US007208312B1

(12) United States Patent
Desnoyers et al.

(10) Patent No.: US 7,208,312 B1
(45) **Date of Patent: *Apr. 24, 2007**

(54) SECRETED AND TRANSMEMBRANE POLYPEPTIDES AND NUCLEIC ACIDS ENCODING THE SAME

(75) Inventors: Luc Desnoyers, San Francisco, CA (US); Audrey Goddard, San Francisco, CA (US); Paul J. Godowski, Burlingame, CA (US); Austin L. Gurney, Belmont, CA (US); William I. Wood, Hillsborough, CA (US); Ellen Filvaroff, San Francisco, CA (US)

(73) Assignee: Genentech, Inc., South San Francicso, CA (US)

( * ) Notice: Subject to any disclaimer, the term of this patent is extended or adjusted under 35 U.S.C. 154(b) by 578 days.

This patent is subject to a terminal disclaimer.

(21) Appl. No.: 10/448,580

(22) Filed: May 29, 2003

Related U.S. Application Data

(63) Continuation of application No. 09/907,794, filed on Jul. 17, 2001, now Pat. No. 6,635,468, which is a continuation of application No. 09/665,350, filed on Sep. 18, 2000, now abandoned, which is a continuation of application No. PCT/US00/04414, filed on Feb. 22, 2000, which is a continuation-in-part of application No. PCT/US99/28313, filed on Nov. 30, 1999, which is a continuation-in-part of application No. PCT/US98/19330, filed on Sep. 16, 1998.

(60) Provisional application No. 60/063,128, filed on Oct. 24, 1997.

(51) Int. Cl.

| | |
|---|---|
| *C12N 1/15* | (2006.01) |
| *C12N 1/21* | (2006.01) |
| *C12N 5/16* | (2006.01) |
| *C12N 15/12* | (2006.01) |
| *C12N 15/63* | (2006.01) |

(52) U.S. Cl. ................................ 435/252.3; 435/320.1; 435/358; 435/252.33; 435/254.2; 536/23.1; 536/23.5

(58) Field of Classification Search ..................... None
See application file for complete search history.

(56) References Cited

U.S. PATENT DOCUMENTS 6,635,468 B2 * 10/2003 Ashkenazi et al. ...... 435/252.3

OTHER PUBLICATIONS

Malda et al., 2003, Biomaterials 24:5153-5161.*
Tallheden et al., 2005, Arthritis Research and Therapy 7:R560-R568.*

* cited by examiner

*Primary Examiner*—Elizabeth Kemmerer
(74) *Attorney, Agent, or Firm*—Elizabeth M. Barnes; Mark T. Kresnak; Ginger R. Dreger

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

6 Claims, 124 Drawing Sheets

FIGURE 1

ACTGCACCTCGGTTCTATCGATTGAATTCCCCGGGGATCCTCTAGAGATCCCTCGACCTCGA
CCCACGCGTCCGGGCCGGAGCAGCACGGCCGCAGGACCTGGAGCTCCGGCTGCGTCTTCCCG
CAGCGCTACCCGCCATGCGCCTGCCGCGCCGGGCCGCGCTGGGGCTCCTGCCGCTTCTGCTG
CTGCTGCCGCCCGCGCCGGAGGCCGCCAAGAAGCCGACGCCCTGCCACCGGTGCCGGGGGCT
GGTGGACAAGTTTAACCAGGGGATGGTGGACACCGCAAAGAAGAACTTTGGCGGCGGGAACA
CGGCTTGGGAGGAAAAGACGCTGTCCAAGTACGAGTCCAGCGAGATTCGCCTGCTGGAGATC
CTGGAGGGGCTGTGCGAGAGCAGCGACTTCGAATGCAATCAGATGCTAGAGGCGCAGGAGGA
GCACCTGGAGGCCTGGTGGCTGCAGCTGAAGAGCGAATATCCTGACTTATTCGAGTGGTTTT
GTGTGAAGACACTGAAAGTGTGCTGCTCTCCAGGAACCTACGGTCCCGACTGTCTCGCATGC
CAGGGCGGATCCCAGAGGCCCTGCAGCGGGAATGGCCACTGCAGCGGAGATGGGAGCAGACA
GGGCGACGGGTCCTGCCGGTGCCACATGGGGTACCAGGGCCCGCTGTGCACTGACTGCATGG
ACGGCTACTTCAGCTCGCTCCGGAACGAGACCCACAGCATCTGCACAGCCTGTGACGAGTCC
TGCAAGACGTGCTCGGGCCTGACCAACAGAGACTGCGGCGAGTGTGAAGTGGGCTGGGTGCT
GGACGAGGGCGCCTGTGTGGATGTGGACGAGTGTGCGGCCGAGCCGCCTCCCTGCAGCGCTG
CGCAGTTCTGTAAGAACGCCAACGGCTCCTACACGTGCGAAGAGTGTGACTCCAGCTGTGTG
GGCTGCACAGGGGAAGGCCCAGGAAACTGTAAAGAGTGTATCTCTGGCTACGCGAGGGAGCA
CGGACAGTGTGCAGATGTGGACGAGTGCTCACTAGCAGAAAAAACCTGTGTGAGGAAAAACG
AAAACTGCTACAATACTCCAGGGAGCTACGTCTGTGTGTGTCCTGACGGCTTCGAAGAAACG
GAAGATGCCTGTGTGCCGCCGGCAGAGGCTGAAGCCACAGAAGGAGAAAGCCCGACACAGCT
GCCCTCCCGCGAAGACCTGTAATGTGCCGGACTTACCCTTTAAATTATTCAGAAGGATGTCC
CGTGGAAAATGTGGCCCTGAGGATGCCGTCTCCTGCAGTGGACAGCGGCGGGGAGAGGCTGC
CTGCTCTCTAACGGTTGATTCTCATTTGTCCCTTAAACAGCTGCATTTCTTGGTTGTTCTTA
AACAGACTTGTATATTTTGATACAGTTCTTTGTAATAAAATTGACCATTGTAGGTAATCAGG
AGGAAAAAAAAAAAAAAAAAAAAAAAAGGGCGGCCGCGACTCTAGAGTCGACCTGCAGAAGC
TTGGCCGCCATGGCCCAACTTGTTTATTGCAGCTTATAATGGTTACAAATAAAGCAATAGCA
TCACAAATTTCACAAATAAAGCATTTTTTTCACTGCATTCTAGTTGTGGTTTGTCCAAACTC
ATCAATGTATCTTATCATGTCTGGATCGGGAATTAATTCGGCGCAGCACCATGGCCTGAAAT
AACCTCTGAAAGAGGAACTTGGTTAGGTACCTTCTGAGGCGGAAAGAACCAGCTGTGGAATG
TGTGTCAGTTAGGGTGTGGAAAGTCCCCAGGCTCCCCAGCAGGCAGAAGTATGCAAGCATGC
ATCTCAATTAGTCAGCAACCCAGTTTT

FIGURE 2

><subunit 1 of 1, 353 aa, 0 stop

><MW: 38192, pI: 4.53, NX(S/T): 2

MRLPRRAALGLLPLLLLLPPAPEAAKKPTPCHRCRGLVDKFNQGMVDTAKKNFGGGNTAWEEKTLSKYESSEIRL
LEILEGLCESSDFECNQMLEAQEEHLEAWWLQLKSEYPDLFEWFCVKTLKVCCSPGTYGPDCLACQGGSQRPCSG
NGHCSGDGSRQGDGSCRCHMGYQGPLCTDCMDGYFSSLRNETHSICTACDESCKTCSGLTNRDCGECEVGWVLDE
GACVDVDECAAEPPPCSAAQFCKNANGSYTCEECDSSCVGCTGEGPGNCKECISGYAREHGQCADVDECSLAEKT
CVRKNENCYNTPGSYVCVCPDGFEETEDACVPPAEAEATEGESPTQLPSREDL

Signal peptide:

amino acids 1-24

N-glycosylation sites.

amino acids 190-194 and 251-255

Glycosaminoglycan attachment sites.

amino acids 149-153 and 155-159 cAMP- and cGMP-dependent protein kinase phosphorylation site.

amino acids 26-30

Casein kinase II phosphorylation sites.

amino acids 58-62, 66-70, 86-90, 197-201, 210-214, 255-259, 295-299, 339-343 and 349-353

Tyrosine kinase phosphorylation site.

amino acids 303-310

N-myristoylation sites.

amino acids 44-50, 54-60, 55-61, 81-87, 150-156, 158-164, 164-170, 252-258 and 313-319

Aspartic acid and asparagine hydroxylation site.

amino acids 308-320

EGF-like domain cysteine pattern signature.

amino acids 166-178

Leucine zipper pattern.

amino acids 94-116

FIGURE 3

CAGGTCCAACTGCACCTCGGTTCTATCGATTGAATTCCCCGGGGATCCTCTAGAGATCCCTC
GACCTCGACCCACGCGTCCGCCAGGCCGGGAGGCGACGCGCCCAGCCGTCTAAACGGAACA
GCCCTGGCTGAGGGAGCTGCAGCGCAGCAGAGTATCTGACGGCGCCAGGTTGCGTAGGTGCG
GCACGAGGAGTTTTCCCGGCAGCGAGGAGGTCCTGAGCAGC<u>ATG</u>GCCCGGAGGAGCGCCTTC
CCTGCCGCCGCGCTCTGGCTCTGGAGCATCCTCCTGTGCCTGCTGGCACTGCGGGCGGAGGC
CGGGCCGCCGCAGGAGGAGAGCCTGTACCTATGGATCGATGCTCACCAGGCAAGAGTACTCA
TAGGATTTGAAGAAGATATCCTGATTGTTTCAGAGGGGAAAATGGCACCTTTTACACATGAT
TTCAGAAAAGCGCAACAGAGAATGCCAGCTATTCCTGTCAATATCCATTCCATGAATTTTAC
CTGGCAAGCTGCAGGGCAGGCAGAATACTTCTATGAATTCCTGTCCTTGCGCTCCCTGGATA
AAGGCATCATGGCAGATCCAACCGTCAATGTCCCTCTGCTGGGAACAGTGCCTCACAAGGCA
TCAGTTGTTCAAGTTGGTTTCCCATGTCTTGGAAAACAGGATGGGGTGGCAGCATTTGAAGT
GGATGTGATTGTTATGAATTCTGAAGGCAACACCATTCTCCAAACACCTCAAAATGCTATCT
TCTTTAAAACATGTCAACAAGCTGAGTGCCCAGGCGGGTGCCGAAATGGAGGCTTTTGTAAT
GAAAGACGCATCTGCGAGTGTCCTGATGGGTTCCACGGACCTCACTGTGAGAAAGCCCTTTG
TACCCCACGATGTATGAATGGTGGACTTTGTGTGACTCCTGGTTTCTGCATCTGCCCACCTG
GATTCTATGGAGTGAACTGTGACAAAGCAAACTGCTCAACCACCTGCTTTAATGGAGGGACC
TGTTTCTACCCTGGAAAATGTATTTGCCCTCCAGGACTAGAGGGAGAGCAGTGTGAAATCAG
CAAATGCCCACAACCCTGTCGAAATGGAGGTAAATGCATTGGTAAAAGCAAATGTAAGTGTT
CCAAAGGTTACCAGGGAGACCTCTGTTCAAAGCCTGTCTGCGAGCCTGGCTGTGGTGCACAT
GGAACCTGCCATGAACCCAACAAATGCCAATGTCAAGAAGGTTGGCATGGAAGACACTGCAA
TAAAAGGTACGAAGCCAGCCTCATACATGCCCTGAGGCCAGCAGGCGCCCAGCTCAGGCAGC
ACACGCCTTCACTTAAAAAGGCCGAGGAGCGGCGGGATCCACCTGAATCCAATTACATCTGG
<u>TGA</u>ACTCCGACATCTGAAACGTTTTAAGTTACACCAAGTTCATAGCCTTTGTTAACCTTTCA
TGTGTTGAATGTTCAAATAATGTTCATTACACTTAAGAATACTGGCCTGAATTTTATTAGCT
TCATTATAAATCACTGAGCTGATATTTACTCTTCCTTTTAAGTTTTCTAAGTACGTCTGTAG
CATGATGGTATAGATTTTCTTGTTTCAGTGCTTTGGGACAGATTTTATATTATGTCAATTGA
TCAGGTTAAAATTTTCAGTGTGTAGTTGGCAGATATTTTCAAAATTACAATGCATTTATGGT
GTCTGGGGGCAGGGGAACATCAGAAAGGTTAAATTGGGCAAAAATGCGTAAGTCACAAGAAT
TTGGATGGTGCAGTTAATGTTGAAGTTACAGCATTTCAGATTTTATTGTCAGATATTTAGAT
GTTTGTTACATTTTTAAAAATTGCTCTTAATTTTTAAACTCTCAATACAATATATTTTGACC
TTACCATTATTCCAGAGATTCAGTATTAAAAAAAAAAAAATTACACTGTGGTAGTGGCATTT
AAACAATATAATATATTCTAAACACAATGAAATAGGGAATATAATGTATGAACTTTTTGCAT
TGGCTTGAAGCAATATAATATATTGTAAACAAAACACAGCTCTTACCTAATAAACATTTTAT
ACTGTTTGTATGTATAAAATAAAGGTGCTGCTTTAGTTTTTGGAAAAAAAAAAAAAAAAAAA
AAAAAAAAAAAAAAAAAAAAAAAGGCGGCCGCGACTCTAGAGTCGACCTGCAGAAGCTTGGC
CGCCATGGCCCAACTTGTTTATTGCAGCTTATAATG

FIGURE 4

></usr/seqdb2/sst/DNA/Dnaseqs.min/ss.DNA33094
><subunit 1 of 1, 379 aa, 0 stop
><MW: 41528, pI: 7.97, NX(S/T): 2

MARRSAFPAAALWLWSILLCLLALRAEAGPPQEESLYLWIDAHQARVLIGFEEDILIVSEGK
MAPFTHDFRKAQQRMPAIPVNIHSMNFTWQAAGQAEYFYEFLSLRSLDKGIMADPTVNVPLL
GTVPHKASVVQVGFPCLGKQDGVAAFEVDVIVMNSEGNTILQTPQNAIFFKTCQQAECPGGC
RNGGFCNERRICECPDGFHGPHCEKALCTPRCMNGGLCVTPGFCICPPGFYGVNCDKANCST
TCFNGGTCFYPGKCICPPGLEGEQCEISKCPQPCRNGGKCIGKSKCKCSKGYQGDLCSKPVC
EPGCGAHGTCHEPNKCQCQEGWHGRHCNKRYEASLIHALRPAGAQLRQHTPSLKKAEERRDP
PESNYIW

Signal peptide:
amino acids 1-28

N-glycosylation site.
amino acids 88-92, 245-249

Casein kinase II phosphorylation site.
amino acids 319-323

Tyrosine kinase phosphorylation site.
amino acids 370-378

N-myristoylation sites.
amino acids 184-190, 185-191, 189-195, 315-321

ATP/GTP-binding site motif A (P-loop).
amino acids 285-293

EGF-like domain cysteine pattern signature.
amino acids 198-210, 230-242, 262-274, 294-306, 326-338

FIGURE 5

CGGACGCGTGGGCGTCCGGCGGTCGCAGAGCCAGGAGGCGGAGGCGCGCGGGCCAGCCTGGG
CCCCAGCCCACACCTTCACCAGGGCCCAGGAGCCACCATGTGGCGATGTCCACTGGGGCTAC
TGCTGTTGCTGCCGCTGGCTGGCCACTTGGCTCTGGGTGCCCAGCAGGGTCGTGGGCGCCGG
GAGCTAGCACCGGGTCTGCACCTGCGGGGCATCCGGGACGCGGGAGGCCGGTACTGCCAGGA
GCAGGACCTGTGCTGCCGCGGCCGTGCCGACGACTGTGCCCTGCCCTACCTGGGCGCCATCT
GTTACTGTGACCTCTTCTGCAACCGCACGGTCTCCGACTGCTGCCCTGACTTCTGGGACTTC
TGCCTCGGCGTGCCACCCCCTTTTCCCCCGATCCAAGGATGTATGCATGGAGGTCGTATCTA
TCCAGTCTTGGGAACGTACTGGGACAACTGTAACCGTTGCACCTGCCAGGAGAACAGGCAGT
GGCATGGTGGATCCAGACATGATCAAAGCCATCAACCAGGGCAACTATGGCTGGCAGGCTGG
GAACCACAGCGCCTTCTGGGGCATGACCCTGGATGAGGGCATTCGCTACCGCCTGGGCACCA
TCCGCCCATCTTCCTCGGTCATGAACATGCATGAAATTTATACAGTGCTGAACCCAGGGGAG
GTGCTTCCCACAGCCTTCGAGGCCTCTGAGAAGTGGCCCAACCTGATTCATGAGCCTCTTGA
CCAAGGCAACTGTGCAGGCTCCTGGGCCTTCTCCACAGCAGCTGTGGCATCCGATCGTGTCT
CAATCCATTCTCTGGGACACATGACGCCTGTCCTGTCGCCCCAGAACCTGCTGTCTTGTGAC
ACCCACCAGCAGCAGGGCTGCCGCGGTGGGCGTCTCGATGGTGCCTGGTGGTTCCTGCGTCG
CCGAGGGGTGGTGTCTGACCACTGCTACCCCTTCTCGGGCCGTGAACGAGACGAGGCTGGCC
CTGCGCCCCCCTGTATGATGCACAGCCGAGCCATGGGTCGGGGCAAGCGCCAGGCCACTGCC
CACTGCCCCAACAGCTATGTTAATAACAATGACATCTACCAGGTCACTCCTGTCTACCGCCT
CGGCTCCAACGACAAGGAGATCATGAAGGAGCTGATGGAGAATGGCCCTGTCCAAGCCCTCA
TGGAGGTGCATGAGGACTTCTTCCTATACAAGGGAGGCATCTACAGCCACACGCCAGTGAGC
CTTGGGAGGCCAGAGAGATACCGCCGGCATGGACCCACTCAGTCAAGATCACAGGATGGGG
AGAGGAGACGCTGCCAGATGGAAGGACGCTCAAATACTGGACTGCGGCCAACTCCTGGGGCC
CAGCCTGGGGCGAGAGGGGCCACTTCCGCATCGTGCGCGGCGTCAATGAGTGCGACATCGAG
AGCTTCGTGCTGGGCGTCTGGGGCCGCGTGGGCATGGAGGACATGGGTCATCACTGAGGCTG
CGGGCACCACGCGGGGTCCGGCCTGGGATCCAGGCTAAGGGCCGGCGGAAGAGGCCCCAATG
GGGCGGTGACCCCAGCCTCGCCCGACAGAGCCCGGGGCGCAGGCGGGCGCCAGGGCGCTAAT
CCCGGCGCGGGTTCCGCTGACGCAGCGCCCCGCCTGGGAGCCGCGGGCAGGCGAGACTGGCG
GAGCCCCCAGACCTCCCAGTGGGGACGGGGCAGGGCCTGGCCTGGGAAGAGCACAGCTGCAG
ATCCCAGGCCTCTGGCGCCCCCACTCAAGACTACCAAAGCCAGGACACCTCAAGTCTCCAGC
CCCAATACCCCACCCCAATCCCGTATTCTTTTTTTTTTTTTTTAGACAGGGTCTTGCTCCG
TTGCCCAGGTTGGAGTGCAGTGGCCCATCAGGGCTCACTGTAACCTCCGACTCCTGGGTTCA
AGTGACCCTCCCACCTCAGCCTCTCAAGTAGCTGGGACTACAGGTGCACCACCACACCTGGC
TAATTTTTGTATTTTTTGTAAAGAGGGGGGTCTCACTGTGTTGCCCAGGCTGGTTTCGAACT
CCTGGGCTCAAGCGGTCCACCTGCCTCCGCCTCCCAAAGTGCTGGGATTGCAGGCATGAGCC
ACTGCACCCAGCCCTGTATTCTTATTCTTCAGATATTTATTTTTCTTTTCACTGTTTTAAAA
TAAAACCAAAGTATTGATAAAAAAAAA

FIGURE 6

></usr/seqdb2/sst/DNA/Dnaseqs.min/ss.DNA33223
><subunit 1 of 1, 164 aa, 1 stop
><MW: 18359, pI: 7.45, NX(S/T): 1
MWRCPLGLLLLLPLAGHLALGAQQGRGRRELAPGLHLRGIRDAGGRYCQEQDLCCRGRADDC
ALPYLGAICYCDLFCNRTVSDCCPDFWDFCLGVPPPFPPIQGCMHGGRIYPVLGTYWDNCNR
CTCQENRQWHGGSRHDQSHQPGQLWLAGWEPQRLLGHDPG

N-glycosylation site.
amino acids 78-82, 161-165

Casein kinase II phosphorylation site.
amino acids 80-84, 117-121, 126-130, 169-173, 205-209, 296-300, 411-415

N-myristoylation site.
amino acids 21-27, 39-45, 44-50, 104-110, 160-164, 224-230, 269-275, 378-384, 442-448

Amidation site.
amino acids 26-30, 318-322

Eukaryotic thiol (cysteine) proteases histidine active site.
amino acids 398-409

FIGURE 7

AGGCTCCTTGGCCCTTTTTCCACAGCAAGCTTNTGCNATCCCGATTCGTTGTCTCAAATCCA
ATTCTCTTGGGACACATNACGCCTGTCCTTTNGCCCCAGAACCTGCTGTCTTGTACACCCAC
CAGCAGCAGGGCTGCCGCGNTGGGCGTCTCGATGGTGCCTGGTGGTTCCTGCGTCGCCGAGG
GNTGGTGTCTGACCACTGCTACCCCTTCTCGGGCCGTGAACGAGACGAGGCTGGCCCTGCGC
CCCCCTGTATGATGCACAGCCGAGCCATGGGTCGGGGCAAGCGCCAGGCCACTGCCCACTGC
CCCAACAGCTATGTTAATAACAATGACATCTACCAGGTCACTCCTGTCTACCGCCTCGGCTC
CAACGACAAGGAGATCATGAAGGAGCTGATGGAGAATGGCCCTGTCCAAGCCCTCATGGAGG
TGCATGAGGACTTCTTCCTATACAAGGGAGGCATCTACAGCCACACGCCAGTGAGCCTTGGG
AGGCCAGAGAGATACCGCCGGCATGGGACCCACTCAG

FIGURE 8

GCTGCTTGCCCTGTTGATGGCAGGCTTGGCCCTGCAGCCAGGCACTGCCCTGCTGTGCTACT
CCTGCAAAGCCCAGGTGAGCAACGAGGACTGCCTGCAGGTGGAGAACTGCACCCAGCTGGGG
GAGCAGTGCTGGACCGCGCGCATCCGCGCAGTTGGCCTCCTGACCGTCATCAGCAAAGGCTG
CAGCTTGAACTGCGTGGATGACTCACAGGACTACTACGTGGGCAAGAAGAACATCACGTGCT
GTGACACCGACTTGTGCAACGCCAGCGGGGCCCATGCCCTGCAGCCGGCTGCCGCCATCCTT
GCGCTGCTCCCTGCACTCGGCCTGCTGCTCTGGGGACCCGGCCAGCTATAGGCTCTGGGGGG
CCCCGCTGCAGCCCACACTGGGTGTGGTGCCCCAGGCCTCTGTGCCACTCCTCACAGACCTG
GCCCAGTGGGAGCCTGTCCTGGTTCCTGAGGCACATCCTAACGCAAGTCTGACCATGTATGT
CTGCACCCCTGTCCCCCACCCTGACCCTCCCATGGCCCTCTCCAGGACTCCCACCCGGCAGA
TCAGCTCTAGTGACACAGATCCGCCTGCAGATGGCCCCTCCAACCCTCTCTGCTGCTGTTTC
CATGGCCCAGCATTCTCCACCCTTAACCCTGTGCTCAGGCACCTCTTCCCCCAGGAAGCCTT
CCCTGCCCACCCCATCTATGACTTGAGCCAGGTCTGGTCCGTGGTGTCCCCCGCACCCAGCA
GGGGACAGGCACTCAGGAGGGCCCAGTAAAGGCTGAGATGAAGTGGACTGAGTAGAACTGGA
GGACAAGAGTCGACGTGAGTTCCTGGGAGTCTCCAGAGATGGGGCCTGGAGGCCTGGAGGAA
GGGGCCAGGCCTCACATTCGTGGGGCTCCCTGAATGGCAGCCTGAGCACAGCGTAGGCCCTT
AATAAACACCTGTTGGATAAGCCAAAAAAA

FIGURE 9

MTHRTTTWARRTSRAVTPTCATPAGPMPCSRLPPSLRCSLHSACCSGDPASYRLWGAPLQPT
LGVVPQASVPLLTDLAQWEPVLVPEAHPNASLTMYVCTPVPHPDPPMALSRTPTRQISSSDT
DPPADGPSNPLCCCFHGPAFSTLNPVLRHLFPQEAFPAHPIYDLSQVWSVVSPAPSRGQALRRAQ

Signal peptide:
amino acids 1-47

N-glycosylation site.
amino acids 31-35, 74-78, 84-88

Casein kinase II phosphorylation site.
amino acids 22-26, 76-80

N-myristoylation site.
amino acids 56-60

Amidation site.
amino acids 70-74

FIGURE 10

CCCACGCGTCCGAACCTCTCCAGCGATGGGAGCCGCCCGCCTGCTGCCCAACCTCACTCTGT
GCTTACAGCTGCTGATTCTCTGCTGTCAAACTCAGTACGTGAGGGACCAGGGCGCCATGACC
GACCAGCTGAGCAGGCGGCAGATCCGCGAGTACCAACTCTACAGCAGGACCAGTGGCAAGCA
CGTGCAGGTCACCGGGCGTCGCATCTCCGCCACCGCCGAGGACGGCAACAAGTTTGCCAAGC
TCATAGTGGAGACGGACACGTTTGGCAGCCGGGTTCGCATCAAAGGGGCTGAGAGTGAGAAG
TACATCTGTATGAACAAGAGGGGCAAGCTCATCGGGAAGCCCAGCGGGAAGAGCAAAGACTG
CGTGTTCACGGAGATCGTGCTGGAGAACAACTATACGGCCTTCCAGAACGCCCGGCACGAGG
GCTGGTTCATGGCCTTCACGCGGCAGGGGCGGCCCCGCCAGGCTTCCCGCAGCCGCCAGAAC
CAGCGCGAGGCCCACTTCATCAAGCGCCTCTACCAAGGCCAGCTGCCCTTCCCCAACCACGC
CGAGAAGCAGAAGCAGTTCGAGTTTGTGGGCTCCGCCCCCACCCGCCGGACCAAGCGCACAC
GGCGGCCCCAGCCCCTCACGTAGTCTGGGAGGCAGGGGGCAGCAGCCCCTGGGCCGCCTCCC
CACCCCTTTCCCTTCTTAATCCAAGGACTGGGCTGGGGTGGCGGGAGGGGAGCCAGATCCCC
GAGGGAGGACCCTGAGGGCCGCGAAGCATCCGAGCCCCCAGCTGGGAAGGGGCAGGCCGGTG
CCCCAGGGGCGGCTGGCACAGTGCCCCCTTCCCGGACGGGTGGCAGGCCCTGGAGAGGAACT
GAGTGTCACCCTGATCTCAGGCCACCAGCCTCTGCCGGCCTCCCAGCCGGGCTCCTGAAGCC
CGCTGAAAGGTCAGCGACTGAAGGCCTTGCAGACAACCGTCTGGAGGTGGCTGTCCTCAAAA
TCTGCTTCTCGGATCTCCCTCAGTCTGCCCCCAGCCCCCAAACTCCTCCTGGCTAGACTGTA
GGAAGGGACTTTTGTTTGTTTGTTTGTTTCAGGAAAAAAGAAAGGGAGAGAGAGGAAAATAG
AGGGTTGTCCACTCCTCACATTCCACGACCCAGGCCTGCACCCCACCCCCAACTCCCAGCCC
CGGAATAAAACCATTTTCCTGC

FIGURE 11

MGAARLLPNLTLCLQLLILCCQTQYVRDQGAMTDQLSRRQIREYQLYSRTSGKHVQVTGRRI
SATAEDGNKFAKLIVETDTFGSRVRIKGAESEKYICMNKRGKLIGKPSGKSKDCVFTEIVLE
NNYTAFQNARHEGWFMAFTRQGRPRQASRSRQNQREAHFIKRLYQGQLPFPNHAEKQKQFEF
VGSAPTRRTKRTRRPQPLT

Signal peptide:

amino acids 1-22

N-glycosylation site.

amino acids 9-13, 126-130 cAMP- and cGMP-dependent protein kinase phosphorylation site.

amino acids 60-64

Casein kinase II phosphorylation site.

amino acids 65-69

Tyrosine kinase phosphorylation site.

amino acids 39-48, 89-97

N-myristoylation site.

amino acids 69-75, 188-194

Amidation site.

amino acids 58-62

HBGF/FGF family signature.

amino acids 103-128

FIGURE 12

ACTTGCCATCACCTGTTGCCAGTGTGGAAAAATTCTCCCTGTTGAATTTTTTGCACATGGAG
GACAGCAGCAAAGAGGGCAACACAGGCTGATAAGACCAGAGACAGCAGGGAGATTATTTTAC
CATACGCCCTCAGGACGTTCCCTCTAGCTGGAGTTCTGGACTTCAACAGAACCCCATCCAGT
CATTTTGATTTTGCTGTTTATTTTTTTTTTCTTTTTCTTTTTCCCACCACATTGTATTTTAT
TTCCGTACTTCAGAAATGGGCCTACAGACCACAAAGTGGCCCAGCCATGGGGCTTTTTTCCT
GAAGTCTTGGCTTATCATTTCCCTGGGGCTCTACTCACAGGTGTCCAAACTCCTGGCCTGCC
CTAGTGTGTGCCGCTGCGACAGGAACTTTGTCTACTGTAATGAGCGAAGCTTGACCTCAGTG
CCTCTTGGGATCCCGGAGGGCGTAACCGTACTCTACCTCCACAACAACCAAATTAATAATGC
TGGATTTCCTGCAGAACTGCACAATGTACAGTCGGTGCACACGGTCTACCTGTATGGCAACC
AACTGGACGAATTCCCCATGAACCTTCCCAAGAATGTCAGAGTTCTCCATTTGCAGGAAAAC
AATATTCAGACCATTTCACGGGCTGCTCTTGCCCAGCTCTTGAAGCTTGAAGAGCTGCACCT
GGATGACAACTCCATATCCACAGTGGGGGTGGAAGACGGGGCCTTCCGGGAGGCTATTAGCC
TCAAATTGTTGTTTTTGTCTAAGAATCACCTGAGCAGTGTGCCTGTTGGGCTTCCTGTGGAC
TTGCAAGAGCTGAGAGTGGATGAAAATCGAATTGCTGTCATATCCGACATGGCCTTCCAGAA
TCTCACGAGCTTGGAGCGTCTTATTGTGGACGGGAACCTCCTGACCAACAAGGGTATCGCCG
AGGGCACCTTCAGCCATCTCACCAAGCTCAAGGAATTTTCAATTGTACGTAATTCGCTGTCC
CACCCTCCTCCCGATCTCCCAGGTACGCATCTGATCAGGCTCTATTTGCAGGACAACCAGAT
AAACCACATTCCTTTGACAGCCTTCTCAAATCTGCGTAAGCTGGAACGGCTGGATATATCCA
ACAACCAACTGCGGATGCTGACTCAAGGGGTTTTTGATAATCTCTCCAACCTGAAGCAGCTC
ACTGCTCGGAATAACCCTTGGTTTTGTGACTGCAGTATTAAATGGGTCACAGAATGGCTCAA
ATATATCCCTTCATCTCTCAACGTGCGGGGTTTCATGTGCCAAGGTCCTGAACAAGTCCGGG
GGATGGCCGTCAGGGAATTAAATATGAATCTTTTGTCCTGTCCCACCACGACCCCCGGCCTG
CCTCTCTTCACCCCAGCCCCAAGTACAGCTTCTCCGACCACTCAGCCTCCCACCCTCTCTAT
TCCAAACCCTAGCAGAAGCTACACGCCTCCAACTCCTACCACATCGAAACTTCCCACGATTC
CTGACTGGGATGGCAGAGAAAGAGTGACCCCACCTATTTCTGAACGGATCCAGCTCTCTATC
CATTTTGTGAATGATACTTCCATTCAAGTCAGCTGGCTCTCTCTCTTCACCGTGATGGCATA
CAAACTCACATGGGTGAAAATGGGCCACAGTTTAGTAGGGGGCATCGTTCAGGAGCGCATAG
TCAGCGGTGAGAAGCAACACCTGAGCCTGGTTAACTTAGAGCCCCGATCCACCTATCGGATT
TGTTTAGTGCCACTGGATGCTTTTAACTACCGCGCGGTAGAAGACACCATTTGTTCAGAGGC
CACCACCCATGCCTCCTATCTGAACAACGGCAGCAACACAGCGTCCAGCCATGAGCAGACGA
CGTCCCACAGCATGGGCTCCCCCTTTCTGCTGGCGGGCTTGATCGGGGGCGCGGTGATATTT
GTGCTGGTGGTCTTGCTCAGCGTCTTTTGCTGGCATATGCACAAAAAGGGGCGCTACACCTC
CCAGAAGTGGAAATACAACCGGGGCCGGCGGAAAGATGATTATTGCGAGGCAGGCACCAAGA
AGGACAACTCCATCCTGGAGATGACAGAAACCAGTTTTCAGATCGTCTCCTTAAATAACGAT
CAACTCCTTAAAGGAGATTTCAGACTGCAGCCCATTTACACCCCAAATGGGGGCATTAATTA
CACAGACTGCCATATCCCCAACAACATGCGATACTGCAACAGCAGCGTGCCAGACCTGGAGC
ACTGCCATACGTGACAGCCAGAGGCCCAGCGTTATCAAGGCGGACAATTAGACTCTTGAGAA
CACACTCGTGTGTGCACATAAAGACACGCAGATTACATTTGATAAATGTTACACAGATGCAT
TTGTGCATTTGAATACTCTGTAATTTATACGGTGTACTATATAATGGGATTTAAAAAAAGTG
CTATCTTTTCTATTTCAAGTTAATTACAAACAGTTTTGTAACTCTTTGCTTTTAAATCTT

FIGURE 13

MGLQTTKWPSHGAFFLKSWLIISLGLYSQVSKLLACPSVCRCDRNFVYCNERSLTSVPLGIP
EGVTVLYLHNNQINNAGFPAELHNVQSVHTVYLYGNQLDEFPMNLPKNVRVLHLQENNIQTI
SRAALAQLLKLEELHLDDNSISTVGVEDGAFREAISLKLLFLSKNHLSSVPVGLPVDLQELR
VDENRIAVISDMAFQNLTSLERLIVDGNLLTNKGIAEGTFSHLTKLKEFSIVRNSLSHPPPD
LPGTHLIRLYLQDNQINHIPLTAFSNLRKLERLDISNNQLRMLTQGVFDNLSNLKQLTARNN
PWFCDCSIKWVTEWLKYIPSSLNVRGFMCQGPEQVRGMAVRELNMNLLSCPTTTPGLPLFTP
APSTASPTTQPPTLSIPNPSRSYTPPTPTTSKLPTIPDWDGRERVTPPISERIQLSIHFVND
TSIQVSWLSLFTVMAYKLTWVKMGHSLVGGIVQERIVSGEKQHLSLVNLEPRSTYRICLVPL
DAFNYRAVEDTICSEATTHASYLNNGSNTASSHEQTTSHSMGSPFLLAGLIGGAVIFVLVVL
LSVFCWHMHKKGRYTSQKWKYNRGRRKDDYCEAGTKKDNSILEMTETSFQIVSLNNDQLLKG
DFRLQPIYTPNGGINYTDCHIPNNMRYCNSSVPDLEHCHT

Signal peptide:

amino acids 1-42

Transmembrane domain:

amino acids 542-561

N-glycosylation site.

amino acids 202-206, 298-302, 433-437, 521-525, 635-639, 649-653

Casein kinase II phosphorylation site.

amino acids 204-208, 407-411, 527-531, 593-597, 598-602, 651-655

Tyrosine kinase phosphorylation site.

amino acids 319-328

N-myristoylation site.

amino acids 2-8, 60-66, 149-155, 213-219, 220-226, 294-300, 522-528, 545-551, 633-639

Amidation site.

amino acids 581-585

Leucine zipper pattern.

amino acids 164-186

Phospholipase A2 aspartic acid active site.

amino acids 39-50

FIGURE 14

ACTTGGAGCAAGCGGCGGCGGCGGAGACAGAGGCAGAGGCAGAAGCTGGGGCTCCGTCCTCGCCTCCCACGAGCG
ATCCCCGAGGAGAGCCGCGGCCCTCGGCGAGGCGAAGAGGCCGACGAGGAAGACCCGGGTGGCTGCGCCCCTGCC
TCGCTTCCCAGGCGCCGGCGGCTGCAGCCTTGCCCCTCTTGCTCGCCTTGAAA<u>ATG</u>GAAAAGATGCTCGCAGGCT
GCTTTCTGCTGATCCTCGGACAGATCGTCCTCCTCCCTGCCGAGGCCAGGGAGCGGTCACGTGGGAGGTCCATCT
CTAGGGGCAGACACGCTCGGACCCACCCGCAGACGGCCCTTCTGGAGAGTTCCTGTGAGAACAAGCGGGCAGACC
TGGTTTTCATCATTGACAGCTCTCGCAGTGTCAACACCCATGACTATGCAAAGGTCAAGGAGTTCATCGTGGACA
TCTTGCAATTCTTGGACATTGGTCCTGATGTCACCCGAGTGGGCCTGCTCCAATATGGCAGCACTGTCAAGAATG
AGTTCTCCCTCAAGACCTTCAAGAGGAAGTCCGAGGTGGAGCGTGCTGTCAAGAGGATGCGGCATCTGTCCACGG
GCACCATGACTGGGCTGGCCATCCAGTATGCCCTGAACATCGCATTCTCAGAAGCAGAGGGGGCCCGGCCCCTGA
GGGAGAATGTGCCACGGGTCATAATGATCGTGACAGATGGGAGACCTCAGGACTCCGTGGCCGAGGTGGCTGCTA
AGGCACGGGACACGGGCATCCTAATCTTTGCCATTGGTGTGGGCCAGGTAGACTTCAACACCTTGAAGTCCATTG
GGAGTGAGCCCCATGAGGACCATGTCTTCCTTGTGGCCAATTTCAGCCAGATTGAGACGCTGACCTCCGTGTTCC
AGAAGAAGTTGTGCACGGCCCACATGTGCAGCACCCTGGAGCATAACTGTGCCCACTTCTGCATCAACATCCCTG
GCTCATACGTCTGCAGGTGCAAACAAGGCTACATTCTCAACTCGGATCAGACGACTTGCAGAATCCAGGATCTGT
GTGCCATGGAGGACCACAACTGTGAGCAGCTCTGTGTGAATGTGCCGGGCTCCTTCGTCTGCCAGTGCTACAGTG
GCTACGCCCTGGCTGAGGATGGGAAGAGGTGTGTGGCTGTGGACTACTGTGCCTCAGAAAACCACGGATGTGAAC
ATGAGTGTGTAAATGCTGATGGCTCCTACCTTTGCCAGTGCCATGAAGGATTTGCTCTTAACCCAGATGAAAAAA
CGTGCACAAGGATCAACTACTGTGCACTGAACAAACCGGGCTGTGAGCATGAGTGCGTCAACATGGAGGAGAGCT
ACTACTGCCGCTGCCACCGTGGCTACACTCTGGACCCCAATGGCAAAACCTGCAGCCGAGTGGACCACTGTGCAC
AGCAGGACCATGGCTGTGAGCAGCTGTGTCTGAACACGGAGGATTCCTTCGTCTGCCAGTGCTCAGAAGGCTTCC
TCATCAACGAGGACCTCAAGACCTGCTCCCGGGTGGATTACTGCCTGCTGAGTGACCATGGTTGTGAATACTCCT
GTGTCAACATGGACAGATCCTTTGCCTGTCAGTGTCCTGAGGGACACGTGCTCCGCAGCGATGGGAAGACGTGTG
CAAAATTGGACTCTTGTGCTCTGGGGGACCACGGTTGTGAACATTCGTGTGTAAGCAGTGAAGATTCGTTTGTGT
GCCAGTGCTTTGAAGGTTATATACTCCGTGAAGATGGAAAAACCTGCAGAAGGAAAGATGTCTGCCAAGCTATAG
ACCATGGCTGTGAACACATTTGTGTGAACAGTGACGACTCATACACGTGCGAGTGCTTGGAGGGATTCCGGCTCG
CTGAGGATGGGAAACGCTGCCGAAGGAAGGATGTCTGCAAATCAACCCACCATGGCTGCGAACACATTTGTGTTA
ATAATGGGAATTCCTACATCTGCAAATGCTCAGAGGGATTTGTTCTAGCTGAGGACGGAAGACGGTGCAAGAAAT
GCACTGAAGGCCCAATTGACCTGGTCTTTGTGATCGATGGATCCAAGAGTCTTGGAGAAGAGAATTTTGAGGTCG
TGAAGCAGTTTGTCACTGGAATTATAGATTCCTTGACAATTTCCCCCAAAGCCGCTCGAGTGGGGCTGCTCCAGT
ATTCCACACAGGTCCACACAGAGTTCACTCTGAGAAACTTCAACTCAGCCAAAGACATGAAAAAAGCCGTGGCCC
ACATGAAATACATGGGAAAGGGCTCTATGACTGGGCTGGCCCTGAAACACATGTTTGAGAGAAGTTTTACCCAAG
GAGAAGGGGCCAGGCCCCTTTCCACAAGGGTGCCCAGAGCAGCCATTGTGTTCACCGACGGACGGGCTCAGGATG
ACGTCTCCGAGTGGGCCAGTAAAGCCAAGGCCAATGGTATCACTATGTATGCTGTTGGGGTAGGAAAAGCCATTG
AGGAGGAACTACAAGAGATTGCCTCTGAGCCCACAAACAAGCATCTCTTCTATGCCGAAGACTTCAGCACAATGG
ATGAGATAAGTGAAAAACTCAAGAAAGGCATCTGTGAAGCTCTAGAAGACTCCGATGGAAGACAGGACTCTCCAG
CAGGGGAACTGCCAAAAACGGTCCAACAGCCAACAGAATCTGAGCCAGTCACCATAAATATCCAAGACCTACTTT
CCTGTTCTAATTTTGCAGTGCAACACAGATATCTGTTTGAAGAAGACAATCTTTTACGGTCTACACAAAAGCTTT
CCCATTCAACAAAACCTTCAGGAAGCCCTTTGGAAGAAAAACACGATCAATGCAAATGTGAAAACCTTATAATGT
TCCAGAACCTTGCAAACGAAGAAGTAAGAAAATTAACACAGCGCTTAGAAGAAATGACACAGAGAATGGAAGCCC
TGGAAAATCGCCTGAGATACAGA<u>TGA</u>AGATTAGAAATCGCGACACATTTGTAGTCATTGTATCACGGATTACAAT
GAACGCAGTGCAGAGCCCCAAAGCTCAGGCTATTGTTAAATCAATAATGTTGTGAAGTAAAACAATCAGTACTGA
GAAACCTGGTTTGCCACAGAACAAAGACAAGAAGTATACACTAACTTGTATAAATTTATCTAGGAAAAAAATCCT
TCAGAATTCTAAGATGAATTTACCAGGTGAGAATGAATAAGCTATGCAAGGTATTTTGTAATATACTGTGGACAC
AACTTGCTTCTGCCTCATCCTGCCTTAGTGTGCAATCTCATTTGACTATACGATAAAGTTTGCACAGTCTTACTT
CTGTAGAACACTGGCCATAGGAAATGCTGTTTTTTTGTACTGGACTTTACCTTGATATATGTATATGGATGTATG
CATAAAATCATAGGACATATGTACTTGTGGAACAAGTTGGATTTTTTATACAATATTAAAATTCACCACTTCAG

FIGURE 15

MEKMLAGCFLLILGQIVLLPAEARERSRGRSISRGRHARTHPQTALLESSCENKRADLVFII
DSSRSVNTHDYAKVKEFIVDILQFLDIGPDVTRVGLLQYGSTVKNEFSLKTFKRKSEVERAV
KRMRHLSTGTMTGLAIQYALNIAFSEAEGARPLRENVPRVIMIVTDGRPQDSVAEVAAKARD
TGILIFAIGVGQVDFNTLKSIGSEPHEDHVFLVANFSQIETLTSVFQKKLCTAHMCSTLEHN
CAHFCINIPGSYVCRCKQGYILNSDQTTCRIQDLCAMEDHNCEQLCVNVPGSFVCQCYSGYA
LAEDGKRCVAVDYCASENHGCEHECVNADGSYLCQCHEGFALNPDEKTCTRINYCALNKPGC
EHECVNMEESYYCRCHRGYTLDPNGKTCSRVDHCAQQDHGCEQLCLNTEDSFVCQCSEGFLI
NEDLKTCSRVDYCLLSDHGCEYSCVNMDRSFACQCPEGHVLRSDGKTCAKLDSCALGDHGCE
HSCVSSEDSFVCQCFEGYILREDGKTCRRKDVCQAIDHGCEHICVNSDDSYTCECLEGFRLA
EDGKRCRRKDVCKSTHHGCEHICVNNGNSYICKCSEGFVLAEDGRRCKKCTEGPIDLVFVID
GSKSLGEENFEVVKQFVTGIIDSLTISPKAARVGLLQYSTQVHTEFTLRNFNSAKDMKKAVA
HMKYMGKGSMTGLALKHMFERSFTQGEGARPLSTRVPRAAIVFTDGRAQDDVSEWASKAKAN
GITMYAVGVGKAIEEELQEIASEPTNKHLFYAEDFSTMDEISEKLKKGICEALEDSDGRQDS
PAGELPKTVQQPTESEPVTINIQDLLSCSNFAVQHRYLFEEDNLLRSTQKLSHSTKPSGSPL
EEKHDQCKCENLIMFQNLANEEVRKLTQRLEEMTQRMEALENRLRYR

Signal peptide:

amino acids 1-23

N-glycosylation site.

amino acids 221-225 cAMP- and cGMP-dependent protein kinase phosphorylation site.

amino acids 115-119, 606-610, 892-896

Casein kinase II phosphorylation site.

amino acids 49-53, 118-122, 149-153, 176-180, 223-227, 243-247, 401-405, 442-446, 501-505, 624-628, 673-677, 706-710, 780-784, 781-785, 819-823, 866-870

N-myristoylation site.

amino acids 133-139, 258-264, 299-305, 340-346, 453-459, 494-500, 639-645, 690-696, 752-758, 792-798

Amidation site.

amino acids 314-318, 560-564, 601-605

Aspartic acid and asparagine hydroxylation site.

amino acids 253-265, 294-306, 335-347, 376-388, 417-423, 458-464, 540-546, 581-587

FIGURE 16

GGAGCCGCCCTGGGTGTCAGCGGCTCGGCTCCCGCGCACGCTCCGGCCGTCGCGCAGCCTCG
GCACCTGCAGGTCCGTGCGTCCCGCGGCTGGCGCCCCTGACTCCGTCCCGGCCAGGGAGGGC
CATGATTTCCCTCCCGGGGCCCCTGGTGACCAACTTGCTGCGGTTTTTGTTCCTGGGGCTGA
GTGCCCTCGCGCCCCCCTCGCGGGCCCAGCTGCAACTGCACTTGCCCGCCAACCGGTTGCAG
GCGGTGGAGGGAGGGGAAGTGGTGCTTCCAGCGTGGTACACCTTGCACGGGGAGGTGTCTTC
ATCCCAGCCATGGGAGGTGCCCTTTGTGATGTGGTTCTTCAAACAGAAAGAAAAGGAGGATC
AGGTGTTGTCCTACATCAATGGGGTCACAACAAGCAAACCTGGAGTATCCTTGGTCTACTCC
ATGCCCTCCCGGAACCTGTCCCTGCGGCTGGAGGGTCTCCAGGAGAAAGACTCTGGCCCCTA
CAGCTGCTCCGTGAATGTGCAAGACAAACAAGGCAAATCTAGGGGCCACAGCATCAAAACCT
TAGAACTCAATGTACTGGTTCCTCCAGCTCCTCCATCCTGCCGTCTCCAGGGTGTGCCCCAT
GTGGGGGCAAACGTGACCCTGAGCTGCCAGTCTCCAAGGAGTAAGCCCGCTGTCCAATACCA
GTGGGATCGGCAGCTTCCATCCTTCCAGACTTTCTTTGCACCAGCATTAGATGTCATCCGTG
GGTCTTTAAGCCTCACCAACCTTTCGTCTTCCATGGCTGGAGTCTATGTCTGCAAGGCCCAC
AATGAGGTGGGCACTGCCCAATGTAATGTGACGCTGGAAGTGAGCACAGGGCCTGGAGCTGC
AGTGGTTGCTGGAGCTGTTGTGGGTACCCTGGTTGGACTGGGGTTGCTGGCTGGGCTGGTCC
TCTTGTACCACCGCCGGGGCAAGGCCCTGGAGGAGCCAGCCAATGATATCAAGGAGGATGCC
ATTGCTCCCCGGACCCTGCCCTGGCCCAAGAGCTCAGACACAATCTCCAAGAATGGGACCCT
TTCCTCTGTCACCTCCGCACGAGCCCTCCGGCCACCCCATGGCCCTCCCAGGCCTGGTGCAT
TGACCCCCACGCCCAGTCTCTCCAGCCAGGCCCTGCCCTCACCAAGACTGCCCACGACAGAT
GGGGCCCACCCTCAACCAATATCCCCCATCCCTGGTGGGGTTTCTTCCTCTGGCTTGAGCCG
CATGGGTGCTGTGCCTGTGATGGTGCCTGCCCAGAGTCAAGCTGGCTCTCTGGTATGATGAC
CCCACCACTCATTGGCTAAAGGATTTGGGGTCTCTCCTTCCTATAAGGGTCACCTCTAGCAC
AGAGGCCTGAGTCATGGGAAAGAGTCACACTCCTGACCCTTAGTACTCTGCCCCCACCTCTC
TTTACTGTGGGAAAACCATCTCAGTAAGACCTAAGTGTCCAGGAGACAGAAGGAGAAGAGGA
AGTGGATCTGGAATTGGGAGGAGCCTCCACCCACCCCTGACTCCTCCTTATGAAGCCAGCTG
CTGAAATTAGCTACTCACCAAGAGTGAGGGGCAGAGACTTCCAGTCACTGAGTCTCCCAGGC
CCCCTTGATCTGTACCCCACCCCTATCTAACACCACCCTTGGCTCCCACTCCAGCTCCCTGT
ATTGATATAACCTGTCAGGCTGGCTTGGTTAGGTTTTACTGGGGCAGAGGATAGGGAATCTC
TTATTAAAACTAACATGAAATATGTGTTGTTTTCATTTGCAAATTTAAATAAAGATACATAA
TGTTTGTATGAAAAA

FIGURE 17

MISLPGPLVTNLLRFLFLGLSALAPPSRAQLQLHLPANRLQAVEGGEVVLPAWYTLHGEVSS
SQPWEVPFVMWFFKQKEKEDQVLSYINGVTTSKPGVSLVYSMPSRNLSLRLEGLQEKDSGPY
SCSVNVQDKQGKSRGHSIKTLELNVLVPPAPPSCRLQGVPHVGANVTLSCQSPRSKPAVQYQ
WDRQLPSFQTFFAPALDVIRGSLSLTNLSSSMAGVYVCKAHNEVGTAQCNVTLEVSTGPGAA
VVAGAVVGTLVGLGLLAGLVLLYHRRGKALEEPANDIKEDAIAPRTLPWPKSSDTISKNGTL
SSVTSARALRPPHGPPRPGALTPTPSLSSQALPSPRLPTTDGAHPQPISPIPGGVSSSGLSR
MGAVPVMVPAQSQAGSLV

Signal peptide:

amino acids 1-29

Transmembrane domain:

amino acids 245-267

N-glycosylation site.

amino acids 108-112, 169-173, 213-217, 236-240, 307-311

N-myristoylation site.

amino acids 90-96, 167-173, 220-226, 231-237, 252-258, 256-262, 262-268, 308-314, 363-369, 364-370

Prokaryotic membrane lipoprotein lipid attachment site.

amino acids 164-175

FIGURE 18

CGCCACCACTGCGGCCACCGCCAATGAAACGCCTCCCGCTCCTAGTGGTTTTTTCCACTTTG
TTGAATTGTTCCTATACTCAAAATTGCACCAAGACACCTTGTCTCCCAAATGCAAAATGTGA
AATACGCAATGGAATTGAAGCCTGCTATTGCAACATGGGATTTTCAGGAAATGGTGTCACAA
TTTGTGAAGATGATAATGAATGTGGAAATTTAACTCAGTCCTGTGGCGAAAATGCTAATTGC
ACTAACACAGAAGGAAGTTATTATTGTATGTGTGTACCTGGCTTCAGATCCAGCAGTAACCA
AGACAGGTTTATCACTAATGATGGAACCGTCTGTATAGAAAATGTGAATGCAAACTGCCATT
TAGATAATGTCTGTATAGCTGCAAATATTAATAAAACTTTAACAAAAATCAGATCCATAAAA
GAACCTGTGGCTTTGCTACAAGAAGTCTATAGAAATTCTGTGACAGATCTTTCACCAACAGA
TATAATTACATATATAGAAATATTAGCTGAATCATCTTCATTACTAGGTTACAAGAACAACA
CTATCTCAGCCAAGGACACCCTTTCTAACTCAACTCTTACTGAATTTGTAAAAACCGTGAAT
AATTTTGTTCAAAGGGATACATTTGTAGTTTGGGACAAGTTATCTGTGAATCATAGGAGAAC
ACATCTTACAAAACTCATGCACACTGTTGAACAAGCTACTTTAAGGATATCCCAGAGCTTCC
AAAAGACCACAGAGTTTGATACAAATTCAACGGATATAGCTCTCAAAGTTTTCTTTTTTGAT
TCATATAACATGAAACATATTCATCCTCATATGAATATGGATGGAGACTACATAAATATATT
TCCAAAGAGAAAAGCTGCATATGATTCAAATGGCAATGTTGCAGTTGCATTTTTATATTATA
AGAGTATTGGTCCTTTGCTTTCATCATCTGACAACTTCTTATTGAAACCTCAAAATTATGAT
AATTCTGAAGAGGAGGAAAGAGTCATATCTTCAGTAATTTCAGTCTCAATGAGCTCAAACCC
ACCCACATTATATGAACTTGAAAAAATAACATTTACATTAAGTCATCGAAAGGTCACAGATA
GGTATAGGAGTCTATGTGCATTTTGGAATTACTCACCTGATACCATGAATGGCAGCTGGTCT
TCAGAGGGCTGTGAGCTGACATACTCAAATGAGACCCACACCTCATGCCGCTGTAATCACCT
GACACATTTTGCAATTTTGATGTCCTCTGGTCCTTCCATTGGTATTAAAGATTATAATATTC
TTACAAGGATCACTCAACTAGGAATAATTATTTCACTGATTTGTCTTGCCATATGCATTTTT
ACCTTCTGGTTCTTCAGTGAAATTCAAAGCACCAGGACAACAATTCACAAAAATCTTTGCTG
TAGCCTATTTCTTGCTGAACTTGTTTTTCTTGTTGGGATCAATACAAATACTAATAAGCTCT
TCTGTTCAATCATTGCCGGACTGCTACACTACTTCTTTTTAGCTGCTTTTGCATGGATGTGC
ATTGAAGGCATACATCTCTATCTCATTGTTGTGGGTGTCATCTACAACAAGGGATTTTTGCA
CAAGAATTTTTATATCTTTGGCTATCTAAGCCCAGCCGTGGTAGTTGGATTTTCGGCAGCAC
TAGGATACAGATATTATGGCACAACCAAAGTATGTTGGCTTAGCACCGAAAACAACTTTATT
TGGAGTTTTATAGGACCAGCATGCCTAATCATTCTTGTTAATCTCTTGGCTTTTGGAGTCAT
CATATACAAAGTTTTTCGTCACACTGCAGGGTTGAAACCAGAAGTTAGTTGCTTTGAGAACA
TAAGGTCTTGTGCAAGAGGAGCCCTCGCTCTTCTGTTCCTTCTCGGCACCACCTGGATCTTT
GGGGTTCTCCATGTTGTGCACGCATCAGTGGTTACAGCTTACCTCTTCACAGTCAGCAATGC
TTTCCAGGGGATGTTCATTTTTTTATTCCTGTGTGTTTTATCTAGAAAGATTCAAGAAGAAT
ATTACAGATTGTTCAAAAATGTCCCCTGTTGTTTTGGATGTTTAAGGTAAACATAGAGAATG
GTGGATAATTACAACTGCACAAAAATAAAAATTCCAAGCTGTGGATGACCAATGTATAAAAA
TGACTCATCAAATTATCCAATTATTAACTACTAGACAAAAAGTATTTTAAATCAGTTTTTCT
GTTTATGCTATAGGAACTGTAGATAATAAGGTAAAATTATGTATCATATAGATATACTATGT
TTTTCTATGTGAAATAGTTCTGTCAAAAATAGTATTGCAGATATTTGGAAAGTAATTGGTTT
CTCAGGAGTGATATCACTGCACCCAAGGAAAGATTTTCTTTCTAACACGAGAAGTATATGAA
TGTCCTGAAGGAAACCACTGGCTTGATATTTCTGTGACTCGTGTTGCCTTTGAAACTAGTCC
CCTACCACCTCGGTAATGAGCTCCATTACAGAAAGTGGAACATAAGAGAATGAAGGGGCAGA
ATATCAAACAGTGAAAAGGGAATGATAAGATGTATTTTGAATGAACTGTTTTTTCTGTAGAC
TAGCTGAGAAATTGTTGACATAAAATAAAGAATTGAAGAAACACATTTTACCATTTTGTGAA
TTGTTCTGAACTTAAATGTCCACTAAAACAACTTAGACTTCTGTTTGCTAAATCTGTTTCTT
TTTCTAATATTCTAAAAAAAAAAAAAAAAGGTTTACCTCCACAAATTGAAAAAAAAAAAAAAAAAA
AAAAAAAAAAAAAAAAAAAAAAAAAAAAAAAAAAAA

FIGURE 19

```
MKRLPLLVVFSTLLNCSYTQNCTKTPCLPNAKCEIRNGIEACYCNMGFSGNGVTICEDDNEC
GNLTQSCGENANCTNTEGSYYCMCVPGFRSSSNQDRFITNDGTVCIENVNANCHLDNVCIAA
NINKTLTKIRSIKEPVALLQEVYRNSVTDLSPTDIITYIEILAESSSLLGYKNNTISAKDTL
SNSTLTEFVKTVNNFVQRDTFVVWDKLSVNHRRTHLTKLMHTVEQATLRISQSFQKTTEFDT
NSTDIALKVFFFDSYNMKHIHPHMNMDGDYINIFPKRKAAYDSNGNVAVAFLYYKSIGPLLS
SSDNFLLKPQNYDNSEEEERVISSVISVSMSSNPPTLYELEKITFTLSHRKVTDRYRSLCAF
WNYSPDTMNGSWSSEGCELTYSNETHTSCRCNHLTHFAILMSSGPSIGIKDYNILTRITQLG
IIISLICLAICIFTFWFFSEIQSTRTTIHKNLCCSLFLAELVFLVGINTNTNKLFCSIIAGL
LHYFFLAAFAWMCIEGIHLYLIVVGVIYNKGFLHKNFYIFGYLSPAVVVGFSAALGYRYYGT
TKVCWLSTENNFIWSFIGPACLIILVNLLAFGVIIYKVFRHTAGLKPEVSCFENIRSCARGA
LALLFLLGTTWIFGVLHVVHASVVTAYLFTVSNAFQGMFIFLFLCVLSRKIQEEYYRLFKNV
PCCFGCLR
```

Signal peptide:

amino acids 1-19

Transmembrane domain:

amino acids 430-450, 465-486, 499-513, 535-549, 573-593, 619-636, 648-664

N-glycosylation site.

amino acids 15-19, 21-25, 64-68, 74-78, 127-131, 177-181, 188-192, 249-253, 381-385, 395-399

Glycosaminoglycan attachment site.

amino acids 49-53 cAMP- and cGMP-dependent protein kinase phosphorylation site.

amino acids 360-364

Casein kinase II phosphorylation site.

amino acids 54-58, 68-72, 76-80, 94-98, 135-139, 150-154, 155-159, 161-165, 181-185, 190-194, 244-248, 310-314, 325-329, 346-350, 608-612

Tyrosine kinase phosphorylation site.

amino acids 36-44, 669-677, 670-678

N-myristoylation site.

amino acids 38-44, 50-56, 52-58, 80-86, 382-388, 388-394, 434-440, 480-486, 521-527

Aspartic acid and asparagine hydroxylation site.

amino acids 75-87

FIGURE 20

TGGAAACATATCCTCCCTCATATGAATATGGATGGAGACTACATAAATATATTTCCAAAGNG
AAAAGCCGGCATATGGATTCAAATGGCAATGTTGCAGTTGCATTTTTATATTATAAGAGTAT
TGGTCCCTTTGCTTTCATCATCTGACAACTTCTTATTGAAACCTCAAAATTATGATAATTCT
GAAGAGGAGGAAAGAGTCATATCTTCAGTAATTTCAGTCTCAATGAGCTCAAACCCACCCAC
ATTATATGAACTTGAAAAAATAACATTTACATTAAGTCATCGAAAGGTCACAGATAGGTATA
GGAGTCTATGTGGCATTTTGGAATACTCACCTGATACCATGAATGGCAGCTGGTCTTCAGAG
GGCTGTGAGCTGACATACTCAAATGAGACCCACACCTCATGCCGCTGTAATCACCTGACACA
TTTTGCAATTTTGATGTCCTCTGGTCCTTCCATTGGTATTAAAGATTATAATATTCTTACAA
GGATCACTCAACTAGGAATAATTATTTCACTGATTTGTCTTGCCATATGCATTTTTACCTTC
TGGTTCTTCAGTGAAATTCAAAGCACCAGGA

FIGURE 21

GCTCCCAGCCAAGAACCTCGGGGCCGCTGCGCGGTGGGAGGAGTTCCCCGAAACCCGGCCG
CTAAGCGAGGCCTCCTCCTCCCGCAGATCCGAACGGCCTGGGCGGGGTCACCCCGGCTGGGA
CAAGAAGCCGCCGCCTGCCTGCCCGGGCCCGGGGAGGGGGCTGGGGCTGGGGCCGGAGGCGG
GGTGTGAGTGGGTGTGTGCGGGGGGCGGAGGCTTGATGCAATCCCGATAAGAAATGCTCGGG
TGTCTTGGGCACCTACCCGTGGGGCCCGTAAGGCGCTACTATATAAGGCTGCCGGCCCGGAG
CCGCCGCGCCGTCAGAGCAGGAGCGCTGCGTCCAGGATCTAGGGCCACGACCATCCCAACCC
GGCACTCACAGCCCCGCAGCGCATCCCGGTCGCCGCCCAGCCTCCCGCACCCCCATCGCCGG
AGCTGCGCCGAGAGCCCCAGGGAGGTGCCATGCGGAGCGGGTGTGTGGTGGTCCACGTATGG
ATCCTGGCCGGCCTCTGGCTGGCCGTGGCCGGGCGCCCCCTCGCCTTCTCGGACGCGGGGCC
CCACGTGCACTACGGCTGGGGCGACCCCATCCGCCTGCGGCACCTGTACACCTCCGGCCCCC
ACGGGCTCTCCAGCTGCTTCCTGCGCATCCGTGCCGACGGCGTCGTGGACTGCGCGCGGGGC
CAGAGCGCGCACAGTTTGCTGGAGATCAAGGCAGTCGCTCTGCGGACCGTGGCCATCAAGGG
CGTGCACAGCGTGCGGTACCTCTGCATGGGCGCCGACGGCAAGATGCAGGGGCTGCTTCAGT
ACTCGGAGGAAGACTGTGCTTTCGAGGAGGAGATCCGCCCAGATGGCTACAATGTGTACCGA
TCCGAGAAGCACCGCCTCCCGGTCTCCCTGAGCAGTGCCAAACAGCGGCAGCTGTACAAGAA
CAGAGGCTTTCTTCCACTCTCTCATTTCCTGCCCATGCTGCCCATGGTCCCAGAGGAGCCTG
AGGACCTCAGGGGCCACTTGGAATCTGACATGTTCTCTTCGCCCCTGGAGACCGACAGCATG
GACCCATTTGGGCTTGTCACCGGACTGGAGGCCGTGAGGAGTCCCAGCTTTGAGAAGTAACT
GAGACCATGCCCGGGCCTCTTCACTGCTGCCAGGGGCTGTGGTACCTGCAGCGTGGGGGACG
TGCTTCTACAAGAACAGTCCTGAGTCCACGTTCTGTTTAGCTTTAGGAAGAAACATCTAGAA
GTTGTACATATTCAGAGTTTTCCATTGGCAGTGCCAGTTTCTAGCCAATAGACTTGTCTGAT
CATAACATTGTAAGCCTGTAGCTTGCCCAGCTGCTGCCTGGGCCCCCATTCTGCTCCCTCGA
GGTTGCTGGACAAGCTGCTGCACTGTCTCAGTTCTGCTTGAATACCTCCATCGATGGGGAAC
TCACTTCCTTTGGAAAAATTCTTATGTCAAGCTGAAATTCTCTAATTTTTTCTCATCACTTC
CCCAGGAGCAGCCAGAAGACAGGCAGTAGTTTTAATTTCAGGAACAGGTGATCCACTCTGTA
AAACAGCAGGTAAATTTCACTCAACCCCATGTGGGAATTGATCTATATCTCTACTTCCAGGG
ACCATTTGCCCTTCCCAAATCCCTCCAGGCCAGAACTGACTGGAGCAGGCATGGCCCACCAG
GCTTCAGGAGTAGGGGAAGCCTGGAGCCCCACTCCAGCCCTGGGACAACTTGAGAATTCCCC
CTGAGGCCAGTTCTGTCATGGATGCTGTCCTGAGAATAACTTGCTGTCCCGGTGTCACCTGC
TTCCATCTCCCAGCCCACCAGCCCTCTGCCCACCTCACATGCCTCCCCATGGATTGGGGCCT
CCCAGGCCCCCCACCTTATGTCAACCTGCACTTCTTGTTCAAAAATCAGGAAAAGAAAAGAT
TTGAAGACCCCAAGTCTTGTCAATAACTTGCTGTGTGGAAGCAGCGGGGGAAGACCTAGAAC
CCTTTCCCCAGCACTTGGTTTTCCAACATGATATTTATGAGTAATTTATTTTGATATGTACA
TCTCTTATTTTCTTACATTATTTATGCCCCCAAATTATATTTATGTATGTAAGTGAGGTTTG
TTTTGTATATTAAAATGGAGTTTGTTTGT

FIGURE 22

MRSGCVVVHVWILAGLWLAVAGRPLAFSDAGPHVHYGWGDPIRLRHLYTSGPHGLSSCFLRI
RADGVVDCARGQSAHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVPEEPEDLRGHLESD
MFSSPLETDSMDPFGLVTGLEAVRSPSFEK

Signal peptide:

amino acids 1-22

Casein kinase II phosphorylation site.

amino acids 78-82, 116-120, 190-194, 204-208

N-myristoylation site.

amino acids 15-21, 54-60, 66-72, 201-207

Prokaryotic membrane lipoprotein lipid attachment site.

amino acids 48-59

FIGURE 23

CCCAGAAGTTCAAGGGCCCCCGGCCTCCTGCGCTCCTGCCGCCGGGACCCTCGACCTCCTCA
GAGCAGCCGGCTGCCGCCCCGGGAAGATGGCGAGGAGGAGCCGCCACCGCCTCCTCCTGCTG
CTGCTGCGCTACCTGGTGGTCGCCCTGGGCTATCATAAGGCCTATGGGTTTTCTGCCCCAAA
AGACCAACAAGTAGTCACAGCAGTAGAGTACCAAGAGGCTATTTTAGCCTGCAAAACCCCAA
AGAAGACTGTTTCCTCCAGATTAGAGTGGAAGAAACTGGGTCGGAGTGTCTCCTTTGTCTAC
TATCAACAGACTCTTCAAGGTGATTTTAAAAATCGAGCTGAGATGATAGATTTCAATATCCG
GATCAAAAATGTGACAAGAAGTGATGCGGGGAAATATCGTTGTGAAGTTAGTGCCCCATCTG
AGCAAGGCCAAAACCTGGAAGAGGATACAGTCACTCTGGAAGTATTAGTGGCTCCAGCAGTT
CCATCATGTGAAGTACCCTCTTCTGCTCTGAGTGGAACTGTGGTAGAGCTACGATGTCAAGA
CAAAGAAGGGAATCCAGCTCCTGAATACACATGGTTTAAGGATGGCATCCGTTTGCTAGAAA
ATCCCAGACTTGGCTCCCAAAGCACCAACAGCTCATACACAATGAATACAAAAACTGGAACT
CTGCAATTTAATACTGTTTCCAAACTGGACACTGGAGAATATTCCTGTGAAGCCCGCAATTC
TGTTGGATATCGCAGGTGTCCTGGGAAACGAATGCAAGTAGATGATCTCAACATAAGTGGCA
TCATAGCAGCCGTAGTAGTTGTGGCCTTAGTGATTTCCGTTTGTGGCCTTGGTGTATGCTAT
GCTCAGAGGAAAGGCTACTTTTCAAAAGAAACCTCCTTCCAGAAGAGTAATTCTTCATCTAA
AGCCACGACAATGAGTGAAAATGTGCAGTGGCTCACGCCTGTAATCCCAGCACTTTGGAAGG
CCGCGGCGGGCGGATCACGAGGTCAGGAGTTCTAGACCAGTCTGGCCAATATGGTGAAACCC
CATCTCTACTAAAATACAAAAATTAGCTGGGCATGGTGGCATGTGCCTGCAGTTCCAGCTGC
TTGGGAGACAGGAGAATCACTTGAACCCGGGAGGCGGAGGTTGCAGTGAGCTGAGATCACGC
CACTGCAGTCCAGCCTGGGTAACAGAGCAAGATTCCATCTCAAAAAATAAAATAAATAAATA
AATAAATACTGGTTTTTACCTGTAGAATTCTTACAATAAATATAGCTTGATATTC

FIGURE 24

MARRSRHRLLLLLLRYLVVALGYHKAYGFSAPKDQQVVTAVEYQEAILACKTPKKTVSSRLE
WKKLGRSVSFVYYQQTLQGDFKNRAEMIDFNIRIKNVTRSDAGKYRCEVSAPSEQGQNLEED
TVTLEVLVAPAVPSCEVPSSALSGTVVELRCQDKEGNPAPEYTWFKDGIRLLENPRLGSQST
NSSYTMNTKTGTLQFNTVSKLDTGEYSCEARNSVGYRRCPGKRMQVDDLNISGIIAAVVVVA
LVISVCGLGVCYAQRKGYFSKETSFQKSNSSSKATTMSENVQWLTPVIPALWKAAAGGSRGQEF

Signal peptide:

amino acids 1-20

Transmembrane domain:

amino acids 130-144, 238-258

N-glycosylation site.

amino acids 98-102, 187-191, 236-240, 277-281

Casein kinase II phosphorylation site.

amino acids 39-43, 59-63, 100-104, 149-153, 205-209, 284-288

N-myristoylation site.

amino acids 182-188, 239-245, 255-261, 257-263, 305-311

Amidation site.

amino acids 226-230

FIGURE 25

GACATCGGAGGTGGGCTAGCACTGAAACTGCTTTTCAAGACGAGGAAGAGGAGGAGAAAGAG
AAAGAAGAGGAAGATGTTGGGCAACATTTATTTAACATGCTCCACAGCCCGGACCCTGGCAT
CATGCTGCTATTCCTGCAAATACTGAAGAAGCATGGGATTTAAATATTTTACTTCTAAATAA
ATGAATTACTCAATCTCCTATGACCATCTATACATACTCCACCTTCAAAAAGTACATCAATA
TTATATCATTAAGGAAATAGTAACCTTCTCTTCTCCAATATGCATGACATTTTTGGACAATG
CAATTGTGGCACTGGCACTTATTTCAGTGAAGAAAAACTTTGTGGTTCTATGGCATTCATCA
TTTGACAAATGCAAGCATCTTCCTTATCAATCAGCTCCTATTGAACTTACTAGCACTGACTG
TGGAATCCTTAAGGGCCCATTACATTTCTGAAGAAGAAAGCTAAGATGAAGGACATGCCACT
CCGAATTCATGTGCTACTTGGCCTAGCTATCACTACACTAGTACAAGCTGTAGATAAAAAAG
TGGATTGTCCACGGTTATGTACGTGTGAAATCAGGCCTTGGTTTACACCCAGATCCATTTAT
ATGGAAGCATCTACAGTGGATTGTAATGATTTAGGTCTTTTAACTTTCCCAGCCAGATTGCC
AGCTAACACACAGATTCTTCTCCTACAGACTAACAATATTGCAAAAATTGAATACTCCACAG
ACTTTCCAGTAAACCTTACTGGCCTGGATTTATCTCAAAACAATTTATCTTCAGTCACCAAT
ATTAATGTAAAAAAGATGCCTCAGCTCCTTTCTGTGTACCTAGAGGAAAACAAACTTACTGA
ACTGCCTGAAAAATGTCTGTCCGAACTGAGCAACTTACAAGAACTCTATATTAATCACAACT
TGCTTTCTACAATTTCACCTGGAGCCTTTATTGGCCTACATAATCTTCTTCGACTTCATCTC
AATTCAAATAGATTGCAGATGATCAACAGTAAGTGGTTTGATGCTCTTCCAAATCTAGAGAT
TCTGATGATTGGGGAAAATCCAATTATCAGAATCAAAGACATGAACTTTAAGCCTCTTATCA
ATCTTCGCAGCCTGGTTATAGCTGGTATAAACCTCACAGAAATACCAGATAACGCCTTGGTT
GGACTGGAAAACTTAGAAAGCATCTCTTTTTACGATAACAGGCTTATTAAAGTACCCCATGT
TGCTCTTCAAAAAGTTGTAAATCTCAAATTTTTGGATCTAAATAAAAATCCTATTAATAGAA
TACGAAGGGGTGATTTTAGCAATATGCTACACTTAAAAGAGTTGGGGATAAATAATATGCCT
GAGCTGATTTCCATCGATAGTCTTGCTGTGGATAACCTGCCAGATTTAAGAAAAATAGAAGC
TACTAACAACCCTAGATTGTCTTACATTCACCCCAATGCATTTTTCAGACTCCCCAAGCTGG
AATCACTCATGCTGAACAGCAATGCTCTCAGTGCCCTGTACCATGGTACCATTGAGTCTCTG
CCAAACCTCAAGGAAATCAGCATACACAGTAACCCCATCAGGTGTGACTGTGTCATCCGTTG
GATGAACATGAACAAAACCAACATTCGATTCATGGAGCCAGATTCACTGTTTTGCGTGGACC
CACCTGAATTCCAAGGTCAGAATGTTCGGCAAGTGCATTTCAGGGACATGATGGAAATTTGT
CTCCCTCTTATAGCTCCTGAGAGCTTTCCTTCTAATCTAAATGTAGAAGCTGGGAGCTATGT
TTCCTTTCACTGTAGAGCTACTGCAGAACCACAGCCTGAAATCTACTGGATAACACCTTCTG
GTCAAAAACTCTTGCCTAATACCCTGACAGACAAGTTCTATGTCCATTCTGAGGGAACACTA
GATATAAATGGCGTAACTCCCAAAGAAGGGGGTTTATATACTTGTATAGCAACTAACCTAGT
TGGCGCTGACTTGAAGTCTGTTATGATCAAAGTGGATGGATCTTTTCCACAAGATAACAATG
GCTCTTTGAATATTAAAATAAGAGATATTCAGGCCAATTCAGTTTTGGTGTCCTGGAAAGCA
AGTTCTAAAATTCTCAAATCTAGTGTTAAATGGACAGCCTTTGTCAAGACTGAAAATTCTCA
TGCTGCGCAAAGTGCTCGAATACCATCTGATGTCAAGGTATATAATCTTACTCATCTGAATC
CATCAACTGAGTATAAAATTTGTATTGATATTCCCACCATCTATCAGAAAAACAGAAAAAAA
TGTGTAAATGTCACCACCAAAGGTTTGCACCCTGATCAAAAAGAGTATGAAAAGAATAATAC
CACAACACTTATGGCCTGTCTTGGAGGCCTTCTGGGGATTATTGGTGTGATATGTCTTATCA
GCTGCCTCTCTCCAGAAATGAACTGTGATGGTGGACACAGCTATGTGAGGAATTACTTACAG
AAACCAACCTTTGCATTAGGTGAGCTTTATCCTCCTCTGATAAATCTCTGGGAAGCAGGAAA
AGAAAAAAGTACATCACTGAAAGTAAAAGCAACTGTTATAGGTTTACCAACAAATATGTCCT
AAAAACCACCAAGGAAACCTACTCCAAAAATGAAC

FIGURE 26

MKDMPLRIHVLLGLAITTLVQAVDKKVDCPRLCTCEIRPWFTPRSIYMEASTVDCNDLGLLT
FPARLPANTQILLLQTNNIAKIEYSTDFPVNLTGLDLSQNNLSSVTNINVKKMPQLLSVYLE
ENKLTELPEKCLSELSNLQELYINHNLLSTISPGAFIGLHNLLRLHLNSNRLQMINSKWFDA
LPNLEILMIGENPIIRIKDMNFKPLINLRSLVIAGINLTEIPDNALVGLENLESISFYDNRL
IKVPHVALQKVVNLKFLDLNKNPINRIRRGDFSNMLHLKELGINNMPELISIDSLAVDNLPD
LRKIEATNNPRLSYIHPNAFFRLPKLESLMLNSNALSALYHGTIESLPNLKEISIHSNPIRC
DCVIRWMNMNKTNIRFMEPDSLFCVDPPEFQGQNVRQVHFRDMMEICLPLIAPESFPSNLNV
EAGSYVSFHCRATAEPQPEIYWITPSGQKLLPNTLTDKFYVHSEGTLDINGVTPKEGGLYTC
IATNLVGADLKSVMIKVDGSFPQDNNGSLNIKIRDIQANSVLVSWKASSKILKSSVKWTAFV
KTENSHAAQSARIPSDVKVYNLTHLNPSTEYKICIDIPTIYQKNRKKCVNVTTKGLHPDQKE
YEKNNTTTLMACLGGLLGIIGVICLISCLSPEMNCDGGHSYVRNYLQKPTFALGELYPPLIN
LWEAGKEKSTSLKVKATVIGLPTNMS

Signal sequence:

amino acids 1-22

Transmembrane domain:

amino acids 633-650

N-glycosylation site.

amino acids 93-97, 103-107, 223-227, 382-386, 522-526, 579-583, 608-612, 624-628, 625-629

Casein kinase II phosphorylation site.

amino acids 51-55, 95-99, 242-246, 468-472, 487-491

Tyrosine kinase phosphorylation site.

amino acids 570-579

N-myristoylation site.

amino acids 13-19, 96-102, 158-164, 221-227, 352-358, 437-443, 491-497, 492-498, 634-640, 702-708

Cell attachment sequence.

amino acids 277-280

FIGURE 27

GCCCGGGACTGGCGCAAGGTGCCCAAGCAAGGAAAGAAATAATGAAGAGACACATGTGTTAG
CTGCAGCCTTTTGAAACACGCAAGAAGGAAATCAATAGTGTGGACAGGGCTGGAACCTTTAC
CACGCTTGTTGGAGTAGATGAGGAATGGGCTCGTGATTATGCTGACATTCCAGCATGAATCT
GGTAGACCTGTGGTTAACCCGTTCCCTCTCCATGTGTCTCCTCCTACAAAGTTTTGTTCTTA
TGATACTGTGCTTTCATTCTGCCAGTATGTGTCCCAAGGGCTGTCTTTGTTCTTCCTCTGGG
GGTTTAAATGTCACCTGTAGCAATGCAAATCTCAAGGAAATACCTAGAGATCTTCCTCCTGA
AACAGTCTTACTGTATCTGGACTCCAATCAGATCACATCTATTCCCAATGAAATTTTTAAGG
ACCTCCATCAACTGAGAGTTCTCAACCTGTCCAAAAATGGCATTGAGTTTATCGATGAGCAT
GCCTTCAAAGGAGTAGCTGAAACCTTGCAGACTCTGGACTTGTCCGACAATCGGATTCAAAG
TGTGCACAAAAATGCCTTCAATAACCTGAAGGCCAGGGCCAGAATTGCCAACAACCCCTGGC
ACTGCGACTGTACTCTACAGCAAGTTCTGAGGAGCATGGCGTCCAATCATGAGACAGCCCAC
AACGTGATCTGTAAAACGTCCGTGTTGGATGAACATGCTGGCAGACCATTCCTCAATGCTGC
CAACGACGCTGACCTTTGTAACCTCCCTAAAAAAACTACCGATTATGCCATGCTGGTCACCA
TGTTTGGCTGGTTCACTATGGTGATCTCATATGTGGTATATTATGTGAGGCAAAATCAGGAG
GATGCCCGGAGACACCTCGAATACTTGAAATCCCTGCCAAGCAGGCAGAAGAAAGCAGATGA
ACCTGATGATATTAGCACTGTGGTATAGTGTCCAAACTGACTGTCATTGAGAAAGAAAGAAA
GTAGTTTGCGATTGCAGTAGAAATAAGTGGTTTACTTCTCCCATCCATTGTAAACATTTGAA
ACTTTGTATTTCAGTTTTTTTTGAATTATGCCACTGCTGAACTTTTAACAAACACTACAACA
TAAATAATTTGAGTTTAGGTGATCCACCCCTTAATTGTACCCCCGATGGTATATTTCTGAGT
AAGCTACTATCTGAACATTAGTTAGATCCATCTCACTATTTAATAATGAAATTTATTTTTTT
AATTTAAAAGCAAATAAAAGCTTAACTTTGAACCATGGGAAAAAAAAAAAAAAAAAAAAACA

FIGURE 28

MNLVDLWLTRSLSMCLLLQSFVLMILCFHSASMCPKGCLCSSSGGLNVTCSNANLKEIPRDL
PPETVLLYLDSNQITSIPNEIFKDLHQLRVLNLSKNGIEFIDEHAFKGVAETLQTLDLSDNR
IQSVHKNAFNNLKARARIANNPWHCDCTLQQVLRSMASNHETAHNVICKTSVLDEHAGRPFL
NAANDADLCNLPKKTTDYAMLVTMFGWFTMVISYVVYYVRQNQEDARRHLEYLKSLPSRQKK
ADEPDDISTVV

Signal sequence:
amino acids 1-33

Transmembrane domain:
amino acids 205-220

N-glycosylation site.
amino acids 47-51, 94-98 cAMP- and cGMP-dependent protein kinase phosphorylation site.
amino acids 199-203

Casein kinase II phosphorylation site.
amino acids 162-166, 175-179

N-myristoylation site.
amino acids 37-43, 45-51, 110-116

FIGURE 29

ACCGAGCCGAGCGGACCGAAGGCGCGCCCGAGATGCAGGTGAGCAAGAGGATGCTGGCGGGG
GGCGTGAGGAGCATGCCCAGCCCCCTCCTGGCCTGCTGGCAGCCCATCCTCCTGCTGGTGCT
GGGCTCAGTGCTGTCAGGCTCGGCCACGGGCTGCCCGCCCCGCTGCGAGTGCTCCGCCCAGG
ACCGCGCTGTGCTGTGCCACCGCAAGTGCTTTGTGGCAGTCCCCGAGGGCATCCCCACCGAG
ACGCGCCTGCTGGACCTAGGCAAGAACCGCATCAAAACGCTCAACCAGGACGAGTTCGCCAG
CTTCCCGCACCTGGAGGAGCTGGAGCTCAACGAGAACATCGTGAGCGCCGTGGAGCCCGGCG
CCTTCAACAACCTCTTCAACCTCCGGACGCTGGGTCTCCGCAGCAACCGCCTGAAGCTCATC
CCGCTAGGCGTCTTCACTGGCCTCAGCAACCTGACCAAGCAGGACATCAGCGAGAACAAGAT
CGTTATCCTACTGGACTACATGTTTCAGGACCTGTACAACCTCAAGTCACTGGAGGTTGGCG
ACAATGACCTCGTCTACATCTCTCACCGCGCCTTCAGCGGCCTCAACAGCCTGGAGCAGCTG
ACGCTGGAGAAATGCAACCTGACCTCCATCCCCACCGAGGCGCTGTCCCACCTGCACGGCCT
CATCGTCCTGAGGCTCCGGCACCTCAACATCAATGCCATCCGGGACTACTCCTTCAAGAGGC
TGTACCGACTCAAGGTCTTGGAGATCTCCCACTGGCCCTACTTGGACACCATGACACCCAAC
TGCCTCTACGGCCTCAACCTGACGTCCCTGTCCATCACACACTGCAATCTGACCGCTGTGCC
CTACCTGGCCGTCCGCCACCTAGTCTATCTCCGCTTCCTCAACCTCTCCTACAACCCCATCA
GCACCATTGAGGGCTCCATGTTGCATGAGCTGCTCCGGCTGCAGGAGATCCAGCTGGTGGGC
GGGCAGCTGGCCGTGGTGGAGCCCTATGCCTTCCGCGGCCTCAACTACCTGCGCGTGCTCAA
TGTCTCTGGCAACCAGCTGACCACACTGGAGGAATCAGTCTTCCACTCGGTGGGCAACCTGG
AGACACTCATCCTGGACTCCAACCCGCTGGCCTGCGACTGTCGGCTCCTGTGGGTGTTCCGG
CGCCGCTGGCGGCTCAACTTCAACCGGCAGCAGCCCACGTGCGCCACGCCCGAGTTTGTCCA
GGGCAAGGAGTTCAAGGACTTCCCTGATGTGCTACTGCCCAACTACTTCACCTGCCGCCGCG
CCCGCATCCGGGACCGCAAGGCCCAGCAGGTGTTTGTGGACGAGGGCCACACGGTGCAGTTT
GTGTGCCGGGCCGATGGCGACCCGCCGCCCGCCATCCTCTGGCTCTCACCCCGAAAGCACCT
GGTCTCAGCCAAGAGCAATGGGCGGCTCACAGTCTTCCCTGATGGCACGCTGGAGGTGCGCT
ACGCCCAGGTACAGGACAACGGCACGTACCTGTGCATCGCGGCCAACGCGGGCGGCAACGAC
TCCATGCCCGCCCACCTGCATGTGCGCAGCTACTCGCCCGACTGGCCCCATCAGCCCAACAA
GACCTTCGCTTTCATCTCCAACCAGCCGGGCGAGGGAGAGGCCAACAGCACCCGCGCCACTG
TGCCTTTCCCCTTCGACATCAAGACCCTCATCATCGCCACCACCATGGGCTTCATCTCTTTC
CTGGGCGTCGTCCTCTTCTGCCTGGTGCTGCTGTTTCTCTGGAGCCGGGGCAAGGGCAACAC
AAAGCACAACATCGAGATCGAGTATGTGCCCCGAAAGTCGGACGCAGGCATCAGCTCCGCCG
ACGCGCCCCGCAAGTTCAACATGAAGATGATATGAGGCCGGGGCGGGGGGCAGGGACCCCCG
GGCGGCCGGGCAGGGGAAGGGGCCTGGTCGCCACCTGCTCACTCTCCAGTCCTTCCCACCTC
CTCCCTACCCTTCTACACACGTTCTCTTTCTCCCTCCCGCCTCCGTCCCCTGCTGCCCCCCG
CCAGCCCTCACCACCTGCCCTCCTTCTACCAGGACCTCAGAAGCCCAGACCTGGGGACCCCA
CCTACACAGGGGCATTGACAGACTGGAGTTGAAAGCCGACGAACCGACACGCGGCAGAGTCA
ATAATTCAATAAAAAGTTACGAACTTTCTCTGTAACTTGGGTTTCAATAATTATGGATTTT
TATGAAAACTTGAAATAATAAAAAGAGAAAAAAACTAAAAAAAAAAAAAAAAAAAAA

FIGURE 30

MQVSKRMLAGGVRSMPSPLLACWQPILLLVLGSVLSGSATGCPPRCECSAQDRAVLCHRKCF
VAVPEGIPTETRLLDLGKNRIKTLNQDEFASFPHLEELELNENIVSAVEPGAFNNLFNLRTL
GLRSNRLKLIPLGVFTGLSNLTKQDISENKIVILLDYMFQDLYNLKSLEVGDNDLVYISHRA
FSGLNSLEQLTLEKCNLTSIPTEALSHLHGLIVLRLRHLNINAIRDYSFKRLYRLKVLEISH
WPYLDTMTPNCLYGLNLTSLSITHCNLTAVPYLAVRHLVYLRFLNLSYNPISTIEGSMLHEL
LRLQEIQLVGGQLAVVEPYAFRGLNYLRVLNVSGNQLTTLEESVFHSVGNLETLILDSNPLA
CDCRLLWVFRRRWRLNFNRQQPTCATPEFVQGKEFKDFPDVLLPNYFTCRRARIRDRKAQQV
FVDEGHTVQFVCRADGDPPPAILWLSPRKHLVSAKSNGRLTVFPDGTLEVRYAQVQDNGTYL
CIAANAGGNDSMPAHLHVRSYSPDWPHQPNKTFAFISNQPGEGEANSTRATVPFPFDIKTLI
IATTMGFISFLGVVLFCLVLLFLWSRGKGNTKHNIEIEYVPRKSDAGISSADAPRKFNMKMI

Signal sequence:

amino acids 1-41

Transmembrane domain:

amino acids 556-578

N-glycosylation site.

amino acids 144-148, 202-206, 264-268, 274-278, 293-297, 341-345, 492-496, 505-509, 526-530, 542-546

Casein kinase II phosphorylation site.

amino acids 49-53, 108-112, 146-150, 300-304, 348-352, 349-353, 607-611

Tyrosine kinase phosphorylation site.

amino acids 590-598

N-myristoylation site.

amino acids 10-16, 32-38, 37-43, 113-119, 125-131, 137-143, 262-268, 320-326, 344-350, 359-365, 493-499, 503-509, 605-611

Prokaryotic membrane lipoprotein lipid attachment site.

amino acids 32-43

FIGURE 31

CCCACGCGTCCGCACCTCGGCCCCGGGCTCCGAAGCGGCTCGGGGGCGCCCTTTCGGTCAAC
ATCGTAGTCCACCCCCTCCCCATCCCCAGCCCCCGGGGATTCAGGCTCGCCAGCGCCCAGCC
AGGGAGCCGGCCGGGAAGCGCGATGGGGGCCCCAGCCGCCTCGCTCCTGCTCCTGCTCCTGC
TGTTCGCCTGCTGCTGGGCGCCCGGCGGGGCCAACCTCTCCCAGGACGACAGCCAGCCCTGG
ACATCTGATGAAACAGTGGTGGCTGGTGGCACCGTGGTGCTCAAGTGCCAAGTGAAAGATCA
CGAGGACTCATCCCTGCAATGGTCTAACCCTGCTCAGCAGACTCTCTACTTTGGGGAGAAGA
GAGCCCTTCGAGATAATCGAATTCAGCTGGTTACCTCTACGCCCCACGAGCTCAGCATCAGC
ATCAGCAATGTGGCCCTGGCAGACGAGGGCGAGTACACCTGCTCAATCTTCACTATGCCTGT
GCGAACTGCCAAGTCCCTCGTCACTGTGCTAGGAATTCCACAGAAGCCCATCATCACTGGTT
ATAAATCTTCATTACGGGAAAAAGACACAGCCACCCTAAACTGTCAGTCTTCTGGGAGCAAG
CCTGCAGCCCGGCTCACCTGGAGAAAGGGTGACCAAGAACTCCACGGAGAACCAACCCGCAT
ACAGGAAGATCCCAATGGTAAAACCTTCACTGTCAGCAGCTCGGTGACATTCCAGGTTACCC
GGGAGGATGATGGGGCGAGCATCGTGTGCTCTGTGAACCATGAATCTCTAAAGGGAGCTGAC
AGATCCACCTCTCAACGCATTGAAGTTTTATACACACCAACTGCGATGATTAGGCCAGACCC
TCCCCATCCTCGTGAGGGCCAGAAGCTGTTGCTACACTGTGAGGGTCGCGGCAATCCAGTCC
CCCAGCAGTACCTATGGGAGAAGGAGGGCAGTGTGCCACCCCTGAAGATGACCCAGGAGAGT
GCCCTGATCTTCCCTTTCCTCAACAAGAGTGACAGTGGCACCTACGGCTGCACAGCCACCAG
CAACATGGGCAGCTACAAGGCCTACTACACCCTCAATGTTAATGACCCCAGTCCGGTGCCCT
CCTCCTCCAGCACCTACCACGCCATCATCGGTGGGATCGTGGCTTTCATTGTCTTCCTGCTG
CTCATCATGCTCATCTTCCTTGGCCACTACTTGATCCGGCACAAAGGAACCTACCTGACACA
TGAGGCAAAAGGCTCCGACGATGCTCCAGACGCGGACACGGCCATCATCAATGCAGAAGGCG
GGCAGTCAGGAGGGGACGACAAGAAGGAATATTTCATCTAGAGGCGCCTGCCCACTTCCTGC
GCCCCCCAGGGGCCCTGTGGGGACTGCTGGGGCCGTCACCAACCCGGACTTGTACAGAGCAA
CCGCAGGGCCGCCCCTCCCGCTTGCTCCCCAGCCCACCCACCCCCCTGTACAGAATGTCTGC
TTTGGGTGCGGTTTTGTACTCGGTTTGGAATGGGGAGGGAGGAGGGCGGGGGGAGGGGAGGG
TTGCCCTCAGCCCTTTCCGTGGCTTCTCTGCATTTGGGTTATTATTATTTTTGTAACAATCC
CAAATCAAATCTGTCTCCAGGCTGGAGAGGCAGGAGCCCTGGGGTGAGAAAAGCAAAAAACA
AACAAAAACA

FIGURE 32

MGAPAASLLLLLLLFACCWAPGGANLSQDDSQPWTSDETVVAGGTVVLKCQVKDHEDSSLQW
SNPAQQTLYFGEKRALRDNRIQLVTSTPHELSISISNVALADEGEYTCSIFTMPVRTAKSLV
TVLGIPQKPIITGYKSSLREKDTATLNCQSSGSKPAARLTWRKGDQELHGEPTRIQEDPNGK
TFTVSSSVTFQVTREDDGASIVCSVNHESLKGADRSTSQRIEVLYTPTAMIRPDPPHPREGQ
KLLLHCEGRGNPVPQQYLWEKEGSVPPLKMTQESALIFPFLNKSDSGTYGCTATSNMGSYKA
YYTLNVNDPSPVPSSSSTYHAIIGGIVAFIVFLLLIMLIFLGHYLIRHKGTYLTHEAKGSDD
APDADTAIINAEGGQSGGDDKKEYFI

Signal sequence:

amino acids 1-20

Transmembrane domain:

amino acids 331-352

N-glycosylation site.

amino acids 25-29, 290-294

Casein kinase II phosphorylation site.

amino acids 27-31, 35-39, 89-93, 141-145, 199-203, 388-392

N-myristoylation site.

amino acids 2-8, 23-29, 156-162, 218-224, 295-301, 298-304, 306-310, 334-340, 360-364, 385-389, 386-390

Prokaryotic membrane lipoprotein lipid attachment site.

amino acids 7-18

FIGURE 33

GGGGGTTAGGGAGGAAGGAATCCACCCCCACCCCCCCAAACCCTTTTCTTCTCCTTTCCTGG
CTTCGGACATTGGAGCACTAAATGAACTTGAATTGTGTCTGTGGCGAGCAGGATGGTCGCTG
TTACTTTGTGATGAGATCGGGGATGAATTGCTCGCTTTAAAAATGCTGCTTTGGATTCTGTT
GCTGGAGACGTCTCTTTGTTTTGCCGCTGGAAACGTTACAGGGGACGTTTGCAAAGAGAAGA
TCTGTTCCTGCAATGAGATAGAAGGGGACCTACACGTAGACTGTGAAAAAAAGGGCTTCACA
AGTCTGCAGCGTTTCACTGCCCCGACTTCCCAGTTTTACCATTTATTTCTGCATGGCAATTC
CCTCACTCGACTTTTCCCTAATGAGTTCGCTAACTTTTATAATGCGGTTAGTTTGCACATGG
AAAACAATGGCTTGCATGAAATCGTTCCGGGGGCTTTTCTGGGGCTGCAGCTGGTGAAAAGG
CTGCACATCAACAACAACAAGATCAAGTCTTTTCGAAAGCAGACTTTTCTGGGGCTGGACGA
TCTGGAATATCTCCAGGCTGATTTTAATTTATTACGAGATATAGACCCGGGGGCCTTCCAGG
ACTTGAACAAGCTGGAGGTGCTCATTTTAAATGACAATCTCATCAGCACCCTACCTGCCAAC
GTGTTCCAGTATGTGCCCATCACCCACCTCGACCTCCGGGGTAACAGGCTGAAAACGCTGCC
CTATGAGGAGGTCTTGGAGCAAATCCCTGGTATTGCGGAGATCCTGCTAGAGGATAACCCTT
GGGACTGCACCTGTGATCTGCTCTCCCTGAAAGAATGGCTGGAAAACATTCCCAAGAATGCC
CTGATCGGCCGAGTGGTCTGCGAAGCCCCCACCAGACTGCAGGGTAAAGACCTCAATGAAAC
CACCGAACAGGACTTGTGTCCTTTGAAAAACCGAGTGGATTCTAGTCTCCCGGCGCCCCCTG
CCCAAGAAGAGACCTTTGCTCCTGGACCCCTGCCAACTCCTTTCAAGACAAATGGGCAAGAG
GATCATGCCACACCAGGGTCTGCTCCAAACGGAGGTACAAAGATCCCAGGCAACTGGCAGAT
CAAAATCAGACCCACAGCAGCGATAGCGACGGGTAGCTCCAGGAACAAACCCTTAGCTAACA
GTTTACCCTGCCCTGGGGGCTGCAGCTGCGACCACATCCCAGGGTCGGGTTTAAAGATGAAC
TGCAACAACAGGAACGTGAGCAGCTTGGCTGATTTGAAGCCCAAGCTCTCTAACGTGCAGGA
GCTTTTCCTACGAGATAACAAGATCCACAGCATCCGAAAATCGCACTTTGTGGATTACAAGA
ACCTCATTCTGTTGGATCTGGGCAACAATAACATCGCTACTGTAGAGAACAACACTTTCAAG
AACCTTTTGGACCTCAGGTGGCTATACATGGATAGCAATTACCTGGACACGCTGTCCCGGGA
GAAATTCGCGGGGCTGCAAAACCTAGAGTACCTGAACGTGGAGTACAACGCTATCCAGCTCA
TCCTCCCGGGCACTTTCAATGCCATGCCCAAACTGAGGATCCTCATTCTCAACAACAACCTG
CTGAGGTCCCTGCCTGTGGACGTGTTCGCTGGGGTCTCGCTCTCTAAACTCAGCCTGCACAA
CAATTACTTCATGTACCTCCCGGTGGCAGGGGTGCTGGACCAGTTAACCTCCATCATCCAGA
TAGACCTCCACGGAAACCCCTGGGAGTGCTCCTGCACAATTGTGCCTTTCAAGCAGTGGGCA
GAACGCTTGGGTTCCGAAGTGCTGATGAGCGACCTCAAGTGTGAGACGCCGGTGAACTTCTT
TAGAAAGGATTTCATGCTCCTCTCCAATGACGAGATCTGCCCTCAGCTGTACGCTAGGATCT
CGCCCACGTTAACTTCGCACAGTAAAAACAGCACTGGGTTGGCGGAGACCGGGACGCACTCC
AACTCCTACCTAGACACCAGCAGGGTGTCCATCTCGGTGTTGGTCCCGGGACTGCTGCTGGT
GTTTGTCACCTCCGCCTTCACCGTGGTGGGCATGCTCGTGTTTATCCTGAGGAACCGAAAGC
GGTCCAAGAGACGAGATGCCAACTCCTCCGCGTCCGAGATTAATTCCCTACAGACAGTCTGT
GACTCTTCCTACTGGCACAATGGGCCTTACAACGCAGATGGGGCCCACAGAGTGTATGACTG
TGGCTCTCACTCGCTCTCAGACTAAGACCCCAACCCCAATAGGGGAGGGCAGAGGGAAGGCG
ATACATCCTTCCCCACCGCAGGCACCCCGGGGGCTGGAGGGGCGTGTACCCAAATCCCCGCG
CCATCAGCCTGGATGGGCATAAGTAGATAAATAACTGTGAGCTCGCACAACCGAAAGGGCCT
GACCCCTTACTTAGCTCCCTCCTTGAAACAAAGAGCAGACTGTGGAGAGCTGGGAGAGCGCA
GCCAGCTCGCTCTTTGCTGAGAGCCCCTTTTGACAGAAAGCCCAGCACGACCCTGCTGGAAG
AACTGACAGTGCCCTCGCCCTCGGCCCCGGGGCCTGTGGGGTTGGATGCCGCGGTTCTATAC
ATATATACATATATCCACATCTATATAGAGAGATAGATATCTATTTTTCCCCTGTGGATTAG
CCCCGTGATGGCTCCCTGTTGGCTACGCAGGGATGGGCAGTTGCACGAAGGCATGAATGTAT
TGTAAATAAGTAACTTTGACTTCTGAC

FIGURE 34

MLLWILLLETSLCFAAGNVTGDVCKEKICSCNEIEGDLHVDCEKKGFTSLQRFTAPTSQFYH
LFLHGNSLTRLFPNEFANFYNAVSLHMENNGLHEIVPGAFLGLQLVKRLHINNNKIKSFRKQ
TFLGLDDLEYLQADFNLLRDIDPGAFQDLNKLEVLILNDNLISTLPANVFQYVPITHLDLRG
NRLKTLPYEEVLEQIPGIAEILLEDNPWDCTCDLLSLKEWLENIPKNALIGRVVCEAPTRLQ
GKDLNETTEQDLCPLKNRVDSSLPAPPAQEETFAPGPLPTPFKTNGQEDHATPGSAPNGGTK
IPGNWQIKIRPTAAIATGSSRNKPLANSLPCPGGCSCDHIPGSGLKMNCNNRNVSSLADLKP
KLSNVQELFLRDNKIHSIRKSHFVDYKNLILLDLGNNNIATVENNTFKNLLDLRWLYMDSNY
LDTLSREKFAGLQNLEYLNVEYNAIQLILPGTFNAMPKLRILILNNNLLRSLPVDVFAGVSL
SKLSLHNNYFMYLPVAGVLDQLTSIIQIDLHGNPWECSCTIVPFKQWAERLGSEVLMSDLKC
ETPVNFFRKDFMLLSNDEICPQLYARISPTLTSHSKNSTGLAETGTHSNSYLDTSRVSISVL
VPGLLLVFVTSAFTVVGMLVFILRNRKRSKRRDANSSASEINSLQTVCDSSYWHNGPYNADG
AHRVYDCGSHSLSD

Signal sequence:

amino acids 1-15

Transmembrane domain:

amino acids 618-638

N-glycosylation site.

amino acids 18-22, 253-257, 363-367, 416-420, 595-599, 655-659 cAMP- and cGMP-dependent protein kinase phosphorylation site.

amino acids 122-126, 646-650

Casein kinase II phosphorylation site.

amino acids 30-34, 180-184, 222-226, 256-260, 366-370, 573-577, 608-612, 657-661, 666-670, 693-697

N-myristoylation site.

amino acids 17-23, 67-73, 100-106, 302-308, 328-334, 343-349, 354-360, 465-471, 493-499, 598-604, 603-609

Prokaryotic membrane lipoprotein lipid attachment site.

amino acids 337-348

FIGURE 35

AGTCGACTGCGTCCCCTGTACCCGGCGCCAGCTGTGTTCCTGACCCCAGAATAACTCAGGGC
TGCACCGGGCCTGGCAGCGCTCCGCACACATTTCCTGTCGCGGCCTAAGGGAAACTGTTGGC
CGCTGGGCCCGCGGGGGGATTCTTGGCAGTTGGGGGGTCCGTCGGGAGCGAGGGCGGAGGGG
AAGGGAGGGGGAACCGGGTTGGGGAAGCCAGCTGTAGAGGGCGGTGACCGCGCTCCAGACAC
AGCTCTGCGTCCTCGAGCGGGACAGATCCAAGTTGGGAGCAGCTCTGCGTGCGGGGCCTCAG
AGAATGAGGCCGGCGTTCGCCCTGTGCCTCCTCTGGCAGGCGCTCTGGCCCGGGCCGGGCGG
CGGCGAACACCCCACTGCCGACCGTGCTGGCTGCTCGGCCTCGGGGGCCTGCTACAGCCTGC
ACCACGCTACCATGAAGCGGCAGGCGGCCGAGGAGGCCTGCATCCTGCGAGGTGGGGCGCTC
AGCACCGTGCGTGCGGGCGCCGAGCTGCGCGCTGTGCTCGCGCTCCTGCGGGCAGGCCCAGG
GCCCGGAGGGGGCTCCAAAGACCTGCTGTTCTGGGTCGCACTGGAGCGCAGGCGTTCCCACT
GCACCCTGGAGAACGAGCCTTTGCGGGGTTTCTCCTGGCTGTCCTCCGACCCCGGCGGTCTC
GAAAGCGACACGCTGCAGTGGGTGGAGGAGCCCCAACGCTCCTGCACCGCGCGGAGATGCGC
GGTACTCCAGGCCACCGGTGGGGTCGAGCCCGCAGGCTGGAAGGAGATGCGATGCCACCTGC
GCGCCAACGGCTACCTGTGCAAGTACCAGTTTGAGGTCTTGTGTCCTGCGCCGCGCCCCGGG
GCCGCCTCTAACTTGAGCTATCGCGCGCCCTTCCAGCTGCACAGCGCCGCTCTGGACTTCAG
TCCACCTGGGACCGAGGTGAGTGCGCTCTGCCGGGGACAGCTCCCGATCTCAGTTACTTGCA
TCGCGGACGAAATCGGCGCTCGCTGGGACAAACTCTCGGGCGATGTGTTGTGTCCCTGCCCC
GGGAGGTACCTCCGTGCTGGCAAATGCGCAGAGCTCCCTAACTGCCTAGACGACTTGGGAGG
CTTTGCCTGCGAATGTGCTACGGGCTTCGAGCTGGGGAAGGACGGCCGCTCTTGTGTGACCA
GTGGGGAAGGACAGCCGACCCTTGGGGGGACCGGGGTGCCCACCAGGCGCCCGCCGGCCACT
GCAACCAGCCCCGTGCCGCAGAGAACATGGCCAATCAGGGTCGACGAGAAGCTGGGAGAGAC
ACCACTTGTCCCTGAACAAGACAATTCAGTAACATCTATTCCTGAGATTCCTCGATGGGGAT
CACAGAGCACGATGTCTACCCTTCAAATGTCCCTTCAAGCCGAGTCAAAGGCCACTATCACC
CCATCAGGGAGCGTGATTTCCAAGTTTAATTCTACGACTTCCTCTGCCACTCCTCAGGCTTT
CGACTCCTCCTCTGCCGTGGTCTTCATATTTGTGAGCACAGCAGTAGTAGTGTTGGTGATCT
TGACCATGACAGTACTGGGGCTTGTCAAGCTCTGCTTTCACGAAAGCCCCTCTTCCCAGCCA
AGGAAGGAGTCTATGGGCCCGCCGGGCCTGGAGAGTGATCCTGAGCCCGCTGCTTTGGGCTC
CAGTTCTGCACATTGCACAAACAATGGGGTGAAAGTCGGGGACTGTGATCTGCGGACAGAG
CAGAGGGTGCCTTGCTGGCGGAGTCCCCTCTTGGCTCTAGTGATGCATAGGGAAACAGGGGA
CATGGGCACTCCTGTGAACAGTTTTTCACTTTTGATGAAACGGGGAACCAAGAGGAACTTAC
TTGTGTAACTGACAATTTCTGCAGAAATCCCCCTTCCTCTAAATTCCCTTTACTCCACTGAG
GAGCTAAATCAGAACTGCACACTCCTTCCCTGATGATAGAGGAAGTGGAAGTGCCTTTAGGA
TGGTGATACTGGGGGACCGGGTAGTGCTGGGGAGAGATATTTTCTTATGTTTATTCGGAGAA
TTTGGAGAAGTGATTGAACTTTTCAAGACATTGGAAACAAATAGAACACAATATAATTTACA
TTAAAAAATAATTTCTACCAAAATGGAAAGGAAATGTTCTATGTTGTTCAGGCTAGGAGTAT
ATTGGTTCGAAATCCCAGGGAAAAAAATAAAAATAAAAAATTAAAGGATTGTTGAT

FIGURE 36

MRPAFALCLLWQALWPGPGGGEHPTADRAGCSASGACYSLHHATMKRQAAEEACILRGGALS
TVRAGAELRAVLALLRAGPGPGGGSKDLLFWVALERRRSHCTLENEPLRGFSWLSSDPGGLE
SDTLQWVEEPQRSCTARRCAVLQATGGVEPAGWKEMRCHLRANGYLCKYQFEVLCPAPRPGA
ASNLSYRAPFQLHSAALDFSPPGTEVSALCRGQLPISVTCIADEIGARWDKLSGDVLCPCPG
RYLRAGKCAELPNCLDDLGGFACECATGFELGKDGRSCVTSGEGQPTLGGTGVPTRRPPATA
TSPVPQRTWPIRVDEKLGETPLVPEQDNSVTSIPEIPRWGSQSTMSTLQMSLQAESKATITP
SGSVISKFNSTTSSATPQAFDSSSAVVFIFVSTAVVVLVILTMTVLGLVKLCFHESPSSQPR
KESMGPPGLESDPEPAALGSSSAHCTNNGVKVGDCDLRDRAEGALLAESPLGSSDA

Signal sequence:

amino acids 1-16

Transmembrane domain:

amino acids 399-418

N-glycosylation site.

amino acids 189-193, 381-385

Glycosaminoglycan attachment site.

amino acids 289-293 cAMP- and cGMP-dependent protein kinase phosphorylation site.

amino acids 98-102, 434-438

Casein kinase II phosphorylation site.

amino acids 275-279, 288-292, 342-346, 445-449

N-myristoylation site.

amino acids 30-36, 35-41, 58-64, 59-65, 121-127, 151-157, 185-191, 209-215, 267-273, 350-356, 374-380, 453-459, 463-469, 477-483

Aspartic acid and asparagine hydroxylation site.

amino acids 262-274

FIGURE 37

CGGACGCGTGGGATTCAGCAGTGGCCTGTGGCTGCCAGAGCAGCTCCTCAGGGGAAACTAAG
CGTCGAGTCAGACGGCACCATAATCGCCTTTAAAAGTGCCTCCGCCCTGCCGGCCGCGTATC
CCCCGGCTACCTGGGCCGCCCCGCGGCGGTGCGCGCGTGAGAGGGAGCGCGCGGGCAGCCGA
GCGCCGGTGTGAGCCAGCGCTGCTGCCAGTGTGAGCGGCGGTGTGAGCGCGGTGGGTGCGGA
GGGGCGTGTGTGCCGGCGCGCGCGCCGTGGGGTGCAAACCCCGAGCGTCTACGCTGCCATGA
GGGGCGCGAACGCCTGGGCGCCACTCTGCCTGCTGCTGGCTGCCGCCACCCAGCTCTCGCGG
CAGCAGTCCCCAGAGAGACCTGTTTTCACATGTGGTGGCATTCTTACTGGAGAGTCTGGATT
TATTGGCAGTGAAGGTTTTCCTGGAGTGTACCCTCCAAATAGCAAATGTACTTGGAAAATCA
CAGTTCCCGAAGGAAAAGTAGTCGTTCTCAATTTCCGATTCATAGACCTCGAGAGTGACAAC
CTGTGCCGCTATGACTTTGTGGATGTGTACAATGGCCATGCCAATGGCCAGCGCATTGGCCG
CTTCTGTGGCACTTTCCGGCCTGGAGCCCTTGTGTCCAGTGGCAACAAGATGATGGTGCAGA
TGATTTCTGATGCCAACACAGCTGGCAATGGCTTCATGGCCATGTTCTCCGCTGCTGAACCA
AACGAAAGAGGGGATCAGTATTGTGGAGGACTCCTTGACAGACCTTCCGGCTCTTTTAAAAC
CCCCAACTGGCCAGACCGGGATTACCCTGCAGGAGTCACTTGTGTGTGGCACATTGTAGCCC
CAAAGAATCAGCTTATAGAATTAAAGTTTGAGAAGTTTGATGTGGAGCGAGATAACTACTGC
CGATATGATTATGTGGCTGTGTTTAATGGCGGGGAAGTCAACGATGCTAGAAGAATTGGAAA
GTATTGTGGTGATAGTCCACCTGCGCCAATTGTGTCTGAGAGAAATGAACTTCTTATTCAGT
TTTTATCAGACTTAAGTTTAACTGCAGATGGGTTTATTGGTCACTACATATTCAGGCCAAAA
AAACTGCCTACAACTACAGAACAGCCTGTCACCACCACATTCCCTGTAACCACGGGTTTAAA
ACCCACCGTGGCCTTGTGTCAACAAAAGTGTAGACGGACGGGGACTCTGGAGGGCAATTATT
GTTCAAGTGACTTTGTATTAGCCGGCACTGTTATCACAACCATCACTCGCGATGGAGTTTG
CACGCCACAGTCTCGATCATCAACATCTACAAAGAGGGAAATTTGGCGATTCAGCAGGCGGG
CAAGAACATGAGTGCCAGGCTGACTGTCGTCTGCAAGCAGTGCCCTCTCCTCAGAAGAGGTC
TAAATTACATTATTATGGGCCAAGTAGGTGAAGATGGGCGAGGCAAAATCATGCCAAACAGC
TTTATCATGATGTTCAAGACCAAGAATCAGAAGCTCCTGGATGCCTTAAAAAATAAGCAATG
TTAACAGTGAACTGTGTCCATTTAAGCTGTATTCTGCCATTGCCTTTGAAAGATCTATGTTC
TCTCAGTAGAAAAAAAAATACTTATAAAATTACATATTCTGAAAGAGGATTCCGAAAGATGG
GACTGGTTGACTCTTCACATGATGGAGGTATGAGGCCTCCGAGATAGCTGAGGGAAGTTCTT
TGCCTGCTGTCAGAGGAGCAGCTATCTGATTGGAAACCTGCCGACTTAGTGCGGTGATAGGA
AGCTAAAAGTGTCAAGCGTTGACAGCTTGGAAGCGTTTATTTATACATCTCTGTAAAAGGAT
ATTTTAGAATTGAGTTGTGTGAAGATGTCAAAAAAAGATTTTAGAAGTGCAATATTTATAGT
GTTATTTGTTTCACCTTCAAGCCTTTGCCCTGAGGTGTTACAATCTTGTCTTGCGTTTTCTA
AATCAATGCTTAATAAAATATTTTTAAAGGAAAAAAAAAAAA

FIGURE 38

MRGANAWAPLCLLLAAATQLSRQQSPERPVFTCGGILTGESGFIGSEGFPGVYPPNSKCTWK
ITVPEGKVVVLNFRFIDLESDNLCRYDFVDVYNGHANGQRIGRFCGTFRPGALVSSGNKMMV
QMISDANTAGNGFMAMFSAAEPNERGDQYCGGLLDRPSGSFKTPNWPDRDYPAGVTCVWHIV
APKNQLIELKFEKFDVERDNYCRYDYVAVFNGGEVNDARRIGKYCGDSPPAPIVSERNELLI
QFLSDLSLTADGFIGHYIFRPKKLPTTTEQPVTTTFPVTTGLKPTVALCQQKCRRTGTLEGN
YCSSDFVLAGTVITTITRDGSLHATVSIINIYKEGNLAIQQAGKNMSARLTVVCKQCPLLRR
GLNYIIMGQVGEDGRGKIMPNSFIMMFKTKNQKLLDALKNKQC

Signal sequence:
amino acids 1-23

N-glycosylation site.
amino acids 355-359

Casein kinase II phosphorylation site.
amino acids 64-68, 142-146, 274-278

Tyrosine kinase phosphorylation site.
amino acids 199-208

N-myristoylation site.
amino acids 34-40, 35-41, 100-106, 113-119, 218-224, 289-295, 305-311, 309-315, 320-326, 330-336

Cell attachment sequence.
amino acids 149-152

FIGURE 39

CGGACGCGTGGGCGGACGCGTGGGCGGCCCACGGCGCCCGCGGGCTGGGGCGGTCGCTTCTT
CCTTCTCCGTGGCCTACGAGGGTCCCCAGCCTGGGTAAAGATGGCCCCATGGCCCCCGAAGG
GCCTAGTCCCAGCTGTGCTCTGGGGCCTCAGCCTCTTCCTCAACCTCCCAGGACCTATCTGG
CTCCAGCCCTCTCCACCTCCCCAGTCTTCTCCCCCGCCTCAGCCCCATCCGTGTCATACCTG
CCGGGGACTGGTTGACAGCTTTAACAAGGGCCTGGAGAGAACCATCCGGGACAACTTTGGAG
GTGGAAACACTGCCTGGGAGGAAGAGAATTTGTCCAAATACAAAGACAGTGAGACCCGCCTG
GTAGAGGTGCTGGAGGGTGTGTGCAGCAAGTCAGACTTCGAGTGCCACCGCCTGCTGGAGCT
GAGTGAGGAGCTGGTGGAGAGCTGGTGGTTTCACAAGCAGCAGGAGGCCCCGGACCTCTTCC
AGTGGCTGTGCTCAGATTCCCTGAAGCTCTGCTGCCCCGCAGGCACCTTCGGGCCCTCCTGC
CTTCCCTGTCCTGGGGGAACAGAGAGGCCCTGCGGTGGCTACGGGCAGTGTGAAGGAGAAGG
GACACGAGGGGGCAGCGGGCACTGTGACTGCCAAGCCGGCTACGGGGGTGAGGCCTGTGGCC
AGTGTGGCCTTGGCTACTTTGAGGCAGAACGCAACGCCAGCCATCTGGTATGTTCGGCTTGT
TTTGGCCCCTGTGCCCGATGCTCAGGACCTGAGGAATCAAACTGTTTGCAATGCAAGAAGGG
CTGGGCCCTGCATCACCTCAAGTGTGTAGACATTGATGAGTGTGGCACAGAGGGAGCCAACT
GTGGAGCTGACCAATTCTGCGTGAACACTGAGGGCTCCTATGAGTGCCGAGACTGTGCCAAG
GCCTGCCTAGGCTGCATGGGGGCAGGGCCAGGTCGCTGTAAGAAGTGTAGCCCTGGCTATCA
GCAGGTGGGCTCCAAGTGTCTCGATGTGGATGAGTGTGAGACAGAGGTGTGTCCGGGAGAGA
ACAAGCAGTGTGAAAACACCGAGGGCGGTTATCGCTGCATCTGTGCCGAGGGCTACAAGCAG
ATGGAAGGCATCTGTGTGAAGGAGCAGATCCCAGAGTCAGCAGGCTTCTTCTCAGAGATGAC
AGAAGACGAGTTGGTGGTGCTGCAGCAGATGTTCTTTGGCATCATCATCTGTGCACTGGCCA
CGCTGGCTGCTAAGGGCGACTTGGTGTTCACCGCCATCTTCATTGGGGCTGTGGCGGCCATG
ACTGGCTACTGGTTGTCAGAGCGCAGTGACCGTGTGCTGGAGGGCTTCATCAAGGGCAGATA
ATCGCGGCCACCACCTGTAGGACCTCCTCCCACCCACGCTGCCCCCAGAGCTTGGGCTGCCC
TCCTGCTGGACACTCAGGACAGCTTGGTTTATTTTTGAGAGTGGGGTAAGCACCCCTACCTG
CCTTACAGAGCAGCCCAGGTACCCAGGCCCGGGCAGACAAGGCCCCTGGGGTAAAAAGTAGC
CCTGAAGGTGGATACCATGAGCTCTTCACCTGGCGGGGACTGGCAGGCTTCACAATGTGTGA
ATTTCAAAAGTTTTTCCTTAATGGTGGCTGCTAGAGCTTTGGCCCCTGCTTAGGATTAGGTG
GTCCTCACAGGGGTGGGGCCATCACAGCTCCCTCCTGCCAGCTGCATGCTGCCAGTTCCTGT
TCTGTGTTCACCACATCCCCACACCCCATTGCCACTTATTTATTCATCTCAGGAAATAAAGA
AAGGTCTTGGAAAGTTAAAAAAAAAAAAAAAAAAAAAA

FIGURE 40

MAPWPPKGLVPAVLWGLSLFLNLPGPIWLQPSPPPQSSPPPQPHPCHTCRGLVDSFNKGLER
TIRDNFGGGNTAWEEENLSKYKDSETRLVEVLEGVCSKSDFECHRLLELSEELVESWWFHKQ
QEAPDLFQWLCSDSLKLCCPAGTFGPSCLPCPGGTERPCGGYGQCEGEGTRGGSGHCDCQAG
YGGEACGQCGLGYFEAERNASHLVCSACFGPCARCSGPEESNCLQCKKGWALHHLKCVDIDE
CGTEGANCGADQFCVNTEGSYECRDCAKACLGCMGAGPGRCKKCSPGYQQVGSKCLDVDECE
TEVCPGENKQCENTEGGYRCICAEGYKQMEGICVKEQIPESAGFFSEMTEDELVVLQQMFFG
IIICALATLAAKGDLVFTAIFIGAVAAMTGYWLSERSDRVLEGFIKGR

Signal sequence:

amino acids 1-29

Transmembrane domain:

amino acids 372-395

N-glycosylation site.

amino acids 79-83, 205-209 cAMP- and cGMP-dependent protein kinase phosphorylation site.

amino acids 290-294

Casein kinase II phosphorylation site.

amino acids 63-67, 73-77, 99-103, 101-105, 222-226, 359-263

N-myristoylation site.

amino acids 8-14, 51-57, 59-65, 69-75, 70-76, 167-173, 173-179, 177-183, 188-194, 250-256, 253-259, 267-273, 280-286, 283-289, 326-332, 372-378, 395-401

Aspartic acid and asparagine hydroxylation site.

amino acids 321-333

EGF-like domain cysteine pattern signature.

amino acids 181-193

FIGURE 41

TGAGACCCTCCTGCAGCCTTCTCAAGGGACAGCCCCACTCTGCCTCTTGCTCCTCCAGGGCA
GCACCATGCAGCCCCTGTGGCTCTGCTGGGCACTCTGGGTGTTGCCCCTGGCCAGCCCCGGG
GCCGCCCTGACCGGGGAGCAGCTCCTGGGCAGCCTGCTGCGGCAGCTGCAGCTCAAAGAGGT
GCCCACCCTGGACAGGGCCGACATGGAGGAGCTGGTCATCCCCACCCACGTGAGGGCCCAGT
ACGTGGCCCTGCTGCAGCGCAGCCACGGGGACCGCTCCCGCGGAAAGAGGTTCAGCCAGAGC
TTCCGAGAGGTGGCCGGCAGGTTCCTGGCGTTGGAGGCCAGCACACACCTGCTGGTGTTCGG
CATGGAGCAGCGGCTGCCGCCCAACAGCGAGCTGGTGCAGGCCGTGCTGCGGCTCTTCCAGG
AGCCGGTCCCCAAGGCCGCGCTGCACAGGCACGGGCGGCTGTCCCCGCGCAGCGCCCGGGCC
CGGGTGACCGTCGAGTGGCTGCGCGTCCGCGACGACGGCTCCAACCGCACCTCCCTCATCGA
CTCCAGGCTGGTGTCCGTCCACGAGAGCGGCTGGAAGGCCTTCGACGTGACCGAGGCCGTGA
ACTTCTGGCAGCAGCTGAGCCGGCCCCGGCAGCCGCTGCTGCTACAGGTGTCGGTGCAGAGG
GAGCATCTGGGCCCGCTGGCGTCCGGCGCCCACAAGCTGGTCCGCTTTGCCTCGCAGGGGGC
GCCAGCCGGGCTTGGGGAGCCCCAGCTGGAGCTGCACACCCTGGACCTTGGGGACTATGGAG
CTCAGGGCGACTGTGACCCTGAAGCACCAATGACCGAGGGCACCCGCTGCTGCCGCCAGGAG
ATGTACATTGACCTGCAGGGGATGAAGTGGGCCGAGAACTGGGTGCTGGAGCCCCCGGGCTT
CCTGGCTTATGAGTGTGTGGGCACCTGCCGGCAGCCCCCGGAGGCCCTGGCCTTCAAGTGGC
CGTTTCTGGGGCCTCGACAGTGCATCGCCTCGGAGACTGACTCGCTGCCCATGATCGTCAGC
ATCAAGGAGGGAGGCAGGACCAGGCCCCAGGTGGTCAGCCTGCCCAACATGAGGGTGCAGAA
GTGCAGCTGTGCCTCGGATGGTGCGCTCGTGCCAAGGAGGCTCCAGCCATAGGCGCCTAGTG
TAGCCATCGAGGGACTTGACTTGTGTGTGTTTCTGAAGTGTTCGAGGGTACCAGGAGAGCTG
GCGATGACTGAACTGCTGATGGACAAATGCTCTGTGCTCTCTAGTGAGCCCTGAATTTGCTT
CCTCTGACAAGTTACCTCACCTAATTTTTGCTTCTCAGGAATGAGAATCTTTGGCCACTGGA
GAGCCCTTGCTCAGTTTTCTCTATTCTTATTATTCACTGCACTATATTCTAAGCACTTACAT
GTGGAGATACTGTAACCTGAGGGCAGAAAGCCCANTGTGTCATTGTTTACTTGTCCTGTCAC
TGGATCTGGGCTAAAGTCCTCCACCACCACTCTGGACCTAAGACCTGGGGTTAAGTGTGGGT
TGTGCATCCCCAATCCAGATAATAAAGACTTTGTAAAACATGAATAAAACACATTTTATTCT
AAAA

FIGURE 42

MQPLWLCWALWVLPLASPGAALTGEQLLGSLLRQLQLKEVPTLDRADMEELVIPTHVRAQYV
ALLQRSHGDRSRGKRFSQSFREVAGRFLALEASTHLLVFGMEQRLPPNSELVQAVLRLFQEP
VPKAALHRHGRLSPRSARARVTVEWLRVRDDGSNRTSLIDSRLVSVHESGWKAFDVTEAVNF
WQQLSRPRQPLLLQVSVQREHLGPLASGAHKLVRFASQGAPAGLGEPQLELHTLDLGDYGAQ
GDCDPEAPMTEGTRCCRQEMYIDLQGMKWAENWVLEPPGFLAYECVGTCRQPPEALAFKWPF
LGPRQCIASETDSLPMIVSIKEGGRTRPQVVSLPNMRVQKCSCASDGALVPRRLQP

Signal sequence:
amino acids 1-18

N-glycosylation site.
amino acids 158-162 cAMP- and cGMP-dependent protein kinase phosphorylation site.
amino acids 76-80

Casein kinase II phosphorylation site.
amino acids 68-72, 81-85, 161-165, 169-173, 319-323, 329-333

N-myristoylation site.
amino acids 19-25, 156-162, 225-231, 260-266, 274-280

Amidation site.
amino acids 74-78

TGF-beta family signature.
amino acids 282-298

FIGURE 43

GTCTGTTCCCAGGAGTCCTTCGGCGGCTGTTGTGTCAGTGGCCTGATCGCGATGGGGACAAA
GGCGCAAGTCGAGAGGAAACTGTTGTGCCTCTTCATATTGGCGATCCTGTTGTGCTCCCTGG
CATTGGGCAGTGTTACAGTGCACTCTTCTGAACCTGAAGTCAGAATTCCTGAGAATAATCCT
GTGAAGTTGTCCTGTGCCTACTCGGGCTTTTCTTCTCCCCGTGTGGAGTGGAAGTTTGACCA
AGGAGACACCACCAGACTCGTTTGCTATAATAACAAGATCACAGCTTCCTATGAGGACCGGG
TGACCTTCTTGCCAACTGGTATCACCTTCAAGTCCGTGACACGGGAAGACACTGGGACATAC
ACTTGTATGGTCTCTGAGGAAGGCGGCAACAGCTATGGGGAGGTCAAGGTCAAGCTCATCGT
GCTTGTGCCTCCATCCAAGCCTACAGTTAACATCCCCTCCTCTGCCACCATTGGGAACCGGG
CAGTGCTGACATGCTCAGAACAAGATGGTTCCCCACCTTCTGAATACACCTGGTTCAAAGAT
GGGATAGTGATGCCTACGAATCCCAAAAGCACCCGTGCCTTCAGCAACTCTTCCTATGTCCT
GAATCCCACAACAGGAGAGCTGGTCTTTGATCCCCTGTCAGCCTCTGATACTGGAGAATACA
GCTGTGAGGCACGGAATGGGTATGGGACACCCATGACTTCAAATGCTGTGCGCATGGAAGCT
GTGGAGCGGAATGTGGGGGTCATCGTGGCAGCCGTCCTTGTAACCCTGATTCTCCTGGGAAT
CTTGGTTTTTGGCATCTGGTTTGCCTATAGCCGAGGCCACTTTGACAGAACAAAGAAAGGGA
CTTCGAGTAAGAAGGTGATTTACAGCCAGCCTAGTGCCCGAAGTGAAGGAGAATTCAAACAG
ACCTCGTCATTCCTGGTGTGAGCCTGGTCGGCTCACCGCCTATCATCTGCATTTGCCTTACT
CAGGTGCTACCGGACTCTGGCCCCTGATGTCTGTAGTTTCACAGGATGCCTTATTTGTCTTC
TACACCCCACAGGGCCCCCTACTTCTTCGGATGTGTTTTTAATAATGTCAGCTATGTGCCCC
ATCCTCCTTCATGCCCTCCCTCCCTTTCCTACCACTGCTGAGTGGCCTGGAACTTGTTTAAA
GTGTTTATTCCCCATTTCTTTGAGGGATCAGGAAGGAATCCTGGGTATGCCATTGACTTCCC
TTCTAAGTAGACAGCAAAAATGGCGGGGGTCGCAGGAATCTGCACTCAACTGCCCACCTGGC
TGGCAGGGATCTTTGAATAGGTATCTTGAGCTTGGTTCTGGGCTCTTTCCTTGTGTACTGAC
GACCAGGGCCAGCTGTTCTAGAGCGGGAATTAGAGGCTAGAGCGGCTGAAATGGTTGTTTGG
TGATGACACTGGGGTCCTTCCATCTCTGGGGCCCACTCTCTTCTGTCTTCCCATGGGAAGTG
CCACTGGGATCCCTCTGCCCTGTCCTCCTGAATACAAGCTGACTGACATTGACTGTGTCTGT
GGAAAATGGGAGCTCTTGTTGTGGAGAGCATAGTAAATTTTCAGAGAACTTGAAGCCAAAAG
GATTTAAAACCGCTGCTCTAAAGAAAAGAAAACTGGAGGCTGGGCGCAGTGGCTCACGCCTG
TAATCCCAGAGGCTGAGGCAGGCGGATCACCTGAGGTCGGGAGTTCGGGATCAGCCTGACCA
ACATGGAGAAACCCTACTGGAAATACAAAGTTAGCCAGGCATGGTGGTGCATGCCTGTAGTC
CCAGCTGCTCAGGAGCCTGGCAACAAGAGCAAAACTCCAGCTCAAAAAAAAAAAAAAA

FIGURE 44

MGTKAQVERKLLCLFILAILLCSLALGSVTVHSSEPEVRIPENNPVKLSCAYSGFSSPRVEW
KFDQGDTTRLVCYNNKITASYEDRVTFLPTGITFKSVTREDTGTYTCMVSEEGGNSYGEVKV
KLIVLVPPSKPTVNIPSSATIGNRAVLTCSEQDGSPPSEYTWFKDGIVMPTNPKSTRAFSNS
SYVLNPTTGELVFDPLSASDTGEYSCEARNGYGTPMTSNAVRMEAVERNVGVIVAAVLVTLI
LLGILVFGIWFAYSRGHFDRTKKGTSSKKVIYSQPSARSEGEFKQTSSFLV

Signal sequence:
amino acids 1-27

Transmembrane domain:
amino acids 238-255

N-glycosylation site.
amino acids 185-189 cAMP- and cGMP-dependent protein kinase phosphorylation site.
amino acids 270-274

Casein kinase II phosphorylation site.
amino acids 34-38, 82-86, 100-104, 118-122, 152-156, 154-158, 193-197, 203-207, 287-291

N-myristoylation site.
amino acids 105-111, 116-122, 158-164, 219-225, 237-243, 256-262

FIGURE 45

CAGCGCGTGGCCGGCGCCGCTGTGGGGACAGCATGAGCGGCGGTTGGATGGCGCAGGTTGGA
GCGTGGCGAACAGGGGCTCTGGGCCTGGCGCTGCTGCTGCTGCTCGGCCTCGGACTAGGCCT
GGAGGCCGCCGCGAGCCCGCTTTCCACCCCGACCTCTGCCCAGGCCGCAGGCCCCAGCTCAG
GCTCGTGCCCACCCACCAAGTTCCAGTGCCGCACCAGTGGCTTATGCGTGCCCCTCACCTGG
CGCTGCGACAGGGACTTGGACTGCAGCGATGGCAGCGATGAGGAGGAGTGCAGGATTGAGCC
ATGTACCCAGAAAGGGCAATGCCCACCGCCCCCTGGCCTCCCCTGCCCCTGCACCGGCGTCA
GTGACTGCTCTGGGGGAACTGACAAGAAACTGCGCAACTGCAGCCGCCTGGCCTGCCTAGCA
GGCGAGCTCCGTTGCACGCTGAGCGATGACTGCATTCCACTCACGTGGCGCTGCGACGGCCA
CCCAGACTGTCCCGACTCCAGCGACGAGCTCGGCTGTGGAACCAATGAGATCCTCCCGGAAG
GGGATGCCACAACCATGGGGCCCCCTGTGACCCTGGAGAGTGTCACCTCTCTCAGGAATGCC
ACAACCATGGGGCCCCCTGTGACCCTGGAGAGTGTCCCCTCTGTCGGGAATGCCACATCCTC
CTCTGCCGGAGACCAGTCTGGAAGCCCAACTGCCTATGGGGTTATTGCAGCTGCTGCGGTGC
TCAGTGCAAGCCTGGTCACCGCCACCCTCCTCCTTTTGTCCTGGCTCCGAGCCCAGGAGCGC
CTCCGCCCACTGGGGTTACTGGTGGCCATGAAGGAGTCCCTGCTGCTGTCAGAACAGAAGAC
CTCGCTGCCCTGAGGACAAGCACTTGCCACCACCGTCACTCAGCCCTGGGCGTAGCCGGACA
GGAGGAGAGCAGTGATGCGGATGGGTACCCGGGCACACCAGCCCTCAGAGACCTGAGTTCTT
CTGGCCACGTGGAACCTCGAACCCGAGCTCCTGCAGAAGTGGCCCTGGAGATTGAGGGTCCC
TGGACACTCCCTATGGAGATCCGGGGAGCTAGGATGGGGAACCTGCCACAGCCAGAACTGAG
GGGCTGGCCCCAGGCAGCTCCCAGGGGGTAGAACGGCCCTGTGCTTAAGACACTCCCTGCTG
CCCCGTCTGAGGGTGGCGATTAAAGTTGCTTC

FIGURE 46

MSGGWMAQVGAWRTGALGLALLLLLGLGLGLEAAASPLSTPTSAQAAGPSSGSCPPTKFQCR
TSGLCVPLTWRCDRDLDCSDGSDEEECRIEPCTQKGQCPPPPGLPCPCTGVSDCSGGTDKKL
RNCSRLACLAGELRCTLSDDCIPLTWRCDGHPDCPDSSDELGCGTNEILPEGDATTMGPPVT
LESVTSLRNATTMGPPVTLESVPSVGNATSSSAGDQSGSPTAYGVIAAAAVLSASLVTATLL
LLSWLRAQERLRPLGLLVAMKESLLLSEQKTSLP

Signal sequence:

amino acids 1-30

Transmembrane domain:

amino acids 230-246

N-glycosylation site.

amino acids 126-130, 195-199, 213-217

Casein kinase II phosphorylation site.

amino acids 84-88, 140-144, 161-165, 218-222

N-myristoylation site.

amino acids 3-9, 10-16, 26-32, 30-36, 112-118, 166-172, 212-218, 224-230, 230-236, 263-269

Prokaryotic membrane lipoprotein lipid attachment site.

amino acids 44-55

Leucine zipper pattern.

amino acids 17-39

FIGURE 47

CCCACGCGTCCGGTCTCGCTCGCTCGCGCAGCGGCGGCAGCAGAGGTCGCGCACAGATGCGG
GTTAGACTGGCGGGGGGAGGAGGCGGAGGAGGGAAGGAAGCTGCATGCATGAGACCCACAGA
CTCTTGCAAGCTGGATGCCCTCTGTGGATGAAAGATGTATCATGGAATGAACCCGAGCAATG
GAGATGGATTTCTAGAGCAGCAGCAGCAGCAGCAGCAACCTCAGTCCCCCCAGAGACTCTTG
GCCGTGATCCTGTGGTTTCAGCTGGCGCTGTGCTTCGGCCCTGCACAGCTCACGGGCGGGTT
CGATGACCTTCAAGTGTGTGCTGACCCCGGCATTCCCGAGAATGGCTTCAGGACCCCCAGCG
GAGGGGTTTTCTTTGAAGGCTCTGTAGCCCGATTTCACTGCCAAGACGGATTCAAGCTGAAG
GGCGCTACAAAGAGACTGTGTTTGAAGCATTTTAATGGAACCCTAGGCTGGATCCCAAGTGA
TAATTCCATCTGTGTGCAAGAAGATTGCCGTATCCCTCAAATCGAAGATGCTGAGATTCATA
ACAAGACATATAGACATGGAGAGAAGCTAATCATCACTTGTCATGAAGGATTCAAGATCCGG
TACCCCGACCTACACAATATGGTTTCATTATGTCGCGATGATGGAACGTGGAATAATCTGCC
CATCTGTCAAGGCTGCCTGAGACCTCTAGCCTCTTCTAATGGCTATGTAAACATCTCTGAGC
TCCAGACCTCCTTCCCGGTGGGGACTGTGATCTCCTATCGCTGCTTTCCCGGATTTAAACTT
GATGGGTCTGCGTATCTTGAGTGCTTACAAAACCTTATCTGGTCGTCCAGCCCACCCCGGTG
CCTTGCTCTGGAAGCCCAAGTCTGTCCACTACCTCCAATGGTGAGTCACGGAGATTTCGTCT
GCCACCCGCGGCCTTGTGAGCGCTACAACCACGGAACTGTGGTGGAGTTTTACTGCGATCCT
GGCTACAGCCTCACCAGCGACTACAAGTACATCACCTGCCAGTATGGAGAGTGGTTTCCTTC
TTATCAAGTCTACTGCATCAAATCAGAGCAAACGTGGCCCAGCACCCATGAGACCCTCCTGA
CCACGTGGAAGATTGTGGCGTTCACGGCAACCAGTGTGCTGCTGGTGCTGCTGCTCGTCATC
CTGGCCAGGATGTTCCAGACCAAGTTCAAGGCCCACTTTCCCCCCAGGGGGCCTCCCCGGAG
TTCCAGCAGTGACCCTGACTTTGTGGTGGTAGACGGCGTGCCCGTCATGCTCCCGTCCTATG
ACGAAGCTGTGAGTGGCGGCTTGAGTGCCTTAGGCCCCGGGTACATGGCCTCTGTGGGCCAG
GGCTGCCCCTTACCCGTGGACGACCAGAGCCCCCCAGCATACCCCGGCTCAGGGGACACGGA
CACAGGCCCAGGGGAGTCAGAAACCTGTGACAGCGTCTCAGGCTCTTCTGAGCTGCTCCAAA
GTCTGTATTCACCTCCCAGGTGCCAAGAGAGCACCCACCCTGCTTCGGACAACCCTGACATA
ATTGCCAGCACGGCAGAGGAGGTGGCATCCACCAGCCCAGGCATCCATCATGCCCACTGGGT
GTTGTTCCTAAGAAACTGATTGATTAAAAAATTTCCCAAAGTGTCCTGAAGTGTCTCTTCAA
ATACATGTTGATCTGTGGAGTTGATTCCTTTCCTTCTCTTGGTTTTAGACAAATGTAAACAA
AGCTCTGATCCTTAAAATTGCTATGCTGATAGAGTGGTGAGGGCTGGAAGCTTGATCAAGTC
CTGTTTCTTCTTGACACAGACTGATTAAAAATTAAAAGNAAAAAA

FIGURE 48

MYHGMNPSNGDGFLEQQQQQQQPQSPQRLLAVILWFQLALCFGPAQLTGGFDDLQVCADPGI
PENGFRTPSGGVFFEGSVARFHCQDGFKLKGATKRLCLKHFNGTLGWIPSDNSICVQEDCRI
PQIEDAEIHNKTYRHGEKLIITCHEGFKIRYPDLHNMVSLCRDDGTWNNLPICQGCLRPLAS
SNGYVNISELQTSFPVGTVISYRCFPGFKLDGSAYLECLQNLIWSSSPPRCLALEAQVCPLP
PMVSHGDFVCHPRPCERYNHGTVVEFYCDPGYSLTSDYKYITCQYGEWFPSYQVYCIKSEQT
WPSTHETLLTTWKIVAFTATSVLLVLLLVILARMFQTKFKAHFPPRGPPRSSSSDPDFVVVD
GVPVMLPSYDEAVSGGLSALGPGYMASVGQGCPLPVDDQSPPAYPGSGDTDTGPGESETCDS
VSGSSELLQSLYSPPRCQESTHPASDNPDIIASTAEEVASTSPGIHHAHWVLFLRN

Signal sequence:
amino acids 1-41

Transmembrane domain:
amino acids 325-344

N-glycosylation site.
amino acids 104-108, 134-138, 192-196

Casein kinase II phosphorylation site.
amino acids 8-12, 146-150, 252-256, 270-274, 313-317, 362-366, 364-368, 380-384, 467-471, 468-472

N-myristoylation site.
amino acids 4-10, 61-67, 169-175, 203-209, 387-393, 418-424, 478-484

Prokaryotic membrane lipoprotein lipid attachment site.
amino acids 394-405

FIGURE 49

CCCACGCGTCCGCTCCGCGCCCTCCCCCCGCCTCCCGTGCGGTCCGTCGGTGGCCTAGAGA
TGCTGCTGCCGCGGTTGCAGTTGTCGCGCACGCCTCTGCCCGCCAGCCCGCTCCACCGCCGT
AGCGCCCGAGTGTCGGGGGCGCACCCGAGTCGGGCCATGAGGCCGGGAACCGCGCTACAGG
CCGTGCTGCTGGCCGTGCTGCTGGTGGGGCTGCGGGCCGCGACGGGTCGCCTGCTGAGTGCC
TCGGATTTGGACCTCAGAGGAGGGCAGCCAGTCTGCCGGGGAGGGACACAGAGGCCTTGTTA
TAAAGTCATTTACTTCCATGATACTTCTCGAAGACTGAACTTTGAGGAAGCCAAAGAAGCCT
GCAGGAGGGATGGAGGCCAGCTAGTCAGCATCGAGTCTGAAGATGAACAGAAACTGATAGAA
AAGTTCATTGAAAACCTCTTGCCATCTGATGGTGACTTCTGGATTGGGCTCAGGAGGCGTGA
GGAGAAACAAAGCAATAGCACAGCCTGCCAGGACCTTTATGCTTGGACTGATGGCAGCATAT
CACAATTTAGGAACTGGTATGTGGATGAGCCGTCCTGCGGCAGCGAGGTCTGCGTGGTCATG
TACCATCAGCCATCGGCACCCGCTGGCATCGGAGGCCCCTACATGTTCCAGTGGAATGATGA
CCGGTGCAACATGAAGAACAATTTCATTTGCAAATATTCTGATGAGAAACCAGCAGTTCCTT
CTAGAGAAGCTGAAGGTGAGGAAACAGAGCTGACAACACCTGTACTTCCAGAAGAAACACAG
GAAGAAGATGCCAAAAAAACATTTAAAGAAAGTAGAGAAGCTGCCTTGAATCTGGCCTACAT
CCTAATCCCCAGCATTCCCCTTCTCCTCCTCCTTGTGGTCACCACAGTTGTATGTTGGGTTT
GGATCTGTAGAAAAAGAAAACGGGAGCAGCCAGACCCTAGCACAAAGAAGCAACACACCATC
TGGCCCTCTCCTCACCAGGGAAACAGCCCGGACCTAGAGGTCTACAATGTCATAAGAAAACA
AAGCGAAGCTGACTTAGCTGAGACCCGGCCAGACCTGAAGAATATTTCATTCCGAGTGTGTT
CGGGAGAAGCCACTCCCGATGACATGTCTTGTGACTATGACAACATGGCTGTGAACCCATCA
GAAAGTGGGTTTGTGACTCTGGTGAGCGTGGAGAGTGGATTTGTGACCAATGACATTTATGA
GTTCTCCCCAGACCAAATGGGGAGGAGTAAGGAGTCTGGATGGGTGGAAAATGAAATATATG
GTTATTAGGACATATAAAAAACTGAAACTGACAACAATGGAAAAGAAATGATAAGCAAAATC
CTCTTATTTTCTATAAGGAAAATACACAGAAGGTCTATGAACAAGCTTAGATCAGGTCCTGT
GGATGAGCATGTGGTCCCCACGACCTCCTGTTGGACCCCCACGTTTTGGCTGTATCCTTTAT
CCCAGCCAGTCATCCAGCTCGACCTTATGAGAAGGTACCTTGCCCAGGTCTGGCACATAGTA
GAGTCTCAATAAATGTCACTTGGTTGGTTGTATCTAACTTTTAAGGGACAGAGCTTTACCTG
GCAGTGATAAAGATGGGCTGTGGAGCTTGGAAAACCACCTCTGTTTTCCTTGCTCTATACAG
CAGCACATATTATCATACAGACAGAAAATCCAGAATCTTTTCAAAGCCCACATATGGTAGCACAG
GTTGGCCTGTGCATCGGCAATTCTCATATCTGTTTTTTTCAAAGAATAAAATCAAATAAAGA
GCAGGAAAAAAAAA

FIGURE 50

MRPGTALQAVLLAVLLVGLRAATGRLLSASDLDLRGGQPVCRGGTQRPCYKVIYFHDTSRRL
NFEEAKEACRRDGGQLVSIESEDEQKLIEKFIENLLPSDGDFWIGLRRREEKQSNSTACQDL
YAWTDGSISQFRNWYVDEPSCGSEVCVVMYHQPSAPAGIGGPYMFQWNDDRCNMKNNFICKY
SDEKPAVPSREAEGEETELTTPVLPEETQEEDAKKTFKESREAALNLAYILIPSIPLLLLLV
VTTVVCWVWICRKRKREQPDPSTKKQHTIWPSPHQGNSPDLEVYNVIRKQSEADLAETRPDL
KNISFRVCSGEATPDDMSCDYDNMAVNPSESGFVTLVSVESGFVTNDIYEFSPDQMGRSKES
GWVENEIYGY

Signal sequence:
amino acids 1-21

Transmembrane domain:
amino acids 235-254

N-glycosylation site.
amino acids 117-121, 312-316 cAMP- and cGMP-dependent protein kinase phosphorylation site.
amino acids 296-300

Casein kinase II phosphorylation site.
amino acids 28-32, 30-34, 83-87, 100-104, 214-218, 222-226, 299-303, 306-310, 323-327

N-myristoylation site.
amino acids 18-24, 37-43, 76-82, 146-152

FIGURE 51

GGGGTCTCCCTCAGGGCCGGGAGGCACAGCGGTCCCTGCTTGCTGAAGGGCTGGATGTACGC
ATCCGCAGGTTCCCGCGGACTTGGGGGCGCCCGCTGAGCCCCGGCGCCCGCAGAAGACTTGT
GTTTGCCTCCTGCAGCCTCAACCCGGAGGGCAGCGAGGGCCTACCACCATGATCACTGGTGT
GTTCAGCATGCGCTTGTGGACCCCAGTGGGCGTCCTGACCTCGCTGGCGTACTGCCTGCACC
AGCGGCGGGTGGCCCTGGCCGAGCTGCAGGAGGCCGATGGCCAGTGTCCGGTCGACCGCAGC
CTGCTGAAGTTGAAAATGGTGCAGGTCGTGTTTCGACACGGGGCTCGGAGTCCTCTCAAGCC
GCTCCCGCTGGAGGAGCAGGTAGAGTGGAACCCCCAGCTATTAGAGGTCCCACCCCAAACTC
AGTTTGATTACACAGTCACCAATCTAGCTGGTGGTCCGAAACCATATTCTCCTTACGACTCT
CAATACCATGAGACCACCCTGAAGGGGGCATGTTTGCTGGGCAGCTGACCAAGGTGGGCAT
GCAGCAAATGTTTGCCTTGGGAGAGAGACTGAGGAAGAACTATGTGGAAGACATTCCCTTTC
TTTCACCAACCTTCAACCCACAGGAGGTCTTTATTCGTTCCACTAACATTTTTCGGAATCTG
GAGTCCACCCGTTGTTTGCTGGCTGGGCTTTTCCAGTGTCAGAAAGAAGGACCCATCATCAT
CCACACTGATGAAGCAGATTCAGAAGTCTTGTATCCCAACTACCAAAGCTGCTGGAGCCTGA
GGCAGAGAACCAGAGGCCGGAGGCAGACTGCCTCTTTACAGCCAGGAATCTCAGAGGATTTG
AAAAAGGTGAAGGACAGGATGGGCATTGACAGTAGTGATAAAGTGGACTTCTTCATCCTCCT
GGACAACGTGGCTGCCGAGCAGGCACACAACCTCCCAAGCTGCCCCATGCTGAAGAGATTTG
CACGGATGATCGAACAGAGAGCTGTGGACACATCCTTGTACATACTGCCCAAGGAAGACAGG
GAAAGTCTTCAGATGGCAGTAGGCCCATTCCTCCACATCCTAGAGAGCAACCTGCTGAAAGC
CATGGACTCTGCCACTGCCCCCGACAAGATCAGAAAGCTGTATCTCTATGCGGCTCATGATG
TGACCTTCATACCGCTCTTAATGACCCTGGGGATTTTTGACCACAAATGGCCACCGTTTGCT
GTTGACCTGACCATGGAACTTTACCAGCACCTGGAATCTAAGGAGTGGTTTGTGCAGCTCTA
TTACCACGGGAAGGAGCAGGTGCCGAGAGGTTGCCCTGATGGGCTCTGCCCGCTGGACATGT
TCTTGAATGCCATGTCAGTTTATACCTTAAGCCCAGAAAAATACCATGCACTCTGCTCTCAA
ACTCAGGTGATGGAAGTTGGAAATGAAGAGTAACTGATTTATAAAAGCAGGATGTGTTGATT
TTAAAATAAAGTGCCTTTATACAATG

FIGURE 52

MITGVFSMRLWTPVGVLTSLAYCLHQRRVALAELQEADGQCPVDRSLLKLKMVQVVFRHGAR
SPLKPLPLEEQVEWNPQLLEVPPQTQFDYTVTNLAGGPKPYSPYDSQYHETTLKGGMFAGQL
TKVGMQQMFALGERLRKNYVEDIPFLSPTFNPQEVFIRSTNIFRNLESTRCLLAGLFQCQKE
GPIIIHTDEADSEVLYPNYQSCWSLRQRTRGRRQTASLQPGISEDLKKVKDRMGIDSSDKVD
FFILLDNVAAEQAHNLPSCPMLKRFARMIEQRAVDTSLYILPKEDRESLQMAVGPFLHILES
NLLKAMDSATAPDKIRKLYLYAAHDVTFIPLLMTLGIFDHKWPPFAVDLTMELYQHLESKEW
FVQLYYHGKEQVPRGCPDGLCPLDMFLNAMSVYTLSPEKYHALCSQTQVMEVGNEE

Signal sequence:

amino acids 1-23 cAMP- and cGMP-dependent protein kinase phosphorylation site.

amino acids 218-222

Casein kinase II phosphorylation site.

amino acids 87-91, 104-108, 320-324

Tyrosine kinase phosphorylation site.

amino acids 280-288

N-myristoylation site.

amino acids 15-21, 117-123, 118-124, 179-185, 240-246, 387-393

Amidation site.

amino acids 216-220

Leucine zipper pattern.

amino acids 10-32

Histidine acid phosphatases phosphohistidine signature.

amino acids 50-65

FIGURE 53

CTCCTCTTAACATACTTGCAGCTAAAACTAAATATTGCTGCTTGGGGACCTCCTTCTAGCCT
TAAATTTCAGCTCATCACCTTCACCTGCCTTGGTCATGGCTCTGCTATTCTCCTTGATCCTT
GCCATTTGCACCAGACCTGGATTCCTAGCGTCTCCATCTGGAGTGCGGCTGGTGGGGGGCCT
CCACCGCTGTGAAGGGCGGGTGGAGGTGGAACAGAAAGGCCAGTGGGGCACCGTGTGTGATG
ACGGCTGGGACATTAAGGACGTGGCTGTGTTGTGCCGGGAGCTGGGCTGTGGAGCTGCCAGC
GGAACCCCTAGTGGTATTTTGTATGAGCCACCAGCAGAAAAAGAGCAAAAGGTCCTCATCCA
ATCAGTCAGTTGCACAGGAACAGAAGATACATTGGCTCAGTGTGAGCAAGAAGAAGTTTATG
ATTGTTCACATGATGAAGATGCTGGGGCATCGTGTGAGAACCCAGAGAGCTCTTTCTCCCCA
GTCCCAGAGGGTGTCAGGCTGGCTGACGGCCCTGGGCATTGCAAGGGACGCGTGGAAGTGAA
GCACCAGAACCAGTGGTATACCGTGTGCCAGACAGGCTGGAGCCTCCGGGCCGCAAAGGTGG
TGTGCCGGCAGCTGGGATGTGGGAGGGCTGTACTGACTCAAAAACGCTGCAACAAGCATGCC
TATGGCCGAAAACCCATCTGGCTGAGCCAGATGTCATGCTCAGGACGAGAAGCAACCCTTCA
GGATTGCCCTTCTGGGCCTTGGGGGAAGAACACCTGCAACCATGATGAAGACACGTGGGTCG
AATGTGAAGATCCCTTTGACTTGAGACTAGTAGGAGGAGACAACCTCTGCTCTGGGCGACTG
GAGGTGCTGCACAAGGGCGTATGGGGCTCTGTCTGTGATGACAACTGGGGAGAAAAGGAGGA
CCAGGTGGTATGCAAGCAACTGGGCTGTGGGAAGTCCCTCTCTCCCTCCTTCAGAGACCGGA
AATGCTATGGCCCTGGGGTTGGCCGCATCTGGCTGGATAATGTTCGTTGCTCAGGGGAGGAG
CAGTCCCTGGAGCAGTGCCAGCACAGATTTTGGGGGTTTCACGACTGCACCCACCAGGAAGA
TGTGGCTGTCATCTGCTCAGTGTAGGTGGGCATCATCTAATCTGTTGAGTGCCTGAATAGAA
GAAAAACACAGAAGAAGGGAGCATTTACTGTCTACATGACTGCATGGGATGAACACTGATCT
TCTTCTGCCCTTGGACTGGGACTTATACTTGGTGCCCCTGATTCTCAGGCCTTCAGAGTTGG
ATCAGAACTTACAACATCAGGTCTAGTTCTCAGGCCATCAGACATAGTTTGGAACTACATCA
CCACCTTTCCTATGTCTCCACATTGCACACAGCAGATTCCCAGCCTCCATAATTGTGTGTAT
CAACTACTTAAATACATTCTCACACACACACACACACACACACACACACACACACACACATA
CACCATTTGTCCTGTTTCTCTGAAGAACTCTGACAAAATACAGATTTTGGTACTGAAAGAGA
TTCTAGAGGAACGGAATTTTAAGGATAAATTTTCTGAATTGGTTATGGGGTTTCTGAAATTG
GCTCTATAATCTAATTAGATATAAAATTCTGGTAACTTTATTTACAATAATAAAGATAGCAC
TATGTGTTCAAA

FIGURE 54

MALLFSLILAICTRPGFLASPSGVRLVGGLHRCEGRVEVEQKGQWGTVCDDGWDIKDVAVLC
RELGCGAASGTPSGILYEPPAEKEQKVLIQSVSCTGTEDTLAQCEQEEVYDCSHDEDAGASC
ENPESSFSPVPEGVRLADGPGHCKGRVEVKHQNQWYTVCQTGWSLRAAKVVCRQLGCGRAVL
TQKRCNKHAYGRKPIWLSQMSCSGREATLQDCPSGPWGKNTCNHDEDTWVECEDPFDLRLVG
GDNLCSGRLEVLHKGVWGSVCDDNWGEKEDQVVCKQLGCGKSLSPSFRDRKCYGPGVGRIWL
DNVRCSGEEQSLEQCQHRFWGFHDCTHQEDVAVICSV

Signal sequence:

amino acids 1-15

Casein kinase II phosphorylation site.

amino acids 47-51, 97-101, 115-119, 209-213, 214-218, 234-238, 267-271, 294-298, 316-320, 336-340

N-myristoylation site.

amino acids 29-35, 43-49, 66-72, 68-74, 72-78, 98-104, 137-143, 180-186, 263-269, 286-292

Amidation site.

amino acids 196-200

Speract receptor repeated domain signature.

amino acids 29-67, 249-287

FIGURE 55

ACTGCACTCGGTTCTATCGATTGAATTCCCCGGGGATCCTCTAGAGATCCCTCGACCTCGAC
CCACGCGTCCGCGGACGCGTGGGCGGACGCGTGGGCCGGCTACCAGGAAGAGTCTGCCGAAG
GTGAAGGCCATGGACTTCATCACCTCCACAGCCATCCTGCCCCTGCTGTTCGGCTGCCTGGG
CGTCTTCGGCCTCTTCCGGCTGCTGCAGTGGGTGCGCGGGAAGGCCTACCTGCGGAATGCTG
TGGTGGTGATCACAGGCGCCACCTCAGGGCTGGGCAAAGAATGTGCAAAAGTCTTCTATGCT
GCGGGTGCTAAACTGGTGCTCTGTGGCCGGAATGGTGGGGCCCTAGAAGAGCTCATCAGAGA
ACTTACCGCTTCTCATGCCACCAAGGTGCAGACACACAAGCCTTACTTGGTGACCTTCGACC
TCACAGACTCTGGGGCCATAGTTGCAGCAGCAGCTGAGATCCTGCAGTGCTTTGGCTATGTC
GACATACTTGTCAACAATGCTGGGATCAGCTACCGTGGTACCATCATGGACACCACAGTGGA
TGTGGACAAGAGGGTCATGGAGACAAACTACTTTGGCCCAGTTGCTCTAACGAAAGCACTCC
TGCCCTCCATGATCAAGAGGAGGCAAGGCCACATTGTCGCCATCAGCAGCATCCAGGGCAAG
ATGAGCATTCCTTTTCGATCAGCATATGCAGCCTCCAAGCACGCAACCCAGGCTTTCTTTGA
CTGTCTGCGTGCCGAGATGGAACAGTATGAAATTGAGGTGACCGTCATCAGCCCCGGCTACA
TCCACACCAACCTCTCTGTAAATGCCATCACCGCGGATGGATCTAGGTATGGAGTTATGGAC
ACCACCACAGCCCAGGGCCGAAGCCCTGTGGAGGTGGCCCAGGATGTTCTTGCTGCTGTGGG
GAAGAAGAAGAAAGATGTGATCCTGGCTGACTTACTGCCTTCCTTGGCTGTTTATCTTCGAA
CTCTGGCTCCTGGGCTCTTCTTCAGCCTCATGGCCTCCAGGGCCAGAAAAGAGCGGAAATCC
AAGAACTCCTAGTACTCTGACCAGCCAGGGCCAGGGCAGAGAAGCAGCACTCTTAGGCTTGC
TTACTCTACAAGGGACAGTTGCATTTGTTGAGACTTTAATGGAGATTTGTCTCACAAGTGGG
AAAGACTGAAGAAACACATCTCGTGCAGATCTGCTGGCAGAGGACAATCAAAAACGACAACA
AGCTTCTTCCCAGGGTGAGGGGAAACACTTAAGGAATAAATATGGAGCTGGGGTTTAACACT
AAAAACTAGAAATAAACATCTCAAACAGTAAAAAAAAAAAAAAAGGGCGGCCGCGACTCTAG
AGTCGACCTGCAGAAGCTTGGCCGCCATGGCCCAACTTGTTTATTGCAGCTTATAATGGTTAC

FIGURE 56

MDFITSTAILPLLFGCLGVFGLFRLLQWVRGKAYLRNAVVVITGATSGLGKECAKVFYAAGA
KLVLCGRNGGALEELIRELTASHATKVQTHKPYLVTFDLTDSGAIVAAAAEILQCFGYVDIL
VNNAGISYRGTIMDTTVDVDKRVMETNYFGPVALTKALLPSMIKRRQGHIVAISSIQGKMSI
PFRSAYAASKHATQAFFDCLRAEMEQYEIEVTVISPGYIHTNLSVNAITADGSRYGVMDTTT
AQGRSPVEVAQDVLAAVGKKKKDVILADLLPSLAVYLRTLAPGLFFSLMASRARKERKSKNS

Signal sequence:

amino acids 1-21

Transmembrane domain:

amino acids 104-120, 278-292

N-glycosylation site.

amino acids 228-232

Glycosaminoglycan attachment site.

amino acids 47-51

Casein kinase II phosphorylation site.

amino acids 135-139, 139-143, 253-257

Tyrosine kinase phosphorylation site.

amino acids 145-153, 146-153

N-myristoylation site.

amino acids 44-50, 105-111, 238-244, 242-248, 291-297

Amidation site.

amino acids 265-269

Prokaryotic membrane lipoprotein lipid attachment site.

amino acids 6-17

FIGURE 57

CCCACGCGTCCGCTGGTGTTAGATCGAGCAACCCTCTAAAAGCAGTTTAGAGTGGTAAAAAA
AAAAAAAAACACACCAAACGCTCGCAGCCACAAAAGGGATGAAATTTCTTCTGGACATCCTC
CTGCTTCTCCCGTTACTGATCGTCTGCTCCCTAGAGTCCTTCGTGAAGCTTTTTATTCCTAA
GAGGAGAAAATCAGTCACCGGCGAAATCGTGCTGATTACAGGAGCTGGGCATGGAATTGGGA
GACTGACTGCCTATGAATTTGCTAAACTTAAAAGCAAGCTGGTTCTCTGGGATATAAATAAG
CATGGACTGGAGGAAACAGCTGCCAAATGCAAGGGACTGGGTGCCAAGGTTCATACCTTTGT
GGTAGACTGCAGCAACCGAGAAGATATTTACAGCTCTGCAAAGAAGGTGAAGGCAGAAATTG
GAGATGTTAGTATTTTAGTAAATAATGCTGGTGTAGTCTATACATCAGATTTGTTTGCTACA
CAAGATCCTCAGATTGAAAAGACTTTTGAAGTTAATGTACTTGCACATTTCTGGACTACAAA
GGCATTTCTTCCTGCAATGACGAAGAATAACCATGGCCATATTGTCACTGTGGCTTCGGCAG
CTGGACATGTCTCGGTCCCCTTCTTACTGGCTTACTGTTCAAGCAAGTTTGCTGCTGTTGGA
TTTCATAAAACTTTGACAGATGAACTGGCTGCCTTACAAATAACTGGAGTCAAAACAACATG
TCTGTGTCCTAATTTCGTAAACACTGGCTTCATCAAAAATCCAAGTACAAGTTTGGGACCCA
CTCTGGAACCTGAGGAAGTGGTAAACAGGCTGATGCATGGGATTCTGACTGAGCAGAAGATG
ATTTTTATTCCATCTTCTATAGCTTTTTTAACAACATTGGAAAGGATCCTTCCTGAGCGTTT
CCTGGCAGTTTTAAAACGAAAAATCAGTGTTAAGTTTGATGCAGTTATTGGATATAAAATGA
AAGCGCAATAAGCACCTAGTTTTCTGAAAACTGATTTACCAGGTTTAGGTTGATGTCATCTA
ATAGTGCCAGAATTTTAATGTTTGAACTTCTGTTTTTTCTAATTATCCCCATTTCTTCAATA
TCATTTTTGAGGCTTTGGCAGTCTTCATTTACTACCACTTGTTCTTTAGCCAAAAGCTGATT
ACATATGATATAAACAGAGAAATACCTTTAGAGGTGACTTTAAGGAAAATGAAGAAAAAGAA
CCAAAATGACTTTATTAAAATAATTTCCAAGATTATTTGTGGCTCACCTGAAGGCTTTGCAA
AATTTGTACCATAACCGTTTATTTAACATATATTTTTATTTTTGATTGCACTTAAATTTTGT
ATAATTTGTGTTTCTTTTTCTGTTCTACATAAAATCAGAAACTTCAAGCTCTCTAAATAAAA
TGAAGGACTATATCTAGTGGTATTTCACAATGAATATCATGAACTCTCAATGGGTAGGTTTC
ATCCTACCCATTGCCACTCTGTTTCCTGAGAGATACCTCACATTCCAATGCCAAACATTTCT
GCACAGGGAAGCTAGAGGTGGATACACGTGTTGCAAGTATAAAAGCATCACTGGGATTTAAG
GAGAATTGAGAGAATGTACCCACAAATGGCAGCAATAATAAATGGATCACACTTAAAAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAA

FIGURE 58

MKFLLDILLLLPLLIVCSLESFVKLFIPKRRKSVTGEIVLITGAGHGIGRLTAYEFAKLKSK
LVLWDINKHGLEETAAKCKGLGAKVHTFVVDCSNREDIYSSAKKVKAEIGDVSILVNNAGVV
YTSDLFATQDPQIEKTFEVNVLAHFWTTKAFLPAMTKNNHGHIVTVASAAGHVSVPFLLAYC
SSKFAAVGFHKTLTDELAALQITGVKTTCLCPNFVNTGFIKNPSTSLGPTLEPEEVVNRLMH
GILTEQKMIFIPSSIAFLTTLERILPERFLAVLKRKISVKFDAVIGYKMKAQ

Signal sequence:

amino acids 1-19 cAMP- and cGMP-dependent protein kinase phosphorylation site.

amino acids 30-34, 283-287

Casein kinase II phosphorylation site.

amino acids 52-56, 95-99, 198-202, 267-271

N-myristoylation site.

amino acids 43-49, 72-78, 122-128, 210-216

FIGURE 59

CCCACGCGTCCGCGGACGCGTGGGTCGACTAGTTCTAGATCGCGAGCGGCCGCCCGCGGCTC
AGGGAGGAGCACCGACTGCGCCGCACCCTGAGAGATGGTTGGTGCCATGTGGAAGGTGATTG
TTTCGCTGGTCCTGTTGATGCCTGGCCCCTGTGATGGGCTGTTTCGCTCCCTATACAGAAGT
GTTTCCATGCCACCTAAGGGAGACTCAGGACAGCCATTATTTCTCACCCCTTACATTGAAGC
TGGGAAGATCCAAAAAGGAAGAGAATTGAGTTTGGTCGGCCCTTTCCCAGGACTGAACATGA
AGAGTTATGCCGGCTTCCTCACCGTGAATAAGACTTACAACAGCAACCTCTTCTTCTGGTTC
TTCCCAGCTCAGATACAGCCAGAAGATGCCCCAGTAGTTCTCTGGCTACAGGGTGGGCCGGG
AGGTTCATCCATGTTTGGACTCTTTGTGGAACATGGGCCTTATGTTGTCACAAGTAACATGA
CCTTGCGTGACAGAGACTTCCCCTGGACCACAACGCTCTCCATGCTTTACATTGACAATCCA
GTGGGCACAGGCTTCAGTTTTACTGATGATACCCACGGATATGCAGTCAATGAGGACGATGT
AGCACGGGATTTATACAGTGCACTAATTCAGTTTTTCCAGATATTTCCTGAATATAAAAATA
ATGACTTTTATGTCACTGGGGAGTCTTATGCAGGGAAATATGTGCCAGCCATTGCACACCTC
ATCCATTCCCTCAACCCTGTGAGAGAGGTGAAGATCAACCTGAACGGAATTGCTATTGGAGA
TGGATATTCTGATCCCGAATCAATTATAGGGGGCTATGCAGAATTCCTGTACCAAATTGGCT
TGTTGGATGAGAAGCAAAAAAAGTACTTCCAGAAGCAGTGCCATGAATGCATAGAACACATC
AGGAAGCAGAACTGGTTTGAGGCCTTTGAAATACTGGATAAACTACTAGATGGCGACTTAAC
AAGTGATCCTTCTTACTTCCAGAATGTTACAGGATGTAGTAATTACTATAACTTTTTGCGGT
GCACGGAACCTGAGGATCAGCTTTACTATGTGAAATTTTTGTCACTCCCAGAGGTGAGACAA
GCCATCCACGTGGGGAATCAGACTTTTAATGATGGAACTATAGTTGAAAAGTACTTGCGAGA
AGATACAGTACAGTCAGTTAAGCCATGGTTAACTGAAATCATGAATAATTATAAGGTTCTGA
TCTACAATGGCCAACTGGACATCATCGTGGCAGCTGCCCTGACAGAGCGCTCCTTGATGGGC
ATGGACTGGAAAGGATCCCAGGAATACAAGAAGGCAGAAAAAAAAGTTTGGAAGATCTTTAA
ATCTGACAGTGAAGTGGCTGGTTACATCCGGCAAGCGGGTGACTTCCATCAGGTAATTATTC
GAGGTGGAGGACATATTTTACCCTATGACCAGCCTCTGAGAGCTTTTGACATGATTAATCGA
TTCATTTATGGAAAAGGATGGGATCCTTATGTTGGATAAACTACCTTCCCAAAAGAGAACAT
CAGAGGTTTTCATTGCTGAAAAGAAAATCGTAAAAACAGAAAATGTCATAGGAATAAAAAAA
TTATCTTTTCATATCTGCAAGATTTTTTTCATCAATAAAAATTATCCTTGAAACAAGTGAGC
TTTTGTTTTTGGGGGGAGATGTTTACTACAAAATTAACATGAGTACATGAGTAAGAATTACA
TTATTTAACTTAAAGGATGAAAGGTATGGATGATGTGACACTGAGACAAGATGTATAAATGA
AATTTTAGGGTCTTGAATAGGAAGTTTTAATTTCTTCTAAGAGTAAGTGAAAAGTGCAGTTG
TAACAAACAAAGCTGTAACATCTTTTTCTGCCAATAACAGAAGTTTGGCATGCCGTGAAGGT
GTTTGGAAATATTATTGGATAAGAATAGCTCAATTATCCCAAATAAATGGATGAAGCTATAA
TAGTTTTGGGGAAAAGATTCTCAAATGTATAAAGTCTTAGAACAAAAGAATTCTTTGAAATA
AAAATATTATATATAAAAGTAAAAAAAAAA

FIGURE 60

MVGAMWKVIVSLVLLMPGPCDGLFRSLYRSVSMPPKGDSGQPLFLTPYIEAGKIQKGRELSL
VGPFPGLNMKSYAGFLTVNKTYNSNLFFWFFPAQIQPEDAPVVLWLQGGPGGSSMFGLFVEH
GPYVVTSNMTLRDRDFPWTTTLSMLYIDNPVGTGFSFTDDTHGYAVNEDDVARDLYSALIQF
FQIFPEYKNNDFYVTGESYAGKYVPAIAHLIHSLNPVREVKINLNGIAIGDGYSDPESIIGG
YAEFLYQIGLLDEKQKKYFQKQCHECIEHIRKQNWFEAFEILDKLLDGDLTSDPSYFQNVTG
CSNYYNFLRCTEPEDQLYYVKFLSLPEVRQAIHVGNQTFNDGTIVEKYLREDTVQSVKPWLT
EIMNNYKVLIYNGQLDIIVAAALTERSLMGMDWKGSQEYKKAEKKVWKIFKSDSEVAGYIRQ
AGDFHQVIIRGGGHILPYDQPLRAFDMINRFIYGKGWDPYVG

Signal sequence:

amino acids 1-22

N-glycosylation site.

amino acids 81-85, 132-136, 307-311, 346-350

Casein kinase II phosphorylation site.

amino acids 134-138, 160-164, 240-244, 321-325, 334-338, 348-352, 353-357, 424-428

Tyrosine kinase phosphorylation site.

amino acids 423-432

N-myristoylation site.

amino acids 22-28, 110-116, 156-162, 232-238

Serine carboxypeptidases, serine active site.

amino acids 200-208

Crystallins beta and gamma 'Greek key' motif signature.

amino acids 375-391

FIGURE 61

CGAGGGCTTTTCCGGCTCCGGAATGGCACATGTGGGAATCCCAGTCTTGTTGGCTACAACAT
TTTTCCCTTTCCTAACAAGTTCTAACAGCTGTTCTAACAGCTAGTGATCAGGGGTTCTTCTT
GCTGGAGAAGAAAGGGCTGAGGGCAGAGCAGGGCACTCTCACTCAGGGTGACCAGCTCCTTG
CCTCTCTGTGGATAACAGAGCATGAGAAAGTGAAGAGATGCAGCGGAGTGAGGTGATGGAAG
TCTAAAATAGGAAGGAATTTTGTGTGCAATATCAGACTCTGGGAGCAGTTGACCTGGAGAGC
CTGGGGGAGGGCCTGCCTAACAAGCTTTCAAAAAACAGGAGCGACTTCCACTGGGCTGGGAT
AAGACGTGCCGGTAGGATAGGGAAGACTGGGTTTAGTCCTAATATCAAATTGACTGGCTGGG
TGAACTTCAACAGCCTTTTAACCTCTCTGGGAGATGAAAACGATGGCTTAAGGGGCCAGAAA
TAGAGATGCTTTGTAAAATAAAATTTTAAAAAAAGCAAGTATTTTATAGCATAAAGGCTAGA
GACCAAAATAGATAACAGGATTCCCTGAACATTCCTAAGAGGGAGAAAGTATGTTAAAAATA
GAAAAACCAAAATGCAGAAGGAGGAGACTCACAGAGCTAAACCAGGATGGGGACCCTGGGTC
AGGCCAGCCTCTTTGCTCCTCCCGGAAATTATTTTTGGTCTGACCACTCTGCCTTGTGTTTT
GCAGAATCATGTGAGGGCCAACCGGGGAAGGTGGAGCAGATGAGCACACACAGGAGCCGTCT
CCTCACCGCCGCCCCTCTCAGCATGGAACAGAGGCAGCCCTGGCCCCGGGCCCTGGAGGTGG
ACAGCCGCTCTGTGGTCCTGCTCTCAGTGGTCTGGGTGCTGCTGGCCCCCCCAGCAGCCGGC
ATGCCTCAGTTCAGCACCTTCCACTCTGAGAATCGTGACTGGACCTTCAACCACTTGACCGT
CCACCAAGGGACGGGGGCCGTCTATGTGGGGGCCATCAACCGGGTCTATAAGCTGACAGGCA
ACCTGACCATCCAGGTGGCTCATAAGACAGGGCCAGAAGAGGACAACAAGTCTCGTTACCCG
CCCCTCATCGTGCAGCCCTGCAGCGAAGTGCTCACCCTCACCAACAATGTCAACAAGCTGCT
CATCATTGACTACTCTGAGAACCGCCTGCTGGCCTGTGGGAGCCTCTACCAGGGGGTCTGCA
AGCTGCTGCGGCTGGATGACCTCTTCATCCTGGTGGAGCCATCCCACAAGAAGGAGCACTAC
CTGTCCAGTGTCAACAAGACGGGCACCATGTACGGGGTGATTGTGCGCTCTGAGGGTGAGGA
TGGCAAGCTCTTCATCGGCACGGCTGTGGATGGGAAGCAGGATTACTTCCCGACCCTGTCCA
GCCGGAAGCTGCCCCGAGACCCTGAGTCCTCAGCCATGCTCGACTATGAGCTACACAGCGAT
TTTGTCTCCTCTCTCATCAAGATCCCTTCAGACACCCTGGCCCTGGTCTCCCACTTTGACAT
CTTCTACATCTACGGCTTTGCTAGTGGGGGCTTTGTCTACTTTCTCACTGTCCAGCCCGAGA
CCCCTGAGGGTGTGGCCATCAACTCCGCTGGAGACCTCTTCTACACCTCACGCATCGTGCGG
CTCTGCAAGGATGACCCCAAGTTCCACTCATACGTGTCCCTGCCCTTCGGCTGCACCCGGGC
CGGGGTGGAATACCGCCTCCTGCAGGCTGCTTACCTGGCCAAGCCTGGGGACTCACTGGCCC
AGGCCTTCAATATCACCAGCCAGGACGATGTACTCTTTGCCATCTTCTCCAAAGGGCAGAAG
CAGTATCACCACCCGCCCGATGACTCTGCCCTGTGTGCCTTCCCTATCCGGGCCATCAACTT
GCAGATCAAGGAGCGCCTGCAGTCCTGCTACCAGGGCGAGGGCAACCTGGAGCTCAACTGGC
TGCTGGGGAAGGACGTCCAGTGCACGAAGGCGCCTGTCCCCATCGATGATAACTTCTGTGGA
CTGGACATCAACCAGCCCCTGGGAGGCTCAACTCCAGTGGAGGGCCTGACCCTGTACACCAC
CAGCAGGGACCGCATGACCTCTGTGGCCTCCTACGTTTACAACGGCTACAGCGTGGTTTTTG
TGGGGACTAAGAGTGGCAAGCTGAAAAAGGTAAGAGTCTATGAGTTCAGATGCTCCAATGCC
ATTCACCTCCTCAGCAAAGAGTCCCTCTTGGAAGGTAGCTATTGGTGGAGATTTAACTATAG
GCAACTTTATTTTCTTGGGGAACAAAGGTGAAATGGGGAGGTAAGAAGGGGTTAATTTTGTG
ACTTAGCTTCTAGCTACTTCCTCCAGCCATCAGTCATTGGGTATGTAAGGAATGCAAGCGTA
TTTCAATATTTCCCAAACTTTAAGAAAAAACTTTAAGAAGGTACATCTGCAAAAGCAAA

FIGURE 62

MGTLGQASLFAPPGNYFWSDHSALCFAESCEGQPGKVEQMSTHRSRLLTAAPLSMEQRQPWP
RALEVDSRSVVLLSVVWVLLAPPAAGMPQFSTFHSENRDWTFNHLTVHQGTGAVYVGAINRV
YKLTGNLTIQVAHKTGPEEDNKSRYPPLIVQPCSEVLTLTNNVNKLLIIDYSENRLLACGSL
YQGVCKLLRLDDLFILVEPSHKKEHYLSSVNKTGTMYGVIVRSEGEDGKLFIGTAVDGKQDY
FPTLSSRKLPRDPESSAMLDYELHSDFVSSLIKIPSDTLALVSHFDIFYIYGFASGGFVYFL
TVQPETPEGVAINSAGDLFYTSRIVRLCKDDPKFHSYVSLPFGCTRAGVEYRLLQAAYLAKP
GDSLAQAFNITSQDDVLFAIFSKGQKQYHHPPDDSALCAFPIRAINLQIKERLQSCYQGEGN
LELNWLLGKDVQCTKAPVPIDDNFCGLDINQPLGGSTPVEGLTLYTTSRDRMTSVASYVYNG
YSVVFVGTKSGKLKKVRVYEFRCSNAIHLLSKESLLEGSYWWRFNYRQLYFLGEQR

Signal sequence:

amino acids 1-32

Transmembrane domain:

amino acids 71-87

N-glycosylation site.

amino acids 130-134, 145-149, 217-221, 381-385

Casein kinase II phosphorylation site.

amino acids 139-143, 229-233, 240-244, 291-295, 324-328, 383-387, 384-388, 471-475, 481-485, 530-534

N-myristoylation site.

amino acids 220-226, 319-325, 353-359, 460-466, 503-509

FIGURE 63

AGGCTCCCGCGCGCGGCTGAGTGCGGACTGGAGTGGGAACCCGGGTCCCCGCGCTTAGAGAACACGCGATGACCA
CGTGGAGCCTCCGGCGGAGGCCGGCCCGCACGCTGGGACTCCTGCTGCTGGTCGTCTTGGGCTTCCTGGTGCTCC
GCAGGCTGGACTGGAGCACCCTGGTCCCTCTGCGGCTCCGCCATCGACAGCTGGGGCTGCAGGCCAAGGGCTGGA
ACTTCATGCTGGAGGATTCCACCTTCTGGATCTTCGGGGGCTCCATCCACTATTTCCGTGTGCCCAGGGAGTACT
GGAGGGACCGCCTGCTGAAGATGAAGGCCTGTGGCTTGAACACCCTCACCACCTATGTTCCGTGGAACCTGCATG
AGCCAGAAAGAGGCAAATTTGACTTCTCTGGGAACCTGGACCTGGAGGCCTTCGTCCTGATGGCCGCAGAGATCG
GGCTGTGGGTGATTCTGCGTCCAGGCCCCTACATCTGCAGTGAGATGGACCTCGGGGGCTTGCCCAGCTGGCTAC
TCCAAGACCCTGGCATGAGGCTGAGGACAACTTACAAGGGCTTCACCGAAGCAGTGGACCTTTATTTTGACCACC
TGATGTCCAGGGTGGTGCCACTCCAGTACAAGCGTGGGGGACCTATCATTGCCGTGCAGGTGGAGAATGAATATG
GTTCCTATAATAAAGACCCCGCATACATGCCCTACGTCAAGAAGGCACTGGAGGACCGTGGCATTGTGGAACTGC
TCCTGACTTCAGACAACAAGGATGGGCTGAGCAAGGGGATTGTCCAGGGAGTCTTGGCCACCATCAACTTGCAGT
CAACACACGAGCTGCAGCTACTGACCACCTTTCTCTTCAACGTCCAGGGGACTCAGCCCAAGATGGTGATGGAGT
ACTGGACGGGGTGGTTTGACTCGTGGGGAGGCCCTCACAATATCTTGGATTCTTCTGAGGTTTTGAAAACCGTGT
CTGCCATTGTGGACGCCGGCTCCTCCATCAACCTCTACATGTTCCACGGAGGCACCAACTTTGGCTTCATGAATG
GAGCCATGCACTTCCATGACTACAAGTCAGATGTCACCAGCTATGACTATGATGCTGTGCTGACAGAAGCCGGCG
ATTACACGGCCAAGTACATGAAGCTTCGAGACTTCTTCGGCTCCATCTCAGGCATCCCTCTCCCTCCCCCACCTG
ACCTTCTTCCCAAGATGCCGTATGAGCCCTTAACGCCAGTCTTGTACCTGTCTCTGTGGGACGCCCTCAAGTACC
TGGGGGAGCCAATCAAGTCTGAAAAGCCCATCAACATGGAGAACCTGCCAGTCAATGGGGGAAATGGACAGTCCT
TCGGGTACATTCTCTATGAGACCAGCATCACCTCGTCTGGCATCCTCAGTGGCCACGTGCATGATCGGGGGCAGG
TGTTTGTGAACACAGTATCCATAGGATTCTTGGACTACAAGACAACGAAGATTGCTGTCCCCCTGATCCAGGGTT
ACACCGTGCTGAGGATCTTGGTGGAGAATCGTGGGCGAGTCAACTATGGGGAGAATATTGATGACCAGCGCAAAG
GCTTAATTGGAAATCTCTATCTGAATGATTCACCCCTGAAAAACTTCAGAATCTATAGCCTGGATATGAAGAAGA
GCTTCTTTCAGAGGTTCGGCCTGGACAAATGGNGTTCCCTCCCAGAAACACCCACATTACCTGCTTTCTTCTTGG
GTAGCTTGTCCATCAGCTCCACGCCTTGTGACACCTTTCTGAAGCTGGAGGGCTGGGAGAAGGGGGTTGTATTCA
TCAATGGCCAGAACCTTGGACGTTACTGGAACATTGGACCCCAGAAGACGCTTTACCTCCCAGGTCCCTGGTTGA
GCAGCGGAATCAACCAGGTCATCGTTTTTGAGGAGACGATGGCGGGCCCTGCATTACAGTTCACGGAAACCCCCC
ACCTGGGCAGGAACCAGTACATTAAGTGAGCGGTGGCACCCCCTCCTGCTGGTGCCAGTGGGAGACTGCCGCCTC
CTCTTGACCTGAAGCCTGGTGGCTGCTGCCCCACCCCTCACTGCAAAAGCATCTCCTTAAGTAGCAACCTCAGGG
ACTGGGGGCTACAGTCTGCCCCTGTCTCAGCTCAAAACCCTAAGCCTGCAGGGAAAGGTGGGATGGCTCTGGGCC
TGGCTTTGTTGATGATGGCTTTCCTACAGCCCTGCTCTTGTGCCGAGGCTGTCGGGCTGTCTCTAGGGTGGAGC
AGCTAATCAGATCGCCCAGCCTTTGGCCCTCAGAAAAAGTGCTGAAACGTGCCCTTGCACCGGACGTCACAGCCC
TGCGAGCATCTGCTGGACTCAGGCGTGCTCTTTGCTGGTTCCTGGGAGGCTTGGCCACATCCCTCATGGCCCCAT
TTTATCCCCGAAATCCTGGGTGTGTCACCAGTGTAGAGGGTGGGGAAGGGGTGTCTCACCTGAGCTGACTTTGTT
CTTCCTTCACAACCTTCTGAGCCTTCTTTGGGATTCTGGAAGGAACTCGGCGTGAGAAACATGTGACTTCCCCTT
TCCCTTCCCACTCGCTGCTTCCCACAGGGTGACAGGCTGGGCTGGAGAAACAGAAATCCTCACCCTGCGTCTTCC
CAAGTTAGCAGGTGTCTCTGGTGTTCAGTGAGGAGGACATGTGAGTCCTGGCAGAAGCCATGGCCCATGTCTGCA
CATCCAGGGAGGAGGACAGAAGGCCCAGCTCACATGTGAGTCCTGGCAGAAGCCATGGCCCATGTCTGCACATCC
AGGGAGGAGGACAGAAGGCCCAGCTCACATGTGAGTCCTGGCAGAAGCCATGGCCCATGTCTGCACATCCAGGGA
GGAGGACAGAAGGCCCAGCTCACATGTGAGTCCTGGCAGAAGCCATGGCCCATGTCTGCACATCCAGGGAGGAGG
ACAGAAGGCCCAGCTCAGTGGCCCCCGCTCCCCACCCCCCACGCCCGAACAGCAGGGGCAGAGCAGCCCTCCTTC
GAAGTGTGTCCAAGTCCGCATTTGAGCCTTGTTCTGGGGCCCAGCCCAACACCTGGCTTGGGCTCACTGTCCTGA
GTTGCAGTAAAGCTATAACCTTGAATCACAA

FIGURE 64

MTTWSLRRRPARTLGLLLLVVLGFLVLRRLDWSTLVPLRLRHRQLGLQAKGWNFMLEDSTFW
IFGGSIHYFRVPREYWRDRLLKMKACGLNTLTTYVPWNLHEPERGKFDFSGNLDLEAFVLMA
AEIGLWVILRPGPYICSEMDLGGLPSWLLQDPGMRLRTTYKGFTEAVDLYFDHLMSRVVPLQ
YKRGGPIIAVQVENEYGSYNKDPAYMPYVKKALEDRGIVELLLTSDNKDGLSKGIVQGVLAT
INLQSTHELQLLTTFLFNVQGTQPKMVMEYWTGWFDSWGGPHNILDSSEVLKTVSAIVDAGS
SINLYMFHGGTNFGFMNGAMHFHDYKSDVTSYDYDAVLTEAGDYTAKYMKLRDFFGSISGIP
LPPPPDLLPKMPYEPLTPVLYLSLWDALKYLGEPIKSEKPINMENLPVNGGNGQSFGYILYE
TSITSSGILSGHVHDRGQVFVNTVSIGFLDYKTTKIAVPLIQGYTVLRILVENRGRVNYGEN
IDDQRKGLIGNLYLNDSPLKNFRIYSLDMKKSFFQRFGLDKWXSLPETPTLPAFFLGSLSIS
STPCDTFLKLEGWEKGVVFINGQNLGRYWNIGPQKTLYLPGPWLSSGINQVIVFEETMAGPA
LQFTETPHLGRNQYIK

Signal sequence:

amino acids 1-27

Casein kinase II phosphorylation site.

amino acids 141-118, 253-257, 340-344, 395-399, 540-544, 560-564

N-myristoylation site.

amino acids 146-152, 236-242, 240-246, 244-250, 287-293, 309-315, 320-326, 366-372, 423-429, 425-431, 441-447, 503-509, 580-586

FIGURE 65

GGGGACGCGGAGCTGAGAGGCTCCGGGCTAGCTAGGTGTAGGGGTGGACGGGTCCCAGGACC
CTGGTGAGGGTTCTCTACTTGGCCTTCGGTGGGGGTCAAGACGCAGGCACCTACGCCAAAGG
GGAGCAAAGCCGGGCTCGGCCCGAGGCCCCCAGGACCTCCATCTCCCAATGTTGGAGGAATC
CGACACGTGACGGTCTGTCCGCCGTCTCAGACTAGAGGAGCGCTGTAAACGCCATGGCTCCC
AAGAAGCTGTCCTGCCTTCGTTCCCTGCTGCTGCCGCTCAGCCTGACGCTACTGCTGCCCCA
GGCAGACACTCGGTCGTTCGTAGTGGATAGGGGTCATGACCGGTTTCTCCTAGACGGGGCCC
CGTTCCGCTATGTGTCTGGCAGCCTGCACTACTTTCGGGTACCGCGGGTGCTTTGGCCGAC
CGGCTTTTGAAGATGCGATGGAGCGGCCTCAACGCCATACAGTTTTATGTGCCCTGGAACTA
CCACGAGCCACAGCCTGGGGTCTATAACTTTAATGGCAGCCGGGACCTCATTGCCTTTCTGA
ATGAGGCAGCTCTAGCGAACCTGTTGGTCATACTGAGACCAGGACCTTACATCTGTGCAGAG
TGGGAGATGGGGGGTCTCCCATCCTGGTTGCTTCGAAAACCTGAAATTCATCTAAGAACCTC
AGATCCAGACTTCCTTGCCGCAGTGGACTCCTGGTTCAAGGTCTTGCTGCCCAAGATATATC
CATGGCTTTATCACAATGGGGGCAACATCATTAGCATTCAGGTGGAGAATGAATATGGTAGC
TACAGAGCCTGTGACTTCAGCTACATGAGGCACTTGGCTGGGCTCTTCCGTGCACTGCTAGG
AGAAAAGATCTTGCTCTTCACCACAGATGGGCCTGAAGGACTCAAGTGTGGCTCCCTCCGGG
GACTCTATACCACTGTAGATTTTGGCCCAGCTGACAACATGACCAAAATCTTTACCCTGCTT
CGGAAGTATGAACCCCATGGGCCATTGGTAAACTCTGAGTACTACACAGGCTGGCTGGATTA
CTGGGGCCAGAATCACTCCACACGGTCTGTGTCAGCTGTAACCAAAGGACTAGAGAACATGC
TCAAGTTGGGAGCCAGTGTGAACATGTACATGTTCCATGGAGGTACCAACTTTGGATATTGG
AATGGTGCCGATAAGAAGGGACGCTTCCTTCCGATTACTACCAGCTATGACTATGATGCACC
TATATCTGAAGCAGGGGACCCCACACCTAAGCTTTTTGCTCTTCGAGATGTCATCAGCAAGT
TCCAGGAAGTTCCTTTGGGACCTTTACCTCCCCCGAGCCCCAAGATGATGCTTGGACCTGTG
ACTCTGCACCTGGTTGGGCATTTACTGGCTTTCCTAGACTTGCTTTGCCCCCGTGGGCCCAT
TCATTCAATCTTGCCAATGACCTTTGAGGCTGTCAAGCAGGACCATGGCTTCATGTTGTACC
GAACCTATATGACCCATACCATTTTTGAGCCAACACCATTCTGGGTGCCAAATAATGGAGTC
CATGACCGTGCCTATGTGATGGTGGATGGGGTGTTCCAGGGTGTTGTGGAGCGAAATATGAG
AGACAAACTATTTTTGACGGGGAAACTGGGGTCCAAACTGGATATCTTGGTGGAGAACATGG
GGAGGCTCAGCTTTGGGTCTAACAGCAGTGACTTCAAGGGCCTGTTGAAGCCACCAATTCTG
GGGCAAACAATCCTTACCCAGTGGATGATGTTCCCTCTGAAAATTGATAACCTTGTGAAGTG
GTGGTTTCCCCTCCAGTTGCCAAAATGGCCATATCCTCAAGCTCCTTCTGGCCCCACATTCT
ACTCCAAAACATTTCCAATTTTAGGCTCAGTTGGGGACACATTTCTATATCTACCTGGATGG
ACCAAGGGCCAAGTCTGGATCAATGGGTTTAACTTGGGCCGGTACTGGACAAAGCAGGGGCC
ACAACAGACCCTCTACGTGCCAAGATTCCTGCTGTTTCCTAGGGGAGCCCTCAACAAAATTA
CATTGCTGGAACTAGAAGATGTACCTCTCCAGCCCCAAGTCCAATTTTTGGATAAGCCTATC
CTCAATAGCACTAGTACTTTGCACAGGACACATATCAATTCCCTTTCAGCTGATACACTGAG
TGCCTCTGAACCAATGGAGTTAAGTGGGCACTGAAAGGTAGGCCGGGCATGGTGGCTCATGC
CTGTAATCCCAGCACTTTGGGAGGCTGAGACGGGTGGATTACCTGAGGTCAGGACTTCAAGA
CCAGCCTGGCCAACATGGTGAAACCCCGTCTCCACTAAAAATACAAAAATTAGCCGGGCGTG
ATGGTGGGCACCTCTAATCCCAGCTACTTGGGAGGCTGAGGGCAGGAGAATTGCTTGAATCC
AGGAGGCAGAGGTTGCAGTGAGTGGAGGTTGTACCACTGCACTCCAGCCTGGCTGACAGTGA
GACACTCCATCTCAAAAAAAAAAAA

FIGURE 66

MAPKKLSCLRSLLLPLSLTLLLPQADTRSFVVDRGHDRFLLDGAPFRYVSGSLHYFRVPRVL
WADRLLKMRWSGLNAIQFYVPWNYHEPQPGVYNFNGSRDLIAFLNEAALANLLVILRPGPYI
CAEWEMGGLPSWLLRKPEIHLRTSDPDFLAAVDSWFKVLLPKIYPWLYHNGGNIISIQVENE
YGSYRACDFSYMRHLAGLFRALLGEKILLFTTDGPEGLKCGSLRGLYTTVDFGPADNMTKIF
TLLRKYEPHGPLVNSEYYTGWLDYWGQNHSTRSVSAVTKGLENMLKLGASVNMYMFHGGTNF
GYWNGADKKGRFLPITTSYDYDAPISEAGDPTPKLFALRDVISKFQEVPLGPLPPPSPKMML
GPVTLHLVGHLLAFLDLLCPRGPIHSILPMTFEAVKQDHGFMLYRTYMTHTIFEPTPFWVPN
NGVHDRAYVMVDGVFQGVVERNMRDKLFLTGKLGSKLDILVENMGRLSFGSNSSDFKGLLKP
PILGQTILTQWMMFPLKIDNLVKWWFPLQLPKWPYPQAPSGPTFYSKTFPILGSVGDTFLYL
PGWTKGQVWINGFNLGRYWTKQGPQQTLYVPRFLLFPRGALNKITLLELEDVPLQPQVQFLD
KPILNSTSTLHRTHINSLSADTLSASEPMELSGH

Signal sequence:

amino acids 1-27

N-glycosylation site.

amino acids 97-101, 243-247, 276-280, 486-490, 625-629 cAMP- and cGMP-dependent protein kinase phosphorylation site.

amino acids 4-8

Casein kinase II phosphorylation site.

amino acids 148-152, 234-238, 327-331, 423-427, 469-473, 550-554, 603-607, 644-648

Tyrosine kinase phosphorylation site.

amino acids 191-198

N-myristoylation site.

amino acids 131-137, 176-182, 188-194, 203-209, 223-229, 227-233, 231-237, 274-280, 296-300, 307-313, 447-453, 484-490

FIGURE 67

GCTTTGAACACGTCTGCAAGCCCAAAGTTGAGCATCTGATTGGTTATGAGGTATTTGAGTGC
ACCCACAATATGGCTTACATGTTGAAAAAGCTTCTCATCAGTTACATATCCATTATTTGTGT
TTATGGCTTTATCTGCCTCTACACTCTCTTCTGGTTATTCAGGATACCTTTGAAGGAATATT
CTTTCGAAAAAGTCAGAGAAGAGAGCAGTTTTAGTGACATTCCAGATGTCAAAAACGATTTT
GCGTTCCTTCTTCACATGGTAGACCAGTATGACCAGCTATATTCCAAGCGTTTTGGTGTGTT
CTTGTCAGAAGTTAGTGAAAATAAACTTAGGGAAATTAGTTTGAACCATGAGTGGACATTTG
AAAAACTCAGGCAGCACATTTCACGCAACGCCCAGGACAAGCAGGAGTTGCATCTGTTCATG
CTGTCGGGGGTGCCCGATGCTGTCTTTGACCTCACAGACCTGGATGTGCTAAAGCTTGAACT
AATTCCAGAAGCTAAAATTCCTGCTAAGATTTCTCAAATGACTAACCTCCAAGAGCTCCACC
TCTGCCACTGCCCTGCAAAAGTTGAACAGACTGCTTTTAGCTTTCTTCGCGATCACTTGAGA
TGCCTTCACGTGAAGTTCACTGATGTGGCTGAAATTCCTGCCTGGGTGTATTTGCTCAAAAA
CCTTCGAGAGTTGTACTTAATAGGCAATTTGAACTCTGAAAACAATAAGATGATAGGACTTG
AATCTCTCCGAGAGTTGCGGCACCTTAAGATTCTCCACGTGAAGAGCAATTTGACCAAAGTT
CCCTCCAACATTACAGATGTGGCTCCACATCTTACAAAGTTAGTCATTCATAATGACGGCAC
TAAACTCTTGGTACTGAACAGCCTTAAGAAAATGATGAATGTCGCTGAGCTGGAACTCCAGA
ACTGTGAGCTAGAGAGAATCCCACATGCTATTTTCAGCCTCTCTAATTTACAGGAACTGGAT
TTAAAGTCCAATAACATTCGCACAATTGAGGAAATCATCAGTTTCCAGCATTTAAAACGACT
GACTTGTTTAAAATTATGGCATAACAAAATTGTTACTATTCCTCCCTCTATTACCCATGTCA
AAAACTTGGAGTCACTTTATTTCTCTAACAACAAGCTCGAATCCTTACCAGTGGCAGTATTT
AGTTTACAGAAACTCAGATGCTTAGATGTGAGCTACAACAACATTTCAATGATTCCAATAGA
AATAGGATTGCTTCAGAACCTGCAGCATTTGCATATCACTGGGAACAAAGTGGACATTCTGC
CAAAACAATTGTTTAAATGCATAAAGTTGAGGACTTTGAATCTGGGACAGAACTGCATCACC
TCACTCCCAGAGAAAGTTGGTCAGCTCTCCCAGCTCACTCAGCTGGAGCTGAAGGGGAACTG
CTTGGACCGCCTGCCAGCCCAGCTGGGCCAGTGTCGGATGCTCAAGAAAAGCGGGCTTGTTG
TGGAAGATCACCTTTTTGATACCCTGCCACTCGAAGTCAAAGAGGCATTGAATCAAGACATA
AATATTCCCTTTGCAAATGGGATTTAAACTAAGATAATATATGCACAGTGATGTGCAGGAAC
AACTTCCTAGATTGCAAGTGCTCACGTACAAGTTATTACAAGATAATGCATTTTAGGAGTAG
ATACATCTTTTAAAATAAAACAGAGAGGATGCATAGAAGGCTGATAGAAGACATAACTGAAT
GTTCAATGTTTGTAGGGTTTTAAGTCATTCATTTCCAAATCATTTTTTTTTTTCTTTTGGGG
AAAGGGAAGGAAAAATTATAATCACTAATCTTGGTTCTTTTTAAATTGTTTGTAACTTGGAT
GCTGCCGCTACTGAATGTTTACAAATTGCTTGCCTGCTAAAGTAAATGATTAAATTGACATT
TTCTTACTAAAAAAAAAAAAAAAAA

FIGURE 68

MAYMLKKLLISYISIICVYGFICLYTLFWLFRIPLKEYSFEKVREESSFSDIPDVKNDFAFL
LHMVDQYDQLYSKRFGVFLSEVSENKLREISLNHEWTFEKLRQHISRNAQDKQELHLFMLSG
VPDAVFDLTDLDVLKLELIPEAKIPAKISQMTNLQELHLCHCPAKVEQTAFSFLRDHLRCLH
VKFTDVAEIPAWVYLLKNLRELYLIGNLNSENNKMIGLESLRELRHLKILHVKSNLTKVPSN
ITDVAPHLTKLVIHNDGTKLLVLNSLKKMMNVAELELQNCELERIPHAIFSLSNLQELDLKS
NNIRTIEEIISFQHLKRLTCLKLWHNKIVTIPPSITHVKNLESLYFSNNKLESLPVAVFSLQ
KLRCLDVSYNNISMIPIEIGLLQNLQHLHITGNKVDILPKQLFKCIKLRTLNLGQNCITSLP
EKVGQLSQLTQLELKGNCLDRLPAQLGQCRMLKKSGLVVEDHLFDTLPLEVKEALNQDINIP
FANGI

Signal sequence:

amino acids 1-20

N-glycosylation site.

amino acids 241-245, 248-252, 383-387 cAMP- and cGMP-dependent protein kinase phosphorylation site.

amino acids 326-330

Casein kinase II phosphorylation site.

amino acids 48-52, 133-137, 226-230, 315-319, 432-436, 444-448

Tyrosine kinase phosphorylation site.

amino acids 349-355, 375-381

N-myristoylation site.

amino acids 78-84, 124-130, 212-218, 392-398

FIGURE 69

CCCACGCGTCCGGCCTTCTCTCTGGACTTTGCATTTCCATTCCTTTTCATTGACAAACTGACTTTTTTTATTTCT
TTTTTTCCATCTCTGGGCCAGCTTGGGATCCTAGGCCGCCCTGGGAAGACATTTGTGTTTTACACACATAAGGAT
CTGTGTTTGGGGTTTCTTCTTCCTCCCCTGACATTGGCATTGCTTAGTGGTTGTGTGGGGAGGGAGACCACGTGG
GCTCAGTGCTTGCTTGCACTTATCTGCCTAGGTACATCGAAGTCTTTTGACCTCCATACAGTGATTATGCCTGTC
ATCGCTGGTGGTATCCTGGCGGCCTTGCTCCTGCTGATAGTTGTCGTGCTCTGTCTTTACTTCAAAATACACAAC
GCGCTAAAAGCTGCAAAGGAACCTGAAGCTGTGGCTGTAAAAAATCACAACCCAGACAAGGTGTGGTGGGCCAAG
AACAGCCAGGCCAAAACCATTGCCACGGAGTCTTGTCCTGCCCTGCAGTGCTGTGAAGGATATAGAATGTGTGCC
AGTTTTGATTCCCTGCCACCTTGCTGTTGCGACATAAATGAGGGCCTCTGAGTTAGGAAAGGCTCCCTTCTCAAA
GCAGAGCCCTGAAGACTTCAATGATGTCAATGAGGCCACCTGTTTGTGATGTGCAGGCACAGAAGAAAGGCACAG
CTCCCCATCAGTTTCATGGAAAATAACTCAGTGCCTGCTGGGAACCAGCTGCTGGAGATCCCTACAGAGAGCTTC
CACTGGGGGCAACCCTTCCAGGAAGGAGTTGGGGAGAGAGAACCCTCACTGTGGGGAATGCTGATAAACCAGTCA
CACAGCTGCTCTATTCTCACACAAATCTACCCCTTGCGTGGCTGGAACTGACGTTTCCCTGGAGGTGTCCAGAAA
GCTGATGTAACACAGAGCCTATAAAAGCTGTCGGTCCTTAAGGCTGCCCAGCGCCTTGCCAAAATGGAGCTTGTA
AGAAGGCTCATGCCATTGACCCTCTTAATTCTCTCCTGTTTGGCGGAGCTGACAATGGCGGAGGCTGAAGGCAAT
GCAAGCTGCACAGTCAGTCTAGGGGGTGCCAATATGGCAGAGACCCACAAAGCCATGATCCTGCAACTCAATCCC
AGTGAGAACTGCACCTGGACAATAGAAAGACCAGAAAACAAAAGCATCAGAATTATCTTTTCCTATGTCCAGCTT
GATCCAGATGGAAGCTGTGAAAGTGAAAACATTAAAGTCTTTGACGGAACCTCCAGCAATGGGCCTCTGCTAGGG
CAAGTCTGCAGTAAAAACGACTATGTTCCTGTATTTGAATCATCATCCAGTACATTGACGTTTCAAATAGTTACT
GACTCAGCAAGAATTCAAAGAACTGTCTTTGTCTTCTACTACTTCTTCTCTCCTAACATCTCTATTCCAAACTGT
GGCGGTTACCTGGATACCTTGGAAGGATCCTTCACCAGCCCCAATTACCCAAAGCCGCATCCTGAGCTGGCTTAT
TGTGTGTGGCACATACAAGTGGAGAAAGATTACAAGATAAAACTAAACTTCAAAGAGATTTTCCTAGAAATAGAC
AAACAGTGCAAATTTGATTTTCTTGCCATCTATGATGGCCCCTCCACCAACTCTGGCCTGATTGGACAAGTCTGT
GGCCGTGTGACTCCCACCTTCGAATCGTCATCAAACTCTCTGACTGTCGTGTTGTCTACAGATTATGCCAATTCT
TACCGGGGATTTTCTGCTTCCTACACCTCAATTTATGCAGAAAACATCAACACTACATCTTTAACTTGCTCTTCT
GACAGGATGAGAGTTATTATAAGCAAATCCTACCTAGAGGCTTTTAACTCTAATGGGAATAACTTGCAACTAAAA
GACCCAACTTGCAGACCAAAATTATCAAATGTTGTGGAATTTTCTGTCCCTCTTAATGGATGTGGTACAATCAGA
AAGGTAGAAGATCAGTCAATTACTTACACCAATATAATCACCTTTTCTGCATCCTCAACTTCTGAAGTGATCACC
CGTCAGAAACAACTCCAGATTATTGTGAAGTGTGAAATGGGACATAATTCTACAGTGGAGATAATATACATAACA
GAAGATGATGTAATACAAAGTCAAAATGCACTGGGCAAATATAACACCAGCATGGCTCTTTTTGAATCCAATTCA
TTTGAAAAGACTATACTTGAATCACCATATTATGTGGATTTGAACCAAACTCTTTTTGTTCAAGTTAGTCTGCAC
ACCTCAGATCCAAATTTGGTGGTGTTTCTTGATACCTGTAGAGCCTCTCCCACCTCTGACTTTGCATCTCCAACC
TACGACCTAATCAAGAGTGGATGTAGTCGAGATGAAACTTGTAAGGTGTATCCCTTATTTGGACACTATGGGAGA
TTCCAGTTTAATGCCTTTAAATTCTTGAGAAGTATGAGCTCTGTGTATCTGCAGTGTAAAGTTTTGATATGTGAT
AGCAGTGACCACCAGTCTCGCTGCAATCAAGGTTGTGTCTCCAGAAGCAAACGAGACATTTCTTCATATAAATGG
AAAACAGATTCCATCATAGGACCCATTCGTCTGAAAAGGGATCGAAGTGCAAGTGGCAATTCAGGATTTCAGCAT
GAAACACATGCGGAAGAAACTCCAAACCAGCCTTTCAACAGTGTGCATCTGTTTTCCTTCATGGTTCTAGCTCTG
AATGTGGTGACTGTAGCGACAATCACAGTGAGGCATTTTGTAAATCAACGGGCAGACTACAAATACCAGAAGCTG
CAGAACTATTAACTAACAGGTCCAACCCTAAGTGAGACATGTTTCTCCAGGATGCCAAAGGAAATGCTACCTCGT
GGCTACACATATTATGAATAAATGAGGAAGGGCCTGAAAGTGACACACAGGCCTGCATGTAAAAAAA

FIGURE 70

MELVRRLMPLTLLILSCLAELTMAEAEGNASCTVSLGGANMAETHKAMILQLNPSENCTWTI
ERPENKSIRIIFSYVQLDPDGSCESENIKVFDGTSSNGPLLGQVCSKNDYVPVFESSSSTLT
FQIVTDSARIQRTVFVFYYFFSPNISIPNCGGYLDTLEGSFTSPNYPKPHPELAYCVWHIQV
EKDYKIKLNFKEIFLEIDKQCKFDFLAIYDGPSTNSGLIGQVCGRVTPTFESSSNSLTVVLS
TDYANSYRGFSASYTSIYAENINTTSLTCSSDRMRVIISKSYLEAFNSNGNNLQLKDPTCRP
KLSNVVEFSVPLNGCGTIRKVEDQSITYTNIITFSASSTSEVITRQKQLQIIVKCEMGHNST
VEIIYITEDDVIQSQNALGKYNTSMALFESNSFEKTILESPYYVDLNQTLFVQVSLHTSDPN
LVVFLDTCRASPTSDFASPTYDLIKSGCSRDETCKVYPLFGHYGRFQFNAFKFLRSMSSVYL
QCKVLICDSSDHQSRCNQGCVSRSKRDISSYKWKTDSIIGPIRLKRDRSASGNSGFQHETHA
EETPNQPFNSVHLFSFMVLALNVVTVATITVRHFVNQRADYKYQKLQNY

Signal sequence:

amino acids 1-24

Transmembrane domain:

amino acids 571-586

N-glycosylation site.

amino acids 29-33, 57-61, 67-71, 148-152, 271-275, 370-374, 394-398, 419-423

Casein kinase II phosphorylation site.

amino acids 22-26, 108-112, 289-293, 348-352, 371-375, 379-383, 408-412, 463-467, 520-524, 556-560

Tyrosine kinase phosphorylation site.

amino acids 172-180, 407-415, 407-416, 519-528

N-myristoylation site.

amino acids 28-34, 38-44, 83-89, 95-101, 104-110, 226-232

Prokaryotic membrane lipoprotein lipid attachment site.

amino acids 7-18

FIGURE 71

GACGGAAGAACAGCGCTCCCGAGGCCGCGGGAGCCTGCAGAGAGGACAGCCGGCCTGCGCCG
GGACATGCGGCCCCAGGAGCTCCCCAGGCTCGCGTTCCCGTTGCTGCTGTTGCTGTTGCTGC
TGCTGCCGCCGCCGCCGTGCCCTGCCCACAGCGCCACGCGCTTCGACCCCACCTGGAGTCC
CTGGACGCCCGCCAGCTGCCCGCGTGGTTTGACCAGGCCAAGTTCGGCATCTTCATCCACTG
GGGAGTGTTTTCCGTGCCCAGCTTCGGTAGCGAGTGGTTCTGGTGGTATTGGCAAAAGGAAA
AGATACCGAAGTATGTGGAATTTATGAAAGATAATTACCCTCCTAGTTTCAAATATGAAGAT
TTTGGACCACTATTTACAGCAAAATTTTTTAATGCCAACCAGTGGGCAGATATTTTTCAGGC
CTCTGGTGCCAAATACATTGTCTTAACTTCCAAACATCATGAAGGCTTTACCTTGTGGGGT
CAGAATATTCGTGGAACTGGAATGCCATAGATGAGGGGCCCAAGAGGGACATTGTCAAGGAA
CTTGAGGTAGCCATTAGGAACAGAACTGACCTGCGTTTTGGACTGTACTATTCCCTTTTTGA
ATGGTTTCATCCGCTCTTCCTTGAGGATGAATCCAGTTCATTCCATAAGCGGCAATTTCCAG
TTTCTAAGACATTGCCAGAGCTCTATGAGTTAGTGAACAACTATCAGCCTGAGGTTCTGTGG
TCGGATGGTGACGGAGGAGCACCGGATCAATACTGGAACAGCACAGGCTTCTTGGCCTGGTT
ATATAATGAAAGCCCAGTTCGGGGCACAGTAGTCACCAATGATCGTTGGGGAGCTGGTAGCA
TCTGTAAGCATGGTGGCTTCTATACCTGCAGTGATCGTTATAACCCAGGACATCTTTTGCCA
CATAAATGGGAAAACTGCATGACAATAGACAAACTGTCCTGGGGCTATAGGAGGGAAGCTGG
AATCTCTGACTATCTTACAATTGAAGAATTGGTGAAGCAACTTGTAGAGACAGTTTCATGTG
GAGGAAATCTTTTGATGAATATTGGGCCCACACTAGATGGCACCATTTCTGTAGTTTTTGAG
GAGCGACTGAGGCAAGTGGGGTCCTGGCTAAAAGTCAATGGAGAAGCTATTTATGAAACCTA
TACCTGGCGATCCCAGAATGACACTGTCACCCCAGATGTGTGGTACACATCCAAGCCTAAAG
AAAAATTAGTCTATGCCATTTTTCTTAAATGGCCCACATCAGGACAGCTGTTCCTTGGCCAT
CCCAAAGCTATTCTGGGGGCAACAGAGGTGAAACTACTGGGCCATGGACAGCCACTTAACTG
GATTTCTTTGGAGCAAAATGGCATTATGGTAGAACTGCCACAGCTAACCATTCATCAGATGC
CGTGTAAATGGGGCTGGGCTCTAGCCCTAACTAATGTGATCTAAAGTGCAGCAGAGTGGCTG
ATGCTGCAAGTTATGTCTAAGGCTAGGAACTATCAGGTGTCTATAATTGTAGCACATGGAGA
AAGCAATGTAAACTGGATAAGAAAATTATTTGGCAGTTCAGCCCTTTCCCTTTTTCCCACTA
AATTTTTCTTAAATTACCCATGTAACCATTTTAACTCTCCAGTGCACTTTGCCATTAAAGTC
TCTTCACATTGATTTGTTTCCATGTGTGACTCAGAGGTGAGAATTTTTTCACATTATAGTAG
CAAGGAATTGGTGGTATTATGGACCGAACTGAAAATTTTATGTTGAAGCCATATCCCCCATG
ATTATATAGTTATGCATCACTTAATATGGGATATTTTCTGGGAAATGCATTGCTAGTCAAT
TTTTTTTTGTGCCAACATCATAGAGTGTATTTACAAAATCCTAGATGGCATAGCCTACTACA
CACCTAATGTGTATGGTATAGACTGTTGCTCCTAGGCTACAGACATATACAGCATGTTACTG
AATACTGTAGGCAATAGTAACAGTGGTATTTGTATATCGAAACATATGGAAACATAGAGAAG
GTACAGTAAAAATACTGTAAAATAAATGGTGCACCTGTATAGGGCACTTACCACGAATGGAG
CTTACAGGACTGGAAGTTGCTCTGGGTGAGTCAGTGAGTGAATGTGAAGGCCTAGGACATTA
TTGAACACTGCCAGACGTTATAAATACTGTATGCTTAGGCTACACTACATTTATAAAAAAAA
GTTTTTCTTTCTTCAATTATAAATTAACATAAGTGTACTGTAACTTTACAAACGTTTTAATT
TTTAAAACCTTTTTGGCTCTTTTGTAATAACACTTAGCTTAAAACATAAACTCATTGTGCAA
ATGTAA

FIGURE 72

MRPQELPRLAFPLLLLLLLLLPPPPCPAHSATRFDPTWESLDARQLPAWFDQAKFGIFIHWG
VFSVPSFGSEWFWWYWQKEKIPKYVEFMKDNYPPSFKYEDFGPLFTAKFFNANQWADIFQAS
GAKYIVLTSKHHEGFTLWGSEYSWNWNAIDEGPKRDIVKELEVAIRNRTDLRFGLYYSLFEW
FHPLFLEDESSSFHKRQFPVSKTLPELYELVNNYQPEVLWSDGDGGAPDQYWNSTGFLAWLY
NESPVRGTVVTNDRWGAGSICKHGGFYTCSDRYNPGHLLPHKWENCMTIDKLSWGYRREAGI
SDYLTIEELVKQLVETVSCGGNLLMNIGPTLDGTISVVFEERLRQVGSWLKVNGEAIYETYT
WRSQNDTVTPDVWYTSKPKEKLVYAIFLKWPTSGQLFLGHPKAILGATEVKLLGHGQPLNWI
SLEQNGIMVELPQLTIHQMPCKWGWALALTNVI

Signal sequence:
amino acids 1-28

N-glycosylation site.
amino acids 171-175, 239-243, 377-381

Casein kinase II phosphorylation site.
amino acids 32-36, 182-186, 209-213, 227-231, 276-280, 315-319, 375-375

Tyrosine kinase phosphorylation site.
amino acids 361-369, 389-397

N-myristoylation site.
amino acids 143-149, 178-184, 255-261, 272-278, 428-434

Leucine zipper pattern.
amino acids 410-432

Alpha-L-fucosidase putative active site.
amino acids 283-295

FIGURE 73

AGCAGGGAAATCCGGATGTCTCGGTTATGAAGTGGAGCAGTGAGTGTGAGCCTCAACATAGT
TCCAGAACTCTCCATCCGGACTAGTTATTGAGCATCTGCCTCTCATATCACCAGTGGCCATC
TGAGGTGTTTCCCTGGCTCTGAAGGGGTAGGCACGATGGCCAGGTGCTTCAGCCTGGTGTTG
CTTCTCACTTCCATCTGGACCACGAGGCTCCTGGTCCAAGGCTCTTTGCGTGCAGAAGAGCT
TTCCATCCAGGTGTCATGCAGAATTATGGGGATCACCCTTGTGAGCAAAAAGGCGAACCAGC
AGCTGAATTTCACAGAAGCTAAGGAGGCCTGTAGGCTGCTGGGACTAAGTTTGGCCGGCAAG
GACCAAGTTGAAACAGCCTTGAAAGCTAGCTTTGAAACTTGCAGCTATGGCTGGGTTGGAGA
TGGATTCGTGGTCATCTCTAGGATTAGCCCAAACCCCAAGTGTGGGAAAAATGGGGTGGGTG
TCCTGATTTGGAAGGTTCCAGTGAGCCGACAGTTTGCAGCCTATTGTTACAACTCATCTGAT
ACTTGGACTAACTCGTGCATTCCAGAAATTATCACCACCAAAGATCCCATATTCAACACTCA
AACTGCAACACAAACAACAGAATTTATTGTCAGTGACAGTACCTACTCGGTGGCATCCCCTT
ACTCTACAATACCTGCCCCTACTACTACTCCTCCTGCTCCAGCTTCCACTTCTATTCCACGG
AGAAAAAAATTGATTTGTGTCACAGAAGTTTTTATGGAAACTAGCACCATGTCTACAGAAAC
TGAACCATTTGTTGAAAATAAAGCAGCATTCAAGAATGAAGCTGCTGGGTTTGGAGGTGTCC
CCACGGCTCTGCTAGTGCTTGCTCTCCTCTTCTTTGGTGCTGCAGCTGGTCTTGGATTTTGC
TATGTCAAAAGGTATGTGAAGGCCTTCCCTTTTACAAACAAGAATCAGCAGAAGGAAATGAT
CGAAACCAAAGTAGTAAAGGAGGAGAAGGCCAATGATAGCAACCCTAATGAGGAATCAAAGA
AAACTGATAAAAACCCAGAAGAGTCCAAGAGTCCAAGCAAAACTACCGTGCGATGCCTGGAA
GCTGAAGTTTAGATGAGACAGAAATGAGGAGACACACCTGAGGCTGGTTTCTTTCATGCTCC
TTACCCTGCCCCAGCTGGGGAAATCAAAAGGGCCAAAGAACCAAAGAAGAAAGTCCACCCTT
GGTTCCTAACTGGAATCAGCTCAGGACTGCCATTGGACTATGGAGTGCACCAAAGAGAATGC
CCTTCTCCTTATTGTAACCCTGTCTGGATCCTATCCTCCTACCTCCAAAGCTTCCCACGGCC
TTTCTAGCCTGGCTATGTCCTAATAATATCCCACTGGGAGAAAGGAGTTTTGCAAAGTGCAA
GGACCTAAAACATCTCATCAGTATCCAGTGGTAAAAAGGCCTCCTGGCTGTCTGAGGCTAGG
TGGGTTGAAAGCCAAGGAGTCACTGAGACCAAGGCTTTCTCTACTGATTCCGCAGCTCAGAC
CCTTTCTTCAGCTCTGAAAGAGAAACACGTATCCCACCTGACATGTCCTTCTGAGCCCGGTA
AGAGCAAAAGAATGGCAGAAAAGTTTAGCCCCTGAAAGCCATGGAGATTCTCATAACTTGAG
ACCTAATCTCTGTAAAGCTAAAATAAAGAAATAGAACAAGGCTGAGGATACGACAGTACACT
GTCAGCAGGGACTGTAAACACAGACAGGGTCAAAGTGTTTTCTCTGAACACATTGAGTTGGA
ATCACTGTTTAGAACACACACACTTACTTTTTCTGGTCTCTACCACTGCTGATATTTTCTCT
AGGAAATATACTTTTACAAGTAACAAAAATAAAAACTCTTATAAATTTCTATTTTTATCTGA
GTTACAGAAATGATTACTAAGGAAGATTACTCAGTAATTTGTTTAAAAAGTAATAAAATTCA
ACAAACATTTGCTGAATAGCTACTATATGTCAAGTGCTGTGCAAGGTATTACACTCTGTAAT
TGAATATTATTCCTCAAAAAATTGCACATAGTAGAACGCTATCTGGGAAGCTATTTTTTTCA
GTTTTGATATTTCTAGCTTATCTACTTCCAAACTAATTTTTATTTTTGCTGAGACTAATCTT
ATTCATTTTCTCTAATATGGCAACCATTATAACCTTAATTTATTATTAACATACCTAAGAAG
TACATTGTTACCTCTATATACCAAAGCACATTTTAAAAGTGCCATTAACAAATGTATCACTA
GCCCTCCTTTTTCCAACAAGAAGGGACTGAGAGATGCAGAAATATTTGTGACAAAAAATTAA
AGCATTTAGAAAACTT

FIGURE 74

MARCFSLVLLLTSIWTTRLLVQGSLRAEELSIQVSCRIMGITLVSKKANQQLNFTEAKEACR
LLGLSLAGKDQVETALKASFETCSYGWVGDGFVVISRISPNPKCGKNGVGVLIWKVPVSRQF
AAYCYNSSDTWTNSCIPEIITTKDPIFNTQTATQTTEFIVSDSTYSVASPYSTIPAPTTTPP
APASTSIPRRKKLICVTEVFMETSTMSTETEPFVENKAAFKNEAAGFGGVPTALLVLALLFF
GAAAGLGFCYVKRYVKAFPFTNKNQQKEMIETKVVKEEKANDSNPNEESKKTDKNPEESKSP
SKTTVRCLEAEV

Signal sequence:
amino acids 1-16

Transmembrane domain:
amino acids 235-254

N-glycosylation site.
amino acids 53-57, 130-134, 289-293

Casein kinase II phosphorylation site.
amino acids 145-149, 214-218

Tyrosine kinase phosphorylation site.
amino acids 79-88

N-myristoylation site.
amino acids 23-29, 65-71, 234-240, 235-239, 249-255, 253-259

FIGURE 75

AGATGGCGGTCTTGGCACCTCTAATTGCTCTCGTGTATTCGGTGCCGCGACTTTCACGATGG
CTCGCCCAACCTTACTACCTTCTGTCGGCCCTGCTCTCTGCTGCCTTCCTACTCGTGAGGAA
ACTGCCGCCGCTCTGCCACGGTCTGCCCACCCAACGCGAAGACGGTAACCCGTGTGACTTTG
ACTGGAGAGAAGTGGAGATCCTGATGTTTCTCAGTGCCATTGTGATGATGAAGAACCGCAGA
TCCATCACTGTGGAGCAACATATAGGCAACATTTTCATGTTTAGTAAAGTGGCCAACACAAT
TCTTTTCTTCCGCTTGGATATTCGCATGGGCCTACTTTACATCACACTCTGCATAGTGTTCC
TGATGACGTGCAAACCCCCCCTATATATGGGCCCTGAGTATATCAAGTACTTCAATGATAAA
ACCATTGATGAGGAACTAGAACGGGACAAGAGGGTCACTTGGATTGTGGAGTTCTTTGCCAA
TTGGTCTAATGACTGCCAATCATTTGCCCCTATCTATGCTGACCTCTCCCTTAAATACAACT
GTACAGGGCTAAATTTTGGGAAGGTGGATGTTGGACGCTATACTGATGTTAGTACGCGGTAC
AAAGTGAGCACATCACCCCTCACCAAGCAACTCCCTACCCTGATCCTGTTCCAAGGTGGCAA
GGAGGCAATGCGGCGGCCACAGATTGACAAGAAAGGACGGGCTGTCTCATGGACCTTCTCTG
AGGAGAATGTGATCCGAGAATTTAACTTAAATGAGCTATACCAGCGGGCCAAGAAACTATCA
AAGGCTGGAGACAATATCCCTGAGGAGCAGCCTGTGGCTTCAACCCCCACCACAGTGTCAGA
TGGGGAAAACAAGAAGGATAAATAAGATCCTCACTTTGGCAGTGCTTCCTCTCCTGTCAATT
CCAGGCTCTTTCCATAACCACAAGCCTGAGGCTGCAGCCTTTNATTNATGTTTTCCCTTTGG
CTGNGACTGGNTGGGGCAGCATGCAGCTTCTGATTTTAAAGAGGCATCTAGGGAATTGTCAG
GCACCCTACAGGAAGGCCTGCCATGCTGTGGCCAACTGTTTCACTGGAGCAAGAAAGAGATC
TCATAGGACGGAGGGGGAAATGGTTTCCCTCCAAGCTTGGGTCAGTGTGTTAACTGCTTATC
AGCTATTCAGACATCTCCATGGTTTCTCCATGAAACTCTGTGGTTTCATCATTCCTTCTTAG
TTGACCTGCACAGCTTGGTTAGACCTAGATTTAACCCTAAGGTAAGATGCTGGGGTATAGAA
CGCTAAGAATTTTCCCCCAAGGACTCTTGCTTCCTTAAGCCCTTCTGGCTTCGTTTATGGTC
TTCATTAAAAGTATAAGCCTAACTTTGTCGCTAGTCCTAAGGAGAAACCTTTAACCACAAAG
TTTTTATCATTGAAGACAATATTGAACAACCCCCTATTTTGTGGGGATTGAGAAGGGGTGAA
TAGAGGCTTGAGACTTTCCTTTGTGTGGTAGGACTTGGAGGAGAAATCCCCTGGACTTTCAC
TAACCCTCTGACATACTCCCCACACCCAGTTGATGGCTTTCCGTAATAAAAAGATTGGGATT
TCCTTTTG

FIGURE 76

MAVLAPLIALVYSVPRLSRWLAQPYYLLSALLSAAFLLVRKLPPLCHGLPTQREDGNPCDFD
WREVEILMFLSAIVMMKNRRSITVEQHIGNIFMFSKVANTILFFRLDIRMGLLYITLCIVFL
MTCKPPLYMGPEYIKYFNDKTIDEELERDKRVTWIVEFFANWSNDCQSFAPIYADLSLKYNC
TGLNFGKVDVGRYTDVSTRYKVSTSPLTKQLPTLILFQGGKEAMRRPQIDKKGRAVSWTFSE
ENVIREFNLNELYQRAKKLSKAGDNIPEEQPVASTPTTVSDGENKKDK

Signal sequence:

amino acids 1-48

Transmembrane domain:

amino acids 111-125

N-glycosylation site.

amino acids 165-169, 185-189 cAMP- and cGMP-dependent protein kinase phosphorylation site.

amino acids 154-158, 265-269

Casein kinase II phosphorylation site.

amino acids 51-55, 145-149, 245-249, 286-290, 288-292

N-myristoylation site.

amino acids 188-194, 225-231

Myb DNA-binding domain repeat signature 1.

amino acids 244-253

FIGURE 77

GGACAGCTCGCGGCCCCCGAGAGCTCTAGCCGTCGAGGAGCTGCCTGGGGACGTTTGCCCTG
GGGCCCCAGCCTGGCCCGGGTCACCCTGGCATGAGGAGATGGGCCTGTTGCTCCTGGTCCCA
TTGCTCCTGCTGCCCGGCTCCTACGGACTGCCCTTCTACAACGGCTTCTACTACTCCAACAG
CGCCAACGACCAGAACCTAGGCAACGGTCATGGCAAAGACCTCCTTAATGGAGTGAAGCTGG
TGGTGGAGACACCCGAGGAGACCCTGTTCACCTACCAAGGGGCCAGTGTGATCCTGCCCTGC
CGCTACCGCTACGAGCCGGCCCTGGTCTCCCCGCGGCGTGTGCGTGTCAAATGGTGGAAGCT
GTCGGAGAACGGGGCCCCAGAGAAGGACGTGCTGGTGGCCATCGGGCTGAGGCACCGCTCCT
TTGGGGACTACCAAGGCCGCGTGCACCTGCGGCAGGACAAAGAGCATGACGTCTCGCTGGAG
ATCCAGGATCTGCGGCTGGAGGACTATGGGCGTTACCGCTGTGAGGTCATTGACGGGCTGGA
GGATGAAAGCGGTCTGGTGGAGCTGGAGCTGCGGGGTGTGGTCTTTCCTTACCAGTCCCCCA
ACGGGCGCTACCAGTTCAACTTCCACGAGGGCCAGCAGGTCTGTGCAGAGCAGGCTGCGGTG
GTGGCCTCCTTTGAGCAGCTCTTCCGGGCCTGGGAGGAGGGCCTGGACTGGTGCAACGCGGG
CTGGCTGCAGGATGCTACGGTGCAGTACCCCATCATGTTGCCCCGGCAGCCCTGCGGTGGCC
CAGGCCTGGCACCTGGCGTGCGAAGCTACGGCCCCCGCCACCGCCGCCTGCACCGCTATGAT
GTATTCTGCTTCGCTACTGCCCTCAAGGGGCGGGTGTACTACCTGGAGCACCCTGAGAAGCT
GACGCTGACAGAGGCAAGGGAGGCCTGCCAGGAAGATGATGCCACGATCGCCAAGGTGGGAC
AGCTCTTTGCCGCCTGGAAGTTCCATGGCCTGGACCGCTGCGACGCTGGCTGGCTGGCAGAT
GGCAGCGTCCGCTACCCTGTGGTTCACCCGCATCCTAACTGTGGGCCCCCAGAGCCTGGGGT
CCGAAGCTTTGGCTTCCCCGACCCGCAGAGCCGCTTGTACGGTGTTTACTGCTACCGCCAGC
ACTAGGACCTGGGGCCCTCCCCTGCCGCATTCCCTCACTGGCTGTGTATTTATTGAGTGGTT
CGTTTTCCCTTGTGGGTTGGAGCCATTTTAACTGTTTTTATACTTCTCAATTTAAATTTTCT
TTAAACATTTTTTTACTATTTTTTGTAAAGCAAACAGAACCCAATGCCTCCCTTTGCTCCTG
GATGCCCCACTCCAGGAATCATGCTTGCTCCCCTGGGCCATTTGCGGTTTTGTGGGCTTCTG
GAGGGTTCCCCGCCATCCAGGCTGGTCTCCCTCCCTTAAGGAGGTTGGTGCCCAGAGTGGGC
GGTGGCCTGTCTAGAATGCCGCCGGGAGTCCGGGCATGGTGGGCACAGTTCTCCCTGCCCCT
CAGCCTGGGGGAAGAAGAGGGCCTCGGGGGCCTCCGGAGCTGGGCTTTGGGCCTCTCCTGCC
CACCTCTACTTCTCTGTGAAGCCGCTGACCCCAGTCTGCCCACTGAGGGGCTAGGGCTGGAA
GCCAGTTCTAGGCTTCCAGGCGAAATCTGAGGGAAGGAAGAAACTCCCCTCCCCGTTCCCCT
TCCCCTCTCGGTTCCAAAGAATCTGTTTTGTTGTCATTTGTTTCTCCTGTTTCCCTGTGTGG
GGAGGGGCCCTCAGGTGTGTGTACTTTGGACAATAAATGGTGCTATGACTGCCTTCCGCCAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAA

FIGURE 78

MGLLLLVPLLLLPGSYGLPFYNGFYYSNSANDQNLGNGHGKDLLNGVKLVVETPEETLFTYQ
GASVILPCRYRYEPALVSPRRVRVKWWKLSENGAPEKDVLVAIGLRHRSFGDYQGRVHLRQD
KEHDVSLEIQDLRLEDYGRYRCEVIDGLEDESGLVELELRGVVFPYQSPNGRYQFNFHEGQQ
VCAEQAAVVASFEQLFRAWEEGLDWCNAGWLQDATVQYPIMLPRQPCGGPGLAPGVRSYGPR
HRRLHRYDVFCFATALKGRVYYLEHPEKLTLTEAREACQEDDATIAKVGQLFAAWKFHGLDR
CDAGWLADGSVRYPVVHPHPNCGPPEPGVRSFGFPDPQSRLYGVYCYRQH

Signal sequence:

amino acids 1-17

Casein kinase II phosphorylation site.

amino acids 29-33, 53-57, 111-115, 278-282

Tyrosine kinase phosphorylation site.

amino acids 137-145

N-myristoylation site.

amino acids 36-42, 184-190, 208-214, 237-243, 297-303, 307-313

FIGURE 79

GGAGAGCGGAGCGAAGCTGGATAACAGGGGACCGATGATGTGGCGACCATCAGTTCTGCTGC
TTCTGTTGCTACTGAGGCACGGGGCCCAGGGGAAGCCATCCCCAGACGCAGGCCCTCATGGC
CAGGGGAGGGTGCACCAGGCGGCCCCCCTGAGCGACGCTCCCCATGATGACGCCCACGGGAA
CTTCCAGTACGACCATGAGGCTTTCCTGGGACGGGAAGTGGCCAAGGAATTCGACCAACTCA
CCCCAGAGGAAAGCCAGGCCCGTCTGGGGCGGATCGTGGACCGCATGGACCGCGCGGGGGAC
GGCGACGGCTGGGTGTCGCTGGCCGAGCTTCGCGCGTGGATCGCGCACACGCAGCAGCGGCA
CATACGGGACTCGGTGAGCGCGGCCTGGGACACGTACGACACGGACCGCGACGGGCGTGTGG
GTTGGGAGGAGCTGCGCAACGCCACCTATGGCCACTACGCGCCCGGTGAAGAATTTCATGAC
GTGGAGGATGCAGAGACCTACAAAAAGATGCTGGCTCGGGACGAGCGGCGTTTCCGGGTGGC
CGACCAGGATGGGGACTCGATGGCCACTCGAGAGGAGCTGACAGCCTTCCTGCACCCCGAGG
AGTTCCCTCACATGCGGGACATCGTGATTGCTGAAACCCTGGAGGACCTGGACAGAAACAAA
GATGGCTATGTCCAGGTGGAGGAGTACATCGCGGATCTGTACTCAGCCGAGCCTGGGGAGGA
GGAGCCGGCGTGGGTGCAGACGGAGAGGCAGCAGTTCCGGGACTTCCGGGATCTGAACAAGG
ATGGGCACCTGGATGGGAGTGAGGTGGGCCACTGGGTGCTGCCCCCTGCCCAGGACCAGCCC
CTGGTGGAAGCCAACCACCTGCTGCACGAGAGCGACACGGACAAGGATGGGCGGCTGAGCAA
AGCGGAAATCCTGGGTAATTGGAACATGTTTGTGGGCAGTCAGGCCACCAACTATGGCGAGG
ACCTGACCCGGCACCACGATGAGCTGTGAGCACCGCGCACCTGCCACAGCCTCAGAGGCCCG
CACAATGACCGGAGGAGGGGCCGCTGTGGTCTGGCCCCCTCCCTGTCCAGGCCCCGCAGGAG
GCAGATGCAGTCCCAGGCATCCTCCTGCCCCTGGGCTCTCAGGGACCCCCTGGGTCGGCTTC
TGTCCCTGTCACACCCCCAACCCCAGGGAGGGGCTGTCATAGTCCCAGAGGATAAGCAATAC
CTATTTCTGACTGAGTCTCCCAGCCCAGACCCAGGGACCCTTGGCCCCAAGCTCAGCTCTAA
GAACCGCCCCAACCCCTCCAGCTCCAAATCTGAGCCTCCACCACATAGACTGAAACTCCCCT
GGCCCCAGCCCTCTCCTGCCTGGCCTGGCCTGGGACACCTCCTCTCTGCCAGGAGGCAATAA
AAGCCAGCGCCGGGACCTTGAAAAAAAAAAAAAAAAAAAAAAAAAAAAAAAAAAAAAAAAAA
AAAAAAAAAAAAAAA

FIGURE 80

MMWRPSVLLLLLLLRHGAQGKPSPDAGPHGQGRVHQAAPLSDAPHDDAHGNFQYDHEAFLGR
EVAKEFDQLTPEESQARLGRIVDRMDRAGDGDGWVSLAELRAWIAHTQQRHIRDSVSAAWDT
YDTDRDGRVGWEELRNATYGHYAPGEEFHDVEDAETYKKMLARDERRFRVADQDGDSMATRE
ELTAFLHPEEFPHMRDIVIAETLEDLDRNKDGYVQVEEYIADLYSAEPGEEEPAWVQTERQQ
FRDFRDLNKDGHLDGSEVGHWVLPPAQDQPLVEANHLLHESDTDKDGRLSKAEILGNWNMFV
GSQATNYGEDLTRHHDEL

```
Signal sequence:
amino acids 1-20

N-glycosylation site.
amino acids 140-144

Casein kinase II phosphorylation site.
amino acids 72-76, 98-102, 127-131, 184-188, 208-212, 289-293,
291-295, 298-302

N-myristoylation site.
amino acids 263-269, 311-317

Endoplasmic reticulum targeting sequence.
amino acids 325-330
```

FIGURE 81

GGGGCCTTGCCTTCCGCACTCGGGCGCAGCCGGGTGGATCTCGAGCAGGTGCGGAGCCCCGG
GCGGCGGGCGCGGGTGCGAGGGATCCCTGACGCCTCTGTCCCTGTTTCTTTGTCGCTCCCAG
CCTGTCTGTCGTCGTTTTGGCGCCCCCGCCTCCCCGCGGTGCGGGGTTGCACACCGATCCTG
GGCTTCGCTCGATTTGCCGCCGAGGCGCCTCCCAGACCTAGAGGGGCGCTGGCCTGGAGCAG
CGGGTCGTCTGTGTCCTCTCTCCTCTGCGCCGCGCCCGGGGATCCGAAGGGTGCGGGGCTCT
GAGGAGGTGACGCGCGGGGCCTCCCGCACCCTGGCCTTGCCCGCATTCTCCCTCTCTCCCAG
GTGTGAGCAGCCTATCAGTCACC<u>ATG</u>TCCGCAGCCTGGATCCCGGCTCTCGGCCTCGGTGTG
TGTCTGCTGCTGCTGCCGGGGCCCGCGGGCAGCGAGGGAGCCGCTCCCATTGCTATCACATG
TTTTACCAGAGGCTTGGACATCAGGAAAGAGAAAGCAGATGTCCTCTGCCCAGGGGGCTGCC
CTCTTGAGGAATTCTCTGTGTATGGGAACATAGTATATGCTTCTGTATCGAGCATATGTGGG
GCTGCTGTCCACAGGGGAGTAATCAGCAACTCAGGGGGACCTGTACGAGTCTATAGCCTACC
TGGTCGAGAAAACTATTCCTCAGTAGATGCCAATGGCATCCAGTCTCAAATGCTTTCTAGAT
GGTCTGCTTCTTTCACAGTAACTAAAGGCAAAAGTAGTACACAGGAGGCCACAGGACAAGCA
GTGTCCACAGCACATCCACCAACAGGTAAACGACTAAAGAAAACACCCGAGAAGAAAACTGG
CAATAAAGATTGTAAAGCAGACATTGCATTTCTGATTGATGGAAGCTTTAATATTGGGCAGC
GCCGATTTAATTTACAGAAGAATTTTGTTGGAAAAGTGGCTCTAATGTTGGGAATTGGAACA
GAAGGACCACATGTGGGCCTTGTTCAAGCCAGTGAACATCCCAAAATAGAATTTTACTTGAA
AAACTTTACATCAGCCAAAGATGTTTTGTTTGCCATAAAGGAAGTAGGTTTCAGAGGGGGTA
ATTCCAATACAGGAAAAGCCTTGAAGCATACTGCTCAGAAATTCTTCACGGTAGATGCTGGA
GTAAGAAAAGGGATCCCCAAAGTGGTGGTGGTATTTATTGATGGTTGGCCTTCTGATGACAT
CGAGGAAGCAGGCATTGTGGCCAGAGAGTTTGGTGTCAATGTATTTATAGTTTCTGTGGCCA
AGCCTATCCCTGAAGAACTGGGGATGGTTCAGGATGTCACATTTGTTGACAAGGCTGTCTGT
CGGAATAATGGCTTCTTCTCTTACCACATGCCCAACTGGTTTGGCACCACAAAATACGTAAA
GCCTCTGGTACAGAAGCTGTGCACTCATGAACAAATGATGTGCAGCAAGACCTGTTATAACT
CAGTGAACATTGCCTTTCTAATTGATGGCTCCAGCAGTGTTGGAGATAGCAATTTCCGCCTC
ATGCTTGAATTTGTTTCCAACATAGCCAAGACTTTTGAAATCTCGGACATTGGTGCCAAGAT
AGCTGCTGTACAGTTTACTTATGATCAGCGCACGGAGTTCAGTTTCACTGACTATAGCACCA
AAGAGAATGTCCTAGCTGTCATCAGAAACATCCGCTATATGAGTGGTGGAACAGCTACTGGT
GATGCCATTTCCTTCACTGTTAGAAATGTGTTTGGCCCTATAAGGGAGAGCCCCAACAAGAA
CTTCCTAGTAATTGTCACAGATGGGCAGTCCTATGATGATGTCCAAGGCCCTGCAGCTGCTG
CACATGATGCAGGAATCACTATCTTCTCTGTTGGTGTGGCTTGGGCACCTCTGGATGACCTG
AAAGATATGGCTTCTAAACCGAAGGAGTCTCACGCTTTCTTCACAAGAGAGTTCACAGGATT
AGAACCAATTGTTTCTGATGTCATCAGAGGCATTTGTAGAGATTTCTTAGAATCCCAGCAA<u>T</u>
<u>AA</u>TGGTAACATTTTGACAACTGAAAGAAAAAGTACAAGGGGATCCAGTGTGTAAATTGTATT
CTCATAATACTGAAATGCTTTAGCATACTAGAATCAGATACAAAACTATTAAGTATGTCAAC
AGCCATTTAGGCAAATAAGCACTCCTTTAAAGCCGCTGCCTTCTGGTTACAATTTACAGTGT
ACTTTGTTAAAAACACTGCTGAGGCTTCATAATCATGGCTCTTAGAAACTCAGGAAAGAGGA
GATAATGTGGATTAAAACCTTAAGAGTTCTAACCATGCCTACTAAATGTACAGATATGCAAA
TTCCATAGCTCAATAAAAGAATCTGATACTTAGACCAAAAAAAAAAA

FIGURE 82

MSAAWIPALGLGVCLLLLPGPAGSEGAAPIAITCFTRGLDIRKEKADVLCPGGCPLEEFSVY
GNIVYASVSSICGAAVHRGVISNSGGPVRVYSLPGRENYSSVDANGIQSQMLSRWSASFTVT
KGKSSTQEATGQAVSTAHPPTGKRLKKTPEKKTGNKDCKADIAFLIDGSFNIGQRRFNLQKN
FVGKVALMLGIGTEGPHVGLVQASEHPKIEFYLKNFTSAKDVLFAIKEVGFRGGNSNTGKAL
KHTAQKFFTVDAGVRKGIPKVVVVFIDGWPSDDIEEAGIVAREFGVNVFIVSVAKPIPEELG
MVQDVTFVDKAVCRNNGFFSYHMPNWFGTTKYVKPLVQKLCTHEQMMCSKTCYNSVNIAFLI
DGSSSVGDSNFRLMLEFVSNIAKTFEISDIGAKIAAVQFTYDQRTEFSFTDYSTKENVLAVI
RNIRYMSGGTATGDAISFTVRNVFGPIRESPNKNFLVIVTDGQSYDDVQGPAAAAHDAGITI
FSVGVAWAPLDDLKDMASKPKESHAFFTREFTGLEPIVSDVIRGICRDFLESQQ

Signal sequence:

amino acids 1-24

N-glycosylation site.

amino acids 100-104, 221-225

Casein kinase II phosphorylation site.

amino acids 102-106, 129-133, 224-228, 316-320, 377-381, 420-424, 425-429, 478-482, 528-532

N-myristoylation site.

amino acids 10-16, 23-29, 81-87, 135-141, 158-164, 205-211, 239-245, 240-246, 261-267, 403-409, 442-448, 443-449

Amidation site.

amino acids 145-149

FIGURE 83

CGCCGCGCTCCCGCACCCGCGGCCCGCCCACCGCGCCGCTCCCGCATCTGCACCCGCAGCCC
GGCGGCCTCCCGGCGGGAGCGAGCAGATCCAGTCCGGCCCGCAGCGCAACTCGGTCCAGTCG
GGGCGGCGGCTGCGGGCGCAGAGCGGAG<u>ATG</u>CAGCGGCTTGGGGCCACCCTGCTGTGCCTGC
TGCTGGCGGCGGCGGTCCCCACGGCCCCCGCGCCCGCTCCGACGGCGACCTCGGCTCCAGTC
AAGCCCGGCCCGGCTCTCAGCTACCCGCAGGAGGAGGCCACCCTCAATGAGATGTTCCGCGA
GGTTGAGGAACTGATGGAGGACACGCAGCACAAATTGCGCAGCGCGGTGGAAGAGATGGAGG
CAGAAGAAGCTGCTGCTAAAGCATCATCAGAAGTGAACCTGGCAAACTTACCTCCCAGCTAT
CACAATGAGACCAACACAGACACGAAGGTTGGAAATAATACCATCCATGTGCACCGAGAAAT
TCACAAGATAACCAACAACCAGACTGGACAAATGGTCTTTTCAGAGACAGTTATCACATCTG
TGGGAGACGAAGAAGGCAGAAGGAGCCACGAGTGCATCATCGACGAGGACTGTGGGCCCAGC
ATGTACTGCCAGTTTGCCAGCTTCCAGTACACCTGCCAGCCATGCCGGGGCCAGAGGATGCT
CTGCACCCGGGACAGTGAGTGCTGTGGAGACCAGCTGTGTGTCTGGGGTCACTGCACCAAAA
TGGCCACCAGGGGCAGCAATGGGACCATCTGTGACAACCAGAGGGACTGCCAGCCGGGGCTG
TGCTGTGCCTTCCAGAGAGGCCTGCTGTTCCCTGTGTGCACACCCCTGCCCGTGGAGGGCGA
GCTTTGCCATGACCCCGCCAGCCGGCTTCTGGACCTCATCACCTGGGAGCTAGAGCCTGATG
GAGCCTTGGACCGATGCCCTTGTGCCAGTGGCCTCCTCTGCCAGCCCCACAGCCACAGCCTG
GTGTATGTGTGCAAGCCGACCTTCGTGGGGAGCCGTGACCAAGATGGGGAGATCCTGCTGCC
CAGAGAGGTCCCCGATGAGTATGAAGTTGGCAGCTTCATGGAGGAGGTGCGCCAGGAGCTGG
AGGACCTGGAGAGGAGCCTGACTGAAGAGATGGCGCTGGGGGAGCCTGCGGCTGCCGCCGCT
GCACTGCTGGGAGGGGAAGAGATT<u>TAG</u>ATCTGGACCAGGCTGTGGGTAGATGTGCAATAGAA
ATAGCTAATTTATTTCCCCAGGTGTGTGCTTTAGGCGTGGGCTGACCAGGCTTCTTCCTACA
TCTTCTTCCCAGTAAGTTTCCCCTCTGGCTTGACAGCATGAGGTGTTGTGCATTTGTTCAGC
TCCCCCAGGCTGTTCTCCAGGCTTCACAGTCTGGTGCTTGGGAGAGTCAGGCAGGGTTAAAC
TGCAGGAGCAGTTTGCCACCCCTGTCCAGATTATTGGCTGCTTTGCCTCTACCAGTTGGCAG
ACAGCCGTTTGTTCTACATGGCTTTGATAATTGTTTGAGGGGAGGAGATGGAAACAATGTGG
AGTCTCCCTCTGATTGGTTTTGGGGAAATGTGGAGAAGAGTGCCCTGCTTTGCAAACATCAA
CCTGGCAAAAATGCAACAAATGAATTTTCCACGCAGTTCTTTCCATGGGCATAGGTAAGCTG
TGCCTTCAGCTGTTGCAGATGAAATGTTCTGTTCACCCTGCATTACATGTGTTTATTCATCC
AGCAGTGTTGCTCAGCTCCTACCTCTGTGCCAGGGCAGCATTTTCATATCCAAGATCAATTC
CCTCTCTCAGCACAGCCTGGGGAGGGGGTCATTGTTCTCCTCGTCCATCAGGGATCTCAGAG
GCTCAGAGACTGCAAGCTGCTTGCCCAAGTCACACAGCTAGTGAAGACCAGAGCAGTTTCAT
CTGGTTGTGACTCTAAGCTCAGTGCTCTCTCCACTACCCCACACCAGCCTTGGTGCCACCAA
AAGTGCTCCCCAAAAGGAAGGAGAATGGGATTTTTCTTGAGGCATGCACATCTGGAATTAAG
GTCAAACTAATTCTCACATCCCTCTAAAAGTAAACTACTGTTAGGAACAGCAGTGTTCTCAC
AGTGTGGGGCAGCCGTCCTTCTAATGAAGACAATGATATTGACACTGTCCCTCTTTGGCAGT
TGCATTAGTAACTTTGAAAGGTATATGACTGAGCGTAGCATACAGGTTAACCTGCAGAAACA
GTACTTAGGTAATTGTAGGGCGAGGATTATAAATGAAATTTGCAAAATCACTTAGCAGCAAC
TGAAGACAATTATCAACCACGTGGAGAAAATCAAACCGAGCAGGGCTGTGTGAAACATGGTT
GTAATATGCGACTGCGAACACTGAACTCTACGCCACTCCACAAATGATGTTTTCAGGTGTCA
TGGACTGTTGCCACCATGTATTCATCCAGAGTTCTTAAAGTTTAAAGTTGCACATGATTGTA
TAAGCATGCTTTCTTTGAGTTTTAAATTATGTATAAACATAAGTTGCATTTAGAAATCAAGC
ATAAATCACTTCAACTGCAAAAAAAAAAAAAAAAAAAAAAAA

FIGURE 84

MQRLGATLLCLLLAAAVPTAPAPAPTATSAPVKPGPALSYPQEEATLNEMFREVEELMEDTQ
HKLRSAVEEMEAEEAAAKASSEVNLANLPPSYHNETNTDTKVGNNTIHVHREIHKITNNQTG
QMVFSETVITSVGDEEGRRSHECIIDEDCGPSMYCQFASFQYTCQPCRGQRMLCTRDSECCG
DQLCVWGHCTKMATRGSNGTICDNQRDCQPGLCCAFQRGLLFPVCTPLPVEGELCHDPASRL
LDLITWELEPDGALDRCPCASGLLCQPHSHSLVYVCKPTFVGSRDQDGEILLPREVPDEYEV
GSFMEEVRQELEDLERSLTEEMALGEPAAAAAALLGGEEI

Signal sequence:

amino acids 1-19

N-glycosylation site.

amino acids 96-100, 106-110, 121-125, 204-208

Casein kinase II phosphorylation site.

amino acids 46-50, 67-71, 98-102, 135-139, 206-210, 312-316, 327-331

N-myristoylation site.

amino acids 202-208, 217-223

Amidation site.

amino acids 140-144

FIGURE 85

AAGGAGGCTGGGAGGAAAGAGGTAAGAAAGGTTAGAGAACCTACCTCACATCTCTCTGGGCTCAGAAGGACTCTG
AAGATAACAATAATTTCAGCCCATCCACTCTCCTTCCCTCCCAAACACACATGTGCATGTACACACACACATACA
CACACATACACCTTCCTCTCCTTCACTGAAGACTCACAGTCACTCACTCTGTGAGCAGGTCATAGAAAAGGACAC
TAAAGCCTTAAGGACAGGCCTGGCCATTACCTCTGCAGCTCCTTTGGCTTGTTGAGTCAAAAAACATGGAGGGG
CCAGGCACGGTGACTCACACCTGTAATCCCAGCATTTTGGGAGACCGAGGTGAGCAGATCACTTGAGGTCAGGAG
TTCGAGACCAGCCTGGCCAACATGGAGAAACCCCCATCTCTACTAAAAATACAAAAATTAGCCAGGAGTGGTGGC
AGGTGCCTGTAATCCCAGCTACTCAGGTGGCTGAGCCAGGAGAATCGCTTGAATCCAGGAGGCGGAGGATGCAGT
CAGCTGAGTGCACCGCTGCACTCCAGCCTGGGTGACAGAATGAGACTCTGTCTCAAACAAACAAACACGGGAGGA
GGGGTAGATACTGCTTCTCTGCAACCTCCTTAACTCTGCATCCTCTTCTTCCAGGGCTGCCCCTGATGGGGCCTG
GCAATGACTGAGCAGGCCCAGCCCCAGAGGACAAGGAAGAGAAGGCATATTGAGGAGGGCAAGAAGTGACGCCCG
GTGTAGAATGACTGCCCTGGGAGGGTGGTTCCTTGGGCCCTGGCAGGGTTGCTGACCCTTACCCTGCAAAACACA
AAGAGCAGGACTCCAGACTCTCCTTGTGAATGGTCCCCTGCCCTGCAGCTCCACCATGAGGCTTCTCGTGGCCCC
ACTCTTGCTAGCTTGGGTGGCTGGTGCCACTGCCACTGTGCCCGTGGTACCCTGGCATGTTCCCTGCCCCCCTCA
GTGTGCCTGCCAGATCCGGCCCTGGTATACGCCCCGCTCGTCCTACCGCGAGGCTACCACTGTGGACTGCAATGA
CCTATTCCTGACGGCAGTCCCCCCGGCACTCCCCGCAGGCACACAGACCCTGCTCCTGCAGAGCAACAGCATTGT
CCGTGTGGACCAGAGTGAGCTGGGCTACCTGGCCAATCTCACAGAGCTGGACCTGTCCCAGAACAGCTTTTCGGA
TGCCCGAGACTGTGATTTCCATGCCCTGCCCCAGCTGCTGAGCCTGCACCTAGAGGAGAACCAGCTGACCCGGCT
GGAGGACCACAGCTTTGCAGGGCTGGCCAGCCTACAGGAACTCTATCTCAACCACAACCAGCTCTACCGCATCGC
CCCCAGGGCCTTTTCTGGCCTCAGCAACTTGCTGCGGCTGCACCTCAACTCCAACCTCCTGAGGGCCATTGACAG
CCGCTGGTTTGAAATGCTGCCCAACTTGGAGATACTCATGATTGGCGGCAACAAGGTAGATGCCATCCTGGACAT
GAACTTCCGGCCCCTGGCCAACCTGCGTAGCCTGGTGCTAGCAGGCATGAACCTGCGGGAGATCTCCGACTATGC
CCTGGAGGGGCTGCAAAGCCTGGAGAGCCTCTCCTTCTATGACAACCAGCTGGCCCGGGTGCCCAGGCGGGCACT
GGAACAGGTGCCCGGGCTCAAGTTCCTAGACCTCAACAAGAACCCGCTCCAGCGGGTAGGGCCGGGGGACTTTGC
CAACATGCTGCACCTTAAGGAGCTGGGACTGAACAACATGGAGGAGCTGGTCTCCATCGACAAGTTTGCCCTGGT
GAACCTCCCCGAGCTGACCAAGCTGGACATCACCAATAACCCACGGCTGTCCTTCATCCACCCCCGCGCCTTCCA
CCACCTGCCCCAGATGGAGACCCTCATGCTCAACAACAACGCTCTCAGTGCCTTGCACCAGCAGACGGTGGAGTC
CCTGCCCAACCTGCAGGAGGTAGGTCTCCACGGCAACCCCATCCGCTGTGACTGTGTCATCCGCTGGGCCAATGC
CACGGGCACCCGTGTCCGCTTCATCGAGCCGCAATCCACCCTGTGTGCGGAGCCTCCGGACCTCCAGCGCCTCCC
GGTCCGTGAGGTGCCCTTCCGGGAGATGACGGACCACTGTTTGCCCCTCATCTCCCCACGAAGCTTCCCCCCAAG
CCTCCAGGTAGCCAGTGGAGAGAGCATGGTGCTGCATTGCCGGGCACTGGCCGAACCCGAACCCGAGATCTACTG
GGTCACTCCAGCTGGGCTTCGACTGACACCTGCCCATGCAGGCAGGAGGTACCGGGTGTACCCCGAGGGGACCCT
GGAGCTGCGGAGGGTGACAGCAGAAGAGGCAGGGCTATACACCTGTGTGGCCCAGAACCTGGTGGGGGCTGACAC
TAAGACGGTTAGTGTGGTTGTGGGCCGTGCTCTCCTCCAGCCAGGCAGGGACGAAGGACAGGGGCTGGAGCTCCG
GGTGCAGGAGACCCACCCCTATCACATCCTGCTATCTTGGGTCACCCCACCCAACACAGTGTCCACCAACCTCAC
CTGGTCCAGTGCCTCCTCCCTCCGGGGCCAGGGGGCCACAGCTCTGGCCCGCCTGCCTCGGGGAACCCACAGCTA
CAACATTACCCGCCTCCTTCAGGCCACGGAGTACTGGGCCTGCCTGCAAGTGGCCTTTGCTGATGCCCACACCCA
GTTGGCTTGTGTATGGGCCAGGACCAAAGAGGCCACTTCTTGCCACAGAGCCTTAGGGGATCGTCCTGGGCTCAT
TGCCATCCTGGCTCTCGCTGTCCTTCTCCTGGCAGCTGGGCTAGCGGCCCACCTTGGCACAGGCCAACCCAGGAA
GGGTGTGGGTGGGAGGCGGCCTCTCCCTCCAGCCTGGGCTTTCTGGGGCTGGAGTGCCCCTTCTGTCCGGGTTGT
GTCTGCTCCCCTCGTCCTGCCCTGGAATCCAGGGAGGAAGCTGCCCAGATCCTCAGAAGGGGAGACACTGTTGCC
ACCATTGTCTCAAAATTCTTGAAGCTCAGCCTGTTCTCAGCAGTAGAGAAATCACTAGGACTACTTTTTACCAAA
AGAGAAGCAGTCTGGGCCAGATGCCCTGCCAGGAAAGGGACATGGACCCACGTGCTTGAGGCCTGGCAGCTGGGC
CAAGACAGATGGGGCTTTGTGGCCCTGGGGGTGCTTCTGCAGCCTTGAAAAAGTTGCCCTTACCTCCTAGGGTCA
CCTCTGCTGCCATTCTGAGGAACATCTCCAAGGAACAGGAGGGACTTTGGCTAGAGCCTCCTGCCTCCCCATCTT
CTCTCTGCCCAGAGGCTCCTGGGCCTGGCTTGGCTGTCCCCTACCTGTGTCCCCGGGCTGCACCCCTTCCTCTTC
TCTTTCTCTGTACAGTCTCAGTTGCTTGCTCTTGTGCCTCCTGGGCAAGGGCTGAAGGAGGCCACTCCATCTCAC
CTCGGGGGGCTGCCCTCAATGTGGGAGTGACCCCAGCCAGATCTGAAGGACATTTGGGAGAGGGATGCCCAGGAA
CGCCTCATCTCAGCAGCCTGGGCTCGGCATTCCGAAGCTGACTTTCTATAGGCAATTTTGTACCTTTGTGGAGAA
ATGTGTCACCTCCCCCAACCCGATTCACTCTTTTCTCCTGTTTTGTAAAAAATAAAAATAAATAATAACAATAAA
AAAA

FIGURE 86

MRLLVAPLLLAWVAGATATVPVVPWHVPCPPQCACQIRPWYTPRSSYREATTVDCNDLFLTA
VPPALPAGTQTLLLQSNSIVRVDQSELGYLANLTELDLSQNSFSDARDCDFHALPQLLSLHL
EENQLTRLEDHSFAGLASLQELYLNHNQLYRIAPRAFSGLSNLLRLHLNSNLLRAIDSRWFE
MLPNLEILMIGGNKVDAILDMNFRPLANLRSLVLAGMNLREISDYALEGLQSLESLSFYDNQ
LARVPRRALEQVPGLKFLDLNKNPLQRVGPGDFANMLHLKELGLNNMEELVSIDKFALVNLP
ELTKLDITNNPRLSFIHPRAFHHLPQMETLMLNNNALSALHQQTVESLPNLQEVGLHGNPIR
CDCVIRWANATGTRVRFIEPQSTLCAEPPDLQRLPVREVPFREMTDHCLPLISPRSFPPSLQ
VASGESMVLHCRALAEPEPEIYWVTPAGLRLTPAHAGRRYRVYPEGTLELRRVTAEEAGLYT
CVAQNLVGADTKTVSVVVGRALLQPGRDEGQGLELRVQETHPYHILLSWVTPPNTVSTNLTW
SSASSLRGQGATALARLPRGTHSYNITRLLQATEYWACLQVAFADAHTQLACVWARTKEATS
CHRALGDRPGLIAILALAVLLLAAGLAAHLGTGQPRKGVGGRRPLPPAWAFWGWSAPSVRVV
SAPLVLPWNPGRKLPRSSEGETLLPPLSQNS

Signal sequence:

amino acids 1-18

Transmembrane domain:

amino acids 629-648

N-glycosylation site.

amino acids 94-98, 381-385, 555-559, 583-587 cAMP- and cGMP-dependent protein kinase phosphorylation site.

amino acids 485-489

Casein kinase II phosphorylation site.

amino acids 46-50, 51-55, 96-100, 104-108, 130-134, 142-146, 243-247, 313-317, 488-492, 700-704

Tyrosine kinase phosphorylation site.

amino acids 532-540

N-myristoylation site.

amino acids 15-21, 493-499, 566-572

Amidation site.

amino acids 470-474, 660-664, 692-696

FIGURE 87

GCAAGCCAAGGCGCTGTTTGAGAAGGTGAAGAAGTTCCGGACCCATGTGGAGGAGGGGACATTGTGTACCGCCT
CTACATGCGGCAGACCATCATCAAGGTGATCAAGTTCATCCTCATCATCTGCTACACCGTCTACTACGTGCACAA
CATCAAGTTCGACGTGGACTGCACCGTGGACATTGAGAGCCTGACGGGCTACCGCACCTACCGCTGTGCCCACCC
CCTGGCCACACTCTTCAAGATCCTGGCGTCCTTCTACATCAGCCTAGTCATCTTCTACGGCCTCATCTGCATGTA
CACACTGTGGTGGATGCTACGGCGCTCCCTCAAGAAGTACTCGTTTGAGTCGATCCGTGAGGAGAGCAGCTACAG
CGACATCCCCGACGTCAAGAACGACTTCGCCTTCATGCTGCACCTCATTGACCAATACGACCCGCTCTACTCCAA
GCGCTTCGCCGTCTTCCTGTCGGAGGTGAGTGAGAACAAGCTGCGGCAGCTGAACCTCAACAACGAGTGGACGCT
GGACAAGCTCCGGCAGCGGCTCACCAAGAACGCGCAGGACAAGCTGGAGCTGCACCTGTTCATGCTCAGTGGCAT
CCCTGACACTGTGTTTGACCTGGTGGAGCTGGAGGTCCTCAAGCTGGAGCTGATCCCCGACGTGACCATCCCGCC
CAGCATTGCCCAGCTCACGGGCCTCAAGGAGCTGTGGCTCTACCACACAGCGGCCAAGATTGAAGCGCCTGCGCT
GGCCTTCCTGCGCGAGAACCTGCGGGCGCTGCACATCAAGTTCACCGACATCAAGGAGATCCCGCTGTGGATCTA
TAGCCTGAAGACACTGGAGGAGCTGCACCTGACGGGCAACCTGAGCGCGGAGAACAACCGCTACATCGTCATCGA
CGGGCTGCGGGAGCTCAAACGCCTCAAGGTGCTGCGGCTCAAGAGCAACCTAAGCAAGCTGCCACAGGTGGTCAC
AGATGTGGGCGTGCACCTGCAGAAGCTGTCCATCAACAATGAGGGCACCAAGCTCATCGTCCTCAACAGCCTCAA
GAAGATGGCGAACCTGACTGAGCTGGAGCTGATCCGCTGCGACCTGGAGCGCATCCCCCACTCCATCTTCAGCCT
CCACAACCTGCAGGAGATTGACCTCAAGGACAACAACCTCAAGACCATCGAGGAGATCATCAGCTTCCAGCACCT
GCACCGCCTCACCTGCCTTAAGCTGTGGTACAACCACATCGCCTACATCCCCATCCAGATCGGCAACCTCACCAA
CCTGGAGCGCCTCTACCTGAACCGCAACAAGATCGAGAAGATCCCCACCCAGCTCTTCTACTGCCGCAAGCTGCG
CTACCTGGACCTCAGCCACAACAACCTGACCTTCCTCCCTGCCGACATCGGCCTCCTGCAGAACCTCCAGAACCT
AGCCATCACGGCCAACCGGATCGAGACGCTCCCTCCGGAGCTCTTCCAGTGCCGGAAGCTGCGGGCCCTGCACCT
GGGCAACAACGTGCTGCAGTCACTGCCCTCCAGGGTGGGCGAGCTGACCAACCTGACGCAGATCGAGCTGCGGGG
CAACCGGCTGGAGTGCCTGCCTGTGGAGCTGGGCGAGTGCCCACTGCTCAAGCGCAGCGGCTTGGTGGTGGAGGA
GGACCTGTTCAACACACTGCCACCCGAGGTGAAGGAGCGGCTGTGGAGGGCTGACAAGGAGCAGGCCTGAGCGAG
GCCGGCCCAGCACAGCAAGCAGCAGGACCGCTGCCCAGTCCTCAGGCCCGGAGGGGCAGGCCTAGCTTCTCCCAG
AACTCCCGGACAGCCAGGACAGCCTCGCGGCTGGGCAGGAGCCTGGGGCCGCTTGTGAGTCAGGCCAGAGCGAGA
GGACAGTATCTGTGGGGCTGGCCCCTTTTCTCCCTCTGAGACTCACGTCCCCCAGGGCAAGTGCTTGTGGAGGAG
AGCAAGTCTCAAGAGCGCAGTATTTGGATAATCAGGGTCTCCTCCCTGGAGGCCAGCTCTGCCCCAGGGGCTGAG
CTGCCACCAGAGGTCCTGGGACCCTCACTTTAGTTCTTGGTATTTATTTTTCTCCATCTCCCACCTCCTTCATCC
AGATAACTTATACATTCCCAAGAAAGTTCAGCCCAGATGGAAGGTGTTCAGGGAAAGGTGGGCTGCCTTTTCCCC
TTGTCCTTATTTAGCGATGCCGCCGGGCATTTAACACCCACCTGGACTTCAGCAGAGTGGTCCGGGGCGAACCAG
CCATGGGACGGTCACCCAGCAGTGCCGGGCTGGGCTCTGCGGTGCGGTCCACGGGAGAGCAGGCCTCCAGCTGGA
AAGGCCAGGCCTGGAGCTTGCCTCTTCAGTTTTTGTGGCAGTTTTAGTTTTTTGTTTTTTTTTTTTTTAATCAAA
AAACAATTTTTTTTAAAAAAAAGCTTTGAAAATGGATGGTTTGGGTATTAAAAAGAAAAAAAAAACTTAAAAAAA
AAAAGACACTAACGGCCAGTGAGTTGGAGTCTCAGGGCAGGGTGGCAGTTTCCCTTGAGCAAAGCAGCCAGACGT
TGAACTGTGTTTCCTTTCCCTGGGCGCAGGGTGCAGGGTGTCTTCCGGATCTGGTGTGACCTTGGTCCAGGAGTT
CTATTTGTTCCTGGGGAGGGAGGTTTTTTTGTTTGTTTTTTGGGTTTTTTTGGTGTCTTGTTTTCTTTCTCCTCC
ATGTGTCTTGGCAGGCACTCATTTCTGTGGCTGTCGGCCAGAGGGAATGTTCTGGAGCTGCCAAGGAGGGAGGAG
ACTCGGGTTGGCTAATCCCCGGATGAACGGTGCTCCATTCGCACCTCCCCTCCTCGTGCCTGCCCTGCCTCTCCA
CGCACAGTGTTAAGGAGCCAAGAGGAGCCACTTCGCCCAGACTTTGTTTCCCCACCTCCTGCGGCATGGGTGTGT
CCAGTGCCACCGCTGGCCTCCGCTGCTTCCATCAGCCCTGTCGCCACCTGGTCCTTCATGAAGAGCAGACACTTA
GAGGCTGGTCGGGAATGGGGAGGTCGCCCCTGGGAGGGCAGGCGTTGGTTCCAAGCCGGTTCCCGTCCCTGGCGC
CTGGAGTGCACACAGCCCAGTCGGCACCTGGTGGCTGGAAGCCAACCTGCTTTAGATCACTCGGGTCCCCACCTT
AGAAGGGTCCCCGCCTTAGATCAATCACGTGGACACTAAGGCACGTTTTAGAGTCTCTTGTCTTAATGATTATGT
CCATCCGTCTGTCCGTCCATTTGTGTTTTCTGCGTCGTGTCATTGGATATAATCCTCAGAAATAATGCACACTAG
CCTCTGACAACCATGAAGCAAAAATCCGTTACATGTGGGTCTGAACTTGTAGACTCGGTCACAGTATCAAATAAA
ATCTATAACAGAAAAAAAAAAAAAAAA

FIGURE 88

MRQTIIKVIKFILIICYTVYYVHNIKFDVDCTVDIESLTGYRTYRCAHPLATLFKILASFYI
SLVIFYGLICMYTLWWMLRRSLKKYSFESIREESSYSDIPDVKNDFAFMLHLIDQYDPLYSK
RFAVFLSEVSENKLRQLNLNNEWTLDKLRQRLTKNAQDKLELHLFMLSGIPDTVFDLVELEV
LKLELIPDVTIPPSIAQLTGLKELWLYHTAAKIEAPALAFLRENLRALHIKFTDIKEIPLWI
YSLKTLEELHLTGNLSAENNRYIVIDGLRELKRLKVLRLKSNLSKLPQVVTDVGVHLQKLSI
NNEGTKLIVLNSLKKMANLTELELIRCDLERIPHSIFSLHNLQEIDLKDNNLKTIEEIISFQ
HLHRLTCLKLWYNHIAYIPIQIGNLTNLERLYLNRNKIEKIPTQLFYCRKLRYLDLSHNNLT
FLPADIGLLQNLQNLAITANRIETLPPELFQCRKLRALHLGNNVLQSLPSRVGELTNLTQIE
LRGNRLECLPVELGECPLLKRSGLVVEEDLFNTLPPEVKERLWRADKEQA

Transmembrane domain:

amino acids 51-75 (type II)

N-glycosylation site.

amino acids 262-266, 290-294, 328-332, 396-400, 432-436, 491-495 cAMP- and cGMP-dependent protein kinase phosphorylation site.

amino acids 85-89

Casein kinase II phosphorylation site.

amino acids 91-95, 97-101, 177-181, 253-257, 330-334, 364-368, 398-402, 493-497

N-myristoylation site.

amino acids 173-179, 261-267, 395-401, 441-447

FIGURE 89

GCCTGTTGCTGATGCTGCCGTGCGGTACTTGTCATGGAGCTGGCACTGCGGCGCTCTCCCGT
CCCGCGGTGGTTGCTGCTGCTGCCGCTGCTGCTGGGCCTGAACGCAGGAGCTGTCATTGACT
GGCCCACAGAGGAGGGCAAGGAAGTATGGGATTATGTGACGGTCCGCAAGGATGCCTACATG
TTCTGGTGGCTCTATTATGCCACCAACTCCTGCAAGAACTTCTCAGAACTGCCCCTGGTCAT
GTGGCTTCAGGGCGGTCCAGGCGGTTCTAGCACTGGATTTGGAAACTTTGAGGAAATTGGGC
CCCTTGACAGTGATCTCAAACCACGGAAAACCACCTGGCTCCAGGCTGCCAGTCTCCTATTT
GTGGATAATCCCGTGGGCACTGGGTTCAGTTATGTGAATGGTAGTGGTGCCTATGCCAAGGA
CCTGGCTATGGTGGCTTCAGACATGATGGTTCTCCTGAAGACCTTCTTCAGTTGCCACAAAG
AATTCCAGACAGTTCCATTCTACATTTTCTCAGAGTCCTATGGAGGAAAAATGGCAGCTGGC
ATTGGTCTAGAGCTTTATAAGGCCATTCAGCGAGGGACCATCAAGTGCAACTTTGCGGGGGT
TGCCTTGGGTGATTCCTGGATCTCCCCTGTTGATTCGGTGCTCTCCTGGGGACCTTACCTGT
ACAGCATGTCTCTTCTCGAAGACAAAGGTCTGGCAGAGGTGTCTAAGGTTGCAGAGCAAGTA
CTGAATGCCGTAAATAAGGGGCTCTACAGAGAGGCCACAGAGCTGTGGGGGAAAGCAGAAAT
GATCATTGAACAGAACACAGATGGGGTGAACTTCTATAACATCTTAACTAAAAGCACTCCCA
CGTCTACAATGGAGTCGAGTCTAGAATTCACACAGAGCCACCTAGTTTGTCTTTGTCAGCGC
CACGTGAGACACCTACAACGAGATGCCTTAAGCCAGCTCATGAATGGCCCCATCAGAAAGAA
GCTCAAAATTATTCCTGAGGATCAATCCTGGGGAGGCCAGGCTACCAACGTCTTTGTGAACA
TGGAGGAGGACTTCATGAAGCCAGTCATTAGCATTGTGGACGAGTTGCTGGAGGCAGGGATC
AACGTGACGGTGTATAATGGACAGCTGGATCTCATCGTAGATACCATGGGTCAGGAGGCCTG
GGTGCGGAAACTGAAGTGGCCAGAACTGCCTAAATTCAGTCAGCTGAAGTGGAAGGCCCTGT
ACAGTGACCCTAAATCTTTGGAAACATCTGCTTTTGTCAAGTCCTACAAGAACCTTGCTTTC
TACTGGATTCTGAAAGCTGGTCATATGGTTCCTTCTGACCAAGGGGACATGGCTCTGAAGAT
GATGAGACTGGTGACTCAGCAAGAATAGGATGGATGGGGCTGGAGATGAGCTGGTTTGGCCT
TGGGGCACAGAGCTGAGCTGAGGCCGCTGAAGCTGTAGGAAGCGCCATTCTTCCCTGTATCT
AACTGGGGCTGTGATCAAGAAGGTTCTGACCAGCTTCTGCAGAGGATAAAATCATTGTCTCT
GGAGGCAATTTGGAAATTATTTCTGCTTCTTAAAAAAACCTAAGATTTTTTAAAAAATTGAT
TTGTTTTGATCAAAATAAAGGATGATAATAGATATTAA

FIGURE 90

MELALRRSPVPRWLLLLPLLLGLNAGAVIDWPTEEGKEVWDYVTVRKDAYMFWWLYYATNSC
KNFSELPLVMWLQGGPGGSSTGFGNFEEIGPLDSDLKPRKTTWLQAASLLFVDNPVGTGFSY
VNGSGAYAKDLAMVASDMMVLLKTFFSCHKEFQTVPFYIFSESYGGKMAAGIGLELYKAIQR
GTIKCNFAGVALGDSWISPVDSVLSWGPYLYSMSLLEDKGLAEVSKVAEQVLNAVNKGLYRE
ATELWGKAEMIIEQNTDGVNFYNILTKSTPTSTMESSLEFTQSHLVCLCQRHVRHLQRDALS
QLMNGPIRKKLKIIPEDQSWGGQATNVFVNMEEDFMKPVISIVDELLEAGINVTVYNGQLDL
IVDTMGQEAWVRKLKWPELPKFSQLKWKALYSDPKSLETSAFVKSYKNLAFYWILKAGHMVP
SDQGDMALKMMRLVTQQE

Signal sequence:

amino acids 1-25

N-glycosylation site.

amino acids 64-68, 126-130, 362-366 cAMP- and cGMP-dependent protein kinase phosphorylation site.

amino acids 101-105

Casein kinase II phosphorylation site.

amino acids 204-208, 220-224, 280-284, 284-288, 351-355, 449-453

N-myristoylation site.

amino acids 22-28, 76-82, 79-85, 80-86, 119-125, 169-175, 187-193, 195-201, 331-337, 332-338, 360-366

FIGURE 91

GGCCGCGGGAGAGGAGGCCATGGGCGCGCGGGGCGCTGCTGCTGGCGCTGCTGCTGGCTC
GGGCTGGACTCAGGAAGCCGGAGTCGCAGGAGGCGGCGCCGTTATCAGGACCATGCGGCCGA
CGGGTCATCACGTCGCGCATCGTGGGTGGAGAGGACGCCGAACTCGGGCGTTGGCCGTGGCA
GGGGAGCCTGCGCCTGTGGGATTCCCACGTATGCGGAGTGAGCCTGCTCAGCCACCGCTGGG
CACTCACGGCGGCGCACTGCTTTGAAACCTATAGTGACCTTAGTGATCCCTCCGGGTGGATG
GTCCAGTTTGGCCAGCTGACTTCCATGCCATCCTTCTGGAGCCTGCAGGCCTACTACACCCG
TTACTTCGTATCGAATATCTATCTGAGCCCTCGCTACCTGGGGAATTCACCCTATGACATTG
CCTTGGTGAAGCTGTCTGCACCTGTCACCTACACTAAACACATCCAGCCCATCTGTCTCCAG
GCCTCCACATTTGAGTTTGAGAACCGGACAGACTGCTGGGTGACTGGCTGGGGGTACATCAA
AGAGGATGAGGCACTGCCATCTCCCCACACCCTCCAGGAAGTTCAGGTCGCCATCATAAACA
ACTCTATGTGCAACCACCTCTTCCTCAAGTACAGTTTCCGCAAGGACATCTTTGGAGACATG
GTTTGTGCTGGCAACGCCCAAGGCGGGAAGGATGCCTGCTTCGGTGACTCAGGTGGACCCTT
GGCCTGTAACAAGAATGGACTGTGGTATCAGATTGGAGTCGTGAGCTGGGGAGTGGGCTGTG
GTCGGCCCAATCGGCCCGGTGTCTACACCAATATCAGCCACCACTTTGAGTGGATCCAGAAG
CTGATGGCCCAGAGTGGCATGTCCCAGCCAGACCCCTCCTGGCCACTACTCTTTTTCCCTCT
TCTCTGGGCTCTCCCACTCCTGGGGCCGGTCTGAGCCTACCTGAGCCCATGCAGCCTGGGGC
CACTGCCAAGTCAGGCCCTGGTTCTCTTCTGTCTTGTTTGGTAATAAACACATTCCAGTTGA
TGCCTTGCAGGGCATTCTTCAAAAAAAAAAAAAAAAAAAAAAAA

FIGURE 92

MGARGALLLALLLARAGLRKPESQEAAPLSGPCGRRVITSRIVGGEDAELGRWPWQGSLRLW
DSHVCGVSLLSHRWALTAAHCFETYSDLSDPSGWMVQFGQLTSMPSFWSLQAYYTRYFVSNI
YLSPRYLGNSPYDIALVKLSAPVTYTKHIQPICLQASTFEFENRTDCWVTGWGYIKEDEALP
SPHTLQEVQVAIINNSMCNHLFLKYSFRKDIFGDMVCAGNAQGGKDACFGDSGGPLACNKNG
LWYQIGVVSWGVGCGRPNRPGVYTNISHHFEWIQKLMAQSGMSQPDPSWPLLFFPLLWALPL
LGPV

Signal sequence:
amino acids 1-18

N-glycosylation site.
amino acids 167-171, 200-204, 273-277

Casein kinase II phosphorylation site.
amino acids 86-90, 134-138, 161-165, 190-194, 291-295

N-myristoylation site.
amino acids 2-8, 44-50, 101-107, 225-231, 229-235, 239-245, 259-265, 269-275

Amidation site.
amino acids 33-37

Prokaryotic membrane lipoprotein lipid attachment site.
amino acids 252-263,

Serine proteases, trypsin family, histidine active site.
amino acids 78-84

FIGURE 93

CCCACGCGTCCGCGGACGCGTGGGAAGGGCAGAATGGGACTCCAAGCCTGCCTCCTAGGGCT
CTTTGCCCTCATCCTCTCTGGCAAATGCAGTTACAGCCCGGAGCCCGACCAGCGGAGGACGC
TGCCCCCAGGCTGGGTGTCCCTGGGCCGTGCGGACCCTGAGGAAGAGCTGAGTCTCACCTTT
GCCCTGAGACAGCAGAATGTGGAAAGACTCTCGGAGCTGGTGCAGGCTGTGTCGGATCCCAG
CTCTCCTCAATACGGAAAATACCTGACCCTAGAGAATGTGGCTGATCTGGTGAGGCCATCCC
CACTGACCCTCCACACGGTGCAAAAATGGCTCTTGGCAGCCGGAGCCCAGAAGTGCCATTCT
GTGATCACACAGGACTTTCTGACTTGCTGGCTGAGCATCCGACAAGCAGAGCTGCTGCTCCC
TGGGGCTGAGTTTCATCACTATGTGGGAGGACCTACGGAAACCCATGTTGTAAGGTCCCCAC
ATCCCTACCAGCTTCCACAGGCCTTGGCCCCCCATGTGGACTTTGTGGGGGGACTGCACCGT
TTTCCCCCAACATCATCCCTGAGGCAACGTCCTGAGCCGCAGGTGACAGGGACTGTAGGCCT
GCATCTGGGGGTAACCCCCTCTGTGATCCGTAAGCGATACAACTTGACCTCACAAGACGTGG
GCTCTGGCACCAGCAATAACAGCCAAGCCTGTGCCCAGTTCCTGGAGCAGTATTTCCATGAC
TCAGACCTGGCTCAGTTCATGCGCCTCTTCGGTGGCAACTTTGCACATCAGGCATCAGTAGC
CCGTGTGGTTGGACAACAGGGCCGGGGCCGGGCCGGGATTGAGGCCAGTCTAGATGTGCAGT
ACCTGATGAGTGCTGGTGCCAACATCTCCACCTGGGTCTACAGTAGCCCTGGCCGGCATGAG
GGACAGGAGCCCTTCCTGCAGTGGCTCATGCTGCTCAGTAATGAGTCAGCCCTGCCACATGT
GCATACTGTGAGCTATGGAGATGATGAGGACTCCCTCAGCAGCGCCTACATCCAGCGGGTCA
ACACTGAGCTCATGAAGGCTGCCGCTCGGGGTCTCACCCTGCTCTTCGCCTCAGGTGACAGT
GGGGCCGGGTGTTGGTCTGTCTCTGGAAGACACCAGTTCCGCCCTACCTTCCCTGCCTCCAG
CCCCTATGTCACCACAGTGGGAGGCACATCCTTCCAGGAACCTTTCCTCATCACAAATGAAA
TTGTTGACTATATCAGTGGTGGTGGCTTCAGCAATGTGTTCCCACGGCCTTCATACCAGGAG
GAAGCTGTAACGAAGTTCCTGAGCTCTAGCCCCCACCTGCCACCATCCAGTTACTTCAATGC
CAGTGGCCGTGCCTACCCAGATGTGGCTGCACTTTCTGATGGCTACTGGGTGGTCAGCAACA
GAGTGCCCATTCCATGGGTGTCCGGAACCTCGGCCTCTACTCCAGTGTTTGGGGGGATCCTA
TCCTTGATCAATGAGCACAGGATCCTTAGTGGCCGCCCCCCTCTTGGCTTTCTCAACCCAAG
GCTCTACCAGCAGCATGGGGCAGGTCTCTTTGATGTAACCCGTGGCTGCCATGAGTCCTGTC
TGGATGAAGAGGTAGAGGGCCAGGGTTTCTGCTCTGGTCCTGGCTGGGATCCTGTAACAGGC
TGGGGAACACCAACTTCCCAGCTTTGCTGAAGACTCTACTCAACCCCTGACCCTTTCCTATC
AGGAGAGATGGCTTGTCCCCTGCCCTGAAGCTGGCAGTTCAGTCCCTTATTCTGCCCTGTTG
GAAGCCCTGCTGAACCCTCAACTATTGACTGCTGCAGACAGCTTATCTCCCTAACCCTGAAA
TGCTGTGAGCTTGACTTGACTCCCAACCCTACCATGCTCCATCATACTCAGGTCTCCCTACT
CCTGCCTTAGATTCCTCAATAAGATGCTGTAACTAGCATTTTTTGAATGCCTCTCCCTCCGC
ATCTCATCTTTCTCTTTTCAATCAGGCTTTTCCAAAGGGTTGTATACAGACTCTGTGCACTA
TTTCACTTGATATTCATTCCCCAATTCACTGCAAGGAGACCTCTACTGTCACCGTTTACTCT
TTCCTACCCTGACATCCAGAAACAATGGCCTCCAGTGCATACTTCTCAATCTTTGCTTTATG
GCCTTTCCATCATAGTTGCCCACTCCCTCTCCTTACTTAGCTTCCAGGTCTTAACTTCTCTG
ACTACTCTTGTCTTCCTCTCTCATCAATTTCTGCTTCTTCATGGAATGCTGACCTTCATTGC
TCCATTTGTAGATTTTTGCTCTTCTCAGTTTACTCATTGTCCCCTGGAACAAATCACTGACA
TCTACAACCATTACCATCTCACTAAATAAGACTTTCTATCCAATAATGATTGATACCTCAAA
TGTAAAAAA

FIGURE 94

MGLQACLLGLFALILSGKCSYSPEPDQRRTLPPGWVSLGRADPEEELSLTFALRQQNVERLS
ELVQAVSDPSSPQYGKYLTLENVADLVRPSPLTLHTVQKWLLAAGAQKCHSVITQDFLTCWL
SIRQAELLLPGAEFHHYVGGPTETHVVRSPHPYQLPQALAPHVDFVGGLHRFPPTSSLRQRP
EPQVTGTVGLHLGVTPSVIRKRYNLTSQDVGSGTSNNSQACAQFLEQYFHDSDLAQFMRLFG
GNFAHQASVARVVGQQGRGRAGIEASLDVQYLMSAGANISTWVYSSPGRHEGQEPFLQWLML
LSNESALPHVHTVSYGDDEDSLSSAYIQRVNTELMKAAARGLTLLFASGDSGAGCWSVSGRH
QFRPTFPASSPYVTTVGGTSFQEPFLITNEIVDYISGGGFSNVFPRPSYQEEAVTKFLSSSP
HLPPSSYFNASGRAYPDVAALSDGYWVVSNRVPIPWVSGTSASTPVFGGILSLINEHRILSG
RPPLGFLNPRLYQQHGAGLFDVTRGCHESCLDEEVEGQGFCSGPGWDPVTGWGTPTSQLC

Signal sequence:
amino acids 1-16

N-glycosylation site.
amino acids 210-214, 222-226, 286-290, 313-317, 443-447

Glycosaminoglycan attachment site.
amino acids 361-365, 408-412, 538-542

Casein kinase II phosphorylation site.
amino acids 212-216, 324-328, 392-396, 420-424, 525-529

N-myristoylation site.
amino acids 2-8, 107-113, 195-201, 199-205, 217-223, 219-225, 248-254, 270-276, 284-290, 409-415, 410-416, 473-479, 482-488, 521-527, 533-539, 549-555

FIGURE 95

GCCGCGCGCTCTCTCCCGGCGCCCACACCTGTCTGAGCGGCGCAGCGAGCCGCGGCCCGGGC
GGGCTGCTCGGCGCGGAACAGTGCTCGGCATGGCAGGGATTCCAGGGCTCCTCTTCCTTCTC
TTCTTTCTGCTCTGTGCTGTTGGGCAAGTGAGCCCTTACAGTGCCCCCTGGAAACCCACTTG
GCCTGCATACCGCCTCCCTGTCGTCTTGCCCCAGTCTACCCTCAATTTAGCCAAGCCAGACT
TTGGAGCCGAAGCCAAATTAGAAGTATCTTCTTCATGTGGACCCCAGTGTCATAAGGGAACT
CCACTGCCCACTTACGAAGAGGCCAAGCAATATCTGTCTTATGAAACGCTCTATGCCAATGG
CAGCCGCACAGAGACGCAGGTGGGCATCTACATCCTCAGCAGTAGTGGAGATGGGGCCCAAC
ACCGAGACTCAGGGTCTTCAGGAAAGTCTCGAAGGAAGCGGCAGATTTATGGCTATGACAGC
AGGTTCAGCATTTTTGGGAAGGACTTCCTGCTCAACTACCCTTTCTCAACATCAGTGAAGTT
ATCCACGGGCTGCACCGGCACCCTGGTGGCAGAGAAGCATGTCCTCACAGCTGCCCACTGCA
TACACGATGGAAAAACCTATGTGAAAGGAACCCAGAAGCTTCGAGTGGGCTTCCTAAAGCCC
AAGTTTAAAGATGGTGGTCGAGGGGCCAACGACTCCACTTCAGCCATGCCCGAGCAGATGAA
ATTTCAGTGGATCCGGGTGAAACGCACCCATGTGCCCAAGGGTTGGATCAAGGGCAATGCCA
ATGACATCGGCATGGATTATGATTATGCCCTCCTGGAACTCAAAAAGCCCCACAAGAGAAAA
TTTATGAAGATTGGGGTGAGCCCTCCTGCTAAGCAGCTGCCAGGGGGCAGAATTCACTTCTC
TGGTTATGACAATGACCGACCAGGCAATTTGGTGTATCGCTTCTGTGACGTCAAAGACGAGA
CCTATGACTTGCTCTACCAGCAATGCGATGCCCAGCCAGGGGCCAGCGGGTCTGGGGTCTAT
GTGAGGATGTGGAAGAGACAGCAGCAGAAGTGGGAGCGAAAAATTATTGGCATTTTTTCAGG
GCACCAGTGGGTGGACATGAATGGTTCCCCACAGGATTTCAACGTGGCTGTCAGAATCACTC
CTCTCAAATATGCCCAGATTTGCTATTGGATTAAAGGAAACTACCTGGATTGTAGGGAGGGG
TGACACAGTGTTCCCTCCTGGCAGCAATTAAGGGTCTTCATGTTCTTATTTTAGGAGAGGCC
AAATTGTTTTTTGTCATTGGCGTGCACACGTGTGTGTGTGTGTGTGTGTGTGTGTAAGGTGT
CTTATAATCTTTTACCTATTTCTTACAATTGCAAGATGACTGGCTTTACTATTTGAAAACTG
GTTTGTGTATCATATCATATATCATTTAAGCAGTTTGAAGGCATACTTTTGCATAGAAATAA
AAAAAATACTGATTTGGGGCAATGAGGAATATTTGACAATTAAGTTAATCTTCACGTTTTTG
CAAACTTTGATTTTTATTTCATCTGAACTTGTTTCAAAGATTTATATTAAATATTTGGCATA
CAAGAGATATGAAAAAAAAAAAAAAA

FIGURE 96

MAGIPGLLFLLFFLLCAVGQVSPYSAPWKPTWPAYRLPVVLPQSTLNLAKPDFGAEAKLEVS
SSCGPQCHKGTPLPTYEEAKQYLSYETLYANGSRTETQVGIYILSSSGDGAQHRDSGSSGKS
RRKRQIYGYDSRFSIFGKDFLLNYPFSTSVKLSTGCTGTLVAEKHVLTAAHCIHDGKTYVKG
TQKLRVGFLKPKFKDGGRGANDSTSAMPEQMKFQWIRVKRTHVPKGWIKGNANDIGMDYDYA
LLELKKPHKRKFMKIGVSPPAKQLPGGRIHFSGYDNDRPGNLVYRFCDVKDETYDLLYQQCD
AQPGASGSGVYVRMWKRQQQKWERKIIGIFSGHQWVDMNGSPQDFNVAVRITPLKYAQICYW
IKGNYLDCREG

Signal sequence:
amino acids 1-19

N-glycosylation site.
amino acids 93-97, 207-211

Glycosaminoglycan attachment site.
amino acids 109-113, 316-320

Casein kinase II phosphorylation site.
amino acids 77-81, 95-99, 108-112, 280-284, 351-355

N-myristoylation site.
amino acids 159-165, 162-168, 202-208, 205-211, 314-320, 338-344

Serine proteases, trypsin family, histidine active site.
amino acids 171-177

FIGURE 97

GCATCGCCCTGGGTCTCTCGAGCCTGCTGCCTGCTCCCCCGCCCCACCAGCCATGGTGGTTT
CTGGAGCGCCCCCAGCCCTGGGTGGGGCTGTCTCGGCACCTTCACCTCCCTGCTGCTGCTG
GCGTCGACAGCCATCCTCAATGCGGCCAGGATACCTGTTCCCCCAGCCTGTGGGAAGCCCCA
GCAGCTGAACCGGGTTGTGGGCGGCGAGGACAGCACTGACAGCGAGTGGCCCTGGATCGTGA
GCATCCAGAAGAATGGGACCCACCACTGCGCAGGTTCTCTGCTCACCAGCCGCTGGGTGATC
ACTGCTGCCCACTGTTTCAAGGACAACCTGAACAAACCATACCTGTTCTCTGTGCTGCTGGG
GGCCTGGCAGCTGGGGAACCCTGGCTCTCGGTCCCAGAAGGTGGGTGTTGCCTGGGTGGAGC
CCCACCCTGTGTATTCCTGGAAGGAAGGTGCCTGTGCAGACATTGCCCTGGTGCGTCTCGAG
CGCTCCATACAGTTCTCAGAGCGGGTCCTGCCCATCTGCCTACCTGATGCCTCTATCCACCT
CCCTCCAAACACCCACTGCTGGATCTCAGGCTGGGGGAGCATCCAAGATGGAGTTCCCTTGC
CCCACCCTCAGACCCTGCAGAAGCTGAAGGTTCCTATCATCGACTCGGAAGTCTGCAGCCAT
CTGTACTGGCGGGGAGCAGGACAGGGACCCATCACTGAGGACATGCTGTGTGCCGGCTACTT
GGAGGGGGAGCGGGATGCTTGTCTGGGCGACTCCGGGGGCCCCCTCATGTGCCAGGTGGACG
GCGCCTGGCTGCTGGCCGGCATCATCAGCTGGGGCGAGGGCTGTGCCGAGCGCAACAGGCCC
GGGGTCTACATCAGCCTCTCTGCGCACCGCTCCTGGGTGGAGAAGATCGTGCAAGGGGTGCA
GCTCCGCGGGCGCGCTCAGGGGGGTGGGGCCCTCAGGGCACCGAGCCAGGGCTCTGGGGCCG
CCGCGCGCTCCTAGGGCGCAGCGGGACGCGGGGCTCGGATCTGAAAGGCGGCCAGATCCACA
TCTGGATCTGGATCTGCGGCGGCCTCGGGCGGTTTCCCCCGCCGTAAATAGGCTCATCTACC
TCTACCTCTGGGGGCCCGGACGGCTGCTGCGGAAAGGAAACCCCCTCCCCGACCCGCCCGAC
GGCCTCAGGCCCCCCTCCAAGGCATCAGGCCCCGCCCAACGGCCTCATGTCCCCGCCCCCAC
GACTTCCGGCCCCGCCCCCGGGCCCCAGCGCTTTTGTGTATATAAATGTTAATGATTTTTAT
AGGTATTTGTAACCCTGCCCACATATCTTATTTATTCCTCCAATTTCAATAAATTATTTATT
CTCCAAAAAAAAAA

FIGURE 98

></usr/seqdb2/sst/DNA/Dnaseqs.full/ss.DNA43318

><subunit 1 of 1, 317 aa, 1 stop

><MW: 33732, pI: 7.90, NX(S/T): 1

MVVSGAPPALGGGCLGTFTSLLLLASTAILNAARIPVPPACGKPQQLNRVVGGEDSTDSEWP
WIVSIQKNGTHHCAGSLLTSRWVITAAHCFKDNLNKPYLFSVLLGAWQLGNPGSRSQKVGVA
WVEPHPVYSWKEGACADIALVRLERSIQFSERVLPICLPDASIHLPPNTHCWISGWGSIQDG
VPLPHPQTLQKLKVPIIDSEVCSHLYWRGAGQGPITEDMLCAGYLEGERDACLGDSGGPLMC
QVDGAWLLAGIISWGEGCAERNRPGVYISLSAHRSWVEKIVQGVQLRGRAQGGGALRAPSQG
SGAAARS

Signal sequence:

amino acids 1-32

N-glycosylation site.

amino acids 62-66, 96-100, 214-218, 382-386, 409-413, 455-459, 628-632, 669-673, 845-849, 927-931, 939-943, 956-960

Glycosaminoglycan attachment site.

amino acids 826-830

Casein kinase II phosphorylation site.

amino acids 17-21, 39-43, 120-124, 203-207, 254-258, 264-268, 314-318, 323-327, 347-351, 464-468, 548-552, 632-636, 649-653, 671-675, 739-743, 783-787, 803-807, 847-851, 943-947, 958-962, 1013-1017, 1019-1023, 1021-1025

Tyrosine kinase phosphorylation site.

amino acids 607-615

N-myristoylation site.

amino acids 179-185, 197-203, 320-326, 367-373, 453-459, 528-534, 612-618, 623-629, 714-720, 873-879

FIGURE 99

GACGGCTGGCCACCATGCACGGCTCCTGCAGTTTCCTGATGCTTCTGCTGCCGCTACTGCTA
CTGCTGGTGGCCACCACAGGCCCCGTTGGAGCCCTCACAGATGAGGAGAAACGTTTGATGGT
GGAGCTGCACAACCTCTACCGGGCCCAGGTATCCCCGACGGCCTCAGACATGCTGCACATGA
GATGGGACGAGGAGCTGGCCGCCTTCGCCAAGGCCTACGCACGGCAGTGCGTGTGGGGCCAC
AACAAGGAGCGCGGGCGCCGCGGCGAGAATCTGTTCGCCATCACAGACGAGGGCATGGACGT
GCCGCTGGCCATGGAGGAGTGGCACCACGAGCGTGAGCACTACAACCTCAGCGCCGCCACCT
GCAGCCCAGGCCAGATGTGCGGCCACTACACGCAGGTGGTATGGGCCAAGACAGAGAGGATC
GGCTGTGGTTCCCACTTCTGTGAGAAGCTCCAGGGTGTTGAGGAGACCAACATCGAATTACT
GGTGTGCAACTATGAGCCTCCGGGGAACGTGAAGGGGAAACGGCCCTACCAGGAGGGGACTC
CGTGCTCCCAATGTCCCTCTGGCTACCACTGCAAGAACTCCCTCTGTGAACCCATCGGAAGC
CCGGAAGATGCTCAGGATTTGCCTTACCTGGTAACTGAGGCCCCATCCTTCCGGGCGACTGA
AGCATCAGACTCTAGGAAAATGGGTACTCCTTCTTCCCTAGCAACGGGGATTCCGGCTTTCT
TGGTAACAGAGGTCTCAGGCTCCCTGGCAACCAAGGCTCTGCCTGCTGTGGAAACCCAGGCC
CCAACTTCCTTAGCAACGAAAGACCCGCCCTCCATGGCAACAGAGGCTCCACCTTGCGTAAC
AACTGAGGTCCCTTCCATTTTGGCAGCTCACAGCCTGCCCTCCTTGGATGAGGAGCCAGTTA
CCTTCCCCAAATCGACCCATGTTCCTATCCCAAAATCAGCAGACAAAGTGACAGACAAAACA
AAAGTGCCCTCTAGGAGCCCAGAGAACTCTCTGGACCCCAAGATGTCCCTGACAGGGGCAAG
GGAACTCCTACCCCATGCCCAGGAGGAGGCTGAGGCTGAGGCTGAGTTGCCTCCTTCCAGTG
AGGTCTTGGCCTCAGTTTTTCCAGCCCAGGACAAGCCAGGTGAGCTGCAGGCCACACTGGAC
CACACGGGGCACACCTCCTCCAAGTCCCTGCCCAATTTCCCCAATACCTCTGCCACCGCTAA
TGCCACGGGTGGGCGTGCCCTGGCTCTGCAGTCGTCCTTGCCAGGTGCAGAGGGCCCTGACA
AGCCTAGCGTTGTGTCAGGGCTGAACTCGGGCCCTGGTCATGTGTGGGGCCCTCTCCTGGGA
CTACTGCTCCTGCCTCCTCTGGTGTTGGCTGGAATCTTCTGAATGGGATACCACTCAAAGGG
TGAAGAGGTCAGCTGTCCTCCTGTCATCTTCCCCACCCTGTCCCCAGCCCCTAAACAAGATA
CTTCTTGGTTAAGGCCCTCCGGAAGGGAAAGGCTACGGGGCATGTGCCTCATCACACCATCC
ATCCTGGAGGCACAAGGCCTGGCTGGCTGCGAGCTCAGGAGGCCGCCTGAGGACTGCACACC
GGGCCCACACCTCTCCTGCCCCTCCCTCCTGAGTCCTGGGGGTGGGAGGATTTGAGGGAGCT
CACTGCCTACCTGGCCTGGGGCTGTCTGCCCACACAGCATGTGCGCTCTCCCTGAGTGCCTG
TGTAGCTGGGGATGGGGATTCCTAGGGGCAGATGAAGGACAAGCCCCACTGGAGTGGGGTTC
TTTGAGTGGGGGAGGCAGGGACGAGGGAAGGAAAGTAACTCCTGACTCTCCAATAAAAACCT
GTCCAACCTGTGAAA

FIGURE 100

MHGSCSFLMLLLPLLLLLVATTGPVGALTDEEKRLMVELHNLYRAQVSPTASDMLHMRWDEE
LAAFAKAYARQCVWGHNKERGRRGENLFAITDEGMDVPLAMEEWHHEREHYNLSAATCSPGQ
MCGHYTQVVWAKTERIGCGSHFCEKLQGVEETNIELLVCNYEPPGNVKGKRPYQEGTPCSQC
PSGYHCKNSLCEPIGSPEDAQDLPYLVTEAPSFRATEASDSRKMGTPSSLATGIPAFLVTEV
SGSLATKALPAVETQAPTSLATKDPPSMATEAPPCVTTEVPSILAAHSLPSLDEEPVTFPKS
THVPIPKSADKVTDKTKVPSRSPENSLDPKMSLTGARELLPHAQEEAEAEAELPPSSEVLAS
VFPAQDKPGELQATLDHTGHTSSKSLPNFPNTSATANATGGRALALQSSLPGAEGPDKPSVV
SGLNSGPGHVWGPLLGLLLLPPLVLAGIF

Signal sequence:

amino acids 1-22

N-glycosylation site.

amino acids 114-118, 403-407, 409-413

Glycosaminoglycan attachment site.

amino acids 439-443

Casein kinase II phosphorylation site.

amino acids 29-33, 50-54, 156-160, 195-199, 202-206, 299-303

N-myristoylation site.

amino acids 123-129, 143-149, 152-158, 169-175, 180-186, 231-237, 250-256

Amidation site.

amino acids 82-86, 172-176

Peroxidases proximal heme-ligand signature.

amino acids 287-298

Extracellular proteins SCP/Tpx-1/Ag5/PR-1/Sc7 signature 1.

amino acids 127-138

Extracellular proteins SCP/Tpx-1/Ag5/PR-1/Sc7 signature 2.

amino acids 160-172

FIGURE 101

GTAACTGAAGTCAGGCTTTTCATTTGGGAAGCCCCCTCAACAGAATTCGGTCATTCTCCAAGTTATGGTGGACGT
ACTTCTGTTGTTCTCCCTCTGCTTGCTTTTTCACATTAGCAGACCGGACTTAAGTCACAACAGATTATCTTTCAT
CAAGGCAAGTTCCATGAGCCACCTTCAAAGCCTTCGAGAAGTGAAACTGAACAACAATGAATTGGAGACCATTCC
AAATCTGGGACCAGTCTCGGCAAATATTACACTTCTCTCCTTGGCTGGAAACAGGATTGTTGAAATACTCCCTGA
ACATCTGAAAGAGTTTCAGTCCCTTGAAACTTTGGACCTTAGCAGCAACAATATTTCAGAGCTCCAAACTGCATT
TCCAGCCCTACAGCTCAAATATCTGTATCTCAACAGCAACCGAGTCACATCAATGGAACCTGGGTATTTTGACAA
TTTGGCCAACACACTCCTTGTGTTAAAGCTGAACAGGAACCGAATCTCAGCTATCCCACCCAAGATGTTTAAACT
GCCCCAACTGCAACATCTCGAATTGAACCGAAACAAGATTAAAAATGTAGATGGACTGACATTCCAAGGCCTTGG
TGCTCTGAAGTCTCTGAAAATGCAAAGAAATGGAGTAACGAAACTTATGGATGGAGCTTTTTGGGGGCTGAGCAA
CATGGAAATTTTGCAGCTGGACCATAACAACCTAACAGAGATTACCAAAGGCTGGCTTTACGGCTTGCTGATGCT
GCAGGAACTTCATCTCAGCCAAAATGCCATCAACAGGATCAGCCCTGATGCCTGGGAGTTCTGCCAGAAGCTCAG
TGAGCTGGACCTAACTTTCAATCACTTATCAAGGTTAGATGATTCAAGCTTCCTTGGCCTAAGCTTACTAAATAC
ACTGCACATTGGGAACAACAGAGTCAGCTACATTGCTGATTGTGCCTTCCGGGGGCTTTCCAGTTTAAAGACTTT
GGATCTGAAGAACAATGAAATTTCCTGGACTATTGAAGACATGAATGGTGCTTTCTCTGGGCTTGACAAACTGAG
GCGACTGATACTCCAAGGAAATCGGATCCGTTCTATTACTAAAAAAGCCTTCACTGGTTTGGATGCATTGGAGCA
TCTAGACCTGAGTGACAACGCAATCATGTCTTTACAAGGCAATGCATTTTCACAAATGAAGAAACTGCAACAATT
GCATTTAAATACATCAAGCCTTTTGTGCGATTGCCAGCTAAAATGGCTCCCACAGTGGGTGGCGGAAAACAACTT
TCAGAGCTTTGTAAATGCCAGTTGTGCCCATCCTCAGCTGCTAAAAGGAAGAAGCATTTTTGCTGTTAGCCCAGA
TGGCTTTGTGTGTGATGATTTTCCCAAACCCCAGATCACGGTTCAGCCAGAAACACAGTCGGCAATAAAAGGTTC
CAATTTGAGTTTCATCTGCTCAGCTGCCAGCAGCAGTGATTCCCCAATGACTTTTGCTTGGAAAAAAGACAATGA
ACTACTGCATGATGCTGAAATGGAAAATTATGCACACCTCCGGGCCCAAGGTGGCGAGGTGATGGAGTATACCAC
CATCCTTCGGCTGCGCGAGGTGGAATTTGCCAGTGAGGGGAAATATCAGTGTGTCATCTCCAATCACTTTGGTTC
ATCCTACTCTGTCAAAGCCAAGCTTACAGTAAATATGCTTCCCTCATTCACCAAGACCCCCATGGATCTCACCAT
CCGAGCTGGGGCCATGGCACGCTTGGAGTGTGCTGCTGTGGGGCACCCAGCCCCCCAGATAGCCTGGCAGAAGGA
TGGGGGCACAGACTTCCCAGCTGCACGGGAGAGACGCATGCATGTGATGCCCGAGGATGACGTGTTCTTTATCGT
GGATGTGAAGATAGAGGACATTGGGGTATACAGCTGCACAGCTCAGAACAGTGCAGGAAGTATTTCAGCAAATGC
AACTCTGACTGTCCTAGAAACACCATCATTTTTGCGGCCACTGTTGGACCGAACTGTAACCAAGGGAGAAACAGC
CGTCCTACAGTGCATTGCTGGAGGAAGCCCTCCCCCTAAACTGAACTGGACCAAAGATGATAGCCCATTGGTGGT
AACCGAGAGGCACTTTTTTGCAGCAGGCAATCAGCTTCTGATTATTGTGGACTCAGATGTCAGTGATGCTGGGAA
ATACACATGTGAGATGTCTAACACCCTTGGCACTGAGAGAGGAAACGTGCGCCTCAGTGTGATCCCCACTCCAAC
CTGCGACTCCCCTCAGATGACAGCCCCATCGTTAGACGATGACGGATGGGCCACTGTGGGTGTCGTGATCATAGC
CGTGGTTTGCTGTGTGGTGGGCACGTCACTCGTGTGGGTGGTCATCATATACCACACAAGGCGGAGGAATGAAGA
TTGCAGCATTACCAACACAGATGAGACCAACTTGCCAGCAGATATTCCTAGTTATTTGTCATCTCAGGGAACGTT
AGCTGACAGGCAGGATGGGTACGTGTCTTCAGAAAGTGGAAGCCACCACCAGTTTGTCACATCTTCAGGTGCTGG
ATTTTTCTTACCACAACATGACAGTAGTGGGACCTGCCATATTGACAATAGCAGTGAAGCTGATGTGGAAGCTGC
CACAGATCTGTTCCTTTGTCCGTTTTTGGATCCACAGGCCCTATGTATTTGAAGGGAAATGTGTATGGCTCAGA
TCCTTTTGAAACATATCATACAGGTTGCAGTCCTGACCCAAGAACAGTTTTAATGGACCACTATGAGCCCAGTTA
CATAAAGAAAAAGGAGTGCTACCCATGTTCTCATCCTTCAGAAGAATCCTGCGAACGGAGCTTCAGTAATATATC
GTGGCCTTCACATGTGAGGAAGCTACTTAACACTAGTTACTCTCACAATGAAGGACCTGGAATGAAAAATCTGTG
TCTAAACAAGTCCTCTTTAGATTTTAGTGCAAATCCAGAGCCAGCGTCGGTTGCCTCGAGTAATTCTTTCATGGG
TACCTTTGGAAAAGCTCTCAGGAGACCTCACCTAGATGCCTATTCAAGCTTTGGACAGCCATCAGATTGTCAGCC
AAGAGCCTTTTATTTGAAAGCTCATTCTTCCCCAGACTTGGACTCTGGGTCAGAGGAAGATGGGAAAGAAAGGAC
AGATTTTCAGGAAGAAAATCACATTTGTACCTTTAAACAGACTTTAGAAAACTACAGGACTCCAAATTTTCAGTC
TTATGACTTGGACACATAGACTGAATGAGACCAAAGGAAAAGCTTAACATACTACCTCAAGTGAACTTTTATTTA
AAAGAGAGAGAATCTTATGTTTTTTAAATGGAGTTATGAATTTTAAAAGGATAAAAATGCTTTATTTATACAGAT
GAACCAAAATTACAAAAAGTTATGAAAATTTTTATACTGGGAATGATGCTCATATAAGAATACCTTTTTAAACTA
TTTTTTAACTTTGTTTTATGCAAAAAAGTATCTTACGTAAATTAATGATATAAATCATGATTATTTTATGTATTT
TTATAATGCCAGATTTCTTTTTATGGAAAATGAGTTACTAAAGCATTTTAAATAATACCTGCCTTGTACCATTTT
TTAAATAGAAGTTACTTCATTATATTTTGCACATTATATTTAATAAAATGTGTCAATTTGAA

FIGURE 102

MVDVLLLFSLCLLFHISRPDLSHNRLSFIKASSMSHLQSLREVKLNNNELETIPNLGPVSAN
ITLLSLAGNRIVEILPEHLKEFQSLETLDLSSNNISELQTAFPALQLKYLYLNSNRVTSMEP
GYFDNLANTLLVLKLNRNRISAIPPKMFKLPQLQHLELNRNKIKNVDGLTFQGLGALKSLKM
QRNGVTKLMDGAFWGLSNMEILQLDHNNLTEITKGWLYGLLMLQELHLSQNAINRISPDAWE
FCQKLSELDLTFNHLSRLDDSSFLGLSLLNTLHIGNNRVSYIADCAFRGLSSLKTLDLKNNE
ISWTIEDMNGAFSGLDKLRRLILQGNRIRSITKKAFTGLDALEHLDLSDNAIMSLQGNAFSQ
MKKLQQLHLNTSSLLCDCQLKWLPQWVAENNFQSFVNASCAHPQLLKGRSIFAVSPDGFVCD
DFPKPQITVQPETQSAIKGSNLSFICSAASSSDSPMTFAWKKDNELLHDAEMENYAHLRAQG
GEVMEYTTILRLREVEFASEGKYQCVISNHFGSSYSVKAKLTVNMLPSFTKTPMDLTIRAGA
MARLECAAVGHPAPQIAWQKDGGTDFPAARERRMHVMPEDDVFFIVDVKIEDIGVYSCTAQN
SAGSISANATLTVLETPSFLRPLLDRTVTKGETAVLQCIAGGSPPPKLNWTKDDSPLVVTER
HFFAAGNQLLIIVDSDVSDAGKYTCEMSNTLGTERGNVRLSVIPTPTCDSPQMTAPSLDDDG
WATVGVVIIAVVCCVVGTSLVWVVIIYHTRRRNEDCSITNTDETNLPADIPSYLSSQGTLAD
RQDGYVSSESGSHHQFVTSSGAGFFLPQHDSSGTCHIDNSSEADVEAATDLFLCPFLGSTGP
MYLKGNVYGSDPFETYHTGCSPDPRTVLMDHYEPSYIKKKECYPCSHPSEESCERSFSNISW
PSHVRKLLNTSYSHNEGPGMKNLCLNKSSLDFSANPEPASVASSNSFMGTFGKALRRPHLDA
YSSFGQPSDCQPRAFYLKAHSSPDLDSGSEEDGKERTDFQEENHICTFKQTLENYRTPNFQS
YDLDT

Signal sequence:

amino acids 1-19

Transmembrane domain:

amino acids 746-765

N-glycosylation site.

amino acids 62-66, 96-100, 214-220, 382-386, 409-413, 455-459, 628-632, 669-673, 845-849, 927-931, 939-943, 956-960

Glycosaminoglycan attachment site.

amino acids 826-830

Casein kinase II phosphorylation site.

amino acids 17-21, 39-43, 120-124, 203-207, 254-258, 264-268, 314-318, 323-327, 347-351, 464-468, 548-552, 632-636, 649-653, 671-675, 739-743, 783-787, 803-807, 847-851, 943-947, 958-962, 1013-1017, 1019-1023, 1021-1025

Tyrosine kinase phosphorylation site.

amino acids 607-615

N-myristoylation site.

amino acids 179-185, 197-203, 320-326, 367-373, 453-459, 528-534, 612-618, 623-629, 714-720, 873-879

FIGURE 103

GGGGAGAGGAATTGACCATGTAAAAGGAGACTTTTTTTTTTGGTGGTGGTGGCTGTTGGGTGCCTTGCAAAAATG
AAGGATGCAGGACGCAGCTTTCTCCTGGAACCGAACGCAATGGATAAACTGATTGTGCAAGAGAGAAGGAAGAAC
GAAGCTTTTTCTTGTGAGCCCTGGATCTTAACACAAATGTGTATATGTGCACACAGGGAGCATTCAAGAATGAAA
TAAACCAGAGTTAGACCCGCGGGGGTTGGTGTGTTCTGACATAAATAAATAATCTTAAAGCAGCTGTTCCCCTCC
CCACCCCCAAAAAAAAGGATGATTGGAAATGAAGAACCGAGGATTCACAAAGAAAAAAGTATGTTCATTTTTCTC
TATAAAGGAGAAAGTGAGCCAAGGAGATATTTTTGGAATGAAAAGTTTGGGGCTTTTTTAGTAAAGTAAAGAACT
GGTGTGGTGGTGTTTTCCTTTCTTTTTGAATTTCCCACAAGAGGAGAGGAAATTAATAATACATCTGCAAAGAAA
TTTCAGAGAAGAAAAGTTGACCGCGGCAGATTGAGGCATTGATTGGGGGAGAGAAACCAGCAGAGCACAGTTGGA
TTTGTGCCTATGTTGACTAAAATTGACGGATAATTGCAGTTGGATTTTTCTTCATCAACCTCCTTTTTTTTAAAT
TTTTATTCCTTTTGGTATCAAGATCATGCGTTTTCTCTTGTTCTTAACCACCTGGATTTCCATCTGGATGTTGCT
GTGATCAGTCTGAAATACAACTGTTTGAATTCCAGAAGGACCAACACCAGATAAATTATGAATGTTGAACAAGAT
GACCTTACATCCACAGCAGATAATGATAGGTCCTAGGTTTAACAGGGCCCTATTTGACCCCCTGCTTGTGGTGCT
GCTGGCTCTTCAACTTCTTGTGGTGGCTGGTCTGGTGCGGGCTCAGACCTGCCCTTCTGTGTGCTCCTGCAGCAA
CCAGTTCAGCAAGGTGATTTGTGTTCGGAAAAACCTGCGTGAGGTTCCGGATGGCATCTCCACCAACACACGGCT
GCTGAACCTCCATGAGAACCAAATCCAGATCATCAAAGTGAACAGCTTCAAGCACTTGAGGCACTTGGAAATCCT
ACAGTTGAGTAGGAACCATATCAGAACCATTGAAATTGGGGCTTTCAATGGTCTGGCGAACCTCAACACTCTGGA
ACTCTTTGACAATCGTCTTACTACCATCCCGAATGGAGCTTTTGTATACTTGTCTAAACTGAAGGAGCTCTGGTT
GCGAAACAACCCCATTGAAAGCATCCCTTCTTATGCTTTTAACAGAATTCCTTCTTTGCGCCGACTAGACTTAGG
GGAATTGAAAAGACTTTCATACATCTCAGAAGGTGCCTTTGAAGGTCTGTCCAACTTGAGGTATTTGAACCTTGC
CATGTGCAACCTTCGGGAAATCCCTAACCTCACACCGCTCATAAAACTAGATGAGCTGGATCTTTCTGGGAATCA
TTTATCTGCCATCAGGCCTGGCTCTTTCCAGGGTTTGATGCACCTTCAAAAACTGTGGATGATACAGTCCCAGAT
TCAAGTGATTGAACGGAATGCCTTTGACAACCTTCAGTCACTAGTGGAGATCAACCTGGCACACAATAATCTAAC
ATTACTGCCTCATGACCTCTTCACTCCCTTGCATCATCTAGAGCGGATACATTTACATCACAACCCTTGGAACTG
TAACTGTGACATACTGTGGCTCAGCTGGTGGATAAAAGACATGGCCCCCTCGAACACAGCTTGTTGTGCCCGGTG
TAACACTCCTCCCAATCTAAAGGGGAGGTACATTGGAGAGCTCGACCAGAATTACTTCACATGCTATGCTCCGGT
GATTGTGGAGCCCCCTGCAGACCTCAATGTCACTGAAGGCATGGCAGCTGAGCTGAAATGTCGGGCCTCCACATC
CCTGACATCTGTATCTTGGATTACTCCAAATGGAACAGTCATGACACATGGGGCGTACAAAGTGCGGATAGCTGT
GCTCAGTGATGGTACGTTAAATTTCACAAATGTAACTGTGCAAGATACAGGCATGTACACATGTATGGTGAGTAA
TTCCGTTGGGAATACTACTGCTTCAGCCACCCTGAATGTTACTGCAGCAACCACTACTCCTTTCTCTTACTTTTC
AACCGTCACAGTAGAGACTATGGAACCGTCTCAGGATGAGGCACGGACCACAGATAACAATGTGGGTCCCACTCC
AGTGGTCGACTGGGAGACCACCAATGTGACCACCTCTCTCACACCACAGAGCACAAGGTCGACAGAGAAAACCTT
CACCATCCCAGTGACTGATATAAACAGTGGGATCCCAGGAATTGATGAGGTCATGAAGACTACCAAAATCATCAT
TGGGTGTTTTGTGGCCATCACACTCATGGCTGCAGTGATGCTGGTCATTTTCTACAAGATGAGGAAGCAGCACCA
TCGGCAAAACCATCACGCCCCAACAAGGACTGTTGAAATTATTAATGTGGATGATGAGATTACGGGAGACACACC
CATGGAAAGCCACCTGCCCATGCCTGCTATCGAGCATGAGCACCTAAATCACTATAACTCATACAAATCTCCCTT
CAACCACACAACAACAGTTAACACAATAAATTCAATACACAGTTCAGTGCATGAACCGTTATTGATCCGAATGAA
CTCTAAAGACAATGTACAAGAGACTCAAATCTAAAACATTTACAGAGTTACAAAAAACAAACAATCAAAAAAAAA
GACAGTTTATTAAAAATGACACAAATGACTGGGCTAAATCTACTGTTTCAAAAAAGTGTCTTTACAAAAAAACAA
AAAAGAAAAGAAATTTATTTATTAAAAATTCTATTGTGATCTAAAGCAGACAAAAA

FIGURE 104

MLNKMTLHPQQIMIGPRFNRALFDPLLVVLLALQLLVVAGLVRAQTCPSVCSCSNQFSKVIC
VRKNLREVPDGISTNTRLLNLHENQIQIIKVNSFKHLRHLEILQLSRNHIRTIEIGAFNGLA
NLNTLELFDNRLTTIPNGAFVYLSKLKELWLRNNPIESIPSYAFNRIPSLRRLDLGELKRLS
YISEGAFEGLSNLRYLNLAMCNLREIPNLTPLIKLDELDLSGNHLSAIRPGSFQGLMHLQKL
WMIQSQIQVIERNAFDNLQSLVEINLAHNNLTLLPHDLFTPLHHLERIHLHHNPWNCNCDIL
WLSWWIKDMAPSNTACCARCNTPPNLKGRYIGELDQNYFTCYAPVIVEPPADLNVTEGMAAE
LKCRASTSLTSVSWITPNGTVMTHGAYKVRIAVLSDGTLNFTNVTVQDTGMYTCMVSNSVGN
TTASATLNVTAATTTPFSYFSTVTVETMEPSQDEARTTDNNVGPTPVVDWETTNVTTSLTPQ
STRSTEKTFTIPVTDINSGIPGIDEVMKTTKIIIGCFVAITLMAAVMLVIFYKMRKQHHRQN
HHAPTRTVEIINVDDEITGDTPMESHLPMPAIEHEHLNHYNSYKSPFNHTTTVNTINSIHSS
VHEPLLIRMNSKDNVQETQI

Signal sequence:
amino acids 1-44

Transmembrane domain:
amino acids 523-543

N-glycosylation site.
amino acids 278-282, 364-368, 390-394, 412-416, 415-419, 434-438, 442-446, 488-492, 606-610 cAMP- and cGMP-dependent protein kinase phosphorylation site.
amino acids 183-187

Casein kinase II phosphorylation site.
amino acids 268-272, 417-421, 465-469, 579-583, 620-624

N-myristoylation site.
amino acids 40-46, 73-79, 118-124, 191-197, 228-234, 237-243, 391-397, 422-428, 433-439, 531-537

FIGURE 105

AGCCGACGCTGCTCAAGCTGCAACTCTGTTGCAGTTGGCAGTTCTTTTCGGTTTCCCTCCTGCTGTTTGGGGGCA
TGAAAGGGCTTCGCCGCCGGGAGTAAAAGAAGGAATTGACCGGGCAGCGCGAGGGAGGAGCGCGCACGCGACCGC
GAGGGCGGGCGTGCACCCTCGGCTGGAAGTTTGTGCCGGGCCCCGAGCGCGCGCCGGCTGGGAGCTTCGGGTAGA
GACCTAGGCCGCTGGACCGCGATGAGCGCGCCGAGCCTCCGTGCGCGCGCCGCGGGGTTGGGGCTGCTGCTGTGC
GCGGTGCTGGGGCGCGCTGGCCGGTCCGACAGCGGCGGTCGCGGGGAACTCGGGCAGCCCTCTGGGGTAGCCGCC
GAGCGCCCATGCCCCACTACCTGCCGCTGCCTCGGGGACCTGCTGGACTGCAGTCGTAAGCGGCTAGCGCGTCTT
CCCGAGCCACTCCCGTCCTGGGTCGCTCGGCTGGACTTAAGTCACAACAGATTATCTTTCATCAAGGCAAGTTCC
ATGAGCCACCTTCAAAGCCTTCGAGAAGTGAAACTGAACAACAATGAATTGGAGACCATTCCAAATCTGGACCA
GTCTCGGCAAATATTACACTTCTCTCCTTGGCTGGAAACAGGATTGTTGAAATACTCCCTGAACATCTGAAAGAG
TTTCAGTCCCTTGAAACTTTGGACCTTAGCAGCAACAATATTTCAGAGCTCCAAACTGCATTTCCAGCCCTACAG
CTCAAATATCTGTATCTCAACAGCAACCGAGTCACATCAATGGAACCTGGGTATTTTGACAATTTGGCCAACACA
CTCCTTGTGTTAAAGCTGAACAGGAACCGAATCTCAGCTATCCCACCCAAGATGTTTAAACTGCCCCAACTGCAA
CATCTCGAATTGAACCGAAACAAGATTAAAAATGTAGATGGACTGACATTCCAAGGCCTTGGTGCTCTGAAGTCT
CTGAAAATGCAAAGAAATGGAGTAACGAAACTTATGGATGGAGCTTTTTGGGGGCTGAGCAACATGGAAATTTTG
CAGCTGGACCATAACAACCTAACAGAGATTACCAAAGGCTGGCTTTACGGCTTGCTGATGCTGCAGGAACTTCAT
CTCAGCCAAAATGCCATCAACAGGATCAGCCCTGATGCCTGGGAGTTCTGCCAGAAGCTCAGTGAGCTGGACCTA
ACTTTCAATCACTTATCAAGGTTAGATGATTCAAGCTTCCTTGGCCTAAGCTTACTAAATACACTGCACATTGGG
AACAACAGAGTCAGCTACATTGCTGATTGTGCCTTCCGGGGGCTTTCCAGTTTAAAGACTTTGGATCTGAAGAAC
AATGAAATTTCCTGGACTATTGAAGACATGAATGGTGCTTTCTCTGGGCTTGACAAACTGAGGCGACTGATACTC
CAAGGAAATCGGATCCGTTCTATTACTAAAAAAGCCTTCACTGGTTTGGATGCATTGGAGCATCTAGACCTGAGT
GACAACGCAATCATGTCTTTACAAGGCAATGCATTTTCACAAATGAAGAAACTGCAACAATTGCATTTAAATACA
TCAAGCCTTTTGTGCGATTGCCAGCTAAAATGGCTCCCACAGTGGGTGGCGGAAAACAACTTTCAGAGCTTTGTA
AATGCCAGTTGTGCCCATCCTCAGCTGCTAAAAGGAAGAAGCATTTTTGCTGTTAGCCCAGATGGCTTTGTGTGT
GATGATTTTCCCAAACCCCAGATCACGGTTCAGCCAGAAACACAGTCGGCAATAAAAGGTTCCAATTTGAGTTTC
ATCTGCTCAGCTGCCAGCAGCAGTGATTCCCCAATGACTTTTGCTTGGAAAAAAGACAATGAACTACTGCATGAT
GCTGAAATGGAAAATTATGCACACCTCCGGGCCCAAGGTGGCGAGGTGATGGAGTATACCACCATCCTTCGGCTG
CGCGAGGTGGAATTTGCCAGTGAGGGGAAATATCAGTGTGTCATCTCCAATCACTTTGGTTCATCCTACTCTGTC
AAAGCCAAGCTTACAGTAAATATGCTTCCCTCATTCACCAAGACCCCCATGGATCTCACCATCCGAGCTGGGGCC
ATGGCACGCTTGGAGTGTGCTGCTGTGGGGCACCCAGCCCCCCAGATAGCCTGGCAGAAGGATGGGGGCACAGAC
TTCCCAGCTGCACGGGAGAGACGCATGCATGTGATGCCCGAGGATGACGTGTTCTTTATCGTGGATGTGAAGATA
GAGGACATTGGGGTATACAGCTGCACAGCTCAGAACAGTGCAGGAAGTATTTCAGCAAATGCAACTCTGACTGTC
CTAGAAACACCATCATTTTTGCGGCCACTGTTGGACCGAACTGTAACCAAGGGAGAAACAGCCGTCCTACAGTGC
ATTGCTGGAGGAAGCCCTCCCCCTAAACTGAACTGGACCAAAGATGATAGCCCATTGGTGGTAACCGAGAGGCAC
TTTTTTGCAGCAGGCAATCAGCTTCTGATTATTGTGGACTCAGATGTCAGTGATGCTGGGAAATACACATGTGAG
ATGTCTAACACCCTTGGCACTGAGAGAGGAAACGTGCGCCTCAGTGTGATCCCCACTCCAACCTGCGACTCCCCT
CAGATGACAGCCCCATCGTTAGACGATGACGGATGGGCCACTGTGGGTGTCGTGATCATAGCCGTGGTTTGCTGT
GTGGTGGGCACGTCACTCGTGTGGGTGGTCATCATATACCACACAAGGCGGAGGAATGAAGATTGCAGCATTACC
AACACAGATGAGACCAACTTGCCAGCAGATATTCCTAGTTATTTGTCATCTCAGGGAACGTTAGCTGACAGGCAG
GATGGGTACGTGTCTTCAGAAAGTGGAAGCCACCACCAGTTTGTCACATCTTCAGGTGCTGGATTTTTCTTACCA
CAACATGACAGTAGTGGGACCTGCCATATTGACAATAGCAGTGAAGCTGATGTGGAAGCTGCCACAGATCTGTTC
CTTTGTCCGTTTTTGGGATCCACAGGCCCTATGTATTTGAAGGGAAATGTGTATGGCTCAGATCCTTTTGAAACA
TATCATACAGGTTGCAGTCCTGACCCAAGAACAGTTTTAATGGACCACTATGAGCCCAGTTACATAAAGAAAAAG
GAGTGCTACCCATGTTCTCATCCTTCAGAAGAATCCTGCGAACGGAGCTTCAGTAATATATCGTGGCCTTCACAT
GTGAGGAAGCTACTTAACACTAGTTACTCTCACAATGAAGGACCTGGAATGAAAAATCTGTGTCTAAACAAGTCC
TCTTTAGATTTTAGTGCAAATCCAGAGCCAGCGTCGGTTGCCTCGAGTAATTCTTTCATGGGTACCTTTGGAAAA
GCTCTCAGGAGACCTCACCTAGATGCCTATTCAAGCTTTGGACAGCCATCAGATTGTCAGCCAAGAGCCTTTTAT
TTGAAAGCTCATTCTTCCCCAGACTTGGACTCTGGGTCAGAGGAAGATGGGAAAGAAAGGACAGATTTTCAGGAA
GAAAATCACATTTGTACCTTTAAACAGACTTTAGAAAACTACAGGACTCCAAATTTTCAGTCTTATGACTTGGAC
ACATAGACTGAATGAGACCAAAGGAAAAGCTTAACATACTACCTCAAGTGAACTTTTATTTAAAAGAGAGAGAAT
CTTATGTTTTTTAAATGGAGTTATGAATTTTAAAAGGATAAAAATGCTTTATTTATACAGATGAACCAAAATTAC
AAAAAGTTATGAAAATTTTTATACTGGGAATGATGCTCATATAAGAATACCTTTTTAAACTATTTTTTAACTTTG
TTTTATGCAAAAAAGTATCTTACGTAAATTAATGATATAAATCATGATTATTTTATGTATTTTTATAATGCCAGA
TTTCTTTTTATGGAAAATGAGTTACTAAAGCATTTTAAATAATACCTGCCTTGTACCATTTTTTAAATAGAAGTT
ACTTCATTATATTTTGCACATTATATTTAATAAAATGTGTCAATTTGAAAAAAAAAAAAAAAAAAAAAAAAAAAAA

FIGURE 106

MSAPSLRARAAGLGLLLCAVLGRAGRSDSGGRGELGQPSGVAAERPCPTTCRCLGDLLDCSR
KRLARLPEPLPSWVARLDLSHNRLSFIKASSMSHLQSLREVKLNNNELETIPNLGPVSANIT
LLSLAGNRIVEILPEHLKEFQSLETLDLSSNNISELQTAFPALQLKYLYLNSNRVTSMEPGY
FDNLANTLLVLKLNRNRISAIPPKMFKLPQLQHLELNRNKIKNVDGLTFQGLGALKSLKMQR
NGVTKLMDGAFWGLSNMEILQLDHNNLTEITKGWLYGLLMLQELHLSQNAINRISPDAWEFC
QKLSELDLTFNHLSRLDDSSFLGLSLLNTLHIGNNRVSYIADCAFRGLSSLKTLDLKNNEIS
WTIEDMNGAFSGLDKLRRLILQGNRIRSITKKAFTGLDALEHLDLSDNAIMSLQGNAFSQMK
KLQQLHLNTSSLLCDCQLKWLPQWVAENNFQSFVNASCAHPQLLKGRSIFAVSPDGFVCDDF
PKPQITVQPETQSAIKGSNLSFICSAASSSDSPMTFAWKKDNELLHDAEMENYAHLRAQGGE
VMEYTTILRLREVEFASEGKYQCVISNHFGSSYSVKAKLTVNMLPSFTKTPMDLTIRAGAMA
RLECAAVGHPAPQIAWQKDGGTDFPAARERRMHVMPEDDVFFIVDVKIEDIGVYSCTAQNSA
GSISANATLTVLETPSFLRPLLDRTVTKGETAVLQCIAGGSPPPKLNWTKDDSPLVVTERHF
FAAGNQLLIIVDSDVSDAGKYTCEMSNTLGTERGNVRLSVIPTPTCDSPQMTAPSLDDDGWA
TVGVVIIAVVCCVVGTSLVWVVIIYHTRRRNEDCSITNTDETNLPADIPSYLSSQGTLADRQ
DGYVSSESGSHHQFVTSSGAGFFLPQHDSSGTCHIDNSSEADVEAATDLFLCPFLGSTGPMY
LKGNVYGSDPFETYHTGCSPDPRTVLMDHYEPSYIKKKECYPCSHPSEESCERSFSNISWPS
HVRKLLNTSYSHNEGPGMKNLCLNKSSLDFSANPEPASVASSNSFMGTFGKALRRPHLDAYS
SFGQPSDCQPRAFYLKAHSSPDLDSGSEEDGKERTDFQEENHICTFKQTLENYRTPNFQSYDLDT

Signal sequence:
amino acids 1-27
Transmembrane domain:
amino acids 808-828
N-glycosylation site.
amino acids 122-126, 156-160, 274-278, 442-446, 469-473, 515-519, 688-692, 729-733, 905-909, 987-991, 999-1003, 1016-1020
Glycosaminoglycan attachment site.
amino acids 886-890
Casein kinase II phosphorylation site.
amino acids 99-103, 180-184, 263-267, 314-318, 324-328, 374-378, 383-387, 407-411, 524-528, 608-612, 692-696, 709-713, 731-735, 799-803, 843-847, 863-867, 907-911, 1003-1007, 1018-1022, 1073-1077, 1079-1083, 1081-1085
Tyrosine kinase phosphorylation site.
amino acids 667-675
N-myristoylation site.
amino acids 14-20, 36-42, 239-245, 257-263, 380-386, 427-433, 513-519, 588-594, 672-678, 683-687, 774-780, 933-939
Leucine zipper pattern.
amino acids 58-80, 65-87

FIGURE 107

CAAAACTTGCGTCGCGGAGAGCGCCCAGCTTGACTTGAATGGAAGGAGCCCGAGCCCGCGGAGCGCAGCTGAGAC
TGGGGGAGCGCGTTCGGCCTGTGGGGCGCCGCTCGGCGCCGGGGCGCAGCAGGGAAGGGGAAGCTGTGGTCTGCC
CTGCTCCACGAGGCGCCACTGGTGTGAACCGGGAGAGCCCCTGGGTGGTCCCGTCCCCTATCCCTCCTTTATATA
GAAACCTTCCACACTGGGAAGGCAGCGGCGAGGCAGGAGGGCTCATGGTGAGCAAGGAGGCCGGCTGATCTGCAG
GCGCACAGCATTCCGAGTTTACAGATTTTTACAGATACCAAATGGAAGGCGAGGAGGCAGAACAGCCTGCCTGGT
TCCATCAGCCCTGGCGCCCAGGCGCATCTGACTCGGCACCCCCTGCAGGCACCATGGCCCAGAGCCGGGTGCTGC
TGCTCCTGCTGCTGCTGCCGCCACAGCTGCACCTGGGACCTGTGCTTGCCGTGAGGGCCCCAGGATTTGGCCGAA
GTGGCGGCCACAGCCTGAGCCCCGAAGAGAACGAATTTGCGGAGGAGGAGCCGGTGCTGGTACTGAGCCCTGAGG
AGCCCGGGCCTGGCCCAGCCGCGGTCAGCTGCCCCCGAGACTGTGCCTGTTCCCAGGAGGGCGTCGTGGACTGTG
GCGGTATTGACCTGCGTGAGTTCCCGGGGGACCTGCCTGAGCACACCAACCACCTATCTCTGCAGAACAACCAGC
TGGAAAAGATCTACCCTGAGGAGCTCTCCCGGCTGCACCGGCTGGAGACACTGAACCTGCAAAACAACCGCCTGA
CTTCCCGAGGGCTCCCAGAGAAGGCGTTTGAGCATCTGACCAACCTCAATTACCTGTACTTGGCCAATAACAAGC
TGACCTTGGCACCCCGCTTCCTGCCAAACGCCCTGATCAGTGTGGACTTTGCTGCCAACTATCTCACCAAGATCT
ATGGGCTCACCTTTGGCCAGAAGCCAAACTTGAGGTCTGTGTACCTGCACAACAACAAGCTGGCAGACGCCGGGC
TGCCGGACAACATGTTCAACGGCTCCAGCAACGTCGAGGTCCTCATCCTGTCCAGCAACTTCCTGCGCCACGTGC
CCAAGCACCTGCCGCCTGCCCTGTACAAGCTGCACCTCAAGAACAACAAGCTGGAGAAGATCCCCCCGGGGGCCT
TCAGCGAGCTGAGCAGCCTGCGCGAGCTATACCTGCAGAACAACTACCTGACTGACGAGGGCCTGGACAACGAGA
CCTTCTGGAAGCTCTCCAGCCTGGAGTACCTGGATCTGTCCAGCAACAACCTGTCTCGGGTCCCAGCTGGGCTGC
CGCGCAGCCTGGTGCTGCTGCACTTGGAGAAGAACGCCATCCGGAGCGTGGACGCGAATGTGCTGACCCCCATCC
GCAGCCTGGAGTACCTGCTGCTGCACAGCAACCAGCTGCGGGAGCAGGGCATCCACCCACTGGCCTTCCAGGGCC
TCAAGCGGTTGCACACGGTGCACCTGTACAACAACGCGCTGGAGCGCGTGCCCAGTGGCCTGCCTCGCCGCGTGC
GCACCCTCATGATCCTGCACAACCAGATCACAGGCATTGGCCGCGAAGACTTTGCCACCACCTACTTCCTGGAGG
AGCTCAACCTCAGCTACAACCGCATCACCAGCCCACAGGTGCACCGCGACGCCTTCCGCAAGCTGCGCCTGCTGC
GCTCGCTGGACCTGTCGGGCAACCGGCTGCACACGCTGCCACCTGGGCTGCCTCGAAATGTCCATGTGCTGAAGG
TCAAGCGCAATGAGCTGGCTGCCTTGGCACGAGGGGCGCTGGCGGGCATGGCTCAGCTGCGTGAGCTGTACCTCA
CCAGCAACCGACTGCGCAGCCGAGCCCTGGGCCCCCGTGCCTGGGTGGACCTCGCCCATCTGCAGCTGCTGGACA
TCGCCGGGAATCAGCTCACAGAGATCCCCGAGGGGCTCCCCGAGTCACTTGAGTACCTGTACCTGCAGAACAACA
AGATTAGTGCGGTGCCCGCCAATGCCTTCGACTCCACGCCCAACCTCAAGGGGATCTTTCTCAGGTTTAACAAGC
TGGCTGTGGGCTCCGTGGTGGACAGTGCCTTCCGGAGGCTGAAGCACCTGCAGGTCTTGGACATTGAAGGCAACT
TAGAGTTTGGTGACATTTCCAAGGACCGTGGCCGCTTGGGGAAGGAAAAGGAGGAGGAGGAAGAGGAGGAGGAGG
AGGAAGAGGAAACAAGATAGTGACAAGGTGATGCAGATGTGACCTAGGATGATGGACCGCCGGACTCTTTTCTGC
AGCACACGCCTGTGTGCTGTGAGCCCCCCACTCTGCCGTGCTCACACAGACACACCCAGCTGCACACATGAGGCA
TCCCACATGACACGGGCTGACACAGTCTCATATCCCCACCCCTTCCCACGGCGTGTCCCACGGCCAGACACATGC
ACACACATCACACCCTCAAACACCCAGCTCAGCCACACACAACTACCCTCCAAACCACCACAGTCTCTGTCACAC
CCCCACTACCGCTGCCACGCCCTCTGAATCATGCAGGGAAGGGTCTGCCCCTGCCCTGGCACACACAGGCACCCA
TTCCCTCCCCCTGCTGACATGTGTATGCGTATGCATACACACCACACACACACACATGCACAAGTCATGTGCGAA
CAGCCCTCCAAAGCCTATGCCACAGACAGCTCTTGCCCCAGCCAGAATCAGCCATAGCAGCTCGCCGTCTGCCCT
GTCCATCTGTCCGTCCGTTCCCTGGAGAAGACACAAGGGTATCCATGCTCTGTGGCCAGGTGCCTGCCACCCTCT
GGAACTCACAAAAGCTGGCTTTTATTCCTTTCCCATCCTATGGGGACAGGAGCCTTCAGGACTGCTGGCCTGGCC
TGGCCCACCCTGCTCCTCCAGGTGCTGGGCAGTCACTCTGCTAAGAGTCCCTCCCTGCCACGCCCTGGCAGGACA
CAGGCACTTTTCCAATGGGCAAGCCCAGTGGAGGCAGGATGGGAGAGCCCCCTGGGTGCTGCTGGGGCCTTGGGG
CAGGAGTGAAGCAGAGGTGATGGGGCTGGGCTGAGCCAGGGAGGAAGGACCCAGCTGCACCTAGGAGACACCTTT
GTTCTTCAGGCCTGTGGGGGAAGTTCCGGGTGCCTTTATTTTTATTCTTTTCTAAGGAAAAAAATGATAAAAAT
CTCAAAGCTGATTTTTCTTGTTATAGAAAAACTAATATAAAAGCATTATCCCTATCCCTGCAAAAAAAAAA

FIGURE 108

MEGEEAEQPAWFHQPWRPGASDSAPPAGTMAQSRVLLLLLLLPPQLHLGPVLAVRAPGFGRS
GGHSLSPEENEFAEEEPVLVLSPEEPGPGPAAVSCPRDCACSQEGVVDCGGIDLREFPGDLP
EHTNHLSLQNNQLEKIYPEELSRLHRLETLNLQNNRLTSRGLPEKAFEHLTNLNYLYLANNK
LTLAPRFLPNALISVDFAANYLTKIYGLTFGQKPNLRSVYLHNNKLADAGLPDNMFNGSSNV
EVLILSSNFLRHVPKHLPPALYKLHLKNNKLEKIPPGAFSELSSLRELYLQNNYLTDEGLDN
ETFWKLSSLEYLDLSSNNLSRVPAGLPRSLVLLHLEKNAIRSVDANVLTPIRSLEYLLLHSN
QLREQGIHPLAFQGLKRLHTVHLYNNALERVPSGLPRRVRTLMILHNQITGIGREDFATTYF
LEELNLSYNRITSPQVHRDAFRKLRLLRSLDLSGNRLHTLPPGLPRNVHVLKVKRNELAALA
RGALAGMAQLRELYLTSNRLRSRALGPRAWVDLAHLQLLDIAGNQLTEIPEGLPESLEYLYL
QNNKISAVPANAFDSTPNLKGIFLRFNKLAVGSVVDSAFRRLKHLQVLDIEGNLEFGDISKD
RGRLGKEKEEEEEEEEEEEETR

Signal sequence:
amino acids 1-48

N-glycosylation site.
amino acids 243-247, 310-314, 328-332, 439-443

Casein kinase II phosphorylation site.
amino acids 68-72, 84-88, 246-250, 292-296, 317-321, 591-595

N-myristoylation site.
amino acids 19-25, 107-113, 213-219, 217-223, 236-242, 335-341, 477-483, 498-502, 539-545, 548-554

Leucine zipper pattern.
amino acids 116-138, 251-273, 258-280, 322-344, 464-486, 471-493, 535-557

FIGURE 109

GGGAGGGGGCTCCGGGCGCCGCGCAGCAGACCTGCTCCGGCCGCGCGCCTCGCCGCTGTCCTCCGGGAGCGGCAG
CAGTAGCCCGGGCGGCGAGGGCTGGGGGTTCCTCGAGACTCTCAGAGGGGCGCCTCCCATCGGCGCCCACCACCC
CAACCTGTTCCTCGCGCGCCACTGCGCTGCGCCCCAGGACCCGCTGCCCAACATGGATTTTCTCCTGGCGCTGGT
GCTGGTATCCTCGCTCTACCTGCAGGCGGCCGCCGAGTTCGACGGGAGGTGGCCCAGGCAAATAGTGTCATCGAT
TGGCCTATGTCGTTATGGTGGAGGATTGACTGCTGCTGGGGCTGGGCTCGCCAGTCTTGGGGACAGTGTCAGCC
TGTGTGCCAACCACGATGCAAACATGGTGAATGTATCGGGCCAAACAAGTGCAAGTGTCATCCTGGTTATGCTGG
AAAAACCTGTAATCAAGATCTAAATGAGTGTGGCCTGAAGCCCCGGCCCTGTAAGCACAGGTGCATGAACACTTA
CGGCAGCTACAAGTGCTACTGTCTCAACGGATATATGCTCATGCCGGATGGTTCCTGCTCAAGTGCCCTGACCTG
CTCCATGGCAAACTGTCAGTATGGCTGTGATGTTGTTAAAGGACAAATACGGTGCCAGTGCCCATCCCCTGGCCT
GCACCTGGCTCCTGATGGGAGGACCTGTGTAGATGTTGATGAATGTGCTACAGGAAGAGCCTCCTGCCCTAGATT
TAGGCAATGTGTCAACACTTTTGGGAGCTACATCTGCAAGTGTCATAAAGGCTTCGATCTCATGTATATTGGAGG
CAAATATCAATGTCATGACATAGACGAATGCTCACTTGGTCAGTATCAGTGCAGCAGCTTTGCTCGATGTTATAA
CGTACGTGGGTCCTACAAGTGCAAATGTAAAGAAGGATACCAGGGTGATGGACTGACTTGTGTGTATATCCCAAA
AGTTATGATTGAACCTTCAGGTCCAATTCATGTACCAAAGGGAAATGGTACCATTTTAAAGGGTGACACAGGAAA
TAATAATTGGATTCCTGATGTTGGAAGTACTTGGTGGCCTCCGAAGACACCATATATTCCTCCTATCATTACCAA
CAGGCCTACTTCTAAGCCAACAACAAGACCTACACCAAAGCCAACACCAATTCCTACTCCACCACCACCACCACC
CCTGCCAACAGAGCTCAGAACACCTCTACCACCTACAACCCCAGAAAGGCCAACCACCGGACTGACAACTATAGC
ACCAGCTGCCAGTACACCTCCAGGAGGGATTACAGTTGACAACAGGGTACAGACAGACCCTCAGAAACCCAGAGG
AGATGTGTTCAGTGTTCTGGTACACAGTTGTAATTTTGACCATGGACTTTGTGGATGGATCAGGGAGAAAGACAA
TGACTTGCACTGGGAACCAATCAGGGACCCAGCAGGTGGACAATATCTGACAGTGTCGGCAGCCAAAGCCCCAGG
GGGAAAAGCTGCACGCTTGGTGCTACCTCTCGGCCGCCTCATGCATTCAGGGGACCTGTGCCTGTCATTCAGGCA
CAAGGTGACGGGGCTGCACTCTGGCACACTCCAGGTGTTTGTGAGAAAACACGGTGCCCACGGAGCAGCCCTGTG
GGGAAGAAATGGTGGCCATGGCTGGAGGCAAACACAGATCACCTTGCGAGGGGCTGACATCAAGAGCGAATCACA
AAGATGATTAAAGGGTTGGAAAAAAAGATCTATGATGGAAAATTAAAGGAACTGGGATTATTGAGCCTGGAGAAG
AGAAGACTGAGGGGCAAACCATTGATGGTTTTCAAGTATATGAAGGGTTGGCACAGAGAGGGTGGCGACCAGCTG
TTCTCCATATGCACTAAGAATAGAACAAGAGGAAACTGGCTTAGACTAGAGTATAAGGGAGCATTTCTTGGCAGG
GGCCATTGTTAGAATACTTCATAAAAAAAGAAGTGTGAAAATCTCAGTATCTCTCTCTCTTTCTAAAAAATTAGA
TAAAAATTTGTCTATTTAAGATGGTTAAAGATGTTCTTACCCAAGGAAAAGTAACAAATTATAGAATTTCCCAAA
AGATGTTTTGATCCTACTAGTAGTATGCAGTGAAAATCTTTAGAACTAAATAATTTGGACAAGGCTTAATTTAGG
CATTTCCCTCTTGACCTCCTAATGGAGAGGGATTGAAAGGGGAAGAGCCCACCAAATGCTGAGCTCACTGAAATA
TCTCTCCCTTATGGCAATCCTAGCAGTATTAAAGAAAAAAGGAAACTATTTATTCCAAATGAGAGTATGATGGAC
AGATATTTTAGTATCTCAGTAATGTCCTAGTGTGGCGGTGGTTTTCAATGTTTCTTCATGGTAAAGGTATAAGCC
TTTCATTTGTTCAATGGATGATGTTTCAGATTTTTTTTTTTTTAAGAGATCCTTCAAGGAACACAGTTCAGAGAG
ATTTTCATCGGGTGCATTCTCTCTGCTTCGTGTGTGACAAGTTATCTTGGCTGCTGAGAAAGAGTGCCCTGCCCC
ACACCGGCAGACCTTTCCTTCACCTCATCAGTATGATTCAGTTTCTCTTATCAATTGGACTCTCCCAGGTTCCAC
AGAACAGTAATATTTTTTGAACAATAGGTACAATAGAAGGTCTTCTGTCATTTAACCTGGTAAAGGCAGGGCTGG
AGGGGGAAAATAAATCATTAAGCCTTTGAGTAACGGCAGAATATATGGCTGTAGATCCATTTTTAATGGTTCATT
TCCTTTATGGTCATATAACTGCACAGCTGAAGATGAAAGGGGAAAATAAATGAAAATTTTACTTTTCGATGCCAA
TGATACATTGCACTAAACTGATGGAAGAAGTTATCCAAAGTACTGTATAACATCTTGTTTATTATTTAATGTTTT
CTAAAATAAAAAATGTTAGTGGTTTTCCAAATGGCCTAATAAAAACAATTATTTGTAAATAAAAACACTGTTAGTAAT

FIGURE 110

MDFLLALVLVSSLYLQAAAEFDGRWPRQIVSSIGLCRYGGRIDCCWGWARQSWGQCQPVCQP
RCKHGECIGPNKCKCHPGYAGKTCNQDLNECGLKPRPCKHRCMNTYGSYKCYCLNGYMLMPD
GSCSSALTCSMANCQYGCDVVKGQIRCQCPSPGLHLAPDGRTCVDVDECATGRASCPRFRQC
VNTFGSYICKCHKGFDLMYIGGKYQCHDIDECSLGQYQCSSFARCYNVRGSYKCKCKEGYQG
DGLTCVYIPKVMIEPSGPIHVPKGNGTILKGDTGNNNWIPDVGSTWWPPKTPYIPPIITNRP
TSKPTTRPTPKPTPIPTPPPPPPLPTELRTPLPPTTPERPTTGLTTIAPAASTPPGGITVDN
RVQTDPQKPRGDVFSVLVHSCNFDHGLCGWIREKDNDLHWEPIRDPAGGQYLTVSAAKAPGG
KAARLVLPLGRLMHSGDLCLSFRHKVTGLHSGTLQVFVRKHGAHGAALWGRNGGHGWRQTQI
TLRGADIKSESQR

Signal sequence:

amino acids 1-17

N-glycosylation site.

amino acids 273-277

Casein kinase II phosphorylation site.

amino acids 166-170, 345-349

Tyrosine kinase phosphorylation site.

amino acids 199-206

N-myristoylation site.

amino acids 109-115, 125-131, 147-153, 191-197, 221-227, 236-242, 421-427, 433-439, 462-468, 476-482

Aspartic acid and asparagine hydroxylation site.

amino acids 104-116, 186-198, 231-243

Cell attachment sequence.

amino acids 382-385

EGF-like domain cysteine pattern signature.

amino acids 75-87

FIGURE 111

CTTCTTTGAAAAGGATTATCACCTGATCAGGTTCTCTCTGCATTTGCCCCTTTAGATTGTGA
AATGTGGCTCAAGGTCTTCACAACTTTCCTTTCCTTTGCAACAGGTGCTTGCTCGGGGCTGA
AGGTGACAGTGCCATCACACACTGTCCATGGCGTCAGAGGTCAGGCCCTCTACCTACCCGTC
CACTATGGCTTCCACACTCCAGCATCAGACATCCAGATCATATGGCTATTTGAGAGACCCCA
CACAATGCCCAAATACTTACTGGGCTCTGTGAATAAGTCTGTGGTTCCTGACTTGGAATACC
AACACAAGTTCACCATGATGCCACCCAATGCATCTCTGCTTATCAACCCACTGCAGTTCCCT
GATGAAGGCAATTACATCGTGAAGGTCAACATTCAGGGAAATGGAACTCTATCTGCCAGTCA
GAAGATACAAGTCACGGTTGATGATCCTGTCACAAAGCCAGTGGTGCAGATTCATCCTCCCT
CTGGGGCTGTGGAGTATGTGGGGAACATGACCCTGACATGCCATGTGGAAGGGGGCACTCGG
CTAGCTTACCAATGGCTAAAAAATGGGAGACCTGTCCACACCAGCTCCACCTACTCCTTTTC
TCCCCAAAACAATACCCTTCATATTGCTCCAGTAACCAAGGAAGACATTGGGAATTACAGCT
GCCTGGTGAGGAACCCTGTCAGTGAAATGGAAAGTGATATCATTATGCCCATCATATATTAT
GGACCTTATGGACTTCAAGTGAATTCTGATAAAGGGCTAAAAGTAGGGGAAGTGTTTACTGT
TGACCTTGGAGAGGCCATCCTATTTGATTGTTCTGCTGATTCTCATCCCCCCAACACCTACT
CCTGGATTAGGAGGACTGACAATACTACATATATCATTAAGCATGGGCCTCGCTTAGAAGTT
GCATCTGAGAAAGTAGCCCAGAAGACAATGGACTATGTGTGCTGTGCTTACAACAACATAAC
CGGCAGGCAAGATGAAACTCATTTCACAGTTATCATCACTTCCGTAGGACTGGAGAAGCTTG
CACAGAAAGGAAAATCATTGTCACCTTTAGCAAGTATAACTGGAATATCACTATTTTTGATT
ATATCCATGTGTCTTCTCTTCCTATGGAAAAAATATCAACCCTACAAAGTTATAAAACAGAA
ACTAGAAGGCAGGCCAGAAACAGAATACAGGAAAGCTCAAACATTTTCAGGCCATGAAGATG
CTCTGGATGACTTCGGAATATATGAATTTGTTGCTTTTCCAGATGTTTCTGGTGTTTCCAGG
ATTCCAAGCAGGTCTGTTCCAGCCTCTGATTGTGTATCGGGGCAAGATTTGCACAGTACAGT
GTATGAAGTTATTCAGCACATCCCTGCCCAGCAGCAAGACCATCCAGAGTGAACTTTCATGG
GCTAAACAGTACATTCGAGTGAAATTCTGAAGAAACATTTTAAGGAAAAACAGTGGAAAAGT
ATATTAATCTGGAATCAGTGAAGAAACCAGGACCAACACCTCTTACTCATTATTCCTTTACA
TGCAGAATAGAGGCATTTATGCAAATTGAACTGCAGGTTTTTCAGCATATACACAATGTCTT
GTGCAACAGAAAAACATGTTGGGGAAATATTCCTCAGTGGAGAGTCGTTCTCATGCTGACGG
GGAGAACGAAAGTGACAGGGGTTTCCTCATAAGTTTTGTATGAAATATCTCTACAAACCTCA
ATTAGTTCTACTCTACACTTTCACTATCATCAACACTGAGACTATCCTGTCTCACCTACAAA
TGTGGAAACTTTACATTGTTCGATTTTTCAGCAGACTTTGTTTTATTAAATTTTTATTAGTG
TTAAGAATGCTAAATTTATGTTTCAATTTTATTTCCAAATTTCTATCTTGTTATTTGTACAA
CAAAGTAATAAGGATGGTTGTCACAAAAACAAAACTATGCCTTCTCTTTTTTTTCAATCACC
AGTAGTATTTTTGAGAAGACTTGTGAACACTTAAGGAAATGACTATTAAAGTCTTATTTTTA
TTTTTTTCAAGGAAAGATGGATTCAAATAAATTATTCTGTTTTTGCTTTTAAAAAAAAAAAAAA

FIGURE 112

MWLKVFTTFLSFATGACSGLKVTVPSHTVHGVRGQALYLPVHYGFHTPASDIQIIWLFERPH
TMPKYLLGSVNKSVVPDLEYQHKFTMMPPNASLLINPLQFPDEGNYIVKVNIQGNGTLSASQ
KIQVTVDDPVTKPVVQIHPPSGAVEYVGNMTLTCHVEGGTRLAYQWLKNGRPVHTSSTYSFS
PQNNTLHIAPVTKEDIGNYSCLVRNPVSEMESDIIMPIIYYGPYGLQVNSDKGLKVGEVFTV
DLGEAILFDCSADSHPPNTYSWIRRTDNTTYIIKHGPRLEVASEKVAQKTMDYVCCAYNNIT
GRQDETHFTVIITSVGLEKLAQKGKSLSPLASITGISLFLIISMCLLFLWKKYQPYKVIKQK
LEGRPETEYRKAQTFSGHEDALDDFGIYEFVAFPDVSGVSRIPSRSVPASDCVSGQDLHSTV
YEVIQHIPAQQQDHPE

Signal sequence:
amino acids 1-18

Transmembrane domain:
amino acids 341-359

N-glycosylation site.
amino acids 73-77, 92-96, 117-121, 153-157, 189-193, 204-208, 276-280, 308-312

Casein kinase II phosphorylation site.
amino acids 129-133, 198-202, 214-218, 388-392, 426-430, 433-437

Tyrosine kinase phosphorylation site.
amino acids 272-280

N-myristoylation site.
amino acids 15-21, 19-25, 118-124, 163-167, 203-209, 231-237, 239-245

Prokaryotic membrane lipoprotein lipid attachment site.
amino acids 7-18

FIGURE 113

GCAAGCGGCGAA<u>ATG</u>GCGCCCTCCGGGAGTCTTGCAGTTCCCCTGGCAGTCCTGGTGCTGTT
GCTTTGGGGTGCTCCCTGGACGCACGGGCGGCGGAGCAACGTTCGCGTCATCACGGACGAGA
ACTGGAGAGAACTGCTGGAAGGAGACTGGATGATAGAATTTTATGCCCCGTGGTGCCCTGCT
TGTCAAAATCTTCAACCGGAATGGGAAAGTTTTGCTGAATGGGGAGAAGATCTTGAGGTTAA
TATTGCGAAAGTAGATGTCACAGAGCAGCCAGGACTGAGTGGACGGTTTATCATAACTGCTC
TTCCTACTATTTATCATTGTAAAGATGGTGAATTTAGGCGCTATCAGGGTCCAAGGACTAAG
AAGGACTTCATAAACTTTATAAGTGATAAAGAGTGGAAGAGTATTGAGCCCGTTTCATCATG
GTTTGGTCCAGGTTCTGTTCTGATGAGTAGTATGTCAGCACTCTTTCAGCTATCTATGTGGA
TCAGGACGTGCCATAACTACTTTATTGAAGACCTTGGATTGCCAGTGTGGGGATCATATACT
GTTTTTGCTTTAGCAACTCTGTTTTCCGGACTGTTATTAGGACTCTGTATGATATTTGTGGC
AGATTGCCTTTGTCCTTCAAAAAGGCGCAGACCACAGCCATACCCATACCCTTCAAAAAAAT
TATTATCAGAATCTGCACAACCTTTGAAAAAAGTGGAGGAGGAACAAGAGGCGGATGAAGAA
GATGTTTCAGAAGAAGAAGCTGAAAGTAAAGAAGGAACAAACAAAGACTTTCCACAGAATGC
CATAAGACAACGCTCTCTGGGTCCATCATTGGCCACAGATAAATCC<u>TAG</u>TTAAATTTTATAG
TTATCTTAATATTATGATTTTGATAAAAACAGAAGATTGATCATTTTGTTTGGTTTGAAGTG
AACTGTGACTTTTTTGAATATTGCAGGGTTCAGTCTAGATTGTCATTAAATTGAAGAGTCTA
CATTCAGAACATAAAAGCACTAGGTATACAAGTTTGAAATATGATTTAAGCACAGTATGATG
GTTTAAATAGTTCTCTAATTTTTGAAAAATCGTGCCAAGCAATAAGATTTATGTATATTTGT
TTAATAATAACCTATTTCAAGTCTGAGTTTTGAAAATTTACATTTCCCAAGTATTGCATTAT
TGAGGTATTTAAGAAGATTATTTTAGAGAAAAATATTTCTCATTTGATATAATTTTTCTCTG
TTTCACTGTGTGAAAAAAAGAAGATATTTCCCATAAATGGGAAGTTTGCCCATTGTCTCAAG
AAATGTGTATTTCAGTGACAATTTCGTGGTCTTTTTAGAGGTATATTCCAAAATTTCCTTGT
ATTTTTAGGTTATGCAACTAATAAAAACTACCTTACATTAATTAATTACAGTTTTCTACACA
TGGTAATACAGGATATGCTACTGATTTAGGAAGTTTTTAAGTTCATGGTATTCTCTTGATTC
CAACAAAGTTTGATTTTCTCTTGTATTTTTCTTACTTACTATGGGTTACATTTTTTATTTTT
CAAATTGGATGATAATTTCTTGGAAACATTTTTTATGTTTTAGTAAACAGTATTTTTTTGTT
GTTTCAAACTGAAGTTTACTGAGAGATCCATCAAATTGAACAATCTGTTGTAATTTAAAATT
TTGGCCACTTTTTTCAGATTTTACATCATTCTTGCTGAACTTCAACTTGAAATTGTTTTTTT
TTTCTTTTTGGATGTGAAGGTGAACATTCCTGATTTTTGTCTGATGTGAAAAAGCCTTGGTA
TTTTACATTTTGAAAATTCAAAGAAGCTTAATATAAAAGTTTGCATTCTACTCAGGAAAAAG
CATCTTCTTGTATATGTCTTAAATGTATTTTTGTCCTCATATACAGAAAGTTCTTAATTGAT
TTTACAGTCTGTAATGCTTGATGTTTTAAAATAATAACATTTTTATATTTTTTAAAAGACAA
ACTTCATATTATCCTGTGTTCTTTCCTGACTGGTAATATTGTGTGGGATTTCACAGGTAAAA
GTCAGTAGGATGGAACATTTTAGTGTATTTTTACTCCTTAAAGAGCTAGAATACATAGTTTT
CACCTTAAAAGAAGGGGGAAAATCATAAATACAATGAATCAACTGACCATTACGTAGTAGAC
AATTTCTGTAATGTCCCCTTCTTTCTAGGCTCTGTTGCTGTGTGAATCCATTAGATTTACAG
TATCGTAATATACAAGTTTTCTTTAAAGCCCTCTCCTTTAGAATTTAAAATATTGTACCATT
AAAGAGTTTGGATGTGTAACTTGTGATGCCTTAGAAAAATATCCTAAGCACAAAATAAACCT
TTCTAACCACTTCATTAAAGCTGAAAAAAAAAAAAAAAAAA

FIGURE 114

MAPSGSLAVPLAVLVLLLWGAPWTHGRRSNVRVITDENWRELLEGDWMIEFYAPWCPACQNL
QPEWESFAEWGEDLEVNIAKVDVTEQPGLSGRFIITALPTIYHCKDGEFRRYQGPRTKKDFI
NFISDKEWKSIEPVSSWFGPGSVLMSSMSALFQLSMWIRTCHNYFIEDLGLPVWGSYTVFAL
ATLFSGLLLGLCMIFVADCLCPSKRRRPQPYPYPSKKLLSESAQPLKKVEEEQEADEEDVSE
EEAESKEGTNKDFPQNAIRQRSLGPSLATDKS

Signal sequence:
amino acids 1-26

Transmembrane domain:
amino acids 182-201

Casein kinase II phosphorylation site.
amino acids 68-72, 119-123, 128-132, 247-251, 257-261

Tyrosine kinase phosphorylation site.
amino acids 107-115

N-myristoylation site.
amino acids 20-26, 192-198

Amidation site.
amino acids 25-29

FIGURE 115

GCGAGTGTCCAGCTGCGGAGACCCGTGATAATTCGTTAACTAATTCAACAAACGGGACCCTT
CTGTGTGCCAGAAACCGCAAGCAGTTGCTAACCCAGTGGGACAGGCGGATTGGAAGAGCGGG
AAGGTCCTGGCCCAGAGCAGTGTGACACTTCCCTCTGTGACCATGAAACTCTGGGTGTCTGC
ATTGCTGATGGCCTGGTTTGGTGTCCTGAGCTGTGTGCAGGCCGAATTCTTCACCTCTATTG
GGCACATGACTGACCTGATTTATGCAGAGAAAGAGCTGGTGCAGTCTCTGAAAGAGTACATC
CTTGTGGAGGAAGCCAAGCTTTCCAAGATTAAGAGCTGGGCCAACAAAATGGAAGCCTTGAC
TAGCAAGTCAGCTGCTGATGCTGAGGGCTACCTGGCTCACCCTGTGAATGCCTACAAACTGG
TGAAGCGGCTAAACACAGACTGGCCTGCGCTGGAGGACCTTGTCCTGCAGGACTCAGCTGCA
GGTTTTATCGCCAACCTCTCTGTGCAGCGGCAGTTCTTCCCCACTGATGAGGACGAGATAGG
AGCTGCCAAAGCCCTGATGAGACTTCAGGACACATACAGGCTGGACCCAGGCACAATTTCCA
GAGGGGAACTTCCAGGAACCAAGTACCAGGCAATGCTGAGTGTGGATGACTGCTTTGGGATG
GGCCGCTCGGCCTACAATGAAGGGGACTATTATCATACGGTGTTGTGGATGGAGCAGGTGCT
AAAGCAGCTTGATGCCGGGGAGGAGGCCACCACAACCAAGTCACAGGTGCTGGACTACCTCA
GCTATGCTGTCTTCCAGTTGGGTGATCTGCACCGTGCCCTGGAGCTCACCCGCCGCCTGCTC
TCCCTTGACCCAAGCCACGAACGAGCTGGAGGGAATCTGCGGTACTTTGAGCAGTTATTGGA
GGAAGAGAGAGAAAAAACGTTAACAAATCAGACAGAAGCTGAGCTAGCAACCCCAGAAGGCA
TCTATGAGAGGCCTGTGGACTACCTGCCTGAGAGGGATGTTTACGAGAGCCTCTGTCGTGGG
GAGGGTGTCAAACTGACACCCCGTAGACAGAAGAGGCTTTTCTGTAGGTACCACCATGGCAA
CAGGGCCCCACAGCTGCTCATTGCCCCCTTCAAAGAGGAGGACGAGTGGGACAGCCCGCACA
TCGTCAGGTACTACGATGTCATGTCTGATGAGGAAATCGAGAGGATCAAGGAGATCGCAAAA
CCTAAACTTGCACGAGCCACCGTTCGTGATCCCAAGACAGGAGTCCTCACTGTCGCCAGCTA
CCGGGTTTCCAAAAGCTCCTGGCTAGAGGAAGATGATGACCCTGTTGTGGCCCGAGTAAATC
GTCGGATGCAGCATATCACAGGGTTAACAGTAAAGACTGCAGAATTGTTACAGGTTGCAAAT
TATGGAGTGGGAGGACAGTATGAACCGCACTTCGACTTCTCTAGGCGACCTTTTGACAGCGG
CCTCAAAACAGAGGGGAATAGGTTAGCGACGTTTCTTAACTACATGAGTGATGTAGAAGCTG
GTGGTGCCACCGTCTTCCCTGATCTGGGGGCTGCAATTTGGCCTAAGAAGGGTACAGCTGTG
TTCTGGTACAACCTCTTGCGGAGCGGGGAAGGTGACTACCGAACAAGACATGCTGCCTGCCC
TGTGCTTGTGGGCTGCAAGTGGGTCTCCAATAAGTGGTTCCATGAACGAGGACAGGAGTTCT
TGAGACCTTGTGGATCAACAGAAGTTGACTGACATCCTTTTCTGTCCTTCCCCTTCCTGGTC
CTTCAGCCCATGTCAACGTGACAGACACCTTTGTATGTTCCTTTGTATGTTCCTATCAGGCT
GATTTTTGGAGAAATGAATGTTTGTCTGGAGCAGAGGGAGACCATACTAGGGCGACTCCTGT
GTGACTGAAGTCCCAGCCCTTCCATTCAGCCTGTGCCATCCCTGGCCCCAAGGCTAGGATCA
AAGTGGCTGCAGCAGAGTTAGCTGTCTAGCGCCTAGCAAGGTGCCTTTGTACCTCAGGTGTT
TTAGGTGTGAGATGTTTCAGTGAACCAAAGTTCTGATACCTTGTTTACATGTTTGTTTTTAT
GGCATTTCTATCTATTGTGGCTTTACCAAAAAATAAAATGTCCCTACCAGAAAAAAAAAA

FIGURE 116

MKLWVSALLMAWFGVLSCVQAEFFTSIGHMTDLIYAEKELVQSLKEYILVEEAKLSKIKSWA
NKMEALTSKSAADAEGYLAHPVNAYKLVKRLNTDWPALEDLVLQDSAAGFIANLSVQRQFFP
TDEDEIGAAKALMRLQDTYRLDPGTISRGELPGTKYQAMLSVDDCFGMGRSAYNEGDYYHTV
LWMEQVLKQLDAGEEATTTKSQVLDYLSYAVFQLGDLHRALELTRRLLSLDPSHERAGGNLR
YFEQLLEEEREKTLTNQTEAELATPEGIYERPVDYLPERDVYESLCRGEGVKLTPRRQKRLF
CRYHHGNRAPQLLIAPFKEEDEWDSPHIVRYYDVMSDEEIERIKEIAKPKLARATVRDPKTG
VLTVASYRVSKSSWLEEDDDPVVARVNRRMQHITGLTVKTAELLQVANYGVGGQYEPHFDFS
RRPFDSGLKTEGNRLATFLNYMSDVEAGGATVFPDLGAAIWPKKGTAVFWYNLLRSGEGDYR
TRHAACPVLVGCKWVSNKWFHERGQEFLRPCGSTEVD

Signal sequence:

amino acids 1-17

N-glycosylation site.

amino acids 115-119, 264-268

Glycosaminoglycan attachment site.

amino acids 490-494 cAMP- and cGMP-dependent protein kinase phosphorylation site.

amino acids 477-481

Casein kinase II phosphorylation site.

amino acids 43-47, 72-76, 125-129, 151-155, 165-169, 266-270, 346-350, 365-369, 385-389, 457-461, 530-534

Tyrosine kinase phosphorylation site.

amino acids 71-80, 489-496

N-myristoylation site.

amino acids 14-20, 131-137, 171-177, 446-452

Prokaryotic membrane lipoprotein lipid attachment site.

amino acids 8-19

Leucine zipper pattern.

amino acids 213-235

FIGURE 117

GCAGTATTGAGTTTTACTTCCTCCTCTTTTTAGTGGAAGACAGACCATAATCCCAGTGTGAGTGAAATTGATTGT
TTCATTTATTACCGTTTTGGCTGGGGGTTAGTTCCGACACCTTCACAGTTGAAGAGCAGGCAGAAGGAGTTGTGA
AGACAGGACAATCTTCTTGGGGATGCTGGTCCTGGAAGCCAGCGGGCCTTGCTCTGTCTTTGGCCTCATTGACCC
CAGGTTCTCTGGTTAAAACTGAAAGCCTACTACTGGCCTGGTGCCCATCAATCCATTGATCCTTGAGGCTGTGCC
CCTGGGGCACCCACCTGGCAGGGCCTACCACCATGCGACTGAGCTCCCTGTTGGCTCTGCTGCGGCCAGCGCTTC
CCCTCATCTTAGGGCTGTCTCTGGGGTGCAGCCTGAGCCTCCTGCGGGTTTCCTGGATCCAGGGGGAGGGAGAAG
ATCCCTGTGTCGAGGCTGTAGGGGAGCGAGGAGGGCCACAGAATCCAGATTCGAGAGCTCGGCTAGACCAAAGTG
ATGAAGACTTCAAACCCCGGATTGTCCCCTACTACAGGGACCCCAACAAGCCCTACAAGAAGGTGCTCAGGACTC
GGTACATCCAGACAGAGCTGGGCTCCCGTGAGCGGTTGCTGGTGGCTGTCCTGACCTCCCGAGCTACACTGTCCA
CTTTGGCCGTGGCTGTGAACCGTACGGTGGCCCATCACTTCCCTCGGTTACTCTACTTCACTGGGCAGCGGGGGG
CCCGGGCTCCAGCAGGGATGCAGGTGGTGTCTCATGGGGATGAGCGGCCCGCCTGGCTCATGTCAGAGACCCTGC
GCCACCTTCACACACACTTTGGGGCCGACTACGACTGGTTCTTCATCATGCAGGATGACACATATGTGCAGGCCC
CCCGCCTGGCAGCCCTTGCTGGCCACCTCAGCATCAACCAAGACCTGTACTTAGGCCGGGCAGAGGAGTTCATTG
GCGCAGGCGAGCAGGCCCGGTACTGTCATGGGGGCTTTGGCTACCTGTTGTCACGGAGTCTCCTGCTTCGTCTGC
GGCCACATCTGGATGGCTGCCGAGGAGACATTCTCAGTGCCCGTCCTGACGAGTGGCTTGGACGCTGCCTCATTG
ACTCTCTGGGCGTCGGCTGTGTCTCACAGCACCAGGGGCAGCAGTATCGCTCATTTGAACTGGCCAAAAATAGGG
ACCCTGAGAAGGAAGGGAGCTCGGCTTTCCTGAGTGCCTTCGCCGTGCACCCTGTCTCCGAAGGTACCCTCATGT
ACCGGCTCCACAAACGCTTCAGCGCTCTGGAGTTGGAGCGGGCTTACAGTGAAATAGAACAACTGCAGGCTCAGA
TCCGGAACCTGACCGTGCTGACCCCCGAAGGGGAGGCAGGGCTGAGCTGGCCCGTTGGGCTCCCTGCTCCTTTCA
CACCACACTCTCGCTTTGAGGTGCTGGGCTGGGACTACTTCACAGAGCAGCACACCTTCTCCTGTGCAGATGGGG
CTCCCAAGTGCCCACTACAGGGGGCTAGCAGGGCGGACGTGGGTGATGCGTTGGAGACTGCCCTGGAGCAGCTCA
ATCGGCGCTATCAGCCCCGCCTGCGCTTCCAGAAGCAGCGACTGCTCAACGGCTATCGGCGCTTCGACCCAGCAC
GGGGCATGGAGTACACCCTGGACCTGCTGTTGGAATGTGTGACACAGCGTGGGCACCGGCGGGCCCTGGCTCGCA
GGGTCAGCCTGCTGCGGCCACTGAGCCGGGTGGAAATCCTACCTATGCCCTATGTCACTGAGGCCACCCGAGTGC
AGCTGGTGCTGCCACTCCTGGTGGCTGAAGCTGCTGCAGCCCCGGCTTTCCTCGAGGCGTTTGCAGCCAATGTCC
TGGAGCCACGAGAACATGCATTGCTCACCCTGTTGCTGGTCTACGGGCCACGAGAAGGTGGCCGTGGAGCTCCAG
ACCCATTTCTTGGGGTGAAGGCTGCAGCAGCGGAGTTAGAGCGACGGTACCCTGGGACGAGGCTGGCCTGGCTCG
CTGTGCGAGCAGAGGCCCCTTCCCAGGTGCGACTCATGGACGTGGTCTCGAAGAAGCACCCTGTGGACACTCTCT
TCTTCCTTACCACCGTGTGGACAAGGCCTGGGCCCGAAGTCCTCAACCGCTGTCGCATGAATGCCATCTCTGGCT
GGCAGGCCTTCTTTCCAGTCCATTTCCAGGAGTTCAATCCTGCCCTGTCACCACAGAGATCACCCCCAGGGCCCC
CGGGGGCTGGCCCTGACCCCCCCTCCCCTCCTGGTGCTGACCCCTCCCGGGGGGCTCCTATAGGGGGGAGATTTG
ACCGGCAGGCTTCTGCGGAGGGCTGCTTCTACAACGCTGACTACCTGGCGGCCCGAGCCCGGCTGGCAGGTGAAC
TGGCAGGCCAGGAAGAGGAGGAAGCCCTGGAGGGGCTGGAGGTGATGGATGTTTTCCTCCGGTTCTCAGGGCTCC
ACCTCTTTCGGGCCGTAGAGCCAGGGCTGGTGCAGAAGTTCTCCCTGCGAGACTGCAGCCCACGGCTCAGTGAAG
AACTCTACCACCGCTGCCGCCTCAGCAACCTGGAGGGGCTAGGGGGCCGTGCCCAGCTGGCTATGGCTCTCTTTG
AGCAGGAGCAGGCCAATAGCACTTAGCCCGCCTGGGGGCCCTAACCTCATTACCTTTCCTTTGTCTGCCTCAGCC
CCAGGAAGGGCAAGGCAAGATGGTGGACAGATAGAGAATTGTTGCTGTATTTTTTAAATATGAAAATGTTATTAA
ACATGTCTTCTGCC

FIGURE 118

MRLSSLLALLRPALPLILGLSLGCSLSLLRVSWIQGEGEDPCVEAVGERGGPQNPDSRARLD
QSDEDFKPRIVPYYRDPNKPYKKVLRTRYIQTELGSRERLLVAVLTSRATLSTLAVAVNRTV
AHHFPRLLYFTGQRGARAPAGMQVVSHGDERPAWLMSETLRHLHTHFGADYDWFFIMQDDTY
VQAPRLAALAGHLSINQDLYLGRAEEFIGAGEQARYCHGGFGYLLSRSLLLRLRPHLDGCRG
DILSARPDEWLGRCLIDSLGVGCVSQHQGQQYRSFELAKNRDPEKEGSSAFLSAFAVHPVSE
GTLMYRLHKRFSALELERAYSEIEQLQAQIRNLTVLTPEGEAGLSWPVGLPAPFTPHSRFEV
LGWDYFTEQHTFSCADGAPKCPLQGASRADVGDALETALEQLNRRYQPRLRFQKQRLLNGYR
RFDPARGMEYTLDLLLECVTQRGHRRALARRVSLLRPLSRVEILPMPYVTEATRVQLVLPLL
VAEAAAAPAFLEAFAANVLEPREHALLTLLLVYGPREGGRGAPDPFLGVKAAAAELERRYPG
TRLAWLAVRAEAPSQVRLMDVVSKKHPVDTLFFLTTVWTRPGPEVLNRCRMNAISGWQAFFP
VHFQEFNPALSPQRSPPGPPGAGPDPPSPPGADPSRGAPIGGRFDRQASAEGCFYNADYLAA
RARLAGELAGQEEEEALEGLEVMDVFLRFSGLHLFRAVEPGLVQKFSLRDCSPRLSEELYHR
CRLSNLEGLGGRAQLAMALFEQEQANST

Signal sequence:

amino acids 1-15

Transmembrane domain:

amino acids 489-507

N-glycosylation site.

amino acids 121-125, 342-346 cAMP- and cGMP-dependent protein kinase phosphorylation site.

amino acids 319-323, 464-468

Casein kinase II phosphorylation site.

amino acids 64-68, 150-154, 322-326, 331-337, 368-372, 385-389, 399-403, 409-413, 473-477, 729-733, 748-752

Tyrosine kinase phosphorylation site.

amino acids 736-743

N-myristoylation site.

amino acids 19-25, 23-29, 136-142, 397-403, 441-447, 544-550, 558-564, 651-657, 657-663, 672-678

Prokaryotic membrane lipoprotein lipid attachment site.

amino acids 14-25

Cell attachment sequence.

amino acids 247-250

FIGURE 119

CGGAGTGGTGCGCCAACGTGAGAGGAAACCCGTGCGCGGCTGCGCTTTCCTGTCCCCAAGCC
GTTCTAGACGCGGGAAAAATGCTTTCTGAAAGCAGCTCCTTTTTGAAGGGTGTGATGCTTGG
AAGCATTTTCTGTGCTTTGATCACTATGCTAGGACACATTAGGATTGGTCATGGAAATAGAA
TGCACCACCATGAGCATCATCACCTACAAGCTCCTAACAAAGAAGATATCTTGAAAATTTCA
GAGGATGAGCGCATGGAGCTCAGTAAGAGCTTTCGAGTATACTGTATTATCCTTGTAAAACC
CAAAGATGTGAGTCTTTGGGCTGCAGTAAAGGAGACTTGGACCAAACACTGTGACAAAGCAG
AGTTCTTCAGTTCTGAAAATGTTAAAGTGTTTGAGTCAATTAATATGGACACAAATGACATG
TGGTTAATGATGAGAAAAGCTTACAAATACGCCTTTGATAAGTATAGAGACCAATACAACTG
GTTCTTCCTTGCACGCCCCACTACGTTTGCTATCATTGAAAACCTAAAGTATTTTTTGTTAA
AAAAGGATCCATCACAGCCTTTCTATCTAGGCCACACTATAAAATCTGGAGACCTTGAATAT
GTGGGTATGGAAGGAGGAATTGTCTTAAGTGTAGAATCAATGAAAAGACTTAACAGCCTTCT
CAATATCCCAGAAAAGTGTCCTGAACAGGGAGGGATGATTTGGAAGATATCTGAAGATAAAC
AGCTAGCAGTTTGCCTGAAATATGCTGGAGTATTTGCAGAAAATGCAGAAGATGCTGATGGA
AAAGATGTATTTAATACCAAATCTGTTGGGCTTTCTATTAAAGAGGCAATGACTTATCACCC
CAACCAGGTAGTAGAAGGCTGTTGTTCAGATATGGCTGTTACTTTTAATGGACTGACTCCAA
ATCAGATGCATGTGATGATGTATGGGGTATACCGCCTTAGGGCATTTGGGCATATTTTCAAT
GATGCATTGGTTTTCTTACCTCCAAATGGTTCTGACAATGACTGAGAAGTGGTAGAAAAGCG
TGAATATGATCTTTGTATAGGACGTGTGTTGTCATTATTTGTAGTAGTAACTACATATCCAA
TACAGCTGTATGTTTCTTTTTCTTTTCTAATTTGGTGGCACTGGTATAACCACACATTAAAG
TCAGTAGTACATTTTTAAATGAGGGTGGTTTTTTTCTTTAAAACACATGAACATTGTAAATG
TGTTGGAAAGAAGTGTTTTAAGAATAATAATTTTGCAAATAAACTATTAATAAATATTATAT
GTGATAAATTCTAAATTATGAACATTAGAAATCTGTGGGGCACATATTTTTGCTGATTGGTT
AAAAAATTTTAACAGGTCTTTAGCGTTCTAAGATATGCAAATGATATCTCTAGTTGTGAATT
TGTGATTAAAGTAAAACTTTTAGCTGTGTGTTCCCTTTACTTCTAATACTGATTTATGTTCT
AAGCCTCCCCAAGTTCCAATGGATTTGCCTTCTCAAAATGTACAACTAAGCAACTAAAGAAA
ATTAAAGTGAAAGTTGAAAAAT

FIGURE 120

MLSESSSFLKGVMLGSIFCALITMLGHIRIGHGNRMHHHEHHHLQAPNKEDILKISEDERME
LSKSFRVYCIILVKPKDVSLWAAVKETWTKHCDKAEFFSSENVKVFESINMDTNDMWLMMRK
AYKYAFDKYRDQYNWFFLARPTTFAIIENLKYFLLKKDPSQPFYLGHTIKSGDLEYVGMEGG
IVLSVESMKRLNSLLNIPEKCPEQGGMIWKISEDKQLAVCLKYAGVFAENAEDADGKDVFNT
KSVGLSIKEAMTYHPNQVVEGCCSDMAVTFNGLTPNQMHVMMYGVYRLRAFGHIFNDALVFL
PPNGSDND

Signal sequence:
amino acids 1-33

N-glycosylation site.
amino acids 121-125, 342-346 cAMP- and cGMP-dependent protein kinase phosphorylation site.
amino acids 319-323, 464-468

Casein kinase II phosphorylation site.
amino acids 64-132, 150-154, 322-326, 331-335, 368-372, 385-389, 399-403, 409-413, 473-477, 729-733, 748-752

Tyrosine kinase phosphorylation site.
amino acids 736-743

N-myristoylation site.
amino acids 19-25, 23-29, 136-142, 397-403, 441-447, 544-550, 558-564, 651-657, 657-663, 672-672

Prokaryotic membrane lipoprotein lipid attachment site.
amino acids 14-25

Cell attachment sequence.
amino acids 247-250

FIGURE 121

CCCACGCGTCCGATCTTACCAACAAAACACTCCTGAGGAGAAAGAAAGAGAGGGAGGGAGAG
AAAAAGAGAGAGAGAGAAACAAAAAACCAAAGAGAGAGAAAAAATGAATTCATCTAAATCAT
CTGAAACACAATGCACAGAGAGAGGATGCTTCTCTTCCCAAATGTTCTTATGGACTGTTGCT
GGGATCCCCATCCTATTTCTCAGTGCCTGTTTCATCACCAGATGTGTTGTGACATTTCGCAT
CTTTCAAACCTGTGATGAGAAAAAGTTTCAGCTACCTGAGAATTTCACAGAGCTCTCCTGCT
ACAATTATGGATCAGGTTCAGTCAAGAATTGTTGTCCATTGAACTGGGAATATTTTCAATCC
AGCTGCTACTTCTTTTCTACTGACACCATTTCCTGGGCGTTAAGTTTAAAGAACTGCTCAGC
CATGGGGGCTCACCTGGTGGTTATCAACTCACAGGAGGAGCAGGAATTCCTTTCCTACAAGA
AACCTAAAATGAGAGAGTTTTTTATTGGACTGTCAGACCAGGTTGTCGAGGGTCAGTGGCAA
TGGGTGGACGGCACACCTTTGACAAAGTCTCTGAGCTTCTGGGATGTAGGGGAGCCCAACAA
CATAGCTACCCTGGAGGACTGTGCCACCATGAGAGACTCTTCAAACCCAAGGCAAAATTGGA
ATGATGTAACCTGTTTCCTCAATTATTTTCGGATTTGTGAAATGGTAGGAATAAATCCTTTG
AACAAAGGAAAATCTCTTTAAGAACAGAAGGCACAACTCAAATGTGTAAAGAAGGAAGAGCA
AGAACATGGCCACACCCACCGCCCCACACGAGAAATTTGTGCGCTGAACTTCAAAGGACTTC
ATAAGTATTTGTTACTCTGATACAAATAAAAATAAGTAGTTTTAAATGTTAAAAAAAAAAAA
AAAAAAAAAAAAAAAAAAAAAAAAAAAAAAAAAAAAAAAAAAAAAAAAAAAAAAAAAAAAAA
AAAAA

FIGURE 122

MNSSKSSETQCTERGCFSSQMFLWTVAGIPILFLSACFITRCVVTFRIFQTCDEKKFQLPEN
FTELSCYNYGSGSVKNCCPLNWEYFQSSCYFFSTDTISWALSLKNCSAMGAHLVVINSQEEQ
EFLSYKKPKMREFFIGLSDQVVEGQWQWVDGTPLTKSLSFWDVGEPNNIATLEDCATMRDSS
NPRQNWNDVTCFLNYFRICEMVGINPLNKGKSL

Signal sequence:

amino acids 1-42

N-glycosylation site.

amino acids 2-6, 62-66, 107-111

Casein kinase II phosphorylation site.

amino acids 51-55, 120-124, 163-167, 175-179, 181-185

N-myristoylation site.

amino acids 15-21, 74-80, 155-161

Prokaryotic membrane lipoprotein lipid attachment site.

amino acids 27-38

FIGURE 123

GGGACTACAAGCCGCGCCGCGCTGCCGCTGGCCCCTCAGCAACCCTCGACATGGCGCTGAGGCGGCCACCGCGAC
TCCGGCTCTGCGCTCGGCTGCCTGACTTCTTCCTGCTGCTGCTTTTCAGGGGCTGCCTGATAGGGGCTGTAAATC
TCAAATCCAGCAATCGAACCCCAGTGGTACAGGAATTTGAAAGTGTGGAACTGTCTTGCATCATTACGGATTCGC
AGACAAGTGACCCCAGGATCGAGTGGAAGAAAATTCAAGATGAACAAACCACATATGTGTTTTTTGACAACAAAA
TTCAGGGAGACTTGGCGGGTCGTGCAGAAATACTGGGGAAGACATCCCTGAAGATCTGGAATGTGACACGGAGAG
ACTCAGCCCTTTATCGCTGTGAGGTCGTTGCTCGAAATGACCGCAAGGAAATTGATGAGATTGTGATCGAGTTAA
CTGTGCAAGTGAAGCCAGTGACCCCTGTCTGTAGAGTGCCGAAGGCTGTACCAGTAGGCAAGATGGCAACACTGC
ACTGCCAGGAGAGTGAGGGCCACCCCCGGCCTCACTACAGCTGGTATCGCAATGATGTACCACTGCCCACGGATT
CCAGAGCCAATCCCAGATTTCGCAATTCTTCTTTCCACTTAAACTCTGAAACAGGCACTTTGGTGTTCACTGCTG
TTCACAAGGACGACTCTGGGCAGTACTACTGCATTGCTTCCAATGACGCAGGCTCAGCCAGGTGTGAGGAGCAGG
AGATGGAAGTCTATGACCTGAACATTGGCGGAATTATTGGGGGGGTTCTGGTTGTCCTTGCTGTACTGGCCCTGA
TCACGTTGGGCATCTGCTGTGCATACAGACGTGGCTACTTCATCAACAATAAACAGGATGGAGAAAGTTACAAGA
ACCCAGGGAAACCAGATGGAGTTAACTACATCCGCACTGACGAGGAGGGCGACTTCAGACACAAGTCATCGTTTG
TGATCTGAGACCCGCGGTGTGGCTGAGAGCGCACAGAGCGCACGTGCACATACCTCTGCTAGAAACTCCTGTCAA
GGCAGCGAGAGCTGATGCACTCGGACAGAGCTAGACACTCATTCAGAAGCTTTTCGTTTTGGCCAAAGTTGACCA
CTACTCTTCTTACTCTAACAAGCCACATGAATAGAAGAATTTTCCTCAAGATGGACCCGGTAAATATAACCACAA
GGAAGCGAAACTGGGTGCGTTCACTGAGTTGGGTTCCTAATCTGTTTCTGGCCTGATTCCCGCATGAGTATTAGG
GTGATCTTAAAGAGTTTGCTCACGTAAACGCCCGTGCTGGGCCCTGTGAAGCCAGCATGTTCACCACTGGTCGTT
CAGCAGCCACGACAGCACCATGTGAGATGGCGAGGTGGCTGGACAGCACCAGCAGCGCATCCCGGCGGGAACCCA
GAAAAGGCTTCTTACACAGCAGCCTTACTTCATCGGCCCACAGACACCACCGCAGTTTCTTCTTAAAGGCTCTGC
TGATCGGTGTTGCAGTGTCCATTGTGGAGAAGCTTTTTGGATCAGCATTTTGTAAAAACAACCAAAATCAGGAAG
GTAAATTGGTTGCTGGAAGAGGGATCTTGCCTGAGGAACCCTGCTTGTCCAACAGGGTGTCAGGATTTAAGGAAA
ACCTTCGTCTTAGGCTAAGTCTGAAATGGTACTGAAATATGCTTTTCTATGGGTCTTGTTTATTTTATAAAATTT
TACATCTAAATTTTTGCTAAGGATGTATTTTGATTATTGAAAAGAAAATTTCTATTTAAACTGTAAATATATTGT
CATACAATGTTAAATAACCTATTTTTTTAAAAAAGTTCAACTTAAGGTAGAAGTTCCAAGCTACTAGTGTTAAAT
TGGAAAATATCAATAATTAAGAGTATTTTACCCAAGGAATCCTCTCATGGAAGTTTACTGTGATGTTCCTTTTCT
CACACAAGTTTTAGCCTTTTTCACAAGGGAACTCATACTGTCTACACATCAGACCATAGTTGCTTAGGAAACCTT
TAAAAATTCCAGTTAAGCAATGTTGAAATCAGTTTGCATCTCTTCAAAAGAAACCTCTCAGGTTAGCTTTGAACT
GCCTCTTCCTGAGATGACTAGGACAGTCTGTACCCAGAGGCCACCCAGAAGCCCTCAGATGTACATACACAGATG
CCAGTCAGCTCCTGGGGTTGCGCCAGGCGCCCCCGCTCTAGCTCACTGTTGCCTCGCTGTCTGCCAGGAGGCCCT
GCCATCCTTGGGCCCTGGCAGTGGCTGTGTCCCAGTGAGCTTTACTCACGTGGCCCTTGCTTCATCCAGCACAGC
TCTCAGGTGGGCACTGCAGGGACACTGGTGTCTTCCATGTAGCGTCCCAGCTTTGGGCTCCTGTAACAGACCTCT
TTTTGGTTATGGATGGCTCACAAAATAGGGCCCCCAATGCTATTTTTTTTTTTTAAGTTTGTTTAATTATTTGTT
AAGATTGTCTAAGGCCAAAGGCAATTGCGAAATCAAGTCTGTCAAGTACAATAACATTTTTAAAAGAAAATGGAT
CCCACTGTTCCTCTTTGCCACAGAGAAAGCACCCAGACGCCACAGGCTCTGTCGCATTTCAAAACAAACCATGAT
GGAGTGGCGGCCAGTCCAGCCTTTTAAAGAACGTCAGGTGGAGCAGCCAGGTGAAAGGCCTGGCGGGGAGGAAAG
TGAAACGCCTGAATCAAAAGCAGTTTTCTAATTTTGACTTTAAATTTTTCATCCGCCGGAGACACTGCTCCCATT
TGTGGGGGACATTAGCAACATCACTCAGAAGCCTGTGTTCTTCAAGAGCAGGTGTTCTCAGCCTCACATGCCCT
GCCGTGCTGGACTCAGGACTGAAGTGCTGTAAAGCAAGGAGCTGCTGAGAAGGAGCACTCCACTGTGTGCCTGGA
GAATGGCTCTCACTACTCACCTTGTCTTTCAGCTTCCAGTGTCTTGGGTTTTTTATACTTTGACAGCTTTTTTTT
AATTGCATACATGAGACTGTGTTGACTTTTTTTAGTTATGTGAAACACTTTGCCGCAGGCCGCCTGGCAGAGGCA
GGAAATGCTCCAGCAGTGGCTCAGTGCTCCCTGGTGTCTGCTGCATGGCATCCTGGATGCTTAGCATGCAAGTTC
CCTCCATCATTGCCACCTTGGTAGAGAGGGATGGCTCCCCACCCTCAGCGTTGGGGATTCACGCTCCAGCCTCCT
TCTTGGTTGTCATAGTGATAGGGTAGCCTTATTGCCCCCTCTTCTTATACCCTAAAACCTTCTACACTAGTGCCA
TGGGAACCAGGTCTGAAAAAGTAGAGAGAAGTGAAAGTAGAGTCTGGGAAGTAGCTGCCTATAACTGAGACTAGA
CGGAAAAGGAATACTCGTGTATTTTAAGATATGAATGTGACTCAAGACTCGAGGCCGATACGAGGCTGTGATTCT
GCCTTTGGATGGATGTTGCTGTACACAGATGCTACAGACTTGTACTAACACACCGTAATTTGGCATTTGTTTAAC
CTCATTTATAAAAGCTTCAAAAAAACCCA

FIGURE 124

></usr/seqdb2/sst/DNA/Dnaseqs.min/ss.DNA77624

><subunit 1 of 1, 310 aa, 1 stop

><MW: 35020, pI: 7.90, NX(S/T): 3

MALRRPPRLRLCARLPDFFLLLLFRGCLIGAVNLKSSNRTPVVQEFESVELSCIITDSQTSD
PRIEWKKIQDEQTTYVFFDNKIQGDLAGRAEILGKTSLKIWNVTRRDSALYRCEVVARNDRK
EIDEIVIELTVQVKPVTPVCRVPKAVPVGKMATLHCQESEGHPRPHYSWYRNDVPLPTDSRA
NPRFRNSSFHLNSETGTLVFTAVHKDDSGQYYCIASNDAGSARCEEQEMEVYDLNIGG[illegible]IGG
VLVVLAVLALITLGICCAYRRGYFINNKQDGESYKNPGKPDGVNYIRTDEEGDFRHKSSFVI

Important features of the protein:

Signal peptide:

amino acids 1-30

Transmembrane domain:

amino acids 243-263

N-glycosylation sites.

amino acids 104-107, 192-195 cAMP- and cGMP-dependent protein kinase phosphorylation site.

amino acids 107-110

Casein kinase II phosphorylation site.

amino acids 106-109, 296-299

Tyrosine kinase phosphorylation site.

amino acids 69-77

N-myristoylation sites.

amino acids 26-31, 215-220, 226-231, 243-248, 244-249, 262-267

SEQUENCE LISTING

<160> NUMBER OF SEQ ID NOS: 423

<210> SEQ ID NO 1
<211> LENGTH: 1825
<212> TYPE: DNA
<213> ORGANISM: Homo sapiens

<400> SEQUENCE: 1
actgcacctc ggttctatcg attgaattcc ccggggatcc tctagagatc cctcgacctc 60
gacccacgcg tccgggccgg agcagcacgg ccgcaggacc tggagctccg gctgcgtctt 120
cccgcagcgc tacccgccat gcgcctgccg cgccgggccg cgctggggct cctgccgctt 180
ctgctgctgc tgccgcccgc gccggaggcc gccaagaagc cgacgccctg ccaccggtgc 240
cgggggctgg tggacaagtt taaccagggg atggtggaca ccgcaaagaa gaactttggc 300
ggcgggaaca cggcttggga ggaaaagacg ctgtccaagt acgagtccag cgagattcgc 360
ctgctggaga tcctggaggg gctgtgcgag agcagcgact tcgaatgcaa tcagatgcta 420
gaggcgcagg aggagcacct ggaggcctgg tggctgcagc tgaagagcga atatcctgac 480
ttattcgagt ggttttgtgt gaagacactg aaagtgtgct gctctccagg aacctacggt 540
cccgactgtc tcgcatgcca gggcggatcc cagaggccct gcagcgggaa tggccactgc 600
agcggagatg ggagcagaca gggcgacggg tcctgccggt gccacatggg gtaccagggc 660
ccgctgtgca ctgactgcat ggacggctac ttcagctcgc tccggaacga gacccacagc 720
atctgcacag cctgtgacga gtcctgcaag acgtgctcgg gcctgaccaa cagagactgc 780
ggcgagtgtg aagtgggctg ggtgctggac gagggcgcct gtgtggatgt ggacgagtgt 840
gcggccgagc cgcctccctg cagcgctgcg cagttctgta agaacgccaa cggctcctac 900
acgtgcgaag agtgtgactc cagctgtgtg ggctgcacag gggaaggccc aggaaactgt 960
aaagagtgta tctctggcta cgcgagggag cacggacagt gtgcagatgt ggacgagtgc 1020
tcactagcag aaaaaacctg tgtgaggaaa aacgaaaact gctacaatac tccagggagc 1080
tacgtctgtg tgtgtcctga cggcttcgaa gaaacggaag atgcctgtgt gccgccggca 1140
gaggctgaag ccacagaagg agaaagcccg acacagctgc cctcccgcga agacctgtaa 1200
tgtgccggac ttaccctta aattattcag aaggatgtcc cgtggaaaat gtggccctga 1260
ggatgccgtc tcctgcagtg gacagcggcg gggagaggct gcctgctctc taacggttga 1320
ttctcatttg tcccttaaac agctgcattt cttggttgtt cttaaacaga cttgtatatt 1380
ttgatacagt tctttgtaat aaaattgacc attgtaggta atcaggagga aaaaaaaaaa 1440
aaaaaaaaaa aaagggcggc cgcgactcta gagtcgacct gcagaagctt ggccgccatg 1500
gcccaacttg tttattgcag cttataatgg ttacaaataa agcaatagca tcacaaattt 1560
cacaaataaa gcattttttt cactgcattc tagttgtggt ttgtccaaac tcatcaatgt 1620

-continued

```
atcttatcat gtctggatcg ggaattaatt cggcgcagca ccatggcctg aaataacctc   1680

tgaaagagga acttggttag gtaccttctg aggcggaaag aaccagctgt ggaatgtgtg   1740

tcagttaggg tgtggaaagt ccccaggctc cccagcaggc agaagtatgc aagcatgcat   1800

ctcaattagt cagcaaccca gtttt                                         1825


<210> SEQ ID NO 2
<211> LENGTH: 353
<212> TYPE: PRT
<213> ORGANISM: Homo sapiens

<400> SEQUENCE: 2

Met Arg Leu Pro Arg Arg Ala Ala Leu Gly Leu Leu Pro Leu Leu Leu
1               5                   10                  15

Leu Leu Pro Pro Ala Pro Glu Ala Ala Lys Lys Pro Thr Pro Cys His
            20                  25                  30

Arg Cys Arg Gly Leu Val Asp Lys Phe Asn Gln Gly Met Val Asp Thr
        35                  40                  45

Ala Lys Lys Asn Phe Gly Gly Gly Asn Thr Ala Trp Glu Glu Lys Thr
    50                  55                  60

Leu Ser Lys Tyr Glu Ser Ser Glu Ile Arg Leu Leu Glu Ile Leu Glu
65                  70                  75                  80

Gly Leu Cys Glu Ser Ser Asp Phe Glu Cys Asn Gln Met Leu Glu Ala
                85                  90                  95

Gln Glu Glu His Leu Glu Ala Trp Trp Leu Gln Leu Lys Ser Glu Tyr
            100                 105                 110

Pro Asp Leu Phe Glu Trp Phe Cys Val Lys Thr Leu Lys Val Cys Cys
        115                 120                 125

Ser Pro Gly Thr Tyr Gly Pro Asp Cys Leu Ala Cys Gln Gly Gly Ser
    130                 135                 140

Gln Arg Pro Cys Ser Gly Asn Gly His Cys Ser Gly Asp Gly Ser Arg
145                 150                 155                 160

Gln Gly Asp Gly Ser Cys Arg Cys His Met Gly Tyr Gln Gly Pro Leu
                165                 170                 175

Cys Thr Asp Cys Met Asp Gly Tyr Phe Ser Ser Leu Arg Asn Glu Thr
            180                 185                 190

His Ser Ile Cys Thr Ala Cys Asp Glu Ser Cys Lys Thr Cys Ser Gly
        195                 200                 205

Leu Thr Asn Arg Asp Cys Gly Glu Cys Glu Val Gly Trp Val Leu Asp
    210                 215                 220

Glu Gly Ala Cys Val Asp Val Asp Glu Cys Ala Ala Glu Pro Pro Pro
225                 230                 235                 240

Cys Ser Ala Ala Gln Phe Cys Lys Asn Ala Asn Gly Ser Tyr Thr Cys
                245                 250                 255

Glu Glu Cys Asp Ser Ser Cys Val Gly Cys Thr Gly Glu Gly Pro Gly
            260                 265                 270

Asn Cys Lys Glu Cys Ile Ser Gly Tyr Ala Arg Glu His Gly Gln Cys
        275                 280                 285

Ala Asp Val Asp Glu Cys Ser Leu Ala Glu Lys Thr Cys Val Arg Lys
    290                 295                 300

Asn Glu Asn Cys Tyr Asn Thr Pro Gly Ser Tyr Val Cys Val Cys Pro
305                 310                 315                 320

Asp Gly Phe Glu Glu Thr Glu Asp Ala Cys Val Pro Pro Ala Glu Ala
                325                 330                 335
```

-continued

Glu Ala Thr Glu Gly Glu Ser Pro Thr Gln Leu Pro Ser Arg Glu Asp
340 345 350

Leu

<210> SEQ ID NO 3
<211> LENGTH: 2206
<212> TYPE: DNA
<213> ORGANISM: Homo sapiens

<400> SEQUENCE: 3
caggtccaac tgcacctcgg ttctatcgat tgaattcccc ggggatcctc tagagatccc 60
tcgacctcga cccacgcgtc cgccaggccg ggaggcgacg cgcccagccg tctaaacggg 120
aacagccctg gctgagggag ctgcagcgca gcagagtatc tgacggcgcc aggttgcgta 180
ggtgcggcac gaggagtttt cccggcagcg aggaggtcct gagcagcatg gcccggagga 240
gcgccttccc tgccgccgcg ctctggctct ggagcatcct cctgtgcctg ctggcactgc 300
gggcggaggc cgggccgccg caggaggaga gcctgtacct atggatcgat gctcaccagg 360
caagagtact cataggattt gaagaagata tcctgattgt ttcagagggg aaaatggcac 420
cttttacaca tgatttcaga aaagcgcaac agagaatgcc agctattcct gtcaatatcc 480
attccatgaa ttttacctgg caagctgcag ggcaggcaga atacttctat gaattcctgt 540
ccttgcgctc cctggataaa ggcatcatgg cagatccaac cgtcaatgtc cctctgctgg 600
gaacagtgcc tcacaaggca tcagttgttc aagttggttt cccatgtctt ggaaaacagg 660
atggggtggc agcatttgaa gtggatgtga ttgttatgaa ttctgaaggc aacaccattc 720
tccaaacacc tcaaaatgct atcttcttta aaacatgtca acaagctgag tgcccaggcg 780
ggtgccgaaa tggaggcttt tgtaatgaaa gacgcatctg cgagtgtcct gatgggttcc 840
acggacctca ctgtgagaaa gccctttgta ccccacgatg tatgaatggt ggactttgtg 900
tgactcctgg tttctgcatc tgcccacctg gattctatgg agtgaactgt gacaaagcaa 960
actgctcaac cacctgcttt aatggaggga cctgtttcta ccctggaaaa tgtatttgcc 1020
ctccaggact agagggagag cagtgtgaaa tcagcaaatg cccacaaccc tgtcgaaatg 1080
gaggtaaatg cattggtaaa agcaaatgta agtgttccaa aggttaccag ggagacctct 1140
gttcaaagcc tgtctgcgag cctggctgtg gtgcacatgg aacctgccat gaacccaaca 1200
aatgccaatg tcaagaaggt tggcatggaa gacactgcaa taaaaggtac gaagccagcc 1260
tcatacatgc cctgaggcca gcaggcgccc agctcaggca gcacacgcct tcacttaaaa 1320
aggccgagga gcggcgggat ccacctgaat ccaattacat ctggtgaact ccgacatctg 1380
aaacgtttta agttacacca agttcatagc ctttgttaac ctttcatgtg ttgaatgttc 1440
aaataatgtt cattacactt aagaatactg gcctgaattt tattagcttc attataaatc 1500
actgagctga tatttactct tccttttaag ttttctaagt acgtctgtag catgatggta 1560
tagattttct tgtttcagtg ctttgggaca gattttatat tatgtcaatt gatcaggtta 1620
aaattttcag tgtgtagttg gcagatattt tcaaaattac aatgcattta tggtgtctgg 1680
gggcagggga acatcagaaa ggttaaattg ggcaaaaatg cgtaagtcac aagaatttgg 1740
atggtgcagt taatgttgaa gttacagcat ttcagatttt attgtcagat atttagatgt 1800
ttgttacatt tttaaaaatt gctcttaatt tttaaactct caatacaata tattttgacc 1860
ttaccattat tccagagatt cagtattaaa aaaaaaaaaa ttacactgtg gtagtggcat 1920
ttaaacaata taatatattc taaacacaat gaaataggga atataatgta tgaacttttt 1980

-continued

```
gcattggctt gaagcaatat aatatattgt aaacaaaaca cagctcttac ctaataaaca   2040

ttttatactg tttgtatgta taaaataaag gtgctgcttt agtttttttgg aaaaaaaaaa   2100

aaaaaaaaaa aaaaaaaaaa aaaaaaaaaa gggcggccgc gactctagag tcgacctgca   2160

gaagcttggc cgccatggcc caacttgttt attgcagctt ataatg                   2206


<210> SEQ ID NO 4
<211> LENGTH: 379
<212> TYPE: PRT
<213> ORGANISM: Homo sapiens

<400> SEQUENCE: 4

Met Ala Arg Arg Ser Ala Phe Pro Ala Ala Ala Leu Trp Leu Trp Ser
  1               5                  10                  15

Ile Leu Leu Cys Leu Leu Ala Leu Arg Ala Glu Ala Gly Pro Pro Gln
             20                  25                  30

Glu Glu Ser Leu Tyr Leu Trp Ile Asp Ala His Gln Ala Arg Val Leu
         35                  40                  45

Ile Gly Phe Glu Glu Asp Ile Leu Ile Val Ser Glu Gly Lys Met Ala
     50                  55                  60

Pro Phe Thr His Asp Phe Arg Lys Ala Gln Gln Arg Met Pro Ala Ile
 65                  70                  75                  80

Pro Val Asn Ile His Ser Met Asn Phe Thr Trp Gln Ala Ala Gly Gln
                 85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
    130                 135                 140

Asp Gly Val Ala Ala Phe Glu Val Asp Val Ile Val Met Asn Ser Glu
145                 150                 155                 160

Gly Asn Thr Ile Leu Gln Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Ile Cys Glu Cys Pro Asp Gly Phe His Gly Pro His
        195                 200                 205

Cys Glu Lys Ala Leu Cys Thr Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Ile Ser Lys Cys Pro Gln Pro Cys Arg Asn Gly Gly Lys Cys
        275                 280                 285

Ile Gly Lys Ser Lys Cys Lys Cys Ser Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Gln Glu Gly Trp His Gly Arg His
                325                 330                 335
```

-continued

```
Cys Asn Lys Arg Tyr Glu Ala Ser Leu Ile His Ala Leu Arg Pro Ala
            340                 345                 350

Gly Ala Gln Leu Arg Gln His Thr Pro Ser Leu Lys Lys Ala Glu Glu
        355                 360                 365

Arg Arg Asp Pro Pro Glu Ser Asn Tyr Ile Trp
    370                 375
```

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 5
agggagcacg gacagtgtgc agatgtggac gagtgctcac tagca 45

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 6
agagtgtatc tctggctacg c 21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 7
taagtccggc acattacagg tc 22

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 8
cccacgatgt atgaatggtg gactttgtgt gactcctggt ttctgcatc 49

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 9
aaagacgcat ctgcgagtgt cc 22

<210> SEQ ID NO 10
<211> LENGTH: 23
<212> TYPE: DNA

-continued

<213> ORGANISM: Artificial Sequence
<220> FEATURE:
<223> OTHER INFORMATION: Description of Artificial Sequence: Synthetic
oligonucleotide probe

<400> SEQUENCE: 10
tgctgatttc acactgctct ccc 23

<210> SEQ ID NO 11
<211> LENGTH: 2197
<212> TYPE: DNA
<213> ORGANISM: Homo sapiens

<400> SEQUENCE: 11
cggacgcgtg ggcgtccggc ggtcgcagag ccaggaggcg gaggcgcgcg ggccagcctg 60
ggccccagcc cacaccttca ccagggccca ggagccacca tgtggcgatg tccactgggg 120
ctactgctgt tgctgccgct ggctggccac ttggctctgg gtgcccagca gggtcgtggg 180
cgccgggagc tagcaccggg tctgcacctg cggggcatcc gggacgcggg aggccggtac 240
tgccaggagc aggacctgtg ctgccgcggc cgtgccgacg actgtgccct gccctacctg 300
ggcgccatct gttactgtga cctcttctgc aaccgcacgg tctccgactg ctgccctgac 360
ttctgggact tctgcctcgg cgtgccaccc ccttttcccc cgatccaagg atgtatgcat 420
ggaggtcgta tctatccagt cttgggaacg tactgggaca actgtaaccg ttgcacctgc 480
caggagaaca ggcagtggca tggtggatcc agacatgatc aaagccatca accagggcaa 540
ctatggctgg caggctggga accacagcgc cttctggggc atgaccctgg atgagggcat 600
tcgctaccgc ctgggcacca tccgcccatc ttcctcggtc atgaacatgc atgaaattta 660
tacagtgctg aacccagggg aggtgcttcc cacagccttc gaggcctctg agaagtggcc 720
caacctgatt catgagcctc ttgaccaagg caactgtgca ggctcctggg ccttctccac 780
agcagctgtg gcatccgatc gtgtctcaat ccattctctg ggacacatga cgcctgtcct 840
gtcgccccag aacctgctgt cttgtgacac ccaccagcag cagggctgcc gcggtgggcg 900
tctcgatggt gcctggtggt tcctgcgtcg ccgagggtg gtgtctgacc actgctaccc 960
cttctcgggc cgtgaacgag acgaggctgg ccctgcgccc ccctgtatga tgcacagccg 1020
agccatgggt cggggcaagc gccaggccac tgcccactgc cccaacagct atgttaataa 1080
caatgacatc taccaggtca ctcctgtcta ccgcctcggc tccaacgaca aggagatcat 1140
gaaggagctg atggagaatg gccctgtcca agccctcatg gaggtgcatg aggacttctt 1200
cctatacaag ggaggcatct acagccacac gccagtgagc cttgggaggc cagagagata 1260
ccgccggcat gggacccact cagtcaagat cacaggatgg ggagaggaga cgctgccaga 1320
tggaaggacg ctcaaatact ggactgcggc caactcctgg ggcccagcct ggggcgagag 1380
gggccacttc cgcatcgtgc gcggcgtcaa tgagtgcgac atcgagagct tcgtgctggg 1440
cgtctggggc cgcgtgggca tggaggacat gggtcatcac tgaggctgcg ggcaccacgc 1500
ggggtccggc ctgggatcca ggctaagggc cggcggaaga ggccccaatg gggcggtgac 1560
cccagcctcg cccgacagag cccggggcgc aggcgggcgc cagggcgcta atcccggcgc 1620
gggttccgct gacgcagcgc cccgcctggg agccgcgggc aggcgagact ggcggagccc 1680
ccagacctcc cagtggggac ggggcagggc ctggcctggg aagagcacag ctgcagatcc 1740
caggcctctg gcgcccccac tcaagactac caaagccagg acacctcaag tctccagccc 1800
caatacccca ccccaatccc gtattctttt tttttttttt ttagacaggg tcttgctccg 1860

-continued

```
ttgcccaggt tggagtgcag tggcccatca gggctcactg taacctccga ctcctgggtt   1920

caagtgaccc tcccacctca gcctctcaag tagctgggac tacaggtgca ccaccacacc   1980

tggctaattt ttgtattttt tgtaaagagg ggggtctcac tgtgttgccc aggctggttt   2040

cgaactcctg ggctcaagcg gtccacctgc ctccgcctcc caaagtgctg ggattgcagg   2100

catgagccac tgcacccagc cctgtattct tattcttcag atatttattt ttcttttcac   2160

tgttttaaaa taaaaccaaa gtattgataa aaaaaaa                            2197
```

<210> SEQ ID NO 12
<211> LENGTH: 164
<212> TYPE: PRT
<213> ORGANISM: Homo sapiens

<400> SEQUENCE: 12

```
Met Trp Arg Cys Pro Leu Gly Leu Leu Leu Leu Leu Pro Leu Ala Gly
  1               5                  10                  15

His Leu Ala Leu Gly Ala Gln Gln Gly Arg Gly Arg Arg Glu Leu Ala
             20                  25                  30

Pro Gly Leu His Leu Arg Gly Ile Arg Asp Ala Gly Gly Arg Tyr Cys
         35                  40                  45

Gln Glu Gln Asp Leu Cys Cys Arg Gly Arg Ala Asp Asp Cys Ala Leu
     50                  55                  60

Pro Tyr Leu Gly Ala Ile Cys Tyr Cys Asp Leu Phe Cys Asn Arg Thr
 65                  70                  75                  80

Val Ser Asp Cys Cys Pro Asp Phe Trp Asp Phe Cys Leu Gly Val Pro
                 85                  90                  95

Pro Pro Phe Pro Pro Ile Gln Gly Cys Met His Gly Gly Arg Ile Tyr
            100                 105                 110

Pro Val Leu Gly Thr Tyr Trp Asp Asn Cys Asn Arg Cys Thr Cys Gln
        115                 120                 125

Glu Asn Arg Gln Trp His Gly Gly Ser Arg His Asp Gln Ser His Gln
    130                 135                 140

Pro Gly Gln Leu Trp Leu Ala Gly Trp Glu Pro Gln Arg Leu Leu Gly
145                 150                 155                 160

His Asp Pro Gly
```

<210> SEQ ID NO 13
<211> LENGTH: 533
<212> TYPE: DNA
<213> ORGANISM: Homo sapiens
<220> FEATURE:
<221> NAME/KEY: modified_base
<222> LOCATION: (33)..(33)
<223> OTHER INFORMATION: a, t, c or g
<220> FEATURE:
<221> NAME/KEY: modified_base
<222> LOCATION: (37)..(37)
<223> OTHER INFORMATION: a, t, c or g
<220> FEATURE:
<221> NAME/KEY: modified_base
<222> LOCATION: (80)..(80)
<223> OTHER INFORMATION: a, t, c or g
<220> FEATURE:
<221> NAME/KEY: modified_base
<222> LOCATION: (94)..(94)
<223> OTHER INFORMATION: a, t, c or g
<220> FEATURE:
<221> NAME/KEY: modified_base
<222> LOCATION: (144)..(144)
<223> OTHER INFORMATION: a, t, c or g
<220> FEATURE:
<221> NAME/KEY: modified_base -continued
<222> LOCATION: (188)..(188)
<223> OTHER INFORMATION: a, t, c or g

<400> SEQUENCE: 13
aggctccttg gcccttttc cacagcaagc ttntgcnatc ccgattcgtt gtctcaaatc 60
caattctctt gggacacatn acgcctgtcc tttngcccca gaacctgctg tcttgtacac 120
ccaccagcag cagggctgcc gcgntgggcg tctcgatggt gcctggtggt tcctgcgtcg 180
ccgagggntg gtgtctgacc actgctaccc cttctcgggc cgtgaacgag acgaggctgg 240
ccctgcgccc ccctgtatga tgcacagccg agccatgggt cggggcaagc gccaggccac 300
tgcccactgc cccaacagct atgttaataa caatgacatc taccaggtca ctcctgtcta 360
ccgcctcggc tccaacgaca aggagatcat gaaggagctg atggagaatg gccctgtcca 420
agccctcatg gaggtgcatg aggacttctt cctatacaag ggaggcatct acagccacac 480
gccagtgagc cttgggaggc cagagagata ccgccggcat gggacccact cag 533

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 14
ttcgaggcct ctgagaagtg gccc 24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 15
ggcggtatct ctctggcctc cc 22

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 16
ttctccacag cagctgtggc atccgatcgt gtctcaatcc attctctggg 50

<210> SEQ ID NO 17
<211> LENGTH: 960
<212> TYPE: DNA
<213> ORGANISM: Homo sapiens

<400> SEQUENCE: 17
gctgcttgcc ctgttgatgg caggcttggc cctgcagcca ggcactgccc tgctgtgcta 60
ctcctgcaaa gcccaggtga gcaacgagga ctgcctgcag gtggagaact gcacccagct 120
gggggagcag tgctggaccg cgcgcatccg cgcagttggc ctcctgaccg tcatcagcaa 180
aggctgcagc ttgaactgcg tggatgactc acaggactac tacgtgggca agaagaacat 240
cacgtgctgt gacaccgact tgtgcaacgc cagcggggcc catgccctgc agccggctgc 300

-continued

```
cgccatcctt gcgctgctcc ctgcactcgg cctgctgctc tggggacccg gccagctata    360

ggctctgggg ggccccgctg cagcccacac tgggtgtggt gccccaggcc tctgtgccac    420

tcctcacaga cctggcccag tgggagcctg tcctggttcc tgaggcacat cctaacgcaa    480

gtctgaccat gtatgtctgc acccctgtcc cccaccctga ccctcccatg gccctctcca    540

ggactcccac ccggcagatc agctctagtg acacagatcc gcctgcagat ggcccctcca    600

accctctctg ctgctgtttc catggcccag cattctccac ccttaaccct gtgctcaggc    660

acctcttccc ccaggaagcc ttccctgccc accccatcta tgacttgagc caggtctggt    720

ccgtggtgtc ccccgcaccc agcaggggac aggcactcag gagggcccag taaaggctga    780

gatgaagtgg actgagtaga actggaggac aagagtcgac gtgagttcct gggagtctcc    840

agagatgggg cctggaggcc tggaggaagg ggccaggcct cacattcgtg gggctccctg    900

aatggcagcc tgagcacagc gtaggccctt aataaacacc tgttggataa gccaaaaaaa    960
```

<210> SEQ ID NO 18
<211> LENGTH: 189
<212> TYPE: PRT
<213> ORGANISM: Homo sapiens

<400> SEQUENCE: 18

```
Met Thr His Arg Thr Thr Thr Trp Ala Arg Arg Thr Ser Arg Ala Val
  1               5                  10                  15

Thr Pro Thr Cys Ala Thr Pro Ala Gly Pro Met Pro Cys Ser Arg Leu
             20                  25                  30

Pro Pro Ser Leu Arg Cys Ser Leu His Ser Ala Cys Cys Ser Gly Asp
         35                  40                  45

Pro Ala Ser Tyr Arg Leu Trp Gly Ala Pro Leu Gln Pro Thr Leu Gly
     50                  55                  60

Val Val Pro Gln Ala Ser Val Pro Leu Leu Thr Asp Leu Ala Gln Trp
 65                  70                  75                  80

Glu Pro Val Leu Val Pro Glu Ala His Pro Asn Ala Ser Leu Thr Met
                 85                  90                  95

Tyr Val Cys Thr Pro Val Pro His Pro Asp Pro Pro Met Ala Leu Ser
            100                 105                 110

Arg Thr Pro Thr Arg Gln Ile Ser Ser Ser Asp Thr Asp Pro Pro Ala
        115                 120                 125

Asp Gly Pro Ser Asn Pro Leu Cys Cys Cys Phe His Gly Pro Ala Phe
    130                 135                 140

Ser Thr Leu Asn Pro Val Leu Arg His Leu Phe Pro Gln Glu Ala Phe
145                 150                 155                 160

Pro Ala His Pro Ile Tyr Asp Leu Ser Gln Val Trp Ser Val Val Ser
                165                 170                 175

Pro Ala Pro Ser Arg Gly Gln Ala Leu Arg Arg Ala Gln
            180                 185
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 19

```
tgctgtgcta ctcctgcaaa gccc                                            24
```

-continued

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 20
tgcacaagtc ggtgtcacag cacg 24

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 21
agcaacgagg actgcctgca ggtggagaac tgcacccagc tggg 44

<210> SEQ ID NO 22
<211> LENGTH: 1200
<212> TYPE: DNA
<213> ORGANISM: Homo sapiens

<400> SEQUENCE: 22
cccacgcgtc cgaacctctc cagcgatggg agccgcccgc ctgctgccca acctcactct 60
gtgcttacag ctgctgattc tctgctgtca aactcagtac gtgagggacc agggcgccat 120
gaccgaccag ctgagcaggc ggcagatccg cgagtaccaa ctctacagca ggaccagtgg 180
caagcacgtg caggtcaccg ggcgtcgcat ctccgccacc gccgaggacg gcaacaagtt 240
tgccaagctc atagtggaga cggacacgtt tggcagccgg gttcgcatca aaggggctga 300
gagtgagaag tacatctgta tgaacaagag gggcaagctc atcgggaagc ccagcgggaa 360
gagcaaagac tgcgtgttca cggagatcgt gctggagaac aactatacgg ccttccagaa 420
cgcccggcac gagggctggt tcatggcctt cacgcggcag gggcggcccc gccaggcttc 480
ccgcagccgc cagaaccagc gcgaggccca cttcatcaag cgcctctacc aaggccagct 540
gcccttcccc aaccacgccg agaagcagaa gcagttcgag tttgtgggct ccgcccccac 600
ccgccggacc aagcgcacac ggcggcccca gcccctcacg tagtctggga ggcagggggc 660
agcagcccct gggccgcctc cccacccctt tcccttctta atccaaggac tgggctgggg 720
tggcgggagg ggagccagat ccccgaggga ggaccctgag ggccgcgaag catccgagcc 780
cccagctggg aaggggcagg ccggtgcccc aggggcggct ggcacagtgc cccttcccg 840 gacgggtggc aggccctgga gaggaactga gtgtcaccct gatctcaggc caccagcctc 900
tgccggcctc ccagccgggc tcctgaagcc cgctgaaagg tcagcgactg aaggccttgc 960
agacaaccgt ctggaggtgg ctgtcctcaa aatctgcttc tcggatctcc ctcagtctgc 1020
ccccagcccc caaactcctc ctggctagac tgtaggaagg gacttttgtt tgtttgtttg 1080
tttcaggaaa aaagaaaggg agagagagga aaatagaggg ttgtccactc ctcacattcc 1140
acgacccagg cctgcacccc acccccaact cccagccccg gaataaaacc attttcctgc 1200

<210> SEQ ID NO 23
<211> LENGTH: 205
<212> TYPE: PRT

-continued

<213> ORGANISM: Homo sapiens

<400> SEQUENCE: 23

```
Met Gly Ala Ala Arg Leu Leu Pro Asn Leu Thr Leu Cys Leu Gln Leu
  1               5                  10                  15

Leu Ile Leu Cys Cys Gln Thr Gln Tyr Val Arg Asp Gln Gly Ala Met
             20                  25                  30

Thr Asp Gln Leu Ser Arg Arg Gln Ile Arg Glu Tyr Gln Leu Tyr Ser
         35                  40                  45

Arg Thr Ser Gly Lys His Val Gln Val Thr Gly Arg Arg Ile Ser Ala
     50                  55                  60

Thr Ala Glu Asp Gly Asn Lys Phe Ala Lys Leu Ile Val Glu Thr Asp
 65                  70                  75                  80

Thr Phe Gly Ser Arg Val Arg Ile Lys Gly Ala Glu Ser Glu Lys Tyr
                 85                  90                  95

Ile Cys Met Asn Lys Arg Gly Lys Leu Ile Gly Lys Pro Ser Gly Lys
            100                 105                 110

Ser Lys Asp Cys Val Phe Thr Glu Ile Val Leu Glu Asn Asn Tyr Thr
        115                 120                 125

Ala Phe Gln Asn Ala Arg His Glu Gly Trp Phe Met Ala Phe Thr Arg
    130                 135                 140

Gln Gly Arg Pro Arg Gln Ala Ser Arg Ser Arg Gln Asn Gln Arg Glu
145                 150                 155                 160

Ala His Phe Ile Lys Arg Leu Tyr Gln Gly Gln Leu Pro Phe Pro Asn
                165                 170                 175

His Ala Glu Lys Gln Lys Gln Phe Glu Phe Val Gly Ser Ala Pro Thr
            180                 185                 190

Arg Arg Thr Lys Arg Thr Arg Arg Pro Gln Pro Leu Thr
        195                 200                 205
```

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 24

```
cagtacgtga gggaccaggg cgccatga                                          28
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 25

```
ccggtgacct gcacgtgctt gcca                                              24
```

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide probe
<220> FEATURE:
<221> NAME/KEY: modified_base
<222> LOCATION: (21)..(21)
<223> OTHER INFORMATION: a, t, c or g

<400> SEQUENCE: 26
gcggatctgc cgcctgctca nctggtcggt catggcgccc t 41

<210> SEQ ID NO 27
<211> LENGTH: 2479
<212> TYPE: DNA
<213> ORGANISM: Homo sapiens

<400> SEQUENCE: 27
acttgccatc acctgttgcc agtgtggaaa aattctccct gttgaatttt ttgcacatgg 60
aggacagcag caaagagggc aacacaggct gataagacca gagacagcag ggagattatt 120
ttaccatacg ccctcaggac gttccctcta gctggagttc tggacttcaa cagaacccca 180
tccagtcatt ttgattttgc tgtttatttt ttttttcttt ttctttttcc caccacattg 240
tattttattt ccgtacttca gaaatgggcc tacagaccac aaagtggccc agccatgggg 300 ctttttttcct gaagtcttgg cttatcattt ccctggggct ctactcacag gtgtccaaac 360
tcctggcctg ccctagtgtg tgccgctgcg acaggaactt tgtctactgt aatgagcgaa 420
gcttgacctc agtgcctctt gggatcccgg agggcgtaac cgtactctac ctccacaaca 480
accaaattaa taatgctgga tttcctgcag aactgcacaa tgtacagtcg gtgcacacgg 540
tctacctgta tggcaaccaa ctggacgaat tccccatgaa ccttcccaag aatgtcagag 600
ttctccattt gcaggaaaac aatattcaga ccatttcacg ggctgctctt gcccagctct 660
tgaagcttga agagctgcac ctggatgaca actccatatc cacagtgggg gtggaagacg 720
gggccttccg ggaggctatt agcctcaaat tgttgttttt gtctaagaat cacctgagca 780
gtgtgcctgt tgggcttcct gtggacttgc aagagctgag agtggatgaa aatcgaattg 840
ctgtcatatc cgacatggcc ttccagaatc tcacgagctt ggagcgtctt attgtggacg 900
ggaacctcct gaccaacaag ggtatcgccg agggcacctt cagccatctc accaagctca 960
aggaattttc aattgtacgt aattcgctgt cccaccctcc tcccgatctc ccaggtacgc 1020
atctgatcag gctctatttg caggacaacc agataaacca cattcctttg acagccttct 1080
caaatctgcg taagctggaa cggctggata tatccaacaa ccaactgcgg atgctgactc 1140
aaggggtttt tgataatctc tccaacctga agcagctcac tgctcggaat aacccttggt 1200
tttgtgactg cagtattaaa tgggtcacag aatggctcaa atatatccct tcatctctca 1260
acgtgcgggg tttcatgtgc caaggtcctg aacaagtccg ggggatggcc gtcagggaat 1320
taaatatgaa tcttttgtcc tgtcccacca cgacccccgg cctgcctctc ttcaccccag 1380
ccccaagtac agcttctccg accactcagc ctcccaccct ctctattcca aaccctagca 1440
gaagctacac gcctccaact cctaccacat cgaaacttcc cacgattcct gactgggatg 1500
gcagagaaag agtgacccca cctatttctg aacggatcca gctctctatc cattttgtga 1560
atgatacttc cattcaagtc agctggctct ctctcttcac cgtgatggca tacaaactca 1620
catgggtgaa aatgggccac agtttagtag ggggcatcgt tcaggagcgc atagtcagcg 1680
gtgagaagca acacctgagc ctggttaact tagagccccg atccacctat cggatttgtt 1740
tagtgccact ggatgctttt aactaccgcg cggtagaaga caccatttgt tcagaggcca 1800
ccacccatgc ctcctatctg aacaacggca gcaacacagc gtccagccat gagcagacga 1860
cgtcccacag catgggctcc ccctttctgc tggcgggctt gatcgggggc gcggtgatat 1920

-continued

```
ttgtgctggt ggtcttgctc agcgtctttt gctggcatat gcacaaaaag gggcgctaca   1980

cctcccagaa gtggaaatac aaccggggcc ggcggaaaga tgattattgc gaggcaggca   2040

ccaagaagga caactccatc ctggagatga cagaaaccag ttttcagatc gtctccttaa   2100

ataacgatca actccttaaa ggagatttca gactgcagcc catttacacc ccaaatgggg   2160

gcattaatta cacagactgc catatcccca acaacatgcg atactgcaac agcagcgtgc   2220

cagacctgga gcactgccat acgtgacagc cagaggccca gcgttatcaa ggcggacaat   2280

tagactcttg agaacacact cgtgtgtgca cataaagaca cgcagattac atttgataaa   2340

tgttacacag atgcatttgt gcatttgaat actctgtaat ttatacggtg tactatataa   2400

tgggatttaa aaaaagtgct atcttttcta tttcaagtta attacaaaca gttttgtaac   2460

tctttgcttt ttaaatctt                                                2479
```

<210> SEQ ID NO 28
<211> LENGTH: 660
<212> TYPE: PRT
<213> ORGANISM: Homo sapiens

<400> SEQUENCE: 28

```
Met Gly Leu Gln Thr Thr Lys Trp Pro Ser His Gly Ala Phe Phe Leu
  1               5                  10                  15

Lys Ser Trp Leu Ile Ile Ser Leu Gly Leu Tyr Ser Gln Val Ser Lys
             20                  25                  30

Leu Leu Ala Cys Pro Ser Val Cys Arg Cys Asp Arg Asn Phe Val Tyr
         35                  40                  45

Cys Asn Glu Arg Ser Leu Thr Ser Val Pro Leu Gly Ile Pro Glu Gly
     50                  55                  60

Val Thr Val Leu Tyr Leu His Asn Asn Gln Ile Asn Asn Ala Gly Phe
 65                  70                  75                  80

Pro Ala Glu Leu His Asn Val Gln Ser Val His Thr Val Tyr Leu Tyr
                 85                  90                  95

Gly Asn Gln Leu Asp Glu Phe Pro Met Asn Leu Pro Lys Asn Val Arg
            100                 105                 110

Val Leu His Leu Gln Glu Asn Asn Ile Gln Thr Ile Ser Arg Ala Ala
        115                 120                 125

Leu Ala Gln Leu Leu Lys Leu Glu Glu Leu His Leu Asp Asp Asn Ser
    130                 135                 140

Ile Ser Thr Val Gly Val Glu Asp Gly Ala Phe Arg Glu Ala Ile Ser
145                 150                 155                 160

Leu Lys Leu Leu Phe Leu Ser Lys Asn His Leu Ser Ser Val Pro Val
                165                 170                 175

Gly Leu Pro Val Asp Leu Gln Glu Leu Arg Val Asp Glu Asn Arg Ile
            180                 185                 190

Ala Val Ile Ser Asp Met Ala Phe Gln Asn Leu Thr Ser Leu Glu Arg
        195                 200                 205

Leu Ile Val Asp Gly Asn Leu Leu Thr Asn Lys Gly Ile Ala Glu Gly
    210                 215                 220

Thr Phe Ser His Leu Thr Lys Leu Lys Glu Phe Ser Ile Val Arg Asn
225                 230                 235                 240

Ser Leu Ser His Pro Pro Pro Asp Leu Pro Gly Thr His Leu Ile Arg
                245                 250                 255

Leu Tyr Leu Gln Asp Asn Gln Ile Asn His Ile Pro Leu Thr Ala Phe
            260                 265                 270
```

-continued

```
Ser Asn Leu Arg Lys Leu Glu Arg Leu Asp Ile Ser Asn Asn Gln Leu
        275                 280                 285

Arg Met Leu Thr Gln Gly Val Phe Asp Asn Leu Ser Asn Leu Lys Gln
    290                 295                 300

Leu Thr Ala Arg Asn Asn Pro Trp Phe Cys Asp Cys Ser Ile Lys Trp
305                 310                 315                 320

Val Thr Glu Trp Leu Lys Tyr Ile Pro Ser Ser Leu Asn Val Arg Gly
                325                 330                 335

Phe Met Cys Gln Gly Pro Glu Gln Val Arg Gly Met Ala Val Arg Glu
            340                 345                 350

Leu Asn Met Asn Leu Leu Ser Cys Pro Thr Thr Thr Pro Gly Leu Pro
        355                 360                 365

Leu Phe Thr Pro Ala Pro Ser Thr Ala Ser Pro Thr Thr Gln Pro Pro
    370                 375                 380

Thr Leu Ser Ile Pro Asn Pro Ser Arg Ser Tyr Thr Pro Pro Thr Pro
385                 390                 395                 400

Thr Thr Ser Lys Leu Pro Thr Ile Pro Asp Trp Asp Gly Arg Glu Arg
                405                 410                 415

Val Thr Pro Pro Ile Ser Glu Arg Ile Gln Leu Ser Ile His Phe Val
            420                 425                 430

Asn Asp Thr Ser Ile Gln Val Ser Trp Leu Ser Leu Phe Thr Val Met
        435                 440                 445

Ala Tyr Lys Leu Thr Trp Val Lys Met Gly His Ser Leu Val Gly Gly
    450                 455                 460

Ile Val Gln Glu Arg Ile Val Ser Gly Glu Lys Gln His Leu Ser Leu
465                 470                 475                 480

Val Asn Leu Glu Pro Arg Ser Thr Tyr Arg Ile Cys Leu Val Pro Leu
                485                 490                 495

Asp Ala Phe Asn Tyr Arg Ala Val Glu Asp Thr Ile Cys Ser Glu Ala
            500                 505                 510

Thr Thr His Ala Ser Tyr Leu Asn Asn Gly Ser Asn Thr Ala Ser Ser
        515                 520                 525

His Glu Gln Thr Thr Ser His Ser Met Gly Ser Pro Phe Leu Leu Ala
    530                 535                 540

Gly Leu Ile Gly Gly Ala Val Ile Phe Val Leu Val Val Leu Leu Ser
545                 550                 555                 560

Val Phe Cys Trp His Met His Lys Lys Gly Arg Tyr Thr Ser Gln Lys
                565                 570                 575

Trp Lys Tyr Asn Arg Gly Arg Arg Lys Asp Asp Tyr Cys Glu Ala Gly
            580                 585                 590

Thr Lys Lys Asp Asn Ser Ile Leu Glu Met Thr Glu Thr Ser Phe Gln
        595                 600                 605

Ile Val Ser Leu Asn Asn Asp Gln Leu Leu Lys Gly Asp Phe Arg Leu
    610                 615                 620

Gln Pro Ile Tyr Thr Pro Asn Gly Gly Ile Asn Tyr Thr Asp Cys His
625                 630                 635                 640

Ile Pro Asn Asn Met Arg Tyr Cys Asn Ser Ser Val Pro Asp Leu Glu
                645                 650                 655

His Cys His Thr
            660
```

<210> SEQ ID NO 29
<211> LENGTH: 21
<212> TYPE: DNA

-continued

<213> ORGANISM: Artificial Sequence
<220> FEATURE:
<223> OTHER INFORMATION: Description of Artificial Sequence: Synthetic oligonucleotide probe

<400> SEQUENCE: 29
cggtctacct gtatggcaac c 21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 30
gcaggacaac cagataaacc ac 22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 31
acgcagattt gagaaggctg tc 22

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 32
ttcacgggct gctcttgccc agctcttgaa gcttgaagag ctgcac 46

<210> SEQ ID NO 33
<211> LENGTH: 3449
<212> TYPE: DNA
<213> ORGANISM: Homo sapiens

<400> SEQUENCE: 33
acttggagca agcggcggcg gcggagacag aggcagaggc agaagctggg gctccgtcct 60
cgcctcccac gagcgatccc cgaggagagc cgcggccctc ggcgaggcga agaggccgac 120
gaggaagacc cgggtggctg cgcccctgcc tcgcttccca ggcgccggcg gctgcagcct 180
tgcccctctt gctcgccttg aaaatggaaa agatgctcgc aggctgcttt ctgctgatcc 240
tcggacagat cgtcctcctc cctgccgagg ccagggagcg gtcacgtggg aggtccatct 300
ctaggggcag acacgctcgg acccacccgc agacggccct tctggagagt tcctgtgaga 360
acaagcgggc agacctggtt ttcatcattg acagctctcg cagtgtcaac acccatgact 420
atgcaaaggt caaggagttc atcgtggaca tcttgcaatt cttggacatt ggtcctgatg 480
tcacccgagt gggcctgctc caatatggca gcactgtcaa gaatgagttc tccctcaaga 540
ccttcaagag gaagtccgag gtggagcgtg ctgtcaagag gatgcggcat ctgtccacgg 600
gcaccatgac tgggctggcc atccagtatg ccctgaacat cgcattctca gaagcagagg 660
gggcccggcc cctgagggag aatgtgccac gggtcataat gatcgtgaca gatgggagac 720

-continued

```
ctcaggactc cgtggccgag gtggctgcta aggcacggga cacgggcatc ctaatctttg    780
ccattggtgt gggccaggta gacttcaaca ccttgaagtc cattgggagt gagccccatg    840
aggaccatgt cttccttgtg gccaatttca gccagattga gacgctgacc tccgtgttcc    900
agaagaagtt gtgcacggcc cacatgtgca gcaccctgga gcataactgt gcccacttct    960
gcatcaacat ccctggctca tacgtctgca ggtgcaaaca aggctacatt ctcaactcgg   1020
atcagacgac ttgcagaatc caggatctgt gtgccatgga ggaccacaac tgtgagcagc   1080
tctgtgtgaa tgtgccgggc tccttcgtct gccagtgcta cagtggctac gccctggctg   1140
aggatgggaa gaggtgtgtg gctgtggact actgtgcctc agaaaaccac ggatgtgaac   1200
atgagtgtgt aaatgctgat ggctcctacc tttgccagtg ccatgaagga tttgctctta   1260
acccagatga aaaaacgtgc acaaggatca actactgtgc actgaacaaa ccgggctgtg   1320
agcatgagtg cgtcaacatg gaggagagct actactgccg ctgccaccgt ggctacactc   1380
tggaccccaa tggcaaaacc tgcagccgag tggaccactg tgcacagcag gaccatggct   1440
gtgagcagct gtgtctgaac acggaggatt ccttcgtctg ccagtgctca gaaggcttcc   1500
tcatcaacga ggacctcaag acctgctccc gggtggatta ctgcctgctg agtgaccatg   1560
gttgtgaata ctcctgtgtc aacatggaca gatcctttgc ctgtcagtgt cctgagggac   1620
acgtgctccg cagcgatggg aagacgtgtg caaaattgga ctcttgtgct ctgggggacc   1680
acggttgtga acattcgtgt gtaagcagtg aagattcgtt tgtgtgccag tgctttgaag   1740
gttatatact ccgtgaagat ggaaaaacct gcagaaggaa agatgtctgc caagctatag   1800
accatggctg tgaacacatt tgtgtgaaca gtgacgactc atacacgtgc gagtgcttgg   1860
agggattccg gctcgctgag gatgggaaac gctgccgaag gaaggatgtc tgcaaatcaa   1920
cccaccatgg ctgcgaacac atttgtgtta ataatgggaa ttcctacatc tgcaaatgct   1980
cagagggatt tgttctagct gaggacggaa gacggtgcaa gaaatgcact gaaggcccaa   2040
ttgacctggt ctttgtgatc gatggatcca agagtcttgg agaagagaat tttgaggtcg   2100
tgaagcagtt tgtcactgga attatagatt ccttgacaat ttcccccaaa gccgctcgag   2160
tggggctgct ccagtattcc acacaggtcc acacagagtt cactctgaga aacttcaact   2220
cagccaaaga catgaaaaaa gccgtggccc acatgaaata catgggaaag ggctctatga   2280
ctgggctggc cctgaaacac atgtttgaga gaagttttac ccaaggagaa ggggccaggc   2340
ccctttccac aagggtgccc agagcagcca ttgtgttcac cgacggacgg gctcaggatg   2400
acgtctccga gtgggccagt aaagccaagg ccaatggtat cactatgtat gctgttgggg   2460
taggaaaagc cattgaggag gaactacaag agattgcctc tgagcccaca aacaagcatc   2520
tcttctatgc cgaagacttc agcacaatgg atgagataag tgaaaaactc aagaaaggca   2580
tctgtgaagc tctagaagac tccgatggaa gacaggactc tccagcaggg gaactgccaa   2640
aaacggtcca acagccaaca gaatctgagc cagtcaccat aaatatccaa gacctacttt   2700
cctgttctaa ttttgcagtg caacacagat atctgtttga agaagacaat cttttacggt   2760
ctacacaaaa gctttcccat tcaacaaaac cttcaggaag ccctttggaa gaaaaacacg   2820
atcaatgcaa atgtgaaaac cttataatgt tccagaacct tgcaaacgaa gaagtaagaa   2880
aattaacaca gcgcttagaa gaaatgacac agagaatgga agccctggaa aatcgcctga   2940
gatacagatg aagattagaa atcgcgacac atttgtagtc attgtatcac ggattacaat   3000
gaacgcagtg cagagcccca aagctcaggc tattgttaaa tcaataatgt tgtgaagtaa   3060
```

-continued

```
aacaatcagt actgagaaac ctggtttgcc acagaacaaa gacaagaagt atacactaac   3120

ttgtataaat ttatctagga aaaaaatcct tcagaattct aagatgaatt taccaggtga   3180

gaatgaataa gctatgcaag gtattttgta atatactgtg gacacaactt gcttctgcct   3240

catcctgcct tagtgtgcaa tctcatttga ctatacgata aagtttgcac agtcttactt   3300

ctgtagaaca ctggccatag gaaatgctgt ttttttgtac tggactttac cttgatatat   3360

gtatatggat gtatgcataa aatcatagga catatgtact tgtggaacaa gttggatttt   3420

ttatacaata ttaaaattca ccacttcag                                    3449


<210> SEQ ID NO 34
<211> LENGTH: 915
<212> TYPE: PRT
<213> ORGANISM: Homo sapiens

<400> SEQUENCE: 34

Met Glu Lys Met Leu Ala Gly Cys Phe Leu Leu Ile Leu Gly Gln Ile
  1               5                  10                  15

Val Leu Leu Pro Ala Glu Ala Arg Glu Arg Ser Arg Gly Arg Ser Ile
             20                  25                  30

Ser Arg Gly Arg His Ala Arg Thr His Pro Gln Thr Ala Leu Leu Glu
         35                  40                  45

Ser Ser Cys Glu Asn Lys Arg Ala Asp Leu Val Phe Ile Ile Asp Ser
     50                  55                  60

Ser Arg Ser Val Asn Thr His Asp Tyr Ala Lys Val Lys Glu Phe Ile
 65                  70                  75                  80

Val Asp Ile Leu Gln Phe Leu Asp Ile Gly Pro Asp Val Thr Arg Val
                 85                  90                  95

Gly Leu Leu Gln Tyr Gly Ser Thr Val Lys Asn Glu Phe Ser Leu Lys
            100                 105                 110

Thr Phe Lys Arg Lys Ser Glu Val Glu Arg Ala Val Lys Arg Met Arg
        115                 120                 125

His Leu Ser Thr Gly Thr Met Thr Gly Leu Ala Ile Gln Tyr Ala Leu
    130                 135                 140

Asn Ile Ala Phe Ser Glu Ala Glu Gly Ala Arg Pro Leu Arg Glu Asn
145                 150                 155                 160

Val Pro Arg Val Ile Met Ile Val Thr Asp Gly Arg Pro Gln Asp Ser
                165                 170                 175

Val Ala Glu Val Ala Ala Lys Ala Arg Asp Thr Gly Ile Leu Ile Phe
            180                 185                 190

Ala Ile Gly Val Gly Gln Val Asp Phe Asn Thr Leu Lys Ser Ile Gly
        195                 200                 205

Ser Glu Pro His Glu Asp His Val Phe Leu Val Ala Asn Phe Ser Gln
    210                 215                 220

Ile Glu Thr Leu Thr Ser Val Phe Gln Lys Lys Leu Cys Thr Ala His
225                 230                 235                 240

Met Cys Ser Thr Leu Glu His Asn Cys Ala His Phe Cys Ile Asn Ile
                245                 250                 255

Pro Gly Ser Tyr Val Cys Arg Cys Lys Gln Gly Tyr Ile Leu Asn Ser
            260                 265                 270

Asp Gln Thr Thr Cys Arg Ile Gln Asp Leu Cys Ala Met Glu Asp His
        275                 280                 285

Asn Cys Glu Gln Leu Cys Val Asn Val Pro Gly Ser Phe Val Cys Gln
    290                 295                 300
```

-continued

```
Cys Tyr Ser Gly Tyr Ala Leu Ala Glu Asp Gly Lys Arg Cys Val Ala
305                 310                 315                 320

Val Asp Tyr Cys Ala Ser Glu Asn His Gly Cys Glu His Glu Cys Val
                325                 330                 335

Asn Ala Asp Gly Ser Tyr Leu Cys Gln Cys His Glu Gly Phe Ala Leu
            340                 345                 350

Asn Pro Asp Glu Lys Thr Cys Thr Arg Ile Asn Tyr Cys Ala Leu Asn
        355                 360                 365

Lys Pro Gly Cys Glu His Glu Cys Val Asn Met Glu Glu Ser Tyr Tyr
    370                 375                 380

Cys Arg Cys His Arg Gly Tyr Thr Leu Asp Pro Asn Gly Lys Thr Cys
385                 390                 395                 400

Ser Arg Val Asp His Cys Ala Gln Gln Asp His Gly Cys Glu Gln Leu
                405                 410                 415

Cys Leu Asn Thr Glu Asp Ser Phe Val Cys Gln Cys Ser Glu Gly Phe
            420                 425                 430

Leu Ile Asn Glu Asp Leu Lys Thr Cys Ser Arg Val Asp Tyr Cys Leu
        435                 440                 445

Leu Ser Asp His Gly Cys Glu Tyr Ser Cys Val Asn Met Asp Arg Ser
    450                 455                 460

Phe Ala Cys Gln Cys Pro Glu Gly His Val Leu Arg Ser Asp Gly Lys
465                 470                 475                 480

Thr Cys Ala Lys Leu Asp Ser Cys Ala Leu Gly Asp His Gly Cys Glu
                485                 490                 495

His Ser Cys Val Ser Ser Glu Asp Ser Phe Val Cys Gln Cys Phe Glu
            500                 505                 510

Gly Tyr Ile Leu Arg Glu Asp Gly Lys Thr Cys Arg Arg Lys Asp Val
        515                 520                 525

Cys Gln Ala Ile Asp His Gly Cys Glu His Ile Cys Val Asn Ser Asp
    530                 535                 540

Asp Ser Tyr Thr Cys Glu Cys Leu Glu Gly Phe Arg Leu Ala Glu Asp
545                 550                 555                 560

Gly Lys Arg Cys Arg Arg Lys Asp Val Cys Lys Ser Thr His His Gly
                565                 570                 575

Cys Glu His Ile Cys Val Asn Asn Gly Asn Ser Tyr Ile Cys Lys Cys
            580                 585                 590

Ser Glu Gly Phe Val Leu Ala Glu Asp Gly Arg Arg Cys Lys Lys Cys
        595                 600                 605

Thr Glu Gly Pro Ile Asp Leu Val Phe Val Ile Asp Gly Ser Lys Ser
    610                 615                 620

Leu Gly Glu Glu Asn Phe Glu Val Val Lys Gln Phe Val Thr Gly Ile
625                 630                 635                 640

Ile Asp Ser Leu Thr Ile Ser Pro Lys Ala Ala Arg Val Gly Leu Leu
                645                 650                 655

Gln Tyr Ser Thr Gln Val His Thr Glu Phe Thr Leu Arg Asn Phe Asn
            660                 665                 670

Ser Ala Lys Asp Met Lys Lys Ala Val Ala His Met Lys Tyr Met Gly
        675                 680                 685

Lys Gly Ser Met Thr Gly Leu Ala Leu Lys His Met Phe Glu Arg Ser
    690                 695                 700

Phe Thr Gln Gly Glu Gly Ala Arg Pro Leu Ser Thr Arg Val Pro Arg
705                 710                 715                 720

Ala Ala Ile Val Phe Thr Asp Gly Arg Ala Gln Asp Asp Val Ser Glu
```

-continued

```
                725                 730                 735

Trp Ala Ser Lys Ala Lys Ala Asn Gly Ile Thr Met Tyr Ala Val Gly
            740                 745                 750

Val Gly Lys Ala Ile Glu Glu Glu Leu Gln Glu Ile Ala Ser Glu Pro
        755                 760                 765

Thr Asn Lys His Leu Phe Tyr Ala Glu Asp Phe Ser Thr Met Asp Glu
    770                 775                 780

Ile Ser Glu Lys Leu Lys Lys Gly Ile Cys Glu Ala Leu Glu Asp Ser
785                 790                 795                 800

Asp Gly Arg Gln Asp Ser Pro Ala Gly Glu Leu Pro Lys Thr Val Gln
                805                 810                 815

Gln Pro Thr Glu Ser Glu Pro Val Thr Ile Asn Ile Gln Asp Leu Leu
            820                 825                 830

Ser Cys Ser Asn Phe Ala Val Gln His Arg Tyr Leu Phe Glu Glu Asp
        835                 840                 845

Asn Leu Leu Arg Ser Thr Gln Lys Leu Ser His Ser Thr Lys Pro Ser
    850                 855                 860

Gly Ser Pro Leu Glu Glu Lys His Asp Gln Cys Lys Cys Glu Asn Leu
865                 870                 875                 880

Ile Met Phe Gln Asn Leu Ala Asn Glu Glu Val Arg Lys Leu Thr Gln
                885                 890                 895

Arg Leu Glu Glu Met Thr Gln Arg Met Glu Ala Leu Glu Asn Arg Leu
            900                 905                 910

Arg Tyr Arg
        915
```

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 35
gtgaccctgg ttgtgaatac tcc 23

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 36
acagccatgg tctatagctt gg 22

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 37
gcctgtcagt gtcctgaggg acacgtgctc cgcagcgatg ggaag 45

<210> SEQ ID NO 38

-continued

<211> LENGTH: 1813
<212> TYPE: DNA
<213> ORGANISM: Homo sapiens

<400> SEQUENCE: 38

```
ggagccgccc tgggtgtcag cggctcggct cccgcgcacg ctccggccgt cgcgcagcct     60
cggcacctgc aggtccgtgc gtcccgcggc tggcgcccct gactccgtcc cggccaggga    120
gggccatgat ttccctcccg gggcccctgg tgaccaactt gctgcggttt ttgttcctgg    180
ggctgagtgc cctcgcgccc ccctcgcggg cccagctgca actgcacttg cccgccaacc    240
ggttgcaggc ggtggaggga ggggaagtgg tgcttccagc gtggtacacc ttgcacgggg    300
aggtgtcttc atcccagcca tgggaggtgc cctttgtgat gtggttcttc aaacagaaag    360
aaaaggagga tcaggtgttg tcctacatca atggggtcac aacaagcaaa cctggagtat    420
ccttggtcta ctccatgccc tcccggaacc tgtccctgcg gctggagggt ctccaggaga    480
aagactctgg cccctacagc tgctccgtga atgtgcaaga caaacaaggc aaatctaggg    540
gccacagcat caaaacctta gaactcaatg tactggttcc tccagctcct ccatcctgcc    600
gtctccaggg tgtgccccat gtgggggcaa acgtgaccct gagctgccag tctccaagga    660
gtaagcccgc tgtccaatac cagtgggatc ggcagcttcc atccttccag actttctttg    720
caccagcatt agatgtcatc cgtgggtctt taagcctcac caacctttcg tcttccatgg    780
ctggagtcta tgtctgcaag gcccacaatg aggtgggcac tgcccaatgt aatgtgacgc    840
tggaagtgag cacagggcct ggagctgcag tggttgctgg agctgttgtg ggtaccctgg    900
ttggactggg gttgctggct gggctggtcc tcttgtacca ccgccggggc aaggccctgg    960
aggagccagc caatgatatc aaggaggatg ccattgctcc ccggaccctg ccctggccca   1020
agagctcaga cacaatctcc aagaatggga ccctttcctc tgtcacctcc gcacgagccc   1080
tccggccacc ccatggccct cccaggcctg gtgcattgac cccccacgccc agtctctcca   1140
gccaggccct gccctcacca agactgccca cgacagatgg ggcccaccct caaccaatat   1200
cccccatccc tggtggggtt tcttcctctg gcttgagccg catgggtgct gtgcctgtga   1260
tggtgcctgc ccagagtcaa gctggctctc tggtatgatg accccaccac tcattggcta   1320
aaggatttgg ggtctctcct tcctataagg gtcacctcta gcacagaggc ctgagtcatg   1380
ggaaagagtc acactcctga cccttagtac tctgccccca cctctcttta ctgtgggaaa   1440
accatctcag taagacctaa gtgtccagga gacagaagga gaagaggaag tggatctgga   1500
attgggagga gcctccaccc acccctgact cctccttatg aagccagctg ctgaaattag   1560
ctactcacca agagtgaggg gcagagactt ccagtcactg agtctcccag gccccccttga   1620
tctgtacccc accccctatct aacaccaccc ttggctccca ctccagctcc ctgtattgat   1680
ataacctgtc aggctggctt ggttaggttt tactggggca gaggataggg aatctcttat   1740
taaaactaac atgaaatatg tgttgttttc atttgcaaat ttaaataaag atacataatg   1800
tttgtatgaa aaa                                                      1813
```

<210> SEQ ID NO 39
<211> LENGTH: 390
<212> TYPE: PRT
<213> ORGANISM: Homo sapiens

<400> SEQUENCE: 39

```
Met Ile Ser Leu Pro Gly Pro Leu Val Thr Asn Leu Leu Arg Phe Leu
  1               5                  10                  15
```

-continued

```
Phe Leu Gly Leu Ser Ala Leu Ala Pro Pro Ser Arg Ala Gln Leu Gln
            20                  25                  30

Leu His Leu Pro Ala Asn Arg Leu Gln Ala Val Glu Gly Gly Glu Val
        35                  40                  45

Val Leu Pro Ala Trp Tyr Thr Leu His Gly Glu Val Ser Ser Ser Gln
    50                  55                  60

Pro Trp Glu Val Pro Phe Val Met Trp Phe Phe Lys Gln Lys Glu Lys
65                  70                  75                  80

Glu Asp Gln Val Leu Ser Tyr Ile Asn Gly Val Thr Thr Ser Lys Pro
                85                  90                  95

Gly Val Ser Leu Val Tyr Ser Met Pro Ser Arg Asn Leu Ser Leu Arg
            100                 105                 110

Leu Glu Gly Leu Gln Glu Lys Asp Ser Gly Pro Tyr Ser Cys Ser Val
        115                 120                 125

Asn Val Gln Asp Lys Gln Gly Lys Ser Arg Gly His Ser Ile Lys Thr
    130                 135                 140

Leu Glu Leu Asn Val Leu Val Pro Pro Ala Pro Pro Ser Cys Arg Leu
145                 150                 155                 160

Gln Gly Val Pro His Val Gly Ala Asn Val Thr Leu Ser Cys Gln Ser
                165                 170                 175

Pro Arg Ser Lys Pro Ala Val Gln Tyr Gln Trp Asp Arg Gln Leu Pro
            180                 185                 190

Ser Phe Gln Thr Phe Phe Ala Pro Ala Leu Asp Val Ile Arg Gly Ser
        195                 200                 205

Leu Ser Leu Thr Asn Leu Ser Ser Ser Met Ala Gly Val Tyr Val Cys
    210                 215                 220

Lys Ala His Asn Glu Val Gly Thr Ala Gln Cys Asn Val Thr Leu Glu
225                 230                 235                 240

Val Ser Thr Gly Pro Gly Ala Ala Val Val Ala Gly Ala Val Val Gly
                245                 250                 255

Thr Leu Val Gly Leu Gly Leu Leu Ala Gly Leu Val Leu Leu Tyr His
            260                 265                 270

Arg Arg Gly Lys Ala Leu Glu Glu Pro Ala Asn Asp Ile Lys Glu Asp
        275                 280                 285

Ala Ile Ala Pro Arg Thr Leu Pro Trp Pro Lys Ser Ser Asp Thr Ile
    290                 295                 300

Ser Lys Asn Gly Thr Leu Ser Ser Val Thr Ser Ala Arg Ala Leu Arg
305                 310                 315                 320

Pro Pro His Gly Pro Pro Arg Pro Gly Ala Leu Thr Pro Thr Pro Ser
                325                 330                 335

Leu Ser Ser Gln Ala Leu Pro Ser Pro Arg Leu Pro Thr Thr Asp Gly
            340                 345                 350

Ala His Pro Gln Pro Ile Ser Pro Ile Pro Gly Gly Val Ser Ser Ser
        355                 360                 365

Gly Leu Ser Arg Met Gly Ala Val Pro Val Met Val Pro Ala Gln Ser
    370                 375                 380

Gln Ala Gly Ser Leu Val
385                 390

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide probe

<400> SEQUENCE: 40

agggtctcca ggagaaagac tc                                              22


<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 41

attgtgggcc ttgcagacat agac                                            24


<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 42

ggccacagca tcaaaacctt agaactcaat gtactggttc ctccagctcc                50


<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 43

gtgtgacaca gcgtgggc                                                   18


<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 44

gaccggcagg cttctgcg                                                   18


<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 45

cagcagcttc agccaccagg agtgg                                           25


<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe
```

<400> SEQUENCE: 46
ctgagccgtg ggctgcagtc tcgc 24

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 47
ccgactacga ctggttcttc atcatgcagg atgacacata tgtgc 45

<210> SEQ ID NO 48
<211> LENGTH: 2822
<212> TYPE: DNA
<213> ORGANISM: Homo sapiens

<400> SEQUENCE: 48
cgccaccact gcggccaccg ccaatgaaac gcctcccgct cctagtggtt ttttccactt 60
tgttgaattg ttcctatact caaaattgca ccaagacacc ttgtctccca aatgcaaaat 120
gtgaaatacg caatggaatt gaagcctgct attgcaacat gggattttca ggaaatggtg 180
tcacaatttg tgaagatgat aatgaatgtg gaaatttaac tcagtcctgt ggcgaaaatg 240
ctaattgcac taacacagaa ggaagttatt attgtatgtg tgtacctggc ttcagatcca 300
gcagtaacca agacaggttt atcactaatg atggaaccgt ctgtatagaa aatgtgaatg 360
caaactgcca tttagataat gtctgtatag ctgcaaatat taataaaact ttaacaaaaa 420
tcagatccat aaaagaacct gtggctttgc tacaagaagt ctatagaaat tctgtgacag 480
atctttcacc aacagatata attacatata tagaaatatt agctgaatca tcttcattac 540
taggttacaa gaacaacact atctcagcca aggacaccct ttctaactca actcttactg 600
aatttgtaaa aaccgtgaat aattttgttc aaagggatac atttgtagtt tgggacaagt 660
tatctgtgaa tcataggaga acacatctta caaaactcat gcacactgtt gaacaagcta 720
ctttaaggat atcccagagc ttccaaaaga ccacagagtt tgatacaaat tcaacggata 780
tagctctcaa agttttcttt tttgattcat ataacatgaa acatattcat cctcatatga 840
atatggatgg agactacata aatatatttc caaagagaaa agctgcatat gattcaaatg 900
gcaatgttgc agttgcattt ttatattata agagtattgg tcctttgctt tcatcatctg 960
acaacttctt attgaaacct caaaattatg ataattctga agaggaggaa agagtcatat 1020
cttcagtaat ttcagtctca atgagctcaa acccacccac attatatgaa cttgaaaaaa 1080
taacatttac attaagtcat cgaaaggtca cagataggta taggagtcta tgtgcatttt 1140
ggaattactc acctgatacc atgaatggca gctggtcttc agagggctgt gagctgacat 1200
actcaaatga gacccacacc tcatgccgct gtaatcacct gacacatttt gcaattttga 1260
tgtcctctgg tccttccatt ggtattaaag attataatat tcttacaagg atcactcaac 1320
taggaataat tatttcactg atttgtcttg ccatatgcat ttttaccttc tggttcttca 1380
gtgaaattca aagcaccagg acaacaattc acaaaaatct ttgctgtagc ctatttcttg 1440
ctgaacttgt ttttcttgtt gggatcaata caaatactaa taagctcttc tgttcaatca 1500
ttgccggact gctacactac ttctttttag ctgcttttgc atggatgtgc attgaaggca 1560
tacatctcta tctcattgtt gtgggtgtca tctacaacaa gggatttttg cacaagaatt 1620

-continued

```
tttatatctt tggctatcta agcccagccg tggtagttgg attttcggca gcactaggat   1680
acagatatta tggcacaacc aaagtatgtt ggcttagcac cgaaaacaac tttatttgga   1740
gttttatagg accagcatgc ctaatcattc ttgttaatct cttggctttt ggagtcatca   1800
tatacaaagt ttttcgtcac actgcagggt tgaaaccaga agttagttgc tttgagaaca   1860
taaggtcttg tgcaagagga gccctcgctc ttctgttcct tctcggcacc acctggatct   1920
ttggggttct ccatgttgtg cacgcatcag tggttacagc ttacctcttc acagtcagca   1980
atgctttcca ggggatgttc attttttttat tcctgtgtgt tttatctaga aagattcaag   2040
aagaatatta cagattgttc aaaaatgtcc cctgttgttt tggatgttta aggtaaacat   2100
agagaatggt ggataattac aactgcacaa aaataaaaat tccaagctgt ggatgaccaa   2160
tgtataaaaa tgactcatca aattatccaa ttattaacta ctagacaaaa agtattttaa   2220
atcagttttt ctgtttatgc tataggaact gtagataata aggtaaaatt atgtatcata   2280
tagatatact atgtttttct atgtgaaata gttctgtcaa aaatagtatt gcagatattt   2340
ggaaagtaat tggtttctca ggagtgatat cactgcaccc aaggaaagat tttctttcta   2400
acacgagaag tatatgaatg tcctgaagga aaccactggc ttgatatttc tgtgactcgt   2460
gttgcctttg aaactagtcc cctaccacct cggtaatgag ctccattaca gaaagtggaa   2520
cataagagaa tgaaggggca gaatatcaaa cagtgaaaag ggaatgataa gatgtatttt   2580
gaatgaactg ttttttctgt agactagctg agaaattgtt gacataaaat aaagaattga   2640
agaaacacat tttaccattt tgtgaattgt tctgaactta aatgtccact aaaacaactt   2700
agacttctgt ttgctaaatc tgtttctttt tctaatattc taaaaaaaaa aaaaaggttt   2760
acctccacaa attgaaaaaa aaaaaaaaaa aaaaaaaaaa aaaaaaaaaa aaaaaaaaaa   2820
aa                                                                  2822
```

<210> SEQ ID NO 49
<211> LENGTH: 690
<212> TYPE: PRT
<213> ORGANISM: Homo sapiens

<400> SEQUENCE: 49

```
Met Lys Arg Leu Pro Leu Leu Val Val Phe Ser Thr Leu Leu Asn Cys
  1               5                  10                  15

Ser Tyr Thr Gln Asn Cys Thr Lys Thr Pro Cys Leu Pro Asn Ala Lys
             20                  25                  30

Cys Glu Ile Arg Asn Gly Ile Glu Ala Cys Tyr Cys Asn Met Gly Phe
         35                  40                  45

Ser Gly Asn Gly Val Thr Ile Cys Glu Asp Asp Asn Glu Cys Gly Asn
     50                  55                  60

Leu Thr Gln Ser Cys Gly Glu Asn Ala Asn Cys Thr Asn Thr Glu Gly
 65                  70                  75                  80

Ser Tyr Tyr Cys Met Cys Val Pro Gly Phe Arg Ser Ser Ser Asn Gln
                 85                  90                  95

Asp Arg Phe Ile Thr Asn Asp Gly Thr Val Cys Ile Glu Asn Val Asn
            100                 105                 110

Ala Asn Cys His Leu Asp Asn Val Cys Ile Ala Ala Asn Ile Asn Lys
        115                 120                 125

Thr Leu Thr Lys Ile Arg Ser Ile Lys Glu Pro Val Ala Leu Leu Gln
    130                 135                 140

Glu Val Tyr Arg Asn Ser Val Thr Asp Leu Ser Pro Thr Asp Ile Ile
```

-continued

```
145                 150                 155                 160

Thr Tyr Ile Glu Ile Leu Ala Glu Ser Ser Ser Leu Leu Gly Tyr Lys
                165                 170                 175

Asn Asn Thr Ile Ser Ala Lys Asp Thr Leu Ser Asn Ser Thr Leu Thr
            180                 185                 190

Glu Phe Val Lys Thr Val Asn Asn Phe Val Gln Arg Asp Thr Phe Val
        195                 200                 205

Val Trp Asp Lys Leu Ser Val Asn His Arg Arg Thr His Leu Thr Lys
    210                 215                 220

Leu Met His Thr Val Glu Gln Ala Thr Leu Arg Ile Ser Gln Ser Phe
225                 230                 235                 240

Gln Lys Thr Thr Glu Phe Asp Thr Asn Ser Thr Asp Ile Ala Leu Lys
                245                 250                 255

Val Phe Phe Phe Asp Ser Tyr Asn Met Lys His Ile His Pro His Met
            260                 265                 270

Asn Met Asp Gly Asp Tyr Ile Asn Ile Phe Pro Lys Arg Lys Ala Ala
        275                 280                 285

Tyr Asp Ser Asn Gly Asn Val Ala Val Ala Phe Leu Tyr Tyr Lys Ser
    290                 295                 300

Ile Gly Pro Leu Leu Ser Ser Ser Asp Asn Phe Leu Leu Lys Pro Gln
305                 310                 315                 320

Asn Tyr Asp Asn Ser Glu Glu Glu Glu Arg Val Ile Ser Ser Val Ile
                325                 330                 335

Ser Val Ser Met Ser Ser Asn Pro Pro Thr Leu Tyr Glu Leu Glu Lys
            340                 345                 350

Ile Thr Phe Thr Leu Ser His Arg Lys Val Thr Asp Arg Tyr Arg Ser
        355                 360                 365

Leu Cys Ala Phe Trp Asn Tyr Ser Pro Asp Thr Met Asn Gly Ser Trp
    370                 375                 380

Ser Ser Glu Gly Cys Glu Leu Thr Tyr Ser Asn Glu Thr His Thr Ser
385                 390                 395                 400

Cys Arg Cys Asn His Leu Thr His Phe Ala Ile Leu Met Ser Ser Gly
                405                 410                 415

Pro Ser Ile Gly Ile Lys Asp Tyr Asn Ile Leu Thr Arg Ile Thr Gln
            420                 425                 430

Leu Gly Ile Ile Ile Ser Leu Ile Cys Leu Ala Ile Cys Ile Phe Thr
        435                 440                 445

Phe Trp Phe Phe Ser Glu Ile Gln Ser Thr Arg Thr Thr Ile His Lys
    450                 455                 460

Asn Leu Cys Cys Ser Leu Phe Leu Ala Glu Leu Val Phe Leu Val Gly
465                 470                 475                 480

Ile Asn Thr Asn Thr Asn Lys Leu Phe Cys Ser Ile Ile Ala Gly Leu
                485                 490                 495

Leu His Tyr Phe Phe Leu Ala Ala Phe Ala Trp Met Cys Ile Glu Gly
            500                 505                 510

Ile His Leu Tyr Leu Ile Val Val Gly Val Ile Tyr Asn Lys Gly Phe
        515                 520                 525

Leu His Lys Asn Phe Tyr Ile Phe Gly Tyr Leu Ser Pro Ala Val Val
    530                 535                 540

Val Gly Phe Ser Ala Ala Leu Gly Tyr Arg Tyr Tyr Gly Thr Thr Lys
545                 550                 555                 560

Val Cys Trp Leu Ser Thr Glu Asn Asn Phe Ile Trp Ser Phe Ile Gly
                565                 570                 575
```

-continued

```
Pro Ala Cys Leu Ile Ile Leu Val Asn Leu Leu Ala Phe Gly Val Ile
            580                 585                 590

Ile Tyr Lys Val Phe Arg His Thr Ala Gly Leu Lys Pro Glu Val Ser
        595                 600                 605

Cys Phe Glu Asn Ile Arg Ser Cys Ala Arg Gly Ala Leu Ala Leu Leu
    610                 615                 620

Phe Leu Leu Gly Thr Thr Trp Ile Phe Gly Val Leu His Val Val His
625                 630                 635                 640

Ala Ser Val Val Thr Ala Tyr Leu Phe Thr Val Ser Asn Ala Phe Gln
                645                 650                 655

Gly Met Phe Ile Phe Leu Phe Leu Cys Val Leu Ser Arg Lys Ile Gln
            660                 665                 670

Glu Glu Tyr Tyr Arg Leu Phe Lys Asn Val Pro Cys Cys Phe Gly Cys
        675                 680                 685

Leu Arg
    690
```

```
<210> SEQ ID NO 50
<211> LENGTH: 589
<212> TYPE: DNA
<213> ORGANISM: Homo sapiens
<220> FEATURE:
<221> NAME/KEY: modified_base
<222> LOCATION: (61)..(61)
<223> OTHER INFORMATION: a, t, c or g

<400> SEQUENCE: 50

tggaaacata tcctccctca tatgaatatg gatggagact acataaatat atttccaaag     60

ngaaaagccg gcatatggat tcaaatggca atgttgcagt tgcattttta tattataaga    120

gtattggtcc ctttgctttc atcatctgac aacttcttat tgaaacctca aaattatgat    180

aattctgaag aggaggaaag agtcatatct tcagtaattt cagtctcaat gagctcaaac    240

ccacccacat tatatgaact tgaaaaaata acatttacat taagtcatcg aaaggtcaca    300

gataggtata ggagtctatg tggcattttg gaatactcac ctgataccat gaatggcagc    360

tggtcttcag agggctgtga gctgacatac tcaaatgaga cccacacctc atgccgctgt    420

aatcacctga cacattttgc aattttgatg tcctctggtc cttccattgg tattaaagat    480

tataatattc ttacaaggat cactcaacta ggaataatta tttcactgat ttgtcttgcc    540

atatgcattt ttaccttctg gttcttcagt gaaattcaaa gcaccagga                589


<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 51

ggtaatgagc tccattacag                                                 20


<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe
```

```
<400> SEQUENCE: 52

ggagtagaaa gcgcatgg                                                    18

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 53

cacctgatac catgaatggc ag                                               22

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 54

cgagctcgaa ttaattcg                                                    18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 55

ggatctcctg agctcagg                                                    18

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 56

cctagttgag tgatccttgt aag                                              23

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 57

atgagaccca cacctcatgc cgctgtaatc acctgacaca ttttgcaatt                 50

<210> SEQ ID NO 58
<211> LENGTH: 2137
<212> TYPE: DNA
<213> ORGANISM: Homo sapiens

<400> SEQUENCE: 58

gctcccagcc aagaacctcg gggccgctgc gcggtgggga ggagttcccc gaaacccggc      60
```

-continued

```
cgctaagcga ggcctcctcc tcccgcagat ccgaacggcc tgggcggggt caccccggct    120
gggacaagaa gccgccgcct gcctgcccgg gcccggggag ggggctgggg ctggggccgg    180
aggcggggtg tgagtgggtg tgtgcggggg gcggaggctt gatgcaatcc cgataagaaa    240
tgctcgggtg tcttgggcac ctacccgtgg ggcccgtaag gcgctactat ataaggctgc    300
cggcccggag ccgccgcgcc gtcagagcag gagcgctgcg tccaggatct agggccacga    360
ccatcccaac ccggcactca cagccccgca gcgcatcccg gtcgccgccc agcctcccgc    420
acccccatcg ccggagctgc gccgagagcc ccagggaggt gccatgcgga gcgggtgtgt    480
ggtggtccac gtatggatcc tggccggcct ctggctggcc gtggccgggc gccccctcgc    540
cttctcggac gcggggcccc acgtgcacta cggctggggc gaccccatcc gcctgcggca    600
cctgtacacc tccggccccc acgggctctc cagctgcttc ctgcgcatcc gtgccgacgg    660
cgtcgtggac tgcgcgcggg gccagagcgc gcacagtttg ctggagatca aggcagtcgc    720
tctgcggacc gtggccatca agggcgtgca cagcgtgcgg tacctctgca tgggcgccga    780
cggcaagatg caggggctgc ttcagtactc ggaggaagac tgtgctttcg aggaggagat    840
ccgcccagat ggctacaatg tgtaccgatc cgagaagcac cgcctcccgg tctccctgag    900
cagtgccaaa cagcggcagc tgtacaagaa cagaggcttt cttccactct ctcatttcct    960
gcccatgctg cccatggtcc cagaggagcc tgaggacctc aggggccact tggaatctga   1020
catgttctct tcgcccctgg agaccgacag catggaccca tttgggcttg tcaccggact   1080
ggaggccgtg aggagtccca gctttgagaa gtaactgaga ccatgcccgg gcctcttcac   1140
tgctgccagg ggctgtggta cctgcagcgt gggggacgtg cttctacaag aacagtcctg   1200
agtccacgtt ctgtttagct ttaggaagaa acatctagaa gttgtacata ttcagagttt   1260
tccattggca gtgccagttt ctagccaata gacttgtctg atcataacat tgtaagcctg   1320
tagcttgccc agctgctgcc tgggccccca ttctgctccc tcgaggttgc tggacaagct   1380
gctgcactgt ctcagttctg cttgaatacc tccatcgatg gggaactcac ttcctttgga   1440
aaaattctta tgtcaagctg aaattctcta atttttctc atcacttccc caggagcagc    1500
cagaagacag gcagtagttt taatttcagg aacaggtgat ccactctgta aaacagcagg   1560
taaatttcac tcaaccccat gtgggaattg atctatatct ctacttccag ggaccatttg   1620
cccttcccaa atccctccag gccagaactg actggagcag gcatggccca ccaggcttca   1680
ggagtagggg aagcctggag ccccactcca gccctgggac aacttgagaa ttccccctga   1740
ggccagttct gtcatggatg ctgtcctgag aataacttgc tgtcccggtg tcacctgctt   1800
ccatctccca gcccaccagc cctctgccca cctcacatgc ctccccatgg attggggcct   1860
cccaggcccc ccaccttatg tcaacctgca cttcttgttc aaaaatcagg aaaagaaaag   1920
atttgaagac cccaagtctt gtcaataact tgctgtgtgg aagcagcggg ggaagaccta   1980
gaaccctttc cccagcactt ggttttccaa catgatattt atgagtaatt tattttgata   2040
tgtacatctc ttattttctt acattattta tgcccccaaa ttatatttat gtatgtaagt   2100
gaggtttgtt ttgtatatta aaatggagtt tgtttgt                            2137
```

<210> SEQ ID NO 59
<211> LENGTH: 216
<212> TYPE: PRT
<213> ORGANISM: Homo sapiens

<400> SEQUENCE: 59

Met Arg Ser Gly Cys Val Val Val His Val Trp Ile Leu Ala Gly Leu

-continued

```
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 60
atccgcccag atggctacaa tgtgta 26

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 61
gcctcccggt ctccctgagc agtgccaaac agcggcagtg ta 42

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 62
ccagtccggt gacaagccca aa 22

-continued

<210> SEQ ID NO 63
<211> LENGTH: 1295
<212> TYPE: DNA
<213> ORGANISM: Homo sapiens

<400> SEQUENCE: 63

```
cccagaagtt caagggcccc cggcctcctg cgctcctgcc gccgggaccc tcgacctcct     60

cagagcagcc ggctgccgcc ccgggaagat ggcgaggagg agccgccacc gcctcctcct    120

gctgctgctg cgctacctgg tggtcgccct gggctatcat aaggcctatg ggttttctgc    180

cccaaaagac caacaagtag tcacagcagt agagtaccaa gaggctattt tagcctgcaa    240

aaccccaaag aagactgttt cctccagatt agagtggaag aaactgggtc ggagtgtctc    300

ctttgtctac tatcaacaga ctcttcaagg tgattttaaa aatcgagctg agatgataga    360

tttcaatatc cggatcaaaa atgtgacaag aagtgatgcg gggaaatatc gttgtgaagt    420

tagtgcccca tctgagcaag gccaaaacct ggaagaggat acagtcactc tggaagtatt    480

agtggctcca gcagttccat catgtgaagt accctcttct gctctgagtg gaactgtggt    540

agagctacga tgtcaagaca aagaagggaa tccagctcct gaatacacat ggtttaagga    600

tggcatccgt ttgctagaaa atcccagact tggctcccaa agcaccaaca gctcatacac    660

aatgaataca aaaactggaa ctctgcaatt taatactgtt tccaaactgg acactggaga    720

atattcctgt gaagcccgca attctgttgg atatcgcagg tgtcctggga aacgaatgca    780

agtagatgat ctcaacataa gtggcatcat agcagccgta gtagttgtgg ccttagtgat    840

ttccgtttgt ggccttggtg tatgctatgc tcagaggaaa ggctactttt caaaagaaac    900

ctccttccag aagagtaatt cttcatctaa agccacgaca atgagtgaaa atgtgcagtg    960

gctcacgcct gtaatcccag cactttggaa ggccgcggcg ggcggatcac gaggtcagga   1020

gttctagacc agtctggcca atatggtgaa accccatctc tactaaaata caaaaattag   1080

ctgggcatgg tggcatgtgc ctgcagttcc agctgcttgg gagacaggag aatcacttga   1140

acccgggagg cggaggttgc agtgagctga gatcacgcca ctgcagtcca gcctgggtaa   1200

cagagcaaga ttccatctca aaaaataaaa taaataaata aataaatact ggtttttacc   1260

tgtagaattc ttacaataaa tatagcttga tattc                              1295
```

<210> SEQ ID NO 64
<211> LENGTH: 312
<212> TYPE: PRT
<213> ORGANISM: Homo sapiens

<400> SEQUENCE: 64

```
Met Ala Arg Arg Ser Arg His Arg Leu Leu Leu Leu Leu Arg Tyr
  1               5                  10                  15

Leu Val Val Ala Leu Gly Tyr His Lys Ala Tyr Gly Phe Ser Ala Pro
             20                  25                  30

Lys Asp Gln Gln Val Val Thr Ala Val Glu Tyr Gln Glu Ala Ile Leu
         35                  40                  45

Ala Cys Lys Thr Pro Lys Lys Thr Val Ser Ser Arg Leu Glu Trp Lys
     50                  55                  60

Lys Leu Gly Arg Ser Val Ser Phe Val Tyr Tyr Gln Gln Thr Leu Gln
 65                  70                  75                  80

Gly Asp Phe Lys Asn Arg Ala Glu Met Ile Asp Phe Asn Ile Arg Ile
                 85                  90                  95
```

-continued

```
Lys Asn Val Thr Arg Ser Asp Ala Gly Lys Tyr Arg Cys Glu Val Ser
            100                 105                 110

Ala Pro Ser Glu Gln Gly Gln Asn Leu Glu Glu Asp Thr Val Thr Leu
        115                 120                 125

Glu Val Leu Val Ala Pro Ala Val Pro Ser Cys Glu Val Pro Ser Ser
    130                 135                 140

Ala Leu Ser Gly Thr Val Val Glu Leu Arg Cys Gln Asp Lys Glu Gly
145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
            180                 185                 190

Asn Thr Lys Thr Gly Thr Leu Gln Phe Asn Thr Val Ser Lys Leu Asp
        195                 200                 205

Thr Gly Glu Tyr Ser Cys Glu Ala Arg Asn Ser Val Gly Tyr Arg Arg
    210                 215                 220

Cys Pro Gly Lys Arg Met Gln Val Asp Asp Leu Asn Ile Ser Gly Ile
225                 230                 235                 240

Ile Ala Ala Val Val Val Val Ala Leu Val Ile Ser Val Cys Gly Leu
                245                 250                 255

Gly Val Cys Tyr Ala Gln Arg Lys Gly Tyr Phe Ser Lys Glu Thr Ser
            260                 265                 270

Phe Gln Lys Ser Asn Ser Ser Ser Lys Ala Thr Thr Met Ser Glu Asn
        275                 280                 285

Val Gln Trp Leu Thr Pro Val Ile Pro Ala Leu Trp Lys Ala Ala Ala
    290                 295                 300

Gly Gly Ser Arg Gly Gln Glu Phe
305                 310
```

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 65
atcgttgtga agttagtgcc cc 22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 66
acctgcgata tccaacagaa ttg 23

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 67

-continued ggaagaggat acagtcactc tggaagtatt agtggctcca gcagttcc 48

<210> SEQ ID NO 68
<211> LENGTH: 2639
<212> TYPE: DNA
<213> ORGANISM: Homo sapiens

<400> SEQUENCE: 68
gacatcggag gtgggctagc actgaaactg cttttcaaga cgaggaagag gaggagaaag 60
agaaagaaga ggaagatgtt gggcaacatt tatttaacat gctccacagc ccggaccctg 120
gcatcatgct gctattcctg caaatactga agaagcatgg gatttaaata ttttacttct 180
aaataaatga attactcaat ctcctatgac catctataca tactccacct tcaaaaagta 240
catcaatatt atatcattaa ggaaatagta accttctctt ctccaatatg catgacattt 300
ttggacaatg caattgtggc actggcactt atttcagtga agaaaaactt tgtggttcta 360
tggcattcat catttgacaa atgcaagcat cttccttatc aatcagctcc tattgaactt 420
actagcactg actgtggaat ccttaagggc ccattacatt tctgaagaag aaagctaaga 480
tgaaggacat gccactccga attcatgtgc tacttggcct agctatcact acactagtac 540
aagctgtaga taaaaaagtg gattgtccac ggttatgtac gtgtgaaatc aggccttggt 600
ttacacccag atccatttat atggaagcat ctacagtgga ttgtaatgat ttaggtcttt 660
taactttccc agccagattg ccagctaaca cacagattct tctcctacag actaacaata 720
ttgcaaaaat tgaatactcc acagactttc cagtaaacct tactggcctg gatttatctc 780
aaaacaattt atcttcagtc accaatatta atgtaaaaaa gatgcctcag ctcctttctg 840
tgtacctaga ggaaaacaaa cttactgaac tgcctgaaaa atgtctgtcc gaactgagca 900
acttacaaga actctatatt aatcacaact tgctttctac aatttcacct ggagccttta 960
ttggcctaca taatcttctt cgacttcatc tcaattcaaa tagattgcag atgatcaaca 1020
gtaagtggtt tgatgctctt ccaaatctag agattctgat gattggggaa aatccaatta 1080
tcagaatcaa agacatgaac tttaagcctc ttatcaatct tcgcagcctg gttatagctg 1140
gtataaacct cacagaaata ccagataacg ccttggttgg actggaaaac ttagaaagca 1200
tctcttttta cgataacagg cttattaaag taccccatgt tgctcttcaa aaagttgtaa 1260
atctcaaatt tttggatcta aataaaaatc ctattaatag aatacgaagg ggtgatttta 1320
gcaatatgct acacttaaaa gagttgggga taaataatat gcctgagctg atttccatcg 1380
atagtcttgc tgtggataac ctgccagatt taagaaaaat agaagctact aacaacccta 1440
gattgtctta cattcacccc aatgcatttt tcagactccc caagctggaa tcactcatgc 1500
tgaacagcaa tgctctcagt gccctgtacc atggtaccat tgagtctctg ccaaacctca 1560
aggaaatcag catacacagt aaccccatca ggtgtgactg tgtcatccgt tggatgaaca 1620
tgaacaaaac caacattcga ttcatggagc cagattcact gttttgcgtg gacccacctg 1680
aattccaagg tcagaatgtt cggcaagtgc atttcaggga catgatggaa atttgtctcc 1740
ctcttatagc tcctgagagc tttccttcta atctaaatgt agaagctggg agctatgttt 1800
cctttcactg tagagctact gcagaaccac agcctgaaat ctactggata acaccttctg 1860
gtcaaaaact cttgcctaat accctgacag acaagttcta tgtccattct gagggaacac 1920
tagatataaa tggcgtaact cccaaagaag gggggtttata tacttgtata gcaactaacc 1980
tagttggcgc tgacttgaag tctgttatga tcaaagtgga tggatctttt ccacaagata 2040
acaatggctc tttgaatatt aaaataagag atattcaggc caattcagtt ttggtgtcct 2100

-continued

```
ggaaagcaag ttctaaaatt ctcaaatcta gtgttaaatg gacagccttt gtcaagactg   2160

aaaattctca tgctgcgcaa agtgctcgaa taccatctga tgtcaaggta tataatctta   2220

ctcatctgaa tccatcaact gagtataaaa tttgtattga tattcccacc atctatcaga   2280

aaaacagaaa aaaatgtgta aatgtcacca ccaaaggttt gcaccctgat caaaaagagt   2340

atgaaaagaa taataccaca acacttatgg cctgtcttgg aggccttctg ggattattgg   2400

gtgtgatatg tcttatcagc tgcctctctc cagaaatgaa ctgtgatggt ggacacagct   2460

atgtgaggaa ttacttacag aaaccaacct ttgcattagg tgagctttat cctcctctga   2520

taaatctctg ggaagcagga aaagaaaaaa gtacatcact gaaagtaaaa gcaactgtta   2580

taggtttacc aacaaatatg tcctaaaaac caccaaggaa acctactcca aaaatgaac    2639


<210> SEQ ID NO 69
<211> LENGTH: 708
<212> TYPE: PRT
<213> ORGANISM: Homo sapiens

<400> SEQUENCE: 69

Met Lys Asp Met Pro Leu Arg Ile His Val Leu Leu Gly Leu Ala Ile
  1               5                  10                  15

Thr Thr Leu Val Gln Ala Val Asp Lys Lys Val Asp Cys Pro Arg Leu
             20                  25                  30

Cys Thr Cys Glu Ile Arg Pro Trp Phe Thr Pro Arg Ser Ile Tyr Met
         35                  40                  45

Glu Ala Ser Thr Val Asp Cys Asn Asp Leu Gly Leu Leu Thr Phe Pro
     50                  55                  60

Ala Arg Leu Pro Ala Asn Thr Gln Ile Leu Leu Leu Gln Thr Asn Asn
 65                  70                  75                  80

Ile Ala Lys Ile Glu Tyr Ser Thr Asp Phe Pro Val Asn Leu Thr Gly
                 85                  90                  95

Leu Asp Leu Ser Gln Asn Asn Leu Ser Ser Val Thr Asn Ile Asn Val
            100                 105                 110

Lys Lys Met Pro Gln Leu Leu Ser Val Tyr Leu Glu Glu Asn Lys Leu
        115                 120                 125

Thr Glu Leu Pro Glu Lys Cys Leu Ser Glu Leu Ser Asn Leu Gln Glu
    130                 135                 140

Leu Tyr Ile Asn His Asn Leu Leu Ser Thr Ile Ser Pro Gly Ala Phe
145                 150                 155                 160

Ile Gly Leu His Asn Leu Leu Arg Leu His Leu Asn Ser Asn Arg Leu
                165                 170                 175

Gln Met Ile Asn Ser Lys Trp Phe Asp Ala Leu Pro Asn Leu Glu Ile
            180                 185                 190

Leu Met Ile Gly Glu Asn Pro Ile Ile Arg Ile Lys Asp Met Asn Phe
        195                 200                 205

Lys Pro Leu Ile Asn Leu Arg Ser Leu Val Ile Ala Gly Ile Asn Leu
    210                 215                 220

Thr Glu Ile Pro Asp Asn Ala Leu Val Gly Leu Glu Asn Leu Glu Ser
225                 230                 235                 240

Ile Ser Phe Tyr Asp Asn Arg Leu Ile Lys Val Pro His Val Ala Leu
                245                 250                 255

Gln Lys Val Val Asn Leu Lys Phe Leu Asp Leu Asn Lys Asn Pro Ile
            260                 265                 270

Asn Arg Ile Arg Arg Gly Asp Phe Ser Asn Met Leu His Leu Lys Glu
```

-continued

```
        275                 280                 285

Leu Gly Ile Asn Asn Met Pro Glu Leu Ile Ser Ile Asp Ser Leu Ala
    290                 295                 300

Val Asp Asn Leu Pro Asp Leu Arg Lys Ile Glu Ala Thr Asn Asn Pro
305                 310                 315                 320

Arg Leu Ser Tyr Ile His Pro Asn Ala Phe Phe Arg Leu Pro Lys Leu
                325                 330                 335

Glu Ser Leu Met Leu Asn Ser Asn Ala Leu Ser Ala Leu Tyr His Gly
            340                 345                 350

Thr Ile Glu Ser Leu Pro Asn Leu Lys Glu Ile Ser Ile His Ser Asn
        355                 360                 365

Pro Ile Arg Cys Asp Cys Val Ile Arg Trp Met Asn Met Asn Lys Thr
    370                 375                 380

Asn Ile Arg Phe Met Glu Pro Asp Ser Leu Phe Cys Val Asp Pro Pro
385                 390                 395                 400

Glu Phe Gln Gly Gln Asn Val Arg Gln Val His Phe Arg Asp Met Met
                405                 410                 415

Glu Ile Cys Leu Pro Leu Ile Ala Pro Glu Ser Phe Pro Ser Asn Leu
            420                 425                 430

Asn Val Glu Ala Gly Ser Tyr Val Ser Phe His Cys Arg Ala Thr Ala
        435                 440                 445

Glu Pro Gln Pro Glu Ile Tyr Trp Ile Thr Pro Ser Gly Gln Lys Leu
    450                 455                 460

Leu Pro Asn Thr Leu Thr Asp Lys Phe Tyr Val His Ser Glu Gly Thr
465                 470                 475                 480

Leu Asp Ile Asn Gly Val Thr Pro Lys Glu Gly Gly Leu Tyr Thr Cys
                485                 490                 495

Ile Ala Thr Asn Leu Val Gly Ala Asp Leu Lys Ser Val Met Ile Lys
            500                 505                 510

Val Asp Gly Ser Phe Pro Gln Asp Asn Asn Gly Ser Leu Asn Ile Lys
        515                 520                 525

Ile Arg Asp Ile Gln Ala Asn Ser Val Leu Val Ser Trp Lys Ala Ser
    530                 535                 540

Ser Lys Ile Leu Lys Ser Ser Val Lys Trp Thr Ala Phe Val Lys Thr
545                 550                 555                 560

Glu Asn Ser His Ala Ala Gln Ser Ala Arg Ile Pro Ser Asp Val Lys
                565                 570                 575

Val Tyr Asn Leu Thr His Leu Asn Pro Ser Thr Glu Tyr Lys Ile Cys
            580                 585                 590

Ile Asp Ile Pro Thr Ile Tyr Gln Lys Asn Arg Lys Lys Cys Val Asn
        595                 600                 605

Val Thr Thr Lys Gly Leu His Pro Asp Gln Lys Glu Tyr Glu Lys Asn
    610                 615                 620

Asn Thr Thr Thr Leu Met Ala Cys Leu Gly Gly Leu Leu Gly Ile Ile
625                 630                 635                 640

Gly Val Ile Cys Leu Ile Ser Cys Leu Ser Pro Glu Met Asn Cys Asp
                645                 650                 655

Gly Gly His Ser Tyr Val Arg Asn Tyr Leu Gln Lys Pro Thr Phe Ala
            660                 665                 670

Leu Gly Glu Leu Tyr Pro Pro Leu Ile Asn Leu Trp Glu Ala Gly Lys
        675                 680                 685

Glu Lys Ser Thr Ser Leu Lys Val Lys Ala Thr Val Ile Gly Leu Pro
    690                 695                 700
```

-continued

```
Thr Asn Met Ser
705


<210> SEQ ID NO 70
<211> LENGTH: 1305
<212> TYPE: DNA
<213> ORGANISM: Homo sapiens

<400> SEQUENCE: 70

gcccgggact ggcgcaaggt gcccaagcaa ggaaagaaat aatgaagaga cacatgtgtt      60

agctgcagcc ttttgaaaca cgcaagaagg aaatcaatag tgtggacagg gctggaacct     120

ttaccacgct tgttggagta gatgaggaat gggctcgtga ttatgctgac attccagcat     180

gaatctggta gacctgtggt taacccgttc cctctccatg tgtctcctcc tacaaagttt     240

tgttcttatg atactgtgct ttcattctgc cagtatgtgt cccaagggct gtctttgttc     300

ttcctctggg ggtttaaatg tcacctgtag caatgcaaat ctcaaggaaa tacctagaga     360

tcttcctcct gaaacagtct tactgtatct ggactccaat cagatcacat ctattcccaa     420

tgaaattttt aaggacctcc atcaactgag agttctcaac ctgtccaaaa atggcattga     480

gtttatcgat gagcatgcct tcaaaggagt agctgaaacc ttgcagactc tggacttgtc     540

cgacaatcgg attcaaagtg tgcacaaaaa tgccttcaat aacctgaagg ccagggccag     600

aattgccaac aacccctggc actgcgactg tactctacag caagttctga ggagcatggc     660

gtccaatcat gagacagccc acaacgtgat ctgtaaaacg tccgtgttgg atgaacatgc     720

tggcagacca ttcctcaatg ctgccaacga cgctgacctt tgtaacctcc ctaaaaaaac     780

taccgattat gccatgctgg tcaccatgtt tggctggttc actatggtga tctcatatgt     840

ggtatattat gtgaggcaaa atcaggagga tgcccggaga cacctcgaat acttgaaatc     900

cctgccaagc aggcagaaga aagcagatga acctgatgat attagcactg tggtatagtg     960

tccaaactga ctgtcattga gaaagaaaga aagtagtttg cgattgcagt agaaataagt    1020

ggtttacttc tcccatccat tgtaaacatt tgaaactttg tatttcagtt ttttttgaat    1080

tatgccactg ctgaactttt aacaaacact acaacataaa taatttgagt ttaggtgatc    1140

caccccttaa ttgtaccccc gatggtatat ttctgagtaa gctactatct gaacattagt    1200

tagatccatc tcactattta ataatgaaat ttattttttt aatttaaaag caaataaaag    1260

cttaactttg aaccatggga aaaaaaaaaa aaaaaaaaaa aaaca                   1305


<210> SEQ ID NO 71
<211> LENGTH: 259
<212> TYPE: PRT
<213> ORGANISM: Homo sapiens

<400> SEQUENCE: 71

Met Asn Leu Val Asp Leu Trp Leu Thr Arg Ser Leu Ser Met Cys Leu
  1               5                  10                  15

Leu Leu Gln Ser Phe Val Leu Met Ile Leu Cys Phe His Ser Ala Ser
             20                  25                  30

Met Cys Pro Lys Gly Cys Leu Cys Ser Ser Ser Gly Gly Leu Asn Val
         35                  40                  45

Thr Cys Ser Asn Ala Asn Leu Lys Glu Ile Pro Arg Asp Leu Pro Pro
     50                  55                  60

Glu Thr Val Leu Leu Tyr Leu Asp Ser Asn Gln Ile Thr Ser Ile Pro
 65                  70                  75                  80
```

-continued

```
Asn Glu Ile Phe Lys Asp Leu His Gln Leu Arg Val Leu Asn Leu Ser
                85                  90                  95

Lys Asn Gly Ile Glu Phe Ile Asp Glu His Ala Phe Lys Gly Val Ala
            100                 105                 110

Glu Thr Leu Gln Thr Leu Asp Leu Ser Asp Asn Arg Ile Gln Ser Val
        115                 120                 125

His Lys Asn Ala Phe Asn Asn Leu Lys Ala Arg Ala Arg Ile Ala Asn
    130                 135                 140

Asn Pro Trp His Cys Asp Cys Thr Leu Gln Gln Val Leu Arg Ser Met
145                 150                 155                 160

Ala Ser Asn His Glu Thr Ala His Asn Val Ile Cys Lys Thr Ser Val
                165                 170                 175

Leu Asp Glu His Ala Gly Arg Pro Phe Leu Asn Ala Ala Asn Asp Ala
            180                 185                 190

Asp Leu Cys Asn Leu Pro Lys Lys Thr Thr Asp Tyr Ala Met Leu Val
        195                 200                 205

Thr Met Phe Gly Trp Phe Thr Met Val Ile Ser Tyr Val Val Tyr Tyr
    210                 215                 220

Val Arg Gln Asn Gln Glu Asp Ala Arg Arg His Leu Glu Tyr Leu Lys
225                 230                 235                 240

Ser Leu Pro Ser Arg Gln Lys Lys Ala Asp Glu Pro Asp Asp Ile Ser
                245                 250                 255

Thr Val Val
```

<210> SEQ ID NO 72
<211> LENGTH: 2290
<212> TYPE: DNA
<213> ORGANISM: Homo sapiens

<400> SEQUENCE: 72

```
accgagccga gcggaccgaa ggcgcgcccg agatgcaggt gagcaagagg atgctggcgg     60

ggggcgtgag gagcatgccc agccccctcc tggcctgctg gcagcccatc ctcctgctgg    120

tgctgggctc agtgctgtca ggctcggcca cgggctgccc gccccgctgc gagtgctccg    180

cccaggaccg cgctgtgctg tgccaccgca agtgctttgt ggcagtcccc gagggcatcc    240

ccaccgagac gcgcctgctg gacctaggca agaaccgcat caaaacgctc aaccaggacg    300

agttcgccag cttcccgcac ctggaggagc tggagctcaa cgagaacatc gtgagcgccg    360

tggagcccgg cgccttcaac aacctcttca acctccggac gctgggtctc cgcagcaacc    420

gcctgaagct catcccgcta ggcgtcttca ctggcctcag caacctgacc aagcaggaca    480

tcagcgagaa caagatcgtt atcctactgg actacatgtt tcaggacctg tacaacctca    540

agtcactgga ggttggcgac aatgacctcg tctacatctc tcaccgcgcc ttcagcggcc    600

tcaacagcct ggagcagctg acgctggaga aatgcaacct gacctccatc cccaccgagg    660

cgctgtccca cctgcacggc ctcatcgtcc tgaggctccg gcacctcaac atcaatgcca    720

tccgggacta ctccttcaag aggctgtacc gactcaaggt cttggagatc tcccactggc    780

cctacttgga caccatgaca cccaactgcc tctacggcct caacctgacg tccctgtcca    840

tcacacactg caatctgacc gctgtgccct acctggccgt ccgccaccta gtctatctcc    900

gcttcctcaa cctctcctac aaccccatca gcaccattga gggctccatg ttgcatgagc    960

tgctccggct gcaggagatc cagctggtgg gcgggcagct ggccgtggtg gagccctatg   1020

ccttccgcgg cctcaactac ctgcgcgtgc tcaatgtctc tggcaaccag ctgaccacac   1080
```

-continued

```
tggaggaatc agtcttccac tcggtgggca acctggagac actcatcctg gactccaacc   1140
cgctggcctg cgactgtcgg ctcctgtggg tgttccggcg ccgctggcgg ctcaacttca   1200
accggcagca gcccacgtgc gccacgcccg agtttgtcca gggcaaggag ttcaaggact   1260
tccctgatgt gctactgccc aactacttca cctgccgccg cgcccgcatc cgggaccgca   1320
aggcccagca ggtgtttgtg gacgagggcc acacggtgca gtttgtgtgc cgggccgatg   1380
gcgacccgcc gcccgccatc ctctggctct caccccgaaa gcacctggtc tcagccaaga   1440
gcaatgggcg gctcacagtc ttccctgatg gcacgctgga ggtgcgctac gcccaggtac   1500
aggacaacgg cacgtacctg tgcatcgcgg ccaacgcggg cggcaacgac tccatgcccg   1560
cccacctgca tgtgcgcagc tactcgcccg actggcccca tcagcccaac aagaccttcg   1620
ctttcatctc caaccagccg ggcgagggag aggccaacag cacccgcgcc actgtgcctt   1680
tccccttcga catcaagacc ctcatcatcg ccaccaccat gggcttcatc tctttcctgg   1740
gcgtcgtcct cttctgcctg gtgctgctgt ttctctggag ccggggcaag ggcaacacaa   1800
agcacaacat cgagatcgag tatgtgcccc gaaagtcgga cgcaggcatc agctccgccg   1860
acgcgccccg caagttcaac atgaagatga tatgaggccg gggcgggggg cagggacccc   1920
cgggcggccg ggcaggggaa ggggcctggt cgccacctgc tcactctcca gtccttccca   1980
cctcctccct acccttctac acacgttctc tttctccctc ccgcctccgt cccctgctgc   2040
cccccgccag ccctcaccac ctgccctcct tctaccagga cctcagaagc ccagacctgg   2100
ggaccccacc tacacagggg cattgacaga ctggagttga aagccgacga accgacacgc   2160
ggcagagtca ataattcaat aaaaaagtta cgaactttct ctgtaacttg ggtttcaata   2220
attatggatt tttatgaaaa cttgaaataa taaaaagaga aaaaaactaa aaaaaaaaaa   2280
aaaaaaaaaa                                                          2290
```

```
<210> SEQ ID NO 73
<211> LENGTH: 620
<212> TYPE: PRT
<213> ORGANISM: Homo sapiens

<400> SEQUENCE: 73

Met Gln Val Ser Lys Arg Met Leu Ala Gly Gly Val Arg Ser Met Pro
1               5                   10                  15

Ser Pro Leu Leu Ala Cys Trp Gln Pro Ile Leu Leu Leu Val Leu Gly
            20                  25                  30

Ser Val Leu Ser Gly Ser Ala Thr Gly Cys Pro Pro Arg Cys Glu Cys
        35                  40                  45

Ser Ala Gln Asp Arg Ala Val Leu Cys His Arg Lys Cys Phe Val Ala
    50                  55                  60

Val Pro Glu Gly Ile Pro Thr Glu Thr Arg Leu Leu Asp Leu Gly Lys
65                  70                  75                  80

Asn Arg Ile Lys Thr Leu Asn Gln Asp Glu Phe Ala Ser Phe Pro His
                85                  90                  95

Leu Glu Glu Leu Glu Leu Asn Glu Asn Ile Val Ser Ala Val Glu Pro
            100                 105                 110

Gly Ala Phe Asn Asn Leu Phe Asn Leu Arg Thr Leu Gly Leu Arg Ser
        115                 120                 125

Asn Arg Leu Lys Leu Ile Pro Leu Gly Val Phe Thr Gly Leu Ser Asn
    130                 135                 140

Leu Thr Lys Gln Asp Ile Ser Glu Asn Lys Ile Val Ile Leu Leu Asp
145                 150                 155                 160
```

-continued

```
Tyr Met Phe Gln Asp Leu Tyr Asn Leu Lys Ser Leu Glu Val Gly Asp
                165                 170                 175

Asn Asp Leu Val Tyr Ile Ser His Arg Ala Phe Ser Gly Leu Asn Ser
            180                 185                 190

Leu Glu Gln Leu Thr Leu Glu Lys Cys Asn Leu Thr Ser Ile Pro Thr
        195                 200                 205

Glu Ala Leu Ser His Leu His Gly Leu Ile Val Leu Arg Leu Arg His
    210                 215                 220

Leu Asn Ile Asn Ala Ile Arg Asp Tyr Ser Phe Lys Arg Leu Tyr Arg
225                 230                 235                 240

Leu Lys Val Leu Glu Ile Ser His Trp Pro Tyr Leu Asp Thr Met Thr
                245                 250                 255

Pro Asn Cys Leu Tyr Gly Leu Asn Leu Thr Ser Leu Ser Ile Thr His
            260                 265                 270

Cys Asn Leu Thr Ala Val Pro Tyr Leu Ala Val Arg His Leu Val Tyr
        275                 280                 285

Leu Arg Phe Leu Asn Leu Ser Tyr Asn Pro Ile Ser Thr Ile Glu Gly
    290                 295                 300

Ser Met Leu His Glu Leu Leu Arg Leu Gln Glu Ile Gln Leu Val Gly
305                 310                 315                 320

Gly Gln Leu Ala Val Val Glu Pro Tyr Ala Phe Arg Gly Leu Asn Tyr
                325                 330                 335

Leu Arg Val Leu Asn Val Ser Gly Asn Gln Leu Thr Thr Leu Glu Glu
            340                 345                 350

Ser Val Phe His Ser Val Gly Asn Leu Glu Thr Leu Ile Leu Asp Ser
        355                 360                 365

Asn Pro Leu Ala Cys Asp Cys Arg Leu Leu Trp Val Phe Arg Arg Arg
    370                 375                 380

Trp Arg Leu Asn Phe Asn Arg Gln Gln Pro Thr Cys Ala Thr Pro Glu
385                 390                 395                 400

Phe Val Gln Gly Lys Glu Phe Lys Asp Phe Pro Asp Val Leu Leu Pro
                405                 410                 415

Asn Tyr Phe Thr Cys Arg Arg Ala Arg Ile Arg Asp Arg Lys Ala Gln
            420                 425                 430

Gln Val Phe Val Asp Glu Gly His Thr Val Gln Phe Val Cys Arg Ala
        435                 440                 445

Asp Gly Asp Pro Pro Pro Ala Ile Leu Trp Leu Ser Pro Arg Lys His
    450                 455                 460

Leu Val Ser Ala Lys Ser Asn Gly Arg Leu Thr Val Phe Pro Asp Gly
465                 470                 475                 480

Thr Leu Glu Val Arg Tyr Ala Gln Val Gln Asp Asn Gly Thr Tyr Leu
                485                 490                 495

Cys Ile Ala Ala Asn Ala Gly Gly Asn Asp Ser Met Pro Ala His Leu
            500                 505                 510

His Val Arg Ser Tyr Ser Pro Asp Trp Pro His Gln Pro Asn Lys Thr
        515                 520                 525

Phe Ala Phe Ile Ser Asn Gln Pro Gly Glu Gly Glu Ala Asn Ser Thr
    530                 535                 540

Arg Ala Thr Val Pro Phe Pro Phe Asp Ile Lys Thr Leu Ile Ile Ala
545                 550                 555                 560

Thr Thr Met Gly Phe Ile Ser Phe Leu Gly Val Val Leu Phe Cys Leu
                565                 570                 575
```

-continued

```
Val Leu Leu Phe Leu Trp Ser Arg Gly Lys Gly Asn Thr Lys His Asn
            580                 585                 590

Ile Glu Ile Glu Tyr Val Pro Arg Lys Ser Asp Ala Gly Ile Ser Ser
        595                 600                 605

Ala Asp Ala Pro Arg Lys Phe Asn Met Lys Met Ile
    610                 615                 620
```

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 74
tcacctggag cctttattgg cc 22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 75
ataccagcta taaccaggct gcg 23

<210> SEQ ID NO 76
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 76
caacagtaag tggtttgatg ctcttccaaa tctagagatt ctgatgattg 50
gg 52

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 77
ccatgtgtct cctcctacaa ag 22

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 78
gggaatagat gtgatctgat tgg 23

<210> SEQ ID NO 79
<211> LENGTH: 50

-continued

<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 79
cacctgtagc aatgcaaatc tcaaggaaat acctagagat cttcctcctg 50

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 80
agcaaccgcc tgaagctcat cc 22

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 81
aaggcgcggt gaaagatgta gacg 24

<210> SEQ ID NO 82
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 82
gactacatgt ttcaggacct gtacaacctc aagtcactgg aggttggcga 50

<210> SEQ ID NO 83
<211> LENGTH: 1685
<212> TYPE: DNA
<213> ORGANISM: Homo sapiens

<400> SEQUENCE: 83
cccacgcgtc cgcacctcgg ccccgggctc cgaagcggct cgggggcgcc ctttcggtca 60
acatcgtagt ccaccccctc cccatcccca gcccccgggg attcaggctc gccagcgccc 120
agccagggag ccggccggga agcgcgatgg gggccccagc cgcctcgctc ctgctcctgc 180
tcctgctgtt cgcctgctgc tgggcgcccg gcggggccaa cctctcccag gacgacagcc 240
agccctggac atctgatgaa acagtggtgg ctggtggcac cgtggtgctc aagtgccaag 300
tgaaagatca cgaggactca tccctgcaat ggtctaaccc tgctcagcag actctctact 360
ttggggagaa gagagccctt cgagataatc gaattcagct ggttacctct acgccccacg 420
agctcagcat cagcatcagc aatgtggccc tggcagacga gggcgagtac acctgctcaa 480
tcttcactat gcctgtgcga actgccaagt ccctcgtcac tgtgctagga attccacaga 540
agcccatcat cactggttat aaatcttcat tacgggaaaa agacacagcc accctaaact 600
gtcagtcttc tgggagcaag cctgcagccc ggctcacctg gagaaagggt gaccaagaac 660

-continued

```
tccacggaga accaacccgc atacaggaag atcccaatgg taaaaccttc actgtcagca    720

gctcggtgac attccaggtt acccgggagg atgatggggc gagcatcgtg tgctctgtga    780

accatgaatc tctaaaggga gctgacagat ccacctctca acgcattgaa gttttataca    840

caccaactgc gatgattagg ccagaccctc cccatcctcg tgagggccag aagctgttgc    900

tacactgtga gggtcgcggc aatccagtcc cccagcagta cctatgggag aaggagggca    960

gtgtgccacc cctgaagatg acccaggaga gtgccctgat cttccctttc ctcaacaaga   1020

gtgacagtgg cacctacggc tgcacagcca ccagcaacat gggcagctac aaggcctact   1080

acaccctcaa tgttaatgac cccagtccgg tgccctcctc ctccagcacc taccacgcca   1140

tcatcggtgg gatcgtggct ttcattgtct tcctgctgct catcatgctc atcttccttg   1200

gccactactt gatccggcac aaaggaacct acctgacaca tgaggcaaaa ggctccgacg   1260

atgctccaga cgcggacacg gccatcatca atgcagaagg cgggcagtca ggaggggacg   1320

acaagaagga atatttcatc tagaggcgcc tgcccacttc ctgcgccccc caggggccct   1380

gtggggactg ctggggccgt caccaacccg gacttgtaca gagcaaccgc agggccgccc   1440

ctcccgcttg ctccccagcc cacccacccc cctgtacaga atgtctgctt tgggtgcggt   1500

tttgtactcg gtttggaatg gggagggagg agggcggggg gaggggaggg ttgccctcag   1560

ccctttccgt ggcttctctg catttgggtt attattattt ttgtaacaat cccaaatcaa   1620

atctgtctcc aggctggaga ggcaggagcc ctggggtgag aaaagcaaaa aacaaacaaa   1680

aaaca                                                               1685
```

<210> SEQ ID NO 84
<211> LENGTH: 398
<212> TYPE: PRT
<213> ORGANISM: Homo sapiens

<400> SEQUENCE: 84

```
Met Gly Ala Pro Ala Ala Ser Leu Leu Leu Leu Leu Leu Leu Phe Ala
  1               5                  10                  15

Cys Cys Trp Ala Pro Gly Gly Ala Asn Leu Ser Gln Asp Asp Ser Gln
             20                  25                  30

Pro Trp Thr Ser Asp Glu Thr Val Val Ala Gly Gly Thr Val Val Leu
         35                  40                  45

Lys Cys Gln Val Lys Asp His Glu Asp Ser Ser Leu Gln Trp Ser Asn
     50                  55                  60

Pro Ala Gln Gln Thr Leu Tyr Phe Gly Glu Lys Arg Ala Leu Arg Asp
 65                  70                  75                  80

Asn Arg Ile Gln Leu Val Thr Ser Thr Pro His Glu Leu Ser Ile Ser
                 85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
        115                 120                 125

Ile Pro Gln Lys Pro Ile Ile Thr Gly Tyr Lys Ser Ser Leu Arg Glu
    130                 135                 140

Lys Asp Thr Ala Thr Leu Asn Cys Gln Ser Ser Gly Ser Lys Pro Ala
145                 150                 155                 160

Ala Arg Leu Thr Trp Arg Lys Gly Asp Gln Glu Leu His Gly Glu Pro
                165                 170                 175

Thr Arg Ile Gln Glu Asp Pro Asn Gly Lys Thr Phe Thr Val Ser Ser
            180                 185                 190
```

-continued

```
Ser Val Thr Phe Gln Val Thr Arg Glu Asp Asp Gly Ala Ser Ile Val
        195                 200                 205

Cys Ser Val Asn His Glu Ser Leu Lys Gly Ala Asp Arg Ser Thr Ser
    210                 215                 220

Gln Arg Ile Glu Val Leu Tyr Thr Pro Thr Ala Met Ile Arg Pro Asp
225                 230                 235                 240

Pro Pro His Pro Arg Glu Gly Gln Lys Leu Leu Leu His Cys Glu Gly
                245                 250                 255

Arg Gly Asn Pro Val Pro Gln Gln Tyr Leu Trp Glu Lys Glu Gly Ser
            260                 265                 270

Val Pro Pro Leu Lys Met Thr Gln Glu Ser Ala Leu Ile Phe Pro Phe
        275                 280                 285

Leu Asn Lys Ser Asp Ser Gly Thr Tyr Gly Cys Thr Ala Thr Ser Asn
    290                 295                 300

Met Gly Ser Tyr Lys Ala Tyr Tyr Thr Leu Asn Val Asn Asp Pro Ser
305                 310                 315                 320

Pro Val Pro Ser Ser Ser Ser Thr Tyr His Ala Ile Ile Gly Gly Ile
                325                 330                 335

Val Ala Phe Ile Val Phe Leu Leu Leu Ile Met Leu Ile Phe Leu Gly
            340                 345                 350

His Tyr Leu Ile Arg His Lys Gly Thr Tyr Leu Thr His Glu Ala Lys
        355                 360                 365

Gly Ser Asp Asp Ala Pro Asp Ala Asp Thr Ala Ile Ile Asn Ala Glu
    370                 375                 380

Gly Gly Gln Ser Gly Gly Asp Asp Lys Lys Glu Tyr Phe Ile
385                 390                 395
```

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 85
gctaggaatt ccacagaagc cc 22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 86
aacctggaat gtcaccgagc tg 22

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 87
cctagcacag tgacgaggga cttggc 26

<210> SEQ ID NO 88
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 88
aagacacagc caccctaaac tgtcagtctt ctgggagcaa gcctgcagcc 50

<210> SEQ ID NO 89
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 89
gccctggcag acgagggcga gtacacctgc tcaatcttca ctatgcctgt 50

<210> SEQ ID NO 90
<211> LENGTH: 2755
<212> TYPE: DNA
<213> ORGANISM: Homo sapiens

<400> SEQUENCE: 90
gggggttagg gaggaaggaa tccaccccca cccccccaaa cccttttctt ctcctttcct 60
ggcttcggac attggagcac taaatgaact tgaattgtgt ctgtggcgag caggatggtc 120
gctgttactt tgtgatgaga tcggggatga attgctcgct ttaaaaatgc tgctttggat 180
tctgttgctg gagacgtctc tttgttttgc cgctggaaac gttacagggg acgtttgcaa 240
agagaagatc tgttcctgca atgagataga aggggaccta cacgtagact gtgaaaaaaa 300
gggcttcaca agtctgcagc gtttcactgc cccgacttcc cagttttacc atttatttct 360
gcatggcaat tccctcactc gacttttccc taatgagttc gctaactttt ataatgcggt 420
tagtttgcac atggaaaaca atggcttgca tgaaatcgtt ccgggggctt ttctggggct 480
gcagctggtg aaaaggctgc acatcaacaa caacaagatc aagtcttttc gaaagcagac 540
ttttctgggg ctggacgatc tggaatatct ccaggctgat tttaatttat tacgagatat 600
agacccgggg gccttccagg acttgaacaa gctggaggtg ctcattttaa atgacaatct 660
catcagcacc ctacctgcca acgtgttcca gtatgtgccc atcacccacc tcgacctccg 720
gggtaacagg ctgaaaacgc tgccctatga ggaggtcttg gagcaaatcc ctggtattgc 780
ggagatcctg ctagaggata acccttggga ctgcacctgt gatctgctct ccctgaaaga 840
atggctggaa aacattccca agaatgccct gatcggccga gtggtctgcg aagcccccac 900
cagactgcag ggtaaagacc tcaatgaaac caccgaacag gacttgtgtc ctttgaaaaa 960
ccgagtggat tctagtctcc cggcgccccc tgcccaagaa gagacctttg ctcctggacc 1020
cctgccaact cctttcaaga caaatgggca agaggatcat gccacaccag ggtctgctcc 1080
aaacggaggt acaaagatcc caggcaactg gcagatcaaa atcagaccca cagcagcgat 1140
agcgacgggt agctccagga acaaaccctt agctaacagt ttaccctgcc ctgggggctg 1200
cagctgcgac cacatcccag ggtcgggttt aaagatgaac tgcaacaaca ggaacgtgag 1260
cagcttggct gatttgaagc ccaagctctc taacgtgcag gagcttttcc tacgagataa 1320
caagatccac agcatccgaa aatcgcactt tgtggattac aagaacctca ttctgttgga 1380

-continued tctgggcaac aataacatcg ctactgtaga gaacaacact ttcaagaacc ttttggacct 1440
caggtggcta tacatggata gcaattacct ggacacgctg tcccgggaga aattcgcggg 1500
gctgcaaaac ctagagtacc tgaacgtgga gtacaacgct atccagctca tcctcccggg 1560
cactttcaat gccatgccca aactgaggat cctcattctc aacaacaacc tgctgaggtc 1620
cctgcctgtg gacgtgttcg ctggggtctc gctctctaaa ctcagcctgc acaacaatta 1680
cttcatgtac ctcccggtgg caggggtgct ggaccagtta acctccatca tccagataga 1740
cctccacgga aacccctggg agtgctcctg cacaattgtg cctttcaagc agtgggcaga 1800
acgcttgggt tccgaagtgc tgatgagcga cctcaagtgt gagacgccgg tgaacttctt 1860
tagaaaggat ttcatgctcc tctccaatga cgagatctgc cctcagctgt acgctaggat 1920
ctcgcccacg ttaacttcgc acagtaaaaa cagcactggg ttggcggaga ccgggacgca 1980
ctccaactcc tacctagaca ccagcagggt gtccatctcg gtgttggtcc cgggactgct 2040
gctggtgttt gtcacctccg ccttcaccgt ggtgggcatg ctcgtgttta tcctgaggaa 2100
ccgaaagcgg tccaagagac gagatgccaa ctcctccgcg tccgagatta attccctaca 2160
gacagtctgt gactcttcct actggcacaa tgggccttac aacgcagatg gggcccacag 2220
agtgtatgac tgtggctctc actcgctctc agactaagac cccaacccca atagggagg 2280 gcagagggaa ggcgatacat ccttccccac cgcaggcacc ccgggggctg gaggggcgtg 2340
tacccaaatc cccgcgccat cagcctggat gggcataagt agataaataa ctgtgagctc 2400
gcacaaccga aagggcctga ccccttactt agctccctcc ttgaaacaaa gagcagactg 2460
tggagagctg ggagagcgca gccagctcgc tctttgctga gagccccttt tgacagaaag 2520
cccagcacga ccctgctgga agaactgaca gtgccctcgc cctcggcccc ggggcctgtg 2580
gggttggatg ccgcggttct atacatatat acatatatcc acatctatat agagagatag 2640
atatctattt ttcccctgtg gattagcccc gtgatggctc cctgttggct acgcagggat 2700
gggcagttgc acgaaggcat gaatgtattg taaataagta actttgactt ctgac 2755

<210> SEQ ID NO 91
<211> LENGTH: 696
<212> TYPE: PRT
<213> ORGANISM: Homo sapiens

<400> SEQUENCE: 91

Met Leu Leu Trp Ile Leu Leu Leu Glu Thr Ser Leu Cys Phe Ala Ala
1 5 10 15

Gly Asn Val Thr Gly Asp Val Cys Lys Glu Lys Ile Cys Ser Cys Asn
20 25 30

Glu Ile Glu Gly Asp Leu His Val Asp Cys Glu Lys Lys Gly Phe Thr
35 40 45

Ser Leu Gln Arg Phe Thr Ala Pro Thr Ser Gln Phe Tyr His Leu Phe
50 55 60

Leu His Gly Asn Ser Leu Thr Arg Leu Phe Pro Asn Glu Phe Ala Asn
65 70 75 80

Phe Tyr Asn Ala Val Ser Leu His Met Glu Asn Asn Gly Leu His Glu
85 90 95

Ile Val Pro Gly Ala Phe Leu Gly Leu Gln Leu Val Lys Arg Leu His
100 105 110

Ile Asn Asn Asn Lys Ile Lys Ser Phe Arg Lys Gln Thr Phe Leu Gly
115 120 125

-continued

```
Leu Asp Asp Leu Glu Tyr Leu Gln Ala Asp Phe Asn Leu Leu Arg Asp
    130                 135                 140

Ile Asp Pro Gly Ala Phe Gln Asp Leu Asn Lys Leu Glu Val Leu Ile
145                 150                 155                 160

Leu Asn Asp Asn Leu Ile Ser Thr Leu Pro Ala Asn Val Phe Gln Tyr
                165                 170                 175

Val Pro Ile Thr His Leu Asp Leu Arg Gly Asn Arg Leu Lys Thr Leu
            180                 185                 190

Pro Tyr Glu Glu Val Leu Glu Gln Ile Pro Gly Ile Ala Glu Ile Leu
        195                 200                 205

Leu Glu Asp Asn Pro Trp Asp Cys Thr Cys Asp Leu Leu Ser Leu Lys
    210                 215                 220

Glu Trp Leu Glu Asn Ile Pro Lys Asn Ala Leu Ile Gly Arg Val Val
225                 230                 235                 240

Cys Glu Ala Pro Thr Arg Leu Gln Gly Lys Asp Leu Asn Glu Thr Thr
                245                 250                 255

Glu Gln Asp Leu Cys Pro Leu Lys Asn Arg Val Asp Ser Ser Leu Pro
            260                 265                 270

Ala Pro Pro Ala Gln Glu Glu Thr Phe Ala Pro Gly Pro Leu Pro Thr
        275                 280                 285

Pro Phe Lys Thr Asn Gly Gln Glu Asp His Ala Thr Pro Gly Ser Ala
    290                 295                 300

Pro Asn Gly Gly Thr Lys Ile Pro Gly Asn Trp Gln Ile Lys Ile Arg
305                 310                 315                 320

Pro Thr Ala Ala Ile Ala Thr Gly Ser Ser Arg Asn Lys Pro Leu Ala
                325                 330                 335

Asn Ser Leu Pro Cys Pro Gly Gly Cys Ser Cys Asp His Ile Pro Gly
            340                 345                 350

Ser Gly Leu Lys Met Asn Cys Asn Asn Arg Asn Val Ser Ser Leu Ala
        355                 360                 365

Asp Leu Lys Pro Lys Leu Ser Asn Val Gln Glu Leu Phe Leu Arg Asp
    370                 375                 380

Asn Lys Ile His Ser Ile Arg Lys Ser His Phe Val Asp Tyr Lys Asn
385                 390                 395                 400

Leu Ile Leu Leu Asp Leu Gly Asn Asn Asn Ile Ala Thr Val Glu Asn
                405                 410                 415

Asn Thr Phe Lys Asn Leu Leu Asp Leu Arg Trp Leu Tyr Met Asp Ser
            420                 425                 430

Asn Tyr Leu Asp Thr Leu Ser Arg Glu Lys Phe Ala Gly Leu Gln Asn
        435                 440                 445

Leu Glu Tyr Leu Asn Val Glu Tyr Asn Ala Ile Gln Leu Ile Leu Pro
    450                 455                 460

Gly Thr Phe Asn Ala Met Pro Lys Leu Arg Ile Leu Ile Leu Asn Asn
465                 470                 475                 480

Asn Leu Leu Arg Ser Leu Pro Val Asp Val Phe Ala Gly Val Ser Leu
                485                 490                 495

Ser Lys Leu Ser Leu His Asn Asn Tyr Phe Met Tyr Leu Pro Val Ala
            500                 505                 510

Gly Val Leu Asp Gln Leu Thr Ser Ile Ile Gln Ile Asp Leu His Gly
        515                 520                 525

Asn Pro Trp Glu Cys Ser Cys Thr Ile Val Pro Phe Lys Gln Trp Ala
    530                 535                 540

Glu Arg Leu Gly Ser Glu Val Leu Met Ser Asp Leu Lys Cys Glu Thr
```

-continued 545 550 555 560

Pro Val Asn Phe Phe Arg Lys Asp Phe Met Leu Leu Ser Asn Asp Glu
565 570 575

Ile Cys Pro Gln Leu Tyr Ala Arg Ile Ser Pro Thr Leu Thr Ser His
580 585 590

Ser Lys Asn Ser Thr Gly Leu Ala Glu Thr Gly Thr His Ser Asn Ser
595 600 605

Tyr Leu Asp Thr Ser Arg Val Ser Ile Ser Val Leu Val Pro Gly Leu
610 615 620

Leu Leu Val Phe Val Thr Ser Ala Phe Thr Val Val Gly Met Leu Val
625 630 635 640

Phe Ile Leu Arg Asn Arg Lys Arg Ser Lys Arg Arg Asp Ala Asn Ser
645 650 655

Ser Ala Ser Glu Ile Asn Ser Leu Gln Thr Val Cys Asp Ser Ser Tyr
660 665 670

Trp His Asn Gly Pro Tyr Asn Ala Asp Gly Ala His Arg Val Tyr Asp
675 680 685

Cys Gly Ser His Ser Leu Ser Asp
690 695

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 92
gttggatctg ggcaacaata ac 22

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 93
attgttgtgc aggctgagtt taag 24

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 94
ggtggctata catggatagc aattacctgg acacgctgtc ccggg 45

<210> SEQ ID NO 95
<211> LENGTH: 2226
<212> TYPE: DNA
<213> ORGANISM: Homo sapiens

<400> SEQUENCE: 95
agtcgactgc gtcccctgta cccggcgcca gctgtgttcc tgaccccaga ataactcagg 60
gctgcaccgg gcctggcagc gctccgcaca catttcctgt cgcggcctaa gggaaactgt 120

-continued

```
tggccgctgg gcccgcgggg ggattcttgg cagttggggg gtccgtcggg agcgagggcg    180
gaggggaagg gagggggaac cgggttgggg aagccagctg tagagggcgg tgaccgcgct    240
ccagacacag ctctgcgtcc tcgagcggga cagatccaag ttgggagcag ctctgcgtgc    300
ggggcctcag agaatgaggc cggcgttcgc cctgtgcctc ctctggcagg cgctctggcc    360
cgggccgggc ggcggcgaac accccactgc cgaccgtgct ggctgctcgg cctcgggggc    420
ctgctacagc ctgcaccacg ctaccatgaa gcggcaggcg gccgaggagg cctgcatcct    480
gcgaggtggg gcgctcagca ccgtgcgtgc gggcgccgag ctgcgcgctg tgctcgcgct    540
cctgcgggca ggcccagggc ccggaggggg ctccaaagac ctgctgttct gggtcgcact    600
ggagcgcagg cgttcccact gcaccctgga gaacgagcct ttgcggggtt tctcctggct    660
gtcctccgac cccggcggtc tcgaaagcga cacgctgcag tgggtggagg agccccaacg    720
ctcctgcacc gcgcggagat gcgcggtact ccaggccacc ggtggggtcg agcccgcagg    780
ctggaaggag atgcgatgcc acctgcgcgc caacggctac ctgtgcaagt accagtttga    840
ggtcttgtgt cctgcgccgc gccccggggc cgcctctaac ttgagctatc gcgcgccctt    900
ccagctgcac agcgccgctc tggacttcag tccacctggg accgaggtga gtgcgctctg    960
ccggggacag ctcccgatct cagttacttg catcgcggac gaaatcggcg ctcgctggga   1020
caaactctcg ggcgatgtgt tgtgtccctg ccccgggagg tacctccgtg ctggcaaatg   1080
cgcagagctc cctaactgcc tagacgactt gggaggcttt gcctgcgaat gtgctacggg   1140
cttcgagctg ggaaggacg gccgctcttg tgtgaccagt ggggaaggac agccgaccct   1200
tgggggggacc ggggtgccca ccaggcgccc gccggccact gcaaccagcc ccgtgccgca   1260
gagaacatgg ccaatcaggg tcgacgagaa gctgggagag acaccacttg tccctgaaca   1320
agacaattca gtaacatcta ttcctgagat tcctcgatgg ggatcacaga gcacgatgtc   1380
tacccttcaa atgtcccttc aagccgagtc aaaggccact atcaccccat cagggagcgt   1440
gatttccaag tttaattcta cgacttcctc tgccactcct caggctttcg actcctcctc   1500
tgccgtggtc ttcatatttg tgagcacagc agtagtagtg ttggtgatct tgaccatgac   1560
agtactgggg cttgtcaagc tctgctttca cgaaagcccc tcttcccagc caaggaagga   1620
gtctatgggc ccgccgggcc tggagagtga tcctgagccc gctgctttgg gctccagttc   1680
tgcacattgc acaaacaatg gggtgaaagt cggggactgt gatctgcggg acagagcaga   1740
gggtgccttg ctggcggagt cccctcttgg ctctagtgat gcatagggaa acaggggaca   1800
tgggcactcc tgtgaacagt tttcactttt tgatgaaacg gggaaccaag aggaacttac   1860
ttgtgtaact gacaatttct gcagaaatcc cccttcctct aaattccctt tactccactg   1920
aggagctaaa tcagaactgc acactccttc cctgatgata gaggaagtgg aagtgccttt   1980
aggatggtga tactggggga ccgggtagtg ctggggagag atattttctt atgtttattc   2040
ggagaatttg gagaagtgat tgaacttttc aagacattgg aaacaaatag aacacaatat   2100
aatttacatt aaaaaataat ttctaccaaa atggaaagga aatgttctat gttgttcagg   2160
ctaggagtat attggttcga aatcccaggg aaaaaaataa aaataaaaaa ttaaaggatt   2220
gttgat                                                               2226
```

<210> SEQ ID NO 96
<211> LENGTH: 490
<212> TYPE: PRT
<213> ORGANISM: Homo sapiens -continued

<400> SEQUENCE: 96

```
Met Arg Pro Ala Phe Ala Leu Cys Leu Leu Trp Gln Ala Leu Trp Pro
  1               5                  10                  15

Gly Pro Gly Gly Gly Glu His Pro Thr Ala Asp Arg Ala Gly Cys Ser
             20                  25                  30

Ala Ser Gly Ala Cys Tyr Ser Leu His His Ala Thr Met Lys Arg Gln
         35                  40                  45

Ala Ala Glu Glu Ala Cys Ile Leu Arg Gly Gly Ala Leu Ser Thr Val
     50                  55                  60

Arg Ala Gly Ala Glu Leu Arg Ala Val Leu Ala Leu Leu Arg Ala Gly
 65                  70                  75                  80

Pro Gly Pro Gly Gly Gly Ser Lys Asp Leu Leu Phe Trp Val Ala Leu
                 85                  90                  95

Glu Arg Arg Arg Ser His Cys Thr Leu Glu Asn Glu Pro Leu Arg Gly
            100                 105                 110

Phe Ser Trp Leu Ser Ser Asp Pro Gly Gly Leu Glu Ser Asp Thr Leu
        115                 120                 125

Gln Trp Val Glu Glu Pro Gln Arg Ser Cys Thr Ala Arg Arg Cys Ala
    130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr Gln Phe Glu
                165                 170                 175

Val Leu Cys Pro Ala Pro Arg Pro Gly Ala Ala Ser Asn Leu Ser Tyr
            180                 185                 190

Arg Ala Pro Phe Gln Leu His Ser Ala Ala Leu Asp Phe Ser Pro Pro
        195                 200                 205

Gly Thr Glu Val Ser Ala Leu Cys Arg Gly Gln Leu Pro Ile Ser Val
    210                 215                 220

Thr Cys Ile Ala Asp Glu Ile Gly Ala Arg Trp Asp Lys Leu Ser Gly
225                 230                 235                 240

Asp Val Leu Cys Pro Cys Pro Gly Arg Tyr Leu Arg Ala Gly Lys Cys
                245                 250                 255

Ala Glu Leu Pro Asn Cys Leu Asp Asp Leu Gly Gly Phe Ala Cys Glu
            260                 265                 270

Cys Ala Thr Gly Phe Glu Leu Gly Lys Asp Gly Arg Ser Cys Val Thr
        275                 280                 285

Ser Gly Glu Gly Gln Pro Thr Leu Gly Gly Thr Gly Val Pro Thr Arg
    290                 295                 300

Arg Pro Pro Ala Thr Ala Thr Ser Pro Val Pro Gln Arg Thr Trp Pro
305                 310                 315                 320

Ile Arg Val Asp Glu Lys Leu Gly Glu Thr Pro Leu Val Pro Glu Gln
                325                 330                 335

Asp Asn Ser Val Thr Ser Ile Pro Glu Ile Pro Arg Trp Gly Ser Gln
            340                 345                 350

Ser Thr Met Ser Thr Leu Gln Met Ser Leu Gln Ala Glu Ser Lys Ala
        355                 360                 365

Thr Ile Thr Pro Ser Gly Ser Val Ile Ser Lys Phe Asn Ser Thr Thr
    370                 375                 380

Ser Ser Ala Thr Pro Gln Ala Phe Asp Ser Ser Ser Ala Val Val Phe
385                 390                 395                 400

Ile Phe Val Ser Thr Ala Val Val Val Leu Val Ile Leu Thr Met Thr
                405                 410                 415
```

-continued

```
Val Leu Gly Leu Val Lys Leu Cys Phe His Glu Ser Pro Ser Ser Gln
            420                 425                 430

Pro Arg Lys Glu Ser Met Gly Pro Pro Gly Leu Glu Ser Asp Pro Glu
        435                 440                 445

Pro Ala Ala Leu Gly Ser Ser Ser Ala His Cys Thr Asn Asn Gly Val
    450                 455                 460

Lys Val Gly Asp Cys Asp Leu Arg Asp Arg Ala Glu Gly Ala Leu Leu
465                 470                 475                 480

Ala Glu Ser Pro Leu Gly Ser Ser Asp Ala
                485                 490


<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 97

tggaaggaga tgcgatgcca cctg                                            24


<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 98

tgaccagtgg ggaaggacag                                                 20


<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 99

acagagcaga gggtgccttg                                                 20


<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 100

tcagggacaa gtggtgtctc tccc                                            24


<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 101
```

-continued tcagggaagg agtgtgcagt tctg 24

<210> SEQ ID NO 102
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 102
acagctcccg atctcagtta cttgcatcgc ggacgaaatc ggcgctcgct 50

<210> SEQ ID NO 103
<211> LENGTH: 2026
<212> TYPE: DNA
<213> ORGANISM: Homo sapiens

<400> SEQUENCE: 103
cggacgcgtg ggattcagca gtggcctgtg gctgccagag cagctcctca ggggaaacta 60
agcgtcgagt cagacggcac cataatcgcc tttaaaagtg cctccgccct gccggccgcg 120
tatcccccgg ctacctgggc cgccccgcgg cggtgcgcgc gtgagaggga gcgcgcgggc 180
agccgagcgc cggtgtgagc cagcgctgct gccagtgtga gcggcggtgt gagcgcggtg 240
ggtgcggagg ggcgtgtgtg ccggcgcgcg cgccgtgggg tgcaaacccc gagcgtctac 300
gctgccatga ggggcgcgaa cgcctgggcg ccactctgcc tgctgctggc tgccgccacc 360
cagctctcgc ggcagcagtc cccagagaga cctgttttca catgtggtgg cattcttact 420
ggagagtctg gatttattgg cagtgaaggt tttcctggag tgtaccctcc aaatagcaaa 480
tgtacttgga aaatcacagt tcccgaagga aaagtagtcg ttctcaattt ccgattcata 540
gacctcgaga gtgacaacct gtgccgctat gactttgtgg atgtgtacaa tggccatgcc 600
aatggccagc gcattggccg cttctgtggc actttccggc ctggagccct tgtgtccagt 660
ggcaacaaga tgatggtgca gatgatttct gatgccaaca cagctggcaa tggcttcatg 720
gccatgttct ccgctgctga accaaacgaa agaggggatc agtattgtgg aggactcctt 780
gacagacctt ccggctcttt taaaaccccc aactggccag accgggatta ccctgcagga 840
gtcacttgtg tgtggcacat tgtagcccca aagaatcagc ttatagaatt aaagtttgag 900
aagtttgatg tggagcgaga taactactgc cgatatgatt atgtggctgt gtttaatggc 960
ggggaagtca acgatgctag aagaattgga aagtattgtg gtgatagtcc acctgcgcca 1020
attgtgtctg agagaaatga acttcttatt cagtttttat cagacttaag tttaactgca 1080
gatgggttta ttggtcacta catattcagg ccaaaaaaac tgcctacaac tacagaacag 1140
cctgtcacca ccacattccc tgtaaccacg ggtttaaaac ccaccgtggc cttgtgtcaa 1200
caaaagtgta gacggacggg gactctggag ggcaattatt gttcaagtga ctttgtatta 1260
gccggcactg ttatcacaac catcactcgc gatgggagtt tgcacgccac agtctcgatc 1320
atcaacatct acaaagaggg aaatttggcg attcagcagg cgggcaagaa catgagtgcc 1380
aggctgactg tcgtctgcaa gcagtgccct ctcctcagaa gaggtctaaa ttacattatt 1440
atgggccaag taggtgaaga tgggcgaggc aaaatcatgc caaacagctt tatcatgatg 1500
ttcaagacca agaatcagaa gctcctggat gccttaaaaa ataagcaatg ttaacagtga 1560
actgtgtcca tttaagctgt attctgccat tgcctttgaa agatctatgt tctctcagta 1620
gaaaaaaaaa tacttataaa attacatatt ctgaaagagg attccgaaag atgggactgg 1680

-continued

```
ttgactcttc acatgatgga ggtatgaggc ctccgagata gctgagggaa gttctttgcc   1740

tgctgtcaga ggagcagcta tctgattgga aacctgccga cttagtgcgg tgataggaag   1800

ctaaaagtgt caagcgttga cagcttggaa gcgtttattt atacatctct gtaaaaggat   1860

attttagaat tgagttgtgt gaagatgtca aaaaaagatt ttagaagtgc aatatttata   1920

gtgttatttg tttcaccttc aagcctttgc cctgaggtgt tacaatcttg tcttgcgttt   1980

tctaaatcaa tgcttaataa aatattttta aaggaaaaaa aaaaaa                  2026
```

<210> SEQ ID NO 104
<211> LENGTH: 415
<212> TYPE: PRT
<213> ORGANISM: Homo sapiens

<400> SEQUENCE: 104

```
Met Arg Gly Ala Asn Ala Trp Ala Pro Leu Cys Leu Leu Leu Ala Ala
  1               5                  10                  15

Ala Thr Gln Leu Ser Arg Gln Gln Ser Pro Glu Arg Pro Val Phe Thr
             20                  25                  30

Cys Gly Gly Ile Leu Thr Gly Glu Ser Gly Phe Ile Gly Ser Glu Gly
         35                  40                  45

Phe Pro Gly Val Tyr Pro Pro Asn Ser Lys Cys Thr Trp Lys Ile Thr
     50                  55                  60

Val Pro Glu Gly Lys Val Val Val Leu Asn Phe Arg Phe Ile Asp Leu
 65                  70                  75                  80

Glu Ser Asp Asn Leu Cys Arg Tyr Asp Phe Val Asp Val Tyr Asn Gly
                 85                  90                  95

His Ala Asn Gly Gln Arg Ile Gly Arg Phe Cys Gly Thr Phe Arg Pro
            100                 105                 110

Gly Ala Leu Val Ser Ser Gly Asn Lys Met Met Val Gln Met Ile Ser
        115                 120                 125

Asp Ala Asn Thr Ala Gly Asn Gly Phe Met Ala Met Phe Ser Ala Ala
    130                 135                 140

Glu Pro Asn Glu Arg Gly Asp Gln Tyr Cys Gly Gly Leu Leu Asp Arg
145                 150                 155                 160

Pro Ser Gly Ser Phe Lys Thr Pro Asn Trp Pro Asp Arg Asp Tyr Pro
                165                 170                 175

Ala Gly Val Thr Cys Val Trp His Ile Val Ala Pro Lys Asn Gln Leu
            180                 185                 190

Ile Glu Leu Lys Phe Glu Lys Phe Asp Val Glu Arg Asp Asn Tyr Cys
        195                 200                 205

Arg Tyr Asp Tyr Val Ala Val Phe Asn Gly Gly Glu Val Asn Asp Ala
    210                 215                 220

Arg Arg Ile Gly Lys Tyr Cys Gly Asp Ser Pro Pro Ala Pro Ile Val
225                 230                 235                 240

Ser Glu Arg Asn Glu Leu Leu Ile Gln Phe Leu Ser Asp Leu Ser Leu
                245                 250                 255

Thr Ala Asp Gly Phe Ile Gly His Tyr Ile Phe Arg Pro Lys Lys Leu
            260                 265                 270

Pro Thr Thr Thr Glu Gln Pro Val Thr Thr Thr Phe Pro Val Thr Thr
        275                 280                 285

Gly Leu Lys Pro Thr Val Ala Leu Cys Gln Gln Lys Cys Arg Arg Thr
    290                 295                 300

Gly Thr Leu Glu Gly Asn Tyr Cys Ser Ser Asp Phe Val Leu Ala Gly
305                 310                 315                 320
```

-continued

```
Thr Val Ile Thr Thr Ile Thr Arg Asp Gly Ser Leu His Ala Thr Val
                325                 330                 335

Ser Ile Ile Asn Ile Tyr Lys Glu Gly Asn Leu Ala Ile Gln Gln Ala
            340                 345                 350

Gly Lys Asn Met Ser Ala Arg Leu Thr Val Val Cys Lys Gln Cys Pro
        355                 360                 365

Leu Leu Arg Arg Gly Leu Asn Tyr Ile Ile Met Gly Gln Val Gly Glu
    370                 375                 380

Asp Gly Arg Gly Lys Ile Met Pro Asn Ser Phe Ile Met Met Phe Lys
385                 390                 395                 400

Thr Lys Asn Gln Lys Leu Leu Asp Ala Leu Lys Asn Lys Gln Cys
                405                 410                 415


<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 105

ccgattcata gacctcgaga gt                                           22


<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 106

gtcaaggagt cctccacaat ac                                           22


<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 107

gtgtacaatg gccatgccaa tggccagcgc attggccgct tctgt                  45


<210> SEQ ID NO 108
<211> LENGTH: 1838
<212> TYPE: DNA
<213> ORGANISM: Homo sapiens

<400> SEQUENCE: 108

cggacgcgtg ggcggacgcg tgggcggccc acggcgcccg cgggctgggg cggtcgcttc     60

ttccttctcc gtggcctacg agggtcccca gcctgggtaa agatggcccc atggcccccg    120

aagggcctag tcccagctgt gctctggggc ctcagcctct tcctcaacct cccaggacct    180

atctggctcc agccctctcc acctccccag tcttctcccc cgcctcagcc ccatccgtgt    240

catacctgcc ggggactggt tgacagcttt aacaagggcc tggagagaac catccgggac    300

aactttggag gtggaaacac tgcctgggag gaagagaatt tgtccaaata caaagacagt    360

gagacccgcc tggtagaggt gctggagggt gtgtgcagca agtcagactt cgagtgccac    420
```

-continued

```
cgcctgctgg agctgagtga ggagctggtg gagagctggt ggtttcacaa gcagcaggag    480
gccccggacc tcttccagtg gctgtgctca gattccctga agctctgctg ccccgcaggc    540
accttcgggc cctcctgcct tccctgtcct gggggaacag agaggccctg cggtggctac    600
gggcagtgtg aaggagaagg gacacgaggg ggcagcgggc actgtgactg ccaagccggc    660
tacgggggtg aggcctgtgg ccagtgtggc cttggctact ttgaggcaga acgcaacgcc    720
agccatctgg tatgttcggc ttgttttggc ccctgtgccc gatgctcagg acctgaggaa    780
tcaaactgtt tgcaatgcaa gaagggctgg gccctgcatc acctcaagtg tgtagacatt    840
gatgagtgtg gcacagaggg agccaactgt ggagctgacc aattctgcgt gaacactgag    900
ggctcctatg agtgccgaga ctgtgccaag gcctgcctag gctgcatggg ggcagggcca    960
ggtcgctgta agaagtgtag ccctggctat cagcaggtgg gctccaagtg tctcgatgtg   1020
gatgagtgtg agacagaggt gtgtccggga gagaacaagc agtgtgaaaa caccgagggc   1080
ggttatcgct gcatctgtgc cgagggctac aagcagatgg aaggcatctg tgtgaaggag   1140
cagatcccag agtcagcagg cttcttctca gagatgacag aagacgagtt ggtggtgctg   1200
cagcagatgt tctttggcat catcatctgt gcactggcca cgctggctgc taagggcgac   1260
ttggtgttca ccgccatctt cattggggct gtggcggcca tgactggcta ctggttgtca   1320
gagcgcagtg accgtgtgct ggagggcttc atcaagggca gataatcgcg gccaccacct   1380
gtaggacctc ctcccaccca cgctgccccc agagcttggg ctgccctcct gctggacact   1440
caggacagct tggtttattt ttgagagtgg ggtaagcacc cctacctgcc ttacagagca   1500
gcccaggtac ccaggcccgg gcagacaagg cccctggggt aaaaagtagc cctgaaggtg   1560
gataccatga gctcttcacc tggcggggac tggcaggctt cacaatgtgt gaatttcaaa   1620
agtttttcct taatggtggc tgctagagct ttggcccctg cttaggatta ggtggtcctc   1680
acaggggtgg ggccatcaca gctccctcct gccagctgca tgctgccagt tcctgttctg   1740
tgttcaccac atccccacac cccattgcca cttatttatt catctcagga aataaagaaa   1800
ggtcttggaa agttaaaaaa aaaaaaaaaa aaaaaaaa                           1838
```

```
<210> SEQ ID NO 109
<211> LENGTH: 420
<212> TYPE: PRT
<213> ORGANISM: Homo sapiens

<400> SEQUENCE: 109

Met Ala Pro Trp Pro Pro Lys Gly Leu Val Pro Ala Val Leu Trp Gly
  1               5                  10                  15

Leu Ser Leu Phe Leu Asn Leu Pro Gly Pro Ile Trp Leu Gln Pro Ser
             20                  25                  30

Pro Pro Pro Gln Ser Ser Pro Pro Pro Gln Pro His Pro Cys His Thr
         35                  40                  45

Cys Arg Gly Leu Val Asp Ser Phe Asn Lys Gly Leu Glu Arg Thr Ile
     50                  55                  60

Arg Asp Asn Phe Gly Gly Gly Asn Thr Ala Trp Glu Glu Glu Asn Leu
 65                  70                  75                  80

Ser Lys Tyr Lys Asp Ser Glu Thr Arg Leu Val Glu Val Leu Glu Gly
                 85                  90                  95

Val Cys Ser Lys Ser Asp Phe Glu Cys His Arg Leu Leu Glu Leu Ser
            100                 105                 110

Glu Glu Leu Val Glu Ser Trp Trp Phe His Lys Gln Gln Glu Ala Pro
```

-continued

```
        115                 120                 125

Asp Leu Phe Gln Trp Leu Cys Ser Asp Ser Leu Lys Leu Cys Cys Pro
    130                 135                 140

Ala Gly Thr Phe Gly Pro Ser Cys Leu Pro Cys Pro Gly Gly Thr Glu
145                 150                 155                 160

Arg Pro Cys Gly Gly Tyr Gly Gln Cys Glu Gly Glu Gly Thr Arg Gly
                165                 170                 175

Gly Ser Gly His Cys Asp Cys Gln Ala Gly Tyr Gly Gly Glu Ala Cys
            180                 185                 190

Gly Gln Cys Gly Leu Gly Tyr Phe Glu Ala Glu Arg Asn Ala Ser His
        195                 200                 205

Leu Val Cys Ser Ala Cys Phe Gly Pro Cys Ala Arg Cys Ser Gly Pro
    210                 215                 220

Glu Glu Ser Asn Cys Leu Gln Cys Lys Lys Gly Trp Ala Leu His His
225                 230                 235                 240

Leu Lys Cys Val Asp Ile Asp Glu Cys Gly Thr Glu Gly Ala Asn Cys
                245                 250                 255

Gly Ala Asp Gln Phe Cys Val Asn Thr Glu Gly Ser Tyr Glu Cys Arg
            260                 265                 270

Asp Cys Ala Lys Ala Cys Leu Gly Cys Met Gly Ala Gly Pro Gly Arg
        275                 280                 285

Cys Lys Lys Cys Ser Pro Gly Tyr Gln Gln Val Gly Ser Lys Cys Leu
    290                 295                 300

Asp Val Asp Glu Cys Glu Thr Glu Val Cys Pro Gly Glu Asn Lys Gln
305                 310                 315                 320

Cys Glu Asn Thr Glu Gly Gly Tyr Arg Cys Ile Cys Ala Glu Gly Tyr
                325                 330                 335

Lys Gln Met Glu Gly Ile Cys Val Lys Glu Gln Ile Pro Glu Ser Ala
            340                 345                 350

Gly Phe Phe Ser Glu Met Thr Glu Asp Glu Leu Val Val Leu Gln Gln
        355                 360                 365

Met Phe Phe Gly Ile Ile Ile Cys Ala Leu Ala Thr Leu Ala Ala Lys
    370                 375                 380

Gly Asp Leu Val Phe Thr Ala Ile Phe Ile Gly Ala Val Ala Ala Met
385                 390                 395                 400

Thr Gly Tyr Trp Leu Ser Glu Arg Ser Asp Arg Val Leu Glu Gly Phe
                405                 410                 415

Ile Lys Gly Arg
            420
```

<210> SEQ ID NO 110
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 110
cctggctatc agcaggtggg ctccaagtgt ctcgatgtgg atgagtgtga 50

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic -continued oligonucleotide probe

<400> SEQUENCE: 111
attctgcgtg aacactgagg gc 22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 112
atctgcttgt agccctcggc ac 22

<210> SEQ ID NO 113
<211> LENGTH: 1616
<212> TYPE: DNA
<213> ORGANISM: Homo sapiens
<220> FEATURE:
<221> NAME/KEY: modified_base
<222> LOCATION: (1461)..(1461)
<223> OTHER INFORMATION: a, t, c or g

<400> SEQUENCE: 113
tgagaccctc ctgcagcctt ctcaagggac agccccactc tgcctcttgc tcctccaggg 60
cagcaccatg cagcccctgt ggctctgctg ggcactctgg gtgttgcccc tggccagccc 120
cggggccgcc ctgaccgggg agcagctcct gggcagcctg ctgcggcagc tgcagctcaa 180
agaggtgccc accctggaca gggccgacat ggaggagctg gtcatcccca cccacgtgag 240
ggcccagtac gtggccctgc tgcagcgcag ccacggggac cgctcccgcg gaaagaggtt 300
cagccagagc ttccgagagg tggccggcag gttcctggcg ttggaggcca gcacacacct 360
gctggtgttc ggcatggagc agcggctgcc gcccaacagc gagctggtgc aggccgtgct 420
gcggctcttc caggagccgg tccccaaggc cgcgctgcac aggcacgggc ggctgtcccc 480
gcgcagcgcc cgggcccggg tgaccgtcga gtggctgcgc gtccgcgacg acggctccaa 540
ccgcacctcc ctcatcgact ccaggctggt gtccgtccac gagagcggct ggaaggcctt 600
cgacgtgacc gaggccgtga acttctggca gcagctgagc cggcccccggc agccgctgct 660 gctacaggtg tcggtgcaga gggagcatct gggcccgctg gcgtccggcg cccacaagct 720
ggtccgcttt gcctcgcagg gggcgccagc cgggcttggg gagccccagc tggagctgca 780
caccctggac cttggggact atggagctca gggcgactgt gaccctgaag caccaatgac 840
cgagggcacc cgctgctgcc gccaggagat gtacattgac ctgcagggga tgaagtgggc 900
cgagaactgg gtgctggagc ccccgggctt cctggcttat gagtgtgtgg gcacctgccg 960
gcagcccccg gaggccctgg ccttcaagtg gccgtttctg ggccctcgac agtgcatcgc 1020
ctcggagact gactcgctgc ccatgatcgt cagcatcaag gagggaggca ggaccaggcc 1080
ccaggtggtc agcctgccca acatgagggt gcagaagtgc agctgtgcct cggatggtgc 1140
gctcgtgcca aggaggctcc agccataggc gcctagtgta gccatcgagg gacttgactt 1200
gtgtgtgttt ctgaagtgtt cgagggtacc aggagagctg gcgatgactg aactgctgat 1260
ggacaaatgc tctgtgctct ctagtgagcc ctgaatttgc ttcctctgac aagttacctc 1320
acctaatttt tgcttctcag gaatgagaat ctttggccac tggagagccc ttgctcagtt 1380
ttctctattc ttattattca ctgcactata ttctaagcac ttacatgtgg agatactgta 1440

-continued

```
acctgagggc agaaagccca ntgtgtcatt gtttacttgt cctgtcactg gatctgggct   1500

aaagtcctcc accaccactc tggacctaag acctggggtt aagtgtgggt tgtgcatccc   1560

caatccagat aataaagact ttgtaaaaca tgaataaaac acattttatt ctaaaa       1616


<210> SEQ ID NO 114
<211> LENGTH: 366
<212> TYPE: PRT
<213> ORGANISM: Homo sapiens

<400> SEQUENCE: 114

Met Gln Pro Leu Trp Leu Cys Trp Ala Leu Trp Val Leu Pro Leu Ala
  1               5                  10                  15

Ser Pro Gly Ala Ala Leu Thr Gly Glu Gln Leu Leu Gly Ser Leu Leu
             20                  25                  30

Arg Gln Leu Gln Leu Lys Glu Val Pro Thr Leu Asp Arg Ala Asp Met
         35                  40                  45

Glu Glu Leu Val Ile Pro Thr His Val Arg Ala Gln Tyr Val Ala Leu
     50                  55                  60

Leu Gln Arg Ser His Gly Asp Arg Ser Arg Gly Lys Arg Phe Ser Gln
 65                  70                  75                  80

Ser Phe Arg Glu Val Ala Gly Arg Phe Leu Ala Leu Glu Ala Ser Thr
                 85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Arg Ala Arg
    130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
    210                 215                 220

Gly Ala Pro Ala Gly Leu Gly Glu Pro Gln Leu Glu Leu His Thr Leu
225                 230                 235                 240

Asp Leu Gly Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Glu Asn Trp Val Leu Glu Pro Pro Gly Phe
        275                 280                 285

Leu Ala Tyr Glu Cys Val Gly Thr Cys Arg Gln Pro Pro Glu Ala Leu
    290                 295                 300

Ala Phe Lys Trp Pro Phe Leu Gly Pro Arg Gln Cys Ile Ala Ser Glu
305                 310                 315                 320

Thr Asp Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350
```

-continued

```
Cys Ala Ser Asp Gly Ala Leu Val Pro Arg Arg Leu Gln Pro
        355                 360                 365
```

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 115
aggactgcca taacttgcct g 21

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 116
ataggagttg aagcagcgct gc 22

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 117
tgtgtggaca tagacgagtg ccgctaccgc tactgccagc accgc 45

<210> SEQ ID NO 118
<211> LENGTH: 1857
<212> TYPE: DNA
<213> ORGANISM: Homo sapiens

<400> SEQUENCE: 118
gtctgttccc aggagtcctt cggcggctgt tgtgtcagtg gcctgatcgc gatggggaca 60
aaggcgcaag tcgagaggaa actgttgtgc ctcttcatat tggcgatcct gttgtgctcc 120
ctggcattgg gcagtgttac agtgcactct tctgaacctg aagtcagaat tcctgagaat 180
aatcctgtga agttgtcctg tgcctactcg ggcttttctt ctccccgtgt ggagtggaag 240
tttgaccaag gagacaccac cagactcgtt tgctataata acaagatcac agcttcctat 300
gaggaccggg tgaccttctt gccaactggt atcaccttca agtccgtgac acgggaagac 360
actgggacat acacttgtat ggtctctgag gaaggcggca acagctatgg ggaggtcaag 420
gtcaagctca tcgtgcttgt gcctccatcc aagcctacag ttaacatccc ctcctctgcc 480
accattggga accgggcagt gctgacatgc tcagaacaag atggttcccc accttctgaa 540
tacacctggt tcaaagatgg gatagtgatg cctacgaatc ccaaaagcac ccgtgccttc 600
agcaactctt cctatgtcct gaatcccaca acaggagagc tggtctttga tcccctgtca 660
gcctctgata ctggagaata cagctgtgag gcacggaatg ggtatgggac acccatgact 720
tcaaatgctg tgcgcatgga agctgtggag cggaatgtgg gggtcatcgt ggcagccgtc 780
cttgtaaccc tgattctcct gggaatcttg gtttttggca tctggtttgc ctatagccga 840

-continued

```
ggccactttg acagaacaaa gaaagggact tcgagtaaga aggtgattta cagccagcct    900

agtgcccgaa gtgaaggaga attcaaacag acctcgtcat tcctggtgtg agcctggtcg    960

gctcaccgcc tatcatctgc atttgcctta ctcaggtgct accggactct ggcccctgat   1020

gtctgtagtt tcacaggatg ccttatttgt cttctacacc ccacagggcc ccctacttct   1080

tcggatgtgt ttttaataat gtcagctatg tgccccatcc tccttcatgc cctccctccc   1140

tttcctacca ctgctgagtg gcctggaact tgtttaaagt gtttattccc catttctttg   1200

agggatcagg aaggaatcct gggtatgcca ttgacttccc ttctaagtag acagcaaaaa   1260

tggcgggggt cgcaggaatc tgcactcaac tgcccacctg gctggcaggg atctttgaat   1320

aggtatcttg agcttggttc tgggctcttt ccttgtgtac tgacgaccag ggccagctgt   1380

tctagagcgg gaattagagg ctagagcggc tgaaatggtt gtttggtgat gacactgggg   1440

tccttccatc tctggggccc actctcttct gtcttcccat gggaagtgcc actgggatcc   1500

ctctgccctg tcctcctgaa tacaagctga ctgacattga ctgtgtctgt ggaaaatggg   1560

agctcttgtt gtggagagca tagtaaattt tcagagaact tgaagccaaa aggatttaaa   1620

accgctgctc taaagaaaag aaaactggag gctgggcgca gtggctcacg cctgtaatcc   1680

cagaggctga ggcaggcgga tcacctgagg tcgggagttc gggatcagcc tgaccaacat   1740

ggagaaaccc tactggaaat acaaagttag ccaggcatgg tggtgcatgc ctgtagtccc   1800

agctgctcag gagcctggca acaagagcaa aactccagct caaaaaaaaa aaaaaaa      1857


<210> SEQ ID NO 119
<211> LENGTH: 299
<212> TYPE: PRT
<213> ORGANISM: Homo sapiens

<400> SEQUENCE: 119

Met Gly Thr Lys Ala Gln Val Glu Arg Lys Leu Leu Cys Leu Phe Ile
  1               5                  10                  15

Leu Ala Ile Leu Leu Cys Ser Leu Ala Leu Gly Ser Val Thr Val His
             20                  25                  30

Ser Ser Glu Pro Glu Val Arg Ile Pro Glu Asn Asn Pro Val Lys Leu
         35                  40                  45

Ser Cys Ala Tyr Ser Gly Phe Ser Ser Pro Arg Val Glu Trp Lys Phe
     50                  55                  60

Asp Gln Gly Asp Thr Thr Arg Leu Val Cys Tyr Asn Asn Lys Ile Thr
 65                  70                  75                  80

Ala Ser Tyr Glu Asp Arg Val Thr Phe Leu Pro Thr Gly Ile Thr Phe
                 85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
```

-continued

```
        195                 200                 205

Glu Tyr Ser Cys Glu Ala Arg Asn Gly Tyr Gly Thr Pro Met Thr Ser
    210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
            260                 265                 270

Thr Ser Ser Lys Lys Val Ile Tyr Ser Gln Pro Ser Ala Arg Ser Glu
        275                 280                 285

Gly Glu Phe Lys Gln Thr Ser Ser Phe Leu Val
    290                 295


<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 120

tcgcggagct gtgttctgtt tccc                                              24


<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 121

tgatcgcgat ggggacaaag gcgcaagctc gagaggaaac tgttgtgcct                  50


<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 122

acacctggtt caaagatggg                                                   20


<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 123

taggaagagt tgctgaaggc acgg                                              24


<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued oligonucleotide probe

<400> SEQUENCE: 124
ttgccttact caggtgctac 20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 125
actcagcagt ggtaggaaag 20

<210> SEQ ID NO 126
<211> LENGTH: 1210
<212> TYPE: DNA
<213> ORGANISM: Homo sapiens

<400> SEQUENCE: 126
cagcgcgtgg ccggcgccgc tgtggggaca gcatgagcgg cggttggatg gcgcaggttg 60
gagcgtggcg aacaggggct ctgggcctgg cgctgctgct gctgctcggc ctcggactag 120
gcctggaggc cgccgcgagc ccgctttcca ccccgacctc tgcccaggcc gcaggcccca 180
gctcaggctc gtgcccaccc accaagttcc agtgccgcac cagtggctta tgcgtgcccc 240
tcacctggcg ctgcgacagg gacttggact gcagcgatgg cagcgatgag gaggagtgca 300
ggattgagcc atgtacccag aaagggcaat gcccaccgcc ccctggcctc ccctgcccct 360
gcaccggcgt cagtgactgc tctgggggaa ctgacaagaa actgcgcaac tgcagccgcc 420
tggcctgcct agcaggcgag ctccgttgca cgctgagcga tgactgcatt ccactcacgt 480
ggcgctgcga cggccaccca gactgtcccg actccagcga cgagctcggc tgtggaacca 540
atgagatcct cccggaaggg gatgccacaa ccatggggcc ccctgtgacc ctggagagtg 600
tcacctctct caggaatgcc acaaccatgg ggcccccctgt gaccctggag agtgtcccct 660
ctgtcgggaa tgccacatcc tcctctgccg gagaccagtc tggaagccca actgcctatg 720
gggttattgc agctgctgcg gtgctcagtg caagcctggt caccgccacc ctcctccttt 780
tgtcctggct ccgagcccag gagcgcctcc gcccactggg gttactggtg gccatgaagg 840
agtccctgct gctgtcagaa cagaagacct cgctgccctg aggacaagca cttgccacca 900
ccgtcactca gccctgggcg tagccggaca ggaggagagc agtgatgcgg atgggtaccc 960
gggcacacca gccctcagag acctgagttc ttctggccac gtggaacctc gaacccgagc 1020
tcctgcagaa gtggccctgg agattgaggg tccctggaca ctccctatgg agatccgggg 1080
agctaggatg gggaacctgc cacagccaga actgaggggc tggccccagg cagctcccag 1140
ggggtagaac ggccctgtgc ttaagacact ccctgctgcc ccgtctgagg gtggcgatta 1200
aagttgcttc 1210

<210> SEQ ID NO 127
<211> LENGTH: 282
<212> TYPE: PRT
<213> ORGANISM: Homo sapiens

<400> SEQUENCE: 127

Met Ser Gly Gly Trp Met Ala Gln Val Gly Ala Trp Arg Thr Gly Ala
1 5 10 15

-continued

```
Leu Gly Leu Ala Leu Leu Leu Leu Leu Gly Leu Gly Leu Gly Leu Glu
            20                  25                  30

Ala Ala Ala Ser Pro Leu Ser Thr Pro Thr Ser Ala Gln Ala Ala Gly
        35                  40                  45

Pro Ser Ser Gly Ser Cys Pro Pro Thr Lys Phe Gln Cys Arg Thr Ser
    50                  55                  60

Gly Leu Cys Val Pro Leu Thr Trp Arg Cys Asp Arg Asp Leu Asp Cys
65                  70                  75                  80

Ser Asp Gly Ser Asp Glu Glu Glu Cys Arg Ile Glu Pro Cys Thr Gln
                85                  90                  95

Lys Gly Gln Cys Pro Pro Pro Pro Gly Leu Pro Cys Pro Cys Thr Gly
            100                 105                 110

Val Ser Asp Cys Ser Gly Gly Thr Asp Lys Lys Leu Arg Asn Cys Ser
        115                 120                 125

Arg Leu Ala Cys Leu Ala Gly Glu Leu Arg Cys Thr Leu Ser Asp Asp
    130                 135                 140

Cys Ile Pro Leu Thr Trp Arg Cys Asp Gly His Pro Asp Cys Pro Asp
145                 150                 155                 160

Ser Ser Asp Glu Leu Gly Cys Gly Thr Asn Glu Ile Leu Pro Glu Gly
                165                 170                 175

Asp Ala Thr Thr Met Gly Pro Pro Val Thr Leu Glu Ser Val Thr Ser
            180                 185                 190

Leu Arg Asn Ala Thr Thr Met Gly Pro Pro Val Thr Leu Glu Ser Val
        195                 200                 205

Pro Ser Val Gly Asn Ala Thr Ser Ser Ser Ala Gly Asp Gln Ser Gly
    210                 215                 220

Ser Pro Thr Ala Tyr Gly Val Ile Ala Ala Ala Ala Val Leu Ser Ala
225                 230                 235                 240

Ser Leu Val Thr Ala Thr Leu Leu Leu Leu Ser Trp Leu Arg Ala Gln
                245                 250                 255

Glu Arg Leu Arg Pro Leu Gly Leu Leu Val Ala Met Lys Glu Ser Leu
            260                 265                 270

Leu Leu Ser Glu Gln Lys Thr Ser Leu Pro
        275                 280
```

```
<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 128

aagttccagt gccgcaccag tggc                                              24


<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 129

ttggttccac agccgagctc gtcg                                              24
```

-continued

<210> SEQ ID NO 130
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 130
gaggaggagt gcaggattga gccatgtacc cagaaagggc aatgcccacc 50

<210> SEQ ID NO 131
<211> LENGTH: 1843
<212> TYPE: DNA
<213> ORGANISM: Homo sapiens
<220> FEATURE:
<221> NAME/KEY: modified_base
<222> LOCATION: (1837)..(1837)
<223> OTHER INFORMATION: a, t, c or g

<400> SEQUENCE: 131
cccacgcgtc cggtctcgct cgctcgcgca gcggcggcag cagaggtcgc gcacagatgc 60
gggttagact ggcgggggga ggaggcggag gagggaagga agctgcatgc atgagaccca 120
cagactcttg caagctggat gccctctgtg gatgaaagat gtatcatgga atgaacccga 180
gcaatggaga tggatttcta gagcagcagc agcagcagca gcaacctcag tccccccaga 240
gactcttggc cgtgatcctg tggtttcagc tggcgctgtg cttcggccct gcacagctca 300
cgggcgggtt cgatgacctt caagtgtgtg ctgaccccgg cattcccgag aatggcttca 360
ggacccccag cggagggggtt ttctttgaag gctctgtagc ccgatttcac tgccaagacg 420
gattcaagct gaagggcgct acaaagagac tgtgtttgaa gcattttaat ggaaccctag 480
gctggatccc aagtgataat tccatctgtg tgcaagaaga ttgccgtatc cctcaaatcg 540
aagatgctga gattcataac aagacatata gacatggaga gaagctaatc atcacttgtc 600
atgaaggatt caagatccgg taccccgacc tacacaatat ggtttcatta tgtcgcgatg 660
atggaacgtg gaataatctg cccatctgtc aaggctgcct gagacctcta gcctcttcta 720
atggctatgt aaacatctct gagctccaga cctccttccc ggtggggact gtgatctcct 780
atcgctgctt tcccggattt aaacttgatg ggtctgcgta tcttgagtgc ttacaaaacc 840
ttatctggtc gtccagccca ccccggtgcc ttgctctgga agcccaagtc tgtccactac 900
ctccaatggt gagtcacgga gatttcgtct gccacccgcg gccttgtgag cgctacaacc 960
acggaactgt ggtggagttt tactgcgatc ctggctacag cctcaccagc gactacaagt 1020
acatcacctg ccagtatgga gagtggtttc cttcttatca agtctactgc atcaaatcag 1080
agcaaacgtg gcccagcacc catgagaccc tcctgaccac gtggaagatt gtggcgttca 1140
cggcaaccag tgtgctgctg gtgctgctgc tcgtcatcct ggccaggatg ttccagacca 1200
agttcaaggc ccactttccc cccaggggggc ctccccggag ttccagcagt gaccctgact 1260
ttgtggtggt agacggcgtg cccgtcatgc tcccgtccta tgacgaagct gtgagtggcg 1320
gcttgagtgc cttaggcccc gggtacatgg cctctgtggg ccagggctgc cccttacccg 1380
tggacgacca gagcccccca gcataccccg gctcagggga cacggacaca ggcccagggg 1440
agtcagaaac ctgtgacagc gtctcaggct cttctgagct gctccaaagt ctgtattcac 1500
ctcccaggtg ccaagagagc acccaccctg cttcggacaa ccctgacata attgccagca 1560
cggcagagga ggtggcatcc accagcccag gcatccatca tgcccactgg gtgttgttcc 1620
taagaaactg attgattaaa aaatttccca aagtgtcctg aagtgtctct tcaaatacat 1680

-continued

```
gttgatctgt ggagttgatt cctttccttc tcttggtttt agacaaatgt aaacaaagct   1740

ctgatcctta aaattgctat gctgatagag tggtgagggc tggaagcttg atcaagtcct   1800

gtttcttctt gacacagact gattaaaaat taaaagnaaa aaa                     1843


<210> SEQ ID NO 132
<211> LENGTH: 490
<212> TYPE: PRT
<213> ORGANISM: Homo sapiens

<400> SEQUENCE: 132

Met Tyr His Gly Met Asn Pro Ser Asn Gly Asp Gly Phe Leu Glu Gln
  1               5                  10                  15

Gln Gln Gln Gln Gln Gln Pro Gln Ser Pro Gln Arg Leu Leu Ala Val
             20                  25                  30

Ile Leu Trp Phe Gln Leu Ala Leu Cys Phe Gly Pro Ala Gln Leu Thr
         35                  40                  45

Gly Gly Phe Asp Asp Leu Gln Val Cys Ala Asp Pro Gly Ile Pro Glu
     50                  55                  60

Asn Gly Phe Arg Thr Pro Ser Gly Gly Val Phe Phe Glu Gly Ser Val
 65                  70                  75                  80

Ala Arg Phe His Cys Gln Asp Gly Phe Lys Leu Lys Gly Ala Thr Lys
                 85                  90                  95

Arg Leu Cys Leu Lys His Phe Asn Gly Thr Leu Gly Trp Ile Pro Ser
            100                 105                 110

Asp Asn Ser Ile Cys Val Gln Glu Asp Cys Arg Ile Pro Gln Ile Glu
        115                 120                 125

Asp Ala Glu Ile His Asn Lys Thr Tyr Arg His Gly Glu Lys Leu Ile
    130                 135                 140

Ile Thr Cys His Glu Gly Phe Lys Ile Arg Tyr Pro Asp Leu His Asn
145                 150                 155                 160

Met Val Ser Leu Cys Arg Asp Asp Gly Thr Trp Asn Asn Leu Pro Ile
                165                 170                 175

Cys Gln Gly Cys Leu Arg Pro Leu Ala Ser Ser Asn Gly Tyr Val Asn
            180                 185                 190

Ile Ser Glu Leu Gln Thr Ser Phe Pro Val Gly Thr Val Ile Ser Tyr
        195                 200                 205

Arg Cys Phe Pro Gly Phe Lys Leu Asp Gly Ser Ala Tyr Leu Glu Cys
    210                 215                 220

Leu Gln Asn Leu Ile Trp Ser Ser Ser Pro Pro Arg Cys Leu Ala Leu
225                 230                 235                 240

Glu Ala Gln Val Cys Pro Leu Pro Pro Met Val Ser His Gly Asp Phe
                245                 250                 255

Val Cys His Pro Arg Pro Cys Glu Arg Tyr Asn His Gly Thr Val Val
            260                 265                 270

Glu Phe Tyr Cys Asp Pro Gly Tyr Ser Leu Thr Ser Asp Tyr Lys Tyr
        275                 280                 285

Ile Thr Cys Gln Tyr Gly Glu Trp Phe Pro Ser Tyr Gln Val Tyr Cys
    290                 295                 300

Ile Lys Ser Glu Gln Thr Trp Pro Ser Thr His Glu Thr Leu Leu Thr
305                 310                 315                 320

Thr Trp Lys Ile Val Ala Phe Thr Ala Thr Ser Val Leu Leu Val Leu
                325                 330                 335

Leu Leu Val Ile Leu Ala Arg Met Phe Gln Thr Lys Phe Lys Ala His
```

-continued

```
            340                 345                 350

Phe Pro Pro Arg Gly Pro Pro Arg Ser Ser Ser Ser Asp Pro Asp Phe
        355                 360                 365

Val Val Val Asp Gly Val Pro Val Met Leu Pro Ser Tyr Asp Glu Ala
    370                 375                 380

Val Ser Gly Gly Leu Ser Ala Leu Gly Pro Gly Tyr Met Ala Ser Val
385                 390                 395                 400

Gly Gln Gly Cys Pro Leu Pro Val Asp Asp Gln Ser Pro Pro Ala Tyr
                405                 410                 415

Pro Gly Ser Gly Asp Thr Asp Thr Gly Pro Gly Glu Ser Glu Thr Cys
            420                 425                 430

Asp Ser Val Ser Gly Ser Ser Glu Leu Leu Gln Ser Leu Tyr Ser Pro
        435                 440                 445

Pro Arg Cys Gln Glu Ser Thr His Pro Ala Ser Asp Asn Pro Asp Ile
    450                 455                 460

Ile Ala Ser Thr Ala Glu Glu Val Ala Ser Thr Ser Pro Gly Ile His
465                 470                 475                 480

His Ala His Trp Val Leu Phe Leu Arg Asn
                485                 490


<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 133

atctcctatc gctgctttcc cgg                                          23


<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 134

agccaggatc gcagtaaaac tcc                                          23


<210> SEQ ID NO 135
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 135

atttaaactt gatgggtctg cgtatcttga gtgcttacaa aaccttatct             50


<210> SEQ ID NO 136
<211> LENGTH: 1815
<212> TYPE: DNA
<213> ORGANISM: Homo sapiens

<400> SEQUENCE: 136

cccacgcgtc cgctccgcgc cctccccccc gcctcccgtg cggtccgtcg gtggcctaga     60

gatgctgctg ccgcggttgc agttgtcgcg cacgcctctg cccgccagcc cgctccaccg    120
```

-continued

```
ccgtagcgcc cgagtgtcgg ggggcgcacc cgagtcgggc catgaggccg ggaaccgcgc    180

tacaggccgt gctgctggcc gtgctgctgg tggggctgcg ggccgcgacg ggtcgcctgc    240

tgagtgcctc ggatttggac ctcagaggag ggcagccagt ctgccgggga gggacacaga    300

ggccttgtta taaagtcatt tacttccatg atacttctcg aagactgaac tttgaggaag    360

ccaaagaagc ctgcaggagg gatggaggcc agctagtcag catcgagtct gaagatgaac    420

agaaactgat agaaaagttc attgaaaacc tcttgccatc tgatggtgac ttctggattg    480

ggctcaggag gcgtgaggag aaacaaagca atagcacagc ctgccaggac ctttatgctt    540

ggactgatgg cagcatatca caatttagga actggtatgt ggatgagccg tcctgcggca    600

gcgaggtctg cgtggtcatg taccatcagc catcggcacc cgctggcatc ggaggcccct    660

acatgttcca gtggaatgat gaccggtgca acatgaagaa caatttcatt tgcaaatatt    720

ctgatgagaa accagcagtt ccttctagag aagctgaagg tgaggaaaca gagctgacaa    780

cacctgtact tccagaagaa acacaggaag aagatgccaa aaaaacattt aaagaaagta    840

gagaagctgc cttgaatctg gcctacatcc taatccccag cattcccctt ctcctcctcc    900

ttgtggtcac cacagttgta tgttgggttt ggatctgtag aaaaagaaaa cgggagcagc    960

cagaccctag cacaaagaag caacacacca tctggccctc tcctcaccag ggaaacagcc   1020

cggacctaga ggtctacaat gtcataagaa aacaaagcga agctgactta gctgagaccc   1080

ggccagacct gaagaatatt tcattccgag tgtgttcggg agaagccact cccgatgaca   1140

tgtcttgtga ctatgacaac atggctgtga acccatcaga aagtgggttt gtgactctgg   1200

tgagcgtgga gagtggattt gtgaccaatg acatttatga gttctcccca gaccaaatgg   1260

ggaggagtaa ggagtctgga tgggtggaaa atgaaatata tggttattag gacatataaa   1320

aaactgaaac tgacaacaat ggaaaagaaa tgataagcaa aatcctctta ttttctataa   1380

ggaaaataca cagaaggtct atgaacaagc ttagatcagg tcctgtggat gagcatgtgg   1440

tccccacgac ctcctgttgg acccccacgt tttggctgta tcctttatcc cagccagtca   1500

tccagctcga ccttatgaga aggtaccttg cccaggtctg gcacatagta gagtctcaat   1560

aaatgtcact tggttggttg tatctaactt ttaagggaca gagctttacc tggcagtgat   1620

aaagatgggc tgtggagctt ggaaaaccac ctctgttttc cttgctctat acagcagcac   1680

atattatcat acagacagaa aatccagaat cttttcaaag cccacatatg gtagcacagg   1740

ttggcctgtg catcggcaat tctcatatct gtttttttca aagaataaaa tcaaataaag   1800

agcaggaaaa aaaaa                                                    1815
```

```
<210> SEQ ID NO 137
<211> LENGTH: 382
<212> TYPE: PRT
<213> ORGANISM: Homo sapiens

<400> SEQUENCE: 137

Met Arg Pro Gly Thr Ala Leu Gln Ala Val Leu Leu Ala Val Leu Leu
  1               5                  10                  15

Val Gly Leu Arg Ala Ala Thr Gly Arg Leu Leu Ser Ala Ser Asp Leu
             20                  25                  30

Asp Leu Arg Gly Gly Gln Pro Val Cys Arg Gly Gly Thr Gln Arg Pro
         35                  40                  45

Cys Tyr Lys Val Ile Tyr Phe His Asp Thr Ser Arg Arg Leu Asn Phe
     50                  55                  60
```

-continued

```
Glu Glu Ala Lys Glu Ala Cys Arg Arg Asp Gly Gly Gln Leu Val Ser
 65                  70                  75                  80

Ile Glu Ser Glu Asp Glu Gln Lys Leu Ile Glu Lys Phe Ile Glu Asn
                85                  90                  95

Leu Leu Pro Ser Asp Gly Asp Phe Trp Ile Gly Leu Arg Arg Arg Glu
            100                 105                 110

Glu Lys Gln Ser Asn Ser Thr Ala Cys Gln Asp Leu Tyr Ala Trp Thr
        115                 120                 125

Asp Gly Ser Ile Ser Gln Phe Arg Asn Trp Tyr Val Asp Glu Pro Ser
    130                 135                 140

Cys Gly Ser Glu Val Cys Val Val Met Tyr His Gln Pro Ser Ala Pro
145                 150                 155                 160

Ala Gly Ile Gly Gly Pro Tyr Met Phe Gln Trp Asn Asp Asp Arg Cys
                165                 170                 175

Asn Met Lys Asn Asn Phe Ile Cys Lys Tyr Ser Asp Glu Lys Pro Ala
            180                 185                 190

Val Pro Ser Arg Glu Ala Glu Gly Glu Glu Thr Glu Leu Thr Thr Pro
        195                 200                 205

Val Leu Pro Glu Glu Thr Gln Glu Glu Asp Ala Lys Lys Thr Phe Lys
    210                 215                 220

Glu Ser Arg Glu Ala Ala Leu Asn Leu Ala Tyr Ile Leu Ile Pro Ser
225                 230                 235                 240

Ile Pro Leu Leu Leu Leu Leu Val Val Thr Thr Val Val Cys Trp Val
                245                 250                 255

Trp Ile Cys Arg Lys Arg Lys Arg Glu Gln Pro Asp Pro Ser Thr Lys
            260                 265                 270

Lys Gln His Thr Ile Trp Pro Ser Pro His Gln Gly Asn Ser Pro Asp
        275                 280                 285

Leu Glu Val Tyr Asn Val Ile Arg Lys Gln Ser Glu Ala Asp Leu Ala
    290                 295                 300

Glu Thr Arg Pro Asp Leu Lys Asn Ile Ser Phe Arg Val Cys Ser Gly
305                 310                 315                 320

Glu Ala Thr Pro Asp Asp Met Ser Cys Asp Tyr Asp Asn Met Ala Val
                325                 330                 335

Asn Pro Ser Glu Ser Gly Phe Val Thr Leu Val Ser Val Glu Ser Gly
            340                 345                 350

Phe Val Thr Asn Asp Ile Tyr Glu Phe Ser Pro Asp Gln Met Gly Arg
        355                 360                 365

Ser Lys Glu Ser Gly Trp Val Glu Asn Glu Ile Tyr Gly Tyr
    370                 375                 380
```

<210> SEQ ID NO 138
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 138
gttcattgaa aacctcttgc catctgatgg tgacttctgg attgggctca 50

<210> SEQ ID NO 139
<211> LENGTH: 24
<212> TYPE: DNA
<213> ORGANISM: Artificial Sequence
<220> FEATURE:

-continued

<223> OTHER INFORMATION: Description of Artificial Sequence: Synthetic
      oligonucleotide probe

<400> SEQUENCE: 139
aagccaaaga agcctgcagg aggg 24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 140
cagtccaagc ataaaggtcc tggc 24

<210> SEQ ID NO 141
<211> LENGTH: 1514
<212> TYPE: DNA
<213> ORGANISM: Homo sapiens

<400> SEQUENCE: 141
ggggtctccc tcagggccgg gaggcacagc ggtccctgct tgctgaaggg ctggatgtac 60
gcatccgcag gttcccgcgg acttgggggc gcccgctgag ccccggcgcc cgcagaagac 120
ttgtgtttgc ctcctgcagc ctcaacccgg agggcagcga gggcctacca ccatgatcac 180
tggtgtgttc agcatgcgct tgtggacccc agtgggcgtc ctgacctcgc tggcgtactg 240
cctgcaccag cggcgggtgg ccctggccga gctgcaggag gccgatggcc agtgtccggt 300
cgaccgcagc ctgctgaagt tgaaaatggt gcaggtcgtg tttcgacacg gggctcggag 360
tcctctcaag ccgctcccgc tggaggagca ggtagagtgg aacccccagc tattagaggt 420
cccaccccaa actcagtttg attacacagt caccaatcta gctggtggtc cgaaaccata 480
ttctccttac gactctcaat accatgagac caccctgaag gggggcatgt ttgctgggca 540
gctgaccaag gtgggcatgc agcaaatgtt tgccttggga gagagactga ggaagaacta 600
tgtggaagac attccctttc tttcaccaac cttcaaccca caggaggtct ttattcgttc 660
cactaacatt tttcggaatc tggagtccac ccgttgtttg ctggctgggc ttttccagtg 720
tcagaaagaa ggacccatca tcatccacac tgatgaagca gattcagaag tcttgtatcc 780
caactaccaa agctgctgga gcctgaggca gagaaccaga ggccggaggc agactgcctc 840
tttacagcca ggaatctcag aggatttgaa aaaggtgaag gacaggatgg gcattgacag 900
tagtgataaa gtggacttct tcatcctcct ggacaacgtg gctgccgagc aggcacacaa 960
cctcccaagc tgccccatgc tgaagagatt tgcacggatg atcgaacaga gagctgtgga 1020
cacatccttg tacatactgc ccaaggaaga cagggaaagt cttcagatgg cagtaggccc 1080
attcctccac atcctagaga gcaacctgct gaaagccatg gactctgcca ctgcccccga 1140
caagatcaga aagctgtatc tctatgcggc tcatgatgtg accttcatac cgctcttaat 1200
gaccctgggg atttttgacc acaaatggcc accgtttgct gttgacctga ccatggaact 1260
ttaccagcac ctggaatcta aggagtggtt tgtgcagctc tattaccacg ggaaggagca 1320
ggtgccgaga ggttgccctg atgggctctg cccgctggac atgttcttga atgccatgtc 1380
agtttatacc ttaagcccag aaaaatacca tgcactctgc tctcaaactc aggtgatgga 1440
agttggaaat gaagagtaac tgatttataa aagcaggatg tgttgatttt aaaataaagt 1500
gcctttatac aatg 1514

-continued

<210> SEQ ID NO 142
<211> LENGTH: 428
<212> TYPE: PRT
<213> ORGANISM: Homo sapiens

<400> SEQUENCE: 142

```
Met Ile Thr Gly Val Phe Ser Met Arg Leu Trp Thr Pro Val Gly Val
  1               5                  10                  15

Leu Thr Ser Leu Ala Tyr Cys Leu His Gln Arg Arg Val Ala Leu Ala
             20                  25                  30

Glu Leu Gln Glu Ala Asp Gly Gln Cys Pro Val Asp Arg Ser Leu Leu
         35                  40                  45

Lys Leu Lys Met Val Gln Val Val Phe Arg His Gly Ala Arg Ser Pro
     50                  55                  60

Leu Lys Pro Leu Pro Leu Glu Glu Gln Val Glu Trp Asn Pro Gln Leu
 65                  70                  75                  80

Leu Glu Val Pro Pro Gln Thr Gln Phe Asp Tyr Thr Val Thr Asn Leu
                 85                  90                  95

Ala Gly Gly Pro Lys Pro Tyr Ser Pro Tyr Asp Ser Gln Tyr His Glu
            100                 105                 110

Thr Thr Leu Lys Gly Gly Met Phe Ala Gly Gln Leu Thr Lys Val Gly
        115                 120                 125

Met Gln Gln Met Phe Ala Leu Gly Glu Arg Leu Arg Lys Asn Tyr Val
    130                 135                 140

Glu Asp Ile Pro Phe Leu Ser Pro Thr Phe Asn Pro Gln Glu Val Phe
145                 150                 155                 160

Ile Arg Ser Thr Asn Ile Phe Arg Asn Leu Glu Ser Thr Arg Cys Leu
                165                 170                 175

Leu Ala Gly Leu Phe Gln Cys Gln Lys Glu Gly Pro Ile Ile Ile His
            180                 185                 190

Thr Asp Glu Ala Asp Ser Glu Val Leu Tyr Pro Asn Tyr Gln Ser Cys
        195                 200                 205

Trp Ser Leu Arg Gln Arg Thr Arg Gly Arg Arg Gln Thr Ala Ser Leu
    210                 215                 220

Gln Pro Gly Ile Ser Glu Asp Leu Lys Lys Val Lys Asp Arg Met Gly
225                 230                 235                 240

Ile Asp Ser Ser Asp Lys Val Asp Phe Phe Ile Leu Leu Asp Asn Val
                245                 250                 255

Ala Ala Glu Gln Ala His Asn Leu Pro Ser Cys Pro Met Leu Lys Arg
            260                 265                 270

Phe Ala Arg Met Ile Glu Gln Arg Ala Val Asp Thr Ser Leu Tyr Ile
        275                 280                 285

Leu Pro Lys Glu Asp Arg Glu Ser Leu Gln Met Ala Val Gly Pro Phe
    290                 295                 300

Leu His Ile Leu Glu Ser Asn Leu Leu Lys Ala Met Asp Ser Ala Thr
305                 310                 315                 320

Ala Pro Asp Lys Ile Arg Lys Leu Tyr Leu Tyr Ala Ala His Asp Val
                325                 330                 335

Thr Phe Ile Pro Leu Leu Met Thr Leu Gly Ile Phe Asp His Lys Trp
            340                 345                 350

Pro Pro Phe Ala Val Asp Leu Thr Met Glu Leu Tyr Gln His Leu Glu
        355                 360                 365

Ser Lys Glu Trp Phe Val Gln Leu Tyr Tyr His Gly Lys Glu Gln Val
```

-continued 370 375 380

Pro Arg Gly Cys Pro Asp Gly Leu Cys Pro Leu Asp Met Phe Leu Asn
385 390 395 400

Ala Met Ser Val Tyr Thr Leu Ser Pro Glu Lys Tyr His Ala Leu Cys
405 410 415

Ser Gln Thr Gln Val Met Glu Val Gly Asn Glu Glu
420 425

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 143
ccaactacca aagctgctgg agcc 24

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 144
gcagctctat taccacggga agga 24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 145
tccttcccgt ggtaatagag ctgc 24

<210> SEQ ID NO 146
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 146
ggcagagaac cagaggccgg aggagactgc ctctttacag ccagg 45

<210> SEQ ID NO 147
<211> LENGTH: 1686
<212> TYPE: DNA
<213> ORGANISM: Homo sapiens

<400> SEQUENCE: 147
ctcctcttaa catacttgca gctaaaacta aatattgctg cttggggacc tccttctagc 60
cttaaatttc agctcatcac cttcacctgc cttggtcatg gctctgctat tctccttgat 120
ccttgccatt tgcaccagac ctggattcct agcgtctcca tctggagtgc ggctggtggg 180
gggcctccac cgctgtgaag ggcgggtgga ggtggaacag aaaggccagt ggggcaccgt 240

-continued

```
gtgtgatgac ggctgggaca ttaaggacgt ggctgtgttg tgccgggagc tgggctgtgg    300

agctgccagc ggaaccccta gtggtatttt gtatgagcca ccagcagaaa aagagcaaaa    360

ggtcctcatc caatcagtca gttgcacagg aacagaagat acattggctc agtgtgagca    420

agaagaagtt tatgattgtt cacatgatga agatgctggg gcatcgtgtg agaacccaga    480

gagctctttc tccccagtcc cagagggtgt caggctggct gacggccctg ggcattgcaa    540

gggacgcgtg gaagtgaagc accagaacca gtggtatacc gtgtgccaga caggctggag    600

cctccgggcc gcaaaggtgg tgtgccggca gctgggatgt gggagggctg tactgactca    660

aaaacgctgc aacaagcatg cctatggccg aaaacccatc tggctgagcc agatgtcatg    720

ctcaggacga gaagcaaccc ttcaggattg cccttctggg ccttggggga agaacacctg    780

caaccatgat gaagacacgt gggtcgaatg tgaagatccc tttgacttga gactagtagg    840

aggagacaac ctctgctctg ggcgactgga ggtgctgcac aagggcgtat ggggctctgt    900

ctgtgatgac aactggggag aaaaggagga ccaggtggta tgcaagcaac tgggctgtgg    960

gaagtccctc tctccctcct tcagagaccg gaaatgctat ggccctgggg ttggccgcat   1020

ctggctggat aatgttcgtt gctcagggga ggagcagtcc ctggagcagt gccagcacag   1080

attttggggg tttcacgact gcacccacca ggaagatgtg gctgtcatct gctcagtgta   1140

ggtgggcatc atctaatctg ttgagtgcct gaatagaaga aaaacacaga agaagggagc   1200

atttactgtc tacatgactg catgggatga acactgatct tcttctgccc ttggactggg   1260

acttatactt ggtgcccctg attctcaggc cttcagagtt ggatcagaac ttacaacatc   1320

aggtctagtt ctcaggccat cagacatagt ttggaactac atcaccacct ttcctatgtc   1380

tccacattgc acacagcaga ttcccagcct ccataattgt gtgtatcaac tacttaaata   1440

cattctcaca cacacacaca cacacacaca cacacacaca cacacataca ccatttgtcc   1500

tgtttctctg aagaactctg acaaaataca gattttggta ctgaaagaga ttctagagga   1560

acggaatttt aaggataaat tttctgaatt ggttatgggg tttctgaaat tggctctata   1620

atctaattag atataaaatt ctggtaactt tatttacaat aataaagata gcactatgtg   1680

ttcaaa                                                              1686
```

<210> SEQ ID NO 148
<211> LENGTH: 347
<212> TYPE: PRT
<213> ORGANISM: Homo sapiens

<400> SEQUENCE: 148

```
Met Ala Leu Leu Phe Ser Leu Ile Leu Ala Ile Cys Thr Arg Pro Gly
  1               5                  10                  15

Phe Leu Ala Ser Pro Ser Gly Val Arg Leu Val Gly Gly Leu His Arg
             20                  25                  30

Cys Glu Gly Arg Val Glu Val Glu Gln Lys Gly Gln Trp Gly Thr Val
         35                  40                  45

Cys Asp Asp Gly Trp Asp Ile Lys Asp Val Ala Val Leu Cys Arg Glu
     50                  55                  60

Leu Gly Cys Gly Ala Ala Ser Gly Thr Pro Ser Gly Ile Leu Tyr Glu
 65                  70                  75                  80

Pro Pro Ala Glu Lys Glu Gln Lys Val Leu Ile Gln Ser Val Ser Cys
                 85                  90                  95

Thr Gly Thr Glu Asp Thr Leu Ala Gln Cys Glu Gln Glu Glu Val Tyr
            100                 105                 110
```

-continued

```
Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Val
            340                 345
```

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 149
ttcagctcat caccttcacc tgcc 24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 150
ggctcataca aaataccact aggg 24

<210> SEQ ID NO 151
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe -continued

<400> SEQUENCE: 151
gggcctccac cgctgtgaag ggcgggtgga ggtggaacag aaaggccagt 50

<210> SEQ ID NO 152
<211> LENGTH: 1427
<212> TYPE: DNA
<213> ORGANISM: Homo sapiens

<400> SEQUENCE: 152
actgcactcg gttctatcga ttgaattccc cggggatcct ctagagatcc ctcgacctcg 60
acccacgcgt ccgcggacgc gtgggcggac gcgtgggccg gctaccagga agagtctgcc 120
gaaggtgaag gccatggact tcatcacctc cacagccatc ctgcccctgc tgttcggctg 180
cctgggcgtc ttcggcctct tccggctgct gcagtgggtg cgcgggaagg cctacctgcg 240
gaatgctgtg gtggtgatca caggcgccac ctcagggctg ggcaaagaat gtgcaaaagt 300
cttctatgct gcgggtgcta aactggtgct ctgtggccgg aatggtgggg ccctagaaga 360
gctcatcaga gaacttaccg cttctcatgc caccaaggtg cagacacaca agccttactt 420
ggtgaccttc gacctcacag actctggggc catagttgca gcagcagctg agatcctgca 480
gtgctttggc tatgtcgaca tacttgtcaa caatgctggg atcagctacc gtggtaccat 540
catggacacc acagtggatg tggacaagag ggtcatggag acaaactact ttggcccagt 600
tgctctaacg aaagcactcc tgccctccat gatcaagagg aggcaaggcc acattgtcgc 660
catcagcagc atccagggca agatgagcat tccttttcga tcagcatatg cagcctccaa 720
gcacgcaacc caggctttct ttgactgtct gcgtgccgag atggaacagt atgaaattga 780
ggtgaccgtc atcagccccg gctacatcca caccaacctc tctgtaaatg ccatcaccgc 840
ggatggatct aggtatggag ttatggacac caccacagcc cagggccgaa gccctgtgga 900
ggtggcccag gatgttcttg ctgctgtggg gaagaagaag aaagatgtga tcctggctga 960
cttactgcct tccttggctg tttatcttcg aactctggct cctgggctct tcttcagcct 1020
catggcctcc agggccagaa aagagcggaa atccaagaac tcctagtact ctgaccagcc 1080
agggccaggg cagagaagca gcactcttag gcttgcttac tctacaaggg acagttgcat 1140
ttgttgagac tttaatggag atttgtctca caagtgggaa agactgaaga aacacatctc 1200
gtgcagatct gctggcagag gacaatcaaa aacgacaaca agcttcttcc cagggtgagg 1260
ggaaacactt aaggaataaa tatggagctg ggtttaaca ctaaaaacta gaaataaaca 1320
tctcaaacag taaaaaaaaa aaaaaagggc ggccgcgact ctagagtcga cctgcagaag 1380
cttggccgcc atggcccaac ttgtttattg cagcttataa tggttac 1427

<210> SEQ ID NO 153
<211> LENGTH: 310
<212> TYPE: PRT
<213> ORGANISM: Homo sapiens

<400> SEQUENCE: 153

Met Asp Phe Ile Thr Ser Thr Ala Ile Leu Pro Leu Leu Phe Gly Cys
1 5 10 15

Leu Gly Val Phe Gly Leu Phe Arg Leu Leu Gln Trp Val Arg Gly Lys
20 25 30

Ala Tyr Leu Arg Asn Ala Val Val Val Ile Thr Gly Ala Thr Ser Gly
35 40 45

Leu Gly Lys Glu Cys Ala Lys Val Phe Tyr Ala Ala Gly Ala Lys Leu

-continued

```
     50                  55                  60

Val Leu Cys Gly Arg Asn Gly Gly Ala Leu Glu Glu Leu Ile Arg Glu
 65                  70                  75                  80

Leu Thr Ala Ser His Ala Thr Lys Val Gln Thr His Lys Pro Tyr Leu
                 85                  90                  95

Val Thr Phe Asp Leu Thr Asp Ser Gly Ala Ile Val Ala Ala Ala Ala
            100                 105                 110

Glu Ile Leu Gln Cys Phe Gly Tyr Val Asp Ile Leu Val Asn Asn Ala
        115                 120                 125

Gly Ile Ser Tyr Arg Gly Thr Ile Met Asp Thr Thr Val Asp Val Asp
    130                 135                 140

Lys Arg Val Met Glu Thr Asn Tyr Phe Gly Pro Val Ala Leu Thr Lys
145                 150                 155                 160

Ala Leu Leu Pro Ser Met Ile Lys Arg Arg Gln Gly His Ile Val Ala
                165                 170                 175

Ile Ser Ser Ile Gln Gly Lys Met Ser Ile Pro Phe Arg Ser Ala Tyr
            180                 185                 190

Ala Ala Ser Lys His Ala Thr Gln Ala Phe Phe Asp Cys Leu Arg Ala
        195                 200                 205

Glu Met Glu Gln Tyr Glu Ile Glu Val Thr Val Ile Ser Pro Gly Tyr
    210                 215                 220

Ile His Thr Asn Leu Ser Val Asn Ala Ile Thr Ala Asp Gly Ser Arg
225                 230                 235                 240

Tyr Gly Val Met Asp Thr Thr Thr Ala Gln Gly Arg Ser Pro Val Glu
                245                 250                 255

Val Ala Gln Asp Val Leu Ala Ala Val Gly Lys Lys Lys Lys Asp Val
            260                 265                 270

Ile Leu Ala Asp Leu Leu Pro Ser Leu Ala Val Tyr Leu Arg Thr Leu
        275                 280                 285

Ala Pro Gly Leu Phe Phe Ser Leu Met Ala Ser Arg Ala Arg Lys Glu
    290                 295                 300

Arg Lys Ser Lys Asn Ser
305                 310
```

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 154
ggtgctaaac tggtgctctg tggc 24

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 155
cagggcaaga tgagcattcc 20

<210> SEQ ID NO 156
<211> LENGTH: 24

-continued

<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 156
tcatactgtt ccatctcggc acgc 24

<210> SEQ ID NO 157
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 157
aatggtgggg ccctagaaga gctcatcaga gaactcaccg cttctcatgc 50

<210> SEQ ID NO 158
<211> LENGTH: 1771
<212> TYPE: DNA
<213> ORGANISM: Homo sapiens

<400> SEQUENCE: 158
cccacgcgtc cgctggtgtt agatcgagca accctctaaa agcagtttag agtggtaaaa 60
aaaaaaaaaa acacaccaaa cgctcgcagc cacaaaaggg atgaaatttc ttctggacat 120
cctcctgctt ctcccgttac tgatcgtctg ctccctagag tccttcgtga agctttttat 180
tcctaagagg agaaaatcag tcaccggcga aatcgtgctg attacaggag ctgggcatgg 240
aattgggaga ctgactgcct atgaatttgc taaacttaaa agcaagctgg ttctctggga 300
tataaataag catggactgg aggaaacagc tgccaaatgc aagggactgg gtgccaaggt 360
tcataccttt gtggtagact gcagcaaccg agaagatatt tacagctctg caaagaaggt 420
gaaggcagaa attggagatg ttagtatttt agtaaataat gctggtgtag tctatacatc 480
agatttgttt gctacacaag atcctcagat tgaaaagact tttgaagtta atgtacttgc 540
acatttctgg actacaaagg catttcttcc tgcaatgacg aagaataacc atggccatat 600
tgtcactgtg gcttcggcag ctggacatgt ctcggtcccc ttcttactgg cttactgttc 660
aagcaagttt gctgctgttg gatttcataa aactttgaca gatgaactgg ctgccttaca 720
aataactgga gtcaaaacaa catgtctgtg tcctaatttc gtaaacactg gcttcatcaa 780
aaatccaagt acaagtttgg gacccactct ggaacctgag gaagtggtaa acaggctgat 840
gcatgggatt ctgactgagc agaagatgat tttattccca tcttctatag ctttttttaac 900 aacattggaa aggatccttc ctgagcgttt cctggcagtt ttaaaacgaa aaatcagtgt 960
taagtttgat gcagttattg gatataaaat gaaagcgcaa taagcaccta gttttctgaa 1020
aactgattta ccaggtttag gttgatgtca tctaatagtg ccagaatttt aatgtttgaa 1080
cttctgtttt ttctaattat ccccatttct tcaatatcat ttttgaggct ttggcagtct 1140
tcatttacta ccacttgttc tttagccaaa agctgattac atatgatata aacagagaaa 1200
tacctttaga ggtgacttta aggaaaatga agaaaaagaa ccaaaatgac tttattaaaa 1260
taatttccaa gattatttgt ggctcacctg aaggctttgc aaaatttgta ccataaccgt 1320
ttatttaaca tatattttta tttttgattg cacttaaatt ttgtataatt tgtgtttctt 1380
tttctgttct acataaaatc agaaacttca agctctctaa ataaaatgaa ggactatatc 1440

-continued

```
tagtggtatt tcacaatgaa tatcatgaac tctcaatggg taggtttcat cctacccatt   1500

gccactctgt ttcctgagag atacctcaca ttccaatgcc aaacatttct gcacagggaa   1560

gctagaggtg gatacacgtg ttgcaagtat aaaagcatca ctgggattta aggagaattg   1620

agagaatgta cccacaaatg gcagcaataa taaatggatc acacttaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa a                                  1771
```

<210> SEQ ID NO 159
<211> LENGTH: 300
<212> TYPE: PRT
<213> ORGANISM: Homo sapiens

<400> SEQUENCE: 159

```
Met Lys Phe Leu Leu Asp Ile Leu Leu Leu Leu Pro Leu Leu Ile Val
  1               5                  10                  15

Cys Ser Leu Glu Ser Phe Val Lys Leu Phe Ile Pro Lys Arg Arg Lys
             20                  25                  30

Ser Val Thr Gly Glu Ile Val Leu Ile Thr Gly Ala Gly His Gly Ile
         35                  40                  45

Gly Arg Leu Thr Ala Tyr Glu Phe Ala Lys Leu Lys Ser Lys Leu Val
     50                  55                  60

Leu Trp Asp Ile Asn Lys His Gly Leu Glu Glu Thr Ala Ala Lys Cys
 65                  70                  75                  80

Lys Gly Leu Gly Ala Lys Val His Thr Phe Val Val Asp Cys Ser Asn
                 85                  90                  95

Arg Glu Asp Ile Tyr Ser Ser Ala Lys Lys Val Lys Ala Glu Ile Gly
            100                 105                 110

Asp Val Ser Ile Leu Val Asn Asn Ala Gly Val Val Tyr Thr Ser Asp
        115                 120                 125

Leu Phe Ala Thr Gln Asp Pro Gln Ile Glu Lys Thr Phe Glu Val Asn
    130                 135                 140

Val Leu Ala His Phe Trp Thr Thr Lys Ala Phe Leu Pro Ala Met Thr
145                 150                 155                 160

Lys Asn Asn His Gly His Ile Val Thr Val Ala Ser Ala Ala Gly His
                165                 170                 175

Val Ser Val Pro Phe Leu Leu Ala Tyr Cys Ser Ser Lys Phe Ala Ala
            180                 185                 190

Val Gly Phe His Lys Thr Leu Thr Asp Glu Leu Ala Ala Leu Gln Ile
        195                 200                 205

Thr Gly Val Lys Thr Thr Cys Leu Cys Pro Asn Phe Val Asn Thr Gly
    210                 215                 220

Phe Ile Lys Asn Pro Ser Thr Ser Leu Gly Pro Thr Leu Glu Pro Glu
225                 230                 235                 240

Glu Val Val Asn Arg Leu Met His Gly Ile Leu Thr Glu Gln Lys Met
                245                 250                 255

Ile Phe Ile Pro Ser Ser Ile Ala Phe Leu Thr Thr Leu Glu Arg Ile
            260                 265                 270

Leu Pro Glu Arg Phe Leu Ala Val Leu Lys Arg Lys Ile Ser Val Lys
        275                 280                 285

Phe Asp Ala Val Ile Gly Tyr Lys Met Lys Ala Gln
    290                 295                 300
```

<210> SEQ ID NO 160

-continued

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 160
ggtgaaggca gaaattggag atg 23

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 161
atcccatgca tcagcctgtt tacc 24

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 162
gctggtgtag tctatacatc agatttgttt gctacacaag atcctcag 48

<210> SEQ ID NO 163
<211> LENGTH: 2076
<212> TYPE: DNA
<213> ORGANISM: Homo sapiens

<400> SEQUENCE: 163
cccacgcgtc cgcggacgcg tgggtcgact agttctagat cgcgagcggc cgcccgcggc 60
tcagggagga gcaccgactg cgccgcaccc tgagagatgg ttggtgccat gtggaaggtg 120
attgtttcgc tggtcctgtt gatgcctggc ccctgtgatg ggctgtttcg ctccctatac 180
agaagtgttt ccatgccacc taagggagac tcaggacagc cattatttct caccccttac 240
attgaagctg ggaagatcca aaaaggaaga gaattgagtt tggtcggccc tttcccagga 300
ctgaacatga agagttatgc cggcttcctc accgtgaata agacttacaa cagcaacctc 360
ttcttctggt tcttcccagc tcagatacag ccagaagatg ccccagtagt tctctggcta 420
cagggtgggc cgggaggttc atccatgttt ggactctttg tggaacatgg gccttatgtt 480
gtcacaagta acatgacctt gcgtgacaga gacttcccct ggaccacaac gctctccatg 540
ctttacattg acaatccagt gggcacaggc ttcagtttta ctgatgatac ccacggatat 600
gcagtcaatg aggacgatgt agcacgggat ttatacagtg cactaattca gtttttccag 660
atatttcctg aatataaaaa taatgacttt tatgtcactg gggagtctta tgcagggaaa 720
tatgtgccag ccattgcaca cctcatccat tccctcaacc ctgtgagaga ggtgaagatc 780
aacctgaacg gaattgctat tggagatgga tattctgatc ccgaatcaat tatagggggc 840
tatgcagaat tcctgtacca aattggcttg ttggatgaga agcaaaaaaa gtacttccag 900
aagcagtgcc atgaatgcat agaacacatc aggaagcaga actggtttga ggcctttgaa 960
atactggata aactactaga tggcgactta acaagtgatc cttcttactt ccagaatgtt 1020

-continued

```
acaggatgta gtaattacta taactttttg cggtgcacgg aacctgagga tcagctttac   1080

tatgtgaaat ttttgtcact cccagaggtg agacaagcca tccacgtggg gaatcagact   1140

tttaatgatg gaactatagt tgaaaagtac ttgcgagaag atacagtaca gtcagttaag   1200

ccatggttaa ctgaaatcat gaataattat aaggttctga tctacaatgg ccaactggac   1260

atcatcgtgg cagctgccct gacagagcgc tccttgatgg gcatggactg gaaaggatcc   1320

caggaataca agaaggcaga aaaaaaagtt tggaagatct ttaaatctga cagtgaagtg   1380

gctggttaca tccggcaagc gggtgacttc catcaggtaa ttattcgagg tggaggacat   1440

attttaccct atgaccagcc tctgagagct tttgacatga ttaatcgatt catttatgga   1500

aaaggatggg atccttatgt tggataaact accttcccaa aagagaacat cagaggtttt   1560

cattgctgaa aagaaaatcg taaaaacaga aaatgtcata ggaataaaaa aattatcttt   1620

tcatatctgc aagatttttt tcatcaataa aaattatcct tgaaacaagt gagcttttgt   1680

ttttgggggg agatgtttac tacaaaatta acatgagtac atgagtaaga attacattat   1740

ttaacttaaa ggatgaaagg tatggatgat gtgacactga gacaagatgt ataaatgaaa   1800

ttttagggtc ttgaatagga agttttaatt tcttctaaga gtaagtgaaa agtgcagttg   1860

taacaaacaa agctgtaaca tctttttctg ccaataacag aagtttggca tgccgtgaag   1920

gtgtttggaa atattattgg ataagaatag ctcaattatc ccaaataaat ggatgaagct   1980

ataatagttt tggggaaaag attctcaaat gtataaagtc ttagaacaaa agaattcttt   2040

gaaataaaaa tattatatat aaaagtaaaa aaaaaa                              2076
```

```
<210> SEQ ID NO 164
<211> LENGTH: 476
<212> TYPE: PRT
<213> ORGANISM: Homo sapiens

<400> SEQUENCE: 164

Met Val Gly Ala Met Trp Lys Val Ile Val Ser Leu Val Leu Leu Met
  1               5                  10                  15

Pro Gly Pro Cys Asp Gly Leu Phe Arg Ser Leu Tyr Arg Ser Val Ser
             20                  25                  30

Met Pro Pro Lys Gly Asp Ser Gly Gln Pro Leu Phe Leu Thr Pro Tyr
         35                  40                  45

Ile Glu Ala Gly Lys Ile Gln Lys Gly Arg Glu Leu Ser Leu Val Gly
     50                  55                  60

Pro Phe Pro Gly Leu Asn Met Lys Ser Tyr Ala Gly Phe Leu Thr Val
 65                  70                  75                  80

Asn Lys Thr Tyr Asn Ser Asn Leu Phe Phe Trp Phe Phe Pro Ala Gln
                 85                  90                  95

Ile Gln Pro Glu Asp Ala Pro Val Val Leu Trp Leu Gln Gly Gly Pro
            100                 105                 110

Gly Gly Ser Ser Met Phe Gly Leu Phe Val Glu His Gly Pro Tyr Val
        115                 120                 125

Val Thr Ser Asn Met Thr Leu Arg Asp Arg Asp Phe Pro Trp Thr Thr
    130                 135                 140

Thr Leu Ser Met Leu Tyr Ile Asp Asn Pro Val Gly Thr Gly Phe Ser
145                 150                 155                 160

Phe Thr Asp Asp Thr His Gly Tyr Ala Val Asn Glu Asp Asp Val Ala
                165                 170                 175

Arg Asp Leu Tyr Ser Ala Leu Ile Gln Phe Phe Gln Ile Phe Pro Glu
            180                 185                 190
```

-continued

```
Tyr Lys Asn Asn Asp Phe Tyr Val Thr Gly Glu Ser Tyr Ala Gly Lys
        195                 200                 205

Tyr Val Pro Ala Ile Ala His Leu Ile His Ser Leu Asn Pro Val Arg
    210                 215                 220

Glu Val Lys Ile Asn Leu Asn Gly Ile Ala Ile Gly Asp Gly Tyr Ser
225                 230                 235                 240

Asp Pro Glu Ser Ile Ile Gly Gly Tyr Ala Glu Phe Leu Tyr Gln Ile
                245                 250                 255

Gly Leu Leu Asp Glu Lys Gln Lys Lys Tyr Phe Gln Lys Gln Cys His
            260                 265                 270

Glu Cys Ile Glu His Ile Arg Lys Gln Asn Trp Phe Glu Ala Phe Glu
        275                 280                 285

Ile Leu Asp Lys Leu Leu Asp Gly Asp Leu Thr Ser Asp Pro Ser Tyr
    290                 295                 300

Phe Gln Asn Val Thr Gly Cys Ser Asn Tyr Tyr Asn Phe Leu Arg Cys
305                 310                 315                 320

Thr Glu Pro Glu Asp Gln Leu Tyr Tyr Val Lys Phe Leu Ser Leu Pro
                325                 330                 335

Glu Val Arg Gln Ala Ile His Val Gly Asn Gln Thr Phe Asn Asp Gly
            340                 345                 350

Thr Ile Val Glu Lys Tyr Leu Arg Glu Asp Thr Val Gln Ser Val Lys
        355                 360                 365

Pro Trp Leu Thr Glu Ile Met Asn Asn Tyr Lys Val Leu Ile Tyr Asn
    370                 375                 380

Gly Gln Leu Asp Ile Ile Val Ala Ala Ala Leu Thr Glu Arg Ser Leu
385                 390                 395                 400

Met Gly Met Asp Trp Lys Gly Ser Gln Glu Tyr Lys Lys Ala Glu Lys
                405                 410                 415

Lys Val Trp Lys Ile Phe Lys Ser Asp Ser Glu Val Ala Gly Tyr Ile
            420                 425                 430

Arg Gln Ala Gly Asp Phe His Gln Val Ile Ile Arg Gly Gly Gly His
        435                 440                 445

Ile Leu Pro Tyr Asp Gln Pro Leu Arg Ala Phe Asp Met Ile Asn Arg
    450                 455                 460

Phe Ile Tyr Gly Lys Gly Trp Asp Pro Tyr Val Gly
465                 470                 475


<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 165

ttccatgcca cctaagggag actc                                           24


<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 166
```

-continued

```
tggatgaggt gtgcaatggc tggc                                          24


<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 167

agctctcaga ggctggtcat aggg                                          24


<210> SEQ ID NO 168
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 168

gtcggccctt tcccaggact gaacatgaag agttatgccg gcttcctcac              50


<210> SEQ ID NO 169
<211> LENGTH: 2477
<212> TYPE: DNA
<213> ORGANISM: Homo sapiens

<400> SEQUENCE: 169

cgagggcttt tccggctccg gaatggcaca tgtgggaatc ccagtcttgt tggctacaac     60

atttttccct ttcctaacaa gttctaacag ctgttctaac agctagtgat caggggttct    120

tcttgctgga gaagaaaggg ctgagggcag agcagggcac tctcactcag ggtgaccagc    180

tccttgcctc tctgtggata acagagcatg agaaagtgaa gagatgcagc ggagtgaggt    240

gatggaagtc taaaatagga aggaattttg tgtgcaatat cagactctgg gagcagttga    300

cctggagagc ctgggggagg gcctgcctaa caagctttca aaaaacagga gcgacttcca    360

ctgggctggg ataagacgtg ccggtaggat agggaagact gggtttagtc ctaatatcaa    420

attgactggc tgggtgaact tcaacagcct tttaacctct ctgggagatg aaaacgatgg    480

cttaaggggc cagaaataga gatgctttgt aaaataaaat tttaaaaaaa gcaagtattt    540

tatagcataa aggctagaga ccaaaataga taacaggatt ccctgaacat tcctaagagg    600

gagaaagtat gttaaaaata gaaaaaccaa aatgcagaag gaggagactc acagagctaa    660

accaggatgg ggaccctggg tcaggccagc ctctttgctc ctcccggaaa ttatttttgg    720

tctgaccact ctgccttgtg ttttgcagaa tcatgtgagg gccaaccggg gaaggtggag    780

cagatgagca cacacaggag ccgtctcctc accgccgccc ctctcagcat ggaacagagg    840

cagccctggc cccgggccct ggaggtggac agccgctctg tggtcctgct ctcagtggtc    900

tgggtgctgc tggccccccc agcagccggc atgcctcagt tcagcacctt ccactctgag    960

aatcgtgact ggaccttcaa ccacttgacc gtccaccaag ggacgggggc cgtctatgtg   1020

ggggccatca accgggtcta taagctgaca ggcaacctga ccatccaggt ggctcataag   1080

acagggccag aagaggacaa caagtctcgt tacccgcccc tcatcgtgca gccctgcagc   1140

gaagtgctca ccctcaccaa caatgtcaac aagctgctca tcattgacta ctctgagaac   1200

cgcctgctgg cctgtgggag cctctaccag gggggtctgca agctgctgcg gctggatgac   1260

ctcttcatcc tggtggagcc atcccacaag aaggagcact acctgtccag tgtcaacaag   1320
```

acgggcacca tgtacggggt gattgtgcgc tctgagggtg aggatggcaa gctcttcatc 1380
ggcacggctg tggatgggaa gcaggattac ttcccgaccc tgtccagccg gaagctgccc 1440
cgagaccctg agtcctcagc catgctcgac tatgagctac acagcgattt tgtctcctct 1500
ctcatcaaga tcccttcaga caccctggcc ctggtctccc actttgacat cttctacatc 1560
tacggctttg ctagtggggg ctttgtctac tttctcactg tccagcccga gacccctgag 1620
ggtgtggcca tcaactccgc tggagacctc ttctacacct cacgcatcgt gcggctctgc 1680
aaggatgacc ccaagttcca ctcatacgtg tccctgccct tcggctgcac ccgggccggg 1740
gtggaatacc gcctcctgca ggctgcttac ctggccaagc ctggggactc actggcccag 1800
gccttcaata tcaccagcca ggacgatgta ctctttgcca tcttctccaa agggcagaag 1860
cagtatcacc acccgcccga tgactctgcc ctgtgtgcct tccctatccg ggccatcaac 1920
ttgcagatca aggagcgcct gcagtcctgc taccagggcg agggcaacct ggagctcaac 1980
tggctgctgg ggaaggacgt ccagtgcacg aaggcgcctg tccccatcga tgataacttc 2040
tgtggactgg acatcaacca gcccctggga ggctcaactc cagtggaggg cctgaccctg 2100
tacaccacca gcagggaccg catgacctct gtggcctcct acgtttacaa cggctacagc 2160
gtggtttttg tggggactaa gagtggcaag ctgaaaaagg taagagtcta tgagttcaga 2220
tgctccaatg ccattcacct cctcagcaaa gagtccctct tggaaggtag ctattggtgg 2280
agatttaact ataggcaact ttattttctt ggggaacaaa ggtgaaatgg ggaggtaaga 2340
aggggttaat tttgtgactt agcttctagc tacttcctcc agccatcagt cattgggtat 2400
gtaaggaatg caagcgtatt tcaatatttc ccaaacttta agaaaaaact ttaagaaggt 2460
acatctgcaa aagcaaa 2477

<210> SEQ ID NO 170
<211> LENGTH: 552
<212> TYPE: PRT
<213> ORGANISM: Homo sapiens

<400> SEQUENCE: 170

Met Gly Thr Leu Gly Gln Ala Ser Leu Phe Ala Pro Pro Gly Asn Tyr
1 5 10 15

Phe Trp Ser Asp His Ser Ala Leu Cys Phe Ala Glu Ser Cys Glu Gly
20 25 30

Gln Pro Gly Lys Val Glu Gln Met Ser Thr His Arg Ser Arg Leu Leu
35 40 45

Thr Ala Ala Pro Leu Ser Met Glu Gln Arg Gln Pro Trp Pro Arg Ala
50 55 60

Leu Glu Val Asp Ser Arg Ser Val Val Leu Leu Ser Val Val Trp Val
65 70 75 80

Leu Leu Ala Pro Pro Ala Ala Gly Met Pro Gln Phe Ser Thr Phe His
85 90 95

Ser Glu Asn Arg Asp Trp Thr Phe Asn His Leu Thr Val His Gln Gly
100 105 110

Thr Gly Ala Val Tyr Val Gly Ala Ile Asn Arg Val Tyr Lys Leu Thr
115 120 125

Gly Asn Leu Thr Ile Gln Val Ala His Lys Thr Gly Pro Glu Glu Asp
130 135 140

Asn Lys Ser Arg Tyr Pro Pro Leu Ile Val Gln Pro Cys Ser Glu Val
145 150 155 160

-continued

```
Leu Thr Leu Thr Asn Asn Val Asn Lys Leu Leu Ile Ile Asp Tyr Ser
                165                 170                 175

Glu Asn Arg Leu Leu Ala Cys Gly Ser Leu Tyr Gln Gly Val Cys Lys
            180                 185                 190

Leu Leu Arg Leu Asp Asp Leu Phe Ile Leu Val Glu Pro Ser His Lys
        195                 200                 205

Lys Glu His Tyr Leu Ser Ser Val Asn Lys Thr Gly Thr Met Tyr Gly
    210                 215                 220

Val Ile Val Arg Ser Glu Gly Glu Asp Gly Lys Leu Phe Ile Gly Thr
225                 230                 235                 240

Ala Val Asp Gly Lys Gln Asp Tyr Phe Pro Thr Leu Ser Ser Arg Lys
                245                 250                 255

Leu Pro Arg Asp Pro Glu Ser Ser Ala Met Leu Asp Tyr Glu Leu His
            260                 265                 270

Ser Asp Phe Val Ser Ser Leu Ile Lys Ile Pro Ser Asp Thr Leu Ala
        275                 280                 285

Leu Val Ser His Phe Asp Ile Phe Tyr Ile Tyr Gly Phe Ala Ser Gly
    290                 295                 300

Gly Phe Val Tyr Phe Leu Thr Val Gln Pro Glu Thr Pro Glu Gly Val
305                 310                 315                 320

Ala Ile Asn Ser Ala Gly Asp Leu Phe Tyr Thr Ser Arg Ile Val Arg
                325                 330                 335

Leu Cys Lys Asp Asp Pro Lys Phe His Ser Tyr Val Ser Leu Pro Phe
            340                 345                 350

Gly Cys Thr Arg Ala Gly Val Glu Tyr Arg Leu Leu Gln Ala Ala Tyr
        355                 360                 365

Leu Ala Lys Pro Gly Asp Ser Leu Ala Gln Ala Phe Asn Ile Thr Ser
    370                 375                 380

Gln Asp Asp Val Leu Phe Ala Ile Phe Ser Lys Gly Gln Lys Gln Tyr
385                 390                 395                 400

His His Pro Pro Asp Asp Ser Ala Leu Cys Ala Phe Pro Ile Arg Ala
                405                 410                 415

Ile Asn Leu Gln Ile Lys Glu Arg Leu Gln Ser Cys Tyr Gln Gly Glu
            420                 425                 430

Gly Asn Leu Glu Leu Asn Trp Leu Leu Gly Lys Asp Val Gln Cys Thr
        435                 440                 445

Lys Ala Pro Val Pro Ile Asp Asp Asn Phe Cys Gly Leu Asp Ile Asn
    450                 455                 460

Gln Pro Leu Gly Gly Ser Thr Pro Val Glu Gly Leu Thr Leu Tyr Thr
465                 470                 475                 480

Thr Ser Arg Asp Arg Met Thr Ser Val Ala Ser Tyr Val Tyr Asn Gly
                485                 490                 495

Tyr Ser Val Val Phe Val Gly Thr Lys Ser Gly Lys Leu Lys Lys Val
            500                 505                 510

Arg Val Tyr Glu Phe Arg Cys Ser Asn Ala Ile His Leu Leu Ser Lys
        515                 520                 525

Glu Ser Leu Leu Glu Gly Ser Tyr Trp Trp Arg Phe Asn Tyr Arg Gln
    530                 535                 540

Leu Tyr Phe Leu Gly Glu Gln Arg
545                 550
```

<210> SEQ ID NO 171
<211> LENGTH: 20
<212> TYPE: DNA

-continued

<213> ORGANISM: Artificial Sequence
<220> FEATURE:
<223> OTHER INFORMATION: Description of Artificial Sequence: Synthetic
oligonucleotide probe

<400> SEQUENCE: 171
tggaataccg cctcctgcag 20

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 172
cttctgccct ttggagaaga tggc 24

<210> SEQ ID NO 173
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 173
ggactcactg gcccaggcct tcaatatcac cagccaggac gat 43

<210> SEQ ID NO 174
<211> LENGTH: 3106
<212> TYPE: DNA
<213> ORGANISM: Homo sapiens
<220> FEATURE:
<221> NAME/KEY: modified_base
<222> LOCATION: (1683)..(1683)
<223> OTHER INFORMATION: a, t, c or g

<400> SEQUENCE: 174
aggctcccgc gcgcggctga gtgcggactg gagtgggaac ccgggtcccc gcgcttagag 60
aacacgcgat gaccacgtgg agcctccggc ggaggccggc ccgcacgctg ggactcctgc 120
tgctggtcgt cttgggcttc ctggtgctcc gcaggctgga ctggagcacc ctggtccctc 180
tgcggctccg ccatcgacag ctggggctgc aggccaaggg ctggaacttc atgctggagg 240
attccacctt ctggatcttc gggggctcca tccactattt ccgtgtgccc agggagtact 300
ggagggaccg cctgctgaag atgaaggcct gtggcttgaa caccctcacc acctatgttc 360
cgtggaacct gcatgagcca gaaagaggca aatttgactt ctctgggaac ctggacctgg 420
aggccttcgt cctgatggcc gcagagatcg ggctgtgggt gattctgcgt ccaggcccct 480
acatctgcag tgagatggac ctcgggggct tgcccagctg gctactccaa gaccctggca 540
tgaggctgag gacaacttac aagggcttca ccgaagcagt ggacctttat tttgaccacc 600
tgatgtccag ggtggtgcca ctccagtaca agcgtggggg acctatcatt gccgtgcagg 660
tggagaatga atatggttcc tataataaag accccgcata catgccctac gtcaagaagg 720
cactggagga ccgtggcatt gtggaactgc tcctgacttc agacaacaag gatgggctga 780
gcaaggggat tgtccaggga gtcttggcca ccatcaactt gcagtcaaca cacgagctgc 840
agctactgac cacctttctc ttcaacgtcc aggggactca gcccaagatg gtgatggagt 900
actggacggg gtggtttgac tcgtggggag gccctcacaa tatcttggat tcttctgagg 960

-continued

```
ttttgaaaac cgtgtctgcc attgtggacg ccggctcctc catcaacctc tacatgttcc   1020
acggaggcac caactttggc ttcatgaatg gagccatgca cttccatgac tacaagtcag   1080
atgtcaccag ctatgactat gatgctgtgc tgacagaagc cggcgattac acggccaagt   1140
acatgaagct tcgagacttc ttcggctcca tctcaggcat ccctctccct cccccacctg   1200
accttcttcc caagatgccg tatgagccct taacgccagt cttgtacctg tctctgtggg   1260
acgccctcaa gtacctgggg gagccaatca agtctgaaaa gcccatcaac atggagaacc   1320
tgccagtcaa tgggggaaat ggacagtcct tcgggtacat tctctatgag accagcatca   1380
cctcgtctgg catcctcagt ggccacgtgc atgatcgggg gcaggtgttt gtgaacacag   1440
tatccatagg attcttggac tacaagacaa cgaagattgc tgtcccccctg atccagggtt   1500
acaccgtgct gaggatcttg gtggagaatc gtgggcgagt caactatggg gagaatattg   1560
atgaccagcg caaaggctta attggaaatc tctatctgaa tgattcaccc ctgaaaaact   1620
tcagaatcta tagcctggat atgaagaaga gcttctttca gaggttcggc ctggacaaat   1680
ggngttccct cccagaaaca cccacattac ctgctttctt cttgggtagc ttgtccatca   1740
gctccacgcc ttgtgacacc tttctgaagc tggagggctg ggagaagggg gttgtattca   1800
tcaatggcca gaaccttgga cgttactgga acattggacc ccagaagacg ctttacctcc   1860
caggtccctg gttgagcagc ggaatcaacc aggtcatcgt ttttgaggag acgatggcgg   1920
gccctgcatt acagttcacg gaaacccccc acctgggcag gaaccagtac attaagtgag   1980
cggtggcacc ccctcctgct ggtgccagtg ggagactgcc gcctcctctt gacctgaagc   2040
ctggtggctg ctgccccacc cctcactgca aaagcatctc cttaagtagc aacctcaggg   2100
actgggggct acagtctgcc cctgtctcag ctcaaaaccc taagcctgca gggaaaggtg   2160
ggatggctct gggcctggct ttgttgatga tggctttcct acagccctgc tcttgtgccg   2220
aggctgtcgg gctgtctcta gggtgggagc agctaatcag atcgcccagc ctttggccct   2280
cagaaaaagt gctgaaacgt gcccttgcac cggacgtcac agccctgcga gcatctgctg   2340
gactcaggcg tgctctttgc tggttcctgg gaggcttggc cacatccctc atggccccat   2400
tttatccccg aaatcctggg tgtgtcacca gtgtagaggg tggggaaggg gtgtctcacc   2460
tgagctgact ttgttcttcc ttcacaacct tctgagcctt ctttgggatt ctggaaggaa   2520
ctcggcgtga gaaacatgtg acttcccctt tcccttccca ctcgctgctt cccacagggt   2580
gacaggctgg gctggagaaa cagaaatcct caccctgcgt cttcccaagt tagcaggtgt   2640
ctctggtgtt cagtgaggag gacatgtgag tcctggcaga agccatggcc catgtctgca   2700
catccaggga ggaggacaga aggcccagct cacatgtgag tcctggcaga agccatggcc   2760
catgtctgca catccaggga ggaggacaga aggcccagct cacatgtgag tcctggcaga   2820
agccatggcc catgtctgca catccaggga ggaggacaga aggcccagct cacatgtgag   2880
tcctggcaga agccatggcc catgtctgca catccaggga ggaggacaga aggcccagct   2940
cagtggcccc cgctccccac cccccacgcc cgaacagcag gggcagagca gccctccttc   3000
gaagtgtgtc caagtccgca tttgagcctt gttctggggc ccagcccaac acctggcttg   3060
ggctcactgt cctgagttgc agtaaagcta taaccttgaa tcacaa                  3106
```

<210> SEQ ID NO 175
<211> LENGTH: 636
<212> TYPE: PRT
<213> ORGANISM: Homo sapiens
<220> FEATURE:
<221> NAME/KEY: MOD_RES -continued
<222> LOCATION: (539)
<223> OTHER INFORMATION: Any amino acid

<400> SEQUENCE: 175

Met Thr Thr Trp Ser Leu Arg Arg Arg Pro Ala Arg Thr Leu Gly Leu
1 5 10 15

Leu Leu Leu Val Val Leu Gly Phe Leu Val Leu Arg Arg Leu Asp Trp
20 25 30

Ser Thr Leu Val Pro Leu Arg Leu Arg His Arg Gln Leu Gly Leu Gln
35 40 45

Ala Lys Gly Trp Asn Phe Met Leu Glu Asp Ser Thr Phe Trp Ile Phe
50 55 60

Gly Gly Ser Ile His Tyr Phe Arg Val Pro Arg Glu Tyr Trp Arg Asp
65 70 75 80

Arg Leu Leu Lys Met Lys Ala Cys Gly Leu Asn Thr Leu Thr Thr Tyr
85 90 95

Val Pro Trp Asn Leu His Glu Pro Glu Arg Gly Lys Phe Asp Phe Ser
100 105 110

Gly Asn Leu Asp Leu Glu Ala Phe Val Leu Met Ala Ala Glu Ile Gly
115 120 125

Leu Trp Val Ile Leu Arg Pro Gly Pro Tyr Ile Cys Ser Glu Met Asp
130 135 140

Leu Gly Gly Leu Pro Ser Trp Leu Leu Gln Asp Pro Gly Met Arg Leu
145 150 155 160

Arg Thr Thr Tyr Lys Gly Phe Thr Glu Ala Val Asp Leu Tyr Phe Asp
165 170 175

His Leu Met Ser Arg Val Val Pro Leu Gln Tyr Lys Arg Gly Gly Pro
180 185 190

Ile Ile Ala Val Gln Val Glu Asn Glu Tyr Gly Ser Tyr Asn Lys Asp
195 200 205

Pro Ala Tyr Met Pro Tyr Val Lys Lys Ala Leu Glu Asp Arg Gly Ile
210 215 220

Val Glu Leu Leu Leu Thr Ser Asp Asn Lys Asp Gly Leu Ser Lys Gly
225 230 235 240

Ile Val Gln Gly Val Leu Ala Thr Ile Asn Leu Gln Ser Thr His Glu
245 250 255

Leu Gln Leu Leu Thr Thr Phe Leu Phe Asn Val Gln Gly Thr Gln Pro
260 265 270

Lys Met Val Met Glu Tyr Trp Thr Gly Trp Phe Asp Ser Trp Gly Gly
275 280 285

Pro His Asn Ile Leu Asp Ser Ser Glu Val Leu Lys Thr Val Ser Ala
290 295 300

Ile Val Asp Ala Gly Ser Ser Ile Asn Leu Tyr Met Phe His Gly Gly
305 310 315 320

Thr Asn Phe Gly Phe Met Asn Gly Ala Met His Phe His Asp Tyr Lys
325 330 335

Ser Asp Val Thr Ser Tyr Asp Tyr Asp Ala Val Leu Thr Glu Ala Gly
340 345 350

Asp Tyr Thr Ala Lys Tyr Met Lys Leu Arg Asp Phe Phe Gly Ser Ile
355 360 365

Ser Gly Ile Pro Leu Pro Pro Pro Pro Asp Leu Leu Pro Lys Met Pro
370 375 380

Tyr Glu Pro Leu Thr Pro Val Leu Tyr Leu Ser Leu Trp Asp Ala Leu
385 390 395 400

-continued

```
Lys Tyr Leu Gly Glu Pro Ile Lys Ser Glu Lys Pro Ile Asn Met Glu
                405                 410                 415

Asn Leu Pro Val Asn Gly Gly Asn Gly Gln Ser Phe Gly Tyr Ile Leu
            420                 425                 430

Tyr Glu Thr Ser Ile Thr Ser Ser Gly Ile Leu Ser Gly His Val His
        435                 440                 445

Asp Arg Gly Gln Val Phe Val Asn Thr Val Ser Ile Gly Phe Leu Asp
    450                 455                 460

Tyr Lys Thr Thr Lys Ile Ala Val Pro Leu Ile Gln Gly Tyr Thr Val
465                 470                 475                 480

Leu Arg Ile Leu Val Glu Asn Arg Gly Arg Val Asn Tyr Gly Glu Asn
                485                 490                 495

Ile Asp Asp Gln Arg Lys Gly Leu Ile Gly Asn Leu Tyr Leu Asn Asp
            500                 505                 510

Ser Pro Leu Lys Asn Phe Arg Ile Tyr Ser Leu Asp Met Lys Lys Ser
        515                 520                 525

Phe Phe Gln Arg Phe Gly Leu Asp Lys Trp Xaa Ser Leu Pro Glu Thr
    530                 535                 540

Pro Thr Leu Pro Ala Phe Phe Leu Gly Ser Leu Ser Ile Ser Ser Thr
545                 550                 555                 560

Pro Cys Asp Thr Phe Leu Lys Leu Glu Gly Trp Glu Lys Gly Val Val
                565                 570                 575

Phe Ile Asn Gly Gln Asn Leu Gly Arg Tyr Trp Asn Ile Gly Pro Gln
            580                 585                 590

Lys Thr Leu Tyr Leu Pro Gly Pro Trp Leu Ser Ser Gly Ile Asn Gln
        595                 600                 605

Val Ile Val Phe Glu Glu Thr Met Ala Gly Pro Ala Leu Gln Phe Thr
    610                 615                 620

Glu Thr Pro His Leu Gly Arg Asn Gln Tyr Ile Lys
625                 630                 635
```

<210> SEQ ID NO 176
<211> LENGTH: 2505
<212> TYPE: DNA
<213> ORGANISM: Homo sapiens

<400> SEQUENCE: 176

```
ggggacgcgg agctgagagg ctccgggcta gctaggtgta ggggtggacg ggtcccagga     60

ccctggtgag ggttctctac ttggccttcg gtgggggtca agacgcaggc acctacgcca    120

aaggggagca aagccgggct cggcccgagg cccccaggac ctccatctcc caatgttgga    180

ggaatccgac acgtgacggt ctgtccgccg tctcagacta gaggagcgct gtaaacgcca    240

tggctcccaa gaagctgtcc tgccttcgtt ccctgctgct gccgctcagc ctgacgctac    300

tgctgcccca ggcagacact cggtcgttcg tagtggatag gggtcatgac cggtttctcc    360

tagacggggc cccgttccgc tatgtgtctg gcagcctgca ctactttcgg gtaccgcggg    420

tgctttgggc cgaccggctt ttgaagatgc gatggagcgg cctcaacgcc atacagtttt    480

atgtgccctg gaactaccac gagccacagc ctggggtcta taactttaat ggcagccggg    540

acctcattgc ctttctgaat gaggcagctc tagcgaacct gttggtcata ctgagaccag    600

gaccttacat ctgtgcagag tgggagatgg ggggtctccc atcctggttg cttcgaaaac    660

ctgaaattca tctaagaacc tcagatccag acttccttgc cgcagtggac tcctggttca    720

aggtcttgct gcccaagata tatccatggc tttatcacaa tgggggcaac atcattagca    780
```

-continued

```
ttcaggtgga gaatgaatat ggtagctaca gagcctgtga cttcagctac atgaggcact    840
tggctgggct cttccgtgca ctgctaggag aaaagatctt gctcttcacc acagatgggc    900
ctgaaggact caagtgtggc tccctccggg gactctatac cactgtagat tttggcccag    960
ctgacaacat gaccaaaatc tttaccctgc ttcggaagta tgaaccccat gggccattgg   1020
taaactctga gtactacaca ggctggctgg attactgggg ccagaatcac tccacacggt   1080
ctgtgtcagc tgtaaccaaa ggactagaga acatgctcaa gttgggagcc agtgtgaaca   1140
tgtacatgtt ccatggaggt accaactttg gatattggaa tggtgccgat aagaagggac   1200
gcttccttcc gattactacc agctatgact atgatgcacc tatatctgaa gcaggggacc   1260
ccacacctaa gctttttgct cttcgagatg tcatcagcaa gttccaggaa gttcctttgg   1320
gacctttacc tcccccgagc cccaagatga tgcttggacc tgtgactctg cacctggttg   1380
ggcatttact ggctttccta gacttgcttt gccccccgtgg gcccattcat tcaatcttgc   1440
caatgacctt tgaggctgtc aagcaggacc atggcttcat gttgtaccga acctatatga   1500
cccataccat tttgagccca acaccattct gggtgccaaa taatggagtc catgaccgtg   1560
cctatgtgat ggtggatggg gtgttccagg gtgttgtgga gcgaaatatg agagacaaac   1620
tatttttgac ggggaaactg gggtccaaac tggatatctt ggtggagaac atggggaggc   1680
tcagctttgg gtctaacagc agtgacttca agggcctgtt gaagccacca attctggggc   1740
aaacaatcct tacccagtgg atgatgttcc ctctgaaaat tgataacctt gtgaagtggt   1800
ggtttcccct ccagttgcca aaatggccat atcctcaagc tccttctggc cccacattct   1860
actccaaaac atttccaatt ttaggctcag ttggggacac atttctatat ctacctggat   1920
ggaccaaggg ccaagtctgg atcaatgggt ttaacttggg ccggtactgg acaaagcagg   1980
ggccacaaca gaccctctac gtgccaagat tcctgctgtt tcctaggggga gccctcaaca   2040
aaattacatt gctggaacta gaagatgtac ctctccagcc ccaagtccaa tttttggata   2100
agcctatcct caatagcact agtactttgc acaggacaca tatcaattcc ctttcagctg   2160
atacactgag tgcctctgaa ccaatggagt taagtgggca ctgaaaggta ggccgggcat   2220
ggtggctcat gcctgtaatc ccagcacttt gggaggctga gacgggtgga ttacctgagg   2280
tcaggacttc aagaccagcc tggccaacat ggtgaaaccc cgtctccact aaaaatacaa   2340
aaattagccg ggcgtgatgg tgggcacctc taatcccagc tacttgggag gctgagggca   2400
ggagaattgc ttgaatccag gaggcagagg ttgcagtgag tggaggttgt accactgcac   2460
tccagcctgg ctgacagtga gacactccat ctcaaaaaaa aaaaa                   2505
```

<210> SEQ ID NO 177
<211> LENGTH: 654
<212> TYPE: PRT
<213> ORGANISM: Homo sapiens

<400> SEQUENCE: 177

```
Met Ala Pro Lys Lys Leu Ser Cys Leu Arg Ser Leu Leu Leu Pro Leu
  1               5                  10                  15

Ser Leu Thr Leu Leu Leu Pro Gln Ala Asp Thr Arg Ser Phe Val Val
             20                  25                  30

Asp Arg Gly His Asp Arg Phe Leu Leu Asp Gly Ala Pro Phe Arg Tyr
         35                  40                  45

Val Ser Gly Ser Leu His Tyr Phe Arg Val Pro Arg Val Leu Trp Ala
     50                  55                  60
```

-continued

```
Asp Arg Leu Leu Lys Met Arg Trp Ser Gly Leu Asn Ala Ile Gln Phe
 65                 70                  75                  80

Tyr Val Pro Trp Asn Tyr His Glu Pro Gln Pro Gly Val Tyr Asn Phe
                85                  90                  95

Asn Gly Ser Arg Asp Leu Ile Ala Phe Leu Asn Glu Ala Ala Leu Ala
            100                 105                 110

Asn Leu Leu Val Ile Leu Arg Pro Gly Pro Tyr Ile Cys Ala Glu Trp
        115                 120                 125

Glu Met Gly Gly Leu Pro Ser Trp Leu Leu Arg Lys Pro Glu Ile His
    130                 135                 140

Leu Arg Thr Ser Asp Pro Asp Phe Leu Ala Ala Val Asp Ser Trp Phe
145                 150                 155                 160

Lys Val Leu Leu Pro Lys Ile Tyr Pro Trp Leu Tyr His Asn Gly Gly
                165                 170                 175

Asn Ile Ile Ser Ile Gln Val Glu Asn Glu Tyr Gly Ser Tyr Arg Ala
            180                 185                 190

Cys Asp Phe Ser Tyr Met Arg His Leu Ala Gly Leu Phe Arg Ala Leu
        195                 200                 205

Leu Gly Glu Lys Ile Leu Leu Phe Thr Thr Asp Gly Pro Glu Gly Leu
    210                 215                 220

Lys Cys Gly Ser Leu Arg Gly Leu Tyr Thr Thr Val Asp Phe Gly Pro
225                 230                 235                 240

Ala Asp Asn Met Thr Lys Ile Phe Thr Leu Leu Arg Lys Tyr Glu Pro
                245                 250                 255

His Gly Pro Leu Val Asn Ser Glu Tyr Tyr Thr Gly Trp Leu Asp Tyr
            260                 265                 270

Trp Gly Gln Asn His Ser Thr Arg Ser Val Ser Ala Val Thr Lys Gly
        275                 280                 285

Leu Glu Asn Met Leu Lys Leu Gly Ala Ser Val Asn Met Tyr Met Phe
    290                 295                 300

His Gly Gly Thr Asn Phe Gly Tyr Trp Asn Gly Ala Asp Lys Lys Gly
305                 310                 315                 320

Arg Phe Leu Pro Ile Thr Thr Ser Tyr Asp Tyr Asp Ala Pro Ile Ser
                325                 330                 335

Glu Ala Gly Asp Pro Thr Pro Lys Leu Phe Ala Leu Arg Asp Val Ile
            340                 345                 350

Ser Lys Phe Gln Glu Val Pro Leu Gly Pro Leu Pro Pro Pro Ser Pro
        355                 360                 365

Lys Met Met Leu Gly Pro Val Thr Leu His Leu Val Gly His Leu Leu
    370                 375                 380

Ala Phe Leu Asp Leu Leu Cys Pro Arg Gly Pro Ile His Ser Ile Leu
385                 390                 395                 400

Pro Met Thr Phe Glu Ala Val Lys Gln Asp His Gly Phe Met Leu Tyr
                405                 410                 415

Arg Thr Tyr Met Thr His Thr Ile Phe Glu Pro Thr Pro Phe Trp Val
            420                 425                 430

Pro Asn Asn Gly Val His Asp Arg Ala Tyr Val Met Val Asp Gly Val
        435                 440                 445

Phe Gln Gly Val Val Glu Arg Asn Met Arg Asp Lys Leu Phe Leu Thr
    450                 455                 460

Gly Lys Leu Gly Ser Lys Leu Asp Ile Leu Val Glu Asn Met Gly Arg
465                 470                 475                 480

Leu Ser Phe Gly Ser Asn Ser Ser Asp Phe Lys Gly Leu Leu Lys Pro
```

-continued

```
                485                 490                 495

Pro Ile Leu Gly Gln Thr Ile Leu Thr Gln Trp Met Met Phe Pro Leu
            500                 505                 510

Lys Ile Asp Asn Leu Val Lys Trp Trp Phe Pro Leu Gln Leu Pro Lys
        515                 520                 525

Trp Pro Tyr Pro Gln Ala Pro Ser Gly Pro Thr Phe Tyr Ser Lys Thr
    530                 535                 540

Phe Pro Ile Leu Gly Ser Val Gly Asp Thr Phe Leu Tyr Leu Pro Gly
545                 550                 555                 560

Trp Thr Lys Gly Gln Val Trp Ile Asn Gly Phe Asn Leu Gly Arg Tyr
                565                 570                 575

Trp Thr Lys Gln Gly Pro Gln Gln Thr Leu Tyr Val Pro Arg Phe Leu
            580                 585                 590

Leu Phe Pro Arg Gly Ala Leu Asn Lys Ile Thr Leu Leu Glu Leu Glu
        595                 600                 605

Asp Val Pro Leu Gln Pro Gln Val Gln Phe Leu Asp Lys Pro Ile Leu
    610                 615                 620

Asn Ser Thr Ser Thr Leu His Arg Thr His Ile Asn Ser Leu Ser Ala
625                 630                 635                 640

Asp Thr Leu Ser Ala Ser Glu Pro Met Glu Leu Ser Gly His
                645                 650
```

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 178
tggctactcc aagaccctgg catg 24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 179
tggacaaatc cccttgctca gccc 24

<210> SEQ ID NO 180
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 180
gggcttcacc gaagcagtgg acctttattt tgaccacctg atgtccaggg 50

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 181
ccagctatga ctatgatgca cc 22

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 182
tggcacccag aatggtgttg gctc 24

<210> SEQ ID NO 183
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 183
cgagatgtca tcagcaagtt ccaggaagtt cctttgggac ctttacctcc 50

<210> SEQ ID NO 184
<211> LENGTH: 1947
<212> TYPE: DNA
<213> ORGANISM: Homo sapiens

<400> SEQUENCE: 184
gctttgaaca cgtctgcaag cccaaagttg agcatctgat tggttatgag gtatttgagt 60
gcacccacaa tatggcttac atgttgaaaa agcttctcat cagttacata tccattattt 120
gtgtttatgg ctttatctgc ctctacactc tcttctggtt attcaggata cctttgaagg 180
aatattcttt cgaaaaagtc agagaagaga gcagttttag tgacattcca gatgtcaaaa 240
acgattttgc gttccttctt cacatggtag accagtatga ccagctatat tccaagcgtt 300
ttggtgtgtt cttgtcagaa gttagtgaaa ataaacttag ggaaattagt ttgaaccatg 360
agtggacatt tgaaaaactc aggcagcaca tttcacgcaa cgcccaggac aagcaggagt 420
tgcatctgtt catgctgtcg ggggtgcccg atgctgtctt tgacctcaca gacctggatg 480
tgctaaagct tgaactaatt ccagaagcta aaattcctgc taagatttct caaatgacta 540
acctccaaga gctccacctc tgccactgcc ctgcaaaagt tgaacagact gcttttagct 600
ttcttcgcga tcacttgaga tgccttcacg tgaagttcac tgatgtggct gaaattcctg 660
cctgggtgta tttgctcaaa aaccttcgag agttgtactt aataggcaat ttgaactctg 720
aaaacaataa gatgatagga cttgaatctc tccgagagtt gcggcacctt aagattctcc 780
acgtgaagag caatttgacc aaagttccct ccaacattac agatgtggct ccacatctta 840
caaagttagt cattcataat gacggcacta aactcttggt actgaacagc cttaagaaaa 900
tgatgaatgt cgctgagctg gaactccaga actgtgagct agagagaatc ccacatgcta 960
ttttcagcct ctctaattta caggaactgg atttaaagtc caataacatt cgcacaattg 1020
aggaaatcat cagtttccag catttaaaac gactgacttg tttaaaatta tggcataaca 1080
aaattgttac tattcctccc tctattaccc atgtcaaaaa cttggagtca ctttatttct 1140
ctaacaacaa gctcgaatcc ttaccagtgg cagtatttag tttacagaaa ctcagatgct 1200

-continued

```
tagatgtgag ctacaacaac atttcaatga ttccaataga aataggattg cttcagaacc   1260

tgcagcattt gcatatcact gggaacaaag tggacattct gccaaaacaa ttgtttaaat   1320

gcataaagtt gaggactttg aatctgggac agaactgcat cacctcactc ccagagaaag   1380

ttggtcagct ctcccagctc actcagctgg agctgaaggg gaactgcttg gaccgcctgc   1440

cagcccagct gggccagtgt cggatgctca agaaaagcgg gcttgttgtg gaagatcacc   1500

tttttgatac cctgccactc gaagtcaaag aggcattgaa tcaagacata aatattccct   1560

ttgcaaatgg gatttaaact aagataatat atgcacagtg atgtgcagga acaacttcct   1620

agattgcaag tgctcacgta caagttatta caagataatg cattttagga gtagatacat   1680

cttttaaaat aaaacagaga ggatgcatag aaggctgata gaagacataa ctgaatgttc   1740

aatgtttgta gggttttaag tcattcattt ccaaatcatt ttttttttc ttttggggaa   1800

agggaaggaa aaattataat cactaatctt ggttcttttt aaattgtttg taacttggat   1860

gctgccgcta ctgaatgttt acaaattgct tgcctgctaa agtaaatgat taaattgaca   1920

ttttcttact aaaaaaaaaa aaaaaaa                                        1947
```

<210> SEQ ID NO 185
<211> LENGTH: 501
<212> TYPE: PRT
<213> ORGANISM: Homo sapiens

<400> SEQUENCE: 185

```
Met Ala Tyr Met Leu Lys Lys Leu Leu Ile Ser Tyr Ile Ser Ile Ile
  1               5                  10                  15

Cys Val Tyr Gly Phe Ile Cys Leu Tyr Thr Leu Phe Trp Leu Phe Arg
             20                  25                  30

Ile Pro Leu Lys Glu Tyr Ser Phe Glu Lys Val Arg Glu Glu Ser Ser
         35                  40                  45

Phe Ser Asp Ile Pro Asp Val Lys Asn Asp Phe Ala Phe Leu Leu His
     50                  55                  60

Met Val Asp Gln Tyr Asp Gln Leu Tyr Ser Lys Arg Phe Gly Val Phe
 65                  70                  75                  80

Leu Ser Glu Val Ser Glu Asn Lys Leu Arg Glu Ile Ser Leu Asn His
                 85                  90                  95

Glu Trp Thr Phe Glu Lys Leu Arg Gln His Ile Ser Arg Asn Ala Gln
            100                 105                 110

Asp Lys Gln Glu Leu His Leu Phe Met Leu Ser Gly Val Pro Asp Ala
        115                 120                 125

Val Phe Asp Leu Thr Asp Leu Asp Val Leu Lys Leu Glu Leu Ile Pro
    130                 135                 140

Glu Ala Lys Ile Pro Ala Lys Ile Ser Gln Met Thr Asn Leu Gln Glu
145                 150                 155                 160

Leu His Leu Cys His Cys Pro Ala Lys Val Glu Gln Thr Ala Phe Ser
                165                 170                 175

Phe Leu Arg Asp His Leu Arg Cys Leu His Val Lys Phe Thr Asp Val
            180                 185                 190

Ala Glu Ile Pro Ala Trp Val Tyr Leu Leu Lys Asn Leu Arg Glu Leu
        195                 200                 205

Tyr Leu Ile Gly Asn Leu Asn Ser Glu Asn Asn Lys Met Ile Gly Leu
    210                 215                 220

Glu Ser Leu Arg Glu Leu Arg His Leu Lys Ile Leu His Val Lys Ser
225                 230                 235                 240
```

-continued

```
Asn Leu Thr Lys Val Pro Ser Asn Ile Thr Asp Val Ala Pro His Leu
                245                 250                 255

Thr Lys Leu Val Ile His Asn Asp Gly Thr Lys Leu Leu Val Leu Asn
            260                 265                 270

Ser Leu Lys Lys Met Met Asn Val Ala Glu Leu Glu Leu Gln Asn Cys
        275                 280                 285

Glu Leu Glu Arg Ile Pro His Ala Ile Phe Ser Leu Ser Asn Leu Gln
    290                 295                 300

Glu Leu Asp Leu Lys Ser Asn Asn Ile Arg Thr Ile Glu Glu Ile Ile
305                 310                 315                 320

Ser Phe Gln His Leu Lys Arg Leu Thr Cys Leu Lys Leu Trp His Asn
                325                 330                 335

Lys Ile Val Thr Ile Pro Pro Ser Ile Thr His Val Lys Asn Leu Glu
            340                 345                 350

Ser Leu Tyr Phe Ser Asn Asn Lys Leu Glu Ser Leu Pro Val Ala Val
        355                 360                 365

Phe Ser Leu Gln Lys Leu Arg Cys Leu Asp Val Ser Tyr Asn Asn Ile
    370                 375                 380

Ser Met Ile Pro Ile Glu Ile Gly Leu Leu Gln Asn Leu Gln His Leu
385                 390                 395                 400

His Ile Thr Gly Asn Lys Val Asp Ile Leu Pro Lys Gln Leu Phe Lys
                405                 410                 415

Cys Ile Lys Leu Arg Thr Leu Asn Leu Gly Gln Asn Cys Ile Thr Ser
            420                 425                 430

Leu Pro Glu Lys Val Gly Gln Leu Ser Gln Leu Thr Gln Leu Glu Leu
        435                 440                 445

Lys Gly Asn Cys Leu Asp Arg Leu Pro Ala Gln Leu Gly Gln Cys Arg
    450                 455                 460

Met Leu Lys Lys Ser Gly Leu Val Val Glu Asp His Leu Phe Asp Thr
465                 470                 475                 480

Leu Pro Leu Glu Val Lys Glu Ala Leu Asn Gln Asp Ile Asn Ile Pro
                485                 490                 495

Phe Ala Asn Gly Ile
            500
```

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 186
cctccctcta ttacccatgt c 21

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 187
gaccaacttt ctctgggagt gagg 24

<210> SEQ ID NO 188

-continued

<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 188
gtcactttat ttctctaaca acaagctcga atccttacca gtggcag 47

<210> SEQ ID NO 189
<211> LENGTH: 2917
<212> TYPE: DNA
<213> ORGANISM: Homo sapiens

<400> SEQUENCE: 189
cccacgcgtc cggccttctc tctggacttt gcatttccat tccttttcat tgacaaactg 60 actttttttta tttctttttt tccatctctg ggccagcttg ggatcctagg ccgccctggg 120
aagacatttg tgttttacac acataaggat ctgtgtttgg ggtttcttct tcctcccctg 180
acattggcat tgcttagtgg ttgtgtgggg agggagacca cgtgggctca gtgcttgctt 240
gcacttatct gcctaggtac atcgaagtct tttgacctcc atacagtgat tatgcctgtc 300
atcgctggtg gtatcctggc ggccttgctc ctgctgatag ttgtcgtgct ctgtctttac 360
ttcaaaatac acaacgcgct aaaagctgca aaggaacctg aagctgtggc tgtaaaaaat 420
cacaacccag acaaggtgtg gtgggccaag aacagccagg ccaaaaccat tgccacggag 480
tcttgtcctg ccctgcagtg ctgtgaagga tatagaatgt gtgccagttt tgattccctg 540
ccaccttgct gttgcgacat aaatgagggc ctctgagtta ggaaaggctc ccttctcaaa 600
gcagagccct gaagacttca atgatgtcaa tgaggccacc tgtttgtgat gtgcaggcac 660
agaagaaagg cacagctccc catcagtttc atggaaaata actcagtgcc tgctgggaac 720
cagctgctgg agatccctac agagagcttc cactgggggc aacccttcca ggaaggagtt 780
ggggagagag aaccctcact gtggggaatg ctgataaacc agtcacacag ctgctctatt 840
ctcacacaaa tctacccctt gcgtggctgg aactgacgtt tccctggagg tgtccagaaa 900
gctgatgtaa cacagagcct ataaaagctg tcggtcctta aggctgccca gcgccttgcc 960
aaaatggagc ttgtaagaag gctcatgcca ttgaccctct taattctctc ctgtttggcg 1020
gagctgacaa tggcggaggc tgaaggcaat gcaagctgca cagtcagtct agggggtgcc 1080
aatatggcag agacccacaa agccatgatc ctgcaactca atcccagtga gaactgcacc 1140
tggacaatag aaagaccaga aaacaaaagc atcagaatta tcttttccta tgtccagctt 1200
gatccagatg gaagctgtga aagtgaaaac attaaagtct ttgacggaac ctccagcaat 1260
gggcctctgc tagggcaagt ctgcagtaaa aacgactatg ttcctgtatt tgaatcatca 1320
tccagtacat tgacgtttca aatagttact gactcagcaa gaattcaaag aactgtcttt 1380
gtcttctact acttcttctc tcctaacatc tctattccaa actgtggcgg ttacctggat 1440
accttggaag gatccttcac cagccccaat tacccaaagc cgcatcctga gctggcttat 1500
tgtgtgtggc acatacaagt ggagaaagat tacaagataa aactaaactt caaagagatt 1560
ttcctagaaa tagacaaaca gtgcaaattt gattttcttg ccatctatga tggcccctcc 1620
accaactctg gcctgattgg acaagtctgt ggccgtgtga ctcccacctt cgaatcgtca 1680
tcaaactctc tgactgtcgt gttgtctaca gattatgcca attcttaccg gggattttct 1740
gcttcctaca cctcaattta tgcagaaaac atcaacacta catctttaac ttgctcttct 1800

-continued

```
gacaggatga gagttattat aagcaaatcc tacctagagg cttttaactc taatgggaat   1860

aacttgcaac taaaagaccc aacttgcaga ccaaaattat caaatgttgt ggaattttct   1920

gtccctctta atggatgtgg tacaatcaga aaggtagaag atcagtcaat tacttacacc   1980

aatataatca ccttttctgc atcctcaact tctgaagtga tcacccgtca gaaacaactc   2040

cagattattg tgaagtgtga aatgggacat aattctacag tggagataat atacataaca   2100

gaagatgatg taatacaaag tcaaaatgca ctgggcaaat ataacaccag catggctctt   2160

tttgaatcca attcatttga aaagactata cttgaatcac catattatgt ggatttgaac   2220

caaactcttt ttgttcaagt tagtctgcac acctcagatc caaatttggt ggtgtttctt   2280

gatacctgta gagcctctcc cacctctgac tttgcatctc caacctacga cctaatcaag   2340

agtggatgta gtcgagatga aacttgtaag gtgtatccct tatttggaca ctatgggaga   2400

ttccagttta atgcctttaa attcttgaga agtatgagct ctgtgtatct gcagtgtaaa   2460

gttttgatat gtgatagcag tgaccaccag tctcgctgca atcaaggttg tgtctccaga   2520

agcaaacgag acatttcttc atataaatgg aaaacagatt ccatcatagg acccattcgt   2580

ctgaaaaggg atcgaagtgc aagtggcaat tcaggatttc agcatgaaac acatgcggaa   2640

gaaactccaa accagccttt caacagtgtg catctgtttt ccttcatggt tctagctctg   2700

aatgtggtga ctgtagcgac aatcacagtg aggcattttg taaatcaacg ggcagactac   2760

aaataccaga agctgcagaa ctattaacta acaggtccaa ccctaagtga gacatgtttc   2820

tccaggatgc caaaggaaat gctacctcgt ggctacacat attatgaata aatgaggaag   2880

ggcctgaaag tgacacacag gcctgcatgt aaaaaaa                            2917
```

<210> SEQ ID NO 190
<211> LENGTH: 607
<212> TYPE: PRT
<213> ORGANISM: Homo sapiens

<400> SEQUENCE: 190

```
Met Glu Leu Val Arg Arg Leu Met Pro Leu Thr Leu Leu Ile Leu Ser
  1               5                  10                  15

Cys Leu Ala Glu Leu Thr Met Ala Glu Ala Glu Gly Asn Ala Ser Cys
             20                  25                  30

Thr Val Ser Leu Gly Gly Ala Asn Met Ala Glu Thr His Lys Ala Met
         35                  40                  45

Ile Leu Gln Leu Asn Pro Ser Glu Asn Cys Thr Trp Thr Ile Glu Arg
     50                  55                  60

Pro Glu Asn Lys Ser Ile Arg Ile Ile Phe Ser Tyr Val Gln Leu Asp
 65                  70                  75                  80

Pro Asp Gly Ser Cys Glu Ser Glu Asn Ile Lys Val Phe Asp Gly Thr
                 85                  90                  95

Ser Ser Asn Gly Pro Leu Leu Gly Gln Val Cys Ser Lys Asn Asp Tyr
            100                 105                 110

Val Pro Val Phe Glu Ser Ser Ser Ser Thr Leu Thr Phe Gln Ile Val
        115                 120                 125

Thr Asp Ser Ala Arg Ile Gln Arg Thr Val Phe Val Phe Tyr Tyr Phe
    130                 135                 140

Phe Ser Pro Asn Ile Ser Ile Pro Asn Cys Gly Gly Tyr Leu Asp Thr
145                 150                 155                 160

Leu Glu Gly Ser Phe Thr Ser Pro Asn Tyr Pro Lys Pro His Pro Glu
                165                 170                 175
```

-continued

```
Leu Ala Tyr Cys Val Trp His Ile Gln Val Glu Lys Asp Tyr Lys Ile
            180                 185                 190

Lys Leu Asn Phe Lys Glu Ile Phe Leu Glu Ile Asp Lys Gln Cys Lys
        195                 200                 205

Phe Asp Phe Leu Ala Ile Tyr Asp Gly Pro Ser Thr Asn Ser Gly Leu
    210                 215                 220

Ile Gly Gln Val Cys Gly Arg Val Thr Pro Thr Phe Glu Ser Ser Ser
225                 230                 235                 240

Asn Ser Leu Thr Val Val Leu Ser Thr Asp Tyr Ala Asn Ser Tyr Arg
                245                 250                 255

Gly Phe Ser Ala Ser Tyr Thr Ser Ile Tyr Ala Glu Asn Ile Asn Thr
            260                 265                 270

Thr Ser Leu Thr Cys Ser Ser Asp Arg Met Arg Val Ile Ile Ser Lys
        275                 280                 285

Ser Tyr Leu Glu Ala Phe Asn Ser Asn Gly Asn Asn Leu Gln Leu Lys
    290                 295                 300

Asp Pro Thr Cys Arg Pro Lys Leu Ser Asn Val Val Glu Phe Ser Val
305                 310                 315                 320

Pro Leu Asn Gly Cys Gly Thr Ile Arg Lys Val Glu Asp Gln Ser Ile
                325                 330                 335

Thr Tyr Thr Asn Ile Ile Thr Phe Ser Ala Ser Ser Thr Ser Glu Val
            340                 345                 350

Ile Thr Arg Gln Lys Gln Leu Gln Ile Ile Val Lys Cys Glu Met Gly
        355                 360                 365

His Asn Ser Thr Val Glu Ile Ile Tyr Ile Thr Glu Asp Asp Val Ile
    370                 375                 380

Gln Ser Gln Asn Ala Leu Gly Lys Tyr Asn Thr Ser Met Ala Leu Phe
385                 390                 395                 400

Glu Ser Asn Ser Phe Glu Lys Thr Ile Leu Glu Ser Pro Tyr Tyr Val
                405                 410                 415

Asp Leu Asn Gln Thr Leu Phe Val Gln Val Ser Leu His Thr Ser Asp
            420                 425                 430

Pro Asn Leu Val Val Phe Leu Asp Thr Cys Arg Ala Ser Pro Thr Ser
        435                 440                 445

Asp Phe Ala Ser Pro Thr Tyr Asp Leu Ile Lys Ser Gly Cys Ser Arg
    450                 455                 460

Asp Glu Thr Cys Lys Val Tyr Pro Leu Phe Gly His Tyr Gly Arg Phe
465                 470                 475                 480

Gln Phe Asn Ala Phe Lys Phe Leu Arg Ser Met Ser Ser Val Tyr Leu
                485                 490                 495

Gln Cys Lys Val Leu Ile Cys Asp Ser Ser Asp His Gln Ser Arg Cys
            500                 505                 510

Asn Gln Gly Cys Val Ser Arg Ser Lys Arg Asp Ile Ser Ser Tyr Lys
        515                 520                 525

Trp Lys Thr Asp Ser Ile Ile Gly Pro Ile Arg Leu Lys Arg Asp Arg
    530                 535                 540

Ser Ala Ser Gly Asn Ser Gly Phe Gln His Glu Thr His Ala Glu Glu
545                 550                 555                 560

Thr Pro Asn Gln Pro Phe Asn Ser Val His Leu Phe Ser Phe Met Val
                565                 570                 575

Leu Ala Leu Asn Val Val Thr Val Ala Thr Ile Thr Val Arg His Phe
            580                 585                 590

Val Asn Gln Arg Ala Asp Tyr Lys Tyr Gln Lys Leu Gln Asn Tyr
```

-continued 595 600 605

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 191
tctctattcc aaactgtggc g 21

<210> SEQ ID NO 192
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 192
tttgatgacg attcgaaggt gg 22

<210> SEQ ID NO 193
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 193
ggaaggatcc ttcaccagcc ccaattaccc aaagccgcat cctgagc 47

<210> SEQ ID NO 194
<211> LENGTH: 2362
<212> TYPE: DNA
<213> ORGANISM: Homo sapiens

<400> SEQUENCE: 194
gacggaagaa cagcgctccc gaggccgcgg gagcctgcag agaggacagc cggcctgcgc 60
cgggacatgc ggccccagga gctccccagg ctcgcgttcc cgttgctgct gttgctgttg 120
ctgctgctgc cgccgccgcc gtgccctgcc cacagcgcca cgcgcttcga ccccacctgg 180
gagtccctgg acgcccgcca gctgcccgcg tggtttgacc aggccaagtt cggcatcttc 240
atccactggg gagtgttttc cgtgcccagc ttcggtagcg agtggttctg gtggtattgg 300
caaaaggaaa agataccgaa gtatgtggaa tttatgaaag ataattaccc tcctagtttc 360
aaatatgaag attttggacc actatttaca gcaaaatttt ttaatgccaa ccagtgggca 420
gatatttttc aggcctctgg tgccaaatac attgtcttaa cttccaaaca tcatgaaggc 480
tttaccttgt gggggtcaga atattcgtgg aactggaatg ccatagatga ggggcccaag 540
agggacattg tcaaggaact tgaggtagcc attaggaaca gaactgacct gcgttttgga 600
ctgtactatt ccctttttga atggtttcat ccgctcttcc ttgaggatga atccagttca 660
ttccataagc ggcaatttcc agtttctaag acattgccag agctctatga gttagtgaac 720
aactatcagc ctgaggttct gtggtcggat ggtgacggag gagcaccgga tcaatactgg 780
aacagcacag gcttcttggc ctggttatat aatgaaagcc cagttcgggg cacagtagtc 840
accaatgatc gttggggagc tggtagcatc tgtaagcatg gtggcttcta tacctgcagt 900

-continued

```
gatcgttata acccaggaca tcttttgcca cataaatggg aaaactgcat gacaatagac    960

aaactgtcct ggggctatag gagggaagct ggaatctctg actatcttac aattgaagaa   1020

ttggtgaagc aacttgtaga gacagtttca tgtggaggaa atcttttgat gaatattggg   1080

cccacactag atggcaccat ttctgtagtt tttgaggagc gactgaggca agtggggtcc   1140

tggctaaaag tcaatggaga agctatttat gaaacctata cctggcgatc ccagaatgac   1200

actgtcaccc cagatgtgtg gtacacatcc aagcctaaag aaaaattagt ctatgccatt   1260

tttcttaaat ggcccacatc aggacagctg ttccttggcc atcccaaagc tattctgggg   1320

gcaacagagg tgaaactact gggccatgga cagccactta actggatttc tttggagcaa   1380

aatggcatta tggtagaact gccacagcta accattcatc agatgccgtg taaatggggc   1440

tgggctctag ccctaactaa tgtgatctaa agtgcagcag agtggctgat gctgcaagtt   1500

atgtctaagg ctaggaacta tcaggtgtct ataattgtag cacatggaga aagcaatgta   1560

aactggataa gaaaattatt tggcagttca gccctttccc tttttcccac taaatttttc   1620

ttaaattacc catgtaacca ttttaactct ccagtgcact ttgccattaa agtctcttca   1680

cattgatttg tttccatgtg tgactcagag gtgagaattt tttcacatta tagtagcaag   1740

gaattggtgg tattatggac cgaactgaaa attttatgtt gaagccatat cccccatgat   1800

tatatagtta tgcatcactt aatatgggga tatttttctgg gaaatgcatt gctagtcaat  1860

ttttttttgt gccaacatca tagagtgtat ttacaaaatc ctagatggca tagcctacta   1920

cacacctaat gtgtatggta tagactgttg ctcctaggct acagacatat acagcatgtt   1980

actgaatact gtaggcaata gtaacagtgg tatttgtata tcgaaacata tggaaacata   2040

gagaaggtac agtaaaaata ctgtaaaata aatggtgcac ctgtataggg cacttaccac   2100

gaatggagct tacaggactg gaagttgctc tgggtgagtc agtgagtgaa tgtgaaggcc   2160

taggacatta ttgaacactg ccagacgtta taaatactgt atgcttaggc tacactacat   2220

ttataaaaaa aagtttttct ttcttcaatt ataaattaac ataagtgtac tgtaactttta  2280

caaacgtttt aatttttaaa accttttttgg ctcttttgta ataacactta gcttaaaaca  2340

taaactcatt gtgcaaatgt aa                                            2362
```

<210> SEQ ID NO 195
<211> LENGTH: 467
<212> TYPE: PRT
<213> ORGANISM: Homo sapiens

<400> SEQUENCE: 195

```
Met Arg Pro Gln Glu Leu Pro Arg Leu Ala Phe Pro Leu Leu Leu Leu
  1               5                  10                  15

Leu Leu Leu Leu Leu Pro Pro Pro Pro Cys Pro Ala His Ser Ala Thr
             20                  25                  30

Arg Phe Asp Pro Thr Trp Glu Ser Leu Asp Ala Arg Gln Leu Pro Ala
         35                  40                  45

Trp Phe Asp Gln Ala Lys Phe Gly Ile Phe Ile His Trp Gly Val Phe
     50                  55                  60

Ser Val Pro Ser Phe Gly Ser Glu Trp Phe Trp Trp Tyr Trp Gln Lys
 65                  70                  75                  80

Glu Lys Ile Pro Lys Tyr Val Glu Phe Met Lys Asp Asn Tyr Pro Pro
                 85                  90                  95

Ser Phe Lys Tyr Glu Asp Phe Gly Pro Leu Phe Thr Ala Lys Phe Phe
            100                 105                 110
```

-continued

```
Asn Ala Asn Gln Trp Ala Asp Ile Phe Gln Ala Ser Gly Ala Lys Tyr
        115                 120                 125

Ile Val Leu Thr Ser Lys His His Glu Gly Phe Thr Leu Trp Gly Ser
    130                 135                 140

Glu Tyr Ser Trp Asn Trp Asn Ala Ile Asp Glu Gly Pro Lys Arg Asp
145                 150                 155                 160

Ile Val Lys Glu Leu Glu Val Ala Ile Arg Asn Arg Thr Asp Leu Arg
                165                 170                 175

Phe Gly Leu Tyr Tyr Ser Leu Phe Glu Trp Phe His Pro Leu Phe Leu
            180                 185                 190

Glu Asp Glu Ser Ser Ser Phe His Lys Arg Gln Phe Pro Val Ser Lys
        195                 200                 205

Thr Leu Pro Glu Leu Tyr Glu Leu Val Asn Asn Tyr Gln Pro Glu Val
    210                 215                 220

Leu Trp Ser Asp Gly Asp Gly Gly Ala Pro Asp Gln Tyr Trp Asn Ser
225                 230                 235                 240

Thr Gly Phe Leu Ala Trp Leu Tyr Asn Glu Ser Pro Val Arg Gly Thr
                245                 250                 255

Val Val Thr Asn Asp Arg Trp Gly Ala Gly Ser Ile Cys Lys His Gly
            260                 265                 270

Gly Phe Tyr Thr Cys Ser Asp Arg Tyr Asn Pro Gly His Leu Leu Pro
        275                 280                 285

His Lys Trp Glu Asn Cys Met Thr Ile Asp Lys Leu Ser Trp Gly Tyr
    290                 295                 300

Arg Arg Glu Ala Gly Ile Ser Asp Tyr Leu Thr Ile Glu Glu Leu Val
305                 310                 315                 320

Lys Gln Leu Val Glu Thr Val Ser Cys Gly Gly Asn Leu Leu Met Asn
                325                 330                 335

Ile Gly Pro Thr Leu Asp Gly Thr Ile Ser Val Val Phe Glu Glu Arg
            340                 345                 350

Leu Arg Gln Val Gly Ser Trp Leu Lys Val Asn Gly Glu Ala Ile Tyr
        355                 360                 365

Glu Thr Tyr Thr Trp Arg Ser Gln Asn Asp Thr Val Thr Pro Asp Val
    370                 375                 380

Trp Tyr Thr Ser Lys Pro Lys Glu Lys Leu Val Tyr Ala Ile Phe Leu
385                 390                 395                 400

Lys Trp Pro Thr Ser Gly Gln Leu Phe Leu Gly His Pro Lys Ala Ile
                405                 410                 415

Leu Gly Ala Thr Glu Val Lys Leu Leu Gly His Gly Gln Pro Leu Asn
            420                 425                 430

Trp Ile Ser Leu Glu Gln Asn Gly Ile Met Val Glu Leu Pro Gln Leu
        435                 440                 445

Thr Ile His Gln Met Pro Cys Lys Trp Gly Trp Ala Leu Ala Leu Thr
    450                 455                 460

Asn Val Ile
465
```

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 196

-continued tggtttgacc aggccaagtt cgg 23

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 197
ggattcatcc tcaaggaaga gcgg 24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 198
aacttgcagc atcagccact ctgc 24

<210> SEQ ID NO 199
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 199
ttccgtgccc agcttcggta gcgagtggtt ctggtggtat tggca 45

<210> SEQ ID NO 200
<211> LENGTH: 2372
<212> TYPE: DNA
<213> ORGANISM: Homo sapiens

<400> SEQUENCE: 200
agcagggaaa tccggatgtc tcggttatga agtggagcag tgagtgtgag cctcaacata 60
gttccagaac tctccatccg gactagttat tgagcatctg cctctcatat caccagtggc 120
catctgaggt gtttccctgg ctctgaaggg gtaggcacga tggccaggtg cttcagcctg 180
gtgttgcttc tcacttccat ctggaccacg aggctcctgg tccaaggctc tttgcgtgca 240
gaagagcttt ccatccaggt gtcatgcaga attatgggga tcacccttgt gagcaaaaag 300
gcgaaccagc agctgaattt cacagaagct aaggaggcct gtaggctgct gggactaagt 360
ttggccggca aggaccaagt tgaaacagcc ttgaaagcta gctttgaaac ttgcagctat 420
ggctgggttg gagatggatt cgtggtcatc tctaggatta gcccaaaccc caagtgtggg 480
aaaaatgggg tgggtgtcct gatttggaag gttccagtga gccgacagtt tgcagcctat 540
tgttacaact catctgatac ttggactaac tcgtgcattc cagaaattat caccaccaaa 600
gatcccatat tcaacactca aactgcaaca caaacaacag aatttattgt cagtgacagt 660
acctactcgg tggcatcccc ttactctaca atacctgccc ctactactac tcctcctgct 720
ccagcttcca cttctattcc acggagaaaa aaattgattt gtgtcacaga agtttttatg 780
gaaactagca ccatgtctac agaaactgaa ccatttgttg aaaataaagc agcattcaag 840
aatgaagctg ctgggtttgg aggtgtcccc acggctctgc tagtgcttgc tctcctcttc 900

-continued

```
tttggtgctg cagctggtct tggattttgc tatgtcaaaa ggtatgtgaa ggccttccct    960
tttacaaaca agaatcagca gaaggaaatg atcgaaacca aagtagtaaa ggaggagaag   1020
gccaatgata gcaaccctaa tgaggaatca aagaaaactg ataaaaaccc agaagagtcc   1080
aagagtccaa gcaaaactac cgtgcgatgc ctggaagctg aagtttagat gagacagaaa   1140
tgaggagaca cacctgaggc tggtttcttt catgctcctt accctgcccc agctggggaa   1200
atcaaaaggg ccaaagaacc aaagaagaaa gtccaccctt ggttcctaac tggaatcagc   1260
tcaggactgc cattggacta tggagtgcac caaagagaat gcccttctcc ttattgtaac   1320
cctgtctgga tcctatcctc ctacctccaa agcttcccac ggcctttcta gcctggctat   1380
gtcctaataa tatcccactg ggagaaagga gttttgcaaa gtgcaaggac ctaaaacatc   1440
tcatcagtat ccagtggtaa aaaggcctcc tggctgtctg aggctaggtg ggttgaaagc   1500
caaggagtca ctgagaccaa ggctttctct actgattccg cagctcagac cctttcttca   1560
gctctgaaag agaaacacgt atcccacctg acatgtcctt ctgagcccgg taagagcaaa   1620
agaatggcag aaaagtttag cccctgaaag ccatggagat tctcataact tgagacctaa   1680
tctctgtaaa gctaaaataa agaaatagaa caaggctgag gatacgacag tacactgtca   1740
gcagggactg taaacacaga cagggtcaaa gtgttttctc tgaacacatt gagttggaat   1800
cactgtttag aacacacaca cttacttttt ctggtctcta ccactgctga tatttctct    1860
aggaaatata cttttacaag taacaaaaat aaaaactctt ataaatttct atttttatct   1920
gagttacaga aatgattact aaggaagatt actcagtaat ttgtttaaaa agtaataaaa   1980
ttcaacaaac atttgctgaa tagctactat atgtcaagtg ctgtgcaagg tattacactc   2040
tgtaattgaa tattattcct caaaaaattg cacatagtag aacgctatct gggaagctat   2100
ttttttcagt tttgatattt ctagcttatc tacttccaaa ctaattttta tttttgctga   2160
gactaatctt attcattttc tctaatatgg caaccattat aaccttaatt tattattaac   2220
atacctaaga agtacattgt tacctctata taccaaagca cattttaaaa gtgccattaa   2280
caaatgtatc actagccctc ctttttccaa caagaaggga ctgagagatg cagaaatatt   2340
tgtgacaaaa aattaaagca tttagaaaac tt                                   2372
```

<210> SEQ ID NO 201
<211> LENGTH: 322
<212> TYPE: PRT
<213> ORGANISM: Artificial sequence
<220> FEATURE:
<223> OTHER INFORMATION: Synthetic protein

<400> SEQUENCE: 201

```
Met Ala Arg Cys Phe Ser Leu Val Leu Leu Leu Thr Ser Ile Trp Thr
  1               5                  10                  15

Thr Arg Leu Leu Val Gln Gly Ser Leu Arg Ala Glu Glu Leu Ser Ile
             20                  25                  30

Gln Val Ser Cys Arg Ile Met Gly Ile Thr Leu Val Ser Lys Lys Ala
         35                  40                  45

Asn Gln Gln Leu Asn Phe Thr Glu Ala Lys Glu Ala Cys Arg Leu Leu
     50                  55                  60

Gly Leu Ser Leu Ala Gly Lys Asp Gln Val Glu Thr Ala Leu Lys Ala
 65                  70                  75                  80

Ser Phe Glu Thr Cys Ser Tyr Gly Trp Val Gly Asp Gly Phe Val Val
                 85                  90                  95
```

-continued

```
Ile Ser Arg Ile Ser Pro Asn Pro Lys Cys Gly Lys Asn Gly Val Gly
            100                 105                 110

Val Leu Ile Trp Lys Val Pro Val Ser Arg Gln Phe Ala Ala Tyr Cys
        115                 120                 125

Tyr Asn Ser Ser Asp Thr Trp Thr Asn Ser Cys Ile Pro Glu Ile Ile
    130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ala Ser Thr Ser
            180                 185                 190

Ile Pro Arg Arg Lys Lys Leu Ile Cys Val Thr Glu Val Phe Met Glu
        195                 200                 205

Thr Ser Thr Met Ser Thr Glu Thr Glu Pro Phe Val Glu Asn Lys Ala
    210                 215                 220

Ala Phe Lys Asn Glu Ala Ala Gly Phe Gly Gly Val Pro Thr Ala Leu
225                 230                 235                 240

Leu Val Leu Ala Leu Leu Phe Phe Gly Ala Ala Ala Gly Leu Gly Phe
                245                 250                 255

Cys Tyr Val Lys Arg Tyr Val Lys Ala Phe Pro Phe Thr Asn Lys Asn
            260                 265                 270

Gln Gln Lys Glu Met Ile Glu Thr Lys Val Val Lys Glu Glu Lys Ala
        275                 280                 285

Asn Asp Ser Asn Pro Asn Glu Glu Ser Lys Lys Thr Asp Lys Asn Pro
    290                 295                 300

Glu Glu Ser Lys Ser Pro Ser Lys Thr Thr Val Arg Cys Leu Glu Ala
305                 310                 315                 320

Glu Val
```

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 202
gagctttcca tccaggtgtc atgc 24

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 203
gtcagtgaca gtacctactc gg 22

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe -continued

<400> SEQUENCE: 204
tggagcagga ggagtagtag tagg 24

<210> SEQ ID NO 205
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 205
aggaggcctg taggctgctg ggactaagtt tggccggcaa ggaccaagtt 50

<210> SEQ ID NO 206
<211> LENGTH: 1620
<212> TYPE: DNA
<213> ORGANISM: Homo sapiens
<220> FEATURE:
<221> NAME/KEY: modified_base
<222> LOCATION: (973)..(973)
<223> OTHER INFORMATION: a, t, c or g
<220> FEATURE:
<221> NAME/KEY: modified_base
<222> LOCATION: (977)..(977)
<223> OTHER INFORMATION: a, t, c or g
<220> FEATURE:
<221> NAME/KEY: modified_base
<222> LOCATION: (996)..(996)
<223> OTHER INFORMATION: a, t, c or g
<220> FEATURE:
<221> NAME/KEY: modified_base
<222> LOCATION: (1003)..(1003)
<223> OTHER INFORMATION: a, t, c or g

<400> SEQUENCE: 206
agatggcggt cttggcacct ctaattgctc tcgtgtattc ggtgccgcga ctttcacgat 60
ggctcgccca accttactac cttctgtcgg ccctgctctc tgctgccttc ctactcgtga 120
ggaaactgcc gccgctctgc cacggtctgc ccacccaacg cgaagacggt aacccgtgtg 180
actttgactg gagagaagtg gagatcctga tgtttctcag tgccattgtg atgatgaaga 240
accgcagatc catcactgtg gagcaacata taggcaacat tttcatgttt agtaaagtgg 300
ccaacacaat tcttttcttc cgcttggata ttcgcatggg cctactttac atcacactct 360
gcatagtgtt cctgatgacg tgcaaacccc ccctatatat gggccctgag tatatcaagt 420
acttcaatga taaaaccatt gatgaggaac tagaacggga caagagggtc acttggattg 480
tggagttctt tgccaattgg tctaatgact gccaatcatt tgcccctatc tatgctgacc 540
tctcccttaa atacaactgt acagggctaa attttgggaa ggtggatgtt ggacgctata 600
ctgatgttag tacgcggtac aaagtgagca catcacccct caccaagcaa ctccctaccc 660
tgatcctgtt ccaaggtggc aaggaggcaa tgcggcggcc acagattgac aagaaaggac 720
gggctgtctc atggaccttc tctgaggaga atgtgatccg agaatttaac ttaaatgagc 780
tataccagcg ggccaagaaa ctatcaaagg ctggagacaa tatccctgag gagcagcctg 840
tggcttcaac ccccaccaca gtgtcagatg gggaaaacaa gaaggataaa taagatcctc 900
actttggcag tgcttcctct cctgtcaatt ccaggctctt tccataacca caagcctgag 960
gctgcagcct ttnattnatg ttttcccttt ggctgngact ggntggggca gcatgcagct 1020
tctgatttta aagaggcatc tagggaattg tcaggcaccc tacaggaagg cctgccatgc 1080
tgtggccaac tgtttcactg gagcaagaaa gagatctcat aggacggagg gggaaatggt 1140

-continued

```
ttccctccaa gcttgggtca gtgtgttaac tgcttatcag ctattcagac atctccatgg   1200

tttctccatg aaactctgtg gtttcatcat tccttcttag ttgacctgca cagcttggtt   1260

agacctagat ttaaccctaa ggtaagatgc tggggtatag aacgctaaga attttccccc   1320

aaggactctt gcttccttaa gcccttctgg cttcgtttat ggtcttcatt aaaagtataa   1380

gcctaacttt gtcgctagtc ctaaggagaa acctttaacc acaaagtttt tatcattgaa   1440

gacaatattg aacaaccccc tattttgtgg ggattgagaa ggggtgaata gaggcttgag   1500

actttccttt gtgtggtagg acttggagga gaaatcccct ggactttcac taaccctctg   1560

acatactccc cacacccagt tgatggcttt ccgtaataaa aagattggga tttccttttg   1620


<210> SEQ ID NO 207
<211> LENGTH: 296
<212> TYPE: PRT
<213> ORGANISM: Homo sapiens

<400> SEQUENCE: 207

Met Ala Val Leu Ala Pro Leu Ile Ala Leu Val Tyr Ser Val Pro Arg
  1               5                  10                  15

Leu Ser Arg Trp Leu Ala Gln Pro Tyr Tyr Leu Leu Ser Ala Leu Leu
             20                  25                  30

Ser Ala Ala Phe Leu Leu Val Arg Lys Leu Pro Pro Leu Cys His Gly
         35                  40                  45

Leu Pro Thr Gln Arg Glu Asp Gly Asn Pro Cys Asp Phe Asp Trp Arg
     50                  55                  60

Glu Val Glu Ile Leu Met Phe Leu Ser Ala Ile Val Met Met Lys Asn
 65                  70                  75                  80

Arg Arg Ser Ile Thr Val Glu Gln His Ile Gly Asn Ile Phe Met Phe
                 85                  90                  95

Ser Lys Val Ala Asn Thr Ile Leu Phe Phe Arg Leu Asp Ile Arg Met
            100                 105                 110

Gly Leu Leu Tyr Ile Thr Leu Cys Ile Val Phe Leu Met Thr Cys Lys
        115                 120                 125

Pro Pro Leu Tyr Met Gly Pro Glu Tyr Ile Lys Tyr Phe Asn Asp Lys
    130                 135                 140

Thr Ile Asp Glu Glu Leu Glu Arg Asp Lys Arg Val Thr Trp Ile Val
145                 150                 155                 160

Glu Phe Phe Ala Asn Trp Ser Asn Asp Cys Gln Ser Phe Ala Pro Ile
                165                 170                 175

Tyr Ala Asp Leu Ser Leu Lys Tyr Asn Cys Thr Gly Leu Asn Phe Gly
            180                 185                 190

Lys Val Asp Val Gly Arg Tyr Thr Asp Val Ser Thr Arg Tyr Lys Val
        195                 200                 205

Ser Thr Ser Pro Leu Thr Lys Gln Leu Pro Thr Leu Ile Leu Phe Gln
    210                 215                 220

Gly Gly Lys Glu Ala Met Arg Arg Pro Gln Ile Asp Lys Lys Gly Arg
225                 230                 235                 240

Ala Val Ser Trp Thr Phe Ser Glu Glu Asn Val Ile Arg Glu Phe Asn
                245                 250                 255

Leu Asn Glu Leu Tyr Gln Arg Ala Lys Lys Leu Ser Lys Ala Gly Asp
            260                 265                 270

Asn Ile Pro Glu Glu Gln Pro Val Ala Ser Thr Pro Thr Thr Val Ser
        275                 280                 285

Asp Gly Glu Asn Lys Lys Asp Lys
```

-continued 290 295

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 208
gcttggatat tcgcatgggc ctac 24

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 209
tggagacaat atccctgagg 20

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 210
aacagttggc cacagcatgg cagg 24

<210> SEQ ID NO 211
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide probe

<400> SEQUENCE: 211
ccattgatga ggaactagaa cgggacaaga gggtcacttg gattgtggag 50

<210> SEQ ID NO 212
<211> LENGTH: 1985
<212> TYPE: DNA
<213> ORGANISM: Homo sapiens

<400> SEQUENCE: 212
ggacagctcg cggcccccga gagctctagc cgtcgaggag ctgcctgggg acgtttgccc 60
tggggcccca gcctggcccg ggtcaccctg gcatgaggag atgggcctgt tgctcctggt 120
cccattgctc ctgctgcccg gctcctacgg actgcccttc tacaacggct tctactactc 180
caacagcgcc aacgaccaga acctaggcaa cggtcatggc aaagacctcc ttaatggagt 240
gaagctggtg gtggagacac ccgaggagac cctgttcacc taccaagggg ccagtgtgat 300
cctgccctgc cgctaccgct acgagccggc cctggtctcc ccgcggcgtg tgcgtgtcaa 360
atggtggaag ctgtcggaga acggggcccc agagaaggac gtgctggtgg ccatcgggct 420
gaggcaccgc tcctttgggg actaccaagg ccgcgtgcac ctgcggcagg acaaagagca 480
tgacgtctcg ctggagatcc aggatctgcg gctggaggac tatgggcgtt accgctgtga 540

-continued

```
ggtcattgac gggctggagg atgaaagcgg tctggtggag ctggagctgc ggggtgtggt    600
ctttccttac cagtccccca acgggcgcta ccagttcaac ttccacgagg gccagcaggt    660
ctgtgcagag caggctgcgg tggtggcctc ctttgagcag ctcttccggg cctgggagga    720
gggcctggac tggtgcaacg cgggctggct gcaggatgct acggtgcagt accccatcat    780
gttgccccgg cagccctgcg gtggcccagg cctggcacct ggcgtgcgaa gctacggccc    840
ccgccaccgc cgcctgcacc gctatgatgt attctgcttc gctactgccc tcaaggggcg    900
ggtgtactac ctggagcacc ctgagaagct gacgctgaca gaggcaaggg aggcctgcca    960
ggaagatgat gccacgatcg ccaaggtggg acagctcttt gccgcctgga agttccatgg   1020
cctggaccgc tgcgacgctg gctggctggc agatggcagc gtccgctacc ctgtggttca   1080
cccgcatcct aactgtgggc ccccagagcc tggggtccga agctttggct tccccgaccc   1140
gcagagccgc ttgtacggtg tttactgcta ccgccagcac taggacctgg ggccctcccc   1200
tgccgcattc cctcactggc tgtgtattta ttgagtggtt cgttttccct tgtgggttgg   1260
agccatttta actgttttta tacttctcaa tttaaatttt ctttaaacat ttttttacta   1320
tttttttgtaa agcaaacaga acccaatgcc tccctttgct cctggatgcc ccactccagg   1380
aatcatgctt gctcccctgg gccatttgcg gttttgtggg cttctggagg gttccccgcc   1440
atccaggctg gtctccctcc cttaaggagg ttggtgccca gagtgggcgg tggcctgtct   1500
agaatgccgc cgggagtccg ggcatggtgg gcacagttct ccctgcccct cagcctgggg   1560
gaagaagagg gcctcggggg cctccggagc tgggctttgg gcctctcctg cccacctcta   1620
cttctctgtg aagccgctga ccccagtctg cccactgagg ggctagggct ggaagccagt   1680
tctaggcttc caggcgaaat ctgagggaag gaagaaactc ccctccccgt tccccttccc   1740
ctctcggttc caaagaatct gttttgttgt catttgtttc tcctgtttcc ctgtgtgggg   1800
aggggccctc aggtgtgtgt actttggaca ataaatggtg ctatgactgc cttccgccaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaa                                                               1985
```

<210> SEQ ID NO 213
<211> LENGTH: 360
<212> TYPE: PRT
<213> ORGANISM: Homo sapiens

<400> SEQUENCE: 213

```
Met Gly Leu Leu Leu Leu Val Pro Leu Leu Leu Leu Pro Gly Ser Tyr
1               5                   10                  15

Gly Leu Pro Phe Tyr Asn Gly Phe Tyr Tyr Ser Asn Ser Ala Asn Asp
            20                  25                  30

Gln Asn Leu Gly Asn Gly His Gly Lys Asp Leu Leu Asn Gly Val Lys
        35                  40                  45

Leu Val Val Glu Thr Pro Glu Glu Thr Leu Phe Thr Tyr Gln Gly Ala
    50                  55                  60

Ser Val Ile Leu Pro Cys Arg Tyr Arg Tyr Glu Pro Ala Leu Val Ser
65                  70                  75                  80

Pro Arg Arg Val Arg Val Lys Trp Trp Lys Leu Ser Glu Asn Gly Ala
                85                  90                  95

Pro Glu Lys Asp Val Leu Val Ala Ile Gly Leu Arg His Arg Ser Phe
            100                 105                 110
```

-continued

```
Gly Asp Tyr Gln Gly Arg Val His Leu Arg Gln Asp Lys Glu His Asp
        115                 120                 125

Val Ser Leu Glu Ile Gln Asp Leu Arg Leu Glu Asp Tyr Gly Arg Tyr
    130                 135                 140

Arg Cys Glu Val Ile Asp Gly Leu Glu Asp Glu Ser Gly Leu Val Glu
145                 150                 155                 160

Leu Glu Leu Arg Gly Val Val Phe Pro Tyr Gln Ser Pro Asn Gly Arg
                165                 170                 175

Tyr Gln Phe Asn Phe His Glu Gly Gln Gln Val Cys Ala Glu Gln Ala
            180                 185                 190

Ala Val Val Ala Ser Phe Glu Gln Leu Phe Arg Ala Trp Glu Glu Gly
        195                 200                 205

Leu Asp Trp Cys Asn Ala Gly Trp Leu Gln Asp Ala Thr Val Gln Tyr
    210                 215                 220

Pro Ile Met Leu Pro Arg Gln Pro Cys Gly Gly Pro Gly Leu Ala Pro
225                 230                 235                 240

Gly Val Arg Ser Tyr Gly Pro Arg His Arg Arg Leu His Arg Tyr Asp
                245                 250                 255

Val Phe Cys Phe Ala Thr Ala Leu Lys Gly Arg Val Tyr Tyr Leu Glu
            260                 265                 270

His Pro Glu Lys Leu Thr Leu Thr Glu Ala Arg Glu Ala Cys Gln Glu
        275                 280                 285

Asp Asp Ala Thr Ile Ala Lys Val Gly Gln Leu Phe Ala Ala Trp Lys
    290                 295                 300

Phe His Gly Leu Asp Arg Cys Asp Ala Gly Trp Leu Ala Asp Gly Ser
305                 310                 315                 320

Val Arg Tyr Pro Val Val His Pro His Pro Asn Cys Gly Pro Pro Glu
                325                 330                 335

Pro Gly Val Arg Ser Phe Gly Phe Pro Asp Pro Gln Ser Arg Leu Tyr
            340                 345                 350

Gly Val Tyr Cys Tyr Arg Gln His
        355                 360


<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 214

tgcttcgcta ctgccctc                                                    18


<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 215

ttcccttgtg ggttggag                                                    18


<210> SEQ ID NO 216
<211> LENGTH: 18
<212> TYPE: DNA
```

-continued

<213> ORGANISM: Artificial Sequence
<220> FEATURE:
<223> OTHER INFORMATION: Description of Artificial Sequence: Synthetic
      oligonucleotide probe

<400> SEQUENCE: 216
agggctggaa gccagttc 18

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 217
agccagtgag gaaatgcg 18

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 218
tgtccaaagt acacacacct gagg 24

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 219
gatgccacga tcgccaaggt gggacagctc tttgccgcct ggaag 45

<210> SEQ ID NO 220
<211> LENGTH: 1503
<212> TYPE: DNA
<213> ORGANISM: Homo sapiens

<400> SEQUENCE: 220
ggagagcgga gcgaagctgg ataacagggg accgatgatg tggcgaccat cagttctgct 60
gcttctgttg ctactgaggc acggggccca ggggaagcca tccccagacg caggccctca 120
tggccagggg agggtgcacc aggcggcccc cctgagcgac gctccccatg atgacgccca 180
cgggaacttc cagtacgacc atgaggcttt cctgggacgg gaagtggcca aggaattcga 240
ccaactcacc ccagaggaaa gccaggcccg tctggggcgg atcgtggacc gcatggaccg 300
cgcgggggac ggcgacggct gggtgtcgct ggccgagctt cgcgcgtgga tcgcgcacac 360
gcagcagcgg cacatacggg actcggtgag cgcggcctgg gacacgtacg acacggaccg 420
cgacgggcgt gtgggttggg aggagctgcg caacgccacc tatggccact acgcgcccgg 480
tgaagaattt catgacgtgg aggatgcaga gacctacaaa aagatgctgg ctcgggacga 540
gcggcgtttc cgggtggccg accaggatgg ggactcgatg gccactcgag aggagctgac 600
agccttcctg caccccgagg agttccctca catgcgggac atcgtgattg ctgaaaccct 660
ggaggacctg gacagaaaca aagatggcta tgtccaggtg gaggagtaca tcgcggatct 720

-continued

```
gtactcagcc gagcctgggg aggaggagcc ggcgtgggtg cagacggaga ggcagcagtt    780

ccgggacttc cgggatctga acaaggatgg gcacctggat gggagtgagg tgggccactg    840

ggtgctgccc cctgcccagg accagcccct ggtggaagcc aaccacctgc tgcacgagag    900

cgacacggac aaggatgggc ggctgagcaa agcggaaatc ctgggtaatt ggaacatgtt    960

tgtgggcagt caggccacca actatggcga ggacctgacc cggcaccacg atgagctgtg   1020

agcaccgcgc acctgccaca gcctcagagg cccgcacaat gaccggagga ggggccgctg   1080

tggtctggcc ccctccctgt ccaggccccg caggaggcag atgcagtccc aggcatcctc   1140

ctgcccctgg gctctcaggg accccctggg tcggcttctg tccctgtcac acccccaacc   1200

ccagggaggg gctgtcatag tcccagagga taagcaatac ctatttctga ctgagtctcc   1260

cagcccagac ccagggaccc ttggccccaa gctcagctct aagaaccgcc ccaacccctc   1320

cagctccaaa tctgagcctc caccacatag actgaaactc ccctggcccc agccctctcc   1380

tgcctggcct ggcctgggac acctcctctc tgccaggagg caataaaagc cagcgccggg   1440

accttgaaaa aaaaaaaaaa aaaaaaaaaa aaaaaaaaaa aaaaaaaaaa aaaaaaaaaa   1500

aaa                                                                 1503
```

<210> SEQ ID NO 221
<211> LENGTH: 328
<212> TYPE: PRT
<213> ORGANISM: Homo sapiens

<400> SEQUENCE: 221

```
Met Met Trp Arg Pro Ser Val Leu Leu Leu Leu Leu Leu Leu Arg His
  1               5                  10                  15

Gly Ala Gln Gly Lys Pro Ser Pro Asp Ala Gly Pro His Gly Gln Gly
             20                  25                  30

Arg Val His Gln Ala Ala Pro Leu Ser Asp Ala Pro His Asp Asp Ala
         35                  40                  45

His Gly Asn Phe Gln Tyr Asp His Glu Ala Phe Leu Gly Arg Glu Val
     50                  55                  60

Ala Lys Glu Phe Asp Gln Leu Thr Pro Glu Glu Ser Gln Ala Arg Leu
 65                  70                  75                  80

Gly Arg Ile Val Asp Arg Met Asp Arg Ala Gly Asp Gly Asp Gly Trp
                 85                  90                  95

Val Ser Leu Ala Glu Leu Arg Ala Trp Ile Ala His Thr Gln Gln Arg
            100                 105                 110

His Ile Arg Asp Ser Val Ser Ala Ala Trp Asp Thr Tyr Asp Thr Asp
        115                 120                 125

Arg Asp Gly Arg Val Gly Trp Glu Glu Leu Arg Asn Ala Thr Tyr Gly
    130                 135                 140

His Tyr Ala Pro Gly Glu Glu Phe His Asp Val Glu Asp Ala Glu Thr
145                 150                 155                 160

Tyr Lys Lys Met Leu Ala Arg Asp Glu Arg Arg Phe Arg Val Ala Asp
                165                 170                 175

Gln Asp Gly Asp Ser Met Ala Thr Arg Glu Glu Leu Thr Ala Phe Leu
            180                 185                 190

His Pro Glu Glu Phe Pro His Met Arg Asp Ile Val Ile Ala Glu Thr
        195                 200                 205

Leu Glu Asp Leu Asp Arg Asn Lys Asp Gly Tyr Val Gln Val Glu Glu
    210                 215                 220
```

-continued

```
Tyr Ile Ala Asp Leu Tyr Ser Ala Glu Pro Gly Glu Glu Glu Pro Ala
225                 230                 235                 240

Trp Val Gln Thr Glu Arg Gln Gln Phe Arg Asp Phe Arg Asp Leu Asn
                245                 250                 255

Lys Asp Gly His Leu Asp Gly Ser Glu Val Gly His Trp Val Leu Pro
            260                 265                 270

Pro Ala Gln Asp Gln Pro Leu Val Glu Ala Asn His Leu Leu His Glu
        275                 280                 285

Ser Asp Thr Asp Lys Asp Gly Arg Leu Ser Lys Ala Glu Ile Leu Gly
    290                 295                 300

Asn Trp Asn Met Phe Val Gly Ser Gln Ala Thr Asn Tyr Gly Glu Asp
305                 310                 315                 320

Leu Thr Arg His His Asp Glu Leu
                325
```

```
<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 222

cgcaggccct catggccagg                                                   20


<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 223

gaaatcctgg gtaattgg                                                     18


<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 224

gtgcgcggtg ctcacagctc atc                                               23


<210> SEQ ID NO 225
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 225

ccccctgag cgacgctccc ccatgatgac gcccacggga actt                        44


<210> SEQ ID NO 226
<211> LENGTH: 2403
<212> TYPE: DNA
<213> ORGANISM: Homo sapiens
```

-continued

<400> SEQUENCE: 226

```
ggggccttgc cttccgcact cgggcgcagc cgggtggatc tcgagcaggt gcggagcccc     60
gggcggcggg cgcgggtgcg agggatccct gacgcctctg tccctgtttc tttgtcgctc    120
ccagcctgtc tgtcgtcgtt ttggcgcccc cgcctccccg cggtgcgggg ttgcacaccg    180
atcctgggct tcgctcgatt tgccgccgag gcgcctccca gacctagagg ggcgctggcc    240
tggagcagcg ggtcgtctgt gtcctctctc ctctgcgccg cgcccgggga tccgaagggt    300
gcggggctct gaggaggtga cgcgcggggc ctcccgcacc ctggccttgc ccgcattctc    360
cctctctccc aggtgtgagc agcctatcag tcaccatgtc cgcagcctgg atcccggctc    420
tcggcctcgg tgtgtgtctg ctgctgctgc cggggcccgc gggcagcgag ggagccgctc    480
ccattgctat cacatgtttt accagaggct tggacatcag gaaagagaaa gcagatgtcc    540
tctgcccagg gggctgccct cttgaggaat tctctgtgta tgggaacata gtatatgctt    600
ctgtatcgag catatgtggg gctgctgtcc acaggggagt aatcagcaac tcagggggac    660
ctgtacgagt ctatagccta cctggtcgag aaaactattc ctcagtagat gccaatggca    720
tccagtctca aatgctttct agatggtctg cttctttcac agtaactaaa ggcaaaagta    780
gtacacagga ggccacagga caagcagtgt ccacagcaca tccaccaaca ggtaaacgac    840
taaagaaaac acccgagaag aaaactggca ataaagattg taaagcagac attgcatttc    900
tgattgatgg aagctttaat attgggcagc gccgatttaa tttacagaag aattttgttg    960
gaaaagtggc tctaatgttg ggaattggaa cagaaggacc acatgtgggc cttgttcaag   1020
ccagtgaaca tcccaaaata gaattttact tgaaaaactt tacatcagcc aaagatgttt   1080
tgtttgccat aaaggaagta ggtttcagag gggtaattcc caatacagga aaagccttga   1140
agcatactgc tcagaaattc ttcacggtag atgctggagt aagaaaaggg atccccaaag   1200
tggtggtggt atttattgat ggttggcctt ctgatgacat cgaggaagca ggcattgtgg   1260
ccagagagtt tggtgtcaat gtatttatag tttctgtggc caagcctatc cctgaagaac   1320
tggggatggt tcaggatgtc acatttgttg acaaggctgt ctgtcggaat aatggcttct   1380
tctcttacca catgcccaac tggtttggca ccacaaaata cgtaaagcct ctggtacaga   1440
agctgtgcac tcatgaacaa atgatgtgca gcaagacctg ttataactca gtgaacattg   1500
cctttctaat tgatggctcc agcagtgttg gagatagcaa tttccgcctc atgcttgaat   1560
ttgtttccaa catagccaag acttttgaaa tctcggacat tggtgccaag atagctgctg   1620
tacagtttac ttatgatcag cgcacggagt tcagtttcac tgactatagc accaaagaga   1680
atgtcctagc tgtcatcaga aacatccgct atatgagtgg tggaacagct actggtgatg   1740
ccatttcctt cactgttaga aatgtgtttg gccctataag ggagagcccc aacaagaact   1800
tcctagtaat tgtcacagat gggcagtcct atgatgatgt ccaaggccct gcagctgctg   1860
cacatgatgc aggaatcact atcttctctg ttggtgtggc ttgggcacct ctggatgacc   1920
tgaaagatat ggcttctaaa ccgaaggagt ctcacgcttt cttcacaaga gagttcacag   1980
gattagaacc aattgtttct gatgtcatca gaggcatttg tagagatttc ttagaatccc   2040
agcaataatg gtaacatttt gacaactgaa agaaaaagta caaggggatc cagtgtgtaa   2100
attgtattct cataatactg aaatgcttta gcatactaga atcagataca aaactattaa   2160
gtatgtcaac agccatttag gcaaataagc actcctttaa agccgctgcc ttctggttac   2220
aatttacagt gtactttgtt aaaaacactg ctgaggcttc ataatcatgg ctcttagaaa   2280
ctcaggaaag aggagataat gtggattaaa accttaagag ttctaaccat gcctactaaa   2340
```

-continued

```
tgtacagata tgcaaattcc atagctcaat aaaagaatct gatacttaga ccaaaaaaaa   2400

aaa                                                                 2403


<210> SEQ ID NO 227
<211> LENGTH: 550
<212> TYPE: PRT
<213> ORGANISM: Homo sapiens

<400> SEQUENCE: 227

Met Ser Ala Ala Trp Ile Pro Ala Leu Gly Leu Gly Val Cys Leu Leu
  1               5                  10                  15

Leu Leu Pro Gly Pro Ala Gly Ser Glu Gly Ala Ala Pro Ile Ala Ile
             20                  25                  30

Thr Cys Phe Thr Arg Gly Leu Asp Ile Arg Lys Glu Lys Ala Asp Val
         35                  40                  45

Leu Cys Pro Gly Gly Cys Pro Leu Glu Glu Phe Ser Val Tyr Gly Asn
     50                  55                  60

Ile Val Tyr Ala Ser Val Ser Ser Ile Cys Gly Ala Ala Val His Arg
 65                  70                  75                  80

Gly Val Ile Ser Asn Ser Gly Gly Pro Val Arg Val Tyr Ser Leu Pro
                 85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu Ala Thr Gly Gln Ala Val Ser Thr Ala His Pro Pro
    130                 135                 140

Thr Gly Lys Arg Leu Lys Lys Thr Pro Glu Lys Lys Thr Gly Asn Lys
145                 150                 155                 160

Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
    210                 215                 220

Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val Val
            260                 265                 270

Phe Ile Asp Gly Trp Pro Ser Asp Asp Ile Glu Glu Ala Gly Ile Val
        275                 280                 285

Ala Arg Glu Phe Gly Val Asn Val Phe Ile Val Ser Val Ala Lys Pro
    290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350
```

-continued

```
His Glu Gln Met Met Cys Ser Lys Thr Cys Tyr Asn Ser Val Asn Ile
        355                 360                 365

Ala Phe Leu Ile Asp Gly Ser Ser Ser Val Gly Asp Ser Asn Phe Arg
    370                 375                 380

Leu Met Leu Glu Phe Val Ser Asn Ile Ala Lys Thr Phe Glu Ile Ser
385                 390                 395                 400

Asp Ile Gly Ala Lys Ile Ala Ala Val Gln Phe Thr Tyr Asp Gln Arg
                405                 410                 415

Thr Glu Phe Ser Phe Thr Asp Tyr Ser Thr Lys Glu Asn Val Leu Ala
            420                 425                 430

Val Ile Arg Asn Ile Arg Tyr Met Ser Gly Gly Thr Ala Thr Gly Asp
        435                 440                 445

Ala Ile Ser Phe Thr Val Arg Asn Val Phe Gly Pro Ile Arg Glu Ser
    450                 455                 460

Pro Asn Lys Asn Phe Leu Val Ile Val Thr Asp Gly Gln Ser Tyr Asp
465                 470                 475                 480

Asp Val Gln Gly Pro Ala Ala Ala Ala His Asp Ala Gly Ile Thr Ile
                485                 490                 495

Phe Ser Val Gly Val Ala Trp Ala Pro Leu Asp Asp Leu Lys Asp Met
            500                 505                 510

Ala Ser Lys Pro Lys Glu Ser His Ala Phe Phe Thr Arg Glu Phe Thr
        515                 520                 525

Gly Leu Glu Pro Ile Val Ser Asp Val Ile Arg Gly Ile Cys Arg Asp
    530                 535                 540

Phe Leu Glu Ser Gln Gln
545                 550
```

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 228
tggtctcgca caccgatc 18

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 229
ctgctgtcca caggggag 18

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 230
ccttgaagca tactgctc 18

-continued

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 231
gagatagcaa tttccgcc 18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 232
ttcctcaaga gggcagcc 18

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 233
cttggcacca atgtccgaga tttc 24

<210> SEQ ID NO 234
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide probe

<400> SEQUENCE: 234
gctctgagga aggtgacgcg cggggcctcc gaacccttgg ccttg 45

<210> SEQ ID NO 235
<211> LENGTH: 2586
<212> TYPE: DNA
<213> ORGANISM: Homo sapiens

<400> SEQUENCE: 235
cgccgcgctc ccgcacccgc ggcccgccca ccgcgccgct cccgcatctg cacccgcagc 60
ccggcggcct cccggcggga gcgagcagat ccagtccggc ccgcagcgca actcggtcca 120
gtcggggcgg cggctgcggg cgcagagcgg agatgcagcg gcttggggcc accctgctgt 180
gcctgctgct ggcggcggcg gtccccacgg cccccgcgcc cgctccgacg gcgacctcgg 240
ctccagtcaa gcccggcccg gctctcagct acccgcagga ggaggccacc ctcaatgaga 300
tgttccgcga ggttgaggaa ctgatggagg acacgcagca caaattgcgc agcgcggtgg 360
aagagatgga ggcagaagaa gctgctgcta aagcatcatc agaagtgaac ctggcaaact 420
tacctcccag ctatcacaat gagaccaaca cagacacgaa ggttggaaat aataccatcc 480
atgtgcaccg agaaattcac aagataacca acaaccagac tggacaaatg gtcttttcag 540
agacagttat cacatctgtg ggagacgaag aaggcagaag gagccacgag tgcatcatcg 600

-continued

```
acgaggactg tgggcccagc atgtactgcc agtttgccag cttccagtac acctgccagc    660
catgccgggg ccagaggatg ctctgcaccc gggacagtga gtgctgtgga gaccagctgt    720
gtgtctgggg tcactgcacc aaaatggcca ccaggggcag caatgggacc atctgtgaca    780
accagaggga ctgccagccg gggctgtgct gtgccttcca gagaggcctg ctgttccctg    840
tgtgcacacc cctgcccgtg gagggcgagc tttgccatga ccccgccagc cggcttctgg    900
acctcatcac ctgggagcta gagcctgatg gagccttgga ccgatgccct tgtgccagtg    960
gcctcctctg ccagccccac agccacagcc tggtgtatgt gtgcaagccg accttcgtgg   1020
ggagccgtga ccaagatggg gagatcctgc tgcccagaga ggtccccgat gagtatgaag   1080
ttggcagctt catggaggag gtgcgccagg agctggagga cctggagagg agcctgactg   1140
aagagatggc gctgggggag cctgcggctg ccgccgctgc actgctggga ggggaagaga   1200
tttagatctg gaccaggctg tgggtagatg tgcaatagaa atagctaatt tatttcccca   1260
ggtgtgtgct ttaggcgtgg gctgaccagg cttcttccta catcttcttc ccagtaagtt   1320
tcccctctgg cttgacagca tgaggtgttg tgcatttgtt cagctccccc aggctgttct   1380
ccaggcttca cagtctggtg cttgggagag tcaggcaggg ttaaactgca ggagcagttt   1440
gccacccctg tccagattat tggctgcttt gcctctacca gttggcagac agccgtttgt   1500
tctacatggc tttgataatt gtttgagggg aggagatgga aacaatgtgg agtctccctc   1560
tgattggttt tggggaaatg tggagaagag tgccctgctt tgcaaacatc aacctggcaa   1620
aaatgcaaca aatgaatttt ccacgcagtt ctttccatgg gcataggtaa gctgtgcctt   1680
cagctgttgc agatgaaatg ttctgttcac cctgcattac atgtgtttat tcatccagca   1740
gtgttgctca gctcctacct ctgtgccagg gcagcatttt catatccaag atcaattccc   1800
tctctcagca cagcctgggg aggggtcat tgttctcctc gtccatcagg gatctcagag    1860
gctcagagac tgcaagctgc ttgcccaagt cacacagcta gtgaagacca gagcagtttc   1920
atctggttgt gactctaagc tcagtgctct ctccactacc ccacaccagc cttggtgcca   1980
ccaaaagtgc tccccaaaag gaaggagaat gggatttttc ttgaggcatg cacatctgga   2040
attaaggtca aactaattct cacatccctc taaaagtaaa ctactgttag gaacagcagt   2100
gttctcacag tgtggggcag ccgtccttct aatgaagaca atgatattga cactgtccct   2160
ctttggcagt tgcattagta actttgaaag gtatatgact gagcgtagca tacaggttaa   2220
cctgcagaaa cagtacttag gtaattgtag ggcgaggatt ataaatgaaa tttgcaaaat   2280
cacttagcag caactgaaga caattatcaa ccacgtggag aaaatcaaac cgagcagggc   2340
tgtgtgaaac atggttgtaa tatgcgactg cgaacactga actctacgcc actccacaaa   2400
tgatgttttc aggtgtcatg gactgttgcc accatgtatt catccagagt tcttaaagtt   2460
taaagttgca catgattgta taagcatgct ttctttgagt tttaaattat gtataaacat   2520
aagttgcatt tagaaatcaa gcataaatca cttcaactgc aaaaaaaaaa aaaaaaaaaa   2580
aaaaaa                                                               2586
```

<210> SEQ ID NO 236
<211> LENGTH: 350
<212> TYPE: PRT
<213> ORGANISM: Homo sapiens

<400> SEQUENCE: 236

```
Met Gln Arg Leu Gly Ala Thr Leu Leu Cys Leu Leu Leu Ala Ala Ala
  1               5                  10                  15
```

-continued

```
Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Ala Leu Leu Gly Gly Glu Glu Ile
            340                 345                 350
```

<210> SEQ ID NO 237
<211> LENGTH: 17
<212> TYPE: DNA
<213> ORGANISM: Artificial Sequence
<220> FEATURE:
<223> OTHER INFORMATION: Synthetic oligonucleotide probe

<400> SEQUENCE: 237
ggagctgcac cccttgc 17

<210> SEQ ID NO 238
<211> LENGTH: 49
<212> TYPE: DNA

-continued

<213> ORGANISM: Artificial Sequence
<220> FEATURE:
<223> OTHER INFORMATION: Synthetic Oligonucleotide Probe

<400> SEQUENCE: 238
ggaggactgt gccaccatga gagactcttc aaacccaagg caaaattgg 49

<210> SEQ ID NO 239
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 239
gcagagcgga gatgcagcgg cttg 24

<210> SEQ ID NO 240
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 240
ttggcagctt catggagg 18

<210> SEQ ID NO 241
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 241
cctgggcaaa aatgcaac 18

<210> SEQ ID NO 242
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 242
ctccagctcc tggcgcacct cctc 24

<210> SEQ ID NO 243
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 243
ggctctcagc taccgcgcag gagcgaggcc accctcaatg agatg 45

<210> SEQ ID NO 244
<211> LENGTH: 3679
<212> TYPE: DNA
<213> ORGANISM: Homo Sapien

<400> SEQUENCE: 244
aaggaggctg ggaggaaaga ggtaagaaag gttagagaac ctacctcaca 50
tctctctggg ctcagaagga ctctgaagat aacaataatt tcagcccatc 100

-continued

```
cactctcctt ccctcccaaa cacacatgtg catgtacaca cacacataca       150
cacacataca ccttcctctc cttcactgaa gactcacagt cactcactct       200
gtgagcaggt catagaaaag gacactaaag ccttaaggac aggcctggcc       250
attacctctg cagctccttt ggcttgttga gtcaaaaaac atgggagggg       300
ccaggcacgg tgactcacac ctgtaatccc agcattttgg gagaccgagg       350
tgagcagatc acttgaggtc aggagttcga gaccagcctg gccaacatgg       400
agaaaccccc atctctacta aaaatacaaa aattagccag gagtggtggc       450
aggtgcctgt aatcccagct actcaggtgg ctgagccagg agaatcgctt       500
gaatccagga ggcggaggat gcagtcagct gagtgcaccg ctgcactcca       550
gcctgggtga cagaatgaga ctctgtctca aacaaacaaa cacgggagga       600
ggggtagata ctgcttctct gcaacctcct taactctgca tcctcttctt       650
ccagggctgc ccctgatggg gcctggcaat gactgagcag gcccagcccc       700
agaggacaag gaagagaagg catattgagg agggcaagaa gtgacgcccg       750
gtgtagaatg actgccctgg gagggtggtt ccttgggccc tggcagggtt       800
gctgaccctt accctgcaaa acacaaagag caggactcca gactctcctt       850
gtgaatggtc ccctgccctg cagctccacc atgaggcttc tcgtggcccc       900
actcttgcta gcttgggtgg ctggtgccac tgccactgtg cccgtggtac       950
cctggcatgt tccctgcccc cctcagtgtg cctgccagat ccggccctgg      1000
tatacgcccc gctcgtccta ccgcgaggct accactgtgg actgcaatga      1050
cctattcctg acggcagtcc ccccggcact ccccgcaggc acacagaccc      1100
tgctcctgca gagcaacagc attgtccgtg tggaccagag tgagctgggc      1150
tacctggcca atctcacaga gctggacctg tcccagaaca gcttttcgga      1200
tgcccgagac tgtgatttcc atgccctgcc ccagctgctg agcctgcacc      1250
tagaggagaa ccagctgacc cggctggagg accacagctt tgcagggctg      1300
gccagcctac aggaactcta tctcaaccac aaccagctct accgcatcgc      1350
ccccagggcc ttttctggcc tcagcaactt gctgcggctg cacctcaact      1400
ccaacctcct gagggccatt gacagccgct ggtttgaaat gctgcccaac      1450
ttggagatac tcatgattgg cggcaacaag gtagatgcca tcctggacat      1500
gaacttccgg cccctggcca acctgcgtag cctggtgcta gcaggcatga      1550
acctgcggga gatctccgac tatgccctgg aggggctgca aagcctggag      1600
agcctctcct tctatgacaa ccagctggcc cgggtgccca ggcgggcact      1650
ggaacaggtg cccgggctca agttcctaga cctcaacaag aacccgctcc      1700
agcgggtagg gccgggggac tttgccaaca tgctgcacct taaggagctg      1750
ggactgaaca acatggagga gctggtctcc atcgacaagt ttgccctggt      1800
gaacctcccc gagctgacca agctggacat caccaataac ccacggctgt      1850
ccttcatcca cccccgcgcc ttccaccacc tgccccagat ggagaccctc      1900
atgctcaaca acaacgctct cagtgccttg caccagcaga cggtggagtc      1950
cctgcccaac ctgcaggagg taggtctcca cggcaacccc atccgctgtg      2000
actgtgtcat ccgctgggcc aatgccacgg gcacccgtgt ccgcttcatc      2050
```

-continued

```
gagccgcaat ccaccctgtg tgcggagcct ccggacctcc agcgcctccc          2100

ggtccgtgag gtgcccttcc gggagatgac ggaccactgt ttgcccctca          2150

tctccccacg aagcttcccc ccaagcctcc aggtagccag tggagagagc          2200

atggtgctgc attgccgggc actggccgaa cccgaacccg agatctactg          2250

ggtcactcca gctgggcttc gactgacacc tgcccatgca ggcaggaggt          2300

accgggtgta ccccgagggg accctggagc tgcggagggt gacagcagaa          2350

gaggcagggc tatacacctg tgtggcccag aacctggtgg gggctgacac          2400

taagacggtt agtgtggttg tgggccgtgc tctcctccag ccaggcaggg          2450

acgaaggaca ggggctggag ctccgggtgc aggagaccca cccctatcac          2500

atcctgctat cttgggtcac cccacccaac acagtgtcca ccaacctcac          2550

ctggtccagt gcctcctccc tccggggcca gggggccaca gctctggccc          2600

gcctgcctcg ggggaaccac agctacaaca ttacccgcct ccttcaggcc          2650

acggagtact gggcctgcct gcaagtggcc tttgctgatg cccacaccca          2700

gttggcttgt gtatgggcca ggaccaaaga ggccacttct tgccacagag          2750

ccttagggga tcgtcctggg ctcattgcca tcctggctct cgctgtcctt          2800

ctcctggcag ctgggctagc ggcccacctt ggcacaggcc aacccaggaa          2850

gggtgtgggt gggaggcggc ctctccctcc agcctgggct ttctggggct          2900

ggagtgcccc ttctgtccgg gttgtgtctg ctcccctcgt cctgccctgg          2950

aatccaggga ggaagctgcc cagatcctca gaaggggaga cactgttgcc          3000

accattgtct caaaattctt gaagctcagc ctgttctcag cagtagagaa          3050

atcactagga ctacttttta ccaaaagaga agcagtctgg gccagatgcc          3100

ctgccaggaa agggacatgg acccacgtgc ttgaggcctg gcagctgggc          3150

caagacagat ggggctttgt ggccctgggg gtgcttctgc agccttgaaa          3200

aagttgccct tacctcctag ggtcacctct gctgccattc tgaggaacat          3250

ctccaaggaa caggagggac tttggctaga gcctcctgcc tccccatctt          3300

ctctctgccc agaggctcct gggcctggct tggctgtccc ctacctgtgt          3350

ccccgggctg caccccttcc tcttctcttt ctctgtacag tctcagttgc          3400

ttgctcttgt gcctcctggg caagggctga aggaggccac tccatctcac          3450

ctcgggggc tgccctcaat gtgggagtga ccccagccag atctgaagga           3500

catttgggag agggatgccc aggaacgcct catctcagca gcctgggctc          3550

ggcattccga agctgacttt ctataggcaa ttttgtacct ttgtggagaa          3600

atgtgtcacc tcccccaacc cgattcactc ttttctcctg ttttgtaaaa          3650

aataaaaata aataataaca ataaaaaaa                                 3679
```

<210> SEQ ID NO 245
<211> LENGTH: 713
<212> TYPE: PRT
<213> ORGANISM: Homo Sapien

<400> SEQUENCE: 245

```
Met Arg Leu Leu Val Ala Pro Leu Leu Leu Ala Trp Val Ala Gly
  1               5                  10                  15

Ala Thr Ala Thr Val Pro Val Val Pro Trp His Val Pro Cys Pro
                 20                  25                  30
```

-continued

```
Pro Gln Cys Ala Cys Gln Ile Arg Pro Trp Tyr Thr Pro Arg Ser
                35                  40                  45

Ser Tyr Arg Glu Ala Thr Thr Val Asp Cys Asn Asp Leu Phe Leu
                50                  55                  60

Thr Ala Val Pro Pro Ala Leu Pro Ala Gly Thr Gln Thr Leu Leu
                65                  70                  75

Leu Gln Ser Asn Ser Ile Val Arg Val Asp Gln Ser Glu Leu Gly
                80                  85                  90

Tyr Leu Ala Asn Leu Thr Glu Leu Asp Leu Ser Gln Asn Ser Phe
                95                 100                 105

Ser Asp Ala Arg Asp Cys Asp Phe His Ala Leu Pro Gln Leu Leu
               110                 115                 120

Ser Leu His Leu Glu Glu Asn Gln Leu Thr Arg Leu Glu Asp His
               125                 130                 135

Ser Phe Ala Gly Leu Ala Ser Leu Gln Glu Leu Tyr Leu Asn His
               140                 145                 150

Asn Gln Leu Tyr Arg Ile Ala Pro Arg Ala Phe Ser Gly Leu Ser
               155                 160                 165

Asn Leu Leu Arg Leu His Leu Asn Ser Asn Leu Leu Arg Ala Ile
               170                 175                 180

Asp Ser Arg Trp Phe Glu Met Leu Pro Asn Leu Glu Ile Leu Met
               185                 190                 195

Ile Gly Gly Asn Lys Val Asp Ala Ile Leu Asp Met Asn Phe Arg
               200                 205                 210

Pro Leu Ala Asn Leu Arg Ser Leu Val Leu Ala Gly Met Asn Leu
               215                 220                 225

Arg Glu Ile Ser Asp Tyr Ala Leu Glu Gly Leu Gln Ser Leu Glu
               230                 235                 240

Ser Leu Ser Phe Tyr Asp Asn Gln Leu Ala Arg Val Pro Arg Arg
               245                 250                 255

Ala Leu Glu Gln Val Pro Gly Leu Lys Phe Leu Asp Leu Asn Lys
               260                 265                 270

Asn Pro Leu Gln Arg Val Gly Pro Gly Asp Phe Ala Asn Met Leu
               275                 280                 285

His Leu Lys Glu Leu Gly Leu Asn Asn Met Glu Glu Leu Val Ser
               290                 295                 300

Ile Asp Lys Phe Ala Leu Val Asn Leu Pro Glu Leu Thr Lys Leu
               305                 310                 315

Asp Ile Thr Asn Asn Pro Arg Leu Ser Phe Ile His Pro Arg Ala
               320                 325                 330

Phe His His Leu Pro Gln Met Glu Thr Leu Met Leu Asn Asn Asn
               335                 340                 345

Ala Leu Ser Ala Leu His Gln Gln Thr Val Glu Ser Leu Pro Asn
               350                 355                 360

Leu Gln Glu Val Gly Leu His Gly Asn Pro Ile Arg Cys Asp Cys
               365                 370                 375

Val Ile Arg Trp Ala Asn Ala Thr Gly Thr Arg Val Arg Phe Ile
               380                 385                 390

Glu Pro Gln Ser Thr Leu Cys Ala Glu Pro Pro Asp Leu Gln Arg
               395                 400                 405

Leu Pro Val Arg Glu Val Pro Phe Arg Glu Met Thr Asp His Cys
               410                 415                 420
```

-continued

```
Leu Pro Leu Ile Ser Pro Arg Ser Phe Pro Pro Ser Leu Gln Val
                425                 430                 435

Ala Ser Gly Glu Ser Met Val Leu His Cys Arg Ala Leu Ala Glu
                440                 445                 450

Pro Glu Pro Glu Ile Tyr Trp Val Thr Pro Ala Gly Leu Arg Leu
                455                 460                 465

Thr Pro Ala His Ala Gly Arg Arg Tyr Arg Val Tyr Pro Glu Gly
                470                 475                 480

Thr Leu Glu Leu Arg Arg Val Thr Ala Glu Glu Ala Gly Leu Tyr
                485                 490                 495

Thr Cys Val Ala Gln Asn Leu Val Gly Ala Asp Thr Lys Thr Val
                500                 505                 510

Ser Val Val Val Gly Arg Ala Leu Leu Gln Pro Gly Arg Asp Glu
                515                 520                 525

Gly Gln Gly Leu Glu Leu Arg Val Gln Glu Thr His Pro Tyr His
                530                 535                 540

Ile Leu Leu Ser Trp Val Thr Pro Pro Asn Thr Val Ser Thr Asn
                545                 550                 555

Leu Thr Trp Ser Ser Ala Ser Ser Leu Arg Gly Gln Gly Ala Thr
                560                 565                 570

Ala Leu Ala Arg Leu Pro Arg Gly Thr His Ser Tyr Asn Ile Thr
                575                 580                 585

Arg Leu Leu Gln Ala Thr Glu Tyr Trp Ala Cys Leu Gln Val Ala
                590                 595                 600

Phe Ala Asp Ala His Thr Gln Leu Ala Cys Val Trp Ala Arg Thr
                605                 610                 615

Lys Glu Ala Thr Ser Cys His Arg Ala Leu Gly Asp Arg Pro Gly
                620                 625                 630

Leu Ile Ala Ile Leu Ala Leu Ala Val Leu Leu Leu Ala Ala Gly
                635                 640                 645

Leu Ala Ala His Leu Gly Thr Gly Gln Pro Arg Lys Gly Val Gly
                650                 655                 660

Gly Arg Arg Pro Leu Pro Pro Ala Trp Ala Phe Trp Gly Trp Ser
                665                 670                 675

Ala Pro Ser Val Arg Val Val Ser Ala Pro Leu Val Leu Pro Trp
                680                 685                 690

Asn Pro Gly Arg Lys Leu Pro Arg Ser Ser Glu Gly Glu Thr Leu
                695                 700                 705

Leu Pro Pro Leu Ser Gln Asn Ser
                710
```

<210> SEQ ID NO 246
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 246
aacaaggtaa gatgccatcc tg 22

<210> SEQ ID NO 247
<211> LENGTH: 24
<212> TYPE: DNA
<213> ORGANISM: Artificial Sequence
<220> FEATURE:
<223> OTHER INFORMATION: Synthetic Oligonucleotide Probe -continued

<400> SEQUENCE: 247
aaacttgtcg atggagacca gctc 24

<210> SEQ ID NO 248
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 248
aggggctgca aagcctggag agcctctcct tctatgacaa ccagc 45

<210> SEQ ID NO 249
<211> LENGTH: 3401
<212> TYPE: DNA
<213> ORGANISM: Homo Sapien

<400> SEQUENCE: 249
gcaagccaag gcgctgtttg agaaggtgaa gaagttccgg acccatgtgg 50
aggaggggga cattgtgtac cgcctctaca tgcggcagac catcatcaag 100
gtgatcaagt tcatcctcat catctgctac accgtctact acgtgcacaa 150
catcaagttc gacgtggact gcaccgtgga cattgagagc ctgacgggct 200
accgcaccta ccgctgtgcc cacccccctgg ccacactctt caagatcctg 250
gcgtccttct acatcagcct agtcatcttc tacggcctca tctgcatgta 300
cacactgtgg tggatgctac ggcgctccct caagaagtac tcgtttgagt 350
cgatccgtga ggagagcagc tacagcgaca tccccgacgt caagaacgac 400
ttcgccttca tgctgcacct cattgaccaa tacgacccgc tctactccaa 450
gcgcttcgcc gtcttcctgt cggaggtgag tgagaacaag ctgcggcagc 500
tgaacctcaa caacgagtgg acgctggaca agctccggca gcggctcacc 550
aagaacgcgc aggacaagct ggagctgcac ctgttcatgc tcagtggcat 600
ccctgacact gtgtttgacc tggtggagct ggaggtcctc aagctggagc 650
tgatccccga cgtgaccatc ccgcccagca ttgcccagct cacgggcctc 700
aaggagctgt ggctctacca cacagcggcc aagattgaag cgcctgcgct 750
ggccttcctg cgcgagaacc tgcgggcgct gcacatcaag ttcaccgaca 800
tcaaggagat cccgctgtgg atctatagcc tgaagacact ggaggagctg 850
cacctgacgg gcaacctgag cgcggagaac aaccgctaca tcgtcatcga 900
cgggctgcgg gagctcaaac gcctcaaggt gctgcggctc aagagcaacc 950
taagcaagct gccacaggtg gtcacagatg tgggcgtgca cctgcagaag 1000
ctgtccatca acaatgaggg caccaagctc atcgtcctca acagcctcaa 1050
gaagatggcg aacctgactg agctggagct gatccgctgc gacctggagc 1100 gcatcccccca ctccatcttc agcctccaca acctgcagga gattgacctc 1150
aaggacaaca acctcaagac catcgaggag atcatcagct tccagcacct 1200
gcaccgcctc acctgcctta agctgtggta caaccacatc gcctacatcc 1250
ccatccagat cggcaacctc accaacctgg agcgcctcta cctgaaccgc 1300
aacaagatcg agaagatccc cacccagctc ttctactgcc gcaagctgcg 1350

-continued

```
ctacctggac ctcagccaca acaacctgac cttcctccct gccgacatcg        1400
gcctcctgca gaacctccag aacctagcca tcacggccaa ccggatcgag        1450
acgctccctc cggagctctt ccagtgccgg aagctgcggg ccctgcacct        1500
gggcaacaac gtgctgcagt cactgccctc cagggtgggc gagctgacca        1550
acctgacgca gatcgagctg cggggcaacc ggctggagtg cctgcctgtg        1600
gagctgggcg agtgcccact gctcaagcgc agcggcttgg tggtggagga        1650
ggacctgttc aacacactgc cacccgaggt gaaggagcgg ctgtggaggg        1700
ctgacaagga gcaggcctga gcgaggccgg cccagcacag caagcagcag        1750
gaccgctgcc cagtcctcag gcccggaggg gcaggcctag cttctcccag        1800
aactcccgga cagccaggac agcctcgcgg ctgggcagga gcctggggcc        1850
gcttgtgagt caggccagag cgagaggaca gtatctgtgg ggctggcccc        1900
ttttctccct ctgagactca cgtcccccag ggcaagtgct tgtggaggag        1950
agcaagtctc aagagcgcag tatttggata atcagggtct cctccctgga        2000
ggccagctct gccccagggg ctgagctgcc accagaggtc ctgggaccct        2050
cactttagtt cttggtattt atttttctcc atctcccacc tccttcatcc        2100
agataactta tacattccca agaaagttca gcccagatgg aaggtgttca        2150
gggaaaggtg ggctgccttt tccccttgtc cttatttagc gatgccgccg        2200
ggcatttaac acccacctgg acttcagcag agtggtccgg ggcgaaccag        2250
ccatgggacg gtcacccagc agtgccgggc tgggctctgc ggtgcggtcc        2300
acgggagagc aggcctccag ctggaaaggc caggcctgga gcttgcctct        2350
tcagtttttg tggcagtttt agtttttttgt tttttttttt tttaatcaaa        2400
aaacaatttt ttttaaaaaa aagctttgaa aatggatggt ttgggtatta        2450
aaaagaaaaa aaaaacttaa aaaaaaaaag acactaacgg ccagtgagtt        2500
ggagtctcag ggcagggtgg cagtttccct tgagcaaagc agccagacgt        2550
tgaactgtgt ttcctttccc tgggcgcagg gtgcagggtg tcttccggat        2600
ctggtgtgac cttggtccag gagttctatt tgttcctggg gagggaggtt        2650
tttttgtttg ttttttgggt ttttttggtg tcttgttttc tttctcctcc        2700
atgtgtcttg gcaggcactc atttctgtgg ctgtcggcca gagggaatgt        2750
tctggagctg ccaaggaggg aggagactcg ggttggctaa tccccggatg        2800
aacggtgctc cattcgcacc tcccctcctc gtgcctgccc tgcctctcca        2850
cgcacagtgt taaggagcca agaggagcca cttcgcccag actttgtttc        2900
cccacctcct gcggcatggg tgtgtccagt gccaccgctg gcctccgctg        2950
cttccatcag ccctgtcgcc acctggtcct tcatgaagag cagacactta        3000
gaggctggtc gggaatgggg aggtcgcccc tgggagggca ggcgttggtt        3050
ccaagccggt tcccgtccct ggcgcctgga gtgcacacag cccagtcggc        3100
acctggtggc tggaagccaa cctgctttag atcactcggg tccccacctt        3150
agaagggtcc ccgccttaga tcaatcacgt ggacactaag gcacgtttta        3200
gagtctcttg tcttaatgat tatgtccatc cgtctgtccg tccatttgtg        3250
ttttctgcgt cgtgtcattg gatataatcc tcagaaataa tgcacactag        3300
cctctgacaa ccatgaagca aaaatccgtt acatgtgggt ctgaacttgt        3350
```

agactcggtc acagtatcaa ataaaatcta taacagaaaa aaaaaaaaaa 3400
a 3401

<210> SEQ ID NO 250
<211> LENGTH: 546
<212> TYPE: PRT
<213> ORGANISM: Homo Sapien

<400> SEQUENCE: 250

Met Arg Gln Thr Ile Ile Lys Val Ile Lys Phe Ile Leu Ile Ile
1 5 10 15

Cys Tyr Thr Val Tyr Tyr Val His Asn Ile Lys Phe Asp Val Asp
20 25 30

Cys Thr Val Asp Ile Glu Ser Leu Thr Gly Tyr Arg Thr Tyr Arg
35 40 45

Cys Ala His Pro Leu Ala Thr Leu Phe Lys Ile Leu Ala Ser Phe
50 55 60

Tyr Ile Ser Leu Val Ile Phe Tyr Gly Leu Ile Cys Met Tyr Thr
65 70 75

Leu Trp Trp Met Leu Arg Arg Ser Leu Lys Lys Tyr Ser Phe Glu
80 85 90

Ser Ile Arg Glu Glu Ser Ser Tyr Ser Asp Ile Pro Asp Val Lys
95 100 105

Asn Asp Phe Ala Phe Met Leu His Leu Ile Asp Gln Tyr Asp Pro
110 115 120

Leu Tyr Ser Lys Arg Phe Ala Val Phe Leu Ser Glu Val Ser Glu
125 130 135

Asn Lys Leu Arg Gln Leu Asn Leu Asn Asn Glu Trp Thr Leu Asp
140 145 150

Lys Leu Arg Gln Arg Leu Thr Lys Asn Ala Gln Asp Lys Leu Glu
155 160 165

Leu His Leu Phe Met Leu Ser Gly Ile Pro Asp Thr Val Phe Asp
170 175 180

Leu Val Glu Leu Glu Val Leu Lys Leu Glu Leu Ile Pro Asp Val
185 190 195

Thr Ile Pro Pro Ser Ile Ala Gln Leu Thr Gly Leu Lys Glu Leu
200 205 210

Trp Leu Tyr His Thr Ala Ala Lys Ile Glu Ala Pro Ala Leu Ala
215 220 225

Phe Leu Arg Glu Asn Leu Arg Ala Leu His Ile Lys Phe Thr Asp
230 235 240

Ile Lys Glu Ile Pro Leu Trp Ile Tyr Ser Leu Lys Thr Leu Glu
245 250 255

Glu Leu His Leu Thr Gly Asn Leu Ser Ala Glu Asn Asn Arg Tyr
260 265 270

Ile Val Ile Asp Gly Leu Arg Glu Leu Lys Arg Leu Lys Val Leu
275 280 285

Arg Leu Lys Ser Asn Leu Ser Lys Leu Pro Gln Val Val Thr Asp
290 295 300

Val Gly Val His Leu Gln Lys Leu Ser Ile Asn Asn Glu Gly Thr
305 310 315

Lys Leu Ile Val Leu Asn Ser Leu Lys Lys Met Ala Asn Leu Thr
320 325 330

-continued

```
Glu Leu Glu Leu Ile Arg Cys Asp Leu Glu Arg Ile Pro His Ser
                335                 340                 345

Ile Phe Ser Leu His Asn Leu Gln Glu Ile Asp Leu Lys Asp Asn
                350                 355                 360

Asn Leu Lys Thr Ile Glu Glu Ile Ile Ser Phe Gln His Leu His
                365                 370                 375

Arg Leu Thr Cys Leu Lys Leu Trp Tyr Asn His Ile Ala Tyr Ile
                380                 385                 390

Pro Ile Gln Ile Gly Asn Leu Thr Asn Leu Glu Arg Leu Tyr Leu
                395                 400                 405

Asn Arg Asn Lys Ile Glu Lys Ile Pro Thr Gln Leu Phe Tyr Cys
                410                 415                 420

Arg Lys Leu Arg Tyr Leu Asp Leu Ser His Asn Asn Leu Thr Phe
                425                 430                 435

Leu Pro Ala Asp Ile Gly Leu Leu Gln Asn Leu Gln Asn Leu Ala
                440                 445                 450

Ile Thr Ala Asn Arg Ile Glu Thr Leu Pro Pro Glu Leu Phe Gln
                455                 460                 465

Cys Arg Lys Leu Arg Ala Leu His Leu Gly Asn Asn Val Leu Gln
                470                 475                 480

Ser Leu Pro Ser Arg Val Gly Glu Leu Thr Asn Leu Thr Gln Ile
                485                 490                 495

Glu Leu Arg Gly Asn Arg Leu Glu Cys Leu Pro Val Glu Leu Gly
                500                 505                 510

Glu Cys Pro Leu Leu Lys Arg Ser Gly Leu Val Val Glu Glu Asp
                515                 520                 525

Leu Phe Asn Thr Leu Pro Pro Glu Val Lys Glu Arg Leu Trp Arg
                530                 535                 540

Ala Asp Lys Glu Gln Ala
                545
```

<210> SEQ ID NO 251
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 251
caacaatgag ggcaccaagc 20

<210> SEQ ID NO 252
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 252
gatggctagg ttctggaggt tctg 24

<210> SEQ ID NO 253
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 253

-continued caacctgcag gagattgacc tcaaggacaa caacctcaag accatcg 47

<210> SEQ ID NO 254
<211> LENGTH: 1650
<212> TYPE: DNA
<213> ORGANISM: Homo Sapien

<400> SEQUENCE: 254
gcctgttgct gatgctgccg tgcggtactt gtcatggagc tggcactgcg 50
gcgctctccc gtcccgcggt ggttgctgct gctgccgctg ctgctgggcc 100
tgaacgcagg agctgtcatt gactggccca cagaggaggg caaggaagta 150
tgggattatg tgacggtccg caaggatgcc tacatgttct ggtggctcta 200
ttatgccacc aactcctgca agaacttctc agaactgccc ctggtcatgt 250
ggcttcaggg cggtccaggc ggttctagca ctggatttgg aaactttgag 300
gaaattgggc cccttgacag tgatctcaaa ccacggaaaa ccacctggct 350
ccaggctgcc agtctcctat ttgtggataa tcccgtgggc actgggttca 400
gttatgtgaa tggtagtggt gcctatgcca aggacctggc tatggtggct 450
tcagacatga tggttctcct gaagaccttc ttcagttgcc acaaagaatt 500
ccagacagtt ccattctaca ttttctcaga gtcctatgga ggaaaaatgg 550
cagctggcat tggtctagag ctttataagg ccattcagcg agggaccatc 600
aagtgcaact ttgcgggggt tgccttgggt gattcctgga tctcccctgt 650
tgattcggtg ctctcctggg gaccttacct gtacagcatg tctcttctcg 700
aagacaaagg tctggcagag gtgtctaagg ttgcagagca agtactgaat 750
gccgtaaata aggggctcta cagagaggcc acagagctgt gggggaaagc 800
agaaatgatc attgaacaga acacagatgg ggtgaacttc tataacatct 850
taactaaaag cactcccacg tctacaatgg agtcgagtct agaattcaca 900
cagagccacc tagtttgtct ttgtcagcgc cacgtgagac acctacaacg 950
agatgcctta agccagctca tgaatggccc catcagaaag aagctcaaaa 1000
ttattcctga ggatcaatcc tggggaggcc aggctaccaa cgtctttgtg 1050
aacatggagg aggacttcat gaagccagtc attagcattg tggacgagtt 1100
gctggaggca gggatcaacg tgacggtgta taatggacag ctggatctca 1150
tcgtagatac catgggtcag gaggcctggg tgcggaaact gaagtggcca 1200
gaactgccta aattcagtca gctgaagtgg aaggccctgt acagtgaccc 1250
taaatctttg gaaacatctg cttttgtcaa gtcctacaag aaccttgctt 1300
tctactggat tctgaaagct ggtcatatgg ttccttctga ccaaggggac 1350
atggctctga agatgatgag actggtgact cagcaagaat aggatggatg 1400
gggctggaga tgagctggtt tggccttggg gcacagagct gagctgaggc 1450
cgctgaagct gtaggaagcg ccattcttcc ctgtatctaa ctggggctgt 1500
gatcaagaag gttctgacca gcttctgcag aggataaaat cattgtctct 1550
ggaggcaatt tggaaattat ttctgcttct taaaaaaacc taagattttt 1600
taaaaaattg atttgttttg atcaaaataa aggatgataa tagatattaa 1650

<210> SEQ ID NO 255
<211> LENGTH: 452

-continued

<212> TYPE: PRT
<213> ORGANISM: Homo Sapien

<400> SEQUENCE: 255

```
Met Glu Leu Ala Leu Arg Arg Ser Pro Val Pro Arg Trp Leu Leu
  1               5                  10                  15

Leu Leu Pro Leu Leu Leu Gly Leu Asn Ala Gly Ala Val Ile Asp
                 20                  25                  30

Trp Pro Thr Glu Glu Gly Lys Glu Val Trp Asp Tyr Val Thr Val
                 35                  40                  45

Arg Lys Asp Ala Tyr Met Phe Trp Trp Leu Tyr Tyr Ala Thr Asn
                 50                  55                  60

Ser Cys Lys Asn Phe Ser Glu Leu Pro Leu Val Met Trp Leu Gln
                 65                  70                  75

Gly Gly Pro Gly Gly Ser Ser Thr Gly Phe Gly Asn Phe Glu Glu
                 80                  85                  90

Ile Gly Pro Leu Asp Ser Asp Leu Lys Pro Arg Lys Thr Thr Trp
                 95                 100                 105

Leu Gln Ala Ala Ser Leu Leu Phe Val Asp Asn Pro Val Gly Thr
                110                 115                 120

Gly Phe Ser Tyr Val Asn Gly Ser Gly Ala Tyr Ala Lys Asp Leu
                125                 130                 135

Ala Met Val Ala Ser Asp Met Met Val Leu Leu Lys Thr Phe Phe
                140                 145                 150

Ser Cys His Lys Glu Phe Gln Thr Val Pro Phe Tyr Ile Phe Ser
                155                 160                 165

Glu Ser Tyr Gly Gly Lys Met Ala Ala Gly Ile Gly Leu Glu Leu
                170                 175                 180

Tyr Lys Ala Ile Gln Arg Gly Thr Ile Lys Cys Asn Phe Ala Gly
                185                 190                 195

Val Ala Leu Gly Asp Ser Trp Ile Ser Pro Val Asp Ser Val Leu
                200                 205                 210

Ser Trp Gly Pro Tyr Leu Tyr Ser Met Ser Leu Leu Glu Asp Lys
                215                 220                 225

Gly Leu Ala Glu Val Ser Lys Val Ala Glu Gln Val Leu Asn Ala
                230                 235                 240

Val Asn Lys Gly Leu Tyr Arg Glu Ala Thr Glu Leu Trp Gly Lys
                245                 250                 255

Ala Glu Met Ile Ile Glu Gln Asn Thr Asp Gly Val Asn Phe Tyr
                260                 265                 270

Asn Ile Leu Thr Lys Ser Thr Pro Thr Ser Thr Met Glu Ser Ser
                275                 280                 285

Leu Glu Phe Thr Gln Ser His Leu Val Cys Leu Cys Gln Arg His
                290                 295                 300

Val Arg His Leu Gln Arg Asp Ala Leu Ser Gln Leu Met Asn Gly
                305                 310                 315

Pro Ile Arg Lys Lys Leu Lys Ile Ile Pro Glu Asp Gln Ser Trp
                320                 325                 330

Gly Gly Gln Ala Thr Asn Val Phe Val Asn Met Glu Glu Asp Phe
                335                 340                 345

Met Lys Pro Val Ile Ser Ile Val Asp Glu Leu Leu Glu Ala Gly
                350                 355                 360

Ile Asn Val Thr Val Tyr Asn Gly Gln Leu Asp Leu Ile Val Asp
                365                 370                 375
```

-continued

```
Thr Met Gly Gln Glu Ala Trp Val Arg Lys Leu Lys Trp Pro Glu
                380                 385                 390

Leu Pro Lys Phe Ser Gln Leu Lys Trp Lys Ala Leu Tyr Ser Asp
                395                 400                 405

Pro Lys Ser Leu Glu Thr Ser Ala Phe Val Lys Ser Tyr Lys Asn
                410                 415                 420

Leu Ala Phe Tyr Trp Ile Leu Lys Ala Gly His Met Val Pro Ser
                425                 430                 435

Asp Gln Gly Asp Met Ala Leu Lys Met Met Arg Leu Val Thr Gln
                440                 445                 450

Gln Glu
```

<210> SEQ ID NO 256
<211> LENGTH: 1100
<212> TYPE: DNA
<213> ORGANISM: Homo Sapien

<400> SEQUENCE: 256

```
ggccgcggga gaggaggcca tgggcgcgcg cggggcgctg ctgctggcgc          50
tgctgctggc tcgggctgga ctcaggaagc cggagtcgca ggaggcggcg         100
ccgttatcag gaccatgcgg ccgacgggtc atcacgtcgc gcatcgtggg         150
tggagaggac gccgaactcg ggcgttggcc gtggcagggg agcctgcgcc         200
tgtgggattc ccacgtatgc ggagtgagcc tgctcagcca ccgctgggca         250
ctcacggcgg cgcactgctt tgaaacctat agtgacctta gtgatccctc         300
cgggtggatg gtccagtttg gccagctgac ttccatgcca tccttctgga         350
gcctgcaggc ctactacacc cgttacttcg tatcgaatat ctatctgagc         400
cctcgctacc tggggaattc accctatgac attgccttgg tgaagctgtc         450
tgcacctgtc acctacacta aacacatcca gcccatctgt ctccaggcct         500
ccacatttga gtttgagaac cggacagact gctgggtgac tggctggggg         550
tacatcaaag aggatgaggc actgccatct ccccacaccc tccaggaagt         600
tcaggtcgcc atcataaaca actctatgtg caaccacctc ttcctcaagt         650
acagtttccg caaggacatc tttggagaca tggtttgtgc tggcaacgcc         700
caaggcggga aggatgcctg cttcggtgac tcaggtggac ccttggcctg         750
taacaagaat ggactgtggt atcagattgg agtcgtgagc tggggagtgg         800
gctgtggtcg gcccaatcgg cccggtgtct acaccaatat cagccaccac         850
tttgagtgga tccagaagct gatggcccag agtggcatgt cccagccaga         900
cccctcctgg ccactactct tttccctctt tctctgggct ctcccactcc         950
tggggccggt ctgagcctac ctgagcccat gcagcctggg gccactgcca        1000
agtcaggccc tggttctctt ctgtcttgtt tggtaataaa cacattccag        1050
ttgatgcctt gcagggcatt cttcaaaaaa aaaaaaaaaa aaaaaaaaaa        1100
```

<210> SEQ ID NO 257
<211> LENGTH: 314
<212> TYPE: PRT
<213> ORGANISM: Homo Sapien

<400> SEQUENCE: 257

```
Met Gly Ala Arg Gly Ala Leu Leu Leu Ala Leu Leu Leu Ala Arg
```

-continued

```
1               5                   10                  15

Ala Gly Leu Arg Lys Pro Glu Ser Gln Glu Ala Ala Pro Leu Ser
                20                  25                  30

Gly Pro Cys Gly Arg Arg Val Ile Thr Ser Arg Ile Val Gly Gly
                35                  40                  45

Glu Asp Ala Glu Leu Gly Arg Trp Pro Trp Gln Gly Ser Leu Arg
                50                  55                  60

Leu Trp Asp Ser His Val Cys Gly Val Ser Leu Leu Ser His Arg
                65                  70                  75

Trp Ala Leu Thr Ala Ala His Cys Phe Glu Thr Tyr Ser Asp Leu
                80                  85                  90

Ser Asp Pro Ser Gly Trp Met Val Gln Phe Gly Gln Leu Thr Ser
                95                  100                 105

Met Pro Ser Phe Trp Ser Leu Gln Ala Tyr Tyr Thr Arg Tyr Phe
                110                 115                 120

Val Ser Asn Ile Tyr Leu Ser Pro Arg Tyr Leu Gly Asn Ser Pro
                125                 130                 135

Tyr Asp Ile Ala Leu Val Lys Leu Ser Ala Pro Val Thr Tyr Thr
                140                 145                 150

Lys His Ile Gln Pro Ile Cys Leu Gln Ala Ser Thr Phe Glu Phe
                155                 160                 165

Glu Asn Arg Thr Asp Cys Trp Val Thr Gly Trp Gly Tyr Ile Lys
                170                 175                 180

Glu Asp Glu Ala Leu Pro Ser Pro His Thr Leu Gln Glu Val Gln
                185                 190                 195

Val Ala Ile Ile Asn Asn Ser Met Cys Asn His Leu Phe Leu Lys
                200                 205                 210

Tyr Ser Phe Arg Lys Asp Ile Phe Gly Asp Met Val Cys Ala Gly
                215                 220                 225

Asn Ala Gln Gly Gly Lys Asp Ala Cys Phe Gly Asp Ser Gly Gly
                230                 235                 240

Pro Leu Ala Cys Asn Lys Asn Gly Leu Trp Tyr Gln Ile Gly Val
                245                 250                 255

Val Ser Trp Gly Val Gly Cys Gly Arg Pro Asn Arg Pro Gly Val
                260                 265                 270

Tyr Thr Asn Ile Ser His His Phe Glu Trp Ile Gln Lys Leu Met
                275                 280                 285

Ala Gln Ser Gly Met Ser Gln Pro Asp Pro Ser Trp Pro Leu Leu
                290                 295                 300

Phe Phe Pro Leu Leu Trp Ala Leu Pro Leu Leu Gly Pro Val
                305                 310
```

<210> SEQ ID NO 258
<211> LENGTH: 2427
<212> TYPE: DNA
<213> ORGANISM: Homo Sapien

<400> SEQUENCE: 258

```
cccacgcgtc cgcggacgcg tgggaagggc agaatgggac tccaagcctg        50

cctcctaggg ctctttgccc tcatcctctc tggcaaatgc agttacagcc       100

cggagcccga ccagcggagg acgctgcccc caggctgggt gtccctgggc       150

cgtgcggacc ctgaggaaga gctgagtctc acctttgccc tgagacagca       200

gaatgtggaa agactctcgg agctggtgca ggctgtgtcg gatcccagct       250
```

-continued

```
ctcctcaata cggaaaatac ctgaccctag agaatgtggc tgatctggtg        300
aggccatccc cactgaccct ccacacggtg caaaaatggc tcttggcagc        350
cggagcccag aagtgccatt ctgtgatcac acaggacttt ctgacttgct        400
ggctgagcat ccgacaagca gagctgctgc tccctggggc tgagtttcat        450
cactatgtgg gaggacctac ggaaacccat gttgtaaggt ccccacatcc        500
ctaccagctt ccacaggcct tggcccccca tgtggacttt gtgggggac         550
tgcaccgttt tcccccaaca tcatccctga ggcaacgtcc tgagccgcag        600
gtgacaggga ctgtaggcct gcatctgggg gtaacccct ctgtgatccg         650
taagcgatac aacttgacct cacaagacgt gggctctggc accagcaata        700
acagccaagc ctgtgcccag ttcctggagc agtatttcca tgactcagac        750
ctggctcagt tcatgcgcct cttcggtggc aactttgcac atcaggcatc        800
agtagcccgt gtggttggac aacagggccg ggccgggcc gggattgagg         850
ccagtctaga tgtgcagtac ctgatgagtg ctggtgccaa catctccacc        900
tgggtctaca gtagccctgg ccggcatgag ggacaggagc ccttcctgca        950
gtggctcatg ctgctcagta atgagtcagc cctgccacat gtgcatactg       1000
tgagctatgg agatgatgag gactccctca gcagcgccta catccagcgg       1050
gtcaacactg agctcatgaa ggctgccgct cggggtctca ccctgctctt       1100
cgcctcaggt gacagtgggg ccgggtgttg gtctgtctct ggaagacacc       1150
agttccgccc taccttccct gcctccagcc cctatgtcac cacagtggga       1200
ggcacatcct tccaggaacc tttcctcatc acaaatgaaa ttgttgacta       1250
tatcagtggt ggtggcttca gcaatgtgtt cccacggcct tcataccagg       1300
aggaagctgt aacgaagttc ctgagctcta gcccccacct gccaccatcc       1350
agttacttca atgccagtgg ccgtgcctac ccagatgtgg ctgcactttc       1400
tgatggctac tgggtggtca gcaacagagt gcccattcca tgggtgtccg       1450
gaacctcggc ctctactcca gtgtttgggg ggatcctatc cttgatcaat       1500
gagcacagga tccttagtgg ccgcccccct cttggctttc tcaacccaag       1550
gctctaccag cagcatgggg caggtctctt tgatgtaacc cgtggctgcc       1600
atgagtcctg tctggatgaa gaggtagagg gccagggttt ctgctctggt       1650
cctggctggg atcctgtaac aggctgggga acaccaactt cccagctttg       1700
ctgaagactc tactcaaccc ctgacccttt cctatcagga gagatggctt       1750
gtcccctgcc ctgaagctgg cagttcagtc ccttattctg ccctgttgga       1800
agccctgctg aaccctcaac tattgactgc tgcagacagc ttatctccct       1850
aaccctgaaa tgctgtgagc ttgacttgac tcccaaccct accatgctcc       1900
atcatactca ggtctcccta ctcctgcctt agattcctca ataagatgct       1950
gtaactagca ttttttgaat gcctctccct ccgcatctca tctttctctt       2000
ttcaatcagg cttttccaaa gggttgtata cagactctgt gcactatttc       2050
acttgatatt cattccccaa ttcactgcaa ggagacctct actgtcaccg       2100
tttactcttt cctaccctga catccagaaa caatggcctc cagtgcatac       2150
ttctcaatct ttgctttatg gcctttccat catagttgcc cactccctct       2200
```

-continued

```
ccttacttag cttccaggtc ttaacttctc tgactactct tgtcttcctc          2250

tctcatcaat ttctgcttct tcatggaatg ctgaccttca ttgctccatt          2300

tgtagatttt tgctcttctc agtttactca ttgtcccctg gaacaaatca          2350

ctgacatcta caaccattac catctcacta aataagactt tctatccaat          2400

aatgattgat acctcaaatg taaaaaa                                   2427


<210> SEQ ID NO 259
<211> LENGTH: 556
<212> TYPE: PRT
<213> ORGANISM: Homo Sapien

<400> SEQUENCE: 259

Met Gly Leu Gln Ala Cys Leu Leu Gly Leu Phe Ala Leu Ile Leu
  1               5                  10                  15

Ser Gly Lys Cys Ser Tyr Ser Pro Glu Pro Asp Gln Arg Arg Thr
                 20                  25                  30

Leu Pro Pro Gly Trp Val Ser Leu Gly Arg Ala Asp Pro Glu Glu
                 35                  40                  45

Glu Leu Ser Leu Thr Phe Ala Leu Arg Gln Gln Asn Val Glu Arg
                 50                  55                  60

Leu Ser Glu Leu Val Gln Ala Val Ser Asp Pro Ser Ser Pro Gln
                 65                  70                  75

Tyr Gly Lys Tyr Leu Thr Leu Glu Asn Val Ala Asp Leu Val Arg
                 80                  85                  90

Pro Ser Pro Leu Thr Leu His Thr Val Gln Lys Trp Leu Leu Ala
                 95                 100                 105

Ala Gly Ala Gln Lys Cys His Ser Val Ile Thr Gln Asp Phe Leu
                110                 115                 120

Thr Cys Trp Leu Ser Ile Arg Gln Ala Glu Leu Leu Leu Pro Gly
                125                 130                 135

Ala Glu Phe His His Tyr Val Gly Gly Pro Thr Glu Thr His Val
                140                 145                 150

Val Arg Ser Pro His Pro Tyr Gln Leu Pro Gln Ala Leu Ala Pro
                155                 160                 165

His Val Asp Phe Val Gly Gly Leu His Arg Phe Pro Pro Thr Ser
                170                 175                 180

Ser Leu Arg Gln Arg Pro Glu Pro Gln Val Thr Gly Thr Val Gly
                185                 190                 195

Leu His Leu Gly Val Thr Pro Ser Val Ile Arg Lys Arg Tyr Asn
                200                 205                 210

Leu Thr Ser Gln Asp Val Gly Ser Gly Thr Ser Asn Asn Ser Gln
                215                 220                 225

Ala Cys Ala Gln Phe Leu Glu Gln Tyr Phe His Asp Ser Asp Leu
                230                 235                 240

Ala Gln Phe Met Arg Leu Phe Gly Gly Asn Phe Ala His Gln Ala
                245                 250                 255

Ser Val Ala Arg Val Val Gly Gln Gln Gly Arg Gly Arg Ala Gly
                260                 265                 270

Ile Glu Ala Ser Leu Asp Val Gln Tyr Leu Met Ser Ala Gly Ala
                275                 280                 285

Asn Ile Ser Thr Trp Val Tyr Ser Ser Pro Gly Arg His Glu Gly
                290                 295                 300

Gln Glu Pro Phe Leu Gln Trp Leu Met Leu Leu Ser Asn Glu Ser
```

-continued

```
                305                 310                 315

Ala Leu Pro His Val His Thr Val Ser Tyr Gly Asp Asp Glu Asp
                320                 325                 330

Ser Leu Ser Ser Ala Tyr Ile Gln Arg Val Asn Thr Glu Leu Met
                335                 340                 345

Lys Ala Ala Ala Arg Gly Leu Thr Leu Leu Phe Ala Ser Gly Asp
                350                 355                 360

Ser Gly Ala Gly Cys Trp Ser Val Ser Gly Arg His Gln Phe Arg
                365                 370                 375

Pro Thr Phe Pro Ala Ser Ser Pro Tyr Val Thr Thr Val Gly Gly
                380                 385                 390

Thr Ser Phe Gln Glu Pro Phe Leu Ile Thr Asn Glu Ile Val Asp
                395                 400                 405

Tyr Ile Ser Gly Gly Gly Phe Ser Asn Val Phe Pro Arg Pro Ser
                410                 415                 420

Tyr Gln Glu Glu Ala Val Thr Lys Phe Leu Ser Ser Ser Pro His
                425                 430                 435

Leu Pro Pro Ser Ser Tyr Phe Asn Ala Ser Gly Arg Ala Tyr Pro
                440                 445                 450

Asp Val Ala Ala Leu Ser Asp Gly Tyr Trp Val Val Ser Asn Arg
                455                 460                 465

Val Pro Ile Pro Trp Val Ser Gly Thr Ser Ala Ser Thr Pro Val
                470                 475                 480

Phe Gly Gly Ile Leu Ser Leu Ile Asn Glu His Arg Ile Leu Ser
                485                 490                 495

Gly Arg Pro Pro Leu Gly Phe Leu Asn Pro Arg Leu Tyr Gln Gln
                500                 505                 510

His Gly Ala Gly Leu Phe Asp Val Thr Arg Gly Cys His Glu Ser
                515                 520                 525

Cys Leu Asp Glu Glu Val Glu Gly Gln Gly Phe Cys Ser Gly Pro
                530                 535                 540

Gly Trp Asp Pro Val Thr Gly Trp Gly Thr Pro Thr Ser Gln Leu
                545                 550                 555

Cys
```

<210> SEQ ID NO 260
<211> LENGTH: 1638
<212> TYPE: DNA
<213> ORGANISM: Homo Sapien

<400> SEQUENCE: 260

```
gccgcgcgct ctctcccggc gcccacacct gtctgagcgg cgcagcgagc        50

cgcggcccgg gcgggctgct cggcgcggaa cagtgctcgg catggcaggg       100

attccagggc tcctcttcct tctcttcttt ctgctctgtg ctgttgggca       150

agtgagccct tacagtgccc cctggaaacc cacttggcct gcataccgcc       200

tccctgtcgt cttgccccag tctaccctca atttagccaa gccagacttt       250

ggagccgaag ccaaattaga agtatcttct tcatgtggac cccagtgtca       300

taagggaact ccactgccca cttacgaaga ggccaagcaa tatctgtctt       350

atgaaacgct ctatgccaat ggcagccgca cagagacgca ggtgggcatc       400

tacatcctca gcagtagtgg agatggggcc caacaccgag actcagggtc       450

ttcaggaaag tctcgaagga agcggcagat ttatggctat gacagcaggt       500
```

```
tcagcatttt tgggaaggac ttcctgctca actacccttt ctcaacatca           550

gtgaagttat ccacgggctg caccggcacc ctggtggcag agaagcatgt           600

cctcacagct gcccactgca tacacgatgg aaaaacctat gtgaaaggaa           650

cccagaagct tcgagtgggc ttcctaaagc ccaagtttaa agatggtggt           700

cgaggggcca acgactccac ttcagccatg cccgagcaga tgaaatttca           750

gtggatccgg gtgaaacgca cccatgtgcc caagggttgg atcaagggca           800

atgccaatga catcggcatg gattatgatt atgccctcct ggaactcaaa           850

aagccccaca agagaaaatt tatgaagatt ggggtgagcc ctcctgctaa           900

gcagctgcca gggggcagaa ttcacttctc tggttatgac aatgaccgac           950

caggcaattt ggtgtatcgc ttctgtgacg tcaaagacga gacctatgac          1000

ttgctctacc agcaatgcga tgcccagcca ggggccagcg ggtctggggt          1050

ctatgtgagg atgtggaaga gacagcagca gaagtgggag cgaaaaatta          1100

ttggcatttt ttcagggcac cagtgggtgg acatgaatgg ttccccacag          1150

gatttcaacg tggctgtcag aatcactcct ctcaaatatg cccagatttg          1200

ctattggatt aaaggaaact acctggattg tagggagggg tgacacagtg          1250

ttccctcctg gcagcaatta agggtcttca tgttcttatt ttaggagagg          1300

ccaaattgtt ttttgtcatt ggcgtgcaca cgtgtgtgtg tgtgtgtgtg          1350

tgtgtgtaag gtgtcttata atcttttacc tatttcttac aattgcaaga          1400

tgactggctt tactatttga aaactggttt gtgtatcata tcatatatca          1450

tttaagcagt ttgaaggcat acttttgcat agaaataaaa aaaatactga          1500

tttggggcaa tgaggaatat ttgacaatta agttaatctt cacgtttttg          1550

caaactttga tttttatttc atctgaactt gtttcaaaga tttatattaa          1600

atatttggca tacaagagat atgaaaaaaa aaaaaaaa                      1638
```

```
<210> SEQ ID NO 261
<211> LENGTH: 383
<212> TYPE: PRT
<213> ORGANISM: Homo Sapien

<400> SEQUENCE: 261

Met Ala Gly Ile Pro Gly Leu Leu Phe Leu Leu Phe Phe Leu Leu
  1               5                  10                  15

Cys Ala Val Gly Gln Val Ser Pro Tyr Ser Ala Pro Trp Lys Pro
                 20                  25                  30

Thr Trp Pro Ala Tyr Arg Leu Pro Val Val Leu Pro Gln Ser Thr
                 35                  40                  45

Leu Asn Leu Ala Lys Pro Asp Phe Gly Ala Glu Ala Lys Leu Glu
                 50                  55                  60

Val Ser Ser Ser Cys Gly Pro Gln Cys His Lys Gly Thr Pro Leu
                 65                  70                  75

Pro Thr Tyr Glu Glu Ala Lys Gln Tyr Leu Ser Tyr Glu Thr Leu
                 80                  85                  90

Tyr Ala Asn Gly Ser Arg Thr Glu Thr Gln Val Gly Ile Tyr Ile
                 95                 100                 105

Leu Ser Ser Ser Gly Asp Gly Ala Gln His Arg Asp Ser Gly Ser
                110                 115                 120
```

-continued

```
Ser Gly Lys Ser Arg Arg Lys Arg Gln Ile Tyr Gly Tyr Asp Ser
                125                 130                 135

Arg Phe Ser Ile Phe Gly Lys Asp Phe Leu Leu Asn Tyr Pro Phe
                140                 145                 150

Ser Thr Ser Val Lys Leu Ser Thr Gly Cys Thr Gly Thr Leu Val
                155                 160                 165

Ala Glu Lys His Val Leu Thr Ala Ala His Cys Ile His Asp Gly
                170                 175                 180

Lys Thr Tyr Val Lys Gly Thr Gln Lys Leu Arg Val Gly Phe Leu
                185                 190                 195

Lys Pro Lys Phe Lys Asp Gly Gly Arg Gly Ala Asn Asp Ser Thr
                200                 205                 210

Ser Ala Met Pro Glu Gln Met Lys Phe Gln Trp Ile Arg Val Lys
                215                 220                 225

Arg Thr His Val Pro Lys Gly Trp Ile Lys Gly Asn Ala Asn Asp
                230                 235                 240

Ile Gly Met Asp Tyr Asp Tyr Ala Leu Leu Glu Leu Lys Lys Pro
                245                 250                 255

His Lys Arg Lys Phe Met Lys Ile Gly Val Ser Pro Pro Ala Lys
                260                 265                 270

Gln Leu Pro Gly Gly Arg Ile His Phe Ser Gly Tyr Asp Asn Asp
                275                 280                 285

Arg Pro Gly Asn Leu Val Tyr Arg Phe Cys Asp Val Lys Asp Glu
                290                 295                 300

Thr Tyr Asp Leu Leu Tyr Gln Gln Cys Asp Ala Gln Pro Gly Ala
                305                 310                 315

Ser Gly Ser Gly Val Tyr Val Arg Met Trp Lys Arg Gln Gln Gln
                320                 325                 330

Lys Trp Glu Arg Lys Ile Ile Gly Ile Phe Ser Gly His Gln Trp
                335                 340                 345

Val Asp Met Asn Gly Ser Pro Gln Asp Phe Asn Val Ala Val Arg
                350                 355                 360

Ile Thr Pro Leu Lys Tyr Ala Gln Ile Cys Tyr Trp Ile Lys Gly
                365                 370                 375

Asn Tyr Leu Asp Cys Arg Glu Gly
                380
```

<210> SEQ ID NO 262
<211> LENGTH: 1378
<212> TYPE: DNA
<213> ORGANISM: Homo Sapien

<400> SEQUENCE: 262

```
gcatcgccct gggtctctcg agcctgctgc ctgctccccc gccccaccag        50

ccatggtggt ttctggagcg cccccagccc tgggtggggg ctgtctcggc       100

accttcacct ccctgctgct gctggcgtcg acagccatcc tcaatgcggc       150

caggatacct gttcccccag cctgtgggaa gccccagcag ctgaaccggg       200

ttgtgggcgg cgaggacagc actgacagcg agtggccctg gatcgtgagc       250

atccagaaga atgggaccca ccactgcgca ggttctctgc tcaccagccg       300

ctgggtgatc actgctgccc actgtttcaa ggacaacctg aacaaaccat       350

acctgttctc tgtgctgctg ggggcctggc agctggggaa ccctggctct       400

cggtcccaga aggtgggtgt tgcctgggtg gagccccacc ctgtgtattc       450
```

-continued

```
ctggaaggaa ggtgcctgtg cagacattgc cctggtgcgt ctcgagcgct        500

ccatacagtt ctcagagcgg gtcctgccca tctgcctacc tgatgcctct        550

atccacctcc ctccaaacac ccactgctgg atctcaggct gggggagcat        600

ccaagatgga gttcccttgc cccaccctca gaccctgcag aagctgaagg        650

ttcctatcat cgactcggaa gtctgcagcc atctgtactg gcggggagca        700

ggacagggac ccatcactga ggacatgctg tgtgccggct acttggaggg        750

ggagcgggat gcttgtctgg gcgactccgg gggccccctc atgtgccagg        800

tggacggcgc ctggctgctg gccggcatca tcagctgggg cgagggctgt        850

gccgagcgca acaggcccgg ggtctacatc agcctctctg cgcaccgctc        900

ctgggtggag aagatcgtgc aaggggtgca gctccgcggg cgcgctcagg        950

ggggtggggc cctcagggca ccgagccagg gctctggggc cgccgcgcgc       1000

tcctagggcg cagcgggacg cggggctcgg atctgaaagg cggccagatc       1050

cacatctgga tctggatctg cggcggcctc gggcggtttc cccgccgta        1100

aataggctca tctacctcta cctctggggg cccggacggc tgctgcggaa       1150

aggaaacccc ctccccgacc cgcccgacgg cctcaggccc ccctccaagg       1200

catcaggccc cgcccaacgg cctcatgtcc ccgcccccac gacttccggc       1250

cccgcccccg ggccccagcg cttttgtgta tataaatgtt aatgattttt       1300

ataggtattt gtaaccctgc ccacatatct tatttattcc tccaatttca       1350

ataaattatt tattctccaa aaaaaaaa                               1378
```

```
<210> SEQ ID NO 263
<211> LENGTH: 317
<212> TYPE: PRT
<213> ORGANISM: Homo Sapien

<400> SEQUENCE: 263

Met Val Val Ser Gly Ala Pro Pro Ala Leu Gly Gly Gly Cys Leu
  1               5                  10                  15

Gly Thr Phe Thr Ser Leu Leu Leu Leu Ala Ser Thr Ala Ile Leu
                 20                  25                  30

Asn Ala Ala Arg Ile Pro Val Pro Pro Ala Cys Gly Lys Pro Gln
                 35                  40                  45

Gln Leu Asn Arg Val Val Gly Gly Glu Asp Ser Thr Asp Ser Glu
                 50                  55                  60

Trp Pro Trp Ile Val Ser Ile Gln Lys Asn Gly Thr His His Cys
                 65                  70                  75

Ala Gly Ser Leu Leu Thr Ser Arg Trp Val Ile Thr Ala Ala His
                 80                  85                  90

Cys Phe Lys Asp Asn Leu Asn Lys Pro Tyr Leu Phe Ser Val Leu
                 95                 100                 105

Leu Gly Ala Trp Gln Leu Gly Asn Pro Gly Ser Arg Ser Gln Lys
                110                 115                 120

Val Gly Val Ala Trp Val Glu Pro His Pro Val Tyr Ser Trp Lys
                125                 130                 135

Glu Gly Ala Cys Ala Asp Ile Ala Leu Val Arg Leu Glu Arg Ser
                140                 145                 150

Ile Gln Phe Ser Glu Arg Val Leu Pro Ile Cys Leu Pro Asp Ala
                155                 160                 165
```

-continued

Ser Ile His Leu Pro Pro Asn Thr His Cys Trp Ile Ser Gly Trp
170 175 180

Gly Ser Ile Gln Asp Gly Val Pro Leu Pro His Pro Gln Thr Leu
185 190 195

Gln Lys Leu Lys Val Pro Ile Ile Asp Ser Glu Val Cys Ser His
200 205 210

Leu Tyr Trp Arg Gly Ala Gly Gln Gly Pro Ile Thr Glu Asp Met
215 220 225

Leu Cys Ala Gly Tyr Leu Glu Gly Glu Arg Asp Ala Cys Leu Gly
230 235 240

Asp Ser Gly Gly Pro Leu Met Cys Gln Val Asp Gly Ala Trp Leu
245 250 255

Leu Ala Gly Ile Ile Ser Trp Gly Glu Gly Cys Ala Glu Arg Asn
260 265 270

Arg Pro Gly Val Tyr Ile Ser Leu Ser Ala His Arg Ser Trp Val
275 280 285

Glu Lys Ile Val Gln Gly Val Gln Leu Arg Gly Arg Ala Gln Gly
290 295 300

Gly Gly Ala Leu Arg Ala Pro Ser Gln Gly Ser Gly Ala Ala Ala
305 310 315

Arg Ser

<210> SEQ ID NO 264
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 264
gtccgcaagg atgcctacat gttc 24

<210> SEQ ID NO 265
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 265
gcagaggtgt ctaaggttg 19

<210> SEQ ID NO 266
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 266
agctctagac caatgccagc ttcc 24

<210> SEQ ID NO 267
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 267

-continued

```
gccaccaact cctgcaagaa cttctcagaa ctgcccctgg tcatg                 45


<210> SEQ ID NO 268
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 268

ggggaattca ccctatgaca ttgcc                                       25


<210> SEQ ID NO 269
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 269

gaatgccctg caagcatcaa ctgg                                        24


<210> SEQ ID NO 270
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 270

gcacctgtca cctacactaa acacatccag cccatctgtc tccaggcctc            50


<210> SEQ ID NO 271
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 271

gcggaagggc agaatgggac tccaag                                      26


<210> SEQ ID NO 272
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 272

cagccctgcc acatgtgc                                               18


<210> SEQ ID NO 273
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 273

tactgggtgg tcagcaac                                               18


<210> SEQ ID NO 274
<211> LENGTH: 24
<212> TYPE: DNA
<213> ORGANISM: Artificial Sequence
```

-continued

<220> FEATURE:
<223> OTHER INFORMATION: Synthetic Oligonucleotide Probe

<400> SEQUENCE: 274
ggcgaagagc agggtgagac cccg 24

<210> SEQ ID NO 275
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 275
gccctcatcc tctctggcaa atgcagttac agcccggagc ccgac 45

<210> SEQ ID NO 276
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 276
gggcagggat tccagggctc c 21

<210> SEQ ID NO 277
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 277
ggctatgaca gcaggttc 18

<210> SEQ ID NO 278
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 278
tgacaatgac cgaccagg 18

<210> SEQ ID NO 279
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 279
gcatcgcatt gctggtagag caag 24

<210> SEQ ID NO 280
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 280
ttacagtgcc ccctggaaac ccacttggcc tgcataccgc ctccc 45

-continued

<210> SEQ ID NO 281
<211> LENGTH: 34
<212> TYPE: DNA
<213> ORGANISM: Artificial Sequence
<220> FEATURE:
<223> OTHER INFORMATION: Synthetic Oligonucleotide Probe

<400> SEQUENCE: 281
cgtctcgagc gctccataca gttcccttgc ccca 34

<210> SEQ ID NO 282
<211> LENGTH: 61
<212> TYPE: DNA
<213> ORGANISM: Artificial Sequence
<220> FEATURE:
<223> OTHER INFORMATION: Synthetic Oligonucleotide Probe

<400> SEQUENCE: 282
tggaggggga gcgggatgct tgtctgggcg actccggggg ccccctcatg 50
tgccaggtgg a 61

<210> SEQ ID NO 283
<211> LENGTH: 119
<212> TYPE: DNA
<213> ORGANISM: Artificial Sequence
<220> FEATURE:
<223> OTHER INFORMATION: Synthetic Oligonucleotide Probe

<400> SEQUENCE: 283
ccctcagacc ctgcagaagc tgaaggttcc tatcatcgac tcggaagtct 50
gcagccatct gtactggcgg ggagcaggac agggacccat cactgaggac 100
atgctgtgtg ccggctact 119

<210> SEQ ID NO 284
<211> LENGTH: 1875
<212> TYPE: DNA
<213> ORGANISM: Homo Sapien

<400> SEQUENCE: 284
gacggctggc caccatgcac ggctcctgca gtttcctgat gcttctgctg 50
ccgctactgc tactgctggt ggccaccaca ggccccgttg gagccctcac 100
agatgaggag aaacgtttga tggtggagct gcacaacctc taccgggccc 150
aggtatcccc gacggcctca gacatgctgc acatgagatg ggacgaggag 200
ctggccgcct tcgccaaggc ctacgcacgg cagtgcgtgt ggggccacaa 250
caaggagcgc gggcgccgcg gcgagaatct gttcgccatc acagacgagg 300
gcatggacgt gccgctggcc atggaggagt ggcaccacga gcgtgagcac 350
tacaacctca gcgccgccac ctgcagccca ggccagatgt gcggccacta 400
cacgcaggtg gtatgggcca agacagagag gatcggctgt ggttcccact 450
tctgtgagaa gctccagggt gttgaggaga ccaacatcga attactggtg 500
tgcaactatg agcctccggg gaacgtgaag gggaaacggc cctaccagga 550
ggggactccg tgctcccaat gtccctctgg ctaccactgc aagaactccc 600
tctgtgaacc catcggaagc ccggaagatg ctcaggattt gccttacctg 650
gtaactgagg ccccatcctt ccgggcgact gaagcatcag actctaggaa 700
aatgggtact ccttcttccc tagcaacggg gattccggct ttcttggtaa 750

-continued

```
cagaggtctc aggctccctg gcaaccaagg ctctgcctgc tgtggaaacc          800

caggccccaa cttccttagc aacgaaagac ccgccctcca tggcaacaga          850

ggctccacct tgcgtaacaa ctgaggtccc ttccattttg gcagctcaca          900

gcctgccctc cttggatgag gagccagtta ccttccccaa atcgacccat          950

gttcctatcc caaaatcagc agacaaagtg acagacaaaa caaaagtgcc         1000

ctctaggagc ccagagaact ctctggaccc caagatgtcc ctgacagggg         1050

caagggaact cctaccccat gcccaggagg aggctgaggc tgaggctgag         1100

ttgcctcctt ccagtgaggt cttggcctca gtttttccag cccaggacaa         1150

gccaggtgag ctgcaggcca cactggacca cacggggcac acctcctcca         1200

agtccctgcc caatttcccc aatacctctg ccaccgctaa tgccacgggt         1250

gggcgtgccc tggctctgca gtcgtccttg ccaggtgcag agggccctga         1300

caagcctagc gttgtgtcag ggctgaactc gggccctggt catgtgtggg         1350

gccctctcct gggactactg ctcctgcctc ctctggtgtt ggctggaatc         1400

ttctgaatgg gataccactc aaagggtgaa gaggtcagct gtcctcctgt         1450

catcttcccc accctgtccc cagcccctaa acaagatact tcttggttaa         1500

ggccctccgg aagggaaagg ctacggggca tgtgcctcat cacaccatcc         1550

atcctggagg cacaaggcct ggctggctgc gagctcagga ggccgcctga         1600

ggactgcaca ccgggcccac acctctcctg cccctccctc ctgagtcctg         1650

ggggtgggag gatttgaggg agctcactgc ctacctggcc tggggctgtc         1700

tgcccacaca gcatgtgcgc tctccctgag tgcctgtgta gctggggatg         1750

gggattccta ggggcagatg aaggacaagc cccactggag tggggttctt         1800

tgagtggggg aggcagggac gagggaagga aagtaactcc tgactctcca         1850

ataaaaacct gtccaacctg tgaaa                                    1875
```

```
<210> SEQ ID NO 285
<211> LENGTH: 463
<212> TYPE: PRT
<213> ORGANISM: Homo Sapien

<400> SEQUENCE: 285

Met His Gly Ser Cys Ser Phe Leu Met Leu Leu Leu Pro Leu Leu
  1               5                  10                  15

Leu Leu Leu Val Ala Thr Thr Gly Pro Val Gly Ala Leu Thr Asp
                 20                  25                  30

Glu Glu Lys Arg Leu Met Val Glu Leu His Asn Leu Tyr Arg Ala
                 35                  40                  45

Gln Val Ser Pro Thr Ala Ser Asp Met Leu His Met Arg Trp Asp
                 50                  55                  60

Glu Glu Leu Ala Ala Phe Ala Lys Ala Tyr Ala Arg Gln Cys Val
                 65                  70                  75

Trp Gly His Asn Lys Glu Arg Gly Arg Arg Gly Glu Asn Leu Phe
                 80                  85                  90

Ala Ile Thr Asp Glu Gly Met Asp Val Pro Leu Ala Met Glu Glu
                 95                 100                 105

Trp His His Glu Arg Glu His Tyr Asn Leu Ser Ala Ala Thr Cys
                110                 115                 120
```

-continued

```
Ser Pro Gly Gln Met Cys Gly His Tyr Thr Gln Val Val Trp Ala
                125                 130                 135

Lys Thr Glu Arg Ile Gly Cys Gly Ser His Phe Cys Glu Lys Leu
                140                 145                 150

Gln Gly Val Glu Glu Thr Asn Ile Glu Leu Leu Val Cys Asn Tyr
                155                 160                 165

Glu Pro Pro Gly Asn Val Lys Gly Lys Arg Pro Tyr Gln Glu Gly
                170                 175                 180

Thr Pro Cys Ser Gln Cys Pro Ser Gly Tyr His Cys Lys Asn Ser
                185                 190                 195

Leu Cys Glu Pro Ile Gly Ser Pro Glu Asp Ala Gln Asp Leu Pro
                200                 205                 210

Tyr Leu Val Thr Glu Ala Pro Ser Phe Arg Ala Thr Glu Ala Ser
                215                 220                 225

Asp Ser Arg Lys Met Gly Thr Pro Ser Ser Leu Ala Thr Gly Ile
                230                 235                 240

Pro Ala Phe Leu Val Thr Glu Val Ser Gly Ser Leu Ala Thr Lys
                245                 250                 255

Ala Leu Pro Ala Val Glu Thr Gln Ala Pro Thr Ser Leu Ala Thr
                260                 265                 270

Lys Asp Pro Pro Ser Met Ala Thr Glu Ala Pro Pro Cys Val Thr
                275                 280                 285

Thr Glu Val Pro Ser Ile Leu Ala Ala His Ser Leu Pro Ser Leu
                290                 295                 300

Asp Glu Glu Pro Val Thr Phe Pro Lys Ser Thr His Val Pro Ile
                305                 310                 315

Pro Lys Ser Ala Asp Lys Val Thr Asp Lys Thr Lys Val Pro Ser
                320                 325                 330

Arg Ser Pro Glu Asn Ser Leu Asp Pro Lys Met Ser Leu Thr Gly
                335                 340                 345

Ala Arg Glu Leu Leu Pro His Ala Gln Glu Glu Ala Glu Ala Glu
                350                 355                 360

Ala Glu Leu Pro Pro Ser Ser Glu Val Leu Ala Ser Val Phe Pro
                365                 370                 375

Ala Gln Asp Lys Pro Gly Glu Leu Gln Ala Thr Leu Asp His Thr
                380                 385                 390

Gly His Thr Ser Ser Lys Ser Leu Pro Asn Phe Pro Asn Thr Ser
                395                 400                 405

Ala Thr Ala Asn Ala Thr Gly Gly Arg Ala Leu Ala Leu Gln Ser
                410                 415                 420

Ser Leu Pro Gly Ala Glu Gly Pro Asp Lys Pro Ser Val Val Ser
                425                 430                 435

Gly Leu Asn Ser Gly Pro Gly His Val Trp Gly Pro Leu Leu Gly
                440                 445                 450

Leu Leu Leu Leu Pro Pro Leu Val Leu Ala Gly Ile Phe
                455                 460
```

<210> SEQ ID NO 286
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 286

-continued

```
tcctgcagtt tcctgatgc                                                  19


<210> SEQ ID NO 287
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 287

ctcatattgc acaccagtaa ttcg                                            24


<210> SEQ ID NO 288
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 288

atgaggagaa acgtttgatg gtggagctgc acaacctcta ccggg                     45


<210> SEQ ID NO 289
<211> LENGTH: 3662
<212> TYPE: DNA
<213> ORGANISM: Homo Sapien

<400> SEQUENCE: 289

gtaactgaag tcaggctttt catttgggaa gccccctcaa cagaattcgg                50

tcattctcca agttatggtg gacgtacttc tgttgttctc cctctgcttg               100

ctttttcaca ttagcagacc ggacttaagt cacaacagat tatctttcat               150

caaggcaagt tccatgagcc accttcaaag ccttcgagaa gtgaaactga               200

acaacaatga attggagacc attccaaatc tgggaccagt ctcggcaaat               250

attacacttc tctccttggc tggaaacagg attgttgaaa tactccctga               300

acatctgaaa gagtttcagt cccttgaaac tttggacctt agcagcaaca               350

atatttcaga gctccaaact gcatttccag ccctacagct caaatatctg               400

tatctcaaca gcaaccgagt cacatcaatg gaacctgggt attttgacaa               450

tttggccaac acactccttg tgttaaagct gaacaggaac cgaatctcag               500

ctatcccacc caagatgttt aaactgcccc aactgcaaca tctcgaattg               550

aaccgaaaca agattaaaaa tgtagatgga ctgacattcc aaggccttgg               600

tgctctgaag tctctgaaaa tgcaaagaaa tggagtaacg aaacttatgg               650

atggagcttt ttgggggctg agcaacatgg aaattttgca gctggaccat               700

aacaacctaa cagagattac caaaggctgg ctttacggct tgctgatgct               750

gcaggaactt catctcagcc aaaatgccat caacaggatc agccctgatg               800

cctgggagtt ctgccagaag ctcagtgagc tggacctaac tttcaatcac               850

ttatcaaggt tagatgattc aagcttcctt ggcctaagct tactaaatac               900

actgcacatt gggaacaaca gagtcagcta cattgctgat tgtgccttcc               950

gggggctttc cagtttaaag actttggatc tgaagaacaa tgaaatttcc              1000

tggactattg aagacatgaa tggtgctttc tctgggcttg acaaactgag              1050

gcgactgata ctccaaggaa atcggatccg ttctattact aaaaaagcct              1100

tcactggttt ggatgcattg gagcatctag acctgagtga caacgcaatc              1150
```

-continued

```
atgtctttac aaggcaatgc attttcacaa atgaagaaac tgcaacaatt      1200
gcatttaaat acatcaagcc ttttgtgcga ttgccagcta aaatggctcc      1250
cacagtgggt ggcggaaaac aactttcaga gctttgtaaa tgccagttgt      1300
gcccatcctc agctgctaaa aggaagaagc atttttgctg ttagcccaga      1350
tggctttgtg tgtgatgatt ttcccaaacc ccagatcacg gttcagccag      1400
aaacacagtc ggcaataaaa ggttccaatt tgagtttcat ctgctcagct      1450
gccagcagca gtgattcccc aatgactttt gcttggaaaa aagacaatga      1500
actactgcat gatgctgaaa tggaaaatta tgcacacctc cgggcccaag      1550
gtggcgaggt gatggagtat accaccatcc ttcggctgcg cgaggtggaa      1600
tttgccagtg aggggaaata tcagtgtgtc atctccaatc actttggttc      1650
atcctactct gtcaaagcca agcttacagt aaatatgctt ccctcattca      1700
ccaagacccc catggatctc accatccgag ctggggccat ggcacgcttg      1750
gagtgtgctg ctgtggggca cccagccccc cagatagcct ggcagaagga      1800
tgggggcaca gacttcccag ctgcacggga gagacgcatg catgtgatgc      1850
ccgaggatga cgtgttcttt atcgtggatg tgaagataga ggacattggg      1900
gtatacagct gcacagctca gaacagtgca ggaagtattt cagcaaatgc      1950
aactctgact gtcctagaaa caccatcatt tttgcggcca ctgttggacc      2000
gaactgtaac caagggagaa acagccgtcc tacagtgcat tgctggagga      2050
agccctcccc ctaaactgaa ctggaccaaa gatgatagcc cattggtggt      2100
aaccgagagg cactttttttg cagcaggcaa tcagcttctg attattgtgg      2150
actcagatgt cagtgatgct gggaaataca catgtgagat gtctaacacc      2200
cttggcactg agagaggaaa cgtgcgcctc agtgtgatcc ccactccaac      2250
ctgcgactcc cctcagatga cagccccatc gttagacgat gacggatggg      2300
ccactgtggg tgtcgtgatc atagccgtgg tttgctgtgt ggtgggcacg      2350
tcactcgtgt gggtggtcat catataccac acaaggcgga ggaatgaaga      2400
ttgcagcatt accaacacag atgagaccaa cttgccagca gatattccta      2450
gttatttgtc atctcaggga acgttagctg acaggcagga tgggtacgtg      2500
tcttcagaaa gtggaagcca ccaccagttt gtcacatctt caggtgctgg      2550
atttttctta ccacaacatg acagtagtgg gacctgccat attgacaata      2600
gcagtgaagc tgatgtggaa gctgccacag atctgttcct ttgtccgttt      2650
ttgggatcca caggccctat gtatttgaag ggaaatgtgt atggctcaga      2700
tccttttgaa acatatcata caggttgcag tcctgaccca agaacagttt      2750
taatggacca ctatgagccc agttacataa agaaaaagga gtgctaccca      2800
tgttctcatc cttcagaaga atcctgcgaa cggagcttca gtaatatatc      2850
gtggccttca catgtgagga agctacttaa cactagttac tctcacaatg      2900
aaggacctgg aatgaaaaat ctgtgtctaa acaagtcctc tttagatttt      2950
agtgcaaatc cagagccagc gtcggttgcc tcgagtaatt ctttcatggg      3000
tacctttgga aaagctctca ggagacctca cctagatgcc tattcaagct      3050
ttggacagcc atcagattgt cagccaagag ccttttattt gaaagctcat      3100
```

-continued

```
tcttccccag acttggactc tgggtcagag gaagatggga aagaaaggac 3150

agattttcag gaagaaaatc acatttgtac ctttaaacag actttagaaa 3200

actacaggac tccaaatttt cagtcttatg acttggacac atagactgaa 3250

tgagaccaaa ggaaaagctt aacatactac ctcaagtgaa cttttattta 3300

aaagagagag aatcttatgt tttttaaatg gagttatgaa ttttaaaagg 3350

ataaaaatgc tttatttata cagatgaacc aaaattacaa aaagttatga 3400

aaatttttat actgggaatg atgctcatat aagaatacct ttttaaacta 3450

ttttttaact ttgttttatg caaaaaagta tcttacgtaa attaatgata 3500

taaatcatga ttattttatg tatttttata atgccagatt tctttttatg 3550

gaaaatgagt tactaaagca ttttaaataa tacctgcctt gtaccatttt 3600

ttaaatagaa gttacttcat tatattttgc acattatatt taataaaatg 3650

tgtcaatttg aa 3662
```

<210> SEQ ID NO 290
<211> LENGTH: 1059
<212> TYPE: PRT
<213> ORGANISM: Homo Sapien

<400> SEQUENCE: 290

```
Met Val Asp Val Leu Leu Leu Phe Ser Leu Cys Leu Leu Phe His
  1               5                  10                  15

Ile Ser Arg Pro Asp Leu Ser His Asn Arg Leu Ser Phe Ile Lys
                 20                  25                  30

Ala Ser Ser Met Ser His Leu Gln Ser Leu Arg Glu Val Lys Leu
                 35                  40                  45

Asn Asn Asn Glu Leu Glu Thr Ile Pro Asn Leu Gly Pro Val Ser
                 50                  55                  60

Ala Asn Ile Thr Leu Leu Ser Leu Ala Gly Asn Arg Ile Val Glu
                 65                  70                  75

Ile Leu Pro Glu His Leu Lys Glu Phe Gln Ser Leu Glu Thr Leu
                 80                  85                  90

Asp Leu Ser Ser Asn Asn Ile Ser Glu Leu Gln Thr Ala Phe Pro
                 95                 100                 105

Ala Leu Gln Leu Lys Tyr Leu Tyr Leu Asn Ser Asn Arg Val Thr
                110                 115                 120

Ser Met Glu Pro Gly Tyr Phe Asp Asn Leu Ala Asn Thr Leu Leu
                125                 130                 135

Val Leu Lys Leu Asn Arg Asn Arg Ile Ser Ala Ile Pro Pro Lys
                140                 145                 150

Met Phe Lys Leu Pro Gln Leu Gln His Leu Glu Leu Asn Arg Asn
                155                 160                 165

Lys Ile Lys Asn Val Asp Gly Leu Thr Phe Gln Gly Leu Gly Ala
                170                 175                 180

Leu Lys Ser Leu Lys Met Gln Arg Asn Gly Val Thr Lys Leu Met
                185                 190                 195

Asp Gly Ala Phe Trp Gly Leu Ser Asn Met Glu Ile Leu Gln Leu
                200                 205                 210

Asp His Asn Asn Leu Thr Glu Ile Thr Lys Gly Trp Leu Tyr Gly
                215                 220                 225

Leu Leu Met Leu Gln Glu Leu His Leu Ser Gln Asn Ala Ile Asn
                230                 235                 240
```

-continued

```
Arg Ile Ser Pro Asp Ala Trp Glu Phe Cys Gln Lys Leu Ser Glu
                245                 250                 255

Leu Asp Leu Thr Phe Asn His Leu Ser Arg Leu Asp Asp Ser Ser
                260                 265                 270

Phe Leu Gly Leu Ser Leu Leu Asn Thr Leu His Ile Gly Asn Asn
                275                 280                 285

Arg Val Ser Tyr Ile Ala Asp Cys Ala Phe Arg Gly Leu Ser Ser
                290                 295                 300

Leu Lys Thr Leu Asp Leu Lys Asn Asn Glu Ile Ser Trp Thr Ile
                305                 310                 315

Glu Asp Met Asn Gly Ala Phe Ser Gly Leu Asp Lys Leu Arg Arg
                320                 325                 330

Leu Ile Leu Gln Gly Asn Arg Ile Arg Ser Ile Thr Lys Lys Ala
                335                 340                 345

Phe Thr Gly Leu Asp Ala Leu Glu His Leu Asp Leu Ser Asp Asn
                350                 355                 360

Ala Ile Met Ser Leu Gln Gly Asn Ala Phe Ser Gln Met Lys Lys
                365                 370                 375

Leu Gln Gln Leu His Leu Asn Thr Ser Ser Leu Leu Cys Asp Cys
                380                 385                 390

Gln Leu Lys Trp Leu Pro Gln Trp Val Ala Glu Asn Asn Phe Gln
                395                 400                 405

Ser Phe Val Asn Ala Ser Cys Ala His Pro Gln Leu Leu Lys Gly
                410                 415                 420

Arg Ser Ile Phe Ala Val Ser Pro Asp Gly Phe Val Cys Asp Asp
                425                 430                 435

Phe Pro Lys Pro Gln Ile Thr Val Gln Pro Glu Thr Gln Ser Ala
                440                 445                 450

Ile Lys Gly Ser Asn Leu Ser Phe Ile Cys Ser Ala Ala Ser Ser
                455                 460                 465

Ser Asp Ser Pro Met Thr Phe Ala Trp Lys Lys Asp Asn Glu Leu
                470                 475                 480

Leu His Asp Ala Glu Met Glu Asn Tyr Ala His Leu Arg Ala Gln
                485                 490                 495

Gly Gly Glu Val Met Glu Tyr Thr Thr Ile Leu Arg Leu Arg Glu
                500                 505                 510

Val Glu Phe Ala Ser Glu Gly Lys Tyr Gln Cys Val Ile Ser Asn
                515                 520                 525

His Phe Gly Ser Ser Tyr Ser Val Lys Ala Lys Leu Thr Val Asn
                530                 535                 540

Met Leu Pro Ser Phe Thr Lys Thr Pro Met Asp Leu Thr Ile Arg
                545                 550                 555

Ala Gly Ala Met Ala Arg Leu Glu Cys Ala Ala Val Gly His Pro
                560                 565                 570

Ala Pro Gln Ile Ala Trp Gln Lys Asp Gly Gly Thr Asp Phe Pro
                575                 580                 585

Ala Ala Arg Glu Arg Arg Met His Val Met Pro Glu Asp Asp Val
                590                 595                 600

Phe Phe Ile Val Asp Val Lys Ile Glu Asp Ile Gly Val Tyr Ser
                605                 610                 615

Cys Thr Ala Gln Asn Ser Ala Gly Ser Ile Ser Ala Asn Ala Thr
                620                 625                 630
```

-continued

Leu Thr Val Leu Glu Thr Pro Ser Phe Leu Arg Pro Leu Leu Asp
635 640 645

Arg Thr Val Thr Lys Gly Glu Thr Ala Val Leu Gln Cys Ile Ala
650 655 660

Gly Gly Ser Pro Pro Pro Lys Leu Asn Trp Thr Lys Asp Asp Ser
665 670 675

Pro Leu Val Val Thr Glu Arg His Phe Phe Ala Ala Gly Asn Gln
680 685 690

Leu Leu Ile Ile Val Asp Ser Asp Val Ser Asp Ala Gly Lys Tyr
695 700 705

Thr Cys Glu Met Ser Asn Thr Leu Gly Thr Glu Arg Gly Asn Val
710 715 720

Arg Leu Ser Val Ile Pro Thr Pro Thr Cys Asp Ser Pro Gln Met
725 730 735

Thr Ala Pro Ser Leu Asp Asp Asp Gly Trp Ala Thr Val Gly Val
740 745 750

Val Ile Ile Ala Val Val Cys Cys Val Val Gly Thr Ser Leu Val
755 760 765

Trp Val Val Ile Ile Tyr His Thr Arg Arg Arg Asn Glu Asp Cys
770 775 780

Ser Ile Thr Asn Thr Asp Glu Thr Asn Leu Pro Ala Asp Ile Pro
785 790 795

Ser Tyr Leu Ser Ser Gln Gly Thr Leu Ala Asp Arg Gln Asp Gly
800 805 810

Tyr Val Ser Ser Glu Ser Gly Ser His His Gln Phe Val Thr Ser
815 820 825

Ser Gly Ala Gly Phe Phe Leu Pro Gln His Asp Ser Ser Gly Thr
830 835 840

Cys His Ile Asp Asn Ser Ser Glu Ala Asp Val Glu Ala Ala Thr
845 850 855

Asp Leu Phe Leu Cys Pro Phe Leu Gly Ser Thr Gly Pro Met Tyr
860 865 870

Leu Lys Gly Asn Val Tyr Gly Ser Asp Pro Phe Glu Thr Tyr His
875 880 885

Thr Gly Cys Ser Pro Asp Pro Arg Thr Val Leu Met Asp His Tyr
890 895 900

Glu Pro Ser Tyr Ile Lys Lys Lys Glu Cys Tyr Pro Cys Ser His
905 910 915

Pro Ser Glu Glu Ser Cys Glu Arg Ser Phe Ser Asn Ile Ser Trp
920 925 930

Pro Ser His Val Arg Lys Leu Leu Asn Thr Ser Tyr Ser His Asn
935 940 945

Glu Gly Pro Gly Met Lys Asn Leu Cys Leu Asn Lys Ser Ser Leu
950 955 960

Asp Phe Ser Ala Asn Pro Glu Pro Ala Ser Val Ala Ser Ser Asn
965 970 975

Ser Phe Met Gly Thr Phe Gly Lys Ala Leu Arg Arg Pro His Leu
980 985 990

Asp Ala Tyr Ser Ser Phe Gly Gln Pro Ser Asp Cys Gln Pro Arg
995 1000 1005

Ala Phe Tyr Leu Lys Ala His Ser Ser Pro Asp Leu Asp Ser Gly
1010 1015 1020

Ser Glu Glu Asp Gly Lys Glu Arg Thr Asp Phe Gln Glu Glu Asn

-continued

```
             1025                1030                1035

His Ile Cys Thr Phe Lys Gln Thr Leu Glu Asn Tyr Arg Thr Pro
             1040                1045                1050

Asn Phe Gln Ser Tyr Asp Leu Asp Thr
             1055


<210> SEQ ID NO 291
<211> LENGTH: 2906
<212> TYPE: DNA
<213> ORGANISM: Homo Sapien

<400> SEQUENCE: 291

ggggagagga attgaccatg taaaaggaga cttttttttt tggtggtggt          50

ggctgttggg tgccttgcaa aaatgaagga tgcaggacgc agctttctcc         100

tggaaccgaa cgcaatggat aaactgattg tgcaagagag aaggaagaac         150

gaagcttttt cttgtgagcc ctggatctta acacaaatgt gtatatgtgc         200

acacagggag cattcaagaa tgaaataaac cagagttaga cccgcggggg         250

ttggtgtgtt ctgacataaa taaataatct taaagcagct gttcccctcc         300

ccacccccaa aaaaaaggat gattggaaat gaagaaccga ggattcacaa         350

agaaaaaagt atgttcattt ttctctataa aggagaaagt gagccaagga         400

gatatttttg gaatgaaaag tttggggctt ttttagtaaa gtaaagaact         450

ggtgtggtgg tgttttcctt tctttttgaa tttcccacaa gaggagagga         500

aattaataat acatctgcaa agaaatttca gagaagaaaa gttgaccgcg         550

gcagattgag gcattgattg ggggagagaa accagcagag cacagttgga         600

tttgtgccta tgttgactaa aattgacgga taattgcagt tggatttttc         650

ttcatcaacc tccttttttt taaattttta ttccttttgg tatcaagatc         700

atgcgttttc tcttgttctt aaccacctgg atttccatct ggatgttgct         750

gtgatcagtc tgaaatacaa ctgtttgaat tccagaagga ccaacaccag         800

ataaattatg aatgttgaac aagatgacct tacatccaca gcagataatg         850

ataggtccta ggtttaacag ggccctattt gaccccctgc ttgtggtgct         900

gctggctctt caacttcttg tggtggctgg tctggtgcgg gctcagacct         950

gcccttctgt gtgctcctgc agcaaccagt tcagcaaggt gatttgtgtt        1000

cggaaaaacc tgcgtgaggt tccggatggc atctccacca acacacggct        1050

gctgaacctc catgagaacc aaatccagat catcaaagtg aacagcttca        1100

agcacttgag gcacttggaa atcctacagt tgagtaggaa ccatatcaga        1150

accattgaaa ttggggcttt caatggtctg gcgaacctca acactctgga        1200

actctttgac aatcgtctta ctaccatccc gaatggagct tttgtatact        1250

tgtctaaact gaaggagctc tggttgcgaa acaaccccat tgaaagcatc        1300

ccttcttatg cttttaacag aattccttct ttgcgccgac tagacttagg        1350

ggaattgaaa agactttcat acatctcaga aggtgccttt gaaggtctgt        1400

ccaacttgag gtatttgaac cttgccatgt gcaaccttcg ggaaatccct        1450

aacctcacac cgctcataaa actagatgag ctggatcttt ctgggaatca        1500

tttatctgcc atcaggcctg gctctttcca gggtttgatg caccttcaaa        1550

aactgtggat gatacagtcc cagattcaag tgattgaacg gaatgccttt        1600
```

-continued

```
gacaaccttc agtcactagt ggagatcaac ctggcacaca ataatctaac      1650
attactgcct catgacctct tcactccctt gcatcatcta gagcggatac      1700
atttacatca caacccttgg aactgtaact gtgacatact gtggctcagc      1750
tggtggataa aagacatggc cccctcgaac acagcttgtt gtgcccggtg      1800
taacactcct cccaatctaa aggggaggta cattggagag ctcgaccaga      1850
attacttcac atgctatgct ccggtgattg tggagccccc tgcagacctc      1900
aatgtcactg aaggcatggc agctgagctg aaatgtcggg cctccacatc      1950
cctgacatct gtatcttgga ttactccaaa tggaacagtc atgacacatg      2000
gggcgtacaa agtgcggata gctgtgctca gtgatggtac gttaaatttc      2050
acaaatgtaa ctgtgcaaga tacaggcatg tacacatgta tggtgagtaa      2100
ttccgttggg aatactactg cttcagccac cctgaatgtt actgcagcaa      2150
ccactactcc tttctcttac ttttcaaccg tcacagtaga gactatggaa      2200
ccgtctcagg atgaggcacg gaccacagat aacaatgtgg gtcccactcc      2250
agtggtcgac tgggagacca ccaatgtgac cacctctctc acaccacaga      2300
gcacaaggtc gacagagaaa accttcacca tcccagtgac tgatataaac      2350
agtgggatcc caggaattga tgaggtcatg aagactacca aaatcatcat      2400
tgggtgtttt gtggccatca cactcatggc tgcagtgatg ctggtcattt      2450
tctacaagat gaggaagcag caccatcggc aaaaccatca cgccccaaca      2500
aggactgttg aaattattaa tgtggatgat gagattacgg gagacacacc      2550
catggaaagc cacctgccca tgcctgctat cgagcatgag cacctaaatc      2600
actataactc atacaaatct cccttcaacc acacaacaac agttaacaca      2650
ataaattcaa tacacagttc agtgcatgaa ccgttattga tccgaatgaa      2700
ctctaaagac aatgtacaag agactcaaat ctaaaacatt tacagagtta      2750
caaaaaaacaa acaatcaaaa aaaaagacag tttattaaaa atgacacaaa     2800
tgactgggct aaatctactg tttcaaaaaa gtgtctttac aaaaaaacaa      2850
aaaagaaaag aaatttattt attaaaaatt ctattgtgat ctaaagcaga      2900
caaaaa                                                      2906
```

```
<210> SEQ ID NO 292
<211> LENGTH: 640
<212> TYPE: PRT
<213> ORGANISM: Homo Sapien

<400> SEQUENCE: 292

Met Leu Asn Lys Met Thr Leu His Pro Gln Gln Ile Met Ile Gly
  1               5                  10                  15

Pro Arg Phe Asn Arg Ala Leu Phe Asp Pro Leu Leu Val Val Leu
                 20                  25                  30

Leu Ala Leu Gln Leu Leu Val Val Ala Gly Leu Val Arg Ala Gln
                 35                  40                  45

Thr Cys Pro Ser Val Cys Ser Cys Ser Asn Gln Phe Ser Lys Val
                 50                  55                  60

Ile Cys Val Arg Lys Asn Leu Arg Glu Val Pro Asp Gly Ile Ser
                 65                  70                  75

Thr Asn Thr Arg Leu Leu Asn Leu His Glu Asn Gln Ile Gln Ile
```

-continued

```
                80                  85                  90

Ile Lys Val Asn Ser Phe Lys His Leu Arg His Leu Glu Ile Leu
                95                  100                 105

Gln Leu Ser Arg Asn His Ile Arg Thr Ile Glu Ile Gly Ala Phe
                110                 115                 120

Asn Gly Leu Ala Asn Leu Asn Thr Leu Glu Leu Phe Asp Asn Arg
                125                 130                 135

Leu Thr Thr Ile Pro Asn Gly Ala Phe Val Tyr Leu Ser Lys Leu
                140                 145                 150

Lys Glu Leu Trp Leu Arg Asn Asn Pro Ile Glu Ser Ile Pro Ser
                155                 160                 165

Tyr Ala Phe Asn Arg Ile Pro Ser Leu Arg Arg Leu Asp Leu Gly
                170                 175                 180

Glu Leu Lys Arg Leu Ser Tyr Ile Ser Glu Gly Ala Phe Glu Gly
                185                 190                 195

Leu Ser Asn Leu Arg Tyr Leu Asn Leu Ala Met Cys Asn Leu Arg
                200                 205                 210

Glu Ile Pro Asn Leu Thr Pro Leu Ile Lys Leu Asp Glu Leu Asp
                215                 220                 225

Leu Ser Gly Asn His Leu Ser Ala Ile Arg Pro Gly Ser Phe Gln
                230                 235                 240

Gly Leu Met His Leu Gln Lys Leu Trp Met Ile Gln Ser Gln Ile
                245                 250                 255

Gln Val Ile Glu Arg Asn Ala Phe Asp Asn Leu Gln Ser Leu Val
                260                 265                 270

Glu Ile Asn Leu Ala His Asn Asn Leu Thr Leu Leu Pro His Asp
                275                 280                 285

Leu Phe Thr Pro Leu His His Leu Glu Arg Ile His Leu His His
                290                 295                 300

Asn Pro Trp Asn Cys Asn Cys Asp Ile Leu Trp Leu Ser Trp Trp
                305                 310                 315

Ile Lys Asp Met Ala Pro Ser Asn Thr Ala Cys Cys Ala Arg Cys
                320                 325                 330

Asn Thr Pro Pro Asn Leu Lys Gly Arg Tyr Ile Gly Glu Leu Asp
                335                 340                 345

Gln Asn Tyr Phe Thr Cys Tyr Ala Pro Val Ile Val Glu Pro Pro
                350                 355                 360

Ala Asp Leu Asn Val Thr Glu Gly Met Ala Ala Glu Leu Lys Cys
                365                 370                 375

Arg Ala Ser Thr Ser Leu Thr Ser Val Ser Trp Ile Thr Pro Asn
                380                 385                 390

Gly Thr Val Met Thr His Gly Ala Tyr Lys Val Arg Ile Ala Val
                395                 400                 405

Leu Ser Asp Gly Thr Leu Asn Phe Thr Asn Val Thr Val Gln Asp
                410                 415                 420

Thr Gly Met Tyr Thr Cys Met Val Ser Asn Ser Val Gly Asn Thr
                425                 430                 435

Thr Ala Ser Ala Thr Leu Asn Val Thr Ala Ala Thr Thr Thr Pro
                440                 445                 450

Phe Ser Tyr Phe Ser Thr Val Thr Val Glu Thr Met Glu Pro Ser
                455                 460                 465

Gln Asp Glu Ala Arg Thr Thr Asp Asn Asn Val Gly Pro Thr Pro
                470                 475                 480
```

-continued

```
Val Val Asp Trp Glu Thr Thr Asn Val Thr Thr Ser Leu Thr Pro
                485                 490                 495

Gln Ser Thr Arg Ser Thr Glu Lys Thr Phe Thr Ile Pro Val Thr
                500                 505                 510

Asp Ile Asn Ser Gly Ile Pro Gly Ile Asp Glu Val Met Lys Thr
                515                 520                 525

Thr Lys Ile Ile Ile Gly Cys Phe Val Ala Ile Thr Leu Met Ala
                530                 535                 540

Ala Val Met Leu Val Ile Phe Tyr Lys Met Arg Lys Gln His His
                545                 550                 555

Arg Gln Asn His His Ala Pro Thr Arg Thr Val Glu Ile Ile Asn
                560                 565                 570

Val Asp Asp Glu Ile Thr Gly Asp Thr Pro Met Glu Ser His Leu
                575                 580                 585

Pro Met Pro Ala Ile Glu His Glu His Leu Asn His Tyr Asn Ser
                590                 595                 600

Tyr Lys Ser Pro Phe Asn His Thr Thr Thr Val Asn Thr Ile Asn
                605                 610                 615

Ser Ile His Ser Ser Val His Glu Pro Leu Leu Ile Arg Met Asn
                620                 625                 630

Ser Lys Asp Asn Val Gln Glu Thr Gln Ile
                635                 640
```

<210> SEQ ID NO 293
<211> LENGTH: 4053
<212> TYPE: DNA
<213> ORGANISM: Homo Sapien

<400> SEQUENCE: 293

```
agccgacgct gctcaagctg caactctgtt gcagttggca gttcttttcg      50

gtttccctcc tgctgtttgg gggcatgaaa gggcttcgcc gccgggagta     100

aaagaaggaa ttgaccgggc agcgcgaggg aggagcgcgc acgcgaccgc     150

gagggcgggc gtgcaccctc ggctggaagt ttgtgccggg ccccgagcgc     200

gcgccggctg ggagcttcgg gtagagacct aggccgctgg accgcgatga     250

gcgcgccgag cctccgtgcg cgcgccgcgg ggttggggct gctgctgtgc     300

gcggtgctgg ggcgcgctgg ccggtccgac agcggcggtc gcggggaact     350

cgggcagccc tctggggtag ccgccgagcg cccatgcccc actacctgcc     400

gctgcctcgg ggacctgctg gactgcagtc gtaagcggct agcgcgtctt     450

cccgagccac tcccgtcctg ggtcgctcgg ctggacttaa gtcacaacag     500

attatctttc atcaaggcaa gttccatgag ccaccttcaa agccttcgag     550

aagtgaaact gaacaacaat gaattggaga ccattccaaa tctgggacca     600

gtctcggcaa atattacact tctctccttg gctggaaaca ggattgttga     650

aatactccct gaacatctga aagagtttca gtcccttgaa actttggacc     700

ttagcagcaa caatatttca gagctccaaa ctgcatttcc agccctacag     750

ctcaaatatc tgtatctcaa cagcaaccga gtcacatcaa tggaacctgg     800

gtattttgac aatttggcca acacactcct tgtgttaaag ctgaacagga     850

accgaatctc agctatccca cccaagatgt ttaaactgcc ccaactgcaa     900

catctcgaat tgaaccgaaa caagattaaa aatgtagatg gactgacatt     950
```

-continued

```
ccaaggcctt ggtgctctga agtctctgaa aatgcaaaga aatggagtaa      1000
cgaaacttat ggatggagct ttttggggc tgagcaacat ggaaattttg      1050
cagctggacc ataacaacct aacagagatt accaaaggct ggctttacgg      1100
cttgctgatg ctgcaggaac ttcatctcag ccaaaatgcc atcaacagga      1150
tcagccctga tgcctgggag ttctgccaga agctcagtga gctggaccta      1200
actttcaatc acttatcaag gttagatgat tcaagcttcc ttggcctaag      1250
cttactaaat acactgcaca ttgggaacaa cagagtcagc tacattgctg      1300
attgtgcctt ccgggggctt tccagtttaa agactttgga tctgaagaac      1350
aatgaaattt cctggactat tgaagacatg aatggtgctt tctctgggct      1400
tgacaaactg aggcgactga tactccaagg aaatcggatc cgttctatta      1450
ctaaaaaagc cttcactggt ttggatgcat tggagcatct agacctgagt      1500
gacaacgcaa tcatgtcttt acaaggcaat gcattttcac aaatgaagaa      1550
actgcaacaa ttgcatttaa atacatcaag ccttttgtgc gattgccagc      1600
taaaatggct cccacagtgg gtggcggaaa acaactttca gagctttgta      1650
aatgccagtt gtgcccatcc tcagctgcta aaaggaagaa gcatttttgc      1700
tgttagccca gatggctttg tgtgtgatga ttttcccaaa ccccagatca      1750
cggttcagcc agaaacacag tcggcaataa aaggttccaa tttgagtttc      1800
atctgctcag ctgccagcag cagtgattcc ccaatgactt ttgcttggaa      1850
aaaagacaat gaactactgc atgatgctga aatggaaaat tatgcacacc      1900
tccgggccca aggtggcgag gtgatggagt ataccaccat ccttcggctg      1950
cgcgaggtgg aatttgccag tgaggggaaa tatcagtgtg tcatctccaa      2000
tcactttggt tcatcctact ctgtcaaagc caagcttaca gtaaatatgc      2050
ttccctcatt caccaagacc cccatggatc tcaccatccg agctggggcc      2100
atggcacgct tggagtgtgc tgctgtgggg cacccagccc cccagatagc      2150
ctggcagaag gatgggggca cagacttccc agctgcacgg gagagacgca      2200
tgcatgtgat gcccgaggat gacgtgttct ttatcgtgga tgtgaagata      2250
gaggacattg ggtatacag ctgcacagct cagaacagtg caggaagtat      2300
ttcagcaaat gcaactctga ctgtcctaga aacaccatca tttttgcggc      2350
cactgttgga ccgaactgta accaagggag aaacagccgt cctacagtgc      2400
attgctggag gaagccctcc ccctaaactg aactggacca aagatgatag      2450
cccattggtg gtaaccgaga ggcacttttt tgcagcaggc aatcagcttc      2500
tgattattgt ggactcagat gtcagtgatg ctgggaaata cacatgtgag      2550
atgtctaaca cccttggcac tgagagagga aacgtgcgcc tcagtgtgat      2600
ccccactcca acctgcgact cccctcagat gacagcccca tcgttagacg      2650
atgacggatg ggccactgtg ggtgtcgtga tcatagccgt ggtttgctgt      2700
gtggtgggca cgtcactcgt gtgggtggtc atcatatacc acacaaggcg      2750
gaggaatgaa gattgcagca ttaccaacac agatgagacc aacttgccag      2800
cagatattcc tagttatttg tcatctcagg gaacgttagc tgacaggcag      2850
gatgggtacg tgtcttcaga aagtggaagc caccaccagt ttgtcacatc      2900
```

-continued

```
ttcaggtgct ggatttttct taccacaaca tgacagtagt gggacctgcc      2950

atattgacaa tagcagtgaa gctgatgtgg aagctgccac agatctgttc      3000

ctttgtccgt ttttgggatc cacaggccct atgtatttga agggaaatgt      3050

gtatggctca gatccttttg aaacatatca tacaggttgc agtcctgacc      3100

caagaacagt tttaatggac cactatgagc ccagttacat aaagaaaaag      3150

gagtgctacc catgttctca tccttcagaa gaatcctgcg aacggagctt      3200

cagtaatata tcgtggcctt cacatgtgag gaagctactt aacactagtt      3250

actctcacaa tgaaggacct ggaatgaaaa atctgtgtct aaacaagtcc      3300

tctttagatt ttagtgcaaa tccagagcca gcgtcggttg cctcgagtaa      3350

ttctttcatg ggtacctttg gaaaagctct caggagacct cacctagatg      3400

cctattcaag ctttggacag ccatcagatt gtcagccaag agccttttat      3450

ttgaaagctc attcttcccc agacttggac tctgggtcag aggaagatgg      3500

gaaagaaagg acagattttc aggaagaaaa tcacatttgt acctttaaac      3550

agactttaga aaactacagg actccaaatt ttcagtctta tgacttggac      3600

acatagactg aatgagacca aaggaaaagc ttaacatact acctcaagtg      3650

aacttttatt taaaagagag agaatcttat gtttttttaaa tggagttatg     3700

aattttaaaa ggataaaaat gctttattta tacagatgaa ccaaaattac      3750

aaaaagttat gaaaattttt atactgggaa tgatgctcat ataagaatac      3800

ctttttaaac tattttttaa ctttgtttta tgcaaaaaag tatcttacgt      3850

aaattaatga tataaatcat gattatttta tgtattttta taatgccaga      3900

tttcttttta tggaaaatga gttactaaag cattttaaat aatacctgcc      3950

ttgtaccatt ttttaaatag aagttacttc attatatttt gcacattata      4000

tttaataaaa tgtgtcaatt tgaaaaaaaa aaaaaaaaaa aaaaaaaaaa      4050

aaa 4053
```

<210> SEQ ID NO 294
<211> LENGTH: 1119
<212> TYPE: PRT
<213> ORGANISM: Homo Sapien

<400> SEQUENCE: 294

```
Met Ser Ala Pro Ser Leu Arg Ala Arg Ala Ala Gly Leu Gly Leu
  1               5                  10                  15

Leu Leu Cys Ala Val Leu Gly Arg Ala Gly Arg Ser Asp Ser Gly
                 20                  25                  30

Gly Arg Gly Glu Leu Gly Gln Pro Ser Gly Val Ala Ala Glu Arg
                 35                  40                  45

Pro Cys Pro Thr Thr Cys Arg Cys Leu Gly Asp Leu Leu Asp Cys
                 50                  55                  60

Ser Arg Lys Arg Leu Ala Arg Leu Pro Glu Pro Leu Pro Ser Trp
                 65                  70                  75

Val Ala Arg Leu Asp Leu Ser His Asn Arg Leu Ser Phe Ile Lys
                 80                  85                  90

Ala Ser Ser Met Ser His Leu Gln Ser Leu Arg Glu Val Lys Leu
                 95                 100                 105

Asn Asn Asn Glu Leu Glu Thr Ile Pro Asn Leu Gly Pro Val Ser
                110                 115                 120
```

-continued

```
Ala Asn Ile Thr Leu Leu Ser Leu Ala Gly Asn Arg Ile Val Glu
                125                 130                 135

Ile Leu Pro Glu His Leu Lys Glu Phe Gln Ser Leu Glu Thr Leu
                140                 145                 150

Asp Leu Ser Ser Asn Asn Ile Ser Glu Leu Gln Thr Ala Phe Pro
                155                 160                 165

Ala Leu Gln Leu Lys Tyr Leu Tyr Leu Asn Ser Asn Arg Val Thr
                170                 175                 180

Ser Met Glu Pro Gly Tyr Phe Asp Asn Leu Ala Asn Thr Leu Leu
                185                 190                 195

Val Leu Lys Leu Asn Arg Asn Arg Ile Ser Ala Ile Pro Pro Lys
                200                 205                 210

Met Phe Lys Leu Pro Gln Leu Gln His Leu Glu Leu Asn Arg Asn
                215                 220                 225

Lys Ile Lys Asn Val Asp Gly Leu Thr Phe Gln Gly Leu Gly Ala
                230                 235                 240

Leu Lys Ser Leu Lys Met Gln Arg Asn Gly Val Thr Lys Leu Met
                245                 250                 255

Asp Gly Ala Phe Trp Gly Leu Ser Asn Met Glu Ile Leu Gln Leu
                260                 265                 270

Asp His Asn Asn Leu Thr Glu Ile Thr Lys Gly Trp Leu Tyr Gly
                275                 280                 285

Leu Leu Met Leu Gln Glu Leu His Leu Ser Gln Asn Ala Ile Asn
                290                 295                 300

Arg Ile Ser Pro Asp Ala Trp Glu Phe Cys Gln Lys Leu Ser Glu
                305                 310                 315

Leu Asp Leu Thr Phe Asn His Leu Ser Arg Leu Asp Asp Ser Ser
                320                 325                 330

Phe Leu Gly Leu Ser Leu Leu Asn Thr Leu His Ile Gly Asn Asn
                335                 340                 345

Arg Val Ser Tyr Ile Ala Asp Cys Ala Phe Arg Gly Leu Ser Ser
                350                 355                 360

Leu Lys Thr Leu Asp Leu Lys Asn Asn Glu Ile Ser Trp Thr Ile
                365                 370                 375

Glu Asp Met Asn Gly Ala Phe Ser Gly Leu Asp Lys Leu Arg Arg
                380                 385                 390

Leu Ile Leu Gln Gly Asn Arg Ile Arg Ser Ile Thr Lys Lys Ala
                395                 400                 405

Phe Thr Gly Leu Asp Ala Leu Glu His Leu Asp Leu Ser Asp Asn
                410                 415                 420

Ala Ile Met Ser Leu Gln Gly Asn Ala Phe Ser Gln Met Lys Lys
                425                 430                 435

Leu Gln Gln Leu His Leu Asn Thr Ser Ser Leu Leu Cys Asp Cys
                440                 445                 450

Gln Leu Lys Trp Leu Pro Gln Trp Val Ala Glu Asn Asn Phe Gln
                455                 460                 465

Ser Phe Val Asn Ala Ser Cys Ala His Pro Gln Leu Leu Lys Gly
                470                 475                 480

Arg Ser Ile Phe Ala Val Ser Pro Asp Gly Phe Val Cys Asp Asp
                485                 490                 495

Phe Pro Lys Pro Gln Ile Thr Val Gln Pro Glu Thr Gln Ser Ala
                500                 505                 510
```

-continued

```
Ile Lys Gly Ser Asn Leu Ser Phe Ile Cys Ser Ala Ala Ser Ser
                515                 520                 525

Ser Asp Ser Pro Met Thr Phe Ala Trp Lys Lys Asp Asn Glu Leu
                530                 535                 540

Leu His Asp Ala Glu Met Glu Asn Tyr Ala His Leu Arg Ala Gln
                545                 550                 555

Gly Gly Glu Val Met Glu Tyr Thr Thr Ile Leu Arg Leu Arg Glu
                560                 565                 570

Val Glu Phe Ala Ser Glu Gly Lys Tyr Gln Cys Val Ile Ser Asn
                575                 580                 585

His Phe Gly Ser Ser Tyr Ser Val Lys Ala Lys Leu Thr Val Asn
                590                 595                 600

Met Leu Pro Ser Phe Thr Lys Thr Pro Met Asp Leu Thr Ile Arg
                605                 610                 615

Ala Gly Ala Met Ala Arg Leu Glu Cys Ala Ala Val Gly His Pro
                620                 625                 630

Ala Pro Gln Ile Ala Trp Gln Lys Asp Gly Gly Thr Asp Phe Pro
                635                 640                 645

Ala Ala Arg Glu Arg Arg Met His Val Met Pro Glu Asp Asp Val
                650                 655                 660

Phe Phe Ile Val Asp Val Lys Ile Glu Asp Ile Gly Val Tyr Ser
                665                 670                 675

Cys Thr Ala Gln Asn Ser Ala Gly Ser Ile Ser Ala Asn Ala Thr
                680                 685                 690

Leu Thr Val Leu Glu Thr Pro Ser Phe Leu Arg Pro Leu Leu Asp
                695                 700                 705

Arg Thr Val Thr Lys Gly Glu Thr Ala Val Leu Gln Cys Ile Ala
                710                 715                 720

Gly Gly Ser Pro Pro Pro Lys Leu Asn Trp Thr Lys Asp Asp Ser
                725                 730                 735

Pro Leu Val Val Thr Glu Arg His Phe Phe Ala Ala Gly Asn Gln
                740                 745                 750

Leu Leu Ile Ile Val Asp Ser Asp Val Ser Asp Ala Gly Lys Tyr
                755                 760                 765

Thr Cys Glu Met Ser Asn Thr Leu Gly Thr Glu Arg Gly Asn Val
                770                 775                 780

Arg Leu Ser Val Ile Pro Thr Pro Thr Cys Asp Ser Pro Gln Met
                785                 790                 795

Thr Ala Pro Ser Leu Asp Asp Asp Gly Trp Ala Thr Val Gly Val
                800                 805                 810

Val Ile Ile Ala Val Val Cys Cys Val Val Gly Thr Ser Leu Val
                815                 820                 825

Trp Val Val Ile Ile Tyr His Thr Arg Arg Arg Asn Glu Asp Cys
                830                 835                 840

Ser Ile Thr Asn Thr Asp Glu Thr Asn Leu Pro Ala Asp Ile Pro
                845                 850                 855

Ser Tyr Leu Ser Ser Gln Gly Thr Leu Ala Asp Arg Gln Asp Gly
                860                 865                 870

Tyr Val Ser Ser Glu Ser Gly Ser His His Gln Phe Val Thr Ser
                875                 880                 885

Ser Gly Ala Gly Phe Phe Leu Pro Gln His Asp Ser Ser Gly Thr
                890                 895                 900

Cys His Ile Asp Asn Ser Ser Glu Ala Asp Val Glu Ala Ala Thr
```

-continued

```
                905                 910                 915

Asp Leu Phe Leu Cys Pro Phe Leu Gly Ser Thr Gly Pro Met Tyr
                920                 925                 930

Leu Lys Gly Asn Val Tyr Gly Ser Asp Pro Phe Glu Thr Tyr His
                935                 940                 945

Thr Gly Cys Ser Pro Asp Pro Arg Thr Val Leu Met Asp His Tyr
                950                 955                 960

Glu Pro Ser Tyr Ile Lys Lys Lys Glu Cys Tyr Pro Cys Ser His
                965                 970                 975

Pro Ser Glu Glu Ser Cys Glu Arg Ser Phe Ser Asn Ile Ser Trp
                980                 985                 990

Pro Ser His Val Arg Lys Leu Leu Asn Thr Ser Tyr Ser His Asn
                995                1000                1005

Glu Gly Pro Gly Met Lys Asn Leu Cys Leu Asn Lys Ser Ser Leu
               1010                1015                1020

Asp Phe Ser Ala Asn Pro Glu Pro Ala Ser Val Ala Ser Ser Asn
               1025                1030                1035

Ser Phe Met Gly Thr Phe Gly Lys Ala Leu Arg Arg Pro His Leu
               1040                1045                1050

Asp Ala Tyr Ser Ser Phe Gly Gln Pro Ser Asp Cys Gln Pro Arg
               1055                1060                1065

Ala Phe Tyr Leu Lys Ala His Ser Ser Pro Asp Leu Asp Ser Gly
               1070                1075                1080

Ser Glu Glu Asp Gly Lys Glu Arg Thr Asp Phe Gln Glu Glu Asn
               1085                1090                1095

His Ile Cys Thr Phe Lys Gln Thr Leu Glu Asn Tyr Arg Thr Pro
               1100                1105                1110

Asn Phe Gln Ser Tyr Asp Leu Asp Thr
               1115


<210> SEQ ID NO 295
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 295

ggaaccgaat ctcagcta                                                    18


<210> SEQ ID NO 296
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 296

cctaaactga actggacca                                                   19


<210> SEQ ID NO 297
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 297

ggctggagac actgaacct                                                   19
```

-continued

<210> SEQ ID NO 298
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 298
acagctgcac agctcagaac agtg 24

<210> SEQ ID NO 299
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 299
cattcccagt ataaaaattt tc 22

<210> SEQ ID NO 300
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 300
gggtcttggt gaatgagg 18

<210> SEQ ID NO 301
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 301
gtgcctctcg gttaccacca atgg 24

<210> SEQ ID NO 302
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 302
gcggccactg ttggaccgaa ctgtaaccaa gggagaaaca gccgtcctac 50

<210> SEQ ID NO 303
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 303
gcctttgaca accttcagtc actagtgg 28

<210> SEQ ID NO 304
<211> LENGTH: 24
<212> TYPE: DNA
<213> ORGANISM: Artificial Sequence
<220> FEATURE:

-continued

<223> OTHER INFORMATION: Synthetic Oligonucleotide Probe

<400> SEQUENCE: 304
ccccatgtgt ccatgactgt tccc 24

<210> SEQ ID NO 305
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 305
tactgcctca tgacctcttc actcccttgc atcatcttag agcgg 45

<210> SEQ ID NO 306
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 306
actccaagga aatcggatcc gttc 24

<210> SEQ ID NO 307
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 307
ttagcagctg aggatgggca caac 24

<210> SEQ ID NO 308
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 308
actccaagga aatcggatcc gttc 24

<210> SEQ ID NO 309
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 309
gccttcactg gtttggatgc attggagcat ctagacctga gtgacaacgc 50

<210> SEQ ID NO 310
<211> LENGTH: 3296
<212> TYPE: DNA
<213> ORGANISM: Homo Sapien

<400> SEQUENCE: 310
caaaacttgc gtcgcggaga gcgcccagct tgacttgaat ggaaggagcc 50
cgagcccgcg gagcgcagct gagactgggg gagcgcgttc ggcctgtggg 100
gcgccgctcg gcgccggggc gcagcaggga aggggaagct gtggtctgcc 150

-continued

```
ctgctccacg aggcgccact ggtgtgaacc gggagagccc ctgggtggtc    200
ccgtccccta tccctccttt atatagaaac cttccacact gggaaggcag    250
cggcgaggca ggagggctca tggtgagcaa ggaggccggc tgatctgcag    300
gcgcacagca ttccgagttt acagattttt acagatacca aatggaaggc    350
gaggaggcag aacagcctgc ctggttccat cagccctggc gcccaggcgc    400
atctgactcg gcaccccctg caggcaccat ggcccagagc cgggtgctgc    450
tgctcctgct gctgctgccg ccacagctgc acctgggacc tgtgcttgcc    500
gtgagggccc caggatttgg ccgaagtggc ggccacagcc tgagccccga    550
agagaacgaa tttgcggagg aggagccggt gctggtactg agccctgagg    600
agcccgggcc tggcccagcc gcggtcagct gcccccgaga ctgtgcctgt    650
tcccaggagg gcgtcgtgga ctgtggcggt attgacctgc gtgagttccc    700
gggggacctg cctgagcaca ccaaccacct atctctgcag aacaaccagc    750
tggaaaagat ctaccctgag gagctctccc ggctgcaccg gctggagaca    800
ctgaacctgc aaaacaaccg cctgacttcc cgagggctcc cagagaaggc    850
gtttgagcat ctgaccaacc tcaattacct gtacttggcc aataacaagc    900
tgaccttggc accccgcttc ctgccaaacg ccctgatcag tgtggacttt    950
gctgccaact atctcaccaa gatctatggg ctcacctttg gccagaagcc   1000
aaacttgagg tctgtgtacc tgcacaacaa caagctggca gacgccgggc   1050
tgccggacaa catgttcaac ggctccagca acgtcgaggt cctcatcctg   1100
tccagcaact tcctgcgcca cgtgcccaag cacctgccgc ctgccctgta   1150
caagctgcac ctcaagaaca acaagctgga gaagatcccc ccgggggcct   1200
tcagcgagct gagcagcctg cgcgagctat acctgcagaa caactacctg   1250
actgacgagg gcctggacaa cgagaccttc tggaagctct ccagcctgga   1300
gtacctggat ctgtccagca acaacctgtc tcgggtccca gctgggctgc   1350
cgcgcagcct ggtgctgctg cacttggaga agaacgccat ccggagcgtg   1400
gacgcgaatg tgctgacccc catccgcagc ctggagtacc tgctgctgca   1450
cagcaaccag ctgcgggagc agggcatcca cccactggcc ttccagggcc   1500
tcaagcggtt gcacacggtg cacctgtaca acaacgcgct ggagcgcgtg   1550
cccagtggcc tgcctcgccg cgtgcgcacc ctcatgatcc tgcacaacca   1600
gatcacaggc attggccgcg aagactttgc caccacctac ttcctggagg   1650
agctcaacct cagctacaac cgcatcacca gcccacaggt gcaccgcgac   1700
gccttccgca agctgcgcct gctgcgctcg ctggacctgt cgggcaaccg   1750
gctgcacacg ctgccacctg ggctgcctcg aaatgtccat gtgctgaagg   1800
tcaagcgcaa tgagctggct gccttggcac gaggggcgct ggcgggcatg   1850
gctcagctgc gtgagctgta cctcaccagc aaccgactgc gcagccgagc   1900
cctgggcccc cgtgcctggg tggacctcgc ccatctgcag ctgctggaca   1950
tcgccgggaa tcagctcaca gagatccccg aggggctccc cgagtcactt   2000
gagtacctgt acctgcagaa caacaagatt agtgcggtgc ccgccaatgc   2050
cttcgactcc acgcccaacc tcaaggggat ctttctcagg tttaacaagc   2100
```

-continued

```
tggctgtggg ctccgtggtg gacagtgcct tccggaggct gaagcacctg      2150

caggtcttgg acattgaagg caacttagag tttggtgaca tttccaagga      2200

ccgtggccgc ttggggaagg aaaaggagga ggaggaagag gaggaggagg      2250

aggaagagga aacaagatag tgacaaggtg atgcagatgt gacctaggat      2300

gatggaccgc cggactcttt tctgcagcac acgcctgtgt gctgtgagcc      2350

ccccactctg ccgtgctcac acagacacac ccagctgcac acatgaggca      2400

tcccacatga cacgggctga cacagtctca tatccccacc ccttcccacg      2450

gcgtgtccca cggccagaca catgcacaca catcacaccc tcaaacaccc      2500

agctcagcca cacacaacta ccctccaaac caccacagtc tctgtcacac      2550

ccccactacc gctgccacgc cctctgaatc atgcagggaa gggtctgccc      2600

ctgccctggc acacacaggc acccattccc tccccctgct gacatgtgta      2650

tgcgtatgca tacacaccac acacacacac atgcacaagt catgtgcgaa      2700

cagccctcca aagcctatgc cacagacagc tcttgcccca gccagaatca      2750

gccatagcag ctcgccgtct gccctgtcca tctgtccgtc cgttccctgg      2800

agaagacaca agggtatcca tgctctgtgg ccaggtgcct gccaccctct      2850

ggaactcaca aaagctggct tttattcctt tcccatccta tggggacagg      2900

agccttcagg actgctggcc tggcctggcc caccctgctc ctccaggtgc      2950

tgggcagtca ctctgctaag agtccctccc tgccacgccc tggcaggaca      3000

caggcacttt tccaatgggc aagcccagtg gaggcaggat gggagagccc      3050

cctgggtgct gctggggcct tggggcagga gtgaagcaga ggtgatgggg      3100

ctgggctgag ccagggagga aggacccagc tgcacctagg agacaccttt      3150

gttcttcagg cctgtggggg aagttccggg tgcctttatt ttttattctt      3200

ttctaaggaa aaaaatgata aaaatctcaa agctgatttt tcttgttata      3250

gaaaaactaa tataaaagca ttatccctat ccctgcaaaa aaaaaa          3296
```

<210> SEQ ID NO 311
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 311
gcattggccg cgagactttg cc 22

<210> SEQ ID NO 312
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 312
gcggccacgg tccttggaaa tg 22

<210> SEQ ID NO 313
<211> LENGTH: 45
<212> TYPE: DNA
<213> ORGANISM: Artificial Sequence
<220> FEATURE:
<223> OTHER INFORMATION: Synthetic Oligonucleotide Probe -continued

<400> SEQUENCE: 313
tggaggagct caacctcagc tacaaccgca tcaccagccc acagg 45

<210> SEQ ID NO 314
<211> LENGTH: 3003
<212> TYPE: DNA
<213> ORGANISM: Homo Sapien

<400> SEQUENCE: 314
gggagggggc tccgggcgcc gcgcagcaga cctgctccgg ccgcgcgcct 50
cgccgctgtc ctccgggagc ggcagcagta gcccgggcgg cgagggctgg 100
gggttcctcg agactctcag aggggcgcct cccatcggcg cccaccaccc 150
caacctgttc ctcgcgcgcc actgcgctgc gccccaggac ccgctgccca 200
acatggattt tctcctggcg ctggtgctgg tatcctcgct ctacctgcag 250
gcggccgccg agttcgacgg gaggtggccc aggcaaatag tgtcatcgat 300
tggcctatgt cgttatggtg ggaggattga ctgctgctgg ggctgggctc 350
gccagtcttg ggacagtgt cagcctgtgt gccaaccacg atgcaaacat 400
ggtgaatgta tcgggccaaa caagtgcaag tgtcatcctg gttatgctgg 450
aaaaacctgt aatcaagatc taaatgagtg tggcctgaag ccccggccct 500
gtaagcacag gtgcatgaac acttacggca gctacaagtg ctactgtctc 550
aacggatata tgctcatgcc ggatggttcc tgctcaagtg ccctgacctg 600
ctccatggca aactgtcagt atggctgtga tgttgttaaa ggacaaatac 650
ggtgccagtg cccatcccct ggcctgcacc tggctcctga tgggaggacc 700
tgtgtagatg ttgatgaatg tgctacagga agagcctcct gccctagatt 750
taggcaatgt gtcaacactt ttgggagcta catctgcaag tgtcataaag 800
gcttcgatct catgtatatt ggaggcaaat atcaatgtca tgacatagac 850
gaatgctcac ttggtcagta tcagtgcagc agctttgctc gatgttataa 900
cgtacgtggg tcctacaagt gcaaatgtaa agaaggatac cagggtgatg 950
gactgacttg tgtgtatatc ccaaaagtta tgattgaacc ttcaggtcca 1000
attcatgtac caaagggaaa tggtaccatt ttaaagggtg acacaggaaa 1050
taataattgg attcctgatg ttggaagtac ttggtggcct ccgaagacac 1100
catatattcc tcctatcatt accaacaggc ctacttctaa gccaacaaca 1150
agacctacac caaagccaac accaattcct actccaccac caccaccacc 1200
cctgccaaca gagctcagaa cacctctacc acctacaacc ccagaaaggc 1250
caaccaccgg actgacaact atagcaccag ctgccagtac acctccagga 1300
gggattacag ttgacaacag ggtacagaca gaccctcaga aacccagagg 1350
agatgtgttc agtgttctgg tacacagttg taattttgac catggacttt 1400
gtggatggat cagggagaaa gacaatgact tgcactggga accaatcagg 1450
gacccagcag gtggacaata tctgacagtg tcggcagcca aagccccagg 1500
gggaaaagct gcacgcttgg tgctacctct cggccgcctc atgcattcag 1550
gggacctgtg cctgtcattc aggcacaagg tgacggggct gcactctggc 1600
acactccagg tgtttgtgag aaaacacggt gcccacggag cagccctgtg 1650

-continued

```
gggaagaaat ggtggccatg gctggaggca aacacagatc accttgcgag              1700

gggctgacat caagagcgaa tcacaaagat gattaaaggg ttggaaaaaa              1750

agatctatga tggaaaatta aaggaactgg gattattgag cctggagaag              1800

agaagactga ggggcaaacc attgatggtt ttcaagtata tgaagggttg              1850

gcacagagag ggtggcgacc agctgttctc catatgcact aagaatagaa              1900

caagaggaaa ctggcttaga ctagagtata agggagcatt tcttggcagg              1950

ggccattgtt agaatacttc ataaaaaaag aagtgtgaaa atctcagtat              2000

ctctctctct ttctaaaaaa ttagataaaa atttgtctat ttaagatggt              2050

taaagatgtt cttacccaag gaaaagtaac aaattataga atttcccaaa              2100

agatgttttg atcctactag tagtatgcag tgaaaatctt tagaactaaa              2150

taatttggac aaggcttaat ttaggcattt ccctcttgac ctcctaatgg              2200

agagggattg aaaggggaag agcccaccaa atgctgagct cactgaaata              2250

tctctccctt atggcaatcc tagcagtatt aaagaaaaaa ggaaactatt              2300

tattccaaat gagagtatga tggacagata ttttagtatc tcagtaatgt              2350

cctagtgtgg cggtggtttt caatgtttct tcatggtaaa ggtataagcc              2400

tttcatttgt tcaatggatg atgtttcaga tttttttttt tttaagagat              2450

ccttcaagga acacagttca gagagatttt catcgggtgc attctctctg              2500

cttcgtgtgt gacaagttat cttggctgct gagaaagagt gccctgcccc              2550

acaccggcag acctttcctt cacctcatca gtatgattca gtttctctta              2600

tcaattggac tctcccaggt tccacagaac agtaatattt tttgaacaat              2650

aggtacaata gaaggtcttc tgtcatttaa cctggtaaag gcagggctgg              2700

agggggaaaa taaatcatta agcctttgag taacggcaga atatatggct              2750

gtagatccat ttttaatggt tcatttcctt tatggtcata taactgcaca              2800

gctgaagatg aaaggggaaa ataaatgaaa attttacttt tcgatgccaa              2850

tgatacattg cactaaactg atggaagaag ttatccaaag tactgtataa              2900

catcttgttt attatttaat gttttctaaa ataaaaaatg ttagtggttt              2950

tccaaatggc ctaataaaaa caattatttg taaataaaaa cactgttagt              3000

aat 3003


<210> SEQ ID NO 315
<211> LENGTH: 509
<212> TYPE: PRT
<213> ORGANISM: Homo Sapien

<400> SEQUENCE: 315

Met Asp Phe Leu Leu Ala Leu Val Leu Val Ser Ser Leu Tyr Leu
  1               5                  10                  15

Gln Ala Ala Ala Glu Phe Asp Gly Arg Trp Pro Arg Gln Ile Val
                 20                  25                  30

Ser Ser Ile Gly Leu Cys Arg Tyr Gly Gly Arg Ile Asp Cys Cys
                 35                  40                  45

Trp Gly Trp Ala Arg Gln Ser Trp Gly Gln Cys Gln Pro Val Cys
                 50                  55                  60

Gln Pro Arg Cys Lys His Gly Glu Cys Ile Gly Pro Asn Lys Cys
                 65                  70                  75
```

-continued

```
Lys Cys His Pro Gly Tyr Ala Gly Lys Thr Cys Asn Gln Asp Leu
                80                  85                  90

Asn Glu Cys Gly Leu Lys Pro Arg Pro Cys Lys His Arg Cys Met
                95                  100                 105

Asn Thr Tyr Gly Ser Tyr Lys Cys Tyr Cys Leu Asn Gly Tyr Met
                110                 115                 120

Leu Met Pro Asp Gly Ser Cys Ser Ser Ala Leu Thr Cys Ser Met
                125                 130                 135

Ala Asn Cys Gln Tyr Gly Cys Asp Val Val Lys Gly Gln Ile Arg
                140                 145                 150

Cys Gln Cys Pro Ser Pro Gly Leu His Leu Ala Pro Asp Gly Arg
                155                 160                 165

Thr Cys Val Asp Val Asp Glu Cys Ala Thr Gly Arg Ala Ser Cys
                170                 175                 180

Pro Arg Phe Arg Gln Cys Val Asn Thr Phe Gly Ser Tyr Ile Cys
                185                 190                 195

Lys Cys His Lys Gly Phe Asp Leu Met Tyr Ile Gly Gly Lys Tyr
                200                 205                 210

Gln Cys His Asp Ile Asp Glu Cys Ser Leu Gly Gln Tyr Gln Cys
                215                 220                 225

Ser Ser Phe Ala Arg Cys Tyr Asn Val Arg Gly Ser Tyr Lys Cys
                230                 235                 240

Lys Cys Lys Glu Gly Tyr Gln Gly Asp Gly Leu Thr Cys Val Tyr
                245                 250                 255

Ile Pro Lys Val Met Ile Glu Pro Ser Gly Pro Ile His Val Pro
                260                 265                 270

Lys Gly Asn Gly Thr Ile Leu Lys Gly Asp Thr Gly Asn Asn Asn
                275                 280                 285

Trp Ile Pro Asp Val Gly Ser Thr Trp Trp Pro Pro Lys Thr Pro
                290                 295                 300

Tyr Ile Pro Pro Ile Ile Thr Asn Arg Pro Thr Ser Lys Pro Thr
                305                 310                 315

Thr Arg Pro Thr Pro Lys Pro Thr Pro Ile Pro Thr Pro Pro Pro
                320                 325                 330

Pro Pro Pro Leu Pro Thr Glu Leu Arg Thr Pro Leu Pro Pro Thr
                335                 340                 345

Thr Pro Glu Arg Pro Thr Thr Gly Leu Thr Thr Ile Ala Pro Ala
                350                 355                 360

Ala Ser Thr Pro Pro Gly Gly Ile Thr Val Asp Asn Arg Val Gln
                365                 370                 375

Thr Asp Pro Gln Lys Pro Arg Gly Asp Val Phe Ser Val Leu Val
                380                 385                 390

His Ser Cys Asn Phe Asp His Gly Leu Cys Gly Trp Ile Arg Glu
                395                 400                 405

Lys Asp Asn Asp Leu His Trp Glu Pro Ile Arg Asp Pro Ala Gly
                410                 415                 420

Gly Gln Tyr Leu Thr Val Ser Ala Ala Lys Ala Pro Gly Gly Lys
                425                 430                 435

Ala Ala Arg Leu Val Leu Pro Leu Gly Arg Leu Met His Ser Gly
                440                 445                 450

Asp Leu Cys Leu Ser Phe Arg His Lys Val Thr Gly Leu His Ser
                455                 460                 465

Gly Thr Leu Gln Val Phe Val Arg Lys His Gly Ala His Gly Ala
```

-continued

```
                470                 475                 480

Ala Leu Trp Gly Arg Asn Gly Gly His Gly Trp Arg Gln Thr Gln
                485                 490                 495

Ile Thr Leu Arg Gly Ala Asp Ile Lys Ser Glu Ser Gln Arg
                500                 505
```

<210> SEQ ID NO 316
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 316
gatggttcct gctcaagtgc cctg 24

<210> SEQ ID NO 317
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 317
ttgcacttgt aggacccacg tacg 24

<210> SEQ ID NO 318
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 318
ctgatgggag gacctgtgta gatgttgatg aatgtgctac aggaagagcc 50

<210> SEQ ID NO 319
<211> LENGTH: 2110
<212> TYPE: DNA
<213> ORGANISM: Homo Sapien

<400> SEQUENCE: 319
cttctttgaa aaggattatc acctgatcag gttctctctg catttgcccc 50
tttagattgt gaaatgtggc tcaaggtctt cacaactttc ctttcctttg 100
caacaggtgc ttgctcgggg ctgaaggtga cagtgccatc acacactgtc 150
catggcgtca gaggtcaggc cctctaccta cccgtccact atggcttcca 200
cactccagca tcagacatcc agatcatatg gctatttgag agaccccaca 250
caatgcccaa atacttactg ggctctgtga ataagtctgt ggttcctgac 300
ttggaatacc aacacaagtt caccatgatg ccacccaatg catctctgct 350
tatcaaccca ctgcagttcc ctgatgaagg caattacatc gtgaaggtca 400
acattcaggg aaatggaact ctatctgcca gtcagaagat acaagtcacg 450
gttgatgatc ctgtcacaaa gccagtggtg cagattcatc ctccctctgg 500
ggctgtggag tatgtgggga acatgaccct gacatgccat gtggaagggg 550
gcactcggct agcttaccaa tggctaaaaa atgggagacc tgtccacacc 600
agctccacct actccttttc tccccaaaac aatacccttc atattgctcc 650
agtaaccaag gaagacattg ggaattacag ctgcctggtg aggaaccctg 700

-continued

```
tcagtgaaat ggaaagtgat atcattatgc ccatcatata ttatggacct          750
tatggacttc aagtgaattc tgataaaggg ctaaaagtag gggaagtgtt          800
tactgttgac cttggagagg ccatcctatt tgattgttct gctgattctc          850
atcccccaa cacctactcc tggattagga ggactgacaa tactacatat           900
atcattaagc atgggcctcg cttagaagtt gcatctgaga aagtagccca          950
gaagacaatg gactatgtgt gctgtgctta caacaacata accggcaggc         1000
aagatgaaac tcatttcaca gttatcatca cttccgtagg actggagaag         1050
cttgcacaga aaggaaaatc attgtcacct ttagcaagta taactggaat         1100
atcactattt ttgattatat ccatgtgtct tctcttccta tggaaaaaat         1150
atcaacccta caaagttata aaacagaaac tagaaggcag gccagaaaca         1200
gaatacagga aagctcaaac attttcaggc catgaagatg ctctggatga         1250
cttcggaata tatgaatttg ttgcttttcc agatgtttct ggtgtttcca         1300
ggattccaag caggtctgtt ccagcctctg attgtgtatc ggggcaagat         1350
ttgcacagta cagtgtatga agttattcag cacatccctg cccagcagca         1400
agaccatcca gagtgaactt tcatgggcta aacagtacat tcgagtgaaa         1450
ttctgaagaa acattttaag gaaaaacagt ggaaaagtat attaatctgg         1500
aatcagtgaa gaaaccagga ccaacacctc ttactcatta ttcctttaca         1550
tgcagaatag aggcatttat gcaaattgaa ctgcaggttt ttcagcatat         1600
acacaatgtc ttgtgcaaca gaaaaacatg ttggggaaat attcctcagt         1650
ggagagtcgt tctcatgctg acggggagaa cgaaagtgac aggggtttcc         1700
tcataagttt tgtatgaaat atctctacaa acctcaatta gttctactct         1750
acactttcac tatcatcaac actgagacta tcctgtctca cctacaaatg         1800
tggaaacttt acattgttcg atttttcagc agactttgtt ttattaaatt         1850
tttattagtg ttaagaatgc taaatttatg tttcaatttt atttccaaat         1900
ttctatcttg ttatttgtac aacaaagtaa taaggatggt tgtcacaaaa         1950
acaaaactat gccttctctt ttttttcaat caccagtagt atttttgaga         2000
agacttgtga acacttaagg aaatgactat taaagtctta tttttatttt         2050
tttcaaggaa agatggattc aaataaatta ttctgttttt gcttttaaaa         2100
aaaaaaaaaa                                                     2110
```

<210> SEQ ID NO 320
<211> LENGTH: 450
<212> TYPE: PRT
<213> ORGANISM: Homo Sapien

<400> SEQUENCE: 320

```
Met Trp Leu Lys Val Phe Thr Thr Phe Leu Ser Phe Ala Thr Gly
  1               5                  10                  15

Ala Cys Ser Gly Leu Lys Val Thr Val Pro Ser His Thr Val His
                 20                  25                  30

Gly Val Arg Gly Gln Ala Leu Tyr Leu Pro Val His Tyr Gly Phe
                 35                  40                  45

His Thr Pro Ala Ser Asp Ile Gln Ile Ile Trp Leu Phe Glu Arg
                 50                  55                  60
```

-continued

```
Pro His Thr Met Pro Lys Tyr Leu Leu Gly Ser Val Asn Lys Ser
                65                  70                  75

Val Val Pro Asp Leu Glu Tyr Gln His Lys Phe Thr Met Met Pro
                80                  85                  90

Pro Asn Ala Ser Leu Leu Ile Asn Pro Leu Gln Phe Pro Asp Glu
                95                 100                 105

Gly Asn Tyr Ile Val Lys Val Asn Ile Gln Gly Asn Gly Thr Leu
               110                 115                 120

Ser Ala Ser Gln Lys Ile Gln Val Thr Val Asp Asp Pro Val Thr
               125                 130                 135

Lys Pro Val Val Gln Ile His Pro Pro Ser Gly Ala Val Glu Tyr
               140                 145                 150

Val Gly Asn Met Thr Leu Thr Cys His Val Glu Gly Gly Thr Arg
               155                 160                 165

Leu Ala Tyr Gln Trp Leu Lys Asn Gly Arg Pro Val His Thr Ser
               170                 175                 180

Ser Thr Tyr Ser Phe Ser Pro Gln Asn Asn Thr Leu His Ile Ala
               185                 190                 195

Pro Val Thr Lys Glu Asp Ile Gly Asn Tyr Ser Cys Leu Val Arg
               200                 205                 210

Asn Pro Val Ser Glu Met Glu Ser Asp Ile Ile Met Pro Ile Ile
               215                 220                 225

Tyr Tyr Gly Pro Tyr Gly Leu Gln Val Asn Ser Asp Lys Gly Leu
               230                 235                 240

Lys Val Gly Glu Val Phe Thr Val Asp Leu Gly Glu Ala Ile Leu
               245                 250                 255

Phe Asp Cys Ser Ala Asp Ser His Pro Pro Asn Thr Tyr Ser Trp
               260                 265                 270

Ile Arg Arg Thr Asp Asn Thr Thr Tyr Ile Ile Lys His Gly Pro
               275                 280                 285

Arg Leu Glu Val Ala Ser Glu Lys Val Ala Gln Lys Thr Met Asp
               290                 295                 300

Tyr Val Cys Cys Ala Tyr Asn Asn Ile Thr Gly Arg Gln Asp Glu
               305                 310                 315

Thr His Phe Thr Val Ile Ile Thr Ser Val Gly Leu Glu Lys Leu
               320                 325                 330

Ala Gln Lys Gly Lys Ser Leu Ser Pro Leu Ala Ser Ile Thr Gly
               335                 340                 345

Ile Ser Leu Phe Leu Ile Ile Ser Met Cys Leu Leu Phe Leu Trp
               350                 355                 360

Lys Lys Tyr Gln Pro Tyr Lys Val Ile Lys Gln Lys Leu Glu Gly
               365                 370                 375

Arg Pro Glu Thr Glu Tyr Arg Lys Ala Gln Thr Phe Ser Gly His
               380                 385                 390

Glu Asp Ala Leu Asp Asp Phe Gly Ile Tyr Glu Phe Val Ala Phe
               395                 400                 405

Pro Asp Val Ser Gly Val Ser Arg Ile Pro Ser Arg Ser Val Pro
               410                 415                 420

Ala Ser Asp Cys Val Ser Gly Gln Asp Leu His Ser Thr Val Tyr
               425                 430                 435

Glu Val Ile Gln His Ile Pro Ala Gln Gln Gln Asp His Pro Glu
               440                 445                 450
```

-continued

<210> SEQ ID NO 321
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 321
gatcctgtca caaagccagt ggtgc 25

<210> SEQ ID NO 322
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 322
cactgacagg gttcctcacc cagg 24

<210> SEQ ID NO 323
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 323
ctccctctgg gctgtggagt atgtggggaa catgaccctg acatg 45

<210> SEQ ID NO 324
<211> LENGTH: 2397
<212> TYPE: DNA
<213> ORGANISM: Homo Sapien

<400> SEQUENCE: 324
gcaagcggcg aaatggcgcc ctccgggagt cttgcagttc ccctggcagt 50
cctggtgctg ttgctttggg gtgctccctg gacgcacggg cggcggagca 100
acgttcgcgt catcacggac gagaactgga gagaactgct ggaaggagac 150
tggatgatag aattttatgc cccgtggtgc cctgcttgtc aaaatcttca 200
accggaatgg gaaagttttg ctgaatgggg agaagatctt gaggttaata 250
ttgcgaaagt agatgtcaca gagcagccag gactgagtgg acggtttatc 300
ataactgctc ttcctactat ttatcattgt aaagatggtg aatttaggcg 350
ctatcagggt ccaaggacta agaaggactt cataaacttt ataagtgata 400
aagagtggaa gagtattgag cccgtttcat catggtttgg tccaggttct 450
gttctgatga gtagtatgtc agcactcttt cagctatcta tgtggatcag 500
gacgtgccat aactacttta ttgaagacct tggattgcca gtgtggggat 550
catatactgt ttttgcttta gcaactctgt tttccggact gttattagga 600
ctctgtatga tatttgtggc agattgcctt tgtccttcaa aaaggcgcag 650
accacagcca tacccatacc cttcaaaaaa attattatca gaatctgcac 700
aacctttgaa aaaagtggag gaggaacaag aggcggatga agaagatgtt 750
tcagaagaag aagctgaaag taaagaagga acaaacaaag actttccaca 800
gaatgccata agacaacgct ctctgggtcc atcattggcc acagataaat 850
cctagttaaa ttttatagtt atcttaatat tatgattttg ataaaaacag 900

-continued

```
aagattgatc attttgtttg gtttgaagtg aactgtgact tttttgaata        950

ttgcagggtt cagtctagat tgtcattaaa ttgaagagtc tacattcaga       1000

acataaaagc actaggtata caagtttgaa atatgattta agcacagtat       1050

gatggtttaa atagttctct aatttttgaa aaatcgtgcc aagcaataag       1100

atttatgtat atttgtttaa taataaccta tttcaagtct gagttttgaa       1150

aatttacatt tcccaagtat tgcattattg aggtatttaa gaagattatt       1200

ttagagaaaa atatttctca tttgatataa tttttctctg tttcactgtg       1250

tgaaaaaaag aagatatttc ccataaatgg gaagtttgcc cattgtctca       1300

agaaatgtgt atttcagtga caatttcgtg gtctttttag aggtatattc       1350

caaaatttcc ttgtattttt aggttatgca actaataaaa actaccttac       1400

attaattaat tacagttttc tacacatggt aatacaggat atgctactga       1450

tttaggaagt ttttaagttc atggtattct cttgattcca acaaagtttg       1500

attttctctt gtatttttct tacttactat gggttacatt ttttattttt       1550

caaattggat gataatttct tggaaacatt ttttatgttt tagtaaacag       1600

tatttttttg ttgtttcaaa ctgaagttta ctgagagatc catcaaattg       1650

aacaatctgt tgtaatttaa aattttggcc acttttttca gattttacat       1700

cattcttgct gaacttcaac ttgaaattgt tttttttttc tttttggatg       1750

tgaaggtgaa cattcctgat ttttgtctga tgtgaaaaag ccttggtatt       1800

ttacattttg aaaattcaaa gaagcttaat ataaaagttt gcattctact       1850

caggaaaaag catcttcttg tatatgtctt aaatgtattt ttgtcctcat       1900

atacagaaag ttcttaattg attttacagt ctgtaatgct tgatgtttta       1950

aaataataac atttttatat tttttaaaag acaaacttca tattatcctg       2000

tgttctttcc tgactggtaa tattgtgtgg gatttcacag gtaaaagtca       2050

gtaggatgga acattttagt gtatttttac tccttaaaga gctagaatac       2100

atagttttca ccttaaaaga agggggaaaa tcataaatac aatgaatcaa       2150

ctgaccatta cgtagtagac aatttctgta atgtcccctt ctttctaggc       2200

tctgttgctg tgtgaatcca ttagatttac agtatcgtaa tatacaagtt       2250

ttctttaaag ccctctcctt tagaatttaa aatattgtac cattaaagag       2300

tttggatgtg taacttgtga tgccttagaa aaatatccta agcacaaaat       2350

aaacctttct aaccacttca ttaaagctga aaaaaaaaaa aaaaaaa          2397
```

<210> SEQ ID NO 325
<211> LENGTH: 280
<212> TYPE: PRT
<213> ORGANISM: Homo Sapien

<400> SEQUENCE: 325

```
Met Ala Pro Ser Gly Ser Leu Ala Val Pro Leu Ala Val Leu Val
  1               5                  10                  15

Leu Leu Leu Trp Gly Ala Pro Trp Thr His Gly Arg Arg Ser Asn
                 20                  25                  30

Val Arg Val Ile Thr Asp Glu Asn Trp Arg Glu Leu Leu Glu Gly
                 35                  40                  45

Asp Trp Met Ile Glu Phe Tyr Ala Pro Trp Cys Pro Ala Cys Gln
                 50                  55                  60
```

-continued

```
Asn Leu Gln Pro Glu Trp Glu Ser Phe Ala Glu Trp Gly Glu Asp
                65                  70                  75

Leu Glu Val Asn Ile Ala Lys Val Asp Val Thr Glu Gln Pro Gly
                80                  85                  90

Leu Ser Gly Arg Phe Ile Ile Thr Ala Leu Pro Thr Ile Tyr His
                95                  100                 105

Cys Lys Asp Gly Glu Phe Arg Arg Tyr Gln Gly Pro Arg Thr Lys
                110                 115                 120

Lys Asp Phe Ile Asn Phe Ile Ser Asp Lys Glu Trp Lys Ser Ile
                125                 130                 135

Glu Pro Val Ser Ser Trp Phe Gly Pro Gly Ser Val Leu Met Ser
                140                 145                 150

Ser Met Ser Ala Leu Phe Gln Leu Ser Met Trp Ile Arg Thr Cys
                155                 160                 165

His Asn Tyr Phe Ile Glu Asp Leu Gly Leu Pro Val Trp Gly Ser
                170                 175                 180

Tyr Thr Val Phe Ala Leu Ala Thr Leu Phe Ser Gly Leu Leu Leu
                185                 190                 195

Gly Leu Cys Met Ile Phe Val Ala Asp Cys Leu Cys Pro Ser Lys
                200                 205                 210

Arg Arg Arg Pro Gln Pro Tyr Pro Tyr Pro Ser Lys Lys Leu Leu
                215                 220                 225

Ser Glu Ser Ala Gln Pro Leu Lys Lys Val Glu Glu Glu Gln Glu
                230                 235                 240

Ala Asp Glu Glu Asp Val Ser Glu Glu Glu Ala Glu Ser Lys Glu
                245                 250                 255

Gly Thr Asn Lys Asp Phe Pro Gln Asn Ala Ile Arg Gln Arg Ser
                260                 265                 270

Leu Gly Pro Ser Leu Ala Thr Asp Lys Ser
                275                 280
```

<210> SEQ ID NO 326
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 326
tgaggtgggc aagcggcgaa atg 23

<210> SEQ ID NO 327
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 327
tatgtggatc aggacgtgcc 20

<210> SEQ ID NO 328
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 328

-continued

```
tgcagggttc agtctagatt g                                          21


<210> SEQ ID NO 329
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 329

ttgaaggaca aaggcaatct gccac                                      25


<210> SEQ ID NO 330
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 330

ggagtcttgc agttcccctg gcagtcctgg tgctgttgct ttggg                45


<210> SEQ ID NO 331
<211> LENGTH: 2168
<212> TYPE: DNA
<213> ORGANISM: Homo Sapien

<400> SEQUENCE: 331

gcgagtgtcc agctgcggag acccgtgata attcgttaac taattcaaca           50

aacgggaccc ttctgtgtgc cagaaaccgc aagcagttgc taacccagtg          100

ggacaggcgg attggaagag cgggaaggtc ctggcccaga gcagtgtgac          150

acttccctct gtgaccatga aactctgggt gtctgcattg ctgatggcct          200

ggtttggtgt cctgagctgt gtgcaggccg aattcttcac ctctattggg          250

cacatgactg acctgattta tgcagagaaa gagctggtgc agtctctgaa          300

agagtacatc cttgtggagg aagccaagct ttccaagatt aagagctggg          350

ccaacaaaat ggaagccttg actagcaagt cagctgctga tgctgagggc          400

tacctggctc accctgtgaa tgcctacaaa ctggtgaagc ggctaaacac          450

agactggcct gcgctggagg accttgtcct gcaggactca gctgcaggtt          500

ttatcgccaa cctctctgtg cagcggcagt tcttccccac tgatgaggac          550

gagataggag ctgccaaagc cctgatgaga cttcaggaca catacaggct          600

ggacccaggc acaatttcca gaggggaact tccaggaacc aagtaccagg          650

caatgctgag tgtggatgac tgctttggga tgggccgctc ggcctacaat          700

gaaggggact attatcatac ggtgttgtgg atggagcagg tgctaaagca          750

gcttgatgcc ggggaggagg ccaccacaac caagtcacag gtgctggact          800

acctcagcta tgctgtcttc cagttgggtg atctgcaccg tgccctggag          850

ctcacccgcc gcctgctctc ccttgaccca agccacgaac gagctggagg          900

gaatctgcgg tactttgagc agttattgga ggaagagaga gaaaaaacgt          950

taacaaatca gacagaagct gagctagcaa ccccagaagg catctatgag         1000

aggcctgtgg actacctgcc tgagagggat gtttacgaga gcctctgtcg         1050

tggggagggt gtcaaactga caccccgtag acagaagagg cttttctgta         1100
```

-continued

```
ggtaccacca tggcaacagg gccccacagc tgctcattgc cccctcaaa              1150

gaggaggacg agtgggacag cccgcacatc gtcaggtact acgatgtcat             1200

gtctgatgag gaaatcgaga ggatcaagga gatcgcaaaa cctaaacttg             1250

cacgagccac cgttcgtgat cccaagacag gagtcctcac tgtcgccagc             1300

taccgggttt ccaaaagctc ctggctagag gaagatgatg accctgttgt             1350

ggcccgagta aatcgtcgga tgcagcatat cacagggtta acagtaaaga             1400

ctgcagaatt gttacaggtt gcaaattatg gagtgggagg acagtatgaa             1450

ccgcacttcg acttctctag gcgacctttt gacagcggcc tcaaaacaga             1500

ggggaatagg ttagcgacgt ttcttaacta catgagtgat gtagaagctg             1550

gtggtgccac cgtcttccct gatctggggg ctgcaatttg gcctaagaag             1600

ggtacagctg tgttctggta caacctcttg cggagcgggg aaggtgacta             1650

ccgaacaaga catgctgcct gccctgtgct tgtgggctgc aagtgggtct             1700

ccaataagtg gttccatgaa cgaggacagg agttcttgag accttgtgga             1750

tcaacagaag ttgactgaca tccttttctg tccttcccct tcctggtcct             1800

tcagcccatg tcaacgtgac agacaccttt gtatgttcct ttgtatgttc             1850

ctatcaggct gatttttgga gaaatgaatg tttgtctgga gcagagggag             1900

accatactag ggcgactcct gtgtgactga agtcccagcc cttccattca             1950

gcctgtgcca tccctggccc caaggctagg atcaaagtgg ctgcagcaga             2000

gttagctgtc tagcgcctag caaggtgcct ttgtacctca ggtgttttag             2050

gtgtgagatg tttcagtgaa ccaaagttct gataccttgt ttacatgttt             2100

gtttttatgg catttctatc tattgtggct ttaccaaaaa ataaaatgtc             2150

cctaccagaa aaaaaaaa                                                2168
```

<210> SEQ ID NO 332
<211> LENGTH: 533
<212> TYPE: PRT
<213> ORGANISM: Homo Sapien

<400> SEQUENCE: 332

```
Met Lys Leu Trp Val Ser Ala Leu Leu Met Ala Trp Phe Gly Val
  1               5                  10                  15

Leu Ser Cys Val Gln Ala Glu Phe Phe Thr Ser Ile Gly His Met
                 20                  25                  30

Thr Asp Leu Ile Tyr Ala Glu Lys Glu Leu Val Gln Ser Leu Lys
                 35                  40                  45

Glu Tyr Ile Leu Val Glu Glu Ala Lys Leu Ser Lys Ile Lys Ser
                 50                  55                  60

Trp Ala Asn Lys Met Glu Ala Leu Thr Ser Lys Ser Ala Ala Asp
                 65                  70                  75

Ala Glu Gly Tyr Leu Ala His Pro Val Asn Ala Tyr Lys Leu Val
                 80                  85                  90

Lys Arg Leu Asn Thr Asp Trp Pro Ala Leu Glu Asp Leu Val Leu
                 95                 100                 105

Gln Asp Ser Ala Ala Gly Phe Ile Ala Asn Leu Ser Val Gln Arg
                110                 115                 120

Gln Phe Phe Pro Thr Asp Glu Asp Glu Ile Gly Ala Ala Lys Ala
                125                 130                 135
```

-continued

```
Leu Met Arg Leu Gln Asp Thr Tyr Arg Leu Asp Pro Gly Thr Ile
                140                 145                 150

Ser Arg Gly Glu Leu Pro Gly Thr Lys Tyr Gln Ala Met Leu Ser
                155                 160                 165

Val Asp Asp Cys Phe Gly Met Gly Arg Ser Ala Tyr Asn Glu Gly
                170                 175                 180

Asp Tyr Tyr His Thr Val Leu Trp Met Glu Gln Val Leu Lys Gln
                185                 190                 195

Leu Asp Ala Gly Glu Glu Ala Thr Thr Thr Lys Ser Gln Val Leu
                200                 205                 210

Asp Tyr Leu Ser Tyr Ala Val Phe Gln Leu Gly Asp Leu His Arg
                215                 220                 225

Ala Leu Glu Leu Thr Arg Arg Leu Leu Ser Leu Asp Pro Ser His
                230                 235                 240

Glu Arg Ala Gly Gly Asn Leu Arg Tyr Phe Glu Gln Leu Leu Glu
                245                 250                 255

Glu Glu Arg Glu Lys Thr Leu Thr Asn Gln Thr Glu Ala Glu Leu
                260                 265                 270

Ala Thr Pro Glu Gly Ile Tyr Glu Arg Pro Val Asp Tyr Leu Pro
                275                 280                 285

Glu Arg Asp Val Tyr Glu Ser Leu Cys Arg Gly Glu Gly Val Lys
                290                 295                 300

Leu Thr Pro Arg Arg Gln Lys Arg Leu Phe Cys Arg Tyr His His
                305                 310                 315

Gly Asn Arg Ala Pro Gln Leu Leu Ile Ala Pro Phe Lys Glu Glu
                320                 325                 330

Asp Glu Trp Asp Ser Pro His Ile Val Arg Tyr Tyr Asp Val Met
                335                 340                 345

Ser Asp Glu Glu Ile Glu Arg Ile Lys Glu Ile Ala Lys Pro Lys
                350                 355                 360

Leu Ala Arg Ala Thr Val Arg Asp Pro Lys Thr Gly Val Leu Thr
                365                 370                 375

Val Ala Ser Tyr Arg Val Ser Lys Ser Ser Trp Leu Glu Glu Asp
                380                 385                 390

Asp Asp Pro Val Val Ala Arg Val Asn Arg Arg Met Gln His Ile
                395                 400                 405

Thr Gly Leu Thr Val Lys Thr Ala Glu Leu Leu Gln Val Ala Asn
                410                 415                 420

Tyr Gly Val Gly Gly Gln Tyr Glu Pro His Phe Asp Phe Ser Arg
                425                 430                 435

Arg Pro Phe Asp Ser Gly Leu Lys Thr Glu Gly Asn Arg Leu Ala
                440                 445                 450

Thr Phe Leu Asn Tyr Met Ser Asp Val Glu Ala Gly Gly Ala Thr
                455                 460                 465

Val Phe Pro Asp Leu Gly Ala Ala Ile Trp Pro Lys Lys Gly Thr
                470                 475                 480

Ala Val Phe Trp Tyr Asn Leu Leu Arg Ser Gly Glu Gly Asp Tyr
                485                 490                 495

Arg Thr Arg His Ala Ala Cys Pro Val Leu Val Gly Cys Lys Trp
                500                 505                 510

Val Ser Asn Lys Trp Phe His Glu Arg Gly Gln Glu Phe Leu Arg
                515                 520                 525

Pro Cys Gly Ser Thr Glu Val Asp
```

-continued

530

<210> SEQ ID NO 333
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 333
ccaggcacaa tttccaga 18

<210> SEQ ID NO 334
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 334
ggacccttct gtgtgccag 19

<210> SEQ ID NO 335
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 335
ggtctcaaga actcctgtc 19

<210> SEQ ID NO 336
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 336
acactcagca ttgcctggta cttg 24

<210> SEQ ID NO 337
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 337
gggcacatga ctgacctgat ttatgcagag aaagagctgg tgcag 45

<210> SEQ ID NO 338
<211> LENGTH: 2789
<212> TYPE: DNA
<213> ORGANISM: Homo Sapien

<400> SEQUENCE: 338
gcagtattga gttttacttc ctcctctttt tagtggaaga cagaccataa 50
tcccagtgtg agtgaaattg attgtttcat ttattaccgt tttggctggg 100
ggttagttcc gacaccttca cagttgaaga gcaggcagaa ggagttgtga 150
agacaggaca atcttcttgg ggatgctggt cctggaagcc agcgggcctt 200
gctctgtctt tggcctcatt gaccccaggt tctctggtta aaactgaaag 250

-continued

```
cctactactg gcctggtgcc catcaatcca ttgatccttg aggctgtgcc    300
cctggggcac ccacctggca gggcctacca ccatgcgact gagctccctg    350
ttggctctgc tgcggccagc gcttcccctc atcttagggc tgtctctggg    400
gtgcagcctg agcctcctgc gggtttcctg gatccagggg gagggagaag    450
atccctgtgt cgaggctgta ggggagcgag gagggccaca gaatccagat    500
tcgagagctc ggctagacca aagtgatgaa gacttcaaac cccggattgt    550
cccctactac agggacccca acaagcccta caagaaggtg ctcaggactc    600
ggtacatcca gacagagctg ggctcccgtg agcggttgct ggtggctgtc    650
ctgacctccc gagctacact gtccactttg gccgtggctg tgaaccgtac    700
ggtggcccat cacttccctc ggttactcta cttcactggg cagcgggggg    750
cccgggctcc agcagggatg caggtggtgt ctcatgggga tgagcggccc    800
gcctggctca tgtcagagac cctgcgccac cttcacacac actttggggc    850
cgactacgac tggttcttca tcatgcagga tgacacatat gtgcaggccc    900
cccgcctggc agcccttgct ggccacctca gcatcaacca agacctgtac    950
ttaggccggg cagaggagtt cattggcgca ggcgagcagg cccggtactg   1000
tcatgggggc tttggctacc tgttgtcacg gagtctcctg cttcgtctgc   1050
ggccacatct ggatggctgc cgaggagaca ttctcagtgc ccgtcctgac   1100
gagtggcttg gacgctgcct cattgactct ctgggcgtcg gctgtgtctc   1150
acagcaccag gggcagcagt atcgctcatt tgaactggcc aaaaataggg   1200
accctgagaa ggaagggagc tcggctttcc tgagtgcctt cgccgtgcac   1250
cctgtctccg aaggtaccct catgtaccgg ctccacaaac gcttcagcgc   1300
tctggagttg gagcgggctt acagtgaaat agaacaactg caggctcaga   1350
tccggaacct gaccgtgctg acccccgaag gggaggcagg gctgagctgg   1400
cccgttgggc tccctgctcc tttcacacca cactctcgct ttgaggtgct   1450
gggctgggac tacttcacag agcagcacac cttctcctgt gcagatgggg   1500
ctcccaagtg cccactacag gggggctagca gggcggacgt gggtgatgcg   1550
ttggagactg ccctggagca gctcaatcgg cgctatcagc cccgcctgcg   1600
cttccagaag cagcgactgc tcaacggcta tcggcgcttc gacccagcac   1650
ggggcatgga gtacaccctg gacctgctgt tggaatgtgt gacacagcgt   1700
gggcaccggc gggccctggc tcgcagggtc agcctgctgc ggccactgag   1750
ccgggtggaa atcctaccta tgccctatgt cactgaggcc acccgagtgc   1800
agctggtgct gccactcctg gtggctgaag ctgctgcagc cccggctttc   1850
ctcgaggcgt ttgcagccaa tgtcctggag ccacgagaac atgcattgct   1900
caccctgttg ctggtctacg ggccacgaga aggtggccgt ggagctccag   1950
acccatttct tggggtgaag gctgcagcag cggagttaga gcgacggtac   2000
cctgggacga ggctggcctg gctcgctgtg cgagcagagg ccccttccca   2050
ggtgcgactc atggacgtgg tctcgaagaa gcaccctgtg gacactctct   2100
tcttccttac caccgtgtgg acaaggcctg ggcccgaagt cctcaaccgc   2150
tgtcgcatga atgccatctc tggctggcag gccttctttc cagtccattt   2200
```

-continued

```
ccaggagttc aatcctgccc tgtcaccaca gagatcaccc ccagggcccc          2250

cgggggctgg ccctgacccc ccctcccctc ctggtgctga cccctcccgg          2300

ggggctccta tagggggag atttgaccgg caggcttctg cggagggctg          2350

cttctacaac gctgactacc tggcggcccg agcccggctg gcaggtgaac          2400

tggcaggcca ggaagaggag gaagccctgg aggggctgga ggtgatggat          2450

gttttcctcc ggttctcagg gctccacctc tttcgggccg tagagccagg          2500

gctggtgcag aagttctccc tgcgagactg cagcccacgg ctcagtgaag          2550

aactctacca ccgctgccgc ctcagcaacc tggaggggct agggggccgt          2600

gcccagctgg ctatggctct ctttgagcag gagcaggcca atagcactta          2650

gcccgcctgg gggccctaac ctcattacct ttcctttgtc tgcctcagcc          2700

ccaggaaggg caaggcaaga tggtggacag atagagaatt gttgctgtat          2750

tttttaaata tgaaaatgtt attaaacatg tcttctgcc                      2789
```

<210> SEQ ID NO 339
<211> LENGTH: 772
<212> TYPE: PRT
<213> ORGANISM: Homo Sapien

<400> SEQUENCE: 339

```
Met Arg Leu Ser Ser Leu Leu Ala Leu Leu Arg Pro Ala Leu Pro
  1               5                  10                  15

Leu Ile Leu Gly Leu Ser Leu Gly Cys Ser Leu Ser Leu Leu Arg
                 20                  25                  30

Val Ser Trp Ile Gln Gly Glu Gly Glu Asp Pro Cys Val Glu Ala
                 35                  40                  45

Val Gly Glu Arg Gly Gly Pro Gln Asn Pro Asp Ser Arg Ala Arg
                 50                  55                  60

Leu Asp Gln Ser Asp Glu Asp Phe Lys Pro Arg Ile Val Pro Tyr
                 65                  70                  75

Tyr Arg Asp Pro Asn Lys Pro Tyr Lys Lys Val Leu Arg Thr Arg
                 80                  85                  90

Tyr Ile Gln Thr Glu Leu Gly Ser Arg Glu Arg Leu Leu Val Ala
                 95                 100                 105

Val Leu Thr Ser Arg Ala Thr Leu Ser Thr Leu Ala Val Ala Val
                110                 115                 120

Asn Arg Thr Val Ala His His Phe Pro Arg Leu Leu Tyr Phe Thr
                125                 130                 135

Gly Gln Arg Gly Ala Arg Ala Pro Ala Gly Met Gln Val Val Ser
                140                 145                 150

His Gly Asp Glu Arg Pro Ala Trp Leu Met Ser Glu Thr Leu Arg
                155                 160                 165

His Leu His Thr His Phe Gly Ala Asp Tyr Asp Trp Phe Phe Ile
                170                 175                 180

Met Gln Asp Asp Thr Tyr Val Gln Ala Pro Arg Leu Ala Ala Leu
                185                 190                 195

Ala Gly His Leu Ser Ile Asn Gln Asp Leu Tyr Leu Gly Arg Ala
                200                 205                 210

Glu Glu Phe Ile Gly Ala Gly Glu Gln Ala Arg Tyr Cys His Gly
                215                 220                 225

Gly Phe Gly Tyr Leu Leu Ser Arg Ser Leu Leu Leu Arg Leu Arg
                230                 235                 240
```

-continued

```
Pro His Leu Asp Gly Cys Arg Gly Asp Ile Leu Ser Ala Arg Pro
                245                 250                 255

Asp Glu Trp Leu Gly Arg Cys Leu Ile Asp Ser Leu Gly Val Gly
                260                 265                 270

Cys Val Ser Gln His Gln Gly Gln Gln Tyr Arg Ser Phe Glu Leu
                275                 280                 285

Ala Lys Asn Arg Asp Pro Glu Lys Glu Gly Ser Ser Ala Phe Leu
                290                 295                 300

Ser Ala Phe Ala Val His Pro Val Ser Glu Gly Thr Leu Met Tyr
                305                 310                 315

Arg Leu His Lys Arg Phe Ser Ala Leu Glu Leu Glu Arg Ala Tyr
                320                 325                 330

Ser Glu Ile Glu Gln Leu Gln Ala Gln Ile Arg Asn Leu Thr Val
                335                 340                 345

Leu Thr Pro Glu Gly Glu Ala Gly Leu Ser Trp Pro Val Gly Leu
                350                 355                 360

Pro Ala Pro Phe Thr Pro His Ser Arg Phe Glu Val Leu Gly Trp
                365                 370                 375

Asp Tyr Phe Thr Glu Gln His Thr Phe Ser Cys Ala Asp Gly Ala
                380                 385                 390

Pro Lys Cys Pro Leu Gln Gly Ala Ser Arg Ala Asp Val Gly Asp
                395                 400                 405

Ala Leu Glu Thr Ala Leu Glu Gln Leu Asn Arg Arg Tyr Gln Pro
                410                 415                 420

Arg Leu Arg Phe Gln Lys Gln Arg Leu Leu Asn Gly Tyr Arg Arg
                425                 430                 435

Phe Asp Pro Ala Arg Gly Met Glu Tyr Thr Leu Asp Leu Leu Leu
                440                 445                 450

Glu Cys Val Thr Gln Arg Gly His Arg Arg Ala Leu Ala Arg Arg
                455                 460                 465

Val Ser Leu Leu Arg Pro Leu Ser Arg Val Glu Ile Leu Pro Met
                470                 475                 480

Pro Tyr Val Thr Glu Ala Thr Arg Val Gln Leu Val Leu Pro Leu
                485                 490                 495

Leu Val Ala Glu Ala Ala Ala Ala Pro Ala Phe Leu Glu Ala Phe
                500                 505                 510

Ala Ala Asn Val Leu Glu Pro Arg Glu His Ala Leu Leu Thr Leu
                515                 520                 525

Leu Leu Val Tyr Gly Pro Arg Glu Gly Gly Arg Gly Ala Pro Asp
                530                 535                 540

Pro Phe Leu Gly Val Lys Ala Ala Ala Ala Glu Leu Glu Arg Arg
                545                 550                 555

Tyr Pro Gly Thr Arg Leu Ala Trp Leu Ala Val Arg Ala Glu Ala
                560                 565                 570

Pro Ser Gln Val Arg Leu Met Asp Val Val Ser Lys Lys His Pro
                575                 580                 585

Val Asp Thr Leu Phe Phe Leu Thr Thr Val Trp Thr Arg Pro Gly
                590                 595                 600

Pro Glu Val Leu Asn Arg Cys Arg Met Asn Ala Ile Ser Gly Trp
                605                 610                 615

Gln Ala Phe Phe Pro Val His Phe Gln Glu Phe Asn Pro Ala Leu
                620                 625                 630
```

-continued

```
Ser Pro Gln Arg Ser Pro Pro Gly Pro Pro Gly Ala Gly Pro Asp
                635                 640                 645

Pro Pro Ser Pro Pro Gly Ala Asp Pro Ser Arg Gly Ala Pro Ile
                650                 655                 660

Gly Gly Arg Phe Asp Arg Gln Ala Ser Ala Glu Gly Cys Phe Tyr
                665                 670                 675

Asn Ala Asp Tyr Leu Ala Ala Arg Ala Arg Leu Ala Gly Glu Leu
                680                 685                 690

Ala Gly Gln Glu Glu Glu Glu Ala Leu Glu Gly Leu Glu Val Met
                695                 700                 705

Asp Val Phe Leu Arg Phe Ser Gly Leu His Leu Phe Arg Ala Val
                710                 715                 720

Glu Pro Gly Leu Val Gln Lys Phe Ser Leu Arg Asp Cys Ser Pro
                725                 730                 735

Arg Leu Ser Glu Glu Leu Tyr His Arg Cys Arg Leu Ser Asn Leu
                740                 745                 750

Glu Gly Leu Gly Gly Arg Ala Gln Leu Ala Met Ala Leu Phe Glu
                755                 760                 765

Gln Glu Gln Ala Asn Ser Thr
                770
```

<210> SEQ ID NO 340
<211> LENGTH: 1572
<212> TYPE: DNA
<213> ORGANISM: Homo Sapien

<400> SEQUENCE: 340

```
cggagtggtg cgccaacgtg agaggaaacc cgtgcgcggc tgcgctttcc        50

tgtccccaag ccgttctaga cgcgggaaaa atgctttctg aaagcagctc       100

ctttttgaag ggtgtgatgc ttggaagcat tttctgtgct ttgatcacta       150

tgctaggaca cattaggatt ggtcatggaa atagaatgca ccaccatgag       200

catcatcacc tacaagctcc taacaaagaa gatatcttga aaatttcaga       250

ggatgagcgc atggagctca gtaagagctt tcgagtatac tgtattatcc       300

ttgtaaaacc caaagatgtg agtctttggg ctgcagtaaa ggagacttgg       350

accaaacact gtgacaaagc agagttcttc agttctgaaa atgttaaagt       400

gtttgagtca attaatatgg acacaaatga catgtggtta atgatgagaa       450

aagcttacaa atacgccttt gataagtata gagaccaata caactggttc       500

ttccttgcac gccccactac gtttgctatc attgaaaacc taaagtattt       550

tttgttaaaa aaggatccat cacagccttt ctatctaggc cacactataa       600

aatctggaga ccttgaatat gtgggtatgg aaggaggaat tgtcttaagt       650

gtagaatcaa tgaaaagact taacagcctt ctcaatatcc cagaaaagtg       700

tcctgaacag ggagggatga tttggaagat atctgaagat aaacagctag       750

cagtttgcct gaaatatgct ggagtatttg cagaaaatgc agaagatgct       800

gatggaaaag atgtatttaa taccaaatct gttgggcttt ctattaaaga       850

ggcaatgact tatcacccca accaggtagt agaaggctgt tgttcagata       900

tggctgttac ttttaatgga ctgactccaa atcagatgca tgtgatgatg       950

tatggggtat accgccttag ggcatttggg catattttca atgatgcatt      1000

ggttttctta cctccaaatg gttctgacaa tgactgagaa gtggtagaaa      1050
```

-continued

```
agcgtgaata tgatctttgt ataggacgtg tgttgtcatt atttgtagta        1100

gtaactacat atccaataca gctgtatgtt tctttttctt ttctaatttg        1150

gtggcactgg tataaccaca cattaaagtc agtagtacat ttttaaatga        1200

gggtggtttt tttctttaaa acacatgaac attgtaaatg tgttggaaag        1250

aagtgtttta agaataataa ttttgcaaat aaactattaa taaatattat        1300

atgtgataaa ttctaaatta tgaacattag aaatctgtgg ggcacatatt        1350

tttgctgatt ggttaaaaaa ttttaacagg tctttagcgt tctaagatat        1400

gcaaatgata tctctagttg tgaatttgtg attaaagtaa aacttttagc        1450

tgtgtgttcc ctttacttct aatactgatt tatgttctaa gcctccccaa        1500

gttccaatgg atttgccttc tcaaaatgta caactaagca actaaagaaa        1550

attaaagtga aagttgaaaa at                                      1572
```

```
<210> SEQ ID NO 341
<211> LENGTH: 318
<212> TYPE: PRT
<213> ORGANISM: Homo Sapien

<400> SEQUENCE: 341

Met Leu Ser Glu Ser Ser Ser Phe Leu Lys Gly Val Met Leu Gly
  1               5                  10                  15

Ser Ile Phe Cys Ala Leu Ile Thr Met Leu Gly His Ile Arg Ile
                 20                  25                  30

Gly His Gly Asn Arg Met His His His Glu His His His Leu Gln
                 35                  40                  45

Ala Pro Asn Lys Glu Asp Ile Leu Lys Ile Ser Glu Asp Glu Arg
                 50                  55                  60

Met Glu Leu Ser Lys Ser Phe Arg Val Tyr Cys Ile Ile Leu Val
                 65                  70                  75

Lys Pro Lys Asp Val Ser Leu Trp Ala Ala Val Lys Glu Thr Trp
                 80                  85                  90

Thr Lys His Cys Asp Lys Ala Glu Phe Phe Ser Ser Glu Asn Val
                 95                 100                 105

Lys Val Phe Glu Ser Ile Asn Met Asp Thr Asn Asp Met Trp Leu
                110                 115                 120

Met Met Arg Lys Ala Tyr Lys Tyr Ala Phe Asp Lys Tyr Arg Asp
                125                 130                 135

Gln Tyr Asn Trp Phe Phe Leu Ala Arg Pro Thr Thr Phe Ala Ile
                140                 145                 150

Ile Glu Asn Leu Lys Tyr Phe Leu Leu Lys Lys Asp Pro Ser Gln
                155                 160                 165

Pro Phe Tyr Leu Gly His Thr Ile Lys Ser Gly Asp Leu Glu Tyr
                170                 175                 180

Val Gly Met Glu Gly Gly Ile Val Leu Ser Val Glu Ser Met Lys
                185                 190                 195

Arg Leu Asn Ser Leu Leu Asn Ile Pro Glu Lys Cys Pro Glu Gln
                200                 205                 210

Gly Gly Met Ile Trp Lys Ile Ser Glu Asp Lys Gln Leu Ala Val
                215                 220                 225

Cys Leu Lys Tyr Ala Gly Val Phe Ala Glu Asn Ala Glu Asp Ala
                230                 235                 240
```

-continued

```
Asp Gly Lys Asp Val Phe Asn Thr Lys Ser Val Gly Leu Ser Ile
                245                 250                 255

Lys Glu Ala Met Thr Tyr His Pro Asn Gln Val Val Glu Gly Cys
                260                 265                 270

Cys Ser Asp Met Ala Val Thr Phe Asn Gly Leu Thr Pro Asn Gln
                275                 280                 285

Met His Val Met Met Tyr Gly Val Tyr Arg Leu Arg Ala Phe Gly
                290                 295                 300

His Ile Phe Asn Asp Ala Leu Val Phe Leu Pro Pro Asn Gly Ser
                305                 310                 315

Asp Asn Asp


<210> SEQ ID NO 342
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 342

tccccaagcc gttctagacg cgg                                          23


<210> SEQ ID NO 343
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 343

ctggttcttc cttgcacg                                                18


<210> SEQ ID NO 344
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 344

gcccaaatgc cctaaggcgg tatacccc                                     28


<210> SEQ ID NO 345
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 345

gggtgtgatg cttggaagca ttttctgtgc tttgatcact atgctaggac             50


<210> SEQ ID NO 346
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 346

gggatgcagg tggtgtctca tgggg                                        25


<210> SEQ ID NO 347
```

-continued

<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 347
ccctcatgta ccggctcc 18

<210> SEQ ID NO 348
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 348
ggattctaat acgactcact atagggctca gaaaagcgca acagagaa 48

<210> SEQ ID NO 349
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 349
ctatgaaatt aaccctcact aaagggatgt cttccatgcc aaccttc 47

<210> SEQ ID NO 350
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 350
ggattctaat acgactcact atagggcggc gatgtccact ggggctac 48

<210> SEQ ID NO 351
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 351
ctatgaaatt aaccctcact aaagggacga ggaagatggg cggatggt 48

<210> SEQ ID NO 352
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 352
ggattctaat acgactcact atagggcacc cacgcgtccg gctgctt 47

<210> SEQ ID NO 353
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 353

-continued ctatgaaatt aaccctcact aaagggacgg gggacaccac ggaccaga 48

<210> SEQ ID NO 354
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 354
ggattctaat acgactcact atagggcttg ctgcggtttt tgttcctg 48

<210> SEQ ID NO 355
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 355
ctatgaaatt aaccctcact aaagggagct gccgatccca ctggtatt 48

<210> SEQ ID NO 356
<211> LENGTH: 46
<212> TYPE: DNA
<213> ORGANISM: Artificial Sequence
<220> FEATURE:
<223> OTHER INFORMATION: Synthetic Oligonucleotide Probe

<400> SEQUENCE: 356
ggattctaat acgactcact atagggcgga tcctggccgg cctctg 46

<210> SEQ ID NO 357
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 357
ctatgaaatt aaccctcact aaagggagcc cgggcatggt ctcagtta 48

<210> SEQ ID NO 358
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 358
ggattctaat acgactcact atagggcggg aagatggcga ggaggag 47

<210> SEQ ID NO 359
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 359
ctatgaaatt aaccctcact aaagggacca aggccacaaa cggaaatc 48

<210> SEQ ID NO 360
<211> LENGTH: 48
<212> TYPE: DNA

-continued

<213> ORGANISM: Artificial Sequence
<220> FEATURE:
<223> OTHER INFORMATION: Synthetic Oligonucleotide Probe

<400> SEQUENCE: 360
ggattctaat acgactcact atagggctgt gctttcattc tgccagta 48

<210> SEQ ID NO 361
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 361
ctatgaaatt aaccctcact aaagggaggg tacaattaag ggtggat 48

<210> SEQ ID NO 362
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 362
ggattctaat acgactcact atagggcccg cctcgctcct gctcctg 47

<210> SEQ ID NO 363
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 363
ctatgaaatt aaccctcact aaagggagga ttgccgcgac cctcacag 48

<210> SEQ ID NO 364
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 364
ggattctaat acgactcact atagggcccc tcctgccttc cctgtcc 47

<210> SEQ ID NO 365
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 365
ctatgaaatt aaccctcact aaagggagtg gtggccgcga ttatctgc 48

<210> SEQ ID NO 366
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 366
ggattctaat acgactcact atagggcgca gcgatggcag cgatgagg 48

<210> SEQ ID NO 367
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 367
ctatgaaatt aaccctcact aaagggacag acggggcaga gggagtg 47

<210> SEQ ID NO 368
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 368
ggattctaat acgactcact atagggccag gaggcgtgag gagaaac 47

<210> SEQ ID NO 369
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 369
ctatgaaatt aaccctcact aaagggaaag acatgtcatc gggagtgg 48

<210> SEQ ID NO 370
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 370
ggattctaat acgactcact atagggccgg gtggaggtgg aacagaaa 48

<210> SEQ ID NO 371
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 371
ctatgaaatt aaccctcact aaagggacac agacagagcc ccatacgc 48

<210> SEQ ID NO 372
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 372
ggattctaat acgactcact atagggccag ggaaatccgg atgtctc 47

<210> SEQ ID NO 373
<211> LENGTH: 48
<212> TYPE: DNA
<213> ORGANISM: Artificial Sequence
<220> FEATURE:

-continued

<223> OTHER INFORMATION: Synthetic Oligonucleotide Probe

<400> SEQUENCE: 373
ctatgaaatt aaccctcact aaagggagta aggggatgcc accgagta 48

<210> SEQ ID NO 374
<211> LENGTH: 47
<212> TYPE: DNA
<213> ORGANISM: Artificial Sequence
<220> FEATURE:
<223> OTHER INFORMATION: Synthetic Oligonucleotide Probe

<400> SEQUENCE: 374
ggattctaat acgactcact atagggccag ctacccgcag gaggagg 47

<210> SEQ ID NO 375
<211> LENGTH: 48
<212> TYPE: DNA
<213> ORGANISM: Artificial Sequence
<220> FEATURE:
<223> OTHER INFORMATION: Synthetic Oligonucleotide Probe

<400> SEQUENCE: 375
ctatgaaatt aaccctcact aaagggatcc caggtgatga ggtccaga 48

<210> SEQ ID NO 376
<211> LENGTH: 997
<212> TYPE: DNA
<213> ORGANISM: Homo Sapien

<400> SEQUENCE: 376
cccacgcgtc cgatcttacc aacaaaacac tcctgaggag aaagaaagag 50
agggagggag agaaaaagag agagagagaa acaaaaaacc aaagagagag 100
aaaaaatgaa ttcatctaaa tcatctgaaa cacaatgcac agagagagga 150
tgcttctctt cccaaatgtt cttatggact gttgctggga tccccatcct 200
atttctcagt gcctgtttca tcaccagatg tgttgtgaca tttcgcatct 250
ttcaaacctg tgatgagaaa aagtttcagc tacctgagaa tttcacagag 300
ctctcctgct acaattatgg atcaggttca gtcaagaatt gttgtccatt 350
gaactgggaa tattttcaat ccagctgcta cttcttttct actgacacca 400
tttcctgggc gttaagttta aagaactgct cagccatggg ggctcacctg 450
gtggttatca actcacagga ggagcaggaa ttcctttcct acaagaaacc 500
taaaatgaga gagtttttta ttggactgtc agaccaggtt gtcgagggtc 550
agtggcaatg ggtggacggc acacctttga caaagtctct gagcttctgg 600
gatgtagggg agcccaacaa catagctacc ctggaggact gtgccaccat 650
gagagactct tcaaacccaa ggcaaaattg gaatgatgta acctgtttcc 700
tcaattattt tcggatttgt gaaatggtag gaataaatcc tttgaacaaa 750
ggaaaatctc tttaagaaca gaaggcacaa ctcaaatgtg taaagaagga 800
agagcaagaa catggccaca cccaccgccc cacacgagaa atttgtgcgc 850
tgaacttcaa aggacttcat aagtatttgt tactctgata caaataaaaa 900
taagtagttt taaatgttaa aaaaaaaaaa aaaaaaaaaa aaaaaaaaaa 950
aaaaaaaaaa aaaaaaaaaa aaaaaaaaaa aaaaaaaaaa aaaaaaa 997

-continued

<210> SEQ ID NO 377
<211> LENGTH: 219
<212> TYPE: PRT
<213> ORGANISM: Homo Sapien

<400> SEQUENCE: 377

```
Met Asn Ser Ser Lys Ser Ser Glu Thr Gln Cys Thr Glu Arg Gly
  1               5                  10                  15

Cys Phe Ser Ser Gln Met Phe Leu Trp Thr Val Ala Gly Ile Pro
                 20                  25                  30

Ile Leu Phe Leu Ser Ala Cys Phe Ile Thr Arg Cys Val Val Thr
                 35                  40                  45

Phe Arg Ile Phe Gln Thr Cys Asp Glu Lys Lys Phe Gln Leu Pro
                 50                  55                  60

Glu Asn Phe Thr Glu Leu Ser Cys Tyr Asn Tyr Gly Ser Gly Ser
                 65                  70                  75

Val Lys Asn Cys Cys Pro Leu Asn Trp Glu Tyr Phe Gln Ser Ser
                 80                  85                  90

Cys Tyr Phe Phe Ser Thr Asp Thr Ile Ser Trp Ala Leu Ser Leu
                 95                 100                 105

Lys Asn Cys Ser Ala Met Gly Ala His Leu Val Val Ile Asn Ser
                110                 115                 120

Gln Glu Glu Gln Glu Phe Leu Ser Tyr Lys Lys Pro Lys Met Arg
                125                 130                 135

Glu Phe Phe Ile Gly Leu Ser Asp Gln Val Val Glu Gly Gln Trp
                140                 145                 150

Gln Trp Val Asp Gly Thr Pro Leu Thr Lys Ser Leu Ser Phe Trp
                155                 160                 165

Asp Val Gly Glu Pro Asn Asn Ile Ala Thr Leu Glu Asp Cys Ala
                170                 175                 180

Thr Met Arg Asp Ser Ser Asn Pro Arg Gln Asn Trp Asn Asp Val
                185                 190                 195

Thr Cys Phe Leu Asn Tyr Phe Arg Ile Cys Glu Met Val Gly Ile
                200                 205                 210

Asn Pro Leu Asn Lys Gly Lys Ser Leu
                215
```

<210> SEQ ID NO 378
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 378
ttcagcttct gggatgtagg g 21

<210> SEQ ID NO 379
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 379
tattcctacc atttcacaaa tccg 24

<210> SEQ ID NO 380
<211> LENGTH: 49

-continued

<212> TYPE: DNA
<213> ORGANISM: Artificial Sequence
<220> FEATURE:
<223> OTHER INFORMATION: Synthetic oligonucleotide probe

<400> SEQUENCE: 380
ggaggactgt gccaccatga gagactcttc aaacccaagg caaaattgg 49

<210> SEQ ID NO 381
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 381
gcagattttg aggacagcca cctcca 26

<210> SEQ ID NO 382
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 382
ggccttgcag acaaccgt 18

<210> SEQ ID NO 383
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 383
cagactgagg gagatccgag a 21

<210> SEQ ID NO 384
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 384
cagctgccct tccccaacca 20

<210> SEQ ID NO 385
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 385
catcaagcgc ctctacca 18

<210> SEQ ID NO 386
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 386

-continued cacaaactcg aactgcttct g 21

<210> SEQ ID NO 387
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 387
gggccatcac agctccct 18

<210> SEQ ID NO 388
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 388
gggatgtggt gaacacagaa ca 22

<210> SEQ ID NO 389
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 389
tgccagctgc atgctgccag tt 22

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 390
cagaaggatg tcccgtggaa 20

<210> SEQ ID NO 391
<211> LENGTH: 17
<212> TYPE: DNA
<213> ORGANISM: Artificial Sequence
<220> FEATURE:
<223> OTHER INFORMATION: Synthetic oligonucleotide probe

<400> SEQUENCE: 391
gccgctgtcc actgcag 17

<210> SEQ ID NO 392
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 392
gacggcatcc tcagggccac a 21

<210> SEQ ID NO 393
<211> LENGTH: 20
<212> TYPE: DNA
<213> ORGANISM: Artificial Sequence -continued
<220> FEATURE:
<223> OTHER INFORMATION: Synthetic oligonucleotide probe

<400> SEQUENCE: 393
atgtcctcca tgcccacgcg 20

<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 394
gagtgcgaca tcgagagctt 20

<210> SEQ ID NO 395
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 395
ccgcagcctc agtgatga 18

<210> SEQ ID NO 396
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 396
gaagagcaca gctgcagatc c 21

<210> SEQ ID NO 397
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 397
gaggtgtcct ggctttggta gt 22

<210> SEQ ID NO 398
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 398
cctctggcgc ccccactcaa 20

<210> SEQ ID NO 399
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 399
ccaggagagc tggcgatg 18

-continued

<210> SEQ ID NO 400
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 400
gcaaattcag ggctcactag aga 23

<210> SEQ ID NO 401
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 401
cacagagcat ttgtccatca gcagttcag 29

<210> SEQ ID NO 402
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 402
ggcagagact tccagtcact ga 22

<210> SEQ ID NO 403
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 403
gccaagggtg gtgttagata gg 22

<210> SEQ ID NO 404
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 404
caggccccct tgatctgtac ccca 24

<210> SEQ ID NO 405
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 405
gggacgtgct tctacaagaa cag 23

<210> SEQ ID NO 406
<211> LENGTH: 26
<212> TYPE: DNA
<213> ORGANISM: Artificial Sequence
<220> FEATURE:
<223> OTHER INFORMATION: Synthetic oligonucleotide probe -continued

<400> SEQUENCE: 406
caggcttaca atgttatgat cagaca 26

<210> SEQ ID NO 407
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 407
tattcagagt tttccattgg cagtgccagt t 31

<210> SEQ ID NO 408
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 408
tctacatcag cctctctgcg c 21

<210> SEQ ID NO 409
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 409
cgatcttctc cacccaggag cgg 23

<210> SEQ ID NO 410
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 410
gccaggcctc acattcgt 18

<210> SEQ ID NO 411
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 411
ctccctgaat ggcagcctga gca 23

<210> SEQ ID NO 412
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 412
aggtgtttat taagggccta cgct 24

<210> SEQ ID NO 413

-continued

<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 413
cagagcagag ggtgccttg 19

<210> SEQ ID NO 414
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 414
tggcggagtc ccctcttggc t 21

<210> SEQ ID NO 415
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 415
ccctgtttcc ctatgcatca ct 22

<210> SEQ ID NO 416
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 416
tcaacccctg accctttcct a 21

<210> SEQ ID NO 417
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 417
ggcaggggac aagccatctc tcct 24

<210> SEQ ID NO 418
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 418
gggactgaac tgccagcttc 20

<210> SEQ ID NO 419
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 419

-continued

```
gggccctaac ctcattacct tt                                            22


<210> SEQ ID NO 420
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 420

tgtctgcctc agccccagga agg                                           23


<210> SEQ ID NO 421
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 421

tctgtccacc atcttgcctt g                                             21


<210> SEQ ID NO 422
<211> LENGTH: 3554
<212> TYPE: DNA
<213> ORGANISM: Homo Sapien

<400> SEQUENCE: 422

gggactacaa gccgcgccgc gctgccgctg gcccctcagc aaccctcgac              50

atggcgctga ggcggccacc gcgactccgg ctctgcgctc ggctgcctga             100

cttcttcctg ctgctgcttt tcaggggctg cctgataggg gctgtaaatc             150

tcaaatccag caatcgaacc ccagtggtac aggaatttga aagtgtggaa             200

ctgtcttgca tcattacgga ttcgcagaca agtgacccca ggatcgagtg             250

gaagaaaatt caagatgaac aaaccacata tgtgtttttt gacaacaaaa             300

ttcagggaga cttggcgggt cgtgcagaaa tactggggaa gacatccctg             350

aagatctgga atgtgacacg gagagactca gccctttatc gctgtgaggt             400

cgttgctcga aatgaccgca aggaaattga tgagattgtg atcgagttaa             450

ctgtgcaagt gaagccagtg acccctgtct gtagagtgcc gaaggctgta             500

ccagtaggca agatggcaac actgcactgc caggagagtg agggccaccc             550

ccggcctcac tacagctggt atcgcaatga tgtaccactg cccacggatt             600

ccagagccaa tcccagattt cgcaattctt ctttccactt aaactctgaa             650

acaggcactt tggtgttcac tgctgttcac aaggacgact ctgggcagta             700

ctactgcatt gcttccaatg acgcaggctc agccaggtgt gaggagcagg             750

agatggaagt ctatgacctg aacattggcg gaattattgg gggggttctg             800

gttgtccttg ctgtactggc cctgatcacg ttgggcatct gctgtgcata             850

cagacgtggc tacttcatca acaataaaca ggatggagaa agttacaaga             900

acccagggaa accagatgga gttaactaca tccgcactga cgaggagggc             950

gacttcagac acaagtcatc gtttgtgatc tgagacccgc ggtgtggctg            1000

agagcgcaca gagcgcacgt gcacatacct ctgctagaaa ctcctgtcaa            1050

ggcagcgaga gctgatgcac tcggacagag ctagacactc attcagaagc            1100
```

-continued

```
ttttcgtttt ggccaaagtt gaccactact cttcttactc taacaagcca        1150

catgaataga agaattttcc tcaagatgga cccggtaaat ataaccacaa        1200

ggaagcgaaa ctgggtgcgt tcactgagtt gggttcctaa tctgtttctg        1250

gcctgattcc cgcatgagta ttagggtgat cttaaagagt ttgctcacgt        1300

aaacgcccgt gctgggccct gtgaagccag catgttcacc actggtcgtt        1350

cagcagccac gacagcacca tgtgagatgg cgaggtggct ggacagcacc        1400

agcagcgcat cccggcggga acccagaaaa ggcttcttac acagcagcct        1450

tacttcatcg gcccacagac accaccgcag tttcttctta aaggctctgc        1500

tgatcggtgt tgcagtgtcc attgtggaga agctttttgg atcagcattt        1550

tgtaaaaaca accaaaatca ggaaggtaaa ttggttgctg gaagagggat        1600

cttgcctgag gaaccctgct tgtccaacag ggtgtcagga tttaaggaaa        1650

accttcgtct taggctaagt ctgaaatggt actgaaatat gcttttctat        1700

gggtcttgtt tattttataa aattttacat ctaaattttt gctaaggatg        1750

tattttgatt attgaaaaga aaatttctat ttaaactgta aatatattgt        1800

catacaatgt taaataacct atttttttaa aaaagttcaa cttaaggtag        1850

aagttccaag ctactagtgt taaattggaa aatatcaata attaagagta        1900

ttttacccaa ggaatcctct catggaagtt tactgtgatg ttccttttct        1950

cacacaagtt ttagcctttt tcacaaggga actcatactg tctacacatc        2000

agaccatagt tgcttaggaa acctttaaaa attccagtta agcaatgttg        2050

aaatcagttt gcatctcttc aaaagaaacc tctcaggtta gctttgaact        2100

gcctcttcct gagatgacta ggacagtctg tacccagagg ccacccagaa        2150

gccctcagat gtacatacac agatgccagt cagctcctgg ggttgcgcca        2200

ggcgcccccg ctctagctca ctgttgcctc gctgtctgcc aggaggccct        2250

gccatccttg ggccctggca gtggctgtgt cccagtgagc tttactcacg        2300

tggcccttgc ttcatccagc acagctctca ggtgggcact gcagggacac        2350

tggtgtcttc catgtagcgt cccagctttg ggctcctgta acagacctct        2400

ttttggttat ggatggctca caaaataggg cccccaatgc tattttttttt        2450

ttttaagttt gtttaattat ttgttaagat tgtctaaggc caaaggcaat        2500

tgcgaaatca agtctgtcaa gtacaataac atttttaaaa gaaaatggat        2550

cccactgttc ctctttgcca cagagaaagc acccagacgc cacaggctct        2600

gtcgcatttc aaaacaaacc atgatggagt ggcggccagt ccagcctttt        2650

aaagaacgtc aggtggagca gccaggtgaa aggcctggcg gggaggaaag        2700

tgaaacgcct gaatcaaaag cagttttcta attttgactt taaatttttc        2750

atccgccgga gacactgctc ccatttgtgg ggggacatta gcaacatcac        2800

tcagaagcct gtgttcttca agagcaggtg ttctcagcct cacatgccct        2850

gccgtgctgg actcaggact gaagtgctgt aaagcaagga gctgctgaga        2900

aggagcactc cactgtgtgc ctggagaatg gctctcacta ctcaccttgt        2950

ctttcagctt ccagtgtctt gggtttttta tactttgaca gctttttttt        3000

aattgcatac atgagactgt gttgactttt tttagttatg tgaaacactt        3050

tgccgcaggc cgcctggcag aggcaggaaa tgctccagca gtggctcagt        3100
```

-continued

```
gctccctggt gtctgctgca tggcatcctg gatgcttagc atgcaagttc          3150

cctccatcat tgccaccttg gtagagaggg atggctcccc accctcagcg          3200

ttggggattc acgctccagc ctccttcttg gttgtcatag tgatagggta          3250

gccttattgc cccctcttct tataccctaa aaccttctac actagtgcca          3300

tgggaaccag gtctgaaaaa gtagagagaa gtgaaagtag agtctgggaa          3350

gtagctgcct ataactgaga ctagacggaa aaggaatact cgtgtatttt          3400

aagatatgaa tgtgactcaa gactcgaggc cgatacgagg ctgtgattct          3450

gcctttggat ggatgttgct gtacacagat gctacagact tgtactaaca          3500

caccgtaatt tggcatttgt ttaacctcat ttataaaagc ttcaaaaaaa          3550

ccca                                                            3554
```

```
<210> SEQ ID NO 423
<211> LENGTH: 310
<212> TYPE: PRT
<213> ORGANISM: Homo Sapien

<400> SEQUENCE: 423

Met Ala Leu Arg Arg Pro Pro Arg Leu Arg Leu Cys Ala Arg Leu
  1               5                  10                  15

Pro Asp Phe Phe Leu Leu Leu Leu Phe Arg Gly Cys Leu Ile Gly
                 20                  25                  30

Ala Val Asn Leu Lys Ser Ser Asn Arg Thr Pro Val Val Gln Glu
                 35                  40                  45

Phe Glu Ser Val Glu Leu Ser Cys Ile Ile Thr Asp Ser Gln Thr
                 50                  55                  60

Ser Asp Pro Arg Ile Glu Trp Lys Lys Ile Gln Asp Glu Gln Thr
                 65                  70                  75

Thr Tyr Val Phe Phe Asp Asn Lys Ile Gln Gly Asp Leu Ala Gly
                 80                  85                  90

Arg Ala Glu Ile Leu Gly Lys Thr Ser Leu Lys Ile Trp Asn Val
                 95                 100                 105

Thr Arg Arg Asp Ser Ala Leu Tyr Arg Cys Glu Val Val Ala Arg
                110                 115                 120

Asn Asp Arg Lys Glu Ile Asp Glu Ile Val Ile Glu Leu Thr Val
                125                 130                 135

Gln Val Lys Pro Val Thr Pro Val Cys Arg Val Pro Lys Ala Val
                140                 145                 150

Pro Val Gly Lys Met Ala Thr Leu His Cys Gln Glu Ser Glu Gly
                155                 160                 165

His Pro Arg Pro His Tyr Ser Trp Tyr Arg Asn Asp Val Pro Leu
                170                 175                 180

Pro Thr Asp Ser Arg Ala Asn Pro Arg Phe Arg Asn Ser Ser Phe
                185                 190                 195

His Leu Asn Ser Glu Thr Gly Thr Leu Val Phe Thr Ala Val His
                200                 205                 210

Lys Asp Asp Ser Gly Gln Tyr Tyr Cys Ile Ala Ser Asn Asp Ala
                215                 220                 225

Gly Ser Ala Arg Cys Glu Glu Gln Glu Met Glu Val Tyr Asp Leu
                230                 235                 240

Asn Ile Gly Gly Ile Ile Gly Gly Val Leu Val Val Leu Ala Val
                245                 250                 255
```

-continued

```
Leu Ala Leu Ile Thr Leu Gly Ile Cys Cys Ala Tyr Arg Arg Gly
                260                 265                 270

Tyr Phe Ile Asn Asn Lys Gln Asp Gly Glu Ser Tyr Lys Asn Pro
                275                 280                 285

Gly Lys Pro Asp Gly Val Asn Tyr Ile Arg Thr Asp Glu Glu Gly
                290                 295                 300

Asp Phe Arg His Lys Ser Ser Phe Val Ile
                305                 310
```

SECRETED AND TRANSMEMBRANE POLYPEPTIDES AND NUCLEIC ACIDS ENCODING THE SAME

RELATED APPLICATIONS

The application is a continuation of, and claims priority under 35 USC §120 to, U.S. application Ser. No. 09/907,794 filed Jul. 17, 2001, issued as U.S. Pat. No. 6,635,468 on Oct. 21, 2003, which is a continuation of, and claims priority under 35 USC §120 to, U.S. application Ser. No. 09/665,350 filed Sep. 18, 2000 now abandoned, which is a continuation of, and claims priority under 35 USC § 120 to, PCT Application PCT/US00/04414 filed Feb. 22, 2000, which is a continuation-in-part of, and claims priority under 35 USC §120 to, PCT Application PCT/US99/28313 filed Nov. 30, 1999, which is a continuation-in-part of, and claims priority under 35 USC §120 to, PCT Application PCT/US98/19330 filed Sep. 16, 1998, which claims priority under 35 USC §119 to U.S. Provisional Application 60/063,128 filed Oct. 24, 1997.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell—cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

1. PRO211 and PRO217

Epidermal growth factor (EGF) is a conventional mitogenic factor that stimulates the proliferation of various types of cells including epithelial cells and fibroblasts. EGF binds to and activates the EGF receptor (EGFR), which initiates intracellular signaling and subsequent effects. The EGFR is expressed in neurons of the cerebral cortex, cerebellum, and hippocampus in addition to other regions of the central nervous system (CNS). In addition, EGF is also expressed in various regions of the CNS. Therefore, EGF acts not only on mitotic cells, but also on postmitotic neurons. In fact, many studies have indicated that EGF has neurotrophic or neuromodulatory effects on various types of neurons in the CNS. For example, EGF acts directly on cultured cerebral cortical and cerebellar neurons, enhancing neurite outgrowth and survival. On the other hand, EGF also acts on other cell types, including septal cholinergic and mesencephalic dopaminergic neurons, indirectly through glial cells. Evidence of the effects of EGF on neurons in the CNS is accumulating, but the mechanisms of action remain essentially unknown. EGF-induced signaling in mitotic cells is better understood than in postmitotic neurons. Studies of cloned pheochromocytoma PC12 cells and cultured cerebral cortical neurons have suggested that the EGF-induced neurotrophic actions are mediated by sustained activation of the EGFR and mitogen-activated protein kinase (MAPK) in response to EGF. The sustained intracellular signaling correlates with the decreased rate of EGFR down-regulation, which might determine the response of neuronal cells to EGF. It is likely that EGF is a multi-potent growth factor that acts upon various types of cells including mitotic cells and postmitotic neurons.

EGF is produced by the salivary and Brunner's glands of the gastrointestinal system, kidney, pancreas, thyroid gland, pituitary gland, and the nervous system, and is found in body fluids such as saliva, blood, cerebrospinal fluid (CSF), urine, amniotic fluid, prostatic fluid, pancreatic juice, and breast milk, Plata-Salaman, *Peptides* 12: 653–663 (1991).

EGF is mediated by its membrane specific receptor, which contains an intrinsic tyrosine kinase. Stoscheck et al., *J. Cell Biochem.* 31: 135–152 (1986). EGF is believed to function by binding to the extracellular portion of its receptor which induces a transmembrane signal that activates the intrinsic tyrosine kinase.

Purification and sequence analysis of the EGF-like domain has revealed the presence of six conserved cysteine residues which cross-bind to create three peptide loops, Savage et al., *J. Biol. Chem.* 248: 7669–7672 (1979). It is now generally known that several other peptides can react with the EGF receptor which share the same generalized motif $X_nCX_7CX_{4/5}CX_{10}CXCX_5GX_2CX_n$, where X represents any non-cysteine amino acid, and n is a variable repeat number. Non isolated peptides having this motif include TGF-α, amphiregulin, schwannoma-derived growth factor (SDGF), heparin-binding EGF-like growth factors and certain virally encoded peptides (e.g., Vaccinia virus, Reisner, *Nature* 313: 801–803 (1985), Shope fibroma virus, Chang et al., Mol Cell Biol. 7: 535–540 (1987), Molluscurn contagiosum, Porter and Archard, *J. Gen. Virol.* 68: 673–682 (1987), and Myxoma virus, Upton et al., *J. Virol.* 61: 1271–1275 (1987), Prigent and Lemoine, *Prog. Growth Factor Res.* 4: 1–24 (1992).

EGF-like domains are not confined to growth factors but have been observed in a variety of cell-surface and extracellular proteins which have interesting properties in cell adhesion, protein—protein interaction and development, Laurence and Gusterson, *Tumor Biol.* 11: 229–261 (1990). These proteins include blood coagulation factors (factors VI, IX, X, XII, protein C, protein S, protein Z, tissue plasminogen activator, urokinase), extracellular matrix components (laminin, cytotactin, entactin), cell surface receptors (LDL receptor, thrombomodulin receptor) and immunity-related proteins (complement C1r, uromodulin).

Even more interesting, the general structure pattern of EGF-like precursors is preserved through lower organisms as well as in mammalian cells. A number of genes with developmental significance have been identified in invertebrates with EGF-like repeats. For example, the notch gene of *Drosophila* encodes 36 tandemly arranged 40 amino acid repeats which show homology to EGF, Wharton et al., *Cell* 43: 557–581 (1985). Hydropathy plots indicate a putative membrane spanning domain, with the EGF-related sequences being located on the extracellular side of the membrane. Other homeotic genes with EGF-like repeats include Delta, 95F and 5ZD which were identified using probes based on Notch, and the nematode gene Lin-12 which encodes a putative receptor for a developmental signal transmitted between two specified cells.

Specifically, EGF has been shown to have potential in the preservation and maintenance of gastrointestinal mucosa and the repair of acute and chronic mucosal lesions, Konturek et al., *Eur. J. Gastroenterol Hepatol.* 7 (10), 933–37 (1995), including the treatment of necrotizing enterocolitis, Zollinger-Ellison syndrome, gastrointestinal ulceration gastrointestinal ulcerations and congenital microvillus atrophy, Guglietta and Sullivan, *Eur. J. Gastroenterol Hepatol,* 7(10), 945–50 (1995). Additionally, EGF has been implicated in hair follicle differentiation; du Cros, *J. Invest. Dermatol.* 101 (1 Suppl.), 106S–113S (1993), Hillier, *Clin. Endocrinol.* 33(4), 427–28 (1990); kidney function, Hamm et al., *Semin. Nephrol.* 13 (1): 109–15 (1993), Harris, *Am. J. Kidney Dis.* 17(6): 627–30 (1991); tear fluid, van Setten et al., *Int. Ophthalmol* 15(6); 359–62 (1991); vitamin K mediated blood coagulation, Stenflo et al., *Blood* 78(7): 1637–51 (1991). EGF is also implicated various skin disease characterized by abnormal keratinocyte differentiation, e.g., psoriasis, epithelial cancers such as squamous cell-carcinomas of the lung, epidermoid carcinoma of the vulva and gliomas. King et al., *Am. J. Med. Sci.* 296: 154–158 (1988).

Of great interest is mounting evidence that genetic alterations in growth factors signaling pathways are closely linked to developmental abnormalities and to chronic diseases including cancer. Aaronson, *Science* 254: 1146–1153 (1991). For example, c-erb-2 (also known as HER-2), a proto-oncogene with close structural similarity to EGF receptor protein, is overexpressed in human breast cancer. King et al., *Science* 229: 974–976 (1985); Gullick, *Hormones and their actions*, Cooke et al., eds, Amsterdam, Elsevier, pp 349–360 (1986).

We herein describe the identification and characterization of novel polypeptides having homology to EGF, wherein those polypeptides are herein designated PRO211 and PRO217.

2. PRO230

Nephritis is a condition characterized by inflammation of the kidney affecting the structure and normal function of the kidney. This condition can be chronic or acute and is generally caused by infection, degenerative process or vascular disease. In all cases, early detection is desirable so that the patient with nephritis can begin treatment of the condition.

An approach to detecting nephritis is to determine the antigens associated with nephritis and antibodies thereto. In rabbit, a tubulointerstitial nephritis antigen (TIN-ag) has been reported in Nelson, T. R., et al., *J. Biol. Chem.,* 270(27): 16265–70 (July 1995) (GENBANK/U24270). This study reports that the rabbit TIN-ag is a basement membrane glycoprotein having a predicted amino acid sequence which has a carboxyl-terminal region exhibiting 30% homology with human preprocathepsin B, a member of the cystein proteinase family of proteins. It is also reported that the rabbit TIN-ag has a domain in the amino-terminal region containing an epidermal growth factor-like motif that shares homology with laminin A and S chains, alpha 1 chain of type I collagen, von Willebrand's factor and mucin, indicating structural and functional similarities. Studies have also been conducted in mice. However, it is desirable to identify tubulointerstitial nephritis antigens in humans to aid in the development of early detection methods and treatment of nephritis.

Proteins which have homology to tubulointerstitial nephritis antigens are of particular interest to the medical and industrial communities. Often, proteins having homology to each other have similar function. It is also of interest when proteins having homology do not have similar functions, indicating that certain structural motifs identify information other than function, such as locality of function. We herein describe the identification and characterization of a novel polypeptide, designated herein as PRO230, which has homology to tubulointerstitial nephritis antigens.

3. PRO232

Stem cells are undifferentiated cells capable of (a) proliferation, (b) self maintenance, (c) the production of a large number of differentiated functional progeny, (d) regeneration of tissue after injury and/or (e) a flexibility in the use of these options. Stem cells often express cell surface antigens which are capable of serving as cell specific markers that can be exploited to identify stem cells, thereby providing a means for identifying and isolating specific stem cell populations.

Having possession of different stem cell populations will allow for a number of important applications. For example, possessing a specific stem cell population will allow for the identification of growth factors and other proteins which are involved in their proliferation and differentiation. In addition, there may be as yet undiscovered proteins which are associated with (1) the early steps of dedication of the stem cell to a particular lineage, (2) prevention of such dedication, and (3) negative control of stem cell proliferation, all of which may be identified if one has possession of the stem cell population. Moreover, stem cells are important and ideal targets for gene therapy where the inserted genes promote the health of the individual into whom the stem cells are transplanted. Finally, stem cells may play important roles in transplantation of organs or tissues, for example liver regeneration and skin grafting.

Given the importance of stem cells in various different applications, efforts are currently being undertaken by both industry and academia to identify new, native stem cell antigen proteins so as to provide specific cell surface markers for identifying stem cell populations as well as for providing insight into the functional roles played by stem cell antigens in cell proliferation and differentiation. We herein describe the identification and characterization of novel polypeptides having homology to a stem cell antigen, wherein those polypeptides are herein designated as PRO232 polypeptides.

4. PRO187

Growth factors are molecular signals or mediators that enhance cell growth or proliferation, alone or in concert, by binding to specific cell surface receptors. However, there are other cellular reactions than only growth upon expression to growth factors. As a result, growth factors are better characterized as multifunctional and potent cellular regulators. Their biological effects include proliferation, chemotaxis and stimulation of extracellular matrix production. Growth factors can have both stimulatory and inhibitory effects. For example, transforming growth factor (TGF-β) is highly pleiotropic and can stimulate proliferation in some cells, especially connective tissue, while being a potent inhibitor of proliferation in others, such as lymphocytes and epithelial cells.

The physiological effect of growth stimulation or inhibition by growth factors depends upon the state of development and differentiation of the target tissue. The mechanism of local cellular regulation by classical endocrine molecules involves comprehends autocrine (same cell); juxtacrine (neighbor cell), and paracrine (adjacent cells) pathways. Peptide growth factors are elements of a complex biological language, providing the basis for intercellular communication. They permit cells to convey information between each other, mediate interaction between cells and change gene expression. The effect of these multifunctional and pluripotent factors is dependent on the presence or absence of other peptides.

FGF-8 is a member of the fibroblast growth factors (FGFs) which are a family of heparin-binding, potent mitogens for both normal diploid fibroblasts and established cell lines, Gospodarowicz et al. (1984), *Proc. Natl. Acad. Sci. USA* 81:6963. The FGF family comprises acidic FGF (FGF-1), basic FGF (FGF-2), INT-2 (FGF-3), K-FGF/HST (FGF-4), FGF-5, FGF-6, KGF (FGF-7), AIGF (FGF-8) among others. All FGFs have two conserved cysteine residues and share 30–50% sequence homology at the amino acid level. These factors are mitogenic for a wide variety of normal diploid mesoderm-derived and neural crest-derived cells, including granulosa cells, adrenal cortical cells, chondrocytes, myoblasts, corneal and vascular endothelial cells (bovine or human), vascular smooth muscle cells, lens, retina and prostatic epithelial cells, oligodendrocytes, astrocytes, chrondocytes, myoblasts and osteoblasts.

Fibroblast growth factors can also stimulate a large number of cell types in a non-mitogenic manner. These activities include promotion of cell migration into wound area (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival. Baird & Bohlen, Handbook of Exp. Pharmacol. 95(1): 369–418, Springer, (1990). These properties provide a basis for using fibroblast growth factors in therapeutic approaches to accelerate wound healing, nerve repair, collateral blood vessel formation, and the like. For example, fibroblast growth factors have been suggested to minimize myocardium damage in heart disease and surgery (U.S. Pat. No. 4,378,347).

FGF-8, also known as androgen-induced growth factor (AIGF), is a 215 amino acid protein which shares 30–40% sequence homology with the other members of the FGF family. FGF-8 has been proposed to be under androgenic regulation and induction in the mouse mammary carcinoma cell line SC3. Tanaka et al., *Proc. Natl. Acad. Sci. USA* 89: 8928–8932 (1992); Sato et al., *J. Steroid Biochem. Molec. Biol.* 47: 91–98. (1993). As a result, FGF-8 may have a local role in the prostate, which is known to be an androgen-responsive organ. FGF-8 can also be oncogenic, as it displays transforming activity when transfected into NIH-3T3 fibroblasts. Kouhara et al., *Oncogene* 9 455–462 (1994). While FGF-8 has been detected in heart, brain, lung, kidney, testis, prostate and ovary, expression was also detected in the absence of exogenous androgens. Schmitt et al., *J. Steroid Biochem. Mol. Biol.* 57 (3–4): 173–78 (1996).

FGF-8 shares the property with several other FGFs of being expressed at a variety of stages of murine embryogenesis, which supports the theory that the various FGFs have multiple and perhaps coordinated roles in differentiation and embryogenesis. Moreover, FGF-8 has also been identified as a protooncogene that cooperates with Wnt-1 in the process of mammary tumorigenesis (Shackleford et al., *Proc. Natl. Acad. Sci. USA* 90, 740–744 (1993); Heikinheimo et al., *Mech. Dev.* 48: 129–138 (1994)).

In contrast to the other FGFs, FGF-8 exists as three protein isoforms, as a result of alternative splicing of the primary transcript. Tanaka et al., supra. Normal adult expression of FGF-8 is weak and confined to gonadal tissue, however northern blot analysis has indicated that FGF-8 mRNA is present from day 10 through day 12 or murine gestation, which suggests that FGF-8 is important to normal development. Heikinheimo et al., *Mech Dev.* 48(2): 129–38 (1994). Further in situ hybridization assays between day 8 and 16 of gestation indicated initial expression in the surface ectoderm of the first bronchial arches, the frontonasal process, the forebrain and the midbrain-hindbrain junction. At days 10–12, FGF-8 was expressed in the surface ectoderm of the forelimb and hindlimb buds, the nasal its and nasopharynx, the infundibulum and in the telencephalon, diencephalon and metencephalon. Expression continues in the developing hindlimbs through day 13 of gestation, but is undetectable thereafter. The results suggest that FGF-8 has a unique temporal and spatial pattern in embryogenesis and suggests a role for this growth factor in multiple regions of ectodermal differentiation in the post-gastrulation embryo.

We herein describe the identification of novel polypeptides having homology to FGF-8, wherein those polypeptides are herein designated PRO187 polypeptides.

5. PRO265

Protein-protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415–421 (Oct. 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol*. (Germany), 37(4):215–222 (1995), reporting mutations in the leucine rich motif in a complex associated with the bleeding disorder Bernard-Soulier syndrome and Chlemetson, K. J., *Thromb. Haemost*. (Germany), 74(1):111–116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell Endocrinol*., (Ireland), 125(1–2): 65–70 (December 1996) (gonadotropin receptor involvement); Miura, Y., et al., *Nippon Rinsho* (Japan), 54(7): 1784–1789 (July 1996) (apoptosis involvement); Harris, P. C., et al., *J. Am. Soc. Nephrol.,* 6(4):1125–1133 (Oct. 1995) (kidney disease involvement); and Ruoslahti, E. I., et al., WO9110727-A by La Jolla Cancer Research Foundation (decorin binding to transforming growth factor-β involvement for treatment for cancer, wound healing and scarring). Also of particular interest is fibromodulin and its use to prevent or reduce dermal scarring. A study of fibromodulin is found in U.S. Pat. No. 5,654,270 to Ruoslahti, et al.

Efforts are therefore being undertaken by both industry and academia to identify new proteins having leucine rich repeats to better understand protein—protein interactions. Of particular interest are those proteins having leucine rich repeats and homology to known proteins having leucine rich repeats such as fibromodulin, the SLIT protein and platelet glycoprotein V. Many efforts are focused on the screening of mammalian recombinant DNA libraries to identify the coding sequences for novel secreted and membrane-bound proteins having leucine rich repeats. We herein describe the identification and characterization of novel polypeptides having homology to fibromodulin, herein designated as PRO265 polypeptides.

6. PRO219

Human matrilin-2 polypeptide is a member of the von Willebrand factor type A-like module superfamily. von Willebrand factor is a protein which plays an important role in the maintenance of hemostasis. More specifically, von Willebrand factor is a protein which is known to participate in platelet-vessel wall interactions at the site of vascular injury via its ability to interact and form a complex with Factor VIII. The absence of von Willebrand factor in the blood causes an abnormality with the blood platelets that prevents platelet adhesion to the vascular wall at the site of the vascular injury. The result is the propensity for brusing, nose bleeds, intestinal bleeding, and the like comprising von Willebrand's disease.

Given the physiological importance of the blood clotting factors, efforts are currently being undertaken by both industry and academia to identify new, native proteins which may be involved in the coagulation process. We herein describe the identification of a novel full-length polypeptide which possesses homology to the human matrilin-2 precursor polypeptide.

7. PRO246

The cell surface protein HCAR is a membrane-bound protein that acts as a receptor for subgroup C of the adenoviruses and subgroup B of the coxsackieviruses. Thus, HCAR may provide a means for mediating viral infection of cells in that the presence of the HCAR receptor on the cellular surface provides a binding site for viral particles, thereby facilitating viral infection.

In light of the physiological importance of membrane-bound proteins and specifically those which serve a cell surface receptor for viruses, efforts are currently being undertaken by both industry and academia to identify new, native membrane-bound receptor proteins. Many of these efforts are focused on the screening of mammalian recombinant DNA libraries to identify the coding sequences for novel receptor proteins. We herein describe a novel membrane-bound polypeptide (designated herein as PRO246) having homology to the cell surface protein HCAR and to various tumor antigens including A33 and carcinoembryonic antigen, wherein this polypeptide may be a novel cell surface virus receptor or tumor antigen.

8. PRO228

There are a number of known seven transmembrane proteins and within this family is a group which includes CD97 and EMR1. CD97 is a seven-span transmembrane receptor which has a cellular ligand, CD55, DAF. Hamann, et al., *J. Exp. Med*. (U.S.), 184(3):1189 (1996). Additionally, CD97 has been reported as being a dedifferentiation marker in human thyroid carcinomas and as associated with inflammation. Aust, et al., *Cancer Res*. (U.S.), 57(9): 1798 (1997); Gray, et al., J. Immunol. (U.S.), 157(12):5438 (1996). CD97 has also been reported as being related to the secretin receptor superfamily, but unlike known members of that family, CD97 and EMR1 have extended extracellular regions that possess several EGF domains at the N-terminus. Hamann, et al., *Genomics,* 32(1):144 (1996); Harmann, et al., *J. Immunol.,* 155(4):1942 (1995). EMR1 is further described in Lin, et al., *Genomics,* 41(3):301 (1997) and Baud, et al., *Genomics,* 26(2):334 (1995). While CD97 and EMR1 appear to be related to the secretin receptors, a known member of the secretin family of G protein-coupled receptors includes the alpha-latroxin receptor, latrophilin, which has been described as calcium independent and abundant among neuronal tissues. Lelianova, et al., *J. Biol. Chem.*, 272(34), 21504 (1997); Davletov, et al., *J. Biol. Chem.* (U.S.), 271(38):23239 (1996). Both members of the secretin receptor superfamily and non-members which are related to the secretin receptor superfamily, or CRF and calcitonin receptors are of interest. In particular, new members of these families, identified by their homology to known proteins, are of interest.

Efforts are being undertaken by both industry and academia to identify new membrane-bound receptor proteins, particularly transmembrane proteins with EGF repeats and large N-terminuses which may belong to the family of seven-transmembrane proteins of which CD97 and EMR1 are members. We herein describe the identification and characterization of novel polypeptides having homology to CD97 and EMR1, designated herein as PRO228 polypeptides.

9. PRO533

Growth factors are molecular signals or mediators that enhance cell growth or proliferation, alone or in concert, by binding to specific cell surface receptors. However, there are other cellular reactions than only growth upon expression to growth factors. As a result, growth factors are better characterized as multifunctional and potent cellular regulators. Their biological effects include proliferation, chemotaxis and stimulation of extracellular matrix production. Growth factors can have both stimulatory and inhibitory effects. For example, transforming growth factors (TGF-β) is highly pleiotropic and can stimulate proliferation in some cells, especially connective tissues, while being a potent inhibitor of proliferation in others, such as lymphocytes and epithelial cells.

The physiological effect of growth stimulation or inhibition by growth factors depends upon the state of development and differentiation of the target tissue. The mechanism of local cellular regulation by classical endocrine molecules comprehends autocrine (same cell), juxtacrine (neighbor cell), and paracrine (adjacent cell) pathways. Peptide growth factors are elements of a complex biological language, providing the basis for intercellular communication. They permit cells to convey information between each other, mediate interaction between cells and change gene expression. The effect of these multifunctional and pluripotent factors is dependent on the presence or absence of other peptides.

Fibroblast growth factors (FGFs) are a family of heparin-binding, potent mitogens for both normal diploid fibroblasts and established cell lines, Godpodarowicz, D. et al. (1984), Proc. Natl. Acad. Sci. USA 81: 6983. the FGF family comprises acidic FGF (FGF-1), basic FGF (FGF-2), INT-2 (FGF-3), K-FGF/HST (FGF-4), FGF-5, FGF-6, KGF (FGF-7), AIGF (FGF-8) among others. All FGFs have two conserved cysteine residues and share 30–50% sequence homology at the amino acid level. These factors are mitogenic for a wide variety of normal diploid mesoderm-derived and neural crest-derived cells, inducing granulosa cells, adrenal cortical cells, chrondocytes, myoblasts, corneal and vascular endothelial cells (bovine or human), vascular smooth muscle cells, lens, retina and prostatic epithelial cells, oligodendrocytes, astrocytes, chrondocytes, myoblasts and osteoblasts.

Fibroblast growth factors can also stimulate a large number of cell types in a non-mitogenic manner. These activities include promotion of cell migration into a wound area (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival. Baird, A. & Bohlen, P., *Handbook of Exp. Pharmacol.* 95(1): 369–418 (1990). These properties provide a basis for using fibroblast growth factors in therapeutic approaches to accelerate wound healing, nerve repair, collateral blood vessel formation, and the like. For example, fibroblast growth factors, have been suggested to minimize myocardium damage in heart disease and surgery (U.S. Pat. No. 4,378,437).

We herein describe the identification and characterization of novel polypeptides having homology to FGF, herein designated PRO533 polypeptides.

10. PRO245

Some of the most important proteins involved in the above described regulation and modulation of cellular processes are the enzymes which regulate levels of protein phosphorylation in the cell. For example, it is known that the transduction of signals that regulate cell growth and differentiation is regulated at least in part by phosphorylation and dephosphorylation of various cellular proteins. The enzymes that catalyze these processes include the protein kinases, which function to phosphorylate various cellular proteins, and the protein phosphatases, which function to remove phosphate residues from various cellular proteins. The balance of the level of protein phosphorylation in the cell is thus mediated by the relative activities of these two types of enzymes.

Although many protein kinase enzymes have been identified, the physiological role played by many of these catalytic proteins has yet to be elucidated. It is well known, however, that a number of the known protein kinases function to phosphorylate tyrosine residues in proteins, thereby leading to a variety of different effects. Perhaps most importantly, there has been a great deal of interest in the protein tyrosine kinases since the discovery that many oncogene products and growth factors possess intrinsic protein tyrosine kinase activity. There is, therefore, a desire to identify new members of the protein tyrosine kinase family.

Given the physiological importance of the protein kinases, efforts are being undertaken by both industry and academia to identify new, native kinase proteins. Many of these efforts are focused on the screening of mammalian recombinant DNA libraries to identify the coding sequences for novel kinase proteins. We herein describe the identification and characterization of novel polypeptides having homology to tyrosine kinase proteins, designated herein as PRO245 polypeptides.

11. PRO220, PRO221 and PRO227

Protein—protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415–421 (Oct. 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol*. (Germany), 37(4):215–222 (1995), reporting mutations in the leucine rich motif in a complex associated with the bleeding disorder Bernard-Soulier syndrome and Chlemetson, K. J., *Thromb. Haemost*. (Germany), 74(1):111–116 (July 1995), reporting that platelets have leucine rich repeats. Another protein of particular-interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell. Endocrinol*., (Ireland), 125(1–2): 65–70 (December 1996) (gonadotropin receptor involvement); Miura, Y., et al., *Nippon Rinsho* (Japan), 54(7): 1784–1789 (July 1996) (apoptosis involvement); Harris, P. C., et al., *J. Am. Soc. Nephrol.,* 6(4):1125–1133 (Oct. 1995) (kidney disease involvement); and Ruoslahti, E. I., et al., WO9110727-A by La Jolla Cancer Research Foundation (decorin binding to transforming growth factorβ involvement for treatment for cancer, wound healing and scarring).

Efforts are therefore being undertaken by both industry and academia to identify new proteins having leucine rich repeats to better understand protein—protein interactions. Of particular interest are those proteins having leucine rich repeats and homology to known proteins having leucine rich repeats such as the SLIT protein and platelet glycoprotein V.

12. PRO258

Immunoglobulins are antibody molecules, the proteins that function both as receptors for antigen on the B-cell membrane and as the secreted products of the plasma cell. Like all antibody molecules, immunoglobulins perform two major functions: they bind specifically to an antigen and they participate in a limited number of biological effector functions. Therefore, new members of the Ig superfamily are always of interest. Molecules which act as receptors by various viruses and those which act to regulate immune function are of particular interest. Also of particular interest are those molecules which have homology to known Ig family members which act as virus receptors or regulate immune function. Thus, molecules having homology to poliovirus receptors, CRTAM and CD166 (a ligand for lymphocyte antigen CD6) are of particular interest.

Extracellular and membrane-bound proteins play important roles in the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment, usually at a membrane-bound receptor protein.

We herein describe the identification and characterization of novel polypeptides having homology to CRTAM, designated herein as PRO258 polypeptides.

13. PRO266

Protein-protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglobular shape. These two features have been indicated as responsible for the protein-binding functions of proteins containing leucine-rich repeats. See, Kobe and Deisenhofer, *Trends Biochem. Sci.,* 19(10):415–421 (October 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol.* (Germany), 37(4):215–222 (1995), reporting mutations in the leucine rich motif in a complex associated with the bleeding disorder Bernard-Soulier syndrome and Chlemetson, K. J., *Thromb. Haemost*. (Germany), 74(1):111–116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell. Endocrinol*., (Ireland), 125(1–2): 65–70 (December 1996) (gonadotropin receptor involvement); Miura, Y., et al., *Nippon Rinsho* (Japan), 54(7): 184–1789 (July 1996) (apoptosis involvement); Harris, P. C., et al., *J. Am. Soc. Nephrol.,* 6(4):1125–1133 (October 1995) (kidney disease involvement); and Ruoslahti, E. I., et al., WO9110727-A by La Jolla Cancer Research Foundation (decorin binding to transforming growth factorβ involvement for treatment for cancer, wound healing and scarring).

Efforts are therefore being undertaken by both industry and academia to identify new proteins having leucine rich repeats to better understand protein—protein interactions, neuronal development and adhesin molecules. Of particular interest are those proteins having leucine rich repeats and homology to known proteins having leucine rich repeats such as the SLIT protein. We herein describe novel polypeptides having homology to SLIT, designated herein as PRO266 polypeptides.

14. PRO269

Thrombomodulin binds to and regulates the activity of thrombin. It is important in the control of blood coagulation. Thrombomodulin functions as a natural anticoagulant by accelerating the activation of protein C by thrombin. Soluble thrombomodulin may have therapeutic use as an antithrombotic agent with reduced risk for hemorrhage as compared with heparin. Thrombomodulin is a cell surface trans-membrane glycoprotein, present on endothelial cells and platelets. A smaller, functionally active form of thrombomodulin circulates in the plasma and is also found in urine. (In Haeberli, A., Human Protein Data, VCH Oub., N.Y., 1992). Peptides having homology to thrombomodulin are particularly desirable.

We herein describe the identification and characterization of novel polypeptides having homology to thrombomodulin, designated herein as PRO269 polypeptides.

15. PRO287

Procollagen C-proteinase enhancer protein binds to and enhances the activity of bone morphogenic protein "BMP1"/procollagen C-proteinase (PCP). It plays a role in extracellular matrix deposition. BMP1 proteins may be used to induce bone and/or cartilage formation and in wound healing and tissue repair. Therefore, procollagen C-proteinase enhancer protein, BMP1 and proteins having homology thereto, are of interest to the scientific and medical communities.

We herein describe the identification and characterization of novel polypeptides having homology to procollagen C-proteinase enhancer protein precursor and procollagen C-proteinase enhancer protein, designated herein as PRO287 polypeptides.

16. PRO214

Growth factors are molecular signals or mediators that enhances cell growth or proliferation, alone or in concert, by binding to specific cell surface receptors. However, there are other cellular reactions than only growth upon expression to growth factors. As a result, growth factors are better characterized as multifunctional and potent cellular regulators. Their biological effects include proliferation, chemotaxis and stimulation of extracellular matrix production. Growth factors can have both stimulatory and inhibitory effects. For example, transforming growth factor β (TGF-β) is highly pleiotropic and can stimulate proliferation in some cells, especially connective tissue, while being a potent inhibitor of proliferation in others, such as lymphocytes and epithelial cells.

The physiological effect of growth stimulation or inhibition by growth factors depends upon the state of development and differentiation of the target tissue. The mechanism of local cellular regulation by classical endocrine molecules involves comprehends autocrine (same cell), juxtacrine (neighbor cell), and paracrine (adjacent cells) pathways. Peptide growth factors are elements of a complex biological language, providing the basis for intercellular communication. They permit cells to convey information between each other, mediate interaction between cells and change gene expression. The effect of these multifunctional and pluripotent factors is dependent on the presence or absence of other peptides.

Epidermal growth factor (EGF) is a conventional mitogenic factor that stimulates the proliferation of various types of cells including epithelial cells and fibroblasts. EGF binds to and activates the EGF receptor (EGFR), which initiates intracellular signaling and subsequent effects. The EGFR is expressed in neurons of the cerebral cortex, cerebellum, and hippocampus in addition to other regions of the central nervous system (CNS). In addition, EGF is also expressed in various regions of the CNS. Therefore, EGF acts not only on mitotic cells, but also on postmitotic neurons. In fact, many studies have indicated that EGF has neurotrophic or neuromodulatory effects on various types of neurons in the CNS. For example, EGF acts directly on cultured cerebral cortical and cerebellar neurons, enhancing neurite outgrowth and survival. On the other hand, EGF also acts on other cell types, including septal cholinergic and mesencephalic dopaminergic neurons, indirectly through glial cells. Evidence of the effects of EGF on neurons in the CNS is accumulating, but the mechanisms of action remain essentially unknown. EGF-induced signaling in mitotic cells is better understood than in postmitotic neurons. Studies of cloned pheochromocytoma PC12 cells and cultured cerebral cortical neurons have suggested that the EGF-induced neurotrophic actions are mediated by sustained activation of the EGFR and mitogen-activated protein kinase (MAPK) in response to EGF. The sustained intracellular signaling correlates with the decreased rate of EGFR down-regulation, which might determine the response of neuronal cells to EGF. It is likely that EGF is a multi-potent growth factor that acts upon various types of cells including mitotic cells and postmitotic neurons.

EGF is produced by the salivary and Brunner's glands of the gastrointestinal system, kidney, pancreas, thyroid gland, pituitary gland, and the nervous system, and is found in body fluids such as saliva, blood, cerebrospinal fluid (CSF), urine, amniotic fluid, prostatic fluid, pancreatic juice, and breast milk, Plata-Salaman, C R *Peptides* 12: 653–663 (1991).

EGF is mediated by its membrane specific receptor, which contains an intrinsic tyrosine kinase. Stoscheck C M et al., *J. Cell Biochem.* 31: 135–152 (1986). EGF is believed to function by binding to the extracellular portion of its receptor which induces a transmembrane signal that activates the intrinsic tyrosine kinase.

Purification and sequence analysis of the EGF-like domain has revealed the presence of six conserved cysteine residues which cross-bind to create three peptide loops, Savage C R et al., *J. Biol. Chem.* 248: 7669–7672 (1979). It is now generally known that several other peptides can react with the EGF receptor which share the same generalized motif $X_nCX_7CX_{4/5}CX_{10}CXCX_5GX_2CX_n$, where X represents any non-cysteine amino acid, and n is a variable repeat number. Non isolated peptides having this motif include TGF-a, amphiregulin, schwannoma-derived growth factor (SDGF), heparin-binding EGF-like growth factors and certain virally encoded peptides (e.g., Vaccinia virus, Reisner A H, *Nature* 313: 801–803 (1985), Shope fibroma virus, Chang W., et al., Mol Cell Biol. 7: 535–540 (1987), Molluscum contagiosum, Porter C D & Archard L C, *J. Gen. Virol.* 68: 673–682 (1987), and Myxoma virus, Upton C et al., *J. Virol.* 61: 1271–1275 (1987). Prigent S A & Lemoine N. R., *Prog. Growth Factor Res.* 4: 1–24 (1992).

EGF-like domains are not confined to growth factors but have been observed in a variety of cell-surface and extracellular proteins which have interesting properties in cell adhesion, protein—protein interaction and development, Laurence D J R & Gusterson B A, *Tumor Biol.* 11: 229–261 (1990). These proteins include blood coagulation factors (factors VI, IX, X, XII, protein C, protein S, protein Z, tissue plasminogen activator, urokinase), extracellular matrix components (laminin, cytotactin, entactin), cell surface receptors (LDL receptor, thrombomodulin receptor) and immunity-related proteins (complement C1r, uromodulin).

Even more interesting, the general structure pattern of EGF-like precursors is preserved through lower organisms as well as in mammalian cells. A number of genes with developmental significance have been identified in invertebrates with EGF-like repeats. For example, the notch gene of *Drosophila* encodes 36 tandemly arranged 40 amino acid repeats which show homology to EGF, Wharton W et al., *Cell* 43: 557–581 (1985). Hydropathy plots indicate a putative membrane spanning domain, with the EGF-related sequences being located on the extracellular side of the membrane. Other homeotic genes with EGF-like repeats include Delta, 95F and 5ZD which were identified using probes based on Notch, and the nematode gene Lin-12 which encodes a putative receptor for a developmental signal transmitted between two specified cells.

Specifically, EGF has been shown to have potential in the preservation and maintenance of gastrointestinal mucosa and the repair of acute and chronic mucosal lesions, Konturek, P C et al., *Eur. J. Gastroenterol Hepatol.* 7 (10), 933–37 (1995), including the treatment of necrotizing enterocolitis, Zollinger-Ellison syndrome, gastrointestinal ulceration gastrointestinal ulcerations and congenital microvillus atrophy, A. Guglietta & P B Sullivan, Eur. *J. Gastroenterol Hepatol,* 2(10), 945–50 (1995). Additionally, EGF has been implicated in hair follicle differentiation; C. L. du Cros, *J. Invest. Dermatol.* 101 (1 Suppl.), 106s–113S (1993), S G Hillier, *Clin. Endocrinol.* 33(4), 427–28 (1990); kidney function, L. L. Hamm et al., *Semin. Nephrol.* 13 (1): 109–15 (1993), R C Harris, *Am. J. Kidney Dis.* 17(6): 627–30 (1991); tear fluid, G B van Setten et al., *Int. Ophthalmol* 5(6); 359–62 (1991); vitamin K mediated blood coagulation, J. Stenflo et al., *Blood* 78(7): 1637–51 (1991). EGF is also implicated various skin disease characterized by abnormal keratinocyte differentiation, e.g., psoriasis, epithelial cancers such as squamous cell carcinomas of the lung, epidermoid carcinoma of the vulva and gliomas. King, L E et al., *Am. J. Med. Sci.* 296: 154–158 (1988).

Of great interest is mounting evidence that genetic alterations in growth factors signaling pathways are closely linked to developmental abnormalities and to chronic diseases including cancer. Aaronson S A, *Science* 254: 1146–1153 (1991). For example, c-erb-2 (also known as HER-2), a proto-oncogene with close structural similarity to EGF receptor protein, is overexpressed in human breast cancer. King et al., *Science* 229: 974–976 (1985); Gullick, W J, *Hormones and their actions*, Cooke B A et al., eds, Amsterdam, Elsevier, pp 349–360 (1986).

17. PRO317

The TGF-β supergene family, or simply TGF-β superfamily, a group of secreted proteins, includes a large number of related growth and differentiation factors expressed in virtually all phyla. Superfamily members bind to specific cell surface receptors that activate signal transduction mechanisms to elicit their multifunctional cytokine effects. Kolodziejczyk and Hall, *Biochem. Cell. Biol.,* 74: 299–314 (1996); Attisano and Wrana, *Cytokine Growth Factor Rev.,* 7: 327–339 (1996); and Hill, *Cellular Signaling,* 8: 533–544 (1996).

Members of this family include five distinct forms of TGF-β (Sporn and Roberts, in *Peptide Growth Factors and Their Receptors*, Sporn and Roberts, eds. (Springer-Verlag: Berlin, 1990) pp. 419–472), as well as the differentiation factors vg1 (Weeks and Melton, *Cell,* 51: 861–867 (1987)) and DPP-C polypeptide (Padgett et al., *Nature,* 325: 81–84 (1987)), the hormones activin and inhibin (Mason et al., *Nature,* 318: 659–663 (1985); Mason et al., *Growth Factors,* 1: 77–88 (1987)), the Mullerian-inhibiting substance (MIS) (Cate et al., *Cell,* 45: 685–698 (1986)), the bone morphogenetic proteins (BMPs) (Wozney et al., *Science,* 242: 1528–1534 (1988); PCT WO 88/00205 published Jan. 14, 1988; U.S. Pat. No. 4,877,864 issued Oct. 31, 1989), the developmentally regulated proteins Vgr-1 (Lyons et al., *Proc. Natl. Acad. Sci. USA.* 86: 4554–4558 (1989)) and Vgr-2 (Jones et al., *Molec. Endocrinol.,* 6: 1961–1968 (1992)), the mouse growth differentiation factor (GDF), such as GDF-3 and GDF-9 (Kingsley, *Genes Dev.,* 8: 133–146 (1994); McPherron and Lee, *J. Biol. Chem.,* 268: 3444–3449 (1993)), the mouse lefty/Stra1 (Meno et al., *Nature,* 381: 151–155 (1996); Bouillet et al., *Dev. Biol.,* 170: 420–433 (1995)), glial cell line-derived neurotrophic factor (GDNF) (Lin et al., *Science,* 260: 1130–1132 (1993), neurturin (Kotzbauer et al., *Nature,* 384: 467–470 (1996)), and endometrial bleeding-associated factor (EBAF) (Kothapalli et al., *J. Clin. Invest.,* 99: 2342–2350 (1997)). The subset BMP-2A and BMP-2B is approximately 75% homologous in sequence to DPP-C and may represent the mammalian equivalent of that protein.

The proteins of the TGF-β superfamily are disulfide-linked homo- or heterodimers encoded by larger precursor polypeptide chains containing a hydrophobic signal sequence, a long and relatively poorly conserved N-terminal pro region of several hundred amino acids, a cleavage site (usually polybasic), and a shorter and more highly conserved C-terminal region. This C-terminal region corresponds to the processed mature protein and contains approximately 100 amino acids with a characteristic cysteine motif, i.e., the conservation of seven of the nine cysteine residues of TGF-β among all known family members. Although the position of the cleavage site between the mature and pro regions varies among the family members, the C-terminus of all of the proteins is in the identical position, ending in the sequence Cys-X-Cys-X, but differing in every case from the TGF-β consensus C-terminus of Cys-Lys-Cys-Ser. Sporn and Roberts, 1990, supra.

There are at least five forms of TGF-β currently identified, TGF-β1, TGF-β2, TGF-β3, TGF-β4, and TGF-β5. The activated form of TGF-β1 is a homodimer formed by dimerization of the carboxy-terminal 112 amino acids of a 390 amino acid precursor. Recombinant TGF-β1 has been cloned (Derynck et al., *Nature,* 316:701–705 (1985)) and expressed in Chinese hamster ovary cells (Gentry et al., *Mol. Cell. Biol.,* 7: 3418–3427 (1987)). Additionally, recombinant human TGF-β2 (deMartin et al., *EMBO J.,* 6: 3673 (1987)), as well as human and porcine TGF-β3 (Derynck et al., *EMBO J.,* 7: 3737–3743 (1988); ten Dijke et al., *Proc. Natl. Acad. Sci. USA,* 85: 4715 (1988)) have been cloned. TGF-β2 has a precursor form of 414 amino acids and is also processed to a homodimer from the carboxy-terminal 112 amino acids that shares approximately 70% homology with the active form of TGF-β1 (Marquardt et al., *J. Biol. Chem.,* 262: 12127 (1987)). See also EP 200,341; 169,016; 268,561; and 267,463; U.S. Pat. No. 4,774,322; Cheifetz et al., *Cell,* 48: 409–415 (1987); Jakowlew et al., *Molecular Endocrin.,* 2: 747–755 (1988); Derynck et al., *J. Biol. Chem.,* 261: 4377–4379 (1986); Sharples et al., *DNA,* 6: 239–244 (1987); Derynck et al., *Nucl. Acids. Res.,* 15: 3188–3189 (1987); Derynck et al., *Nucl. Acids. Res.,* 15: 3187 (1987); Seyedin et al., *J. Biol. Chem.,* 261: 5693–5695 (1986); Madisen et al., *DNA,* 7: 1–8 (1988); and Hanks et al., *Proc. Natl. Acad. Sci.* (*U.S.A.*), 85: 79–82 (1988).

TGF-β4 and TGF-β5 were cloned from a chicken chondrocyte cDNA library (Jakowlew et al., *Molec. Endocrinol.,* 2: 1186–1195 (1988)) and from a frog oocyte cDNA library, respectively.

The pro region of TGF-β associates non-covalently with the mature TGF-β dimer (Wakefield et al., *J. Biol. Chem.,*

263: 7646–7654 (1988); Wakefield et al., *Growth Factors,* 1: 203–218 (1989)), and the pro regions are found to be necessary for proper folding and secretion of the active mature dimers of both TGF-β and activin (Gray and Mason, *Science,* 247: 1328–1330 (1990)). The association between the mature and pro regions of TGF-β masks the biological activity of the mature dimer, resulting in formation of an inactive latent form. Latency is not a constant of the TGF-β superfamily, since the presence of the pro region has no effect on activin or inhibin biological activity.

A unifying feature of the biology of the proteins from the TGF-β superfamily is their ability to regulate developmental processes. TGF-β has been shown to have numerous regulatory actions on a wide variety of both normal and neoplastic cells. TGF-β is multifunctional, as it can either stimulate or inhibit cell proliferation, differentiation, and other critical processes in cell function (Sporn and Roberts, supra).

One member of the TGF-β superfamily, EBAF, is expressed in endometrium only in the late secretory phase and during abnormal endometrial bleeding. Kothapalli et al., *J. Clin. Invest.,* 99: 2342–2350 (1997). Human endometrium is unique in that it is the only tissue in the body that bleeds at regular intervals. In addition, abnormal endometrial bleeding is one of the most common manifestations of gynecological diseases, and is a prime indication for hysterectomy. In situ hybridization showed that the mRNA of EBAF was expressed in the stroma without any significant mRNA expression in the endometrial glands or endothelial cells.

The predicted protein sequence of EBAF showed a strong homology to the protein encoded by mouse lefty/stra3 of the TGF-β superfamily. A motif search revealed that the predicted EBAF protein contains most of the cysteine residues which are conserved among the TGF-β-related proteins and which are necessary for the formation of the cysteine knot structure. The EBAF sequence contains an additional cysteine residue, 12 amino acids upstream from the first conserved cysteine residue. The only other family members known to contain an additional cysteine residue are TGF-βs, inhibins, and GDF-3. EBAF, similar to LEFTY, GDF-3/Vgr2, and GDF-9, lacks the cysteine residue that is known to form the intermolecular disulfide bond. Therefore, EBAF appears to be an additional member of the TGF-β superfamily with an unpaired cysteine residue that may not exist as a dimer. However, hydrophobic contacts between the two monomer subunits may promote dimer formation. Fluorescence in situ hybridization showed that the ebaf gene is located on human chromosome 1 at band q42.1.

Additional members of the TGF-β superfamily, such as those related to EBAF, are being searched for by industry and academics. We herein describe the identification and characterization of novel polypeptides having homology to EBAF, designated herein as PRO317 polypeptides.

18. PRO301

The widespread occurrence of cancer has prompted the devotion of considerable resources and discovering new treatments of treatment. One particular method involves the creation of tumor or cancer specific monoclonal antibodies (mAbs) which are specific to tumor antigens. Such mAbs, which can distinguish between normal and cancerous cells are useful in the diagnosis, prognosis and treatment of the disease. Particular antigens are known to be associated with neoplastic diseases, such as colorectal cancer.

One particular antigen, the A33 antigen is expressed in more than 90% of primary or metastatic colon cancers as well as normal colon epithelium. Since colon cancer is a widespread disease, early diagnosis and treatment is an important medical goal. Diagnosis and treatment of colon cancer can be implemented using monoclonal antibodies (mAbs) specific therefore having fluorescent, nuclear magnetic or radioactive tags. Radioactive gene, toxins and/or drug tagged mAbs can be used for treatment in situ with minimal patient description. mAbs can also be used to diagnose during the diagnosis and treatment of colon cancers. For example, when the serum levels of the A33 antigen are elevated in a patient, a drop of the levels after surgery would indicate the tumor resection was successful. On the other hand, a subsequent rise in serum A33 antigen levels after surgery would indicate that metastases of the original tumor may have formed or that new primary tumors may have appeared. Such monoclonal antibodies can be used in lieu of, or in conjunction with surgery and/or other chemotherapies. For example, U.S. Pat. No. 4,579,827 and U.S. Ser. No. 424,991 (E.P. 199,141) are directed to therapeutic administration of monoclonal antibodies, the latter of which relates to the application of anti-A33 mAb.

Many cancers of epithelial origin have adenovirus receptors. In fact, adenovirus-derived vectors have been proposed as a means of inserting antisense nucleic acids into tumors (U.S. Pat. No. 5,518,885). Thus, the association of viral receptors with neoplastic tumors is not unexpected.

We herein describe the identification and characterization of novel polypeptides having homology to certain cancer-associated antigens, designated herein as PRO301 polypeptides.

19. PRO224

Cholesterol uptake can have serious implications on one's health. Cholesterol uptake provides cells with most of the cholesterol they require for membrane synthesis. If this uptake is blocked, cholesterol accumulates in the blood and can contribute to the formation of atherosclerotic plaques in blood vessel walls. Most cholesterol is transported in the blood bound to protein in the form of complexes known as low-density lipoproteins (LDLs). LDLs are endocytosed into cells via LDL receptor proteins. Therefore, LDL receptor proteins, and proteins having homology thereto, are of interest to the scientific and medical communities.

Membrane-bound proteins and receptors can play an important role in the formation, differentiation and maintenance of multicellular organisms. The LDL receptors are an example of membrane-bound proteins which are involved in the synthesis and formation of cell membranes, wherein the health of an individual is affected directly and indirectly by its function. Many membrane-bound proteins act as receptors such as the LDL receptor. These receptors can function to endocytose substrates or they can function as a receptor for a channel. Other membrane-bound proteins function as signals or antigens.

Membrane-bound proteins and receptor molecules have various industrial applications, including as pharmaceutical and diagnostic agents. The membrane-bound proteins can also be employed for screening of potential peptide or small molecule regulators of the relevant receptor/ligand interaction. In the case of the LDL receptor, it is desirable to find molecules which enhance endocytosis so as to lower blood cholesterol levels and plaque formation. It is also desirable to identify molecules which inhibit endocytosis so that these molecules can be avoided or regulated by individuals having high blood cholesterol. Polypeptides which are homologous to lipoprotein receptors but which do not function as lipoprotein receptors are also of interest in the determination of the function of the fragments which show homology.

The following studies report on previously known low density lipoprotein receptors and related proteins including apolipoproteins: Sawamura, et al., Nippon Chemiphar Co, Japan patent application J09098787; Novak, S., et al., *J. Biol. Chem.,* 271:(20) 11732–6 (1996); Blaas, D., *J. Virol.,* 69(11) 7244–7 (November 1995); Scott, J., *J. Inherit. Metab. Dis.* (UK), 9/Supp. 1 (3–16) (1986); Yamamoto, et al., *Cell,* 39:27–38 (1984); Rebece, et al., *Neurobiol. Aging,* 15:5117 (1994); Novak, S., et al., *J. Biol. Chemistry,* 271: 11732–11736 (1996); and Sestavel and Fruchart, *Cell Mol. Biol.,* 40(4):461–81 (June 1994). These publications and others published prior to the filing of this application provide further background to peptides already known in the art.

Efforts are being undertaken by both industry and academia to identify new, native membrane-bound receptor proteins, particularly those having homology to lipoprotein receptors. We herein describe the identification and characterization of novel polypeptides having homology to lipoprotein receptors, designated herein as PRO224 polypeptides.

20. PRO222

Complement is a group of proteins found in the blood that are important in humoral immunity and inflammation. Complement proteins are sequentially activated by antigen-antibody complexes or by proteolytic enzymes. When activated, complement proteins kill bacteria and other microorganisms, affect vascular permeability, release histamine and attract white blood cells. Complement also enhances phagocytosis when bound to target cells. In order to prevent harm to autologous cells, the complement activation pathway is tightly regulated.

Deficiencies in the regulation of complement activation or in the complement proteins themselves may lead to immune-complex diseases, such as systemic lupus erythematosus, and may result in increased susceptibility to bacterial infection. In all cases, early detection of complement deficiency is desirable so that the patient can begin treatment. Thus, research efforts are currently directed toward identification of soluble and membrane proteins that regulate complement activation.

Proteins known to be important in regulating complement activation in humans include Factor H and Complement receptor type 1 (CR1). Factor H is a 150 kD soluble serum protein that interacts with complement protein C3b to accelerate the decay of C3 convertase and acts as a cofactor for Factor I-mediated cleavage of complement protein C4b. Complement receptor type 1 is a 190–280 kD membrane bound protein found in mast cells and most blood cells. CR1 interacts with complement proteins C3b, C4b, and iC3b to accelerate dissociation of C3 convertases, acts as a cofactor for Factor I-mediated cleavage of C3b and C4b, and binds immune complexes and promotes their dissolution and phagocytosis.

Proteins which have homology to complement proteins are of particular interest to the medical and industrial communities. Often, proteins having homology to each other have similar function. It is also of interest when proteins having homology do not have similar functions, indicating that certain structural motifs identify information other than function, such as locality of function.

Efforts are being undertaken by both industry and academia to identify new, native secreted and membrane-bound proteins, particularly those having homology to known proteins involved in the complement pathway. Proteins involved in the complement pathway were reviewed in Birmingham D J (1995), *Critical Reviews in Immunology,* 15(2):133–154 and in Abbas A K, et al. (1994) Cellular and Molecular Immunology, 2nd Ed. W.B. Saunders Company, Philadelphia, pp 295–315.

We herein describe the identification and characterization of novel polypeptides having homology to complement receptors, designated herein as PRO222 polypeptides.

21. PRO234

The successful function of many systems within multicellular organisms is dependent on cell—cell interactions. Such interactions are affected by the alignment of particular ligands with particular receptors in a manner which allows for ligand-receptor binding and thus a cell—cell adhesion. While protein—protein interactions in cell recognition have been recognized for some time, only recently has the role of carbohydrates in physiologically relevant recognition been widely considered (see B. K. Brandley et al., *J. Leuk. Biol.* 40: 97 (1986) and N. Sharon et al., *Science* 246: 227 (1989). Oligosaccharides are well positioned to act as recognition novel lectins due to their cell surface location and structural diversity. Many oligosaccharide structures can be created through the differential activities of a smaller number of glycosyltransferases. The diverse structures of oligosaccharides can be generated by transcription of relatively few gene products, which suggests that the oligosaccharides are a plausible mechanism by which is directed a wide range of cell—cell interactions. Examples of differential expression of cell surface carbohydrates and putative carbohydrate binding proteins (lectins) on interacting cells have been described (J. Dodd & T. M. Jessel, *J. Neurosci.* 5: 3278 (1985); L. J. Regan et al., *Proc. Natl. Acad. Sci. USA* 83: 2248 (1986); M. Constantine-Paton et al., *Nature* 324: 459 (1986); and M. Tiemeyer et al., *J. Biol. Chem.* 263: 1671 (1989). One interesting member of the lectin family are selectins.

The migration of leukocytes to sites of acute or chronic inflammation involves adhesive interactions between these cells and the endothelium. This specific adhesion is the initial event in the cascade that is initiated by inflammatory insults, and it is, therefore, of paramount importance to the regulated defense of the organism.

The types of cell adhesion molecules that are involved in the interaction between leukocytes and the endothelium during an inflammatory response currently stands at four: (1) selecting; (2) (carbohydrate and glycoprotein) ligands for selectins; (3) integrins; and (4) integrin ligands, which are members of the immunoglobulin gene superfamily.

The selectins are cell adhesion molecules that are unified both structurally and functionally. Structurally, selectins are characterized by the inclusion of a domain with homology to a calcium-dependent lectin (C-lectins), an epidermal growth factor (egf) like domain and several complement binding-like domains, Bevilacqua, M. P. et al., *Science* 243: 1160–1165 (1989); Johnston et al., *Cell* 56: 1033–1044 (1989); Lasky et al, *Cell* 56: 1045–1055 (1989); Siegalman, M. et al., *Science* 243: 1165–1172 (1989); Stoolman, L. M., *Cell* 56: 907–910 (1989). Functionally, selectins share the common property of their ability to mediate cell binding through interactions between their lectin domains and cell surface carbohydrate ligands (Brandley, B, et al., *Cell* 63, 861–863 (1990); Springer, T. and Lasky, L. A., *Nature* 349, 19–197 (1991); Bevilacqua, M. P. and Nelson, R. M., *J. Clin. Invest.* 91 379–387 (1993) and Tedder et al., *J. Exp. Med.* 170: 123–133 (1989).

There are three members identified so far in the selectin family of cell adhesion molecules: L-selectin (also called peripheral lymph node homing receptor (pnHR), LEC-CAM-1, LAM-1, $gp90^{MEL}$, $gp100^{MEL}$, $gp110^{MEL}$, MEL-14 antigen, Leu-8 antigen, TQ-1 antigen, DREG antigen), E-selectin (LEC-CAM-2, LECAM-2, ELAM-1) and P-selectin (LEC-CAM-3, LECAM-3, GMP-140, PADGEM).

The identification of the C-lectin domain has led to an intense effort to define carbohydrate binding ligands for proteins containing such domains. E-selectin is believed to recognize the carbohydrate sequence NeuNAcα2–3Galβ1–4 (Fucα1–3) GlcNAc (sialyl-Lewis x, or $sLe^x$) and related oligosaccharides, Berg et al., *J. Biol. Chem.* 265: 14869–14872 (1991); Lowe et al., *Cell* 63: 475–484 (1990); Phillips et al., *Science* 250: 1130–1132 (1990); Tiemeyer et al., *Proc. Natl. Acad. Sci. USA* 88: 1138–1142 (1991).

L-selectin, which comprises a lectin domain, performs its adhesive function by recognizing carbohydrate-containing ligands on endothelial cells. L-selectin is expressed on the surface of leukocytes, such as lymphocytes, neutrophils, monocytes and eosinophils, and is involved with the trafficking of lymphocytes to peripheral lymphoid tissues (Gallatin et al., *Nature* 303: 30–34 (1983)) and with acute neutrophil-medicated inflammatory responses (Watson, S. R., *Nature* 349: 164–167 (1991)). The amino acid sequence of L-selectin and the encoding nucleic acid sequence are, for example, disclosed in U.S. Pat. No. 5,098,833 issued 24 Mar. 1992.

L-selectin (LECAM-1) is particularly interesting because of its ability to block neutrophil influx (Watson et al., *Nature* 349: 164–167 (1991). It is expressed in chronic lymphocytic leukemia cells which bind to HEV (Spertini et al., *Nature* 349: 691–694 (1991). It is also believed that HEV structures at sites of chronic inflammation are associated with the symptoms of diseases such as rheumatoid arthritis, psoriasis and multiple sclerosis.

E-selectin (ELAM-1), is particularly interesting because of its transient expression on endothelial cells in response to IL-1 or TNF. Bevilacqua et al., *Science* 243: 1160 (1989). The time course of this induced expression (2–8 h) suggests a role for this receptor in initial neutrophil induced extravasation in response to infection and injury. It has further been reported that anti-ELAM-1 antibody blocks the influx of neutrophils in a primate asthma model and thus is beneficial for preventing airway obstruction resulting from the inflammatory response. Gundel et al., *J. Clin. Invest.* 88: 1407 (1991).

The adhesion of circulating neutrophils to stimulated vascular endothelium is a primary event of the inflammatory response. P-selectin has been reported to recognize the Lewis x structure (Galβ1–4(Fucα1–3) GlcNAc), Larsen et al., *Cell* 63: 467–474(1990). Others report that an additional terminal linked sialic acid is required for high affinity binding, Moore et al., *J. Cell. Biol.* 112: 491–499 (1991). P-selectin has been shown to be significant in acute lung injury. Anti-P-selectin antibody has been shown to have strong protective effects in a rodent lung injury model. M. S. Mulligan et al., *J. Clin. Invest.* 90: 1600 (1991).

We herein describe the identification and characterization of novel polypeptides having homology to lectin proteins, herein designated as PRO234 polypeptides.

22. PRO231

Some of the most important proteins involved in the above described regulation and modulation of cellular processes are the enzymes which regulate levels of protein phosphorylation in the cell. For example, it is known that the transduction of signals that regulate cell growth and differentiation is regulated at least in part by phosphorylation and dephosphorylation of various cellular proteins. The enzymes that catalyze these processes include the protein kinases, which function to phosphorylate various cellular proteins, and the protein phosphatases, which function to remove phosphate residues from various cellular proteins. The balance of the level of protein phosphorylation in the cell is thus mediated by the relative activities of these two types of enzymes.

Protein phosphatases represent a growing family of enzymes that are found in many diverse forms, including both membrane-bound and soluble forms. While many protein phosphatases have been described, the functions of only a very few are beginning to be understood (Tonks, *Semin. Cell Biol.* 4:373–453 (1993) and Dixon, *Recent Prog. Horm. Res.* 51:405–414 (1996)). However, in general, it appears that many of the protein phosphatases function to modulate the positive or negative signals induced by various protein kinases. Therefore, it is likely that protein phosphatases play critical roles in numerous and diverse cellular processes.

Given the physiological importance of the protein phosphatases, efforts are being undertaken by both industry and academia to identify new, native phosphatase proteins. Many of these efforts are focused on the screening of mammalian recombinant DNA libraries to identify the coding sequences for novel phosphatase proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to acid phosphatases, designated herein as PRO231 polypeptides.

23. PRO229

Scavenger receptors are known to protect IgG molecules from catabolic degradation. Riechmann and Hollinger, *Nature Biotechnology,* 15:617 (1997). In particular, studies of the CH2 and CH3 domains have shown that specific sequences of these domains are important in determining the half-lives of antibodies. Ellerson, et al., *J. Immunol.,* 116: 510 (1976); Yasmeen, et al., *J. Immunol.* 116: 518 (1976; Pollock, et al., *Eur. J. Immunol.,* 20: 2021 (1990). Scavenger receptor proteins and antibodies thereto are further reported in U.S. Pat. No. 5,510,466 to Krieger, et al. Due to the ability of scavenger receptors to increase the half-life of polypeptides and their involvement in immune function, molecules having homology to scavenger receptors are of importance to the scientific and medical community.

Efforts are being undertaken by both industry and academia to identify new, native secreted and membrane-bound receptor proteins, particularly those having homology to scavenger receptors. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to scavenger receptors, designated herein as PRO229 polypeptides.

24. PRO238

Oxygen free radicals and antioxidants appear to play an important role in the central nervous system after cerebral ischemia and reperfusion. Moreover, cardiac injury, related to ischaemia and reperfusion has been reported to be caused by the action of free radicals. Additionally, studies have reported that the redox state of the cell is a pivotal determinant of the fate of the cells. Furthermore, reactive oxygen species have been reported to be cytotoxic, causing inflammatory disease, including tissue necrosis, organ failure, atherosclerosis, infertility, birth defects, premature aging, mutations and malignancy. Thus, the control of oxidation and reduction is important for a number of reasons including for control and prevention of strokes, heart attacks, oxidative stress and hypertension. In this regard, reductases, and particularly, oxidoreductases, are of interest. Publications further describing this subject matter include Kelsey, et al., *Br. J. Cancer,* 76(7):852–4 (1997); Friedrich and Weiss, *J. Theor. Biol.,* 187(4):529–40 (1997) and Pieulle, et al., *J. Bacteriol.,* 179(18):5684–92 (1997).

Efforts are being undertaken by both industry and academia to identify new, native secreted and membrane-bound receptor proteins, particularly secreted proteins which have homology to reductase. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to reductase, designated herein as PRO238 polypeptides.

25. PRO233

Studies have reported that the redox state of the cell is an important determinant of the fate of the cell. Furthermore, reactive oxygen species have been reported to be cytotoxic, causing inflammatory disease, including tissue necrosis, organ failure, atherosclerosis, infertility, birth defects, premature aging, mutations and malignancy. Thus, the control of oxidation and reduction is important for a number of reasons, including the control and prevention of strokes, heart attacks, oxidative stress and hypertension. Oxygen free radicals and antioxidants appear to play an important role in the central nervous system after cerebral ischemia and reperfusion. Moreover, cardiac injury, related to ischaemia and reperfusion has been reported to be caused by the action of free radicals. In this regard, reductases, and particularly, oxidoreductases, are of interest. In addition, the transcription factors, NF-kappa B and AP-1, are known to be regulated by redox state and to affect the expression of a large variety of genes thought to be involved in the pathogenesis of AIDS, cancer, atherosclerosis and diabetic complications. Publications further describing this subject matter include Kelsey, et al., *Br. J. Cancer,* 76(7):852–4 (1997); Friedrich and Weiss, *J. Theor. Biol.,* 187(4):529–40 (1997) and Pieulle, et al., *J. Bacteriol.,* 179(18):5684–92 (1997). Given the physiological importance of redox reactions in vivo, efforts are currently being under taken to identify new, native proteins which are involved in redox reactions. We describe herein the identification of novel polypeptides which have homology to reductase, designated herein as PRO233 polypeptides.

26. PRO223

The carboxypeptidase family of exopeptidases constitutes a diverse group of enzymes that hydrolyze carboxyl-terminal amide bonds in polypeptides, wherein a large number of mammalian tissues produce these enzymes. Many of the carboxypeptidase enzymes that have been identified to date exhibit rather strong cleavage specificities for certain amino acids in polypeptides. For example, carboxypeptidase enzymes have been identified which prefer lysine, arginine, serine or amino acids with either aromatic or branched aliphatic side chains as substrates at the carboxyl terminus of the polypeptide.

With regard to the serine carboxypeptidases, such amino acid specific enzymes have been identified from a variety of different mammalian and non-mammalian organisms. The mammalian serine carboxypeptidase enzymes play important roles in many different biological processes including, for example, protein digestion, activation, inactivation, or modulation of peptide hormone activity, and alteration of the physical properties of proteins and enzymes.

In light of the physiological importance of the serine carboxypeptidases, efforts are being undertaken by both industry and academia to identify new, native secreted and membrane-bound receptor proteins and specifically novel carboxypeptidases. Many of these efforts are focused on the screening of mammalian recombinant DNA libraries to identify the coding sequences for novel secreted and membrane-bound receptor proteins. We describe herein novel polypeptides having homology to one or more serine carboxypeptidase polypeptides, designated herein as PRO223 polypeptides.

27. PRO235

Plexin was first identified in *Xenopus* tadpole nervous system as a membrane glycoprotein which was shown to mediate cell adhesion via a homophilic binding mechanism in the presence of calcium ions. Strong evolutionary conservation between *Xenopus*, mouse and human homologs of plexin has been observed. [Kaneyama et al., Biochem. And Biophys. Res. Comm. 226: 524–529 (1996)]. Given the physiological importance of cell adhesion mechanisms in vivo, efforts are currently being under taken to identify new, native proteins which are involved in cell adhesion. We describe herein the identification of a novel polypeptide which has homology to plexin, designated herein as PRO235.

28. PRO236 and PRO262

β-galactosidase is a well known enzymatic protein which functions to hydrolyze β-galactoside molecules. β-galactosidase has been employed for a variety of different applications, both in vitro and in vivo and has proven to be an extremely useful research tool. As such, there is an interest in obtaining novel polypeptides which exhibit homology to the β-galactosidase polypeptide.

Given the strong interest in obtaining novel polypeptides having homology to β-galactosidase, efforts are currently being undertaken by both industry and academia to identify new, native β-galactosidase homolog proteins. Many of these efforts are focused on the screening of mammalian recombinant DNA libraries to identify the coding sequences for novel β-galactosidase-like proteins. Examples of screening methods and techniques are described in the literature [see, for example, Klein et al., *Proc. Natl. Acad. Sci.,* 93:7108–7113 (1996); U.S. Pat. No. 5,536,637)]. We herein describe novel polypeptides having significant homology to the β-galactosidase enzyme, designated herein as PRO236 and PRO262 polypeptides.

29. PRO239

Densin is a glycoprotein which has been isolated from the brain which has all the hallmarks of an adhesion molecule. It is highly concentrated at synaptic sites in the brain and is expressed prominently in dendritic processes in developing neurons. Densin has been characterized as a member of the O-linked sialoglycoproteins. Densin has relevance to medically important processes such as regeneration. Given the physiological importance of synaptic processes and cell adhesion mechanisms in vivo, efforts are currently being under taken to identify new, native proteins which are involved in synaptic machinery and cell adhesion. We describe herein the identification of novel polypeptides which have homology to densin, designated herein as PRO239 polypeptides.

30. PRO257

Ebnerin is a cell surface protein associated with von Ebner glands in mammals. Efforts are being undertaken by both industry and academia to identify new, native cell surface receptor proteins and specifically those which possess sequence homology to cell surface proteins such as ebnerin. Many of these efforts are focused on the screening of mammalian recombinant DNA libraries to identify the coding sequences for novel receptor proteins. We herein describe the identification of novel polypeptides having significant homology to the von Ebner's gland-associated protein ebnerin, designated herein as PRO257 polypeptides.

31. PRO260

Fucosidases are enzymes that remove fucose residues from fucose containing proteoglycans. In some pathological conditions, such as cancer, rheumatoid arthritis, and diabetes, there is an abnormal fucosylation of serum proteins. Therefore, fucosidases, and proteins having homology to fucosidase, are of importance to the study and abrogation of these conditions. In particular, proteins having homology to the alpha-1-fucosidase precursor are of interest. Fucosidases and fucosidase inhibitors are further described in U.S. Pat. Nos. 5,637,490, 5,382,709, 5,240,707, 5,153,325, 5,100,797, 5,096,909 and 5,017,704. Studies are also reported in Valk, et al., *J. Virol.,* 71(9):6796 (1997), Aktogu, et al., *Monaldi. Arch. Chest Dis.* (Italy), 52(2): 118 (1997) and Focarelli, et al., *Biochem. Biophys. Res. Commun.* (U.S.), 234(1):54 (1997).

Efforts are being undertaken by both industry and academia to identify new, native secreted and membrane-bound receptor proteins. Of particular interest are proteins having homology to the alpha-1-fucosidase precursor. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to fucosidases, designated herein as PRO260 polypeptides.

32. PRO263

CD44 is a cell surface adhesion molecule involved in cell—cell and cell-matrix interactions. Hyaluronic acid, a component of the extracellular matrix is a major ligand. Other ligands include collagen, fibronectin, laminin, chrondroitin sulfate, mucosal addressin, serglycin and osteoponin. CD44 is also important in regulating cell traffic, lymph node homing, transmission of growth signals, and presentation of chemokines and growth factors to traveling cells. CD44 surface proteins are associated with metastatic tumors and CD44 has been used as a marker for HIV infection. Certain splice variants are associated with metastasis and poor prognosis of cancer patients. Therefore, molecules having homology with CD44 are of particular interest, as their homology indicates that they may have functions related to those functions of CD44. CD44 is further described in U.S. Pat. Nos. 5,506,119, 5,504,194 and 5,108,904; Gerberick, et al., *Toxicol. Appl. Pharmacol.,* 146(1):1 (1997); Wittig, et al., *Immunol. Letters* (Netherlands), 57(1–3):217 (1997); and Oliveira and Odell, *Oral Oncol.* (England), 33(4):260 (1997).

Efforts are being undertaken by both industry and academia to identify new, native secreted and membrane-bound receptor proteins, particularly transmembrane proteins with homology to CD44 antigen. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to CD44 antigen, designated herein as PRO263 polypeptides.

33. PRO270

Thioredoxins effect reduction-oxidation (redox) state. Many diseases are potentially related to redox state and reactive oxygen species may play a role in many important biological processes. The transcription factors, NF-kappa B and AP-1, are regulated by redox state and are known to affect the expression of a large variety of genes thought to be involved in the pathogenesis of AIDS, cancer, atherosclerosis and diabetic complications. Such proteins may also play a role in cellular antioxidant defense, and in pathological conditions involving oxidative stress such as stroke and inflammation in addition to having a role in apoptosis. Therefore, thioredoxins, and proteins having homology thereto, are of interest to the scientific and medical communities.

We herein describe the identification and characterization of novel polypeptides having homology to thioredoxin, designated herein as PRO270 polypeptides.

34. PRO271

The proteoglycan link protein is a protein which is intimately associated with various extracellular matrix proteins and more specifically with proteins such as collagen. For example, one primary component of collagen is a large proteoglycan called aggrecan. This molecule is retained by binding to the glycosaminoglycan hyaluronan through the amino terminal G1 globular domain of the core protein. This binding is stabilized by the proteoglycan link protein which is a protein that is also associated with other tissues containing hyaluronan binding proteoglycans such as versican.

Link protein has been identified as a potential target for autoimmune antibodies in individuals who suffer from juvenile rheumatoid arthritis (see Guerassimov et al., *J. Rheumatology* 24(5):959–964 (1997)). As such, there is strong interest in identifying novel proteins having homology to link protein. We herein describe the identification and characterization of novel polypeptides having such homology, designated herein as PRO271 polypeptides.

35. PRO272

Reticulocalbin is an endoplasmic reticular protein which may be involved in protein transport and luminal protein processing. Reticulocalbin resides in the lumen of the endopladsmic rerticulum, is known to bind calcium, and may be involved in a luminal retention mechanism of the endoplasmic reticulum. It contains six domains of the EF-hand motif associated with high affinity calcium binding. We describe herein the identification and characterization of a novel polypeptide which has homology to the reticulocalbin protein, designated herein as PRO272.

36. PRO294

Collagen, a naturally occurring protein, finds wide application in industry. Chemically hydrolyzed natural collagen can be denatured and renatured by heating and cooling to produce gelatin, which is used in photographic and medical, among other applications. Collagen has important properties such as the ability to form interchain aggregates having a conformation designated as a triple helix. We herein describe the identification and characterization of a novel polypeptide which has homology to portions of the collagen molecule, designated herein as PRO294.

37. PRO295

The integrins comprise a supergene family of cell-surface glycoprotein receptors that promote cellular adhesion. Each cell has numerous receptors that define its cell adhesive capabilities. Integrins are involved in a wide variety of interaction between cells and other cells or matrix components. The integrins are of particular importance in regulating movement and function of immune system cells. The platelet IIb/IIIA integrin complex is of particular importance in regulating platelet aggregation. A member of the integrin family, integrin β-6, is expressed on epithelial cells and modulates epithelial inflammation. Another integrin, leucocyte-associated antigen-1 (LFA-1) is important in the adhesion of lymphocytes during an immune response. The integrins are expressed as heterodimers of non-covalently associated alpha and beta subunits. Given the physiological importance of cell adhesion mechanisms in vivo, efforts are currently being under taken to identify new, native proteins which are involved in cell adhesion. We describe herein the identification and characterization of a novel polypeptide which has homology to integrin, designated herein as PRO295.

38. PRO293

Protein—protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415–421 (October 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol.* (Germany), 37(4):215–222 (1995), reporting mutations in the leucine rich motif in a complex associated with the bleeding disorder Bernard-Soulier syndrome and Chlemetson, K. J., *Thromb. Haemost.* (Germany), 74(1):111–116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell. Endocrinol.*, (Ireland), 125(1–2): 65–70 (December 1996) (gonadotropin receptor involvement); Miura, Y., et al., *Nippon Rinsho* (Japan), 54(7): 1784–1789 (July 1996) (apoptosis involvement); Harris, P. C., et al., *J. Am. Soc. Nephrol.,* 6(4):1125–1133 (October 1995) (kidney disease involvement); and Ruoslahti, E. I., et al., WO9110727-A by La Jolla Cancer Research Foundation (decorin binding to transforming growth factorβ involvement for treatment for cancer, wound healing and scarring).

Efforts are therefore being undertaken by both industry and academia to identify new proteins having leucine rich repeats to better understand protein—protein interactions. Of particular interest are those proteins having leucine rich repeats and homology to known neuronal leucine rich repeat proteins. Many efforts are focused on the screening of mammalian recombinant DNA libraries to identify the coding sequences for novel secreted and membrane-bound proteins having leucine rich repeats. Examples of screening methods and techniques are described in the literature [see, for example, Klein et al., *Proc. Natl. Acad. Sci.,* 93:7108–7113 (1996); U.S. Pat. No. 5,536,637)].

We describe herein the identification and characterization of a novel polypeptide which has homology to leucine rich repeat proteins, designated herein as PRO293.

39. PRO247

Protein-protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415–421 (Oct. 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol.* (Germany), 37(4):215–222 (1995), reporting mutations in the leucine rich motif in a complex associated with the bleeding disorder Bernard-Soulier syndrome and Chlemetson, K. J., *Thromb. Haemost.* (Germany), 74(1): 111–116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell Endocrinol.*, (Ireland), 125(1–2): 65–70 (December 1996) (gonadotropin receptor involvement); Miura, Y., et al., *Nippon Rinsho* (Japan), 54(7): 1784–1789 (July 1996) (apoptosis involvement); Harris, P. C., et al., *J. Am. Soc. Nephrol.,* 6(4):1125–1133 (October 1995) (kidney disease involvement); and Ruoslahti, E. I., et al., WO9110727-A by La Jolla Cancer Research Foundation (decorin binding to transforming growth factorβ involvement for treatment for cancer, wound healing and scarring).

Densin is a glycoprotein which has been isolated from the brain which has all the hallmarks of an adhesion molecule. It is highly concentrated at synaptic sites in the brain and is expressed prominently in dendritic processes in developing neurons. Densin has been characterized as a member of the O-linked sialoglycoproteins. Densin has relevance to medically important processes such as regeneration. Given the physiological importance of synaptic processes and cell adhesion mechanisms in vivo, efforts are currently being under taken to identify new, native proteins which are involved in synaptic machinery and cell adhesion. Densin is further described in Kennedy, M. B, *Trends Neurosci*. (England), 20(6):264 (1997) and Apperson, et al., *J. Neurosci.,* 16(21):6839 (1996).

Efforts are therefore being undertaken by both industry and academia to identify new proteins having leucine rich repeats to better understand protein—protein interactions. Of particular interest are those proteins having leucine rich repeats and homology to known proteins having leucine rich repeats such as KIAA0231 and densin. Many efforts are focused on the screening of mammalian recombinant DNA libraries to identify the coding-sequences for novel secreted and membrane-bound proteins having leucine rich repeats. Examples of screening methods and techniques are described in the literature [see, for example, Klein et al., *Proc. Natl. Acad. Sci.,* 93:7108–7113 (1996); U.S. Pat. No. 5,536,637)].

We describe herein the identification and characterization of a novel polypeptide which has homology to leucine rich repeat proteins, designated herein as PRO247.

40. PRO302, PRO303, PRO304, PRO307 and PRO343

Proteases are enzymatic proteins which are involved in a large number of very important biological processes in mammalian and non-mammalian organisms. Numerous different protease enzymes from a variety of different mammalian and non-mammalian organisms have been both identified and characterized. The mammalian protease enzymes play important roles in many different biological processes including, for example, protein digestion, activation, inactivation, or modulation of peptide hormone activity, and alteration of the physical properties of proteins and enzymes.

In light of the important physiological roles played by protease enzymes, efforts are currently being undertaken by both industry and academia to identify new, native protease homologs. Many of these efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)]. We herein describe the identification of novel polypeptides having homology to various protease enzymes, designated herein as PRO302, PRO303, PRO304, PRO307 and PRO343 polypeptides.

41. PRO328

The GLIP protein family has been characterized as comprising zinc-finger proteins which play important roles in embryogenesis. These proteins may function as transcriptional regulatory proteins and are known to be amplified in a subset of human tumors. Glioma pathogenesis protein is structurally related to a group of plant pathogenesis-related proteins. It is highly expressed in glioblastoma. See U.S. Pat. No. 5,582,981 (issued Dec. 10, 1996) and U.S. Pat. No. 5,322,801 (issued Jun. 21, 1996), Ellington, A. D. et al., *Nature,* 346:818 (1990), Grindley, J. C. et al., *Dev. Biol.,* 188(2):337 (1997), Marine, J. C. et al., *Mech. Dev.,* 63(2): 211 (1997), The CRISP or cysteine rich secretory protein family are a group of proteins which are also structurally related to a group of plant pathogenesis proteins. [Schwidetzky, U., *Biochem. J.,* 321:325 (1997), Pfisterer, P., *Mol. Cell. Biol.,* 16(11):6160 (1996), Kratzschmar, J., *Eur. J. Biochem.,* 236(3):827 (1996)]. We describe herein the identification of a novel polypeptide which has homology to GLIP and CRISP, designated herein as PRO328 polypeptides.

42. PRO335, PRO331 and PRO326

Protein-protein interactions include receptor and antigen complexes and signaling mechanisms. As more is known about the structural and functional mechanisms underlying protein—protein interactions, protein—protein interactions can be more easily manipulated to regulate the particular result of the protein—protein interaction. Thus, the underlying mechanisms of protein—protein interactions are of interest to the scientific and medical community.

All proteins containing leucine-rich repeats are thought to be involved in protein—protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415–421 (October 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.,* 32(2):141–174 (1997). Others studies implicating leucine rich proteins in wound healing and tissue repair are De La Salle, C., et al., *Vouv. Rev. Fr. Hematol.* (Germany), 37(4):215–222 (1995), reporting mutations in the leucine rich motif in a complex associated with the bleeding disorder Bernard-Soulier syndrome, Chlemetson, K. J., *Thromb. Haemost.* (Germany), 74(1):111–116 (July 1995), reporting that platelets have leucine rich repeats and Ruoslahti, E. I., et al., WO9110727-A by La Jolla Cancer Research Foundation reporting that decorin binding to transforming growth factorβ has involvement in a treatment for cancer, wound healing and scarring. Related by function to this group of proteins is the insulin like growth factor (IGF), in that it is useful in wound-healing and associated therapies concerned with re-growth of tissue, such as connective tissue, skin and bone; in promoting body growth in humans and animals; and in stimulating other growth-related processes. The acid labile subunit of IGF (ALS) is also of interest in that it increases the half-life of IGF and is part of the IGF complex in vivo.

Another protein which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Of particular interest is LIG-1, a membrane glycoprotein that is expressed specifically in glial cells in the mouse brain, and has leucine rich repeats and immunoglobulin-like domains. Suzuki, et al., J. Biol. Chem. (U.S.), 271(37): 22522 (1996). Other studies reporting on the biological functions of proteins having leucine rich repeats include: Tayar, N., et al., *Mol. Cell Endocrinol*., (Ireland), 125(1–2): 65–70 (December 1996) (gonadotropin receptor involvement); Miura, Y., et al., *Nippon Rinsho* (Japan), 54(7): 1784–1789 (July 1996) (apoptosis involvement); Harris, P. C., et al., *J. Am. Soc. Nephrol.,* 6(4):1125–1133 (October 1995) (kidney disease involvement).

Efforts are therefore being undertaken by both industry and academia to identify new proteins having leucine rich repeats to better understand protein—protein interactions. Of particular interest are those proteins having leucine rich repeats and homology to known proteins having leucine rich repeats such as LIG-1, ALS and decorin. Many efforts are focused on the screening of mammalian recombinant DNA libraries to identify the coding sequences for novel secreted and membrane-bound proteins having leucine rich repeats. Examples of screening methods and techniques are described in the literature [see, for example, Klein et al., *Proc. Natl. Acad. Sci.,* 93:7108–7113 (1996); U.S. Pat. No. 5,536,637)].

We describe herein the identification and characterization of novel polypeptides which have homology to proteins of the leucine rich repeat superfamily, designated herein as PRO335, PRO331 and PRO326 polypeptides.

43. PRO332

Secreted proteins comprising a repeat characterized by an arrangement of conserved leucine residues (leucine-rich repeat motif) have diverse biological roles. Certain proteoglycans, such as biglycan, fibromodulin and decorin, are, for example, characterized by the presence of a leucine-rich repeat of about 24 amino acids [Ruoslahti, *Ann. Rev. Cell. Biol.* 4 229–255 (1988); Oldberg et al., *EMBO J.* 8, 2601–2604 (1989)]. In general, proteoglycans are believed to play a role in regulating extracellular matrix, cartilage or bone function. The proteoglycan decorin binds to collagen type I and II and affects the rate of fibril formation. Fibromodulin also binds collagen and delays fibril formation. Both fibromodulin and decorin inhibit the activity of transforming growth factor beta (TGF-β) (U.S. Pat. No. 5,583, 103 issued Dec. 10, 1996). TGF-β is known to play a key role in the induction of extracellular matrix and has been implicated in the development of fibrotic diseases, such as cancer and glomerulonephritis. Accordingly, proteoglycans have been proposed for the treatment of fibrotic cancer, based upon their ability to inhibit TGF-β's growth stimulating activity on the cancer cell. Proteoglycans have also been described as potentially useful in the treatment of other proliferative pathologies, including rheumatoid arthritis, arteriosclerosis, adult respiratory distress syndrome, cirrhosis of the liver, fibrosis of the lungs, post-myocardial infarction, cardiac fibrosis, post-angioplasty restenosis, renal interstitial fibrosis and certain dermal fibrotic conditions, such as keloids and scarring, which might result from burn injuries, other invasive skin injuries, or cosmetic or reconstructive surgery (U.S. Pat. No. 5,654,270, issued Aug. 5, 1997).

We describe herein the identification and characterization of novel polypeptides which have homology to proteins of the leucine rich repeat superfamily, designated herein as PRO332 polypeptides.

44. PRO334

Microfibril bundles and proteins found in association with these bundles, particularly attachment molecules, are of interest in the field of dermatology, particularly in the study of skin which has been damaged from aging, injuries or the sun. Fibrillin nicrofibrils define the continuous elastic network of skin, and are present in dermis as microfibril bundles devoid of measurable elastin extending from the dermal-epithelial junction and as components of the thick elastic fibres present in the deep reticular dermis. Moreover, Marfan syndrome has been linked to mutations which interfere with multimerization of fibrillin monomers or other connective tissue elements.

Fibulin-1 is a modular glycoprotein with amino-terminal anaphlatoxin-like modules followed by nine epidermal growth factor (EGF)-like modules and, depending on alternative splicing, four possible carboxyl termini. Fibulin-2 is a novel extracellular matrix protein frequently found in close association with microfibrils containing either fibronectin or fibrillin. Thus, fibrillin, fibulin, and molecules related thereto are of interest, particularly for the use of preventing skin from being damaged from aging, injuries or the sun, or for restoring skin damaged from same. Moreover, these molecules are generally of interest in the study of connective tissue and attachment molecules and related mechanisms. Fibrillin, fibulin and related molecules are further described in Adams, et al., *J. Mol. Biol.,* 272(2):226–36 (1997); Kielty and Shuttleworth, *Microsc. Res. Tech.,* 38(4):413–27 (1997); and *Child, J. Card. Surg.* 12(2Supp.):131–5 (1997).

Currently, efforts are being undertaken by both industry and academia to identify new, native secreted and membrane-bound receptor proteins, particularly secreted proteins which have homology to fibulin and fibrillin. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)].

We herein describe the identification and characterization of novel polypeptides having homology to fibulin and fibrillin, designated herein as PRO334 polypeptides.

45. PRO346

The widespread occurrence of cancer has prompted the devotion of considerable resources and discovering new treatments of treatment. One particular method involves the creation of tumor or cancer specific monoclonal antibodies (mAbs) which are specific to tumor antigens. Such mAbs, which can distinguish between normal and cancerous cells are useful in the diagnosis, prognosis and treatment of the disease. Particular antigens are known to be associated with neoplastic diseases, such as colorectal and breast cancer. Since colon cancer is a widespread disease, early diagnosis and treatment is an important medical goal. Diagnosis and treatment of cancer can be implemented using monoclonal antibodies (mAbs) specific therefore having fluorescent, nuclear magnetic or radioactive tags. Radioactive genes, toxins and/or drug tagged mAbs can be used for treatment in situ with minimal patient description.

Carcinoembryonic antigen (CEA) is a glycoprotein found in human colon cancer and the digestive organs of a 2–6 month human embryos. CEA is a known human tumor marker and is widely used in the diagnosis of neoplastic diseases, such as colon cancer. For example, when the serum levels of CEA are elevated in a patient, a drop of CEA levels after surgery would indicate the tumor resection was successful. On the other hand, a subsequent rise in serum CEA levels after surgery would indicate that metastases of the original tumor may have formed or that new primary tumors may have appeared. CEA may also be a target for mAb, antisense nucleotides

46. PRO268

Protein disulfide isomerase is an enzymatic protein which is involved in the promotion of correct refolding of proteins through the establishment of correct disulfide bond formation. Protein disulfide isomerase was initially identified based upon its ability to catalyze the renaturation of reduced denatured RNAse (Goldberger et al., *J. Biol. Chem.* 239: 1406–1410 (1964) and Epstein et al., *Cold Spring Harbor Symp. Quant. Biol.* 28:439–449 (1963)). Protein disulfide isomerase has been shown to be a resident enzyme of the endoplasmic reticulum which is retained in the endoplasmic reticulum via a -KDEL or -HDEL amino acid sequence at its C-terminus.

Given the importance of disulfide bond-forming enzymes and their potential uses in a number of different applications, for example in increasing the yield of correct refolding of recombinantly produced proteins, efforts are currently being undertaken by both industry and academia to identify new, native proteins having homology to protein disulfide isomerase. Many of these efforts are focused on the screening of mammalian recombinant DNA libraries to identify the coding sequences for novel protein disulfide isomerase homologs. We herein describe a novel polypeptide having homology to protein disulfide isomerase, designated herein as PRO268.

47. PRO330

Prolyl 4-hydroxylase is an enzyme which functions to post-translationally hydroxylate proline residues at the Y position of the amino acid sequence Gly-X-Y, which is a repeating three amino acid sequence found in both collagen and procollagen. Hydroxylation of proline residues at the Y position of the Gly-X-Y amino acid triplet to form 4-hydroxyproline residues at those positions is required before newly synthesized collagen polypeptide chains may fold into their proper three-dimensional triple-helical conformation. If hydroxylation does not occur, synthesized collagen polypeptides remain non-helical, are poorly secreted by cells and cannot assemble into stable functional collagen fibrils. Vuorio et al., *Proc. Natl. Acad. Sci. USA* 89:7467–7470 (1992). Prolyl 4-hydroxylase is comprised of at least two different polypeptide subunits, alpha and beta.

Efforts are being undertaken by both industry and academia to identify new, native secreted and membrane-bound receptor proteins. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.,* 93:7108–7113 (1996); U.S. Pat. No. 5,536,637)]. Based upon these efforts, Applicants have herein identified and describe a novel polypeptide having homology to the alpha subunit of prolyl 4-hydroxylase, designated herein as PRO330.

48. PRO339 and PRO310

Fringe is a protein which specifically blocks serrate-mediated activation of notch in the dorsal compartment of the *Drosophila* wing imaginal disc. Fleming, et al., *Development,* 124(15):2973–81 (1997). Therefore, fringe is of interest for both its role in development as well as its ability to regulate serrate, particularly serrate's signaling abilities. Also of interest are novel polypeptides which may have a role in development and/or the regulation of serrate-like molecules. Of particular interest are novel polypeptides having homology to fringe as identified and described herein, designated herein as PRO339 and PRO310 polypeptides.

49. PRO244

Lectins are a class of proteins comprising a region that binds carbohydrates specifically and non-covalently. Numerous lectins have been identified in higher animals, both membrane-bound and soluble, and have been implicated in a variety of cell-recognition phenomena and tumor metastasis.

Most lectins can be classified as either C-type (calcium-dependent) or S-type (thiol-dependent).

Lectins are thought to play a role in regulating cellular events that are initiated at the level of the plasma membrane. For example, plasma membrane associated molecules are involved in the activation of various subsets of lymphoid cells, e.g. T-lymphocytes, and it is known that cell surface molecules are responsible for activation of these cells and consequently their response during an immune reaction.

A particular group of cell adhesion molecules, selecting, belong in the superfamily of C-type lectins. This group includes L-selectin (peripheral lymph node homing receptor (pnHR), LEC-CAM-1, LAM-1, $gp90^{MEL}$, $gp100^{MEL}$, $gp110^{MEL}$, MEL-14 antigen, Leu-8 antigen, TQ-1 antigen, DREG antigen), E-selectin (LEC-CAM-2, LECAM-2, ELAM-1), and P-selectin (LEC-CAM-3, LECAM-3, GMP-140, PADGEM). The structure of selectins consists of a C-type lectin (carbohydrate binding) domain, an epidermal growth factor-like (EGF-like) motif, and variable numbers of complement regulatory (CR) motifs. Selectins are associated with leukocyte adhesion, e.g. the attachment of neutrophils to venular endothelial cells adjacent to inflammation (E-selectin), or with the trafficking of lymphocytes from blood to secondary lymphoid organs, e.g. lymph nodes and Peyer's patches (L-selectin).

Another exemplary lectin is the cell-associated macrophage antigen, Mac-2 that is believed to be involved in cell adhesion and immune responses. Macrophages also express a lectin that recognizes Tn Ag, a human carcinoma-associated epitope.

Another C-type lectin is CD95 (Fas antigen/APO-1) that is an important mediator of immunologically relevant regulated or programmed cell death (apoptosis). "Apoptosis" is a non-necrotic cell death that takes place in metazoan animal cells following activation of an intrinsic cell suicide program. The cloning of Fas antigen is described in PCT publication WO 91/10448, and European patent application EP510691. The mature Fas molecule consists of 319 amino acids of which 157 are extracellular, 17 constitute the transmembrane domain, and 145 are intracellular. Increased levels of Fas expression at T cell surface have been associated with tumor cells and HIV-infected cells. Ligation of CD95 triggers apoptosis in the presence of interleukin-1 (IL-2).

C-type lectins also include receptors for oxidized low-density lipoprotein (LDL). This suggests a possible role in the pathogenesis of atherosclerosis.

We herein describe the identification and characterization of novel polypeptides having homology to C-type lectins, designated herein as PRO244 polypeptides.

SUMMARY OF THE INVENTION

1. PRO211 and PRO217

Applicants have identified cDNA clones that encode novel polypeptides having homology to EGF, designated in the present application as "PRO211" and "PRO217" polypeptides.

In one embodiment, the invention provides an isolated nucleic acid molecule comprising DNA encoding a PRO211 or PRO217 polypeptide. In one aspect, the isolated nucleic acid comprises DNA encoding EGF-like homologue PRO211 and PRO217 polypeptides of FIG. 2 (SEQ ID NO:2) and/or 4 (SEQ ID NO:4) indicated in FIG. 1 (SEQ ID NO:1) and/or FIG. 3 (SEQ ID NO:3), respectively, or is complementary to such encoding nucleic acid sequence, and remains stably bound to it under at least moderate, and optionally, under high stringency conditions.

In another embodiment, the invention provides isolated PRO211 and PRO217 EGF-like homologue PRO211 and PRO217 polypeptides. In particular, the invention provides isolated native sequence PRO211 and PRO217 EGF-like homologue polypeptides, which in one embodiment, includes an amino acid sequence comprising residues: 1 to 353 of FIG. 2 (SEQ ID NO:2) or (2) 1 to 379 of FIG. 4 (SEQ ID NO: 4).

2. PRO230

Applicants have identified a cDNA clone that encodes a novel polypeptide, wherein the polypeptide is designated in the present application as "PRO230".

In one embodiment, the invention provides an isolated nucleic acid molecule comprising DNA encoding a PRO230 polypeptide. In one aspect, the isolated nucleic acid comprises DNA encoding the PRO230 polypeptide having amino acid residues 1 through 467 of FIG. 6 (SEQ ID NO: 12), or is complementary to such encoding nucleic acid sequence, and remains stably bound to it under at least moderate, and optionally, under high stringency conditions.

In another embodiment, the invention provides isolated PRO230 polypeptide. In particular, the invention provides isolated native sequence PRO230 polypeptide, which in one embodiment, includes an amino acid sequence comprising residues 1 through 467 of FIG. 6 (SEQ ID NO: 12).

In another embodiment, the invention provides an expressed sequence tag (EST) comprising the nucleotide sequence of SEQ ID NO: 13 (FIG. 7) which is herein designated as DNA20088.

3. PRO232

Applicants have identified a cDNA clone that encodes a novel polypeptide, wherein the polypeptide is designated in the present application as "PRO232".

In one embodiment, the invention provides an isolated nucleic acid molecule comprising DNA encoding a PRO232 polypeptide. In one aspect, the isolated nucleic acid comprises DNA encoding the PRO232 polypeptide having amino acid residues 1 to 114 of FIG. 9 (SEQ ID NO:18), or is complementary to such encoding nucleic acid sequence, and remains stably bound to it under at least moderate, and optionally, under high stringency conditions.

In another embodiment, the invention provides isolated PRO232 polypeptide. In particular, the invention provides isolated native sequence PRO232 polypeptide, which in one embodiment, includes an amino acid sequence comprising residues 1 to 114 of FIG. 9 (SEQ ID NO: 18).

4. PRO187

Applicants have identified a cDNA clone that encodes a novel polypeptide, designated in the present application as "PRO187".

In one embodiment, the invention provides an isolated nucleic acid molecule comprising DNA encoding a PRO187 polypeptide. In one aspect, the isolated nucleic acid comprises DNA encoding the PRO187 polypeptide of FIG. 11 (SEQ ID NO:23), or is complementary to such encoding nucleic acid sequence, and remains stably bound to it under at least moderate, and optionally, under high stringency conditions. In another aspect, the invention provides a nucleic acid comprising the coding sequence of FIG. 10 (SEQ ID NO:22) or its complement. In another aspect, the invention provides a nucleic acid of the full length protein of clone DNA27864-1155, deposited with the ATCC under accession number ATCC 209375, alternatively the coding sequence of clone DNA27864-1155, deposited under accession number ATCC 209375.

In yet another embodiment, the invention provides isolated PRO187 polypeptide. In particular, the invention provides isolated native sequence PRO187 polypeptide, which in one embodiment, includes an amino acid sequence comprising residues 1 to 205 of FIG. 11 (SEQ ID NO:23). Alternatively, the invention provides a polypeptide encoded by the nucleic acid deposited under accession number ATCC 209375.

5. PRO265

Applicants have identified a cDNA clone that encodes a novel polypeptide, wherein the polypeptide is designated in the present application as "PRO265".

In one embodiment, the invention provides an isolated nucleic acid molecule comprising DNA encoding a PRO265 polypeptide. In one aspect, the isolated nucleic acid comprises DNA encoding the PRO265 polypeptide having amino acid residues 1 to 660 of FIG. 13 (SEQ ID NO:28), or is complementary to such encoding nucleic acid sequence, and remains stably bound to it under at least moderate, and optionally, under high stringency conditions.

In another embodiment, the invention provides isolated PRO265 polypeptide. In particular, the invention provides isolated native sequence PRO265 polypeptide, which in one embodiment, includes an amino acid sequence comprising residues 1 to 660 of FIG. 13 (SEQ ID NO:28). An additional embodiment of the present invention is directed to an isolated extracellular domain of a PRO265 polypeptide.

6. PRO219

Applicants have identified a cDNA clone that encodes a novel polypeptide, wherein the polypeptide is designated in the present application as "PRO219".

In one embodiment, the invention provides an isolated nucleic acid molecule comprising DNA encoding a PRO219 polypeptide. In one aspect, the isolated nucleic acid comprises DNA encoding the PRO219 polypeptide having amino acid residues 1 to 915 of FIG. 15 (SEQ ID NO:34), or is complementary to such encoding nucleic acid sequence, and remains stably bound to it under at least moderate, and optionally, under high stringency conditions.

In another embodiment, the invention provides isolated PRO219 polypeptide. In particular, the invention provides isolated native sequence PRO219 polypeptide, which in one embodiment, includes an amino acid sequence comprising residues 1 to 915 of FIG. 15 (SEQ ID NO:34).

7. PRO246

Applicants have identified a cDNA clone that encodes a novel polypeptide, wherein the polypeptide is designated in the present application as "PRO246".

In one embodiment, the invention provides an isolated nucleic acid molecule comprising DNA encoding a PRO246 polypeptide. In one aspect, the isolated nucleic acid comprises DNA encoding the PRO246 polypeptide having amino acid residues 1 to 390 of FIG. 17 (SEQ ID NO:39), or is complementary to such encoding nucleic acid sequence, and remains stably bound to it under at least moderate, and optionally, under high stringency conditions.

In another embodiment, the invention provides isolated PRO246 polypeptide. In particular, the invention provides isolated native sequence PRO246 polypeptide, which in one embodiment, includes an amino acid sequence comprising residues 1 to 390 of FIG. 17 (SEQ ID NO:39). An additional embodiment of the present invention is directed to an isolated extracellular domain of a PRO246 polypeptide.

8. PRO228

Applicants have identified a cDNA clone that encodes a novel polypeptide having homology to CD97, EMR1 and latrophilin, wherein the polypeptide is designated in the present application as "PRO228".

In one embodiment, the invention provides an isolated nucleic acid molecule comprising DNA encoding a PRO228 polypeptide. In one aspect, the isolated nucleic acid comprises DNA encoding the PRO228 polypeptide having amino acid residues 1 to 690 of FIG. 19 (SEQ ID NO:49), or is complementary to such encoding nucleic acid sequence, and remains stably bound to it under at least moderate, and optionally, under high stringency conditions.

In another embodiment, the invention provides isolated PRO228 polypeptide. In particular, the invention provides isolated native sequence PRO228 polypeptide, which in one embodiment, includes an amino acid sequence comprising residues 1 to 690 of FIG. 19 (SEQ ID NO:49). An additional embodiment of the present invention is directed to an isolated extracellular domain of a PRO228 polypeptide.

In another embodiment, the invention provides an expressed sequence tag (EST) comprising the nucleotide sequence of SEQ ID NO:50, designated herein as DNA21951.

9. PRO533

Applicants have identified a cDNA clone (DNA49435-1219) that encodes a novel polypeptide, designated in the present application as PRO533.

In one embodiment; the invention provides an isolated nucleic acid molecule having at least about 80% sequence identity to (a) a DNA molecule encoding a PRO533 polypeptide comprising the sequence of amino acids 23 to 216 of FIG. 22 (SEQ ID NO:59), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 23 to 216 of FIG. 22 (SEQ ID NO:59). Preferably, the highest degree of sequence identity occurs within the secreted portion (amino acids 23 to 216 of FIG. 22, SEQ ID NO:59). In a further embodiment, the isolated nucleic acid molecule comprises DNA encoding a PRO533 polypeptide having amino acid residues 1 to 216 of FIG. 22 (SEQ ID NO:59), or is complementary to such encoding nucleic acid sequence, and remains stably bound to it under at least moderate, and optionally, under high stringency conditions. In another aspect, the invention provides a nucleic acid of the full length protein of clone DNA49435-1219, deposited with the ATCC under accession number ATCC 209480.

In yet another embodiment, the invention provides isolated PRO533 polypeptide. In particular, the invention provides isolated native sequence PRO533 polypeptide, which in one embodiment, includes an amino acid sequence comprising residues 23 to 216 of FIG. 22 (SEQ ID NO:59). Native PRO533 polypeptides with or without the native signal sequence (amino acids 1 to 22 in FIG. 22 (SEQ ID NO:59)), and with or without the initiating methionine are specifically included. Alternatively, the invention provides a PRO533 polypeptide encoded by the nucleic acid deposited under accession number ATCC 209480.

10. PRO245

Applicants have identified a cDNA clone that encodes a novel polypeptide, wherein the polypeptide is designated in the present application as "PRO245".

In one embodiment, the invention provides an isolated nucleic acid molecule comprising DNA encoding a PRO245 polypeptide. In one aspect, the isolated nucleic acid comprises DNA encoding the PRO245 polypeptide having amino acid residues 1 to 312 of FIG. 24 (SEQ ID NO:64), or is complementary to such encoding nucleic acid sequence, and remains stably bound to it under at least moderate, and optionally, under high stringency conditions.

In another embodiment, the invention provides isolated PRO245 polypeptide. In particular, the invention provides isolated native sequence PRO245 polypeptide, which in one embodiment, includes an amino acid sequence comprising residues 1 to 312 of FIG. 24 (SEQ ID NO:64).

11. PRO220, PRO221 and PRO227

Applicants have identified cDNA clones that each encode novel polypeptides, all having leucine rich repeats. These polypeptides are designated in the present application as PRO220, PRO221 and PRO227.

In one embodiment, the invention provides isolated nucleic acid molecules comprising DNA respectively encoding PRO220, PRO221 and PRO227, respectively. In one aspect, provided herein is an isolated nucleic acid comprises DNA encoding the PRO220 polypeptide having amino acid residues 1 through 708 of FIG. 26 (SEQ ID NO:69), or is complementary to such encoding nucleic acid sequence, and remains stably bound to it under at least moderate, and optionally, under high stringency conditions. Also provided herein is an isolated nucleic acid comprises DNA encoding the PRO221 polypeptide having amino acid residues 1 through 259 of FIG. 28 (SEQ ID NO:71), or is complementary to such encoding nucleic acid sequence, and remains stably bound to it under at least moderate, and optionally, under high stringency conditions. Moreover, also provided herein is an isolated nucleic acid comprises DNA encoding the PRO227 polypeptide having amino acid residues 1 through 620 of FIG. 30 (SEQ ID NO:73), or is complementary to such encoding nucleic acid sequence, and remains stably bound to it under at least moderate, and optionally, under high stringency conditions.

In another embodiment, the invention provides isolated PRO220, PRO221 and PRO227 polypeptides. In particular, provided herein is the isolated native sequence for the PRO220 polypeptide, which in one embodiment, includes an amino acid sequence comprising residues 1 to 708 of FIG. 26 (SEQ ID NO:69). Additionally provided herein is the isolated native sequence for the PRO221 polypeptide, which in one embodiment, includes an amino acid sequence comprising residues 1 to 259 of FIG. 28 (SEQ ID) NO:71). Moreover, provided herein is the isolated native sequence for the PRO227 polypeptide, which in one embodiment, includes an amino acid sequence comprising residues 1 to 620 of FIG. 30 (SEQ ID NO:73).

12. PRO258

Applicants have identified a cDNA clone that encodes a novel polypeptide having homology to CRTAM and poliovirus receptor precursors, wherein the polypeptide is designated in the present application as "PRO258".

In one embodiment, the invention provides an isolated nucleic acid molecule comprising DNA encoding a PRO258 polypeptide. In one aspect, the isolated nucleic acid comprises DNA encoding the PRO258 polypeptide having amino acid residues 1 to 398 of FIG. 32 (SEQ ID NO:84), or is complementary to such encoding nucleic acid sequence, and remains stably bound to it under at least moderate, and optionally, under high stringency conditions.

In another embodiment, the invention provides isolated PRO258 polypeptide. In particular, the invention provides isolated native sequence PRO258 polypeptide, which in one embodiment, includes an amino acid sequence comprising residues 1 to 398 of FIG. 32 (SEQ ID NO:84). An additional embodiment of the present invention is directed to an isolated extracellular domain of a PRO258 polypeptide.

13. PRO266

Applicants have identified a cDNA clone that encodes a novel polypeptide, wherein the polypeptide is designated in the present application as "PRO266".

In one embodiment, the invention provides an isolated nucleic acid molecule comprising DNA encoding a PRO266 polypeptide. In one aspect, the isolated nucleic acid comprises DNA encoding the PRO266 polypeptide having amino acid residues 1 to 696 of FIG. 34 (SEQ ID NO:91), or is complementary to such encoding nucleic acid sequence, and remains stably bound to it under at least moderate, and optionally, under high stringency conditions.

In another embodiment, the invention provides isolated PRO266 polypeptide. In particular, the invention provides isolated native sequence PRO266 polypeptide, which in one embodiment, includes an amino acid sequence comprising residues 1 to 696 of FIG. 34 (SEQ ID NO:91).

14. PRO269

Applicants have identified a cDNA clone that encodes a novel polypeptide, wherein the polypeptide is designated in the present application as PRO269.

In one embodiment, the invention provides an isolated nucleic acid molecule comprising DNA encoding a PRO269 polypeptide. In one aspect, the isolated nucleic acid comprises DNA encoding the PRO269 polypeptide having amino acid residues 1 to 490 of FIG. 36 (SEQ ID NO:96), or is complementary to such encoding nucleic acid sequence, and remains stably bound to it under at least moderate, and optionally, under high stringency conditions.

In another embodiment, the invention provides isolated PRO269 polypeptide. In particular, the invention provides isolated native sequence PRO269 polypeptide, which in one embodiment, includes an amino acid sequence comprising residues 1 to 490 of FIG. 36 (SEQ ID NO:96). An additional embodiment of the present invention is directed to an isolated extracellular domain of a PRO269 polypeptide.

15. PRO287

Applicants have identified a cDNA clone that encodes a novel polypeptide, wherein the polypeptide is designated in the present application as "PRO287".

In one embodiment, the invention provides an isolated nucleic acid molecule comprising DNA encoding a PRO287 polypeptide. In one aspect, the isolated nucleic acid comprises DNA encoding the PRO287 polypeptide having amino acid residues 1 to 415 of FIG. 38 (SEQ ID NO:104), or is complementary to such encoding nucleic acid sequence, and remains stably bound to it under at least moderate, and optionally, under high stringency conditions.

In another embodiment, the invention provides isolated PRO287 polypeptide. In particular, the invention provides isolated native sequence PRO287 polypeptide, which in one embodiment, includes an amino acid sequence comprising residues 1 to 415 of FIG. 38 (SEQ ID NO:104).

16. PRO214

Applicants have identified a cDNA clone that encodes a novel polypeptide, designated in the present application as "PRO214".

In one embodiment, the invention provides an isolated nucleic acid molecule comprising DNA encoding a PRO214 polypeptide. In one aspect, the isolated nucleic acid comprises DNA encoding the PRO214 polypeptide of FIG. 40 (SEQ ID NO:109), or is complementary to such encoding nucleic acid sequence, and remains stably bound to it under at least moderate, and optionally, under high stringency conditions. In another aspect, the invention provides a nucleic acid comprising the coding sequence of FIG. 39 (SEQ ID NO:108) or its complement. In another aspect, the invention provides a nucleic acid of the full length protein of clone DNA32286-1191, deposited with ATCC under accession number ATCC 209385.

In yet another embodiment, the invention provides isolated PRO214 polypeptide. In particular, the invention provides isolated native sequence PRO214 polypeptide, which in one embodiment, includes an amino acid sequence comprising the residues of FIG. 40 (SEQ ID NO:109). Alternatively, the invention provides a polypeptide encoded by the nucleic acid deposited under accession number ATCC 209385.

17. PRO317

Applicants have identified a cDNA clone that encodes a novel polypeptide, designated in the present application as "PRO317".

In one embodiment, the invention provides an isolated nucleic acid molecule comprising DNA encoding PRO317 polypeptide. In one aspect, the isolated nucleic acid comprises DNA (SEQ ID NO:113) encoding PRO317 polypeptide having amino acid residues 1 to 366 of FIG. 42, or is complementary to such encoding nucleic acid sequence, and remains stably bound to it under at least moderate, and optionally, under high stringency conditions.

In another embodiment, the invention provides isolated PRO317 polypeptide. In particular, the invention provides isolated native-sequence PRO317 polypeptide, which in one embodiment, includes an amino acid sequence comprising residues 1 to 366 of FIG. 42 (SEQ ID NO:114).

In yet another embodiment, the invention supplies a method of detecting the presence of PRO317 in a sample, the method comprising:

a) contacting a detectable anti-PRO317 antibody with a sample suspected of containing PRO317; and b) detecting binding of the antibody to the sample; wherein the sample is selected from the group consisting of a body fluid, a tissue sample, a cell extract, and a cell culture medium.

In a still further embodiment a method is provided for determining the presence of PRO317 mRNA in a sample, the method comprising:

a) contacting a sample suspected of containing PRO317 mRNA with a detectable nucleic acid probe that hybridizes under moderate to stringent conditions to PRO317 mRNA; and b) detecting hybridization of the probe to the sample.

Preferably, in this method the sample is a tissue sample and the detecting step is by in situ hybridization, or the sample is a cell extract and detection is by Northern analysis.

Further, the invention provides a method for treating a PRO317-associated disorder comprising administering to a mammal an effective amount of the PRO317 polypeptide or a composition thereof containing a carrier, or with an effective amount of a PRO317 agonist or PRO317 antagonist, such as an antibody which binds specifically to PRO317.

18. PRO301

Applicants have identified a cDNA clone (DNA40628-1216) that encodes a novel polypeptide, designated in the present application as "PRO301".

In one embodiment, the invention provides an isolated nucleic acid molecule having at least about 80% sequence identity to (a) a DNA molecule encoding a PRO301 polypeptide comprising the sequence of amino acids 28 to 258 of FIG. 44 (SEQ ID NO:119), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 28 to 258 of FIG. 44 (SEQ ID NO:119). Preferably, the highest degree of sequence identity occurs within the extracellular domains (amino acids 28 to 258 of FIG. 44, SEQ ID NO:119). In a further embodiment, the isolated nucleic acid molecule comprises DNA encoding a PRO301 polypeptide having amino acid residues 28 to 299 of FIG. 44 (SEQ ID NO:119), or is complementary to such encoding nucleic acid sequence, and remains stably bound to it under at least moderate, and optionally, under high stringency conditions. In another aspect, the invention provides a nucleic acid of the full length protein of clone DNA40628-1216, deposited with the ATCC under accession number ATCC 209432, alternatively the coding sequence of clone DNA40628-1216, deposited under accession number ATCC 209432.

In yet another embodiment, the invention provides isolated PRO301 polypeptide. In particular, the invention provides isolated native sequence PRO301 polypeptide, which in one embodiment, includes an amino acid sequence comprising the extracellular domain residues 28 to 258 of FIG. 44 (SEQ ID NO:119). Native PRO301 polypeptides with or without the native signal sequence (amino acids 1 to 27 in FIG. 44 (SEQ ID NO:119), and with or without the initiating methionine are specifically included. Additionally, the sequences of the invention may also comprise the transmembrane domain (residues 236 to about 258 in FIG. 44; SEQ ID NO:119) and/or the intracellular domain (about residue 259 to 299 in FIG. 44; SEQ ID NO:119). Alternatively, the invention provides a PRO301 polypeptide encoded by the nucleic acid deposited under accession number ATCC 209432.

19. PRO224

Applicants have identified a cDNA clone that encodes a novel polypeptide, wherein the polypeptide is designated in the present application as "PRO224".

In one embodiment, the invention provides an isolated nucleic acid molecule comprising DNA encoding a PRO224 polypeptide. In one aspect, the isolated nucleic acid comprises DNA encoding the PRO224 polypeptide having amino acid residues 1 to 282 of FIG. 46 (SEQ ID NO:127), or is complementary to such encoding nucleic acid sequence, and remains stably bound to it under at least moderate, and optionally, under high stringency conditions.

In another embodiment, the invention provides isolated PRO224 polypeptide. In particular, the invention provides isolated native sequence PRO224 polypeptide, which in one embodiment, includes an amino acid sequence comprising residues 1 to 282 of FIG. 46 (SEQ ID NO:127).

20. PRO222

Applicants have identified a cDNA clone that encodes a novel polypeptide, wherein the polypeptide is designated in the present application as "PRO222".

In one embodiment, the invention provides an isolated nucleic acid molecule comprising DNA encoding a PRO222 polypeptide. In one aspect, the isolated nucleic acid comprises DNA encoding the PRO222 polypeptide having amino acid residues 1 to 490 of FIG. 48 (SEQ ID. NO: 132), or is complementary to such encoding nucleic acid sequence, and remains stably bound to it under at least moderate, and optionally, under high stringency conditions.

In another embodiment, the invention provides isolated PRO222 polypeptide. In particular, the invention provides isolated native sequence PRO222 polypeptide, which in one embodiment, includes an amino acid sequence comprising residues 1 to 490 of FIG. 48 (SEQ ID NO:132).

21. PRO234

Applicants have identified a cDNA clone that encodes a novel lectin polypeptide molecule, designated in the present application as "PRO234".

In one embodiment, the invention provides an isolated nucleic acid encoding a novel lectin comprising DNA encoding a PRO234 polypeptide. In one aspect, the isolated nucleic acid comprises the DNA encoding PRO234 polypeptides having amino acid residues 1 to 382 of FIG. 50 (SEQ ID NO:137), or is complementary to such encoding nucleic acid sequence, and remains stably bound to it under at least moderate, and optionally, under high stringency conditions. In another aspect, the invention provides an isolated nucleic acid molecule comprising the nucleotide sequence of FIG. 49 (SEQ ID NO:136).

In another embodiment, the invention provides isolated novel PRO234 polypeptides. In particular, the invention provides isolated native sequence PRO234 polypeptide, which in one embodiment, includes an amino acid sequence comprising residues 1 to 382 of FIG. 50 (SEQ ID NO:137).

In yet another embodiment, the invention provides oligonucleotide probes useful for isolating genomic and cDNA nucleotide sequences.

22. PRO231

Applicants have identified a cDNA clone that encodes a novel polypeptide having homology to a putative acid phosphatase, wherein the polypeptide is designated in the present application as "PRO231".

In one embodiment, the invention provides an isolated nucleic acid molecule comprising DNA encoding a PRO231 polypeptide. In one aspect, the isolated nucleic acid comprises DNA encoding the PRO231 polypeptide having amino acid residues 1 to 428 of FIG. 52 (SEQ ID NO:142), or is complementary to such encoding nucleic acid sequence, and remains stably bound to it under at least moderate, and optionally, under high stringency conditions.

In another embodiment, the invention provides isolated PRO231 polypeptide. In particular, the invention provides isolated native sequence PRO231 polypeptide, which in one embodiment, includes an amino acid sequence comprising residues 1 to 428 of FIG. 52 (SEQ ID NO:142).

23. PRO229

Applicants have identified a cDNA clone that encodes a novel polypeptide having homology to scavenger receptors wherein the polypeptide is designated in the present application as "PRO229".

In one embodiment, the invention provides an isolated nucleic acid molecule comprising DNA encoding a PRO229 polypeptide. In one aspect, the isolated nucleic acid comprises DNA encoding the PRO229 polypeptide having amino acid residues 1 to 347 of FIG. 54 (SEQ ID NO:148), or is complementary to such encoding nucleic acid sequence, and remains stably bound to it under at least moderate, and optionally, under high stringency conditions.

In another embodiment, the invention provides isolated PRO229 polypeptide. In particular, the invention provides isolated native sequence PRO229 polypeptide, which in one embodiment, includes an amino acid sequence comprising residues 1 to 347 of FIG. 54 (SEQ ID NO:148).

24. PRO238

Applicants have identified a cDNA clone that encodes a novel polypeptide having homology to reductase, wherein the polypeptide is designated in the present application as "PRO238".

In one embodiment, the invention provides an isolated nucleic acid molecule comprising DNA encoding a PRO238 polypeptide. In one aspect, the isolated nucleic acid comprises DNA encoding the PRO238 polypeptide having amino acid residues 1 to 310 of FIG. 56 (SEQ ID NO:153), or is complementary to such encoding nucleic acid sequence, and remains stably bound to it under at least moderate, and optionally, under high stringency conditions.

In another embodiment, the invention provides isolated PRO238 polypeptide. In particular, the invention provides isolated native sequence PRO238 polypeptide, which in one embodiment, includes an amino acid sequence comprising residues 1 to 310 of FIG. 56 (SEQ ID NO:153).

25. PRO233

Applicants have identified a cDNA clone that encodes a novel polypeptide, wherein the polypeptide is designated in the present application as "PRO233".

In one embodiment, the invention provides an isolated nucleic acid molecule comprising DNA encoding a PRO233 polypeptide. In one aspect, the isolated nucleic acid comprises DNA encoding the PRO233 polypeptide having amino acid residues 1 to 300 of FIG. 58 (SEQ ID NO:159), or is complementary to such encoding nucleic acid sequence, and remains stably bound to it under at least moderate, and optionally, under high stringency conditions.

In another embodiment, the invention provides isolated PRO233 polypeptide. In particular, the invention provides isolated native sequence PRO233 polypeptide, which in one embodiment, includes an amino acid sequence comprising residues 1 to 300 of FIG. 58 (SEQ ID NO:159).

26. PRO223

Applicants have identified a cDNA clone that encodes a novel polypeptide having homology to serine carboxypeptidase polypeptides, wherein the polypeptide is designated in the present application as "PRO223".

In one embodiment, the invention provides an isolated nucleic acid molecule comprising DNA encoding a PRO223 polypeptide. In one aspect, the isolated nucleic acid comprises DNA encoding the PRO223 polypeptide having amino acid residues 1 to 476 of FIG. 60 (SEQ ID NO:164), or is complementary to such encoding nucleic acid sequence, and remains stably bound to it under at least moderate, and optionally, under high stringency conditions.

In another embodiment, the invention provides isolated PRO223 polypeptide. In particular, the invention provides isolated native sequence PRO223 polypeptide, which in one embodiment, includes an amino acid sequence comprising residues 1 to 476 of FIG. 60 (SEQ ID NO:164).

27. PRO235

Applicants have identified a cDNA clone that encodes a novel polypeptide, wherein the polypeptide is designated in the present application as "PRO235".

In one embodiment, the invention provides an isolated nucleic acid molecule comprising DNA encoding a PRO235 polypeptide. In one aspect, the isolated nucleic acid comprises DNA encoding the PRO235 polypeptide having amino acid residues 1 to 552 of FIG. 62 (SEQ ID NO:170), or is complementary to such encoding nucleic acid sequence, and remains stably bound to it under at least moderate, and optionally, under high stringency conditions.

In another embodiment, the invention provides isolated PRO235 polypeptide. In particular, the invention provides isolated native sequence PRO235 polypeptide, which in one embodiment, includes an amino acid sequence comprising residues 1 to 552 of FIG. 62 (SEQ ID NO:170).

28. PRO236 and PRO262

Applicants have identified cDNA clones that encode novel polypeptides having homology to β-galactosidase, wherein those polypeptides are designated in the present application as "PRO236" and "PRO262".

In one embodiment, the invention provides an isolated nucleic acid molecule comprising DNA encoding a PRO236 polypeptide. In one aspect, the isolated nucleic acid comprises DNA encoding the PRO236 polypeptide having amino acid residues 1 to 636 of FIG. 64 (SEQ ID NO:175), or is complementary to such encoding nucleic acid sequence, and remains stably bound to it under at least moderate, and optionally, under high stringency conditions.

In another embodiment, the invention provides an isolated nucleic acid molecule comprising DNA encoding a PRO262 polypeptide. In one aspect, the isolated nucleic acid comprises DNA encoding the PRO262 polypeptide having amino acid residues 1 to 654 of FIG. 66 (SEQ ID NO:177), or is complementary to such encoding nucleic acid sequence, and remains stably bound to it under at least moderate, and optionally, under high stringency conditions.

In another embodiment, the invention provides isolated PRO236 polypeptide. In particular, the invention provides isolated native sequence PRO236 polypeptide, which in one embodiment, includes an amino acid sequence comprising residues 1 to 636 of FIG. 64 (SEQ ID NO:175).

In another embodiment, the invention provides isolated PRO262 polypeptide. In particular, the invention provides isolated native sequence PRO262 polypeptide, which in one embodiment, includes an amino acid sequence comprising residues 1 to 654 of FIG. 66 (SEQ ID NO:177).

29. PRO239

Applicants have identified a cDNA clone that encodes a novel polypeptide, wherein the polypeptide is designated in the present application as "PRO239".

In one embodiment, the invention provides an isolated nucleic acid molecule comprising DNA encoding a PRO239 polypeptide. In one aspect, the isolated nucleic acid comprises DNA encoding the PRO239 polypeptide having amino acid residues 1 to 501 of FIG. 68 (SEQ ID NO:185), or is complementary to such encoding nucleic acid sequence, and remains stably bound to it under at least moderate, and optionally, under high stringency conditions.

In another embodiment, the invention provides isolated PRO239 polypeptide. In particular, the invention provides isolated native sequence PRO239 polypeptide, which in one embodiment, includes an amino acid sequence comprising residues 1 to 501 of FIG. 68 (SEQ ID NO:185).

30. PRO257

Applicants have identified a cDNA clone that encodes a novel polypeptide, wherein the polypeptide is designated in the present application as "PRO257".

In one embodiment, the invention provides an isolated nucleic acid molecule comprising DNA encoding a PRO257 polypeptide. In one aspect, the isolated nucleic acid comprises DNA encoding the PRO257 polypeptide having amino acid residues 1 to 607 of FIG. 70 (SEQ ID NO:190), or is complementary to such encoding nucleic acid sequence, and remains stably bound to it under at least moderate, and optionally, under high stringency conditions.

In another embodiment, the invention provides isolated PRO257 polypeptide. In particular, the invention provides isolated native sequence PRO257 polypeptide, which in one embodiment, includes an amino acid sequence comprising residues 1 to 607 of FIG. 70 (SEQ ID NO:190). An additional embodiment of the present invention is directed to an isolated extracellular domain of a PRO257 polypeptide.

31. PRO260

Applicants have identified a cDNA clone that encodes a novel polypeptide, wherein the polypeptide is designated in the present application as "PRO260".

In one embodiment, the invention provides an isolated nucleic acid molecule comprising DNA encoding a PRO260 polypeptide. In one aspect, the isolated nucleic acid comprises DNA encoding the PRO260 polypeptide having amino acid residues 1 to 467 of FIG. 72 (SEQ ID NO:195), or is complementary to such encoding nucleic acid sequence, and remains stably bound to it under at least moderate, and optionally, under high stringency conditions.

In another embodiment, the invention provides isolated PRO260 polypeptide. In particular, the invention provides isolated native sequence PRO260 polypeptide, which in one embodiment, includes an amino acid sequence comprising residues 1 to 467 of FIG. 72 (SEQ ID NO:195).

32. PRO263

Applicants have identified a cDNA clone that encodes a novel polypeptide having homology to CD44 antigen, wherein the polypeptide is designated in the present application as "PRO263".

In one embodiment, the invention provides an isolated nucleic acid molecule comprising DNA encoding a PRO263 polypeptide. In one aspect, the isolated nucleic acid comprises DNA encoding the PRO263 polypeptide having amino acid residues 1 to 322 of FIG. 74 (SEQ ID NO:201), or is complementary to such encoding nucleic acid sequence, and remains stably bound to it under at least moderate, and optionally, under high stringency conditions.

In another embodiment, the invention provides isolated PRO263 polypeptide. In particular, the invention provides isolated native sequence PRO263 polypeptide, which in one embodiment, includes an amino acid sequence comprising residues 1 to 322 of FIG. 74 (SEQ ID NO:201). An additional embodiment of the present invention is directed to an isolated extracellular domain of a PRO263 polypeptide.

33. PRO270

Applicants have identified a cDNA clone that encodes a novel polypeptide, wherein the polypeptide is designated in the present application as "PRO270".

In one embodiment, the invention provides an isolated nucleic acid molecule comprising DNA encoding a PRO270 polypeptide. In one aspect, the isolated nucleic acid comprises DNA which includes the sequence encoding the PRO270 polypeptide having amino acid residues 1 to 296 of FIG. 76 (SEQ ID NO:207), or is complementary to such encoding nucleic acid sequence, and remains stably bound to it under at least moderate, and optionally, under high stringency conditions.

In another embodiment, the invention provides isolated PRO270 polypeptide. In particular, the invention provides isolated native sequence PRO270 polypeptide, which in one embodiment, includes an amino acid sequence comprising residues 1 to 296 of FIG. 76 (SEQ ID NO:207).

34. PRO271

Applicants have identified a cDNA clone that encodes a novel polypeptide having homology to the proteoglycan link protein, wherein the polypeptide is designated in the present application as "PRO271".

In one embodiment, the invention provides an isolated nucleic acid molecule comprising DNA encoding a PRO271 polypeptide. In one aspect, the isolated nucleic acid comprises DNA encoding the PRO271 polypeptide having amino acid residues 1 to 360 of FIG. 78 (SEQ ID NO:213), or is complementary to such encoding nucleic acid sequence, and remains stably bound to it under at least moderate, and optionally, under high stringency conditions.

In another embodiment, the invention provides isolated PRO271 polypeptide. In particular, the invention provides isolated native sequence PRO271 polypeptide, which in one embodiment, includes an amino acid sequence comprising residues 1 to 360 of FIG. 78 (SEQ ID NO:213).

35. PRO272

Applicants have identified a cDNA clone that encodes a novel polypeptide, wherein the polypeptide is designated in the present application as "PRO272".

In one embodiment, the invention provides an isolated nucleic acid molecule comprising DNA encoding a PRO272 polypeptide. In one aspect, the isolated nucleic acid comprises DNA encoding the PRO272 polypeptide having amino acid residues 1 to 328 of FIG. 80 (SEQ ID NO:221), or is complementary to such encoding nucleic acid sequence, and remains stably bound to it under at least moderate, and optionally, under high stringency conditions.

In another embodiment, the invention provides isolated PRO272 polypeptide. In particular, the invention provides isolated native sequence PRO272 polypeptide, which in one embodiment, includes an amino acid sequence comprising residues 1 to 328 of FIG. 80 (SEQ ID NO:211).

36. PRO294

Applicants have identified a cDNA clone that encodes a novel polypeptide, wherein the polypeptide is designated in the present application as "PRO294".

In one embodiment, the invention provides an isolated nucleic acid molecule comprising DNA encoding a PRO294 polypeptide. In one aspect, the isolated nucleic acid comprises DNA encoding the PRO294 polypeptide having amino acid residues 1 to 550 of FIG. 82 (SEQ ID NO:227), or is complementary to such encoding nucleic acid sequence, and remains stably bound to it under at least moderate, and optionally, under high stringency conditions.

In another embodiment, the invention provides isolated PRO294 polypeptide. In particular, the invention provides isolated native sequence PRO294 polypeptide, which in one embodiment, includes an amino acid sequence comprising residues 1 to 550 of FIG. 82 (SEQ ID NO:227).

37. PRO295

Applicants have identified a cDNA clone that encodes a novel polypeptide, wherein the polypeptide is designated in the present application as "PRO295".

In one embodiment, the invention provides an isolated nucleic acid molecule comprising DNA encoding a PRO295 polypeptide. In one aspect, the isolated nucleic acid comprises DNA encoding the PRO295 polypeptide having amino acid residues 1 to 350 of FIG. 84 (SEQ ID NO:236), or is complementary to such encoding nucleic acid sequence, and remains stably bound to it under at least moderate, and optionally, under high stringency conditions.

In another embodiment, the invention provides isolated PRO295 polypeptide. In particular, the invention provides isolated native sequence PRO295 polypeptide, which in one embodiment, includes an amino acid sequence comprising residues 1 to 350 of FIG. 84 (SEQ ID NO:236).

38. PRO293

Applicants have identified a cDNA clone that encodes a novel human neuronal leucine rich repeat polypeptide, wherein the polypeptide is designated in the present application as “PRO293”.

In one embodiment, the invention provides an isolated nucleic acid molecule comprising DNA encoding a PRO293 polypeptide. In one aspect, the isolated nucleic acid comprises DNA encoding the PRO293 polypeptide having amino acid residues 1 to 713 of FIG. 86 (SEQ ID NO:245), or is complementary to such encoding nucleic acid sequence, and remains stably bound to it under at least moderate, and optionally, under high stringency conditions.

In another embodiment, the invention provides isolated PRO293 polypeptide. In particular, the invention provides isolated native sequence PRO293 polypeptide, which in one embodiment, includes an amino acid sequence comprising residues 1 to 713 of FIG. 86 (SEQ ID NO:245). An additional embodiment of the present invention is directed to an isolated extracellular domain of a PRO293 polypeptide.

39. PRO247

Applicants have identified a cDNA clone that encodes a novel polypeptide having leucine rich repeats wherein the polypeptide is designated in the present application as “PRO247”.

In one embodiment, the invention provides an isolated nucleic acid molecule comprising DNA encoding a PRO247 polypeptide. In one aspect, the isolated nucleic acid comprises DNA encoding the PRO247 polypeptide having amino acid residues 1 to 546 of FIG. 88 (SEQ ID NO:250), or is complementary to such encoding nucleic acid sequence, and remains stably bound to it under at least moderate, and optionally, under high stringency conditions.

In another embodiment, the invention provides isolated PRO247 polypeptide. In particular, the invention provides isolated native sequence PRO247 polypeptide, which in one embodiment, includes an amino acid sequence comprising residues 1 to 546 of FIG. 88 (SEQ ID NO:250). An additional embodiment of the present invention is directed to an isolated extracellular domain of a PRO247 polypeptide.

40. PRO302, PRO303, PRO304, PRO307 and PRO343

Applicants have identified cDNA clones that encode novel polypeptides having homology to various proteases, wherein those polypeptide are designated in the present application as “PRO302”, “PRO303”, “PRO304”, “PRO307” and “PRO343” polypeptides.

In one embodiment, the invention provides an isolated nucleic acid molecule comprising DNA encoding a PRO302 polypeptide. In one aspect, the isolated nucleic acid comprises DNA encoding the PRO302 polypeptide having amino acid residues 1 to 452 of FIG. 90 (SEQ ID NO:255), or is complementary to such encoding nucleic acid sequence, and remains stably bound to it under at least moderate, and optionally, under high stringency conditions.

In another embodiment, the invention provides an isolated nucleic acid molecule comprising DNA encoding a PRO303 polypeptide. In one aspect, the isolated nucleic acid comprises DNA encoding the PRO303 polypeptide having amino acid residues 1 to 314 of FIG. 92 (SEQ ID NO:257), or is complementary to such encoding nucleic acid sequence, and remains stably bound to it under at least moderate, and optionally, under high stringency conditions.

In yet another embodiment, the invention provides an isolated nucleic acid molecule comprising DNA encoding a PRO304 polypeptide. In one aspect, the isolated nucleic acid comprises DNA encoding the PRO304 polypeptide having amino acid residues 1 to 556 of FIG. 94 (SEQ ID NO:259), or is complementary to such encoding nucleic acid sequence, and remains stably bound to it under at least moderate, and optionally, under high stringency conditions.

In another embodiment, the invention provides an isolated nucleic acid molecule comprising DNA encoding a PRO307 polypeptide. In one aspect, the isolated nucleic acid comprises DNA encoding the PRO307 polypeptide having amino acid residues 1 to 383 of FIG. 96 (SEQ ID NO:261), or is complementary to such encoding nucleic acid sequence, and remains stably bound to it under at least moderate, and optionally, under high stringency conditions.

In another embodiment, the invention provides an isolated nucleic acid molecule comprising DNA encoding a PRO343 polypeptide. In one aspect, the isolated nucleic acid comprises DNA encoding the PRO343 polypeptide having amino acid residues 1 to 317 of FIG. 98 (SEQ ID NO:263), or is complementary to such encoding nucleic acid sequence, and remains stably bound to it under at least moderate, and optionally, under high stringency conditions.

In another embodiment, the invention provides isolated PRO302 polypeptide. In particular, the invention provides isolated native sequence PRO302 polypeptide, which in one embodiment, includes an amino acid sequence comprising residues 1 to 452 of FIG. 90 (SEQ ID NO:255).

In another embodiment, the invention provides isolated PRO303 polypeptide. In particular, the invention provides isolated native sequence PRO303 polypeptide, which in one embodiment, includes an amino acid sequence comprising residues 1 to 314 of FIG. 92 (SEQ ID NO:257).

In another embodiment, the invention provides isolated PRO304 polypeptide. In particular, the invention provides isolated native sequence PRO304 polypeptide, which in one embodiment, includes an amino acid sequence comprising residues 1 to 556 of FIG. 94 (SEQ ID NO:259).

In another embodiment, the invention provides isolated PRO307 polypeptide. In particular, the invention provides isolated native sequence PRO307 polypeptide, which in one embodiment, includes an amino acid sequence comprising residues 1 to 383 of FIG. 96 (SEQ ID NO:261).

In another embodiment, the invention provides isolated PRO343 polypeptide. In particular, the invention provides isolated native sequence PRO343 polypeptide, which in one embodiment, includes an amino acid sequence comprising residues 1 to 317 of FIG. 98 (SEQ ID NO:263).

41. PRO328

Applicants have identified a cDNA clone that encodes a novel polypeptide, wherein the polypeptide is designated in the present application as “PRO328”.

In one embodiment, the invention provides an isolated nucleic acid molecule comprising DNA encoding a PRO328 polypeptide. In one aspect, the isolated nucleic acid comprises DNA encoding the PRO328 polypeptide having amino acid residues 1 to 463 of FIG. 100 (SEQ ID NO:285), or is complementary to such encoding nucleic acid sequence, and remains stably bound to it under at least moderate, and optionally, under high stringency conditions.

In another embodiment, the invention provides isolated PRO328 polypeptide. In particular, the invention provides isolated native sequence PRO328 polypeptide, which in one embodiment, includes an amino acid sequence comprising residues 1 to 463 of FIG. 100 (SEQ ID NO:285). An additional embodiment of the present invention is directed to an isolated extracellular domain of a PRO306 polypeptide.

42, PRO335, PRO331 and PRO326

Applicants have identified three cDNA clones that respectively encode three novel polypeptides, each having leucine rich repeats and homology to LIG-1 and ALS. These polypeptides are designated in the present application as PRO335, PRO331 and PRO326, respectively.

In one embodiment, the invention provides three isolated nucleic acid molecules comprising DNA respectively encoding PRO335, PRO331 and PRO326, respectively. In one aspect, herein is provided an isolated nucleic acid comprising DNA encoding the PRO335 polypeptide having amino acid residues 1 through 1059 of FIG. 102 (SEQ ID NO:290), or is complementary to such encoding nucleic acid sequence, and remains stably bound to it under at least moderate, and optionally, under high stringency conditions. Also provided herein is an isolated nucleic acid comprises DNA encoding the PRO331 polypeptide having amino acid residues 1 through 640 of FIG. 104 (SEQ ID NO:292), or is complementary to such encoding nucleic acid sequence, and remains stably bound to it under at least moderate, and optionally, under high stringency conditions. Additionally provided herein is an isolated nucleic acid comprises DNA encoding the PRO326 polypeptide having amino acid residues 1 through 1119 of FIG. 106 (SEQ ID NO:294), or is complementary to such encoding nucleic acid sequence, and remains stably bound to it under at least moderate, and optionally, under high stringency conditions.

In another embodiment, the invention provides isolated PRO335, PRO331 and PRO326 polypeptides or extracellular domains thereof. In particular, the invention provides isolated native sequence for the PRO335 polypeptide, which in one embodiment, includes an amino acid sequence comprising residues 1 through 1059 of FIG. 102 (SEQ ID NO:290). Also provided herein is the isolated native sequence for the PRO331 polypeptide, which in one embodiment, includes an amino acid sequence comprising residues 1 through 640 of FIG. 104 (SEQ ID NO:292). Also provided herein is the isolated native sequence for the PRO326 polypeptide, which in one embodiment, includes an amino acid sequence comprising residues 1 through 1119 of FIG. 106 (SEQ ID NO:294).

43. PRO332

Applicants have identified a cDNA clone (DNA40982-1235) that encodes a novel polypeptide, designated in the present application as "PRO332."

In one embodiment, the invention provides an isolated nucleic acid molecule comprising DNA having at least about 80% sequence identity to (a) a DNA molecule encoding a PRO358 polypeptide comprising the sequence of amino acids 49 to 642 of FIG. 108 (SEQ ID NO:310), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to 642 of FIG. 108 (SEQ ID NO:310). Preferably, the highest degree of sequence identity occurs within the leucine-rich repeat domains (amino acids 116 to 624 of FIG. 108, SEQ ID NO:310). In a further embodiment, the isolated nucleic acid molecule comprises DNA encoding a PRO332 polypeptide having amino acid residues 49 to 642 of FIG. 108 (SEQ ID NO:310), or is complementary to such encoding nucleic acid sequence, and remains stably bound to it under at least moderate, and optionally, under high stringency conditions.

In another embodiment, the invention provides isolated PRO332 polypeptides. In particular, the invention provides isolated native sequence PRO332 polypeptide, which in one embodiment, includes an amino acid sequence comprising residues 49 to 624 of FIG. 108 (SEQ ID NO:310). Native PRO332 polypeptides with or without the native signal sequence (amino acids 1 to 48 in FIG. 108, SEQ ID NO:310), and with or without the initiating methionine are specifically included.

44. PRO334

Applicants have identified a cDNA clone that encodes a novel polypeptide having homology to fibulin and fibrillin, wherein the polypeptide is designated in the present application as "PRO334".

In one embodiment, the invention provides an isolated nucleic acid molecule comprising DNA encoding a PRO334 polypeptide. In one aspect, the isolated nucleic acid comprises DNA encoding the PRO334 polypeptide having amino acid residues 1 to 509 of FIG. 110 (SEQ ID NO:315), or is complementary to such encoding nucleic acid sequence, and remains stably bound to it under at least moderate, and optionally, under high stringency conditions.

In another embodiment, the invention provides isolated PRO334 polypeptide. In particular, the invention provides isolated native sequence PRO334 polypeptide, which in one embodiment, includes an amino acid sequence comprising residues 1 to 509 of FIG. 110 (SEQ ID NO:315).

45. PRO346

Applicants have identified a cDNA clone (DNA44167-1243) that encodes a novel polypeptide, designated in the present application as "PRO346."

In one embodiment, the invention provides an isolated nucleic acid molecule having at least about 80% sequence identity to (a) a DNA molecule encoding a PRO346 polypeptide comprising the sequence of amino acids 19 to 339 of FIG. 112 (SEQ ID NO: 320), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 19 to 339 of FIG. 112 (SEQ ID NO:320). Preferably, the highest degree of sequence identity occurs within the extracellular domains (amino acids 19 to 339 of FIG. 112, SEQ ID NO:320). In alternative embodiments, the polypeptide by which the homology is measured comprises the residues 1–339, 19–360 or 19–450 of FIG. 112, SEQ ID NO:320). In a further embodiment, the isolated nucleic acid molecule comprises DNA encoding a PRO346 polypeptide having amino acid residues 19 to 339 of FIG. 112 (SEQ ID NO:320), alternatively residues 1–339, 19–360 or 19–450 of FIG. 112 (SEQ ID NO:320) or is complementary to such encoding nucleic acid sequence, and remains stably bound to it under at least moderate, and optionally, under high stringency conditions. In another aspect, the invention provides a nucleic acid of the full length protein of clone DNA44167-1243, deposited with the ATCC under accession number ATCC 209434, alternatively the coding sequence of clone DNA44167-1243, deposited under accession number ATCC 209434.

In yet another embodiment, the invention provides isolated PRO346 polypeptide. In particular, the invention provides isolated native sequence PRO346 polypeptide, which in one embodiment, includes an amino acid sequence comprising residues 19 to 339 of FIG. 112 (SEQ ID NO:320). Native PRO346 polypeptides with or without the native signal sequence (residues 1 to 18 in FIG. 112 (SEQ ID NO:320), with or without the initiating methionine, with or without the transmembrane domain (residues 340 to 360) and with or without the intracellular domain (residues 361 to 450) are specifically included. Alternatively, the invention provides a PRO346 polypeptide encoded by the nucleic acid deposited under accession number ATCC 209434.

46. PRO268

Applicants have identified a cDNA clone that encodes a novel polypeptide having homology to protein disulfide isomerase, wherein the polypeptide is designated in the present application as "PRO268".

In one embodiment, the invention provides an isolated nucleic acid molecule comprising DNA encoding a PRO268 polypeptide. In one aspect, the isolated nucleic acid comprises DNA encoding the PRO268 polypeptide having amino acid residues 1 to 280 of FIG. 114 (SEQ ID NO:325), or is complementary to such encoding nucleic acid sequence, and remains stably bound to it under at least moderate, and optionally, under high stringency conditions.

In another embodiment, the invention provides isolated PRO268 polypeptide. In particular, the invention provides isolated native sequence PRO268 polypeptide, which in one embodiment, includes an amino acid sequence comprising residues 1 to 280 of FIG. 114 (SEQ ID NO:325). An additional embodiment of the present invention is directed to an isolated extracellular domain of a PRO268 polypeptide.

47. PRO330

Applicants have identified a cDNA clone that encodes a novel polypeptide having homology to the alpha subunit of prolyl 4-hydroxylase, wherein the polypeptide is designated in the present application as "PRO330".

In one embodiment, the invention provides an isolated nucleic acid molecule comprising DNA encoding a PRO330 polypeptide. In one aspect, the isolated nucleic acid comprises DNA encoding the PRO330 polypeptide having amino acid residues 1 to 533 of FIG. 116 (SEQ ID NO:332), or is complementary to such encoding nucleic acid sequence, and remains stably bound to it under at least moderate, and optionally, under high stringency conditions.

In another embodiment, the invention provides isolated PRO330 polypeptide. In particular, the invention provides isolated native sequence PRO330 polypeptide, which in one embodiment, includes an amino acid sequence comprising residues 1 to 533 of FIG. 116 (SEQ ID NO:332).

48. PRO339 and PRO310

Applicants have identified two cDNA clones wherein each clone encodes a novel polypeptide having homology to fringe, wherein the polypeptides are designated in the present application as "PRO339" and "PRO310".

In one embodiment, the invention provides isolated nucleic acid molecules comprising DNA encoding a PRO339 and/or a PRO310 polypeptide. In one aspect, the isolated nucleic acid comprises DNA encoding the PRO339 polypeptide having amino acid residues 1 to 772 of FIG. 118 (SEQ ID NO:339), or is complementary to such encoding nucleic acid sequence, and remains stably bound to it under at least moderate, and optionally, under high stringency conditions. In another aspect, the isolated nucleic acid comprises DNA encoding the PRO310 polypeptide having amino acid residues 1 to 318 of FIG. 120 (SEQ ID NO:341), or is complementary to such encoding nucleic acid sequence, and remains stably bound to it under at least moderate, and optionally, under high stringency conditions.

In another embodiment, the invention provides isolated PRO339 as well as isolated PRO310 polypeptides. In particular, the invention provides isolated native sequence PRO339 polypeptide, which in one embodiment, includes an amino acid sequence comprising residues 1 to 772 of FIG. 118 (SEQ ID NO:339). The invention further provides isolated native sequence PRO310 polypeptide, which in one embodiment, includes an amino acid sequence comprising residues 1 to 318 of FIG. 120 (SEQ ID NO:341).

49. PRO244

Applicants have identified a cDNA clone that encodes a novel polypeptide, designated in the present application as "PRO244".

In one embodiment, the invention provides an isolated nucleic acid molecule comprising DNA encoding PRO244 polypeptide. In one aspect, the isolated nucleic acid comprises DNA encoding PRO244 polypeptide having amino acid residues 1 to 219 of FIG. 122 (SEQ ID NO:377), or is complementary to such encoding nucleic acid sequence, and remains stably bound to it under at least moderate, and optionally, under high stringency conditions.

In another embodiment, the invention provides isolated PRO244 polypeptide. In particular, the invention provides isolated native sequence PRO244 polypeptide, which in one embodiment, includes an amino acid sequence comprising residues 1 to 219 of FIG. 122 (SEQ ID NO:377).

50. Additional Embodiments

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO polypeptide having a full-length amino acid sequence as disclosed herein, an amino acid sequence lacking the signal peptide as disclosed herein or an extracellular domain of a transmembrane protein, with or without the signal peptide, as disclosed herein, or (b) the complement of the DNA molecule of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule comprising the coding sequence of a full-length PRO polypeptide cDNA as disclosed herein, the coding sequence of a PRO polypeptide lacking the signal peptide as disclosed herein or the coding sequence of an extracellular domain of a transmembrane PRO polypeptide, with or without the signal peptide, as disclosed herein, or (b) the complement of the DNA molecule of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes or for encoding fragments of a PRO polypeptide that may optionally encode a polypeptide comprising a binding site for an anti-PRO antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to a PRO polypeptide having a full-length amino acid sequence as disclosed herein, an amino acid sequence lacking the signal peptide as disclosed herein or an extracellular domain of a transmembrane protein, with or without the signal peptide, as disclosed herein.

In a further aspect, the invention concerns an isolated PRO polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of a PRO polypeptide having a full-length amino acid sequence as disclosed herein, an amino acid sequence lacking the signal peptide as disclosed herein or an extracellular domain of a transmembrane protein, with or without the signal peptide, as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:1) of a native sequence PRO211 cDNA, wherein SEQ ID NO:1 is a clone designated herein as "DNA32292-1131".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO217 cDNA, wherein SEQ ID NO:3 is a clone designated herein as "DNA33094-1131".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:11) of a native sequence PRO230 cDNA, wherein SEQ ID NO:11 is a clone designated herein as "DNA33223-1136".

FIG. 6 shows the amino acid sequence (SEQ ID NO:12) derived from the coding sequence of SEQ ID NO:11 shown in FIG. 5.

FIG. 7 shows a nucleotide sequence designated herein as DNA20088 (SEQ ID NO:13).

FIG. 8 shows a nucleotide sequence (SEQ ID NO:17) of a native sequence PRO232 cDNA, wherein SEQ ID NO:17 is a clone designated herein as "DNA34435-1140".

FIG. 9 shows the amino acid sequence (SEQ ID NO:18) derived from the coding sequence of SEQ ID NO:17 shown in FIG. 8.

FIG. 10 shows a nucleotide sequence (SEQ ID NO:22) of a native sequence PRO187 cDNA, wherein SEQ ID NO:22 is a clone designated herein as "DNA27864-1155".

FIG. 11 shows the amino acid sequence (SEQ ID NO:23) derived from the coding sequence of SEQ ID NO:22 shown in FIG. 10.

FIG. 12 shows a nucleotide sequence (SEQ ID NO:27) of a native sequence PRO265 cDNA, wherein SEQ ID NO:27 is a clone designated herein as "DNA36350-1158".

FIG. 13 shows the amino acid sequence (SEQ ID NO:28) derived from the coding sequence of SEQ ID NO:27 shown in FIG. 12.

FIG. 14 shows a nucleotide sequence (SEQ ID NO:33) of a native sequence PRO219 cDNA, wherein SEQ ID NO:33 is a clone designated herein as "DNA32290-1164".

FIG. 15 shows the amino acid sequence (SEQ ID NO:34) derived from the coding sequence of SEQ ID NO:33 shown in FIG. 14.

FIG. 16 shows a nucleotide sequence (SEQ ID NO:38) of a native sequence PRO246 cDNA, wherein SEQ ID NO:38 is a clone designated herein as "DNA35639-1172".

FIG. 17 shows the amino acid sequence (SEQ ID NO:39) derived from the coding sequence of SEQ ID NO:38 shown in FIG. 16.

FIG. 18 shows a nucleotide sequence (SEQ ID NO:48) of a native sequence PRO228 cDNA, wherein SEQ ID NO:48 is a clone designated herein as "DNA33092-1202".

FIG. 19 shows the amino acid sequence (SEQ ID NO:49) derived from the coding sequence of SEQ ID NO:48 shown in FIG. 18.

FIG. 20 shows a nucleotide sequence designated herein as DNA21951 (SEQ ID NO:50).

FIG. 21 shows a nucleotide sequence (SEQ ID NO:58) of a native sequence PRO533 cDNA, wherein SEQ ID NO:58 is a clone designated herein as "DNA49435-1219".

FIG. 22 shows the amino acid sequence (SEQ ID NO:59) derived from the coding sequence of SEQ ID NO:58 shown in FIG. 21.

FIG. 23 shows a nucleotide sequence (SEQ ID NO:63) of a native sequence PRO245 cDNA, wherein SEQ ID NO:63 is a clone designated herein as "DNA35638-1141".

FIG. 24 shows the amino acid sequence (SEQ ID NO:64) derived from the coding sequence of SEQ ID NO:63 shown in FIG. 23.

FIG. 25 shows a nucleotide sequence (SEQ ID NO:68) of a native sequence PRO220 cDNA, wherein SEQ ID NO:68 is a clone designated herein as "DNA32298-1132".

FIG. 26 shows the amino acid sequence (SEQ ID NO:69) derived from the coding sequence of SEQ ID NO:68 shown in FIG. 25.

FIG. 27 shows a nucleotide sequence (SEQ ID NO:70) of a native sequence PRO221 cDNA, wherein SEQ ID NO:70 is a clone designated herein as "DNA33089-1132".

FIG. 28 shows the amino acid sequence (SEQ ID NO:71) derived from the coding sequence of SEQ ID NO:70 shown in FIG. 27.

FIG. 29 shows a nucleotide sequence (SEQ ID NO:72) of a native sequence PRO227 cDNA, wherein SEQ ID NO:72 is a clone designated herein as "DNA33786-1132".

FIG. 30 shows the amino acid sequence (SEQ ID NO:73) derived from the coding sequence of SEQ ID NO:72 shown in FIG. 29.

FIG. 31 shows a nucleotide sequence (SEQ ID NO:83) of a native sequence PRO258 cDNA, wherein SEQ ID NO:83 is a clone designated herein as "DNA35918-1174".

FIG. 32 shows the amino acid sequence (SEQ ID NO:84) derived from the coding sequence of SEQ ID NO:83 shown in FIG. 31.

FIG. 33 shows a nucleotide sequence (SEQ ID NO:90) of a native sequence PRO266 cDNA, wherein SEQ ID NO:90 is a clone designated herein as "DNA37150-1178".

FIG. 34 shows the amino acid sequence (SEQ ID NO:91) derived from the coding sequence of SEQ ID NO:90 shown in FIG. 33.

FIG. 35 shows a nucleotide sequence (SEQ ID NO:95) of a native sequence PRO269 cDNA, wherein SEQ ID NO:95 is a clone designated herein as "DNA38260-1180".

FIG. 36 shows the amino acid sequence (SEQ ID NO:96) derived from the coding sequence of SEQ ID NO:95 shown in FIG. 35.

FIG. 37 shows a nucleotide sequence (SEQ ID NO:103) of a native sequence PRO287 cDNA, wherein SEQ ID NO:103 is a clone designated herein as "DNA39969-1185".

FIG. 38 shows the amino acid sequence (SEQ ID NO:104) derived from the coding sequence of SEQ ID NO:103 shown in FIG. 37.

FIG. 39 shows a nucleotide sequence (SEQ ID NO:108) of a native sequence PRO214 cDNA, wherein SEQ ID NO:108 is a clone designated herein as "DNA32286-1191".

FIG. 40 shows the amino acid sequence (SEQ ID NO:109) derived from the coding sequence of SEQ ID NO:108 shown in FIG. 39.

FIG. 41 shows a nucleotide sequence (SEQ ID NO:113) of a native sequence PRO317 cDNA, wherein SEQ ID NO:113 is a clone designated herein as "DNA33461-1199".

FIG. 42 shows the amino acid sequence (SEQ ID NO:114) derived from the coding sequence of SEQ ID NO:113 shown in FIG. 41.

FIG. 43 shows a nucleotide sequence (SEQ ID NO:118) of a native sequence PRO301 cDNA, wherein SEQ ID NO:118 is a clone designated herein as "DNA40628-1216".

FIG. 44 shows the amino acid sequence (SEQ ID NO:119) derived from the coding sequence of SEQ ID NO:118 shown in FIG. 43.

FIG. 45 shows a nucleotide sequence (SEQ ID NO:126) of a native sequence PRO224 cDNA, wherein SEQ ID NO:126 is a clone designated herein as "DNA33221-1133".

FIG. 46 shows the amino acid sequence (SEQ ID NO:127) derived from the coding sequence of SEQ ID NO:126 shown in FIG. 45.

FIG. 47 shows a nucleotide sequence (SEQ ID NO:131) of a native sequence PRO222 cDNA, wherein SEQ ID NO:131 is a clone designated herein as "DNA33107-1135".

FIG. 48 shows the amino acid sequence (SEQ ID NO:132) derived from the coding sequence of SEQ ID NO:131 shown in FIG. 47.

FIG. 49 shows a nucleotide sequence (SEQ ID NO:136) of a native sequence PRO234 cDNA, wherein SEQ ID NO:136 is a clone designated herein as "DNA35557-1137".

FIG. 50 shows the amino acid sequence (SEQ ID NO:137) derived from the coding sequence of SEQ ID NO:136 shown in FIG. 49.

FIG. 51 shows a nucleotide sequence (SEQ ID NO:141) of a native sequence PRO231 cDNA, wherein SEQ ID NO:141 is a clone designated herein as "DNA34434-1139".

FIG. 52 shows the amino acid sequence (SEQ ID NO:142) derived from the coding sequence of SEQ ID NO:141 shown in FIG. 51.

FIG. 53 shows a nucleotide sequence (SEQ ID NO:147) of a native sequence PRO229 cDNA, wherein SEQ ID NO:147 is a clone designated herein as "DNA33100-1159".

FIG. 54 shows the amino acid sequence (SEQ ID NO:148) derived from the coding sequence of SEQ ID NO:147 shown in FIG. 53.

FIG. 55 shows a nucleotide sequence (SEQ ID NO:152) of a native sequence PRO238 cDNA, wherein SEQ ID NO:152 is a clone designated herein as "DNA35600-1162".

FIG. 56 shows the amino acid sequence (SEQ ID NO:153) derived from the coding sequence of SEQ ID NO:152 shown in FIG. 55.

FIG. 57 shows a nucleotide sequence (SEQ ID NO:158) of a native sequence PRO233 cDNA, wherein SEQ ID NO:158 is a clone designated herein as "DNA34436-1238".

FIG. 58 shows the amino acid sequence (SEQ ID NO:159) derived from the coding sequence of SEQ ID NO:158 shown in FIG. 57.

FIG. 59 shows a nucleotide sequence (SEQ ID NO:163) of a native sequence PRO223 cDNA, wherein SEQ ID NO:163 is a clone designated herein as "DNA33206-1165".

FIG. 60 shows the amino acid sequence (SEQ ID NO:164) derived from the coding sequence of SEQ ID NO:163 shown in FIG. 59.

FIG. 61 shows a nucleotide sequence (SEQ ID. NO:169) of a native sequence PRO235 cDNA, wherein SEQ ID NO:169 is a clone designated herein as "DNA35558-1167".

FIG. 62 shows the amino acid sequence (SEQ ID NO:170) derived from the coding sequence of SEQ ID NO:169 shown in FIG. 61.

FIG. 63 shows a nucleotide sequence (SEQ ID NO:174) of a native sequence PRO236 cDNA, wherein SEQ ID NO:174 is a clone designated herein as "DNA35599-1168".

FIG. 64 shows the amino acid sequence (SEQ ID NO:175) derived from the coding sequence of SEQ ID NO:174 shown in FIG. 63.

FIG. 65 shows a nucleotide sequence (SEQ ID NO:176) of a native sequence PRO262 cDNA, wherein SEQ ID NO:176 is a clone designated herein as "DNA36992-1168".

FIG. 66 shows the amino acid sequence (SEQ ID NO:177) derived from the coding sequence of SEQ ID NO:176 shown in FIG. 65.

FIG. 67 shows a nucleotide sequence (SEQ ID NO:184) of a native sequence PRO239 cDNA, wherein SEQ ID NO:184 is a clone designated herein as "DNA34407-1169".

FIG. 68 shows the amino acid sequence (SEQ ID NO:185) derived from the coding sequence of SEQ ID NO:184 shown in FIG. 67.

FIG. 69 shows a nucleotide sequence (SEQ ID NO:189) of a native sequence PRO257 cDNA, wherein SEQ ID NO:189 is a clone designated herein as "DNA35841-1173".

FIG. 70 shows the amino acid sequence (SEQ ID NO:190) derived from the coding sequence of SEQ ID NO:189 shown in FIG. 69.

FIG. 71 shows a nucleotide sequence (SEQ ID NO:194) of a native sequence PRO260 cDNA, wherein SEQ ID NO:194 is a clone designated herein as "DNA33470-1175".

FIG. 72 shows the amino acid sequence (SEQ ID NO:195) derived from the coding sequence of SEQ ID NO:194 shown in FIG. 71.

FIG. 73 shows a nucleotide sequence (SEQ ID NO:200) of a native sequence PRO263 cDNA, wherein SEQ ID NO:200 is a clone designated herein as "DNA34431-1177".

FIG. 74 shows the amino acid sequence (SEQ ID NO:201) derived from the coding sequence of SEQ ID NO:200 shown in FIG. 73.

FIG. 75 shows a nucleotide sequence (SEQ ID NO:206) of a native sequence PRO270 cDNA, wherein SEQ ID NO:206 is a clone designated herein as "DNA39510-1181".

FIG. 76 shows the amino acid sequence (SEQ ID NO:207) derived from the coding sequence of SEQ ID NO:206 shown in FIG. 75.

FIG. 77 shows a nucleotide sequence (SEQ ID NO:212) of a native sequence PRO271 cDNA, wherein SEQ ID NO:212 is a clone designated herein as "DNA39423-1182".

FIG. 78 shows the amino acid sequence (SEQ ID NO:213) derived from the coding sequence of SEQ ID NO:212 shown in FIG. 77.

FIG. 79 shows a nucleotide sequence (SEQ ID NO:220) of a native sequence PRO272 cDNA, wherein SEQ ID NO:220 is a clone designated herein as "DNA40620-1183".

FIG. 80 shows the amino acid sequence (SEQ ID NO:221) derived from the coding sequence of SEQ ID NO:220 shown in FIG. 79.

FIG. 81 shows a nucleotide sequence (SEQ ID NO:226) of a native sequence PRO294 cDNA, wherein SEQ ID NO:226 is a clone designated herein as "DNA40604-1187".

FIG. 82 shows the amino acid sequence (SEQ ID NO:227) derived from the coding sequence of SEQ ID NO:226 shown in FIG. 81.

FIG. 83 shows a nucleotide sequence (SEQ ID NO:235) of a native sequence PRO295 cDNA, wherein SEQ ID NO:235 is a clone designated herein as "DNA38268-1188".

FIG. 84 shows the amino acid sequence (SEQ ID NO:236) derived from the coding sequence of SEQ ID NO:235 shown in FIG. 83.

FIG. 85 shows a nucleotide sequence (SEQ ID NO:244) of a native sequence PRO293 cDNA, wherein SEQ ID NO:244 is a clone designated herein as "DNA37151-1193".

FIG. 86 shows the amino acid sequence (SEQ ID NO:245) derived from the coding sequence of SEQ ID NO:244 shown in FIG. 85.

FIG. 87 shows a nucleotide sequence (SEQ ID NO:249) of a native sequence PRO247 cDNA, wherein SEQ ID NO:249 is a clone designated herein as "DNA35673-1201".

FIG. 88 shows the amino acid sequence (SEQ ID NO:250) derived from the coding sequence of SEQ ID NO:249 shown in FIG. 87.

FIG. 89 shows a nucleotide sequence (SEQ ID NO:254) of a native sequence PRO302 cDNA, wherein SEQ ID NO:254 is a clone designated herein as "DNA40370-1217".

FIG. 90 shows the amino acid sequence (SEQ ID NO:255) derived from the coding sequence of SEQ ID NO:254 shown in FIG. 89.

FIG. 91 shows a nucleotide sequence (SEQ ID NO:256) of a native sequence PRO303 cDNA, wherein SEQ ID NO:256 is a clone designated herein as "DNA42551-1217".

FIG. 92 shows the amino acid sequence (SEQ ID NO:257) derived from the coding sequence of SEQ ID NO:256 shown in FIG. 91.

FIG. 93 shows a nucleotide sequence (SEQ ID NO:258) of a native sequence PRO304 cDNA, wherein SEQ ID NO:258 is a clone designated herein as "DNA39520-1217".

FIG. 94 shows the amino acid sequence (SEQ ID NO:259) derived from the coding sequence of SEQ ID NO:258 shown in FIG. 93.

FIG. 95 shows a nucleotide sequence (SEQ ID NO:260) of a native sequence PRO307 cDNA, wherein SEQ ID NO:260 is a clone designated herein as "DNA41225-1217".

FIG. 96 shows the amino acid sequence (SEQ ID NO:261) derived from the coding sequence of SEQ ID NO:260 shown in FIG. 95.

FIG. 97 shows a nucleotide sequence (SEQ ID NO:262) of a native sequence PRO343 cDNA, wherein SEQ ID NO:262 is a clone designated herein as "DNA43318-1217".

FIG. 98 shows the amino acid sequence (SEQ ID NO:263) derived from the coding sequence of SEQ ID NO:262 shown in FIG. 97.

FIG. 99 shows a nucleotide sequence (SEQ ID NO:284) of a native sequence PRO328 cDNA, wherein SEQ ID NO:284 is a clone designated herein as "DNA40587-1231".

FIG. 100 shows the amino acid sequence (SEQ ID NO:285) derived from the coding sequence of SEQ ID NO:284 shown in FIG. 99.

FIG. 101 shows a nucleotide sequence (SEQ ID NO:289) of a native sequence PRO335 cDNA, wherein SEQ ID NO:289 is a clone designated herein as "DNA41388-1234".

FIG. 102 shows the amino acid sequence (SEQ ID NO:290) derived from the coding sequence of SEQ ID NO:289 shown in FIG. 101.

FIG. 103 shows a nucleotide sequence (SEQ ID NO:291) of a native sequence PRO331 cDNA, wherein SEQ ID NO:291 is a clone designated herein as "DNA40981-1234".

FIG. 104 shows the amino acid sequence (SEQ ID NO:292) derived from the coding sequence of SEQ ID NO:291 shown in FIG. 103.

FIG. 105 shows a nucleotide sequence (SEQ ID NO:293) of a native sequence PRO326 cDNA, wherein SEQ ID NO:293 is a clone designated herein as "DNA37140-1234".

FIG. 106 shows the amino acid sequence (SEQ ID NO:294) derived from the coding sequence of SEQ ID NO:293 shown in FIG. 105.

FIG. 107 shows a nucleotide sequence (SEQ ID NO:309) of a native sequence PRO332 cDNA, wherein SEQ ID NO:309 is a clone designated herein as "DNA40982-1235".

FIG. 108 shows the amino acid sequence (SEQ ID NO:310) derived from the coding sequence of SEQ ID NO:309 shown in FIG. 107.

FIG. 109 shows a nucleotide sequence (SEQ ID NO:314) of a native sequence PRO334 cDNA, wherein SEQ ID NO:314 is a clone designated herein as "DNA41379-1236".

FIG. 110 shows the amino acid sequence (SEQ ID NO:315) derived from the coding sequence of SEQ ID NO:314 shown in FIG. 109.

FIG. 111 shows a nucleotide sequence (SEQ ID NO:319) of a native sequence PRO346 cDNA, wherein SEQ ID NO:319 is a clone designated herein as "DNA44167-1243'.

FIG. 112 shows the amino acid sequence (SEQ ID NO:320) derived from the coding sequence of SEQ ID NO:319 shown in FIG. 111.

FIG. 113 shows a nucleotide sequence (SEQ ID NO:324) of a native sequence PRO268 cDNA, wherein SEQ ID NO:324 is a clone designated herein as "DNA39427-1179".

FIG. 114 shows the amino acid sequence (SEQ ID NO:325) derived from the coding sequence of SEQ ID NO:324 shown in FIG. 113.

FIG. 115 shows a nucleotide sequence (SEQ ID NO:331) of a native sequence PRO330 cDNA, wherein SEQ ID NO:331 is a clone designated herein as "DNA40603-1232".

FIG. 116 shows the amino acid sequence (SEQ ID NO:332) derived from the coding sequence of SEQ ID NO:331 shown in FIG. 115.

FIG. 117 shows a nucleotide sequence (SEQ ID NO:338) of a native sequence PRO339 cDNA, wherein SEQ ID NO:338 is a clone designated herein as "DNA43466-1225".

FIG. 118 shows the amino acid sequence (SEQ ID NO:339) derived from the coding sequence of SEQ ID NO:338 shown in FIG. 117.

FIG. 119 shows a nucleotide sequence (SEQ ID NO:340) of a native sequence PRO310 cDNA, wherein SEQ ID NO:340 is a clone designated herein as "DNA43046-1225".

FIG. 120 shows the amino acid sequence (SEQ ID NO:341) derived from the coding sequence of SEQ ID NO:340 shown in FIG. 119.

FIG. 121 shows a nucleotide sequence (SEQ ID NO:376) of a native sequence PRO244 cDNA, wherein SEQ ID NO:376 is a clone designated herein as "DNA35668-1171".

FIG. 122 shows the amino acid sequence (SEQ ID NO:377) derived from the coding sequence of SEQ ID NO:376 shown in FIG. 121.

FIG. 123 shows a nucleotide sequence (SEQ ID NO:422) of a native sequence PRO1868 cDNA, wherein SEQ ID NO:422 is a clone designated herein as "DNA77624-2515".

FIG. 124 shows the amino acid sequence (SEQ ID NO:423) derived from the coding sequence of SEQ ID NO:422 shown in FIG. 123.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul, et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=" BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least, about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by, Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters, are set by the ALIGN-2 program and do not vary.

In situations where ALIGN-2 is employed for nucleic acid sequence comparisons, the % nucleic acid sequence identity of a given nucleic, acid sequence C to, with, or against a given nucleic acid sequence D (which can alternatively be phrased as, a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence-against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., *Protein Eng.* 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

"PRO317-associated disorder" refers to a pathological condition or disease wherein PRO317 is over- or underexpressed. Such disorders include diseases of the female genital tract or of the endometrium of a mammal, including hyperplasia, endometritis, endometriosis, wherein the patient is at risk for infertility due to endometrial factor, endometrioma, and endometrial cancer, especially those diseases involving abnormal bleeding such as a gynecological disease. They also include diseases involving angiogenesis, wherein the angiogenesis results in a pathological condition, such as cancer involving solid tumors (the therapy for the disorder would result in decreased vascularization and a decline in growth and metastasis of a variety of tumors). Alternatively, the angiogenesis may be beneficial, such as for ischemia, especially coronary ischemia. Hence, these disorders include those found in patients whose hearts are functioning but who have a blocked blood supply due to atherosclerotic coronary artery disease, and those with a functioning but underperfused heart, including patients with coronary arterial disease who are not optimal candidates for angioplasty and coronary artery by-pass surgery. The disorders also include diseases involving the kidney or originating from the kidney tissue, such as polycystic kidney disease and chronic and acute renal failure.

Table 1

```
/*
 *
 * C-C increased from 12 to 15
 * Z is average of EQ
 * B is average of ND
 * match with stop is _M; stop-stop = 0; J (joker) match = 0
 */
#define  _M     -8      /* value of a match with a stop */

int      _day[26][26] = {
/*     A B C D E F G H I J K L M N O P Q R S T U V W X Y Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M, 0,_M,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
 */
#include <stdio.h>
#include <ctype.h>

#define MAXJMP     16     /* max jumps in a diag */
#define MAXGAP     24     /* don't continue to penalize gaps larger than this */
#define JMPS       1024   /* max jmps in an path */
#define MX         4      /* save if there's at least MX-1 bases since last jmp */

#define DMAT       3      /* value of matching bases */
#define DMIS       0      /* penalty for mismatched bases */
#define DINS0      8      /* penalty for a gap */
#define DINS1      1      /* penalty per base */
#define PINS0      8      /* penalty for a gap */
#define PINS1      4      /* penalty per residue */

struct jmp {
        short           n[MAXJMP];      /* size of jmp (neg for dely) */
        unsigned short  x[MAXJMP];      /* base no. of jmp in seq x */
};                                      /* limits seq to 2^16 -1 */

struct diag {
        int             score;          /* score at last jmp */
        long            offset;         /* offset of prev block */
        short           ijmp;           /* current jmp index */
        struct jmp      jp;             /* list of jmps */
};

struct path {
        int     spc;            /* number of leading spaces */
        short   n[JMPS];        /* size of jmp (gap) */
        int     x[JMPS];        /* loc of jmp (last elem before gap) */
};

char            *ofile;                 /* output file name */
char            *namex[2];              /* seq names: getseqs() */
char            *prog;                  /* prog name for err msgs */
char            *seqx[2];                       /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */

char            *calloc(), *malloc(), *index(), *strcpy();
char            *getseq(), *g_calloc();
```

Table 1 (cont')

main

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

        endgaps = 0;                    /* 1 to penalize endgaps */
        ofile = "align.out";            /* output file */

        nw();           /* fill in the matrix, get the possible jmps */
        readjmps();     /* get the actual jmps */
        print();        /* print stats, alignment */

        cleanup(0);     /* unlink any tmp files */
}
```

Table 1 (cont')

nw

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
	char		*px, *py;		/* seqs and ptrs */
	int		*ndely, *dely;	/* keep track of dely */
	int		ndelx, delx;	/* keep track of delx */
	int		*tmp;		/* for swapping row0, row1 */
	int		mis;		/* score for each type */
	int		ins0, ins1;	/* insertion penalties */
	register	id;		/* diagonal index */
	register	ij;		/* jmp index */
	register	*col0, *col1;	/* score for curr, last row */
	register	xx, yy;		/* index into seqs */

	dx = (struct diag *)g_calloc("to get diags", len0+len1+1, sizeof(struct diag));

	ndely = (int *)g_calloc("to get ndely", len1+1, sizeof(int));
	dely = (int *)g_calloc("to get dely", len1+1, sizeof(int));
	col0 = (int *)g_calloc("to get col0", len1+1, sizeof(int));
	col1 = (int *)g_calloc("to get col1", len1+1, sizeof(int));
	ins0 = (dna)? DINS0 : PINS0;
	ins1 = (dna)? DINS1 : PINS1;

	smax = -10000;
	if (endgaps) {
		for (col0[0] = dely[0] = -ins0, yy = 1; yy <= len1; yy++) {
			col0[yy] = dely[yy] = col0[yy-1] - ins1;
			ndely[yy] = yy;
		}
		col0[0] = 0;	/* Waterman Bull Math Biol 84 */
	}
	else
		for (yy = 1; yy <= len1; yy++)
			dely[yy] = -ins0;

	/* fill in match matrix
	 */
	for (px = seqx[0], xx = 1; xx <= len0; px++, xx++) {
		/* initialize first entry in col
		 */
		if (endgaps) {
			if (xx == 1)
				col1[0] = delx = -(ins0+ins1);
			else
				col1[0] = delx = col0[0] - ins1;
			ndelx = xx;
		}
		else {
			col1[0] = 0;
			delx = -ins0;
			ndelx = 0;
		}
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

        /* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

        /* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

        /* pick the maximum score; we're favoring
         * mis over any del and delx over dely
         */
```

Table 1 (cont')

...nw

```
id = xx - yy + len1 - 1;
if (mis >= delx && mis >= dely[yy])
        col1[yy] = mis;
else if (delx >= dely[yy]) {
        col1[yy] = delx;
        ij = dx[id].ijmp;
        if (dx[id].jp.n[0] && (!dna || (ndelx >= MAXJMP
        && xx > dx[id].jp.x[ij]+MX) || mis > dx[id].score+DINS0)) {
                dx[id].ijmp++;
                if (++ij >= MAXJMP) {
                        writejmps(id);
                        ij = dx[id].ijmp = 0;
                        dx[id].offset = offset;
                        offset += sizeof(struct jmp) + sizeof(offset);
                }
        }
        dx[id].jp.n[ij] = ndelx;
        dx[id].jp.x[ij] = xx;
        dx[id].score = delx;
}
else {
        col1[yy] = dely[yy];
        ij = dx[id].ijmp;
if (dx[id].jp.n[0] && (!dna || (ndely[yy] >= MAXJMP
        && xx > dx[id].jp.x[ij]+MX) || mis > dx[id].score+DINS0)) {
                dx[id].ijmp++;
                if (++ij >= MAXJMP) {
                        writejmps(id);
                        ij = dx[id].ijmp = 0;
                        dx[id].offset = offset;
                        offset += sizeof(struct jmp) + sizeof(offset);
                }
        }
        dx[id].jp.n[ij] = -ndely[yy];
        dx[id].jp.x[ij] = xx;
        dx[id].score = dely[yy];
}
if (xx == len0 && yy < len1) {
        /* last col
         */
        if (endgaps)
                col1[yy] -= ins0+ins1*(len1-yy);
        if (col1[yy] > smax) {
                smax = col1[yy];
                dmax = id;
        }
}
}
if (endgaps && xx < len0)
        col1[yy-1] -= ins0+ins1*(len0-xx);
if (col1[yy-1] > smax) {
        smax = col1[yy-1];
        dmax = id;
}
tmp = col0; col0 = col1; col1 = tmp;
}
(void) free((char *)ndely);
(void) free((char *)dely);
(void) free((char *)col0);
(void) free((char *)col1);
```

Table 1 (cont')

print

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */

#include "nw.h"

#define SPC        3
#define P_LINE     256        /* maximum output line */
#define P_SPC      3          /* space between name or num and seq */

extern   _day[26][26];
int      olen;                /* set output line length */
FILE     *fx;                 /* output file */

print()
{
        int       lx, ly, firstgap, lastgap;      /* overlap */

        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {        /* leading gap in x */
                pp[0].spc = firstgap = len1 - dmax - 1;
                ly -= pp[0].spc;
        }
        else if (dmax > len1 - 1) {   /* leading gap in y */
                pp[1].spc = firstgap = dmax - (len1 - 1);
                lx -= pp[1].spc;
        }
        if (dmax0 < len0 - 1) {       /* trailing gap in x */
                lastgap = len0 - dmax0 -1;
                lx -= lastgap;
        }
        else if (dmax0 > len0 - 1) { /* trailing gap in y */
                lastgap = dmax0 - (len0 - 1);
                ly -= lastgap;
        }
        getmat(lx, ly, firstgap, lastgap);
        pr_align();
}
```

Table 1 (cont')

getmat

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Table 1 (cont')

...getmat

```
	fprintf(fx, "<gaps in first sequence: %d", gapx);
	if (gapx) {
		(void) sprintf(outx, " (%d %s%s)",
			ngapx, (dna)? "base":"residue", (ngapx == 1)? "":"s");
		fprintf(fx,"%s", outx);

	fprintf(fx, ", gaps in second sequence: %d", gapy);
	if (gapy) {
		(void) sprintf(outx, " (%d %s%s)",
			ngapy, (dna)? "base":"residue", (ngapy == 1)? "":"s");
		fprintf(fx,"%s", outx);
	}
	if (dna)
		fprintf(fx,
		"\n<score: %d (match = %d, mismatch = %d, gap penalty = %d + %d per base)\n",
		smax, DMAT, DMIS, DINS0, DINS1);
	else
		fprintf(fx,
		"\n<score: %d (Dayhoff PAM 250 matrix, gap penalty = %d + %d per residue)\n",
		smax, PINS0, PINS1);
	if (endgaps)
		fprintf(fx,
		"<endgaps penalized. left endgap: %d %s%s, right endgap: %d %s%s\n",
		firstgap, (dna)? "base" : "residue", (firstgap == 1)? "" : "s",
		lastgap, (dna)? "base" : "residue", (lastgap == 1)? "" : "s");
	else
		fprintf(fx, "<endgaps not penalized\n");
}

static		nm;		/* matches in core -- for checking */
static		lmax;		/* lengths of stripped file names */
static		ij[2];		/* jmp index for a path */
static		nc[2];		/* number at start of current line */
static		ni[2];		/* current elem number -- for gapping */
static		siz[2];
static char	*ps[2];		/* ptr to current element */
static char	*po[2];		/* ptr to next output char slot */
static char	out[2][P_LINE];	/* output line */
static char	star[P_LINE];	/* set by stars() */

/*
 * print alignment of described in struct path pp[]
 */
static
pr_align()
{
	int		nn;	/* char count */
	int		more;
	register	i;

	for (i = 0, lmax = 0; i < 2; i++) {
		nn = stripname(namex[i]);
		if (nn > lmax)
			lmax = nn;

		nc[i] = 1;
		ni[i] = 1;
		siz[i] = ij[i] = 0;
		ps[i] = seqx[i];
		po[i] = out[i];
	}
```

pr_align

Table 1 (cont')

...pr_align

```
for (nn = nm = 0, more = 1; more; ) {
	for (i = more = 0; i < 2; i++) {
		/*
		 * do we have more of this sequence?
		 */
		if (!*ps[i])
			continue;

		more++;

		if (pp[i].spc) {	/* leading space */
			*po[i]++ = ' ';
			pp[i].spc--;
		}
		else if (siz[i]) {	/* in a gap */
			*po[i]++ = '-';
			siz[i]--;
		}
		else {			/* we're putting a seq element
					 */
			*po[i] = *ps[i];
			if (islower(*ps[i]))
				*ps[i] = toupper(*ps[i]);
			po[i]++;
			ps[i]++;

			/*
			 * are we at next gap for this seq?
			 */
			if (ni[i] == pp[i].x[ij[i]]) {
				/*
				 * we need to merge all gaps
				 * at this location
				 */
				siz[i] = pp[i].n[ij[i]++];
				while (ni[i] == pp[i].x[ij[i]])
					siz[i] += pp[i].n[ij[i]++];
			}
			ni[i]++;
		}
	}
	if (++nn == olen || !more && nn) {
		dumpblock();
		for (i = 0; i < 2; i++)
			po[i] = out[i];
		nn = 0;
	}
}
}

/*
 * dump a block of lines, including numbers, stars: pr_align()
 */
static
dumpblock()
{
	register i;

	for (i = 0; i < 2; i++)
		*po[i]-- = '\0';
```

dumpblock

Table 1 (cont')

...dumpblock

```
	(void) putc('\n', fx);
	for (i = 0; i < 2; i++) {
		if (*out[i] && (*out[i] != ' ' || *(po[i]) != ' ')) {
			if (i == 0)
				nums(i);
			if (i == 0 && *out[1])
				stars();
			putline(i);
			if (i == 0 && *out[1])
				fprintf(fx, star);
			if (i == 1)
				nums(i);
		}
	}
}

/*
 * put out a number line: dumpblock()
 */
static
nums(ix)
	int	ix;	/* index in out[] holding seq line */
{
	char		nline[P_LINE];
	register	i, j;
	register char	*pn, *px, *py;

	for (pn = nline, i = 0; i < lmax+P_SPC; i++, pn++)
		*pn = ' ';
	for (i = nc[ix], py = out[ix]; *py; py++, pn++) {
		if (*py == ' ' || *py == '-')
			*pn = ' ';
		else {
			if (i%10 == 0 || (i == 1 && nc[ix] != 1)) {
				j = (i < 0)? -i : i;
				for (px = pn; j; j /= 10, px--)
					*px = j%10 + '0';
				if (i < 0)
					*px = '-';
			}
			else
				*pn = ' ';
			i++;
		}
	}
	*pn = '\0';
	nc[ix] = i;
	for (pn = nline; *pn; pn++)
		(void) putc(*pn, fx);
	(void) putc('\n', fx);
}

/*
 * put out a line (name, [num], seq, [num]): dumpblock()
 */
static
putline(ix)
	int	ix;
{
```

nums putline

Table 1 (cont')

...putline

```
        int             i;
        register char   *px;

        for (px = namex[ix], i = 0; *px && *px != ':'; px++, i++)
                (void) putc(*px, fx);
        for (; i < lmax+P_SPC; i++)
                (void) putc(' ', fx);

        /* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}
```

stars

```
/*
 * put a line of stars (seqs always in out[0], out[1]): dumpblock()
 */
static
stars()
{
        int             i;
        register char   *p0, *p1, cx, *px;

        if (!*out[0] || (*out[0] == ' ' && *(po[0]) == ' ') ||
           !*out[1] || (*out[1] == ' ' && *(po[1]) == ' '))
                return;
        px = star;
        for (i = lmax+P_SPC; i; i--)
                *px++ = ' ';

        for (p0 = out[0], p1 = out[1]; *p0 && *p1; p0++, p1++) {
                if (isalpha(*p0) && isalpha(*p1)) {

                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Table 1 (cont')

stripname

```
/*
 * strip path or prefix from pn, return len: pr_align()
 */
static
stripname(pn)
        char     *pn;     /* file name (may be path) */
{
        register char     *px, *py;

        py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
#include "nw.h"
#include <sys/file.h>

char    *jname = "/tmp/homgXXXXXX";          /* tmp file for jmps */
FILE    *fj;

int     cleanup();                           /* cleanup tmp file */
long    lseek();

/*
 * remove any tmp file if we blow
 */
cleanup(i)                                                              cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                       getseq
        char    *file;  /* file name */
        int     *len;   /* seq len */
{
        char            line[1024], *pseq;
        register char   *px, *py;
        int             natgc, tlen;
        FILE            *fp;

        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
        py = pseq + 4;
        *len = tlen;
        rewind(fp);

        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
```

g_calloc

```
char    *
g_calloc(msg, nx, sz)
        char    *msg;           /* program, calling routine */
        int     nx, sz;         /* number and size of elements */
{
        char            *px, *calloc();

        if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}
```

readjmps

```
/*
 * get final jmps from dx[] or tmp file, set pp[], reset dmax: main()
 */
readjmps()
{
        int             fd = -1;
        int             siz, i0, i1;
        register i, j, xx;

        if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

Table 1 (cont')

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {                  /* gap in second seq */
                        pp[1].n[i1] = -siz;
                        xx += siz;
                        /* id = xx - yy + len1 - 1
                         */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {  /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
}
```

Table 1 (cont')

writejmps

```
/*
 * write a filled jmp struct offset of the prev one (if any): nw()
 */
writejmps(ix)
        int     ix;
{
        char    *mktemp();

        if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity =
(the number of identically matching amino acid residues between the two polypeptide sequences as determined by ALIGN-2) divided by (the total number of amino acid residues of the PRO polypeptide) =
5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity =
(the number of identically matching amino acid residues between the two polypeptide sequences as determined by ALIGN-2) divided by (the total number of amino acid residues of the PRO polypeptide) =
5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) =
6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) =
4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

1. Full-Length PRO211 and PRO217 Polypeptides

The present invention provides newly identified and isolated nucleotide sequences encoding polypeptides referred to in the present application as PRO211 and PRO217. In particular, Applicants have identified and isolated cDNA encoding PRO211 and PRO217 polypeptides, as disclosed in further detail in the Examples below. Using BLAST (FastA format) sequence alignment computer programs, Applicants found that cDNA sequences encoding full-length native sequence PRO211 and PRO217 have homologies to known proteins having EGF-like domains. Specifically, the cDNA sequence DNA32292-1131 (FIG. 1, SEQ ID NO:1) has certain identify and a Blast score of 209 with PAC6_RAT and certain identify and a Blast score of 206 with Fibulin-1, isoform c precursor. The cDNA sequence DNA33094-1131 (FIG. 3, SEQ ID NO:3) has 36% identity and a Blast score of 336 with eastern newt tenascin, and 37% identity and a Blast score of 331 with human tenascin-X precursor. Accordingly, it is presently believed that PRO211 and PRO217 polypeptides disclosed in the present application are newly identified members of the EGF-like family and possesses properties typical of the EGF-like protein family.

2. Full-Length PRO230 Polypeptides

The present invention provides newly identified and isolated nucleotide sequences encoding polypeptides referred to in the present application as PRO230. In particular, Applicants have identified and isolated cDNA encoding a PRO230 polypeptide, as disclosed in further detail in the Examples below. Using known programs such as BLAST and FastA sequence alignment computer programs, Applicants found that a cDNA sequence encoding full-length native sequence PRO230 has 48% amino acid identity with the rabbit tubulointerstitial nephritis antigen precursor. Accordingly, it is presently believed that PRO230 polypeptide disclosed in the present application is a newly identified member of the tubulointerstitial nephritis antigen family and possesses the ability to be recognized by human autoantibodies in certain forms of tubulointerstitial nephritis.

3. Full-Length PRO232 Polypeptides

The present invention provides newly identified and isolated nucleotide sequences encoding polypeptides referred to in the present application as PRO232. In particular, Applicants have identified and isolated cDNA encoding a PRO232 polypeptide, as disclosed in further detail in the Examples below. Using BLAST and FastA sequence alignment computer programs, Applicants found that a portion of the full-length native sequence PRO232 (shown in FIG. 9 and SEQ ID NO:18) has 35% sequence identity with a stem cell surface antigen from *Gallus gallus*. Accordingly, it is presently believed that the PRO232 polypeptide disclosed in the present application may be a newly identified stem cell antigen.

4. Full-Length PRO187 Polypeptides

The present invention provides newly identified and isolated nucleotide sequences encoding polypeptides referred to in the present application as PRO187. In particular, Applicants have identified and isolated cDNA encoding a PRO187 polypeptide, as disclosed in further detail in the Examples below. Using BLAST and FastA sequence alignment computer programs, Applicants found that a full-length native sequence PRO187 (shown in FIG. 15) has 74% amino acid sequence identity and BLAST score of 310 with various androgen-induced growth factors and FGF-8. Accordingly, it is presently believed that PRO187 polypeptide disclosed in the present application is a newly identified member of the FGF-8 protein family and may possess identify activity or property typical of the FGF-8-like protein family.

5. Full-Length PRO265 Polypeptides

The present invention provides newly identified and isolated nucleotide sequences encoding polypeptides referred to in the present application as PRO265. In particular, Applicants have identified and isolated cDNA encoding a PRO265 polypeptide, as disclosed in further detail in the Examples below. Using programs such as BLAST and FastA sequence alignment computer programs, Applicants found that various portions of the PRO265 polypeptide have significant homology with the fibromodulin protein and fibromodulin precursor protein. Applicants have also found that the DNA encoding the PRO265 polypeptide has significant homology with platelet glycoprotein V, a member of the leucine rich related protein family involved in skin and wound repair. Accordingly, it is presently believed that PRO265 polypeptide disclosed in the present application is a newly identified member of the leucine rich repeat family and possesses protein binding capabilities, as well as be involved in skin and wound repair as typical of this family.

6. Full-Length PRO219 Polypeptides

The present invention provides newly identified and isolated nucleotide sequences encoding polypeptides referred to in the present application as PRO219. In particular, Applicants have identified and isolated cDNA encoding a PRO219 polypeptide, as disclosed in further detail in the Examples below. Using BLAST and FastA sequence alignment computer programs, Applicants found that various portions of the PRO219 polypeptide have significant homology with the mouse and human matrilin-2 precursor polypeptides. Accordingly, it is presently believed that PRO219 polypeptide disclosed in the present application is related to the matrilin-2 precursor polypeptide.

7. Full-Length PRO246 Polypeptides

The present invention provides newly identified and isolated nucleotide sequences encoding polypeptides referred to in the present application as PRO246. In particular, Applicants have identified and isolated cDNA encoding a PRO246 polypeptide, as disclosed in further detail in the Examples below. Using BLAST and FastA sequence alignment computer programs, Applicants found that a portion of the PRO246 polypeptide has significant homology with the human cell surface protein HCAR. Accordingly, it is presently believed that PRO246 polypeptide disclosed in the present application may be a newly identified membrane-bound virus receptor or tumor cell-specific antigen.

8. Full-Length PRO228 Polypeptides

The present invention provides newly identified and isolated nucleotide sequences encoding polypeptides referred to in the present application as PRO228. In particular, Applicants have identified and isolated cDNA encoding a PRO228 polypeptide, as disclosed in further detail in the Examples below. Using BLAST and FastA sequence alignment computer programs, Applicants found that various portions of the PRO228 polypeptide have significant homology with the EMR1 protein. Applicants have also found that the DNA encoding the PRO228 polypeptide has significant homology with latrophilin, macrophage-restricted cell surface glycoprotein, B0457.1 and leucocyte antigen CD97 precursor. Accordingly, it is presently believed that PRO228 polypeptide disclosed in the present application is a newly identified member of the seven transmembrane superfamily and possesses characteristics and functional properties typical of this family. In particular, it is believed that PRO228 is a new member of the subgroup within this family to which CD97 and EMR1 belong.

9. Full-Length PRO533 Polypeptides

The present invention provides newly identified and isolated nucleotide sequences encoding polypeptides referred to in the present application as PRO533. In particular, Applicants have identified and isolated cDNA encoding a PRO533 polypeptide, as disclosed in further detail in the Examples below. Using BLAST-2 and FastA sequence alignment computer programs, Applicants found that a full-length native sequence PRO533 (shown in FIG. 22 and SEQ ID NO:59) has a Blast score of 509 and 53% amino acid sequence identity with fibroblast growth factor (FGF). Accordingly, it is presently believed that PRO533 disclosed in the present application is a newly identified member of the fibroblast growth factor family and may possess activity typical of such polypeptides.

10. Full-Length PRO245 Polypeptides

The present invention provides newly identified and isolated nucleotide sequences encoding polypeptides referred to in the present application as PRO245. In particular, Applicants have identified and isolated cDNA encoding a PRO245 polypeptide, as disclosed in further detail in the Examples below. Using BLAST and FastA sequence alignment computer programs, Applicants found that a portion of the amino acid sequence of the PRO245 polypeptide has 60% amino acid identity with the human c-myb protein. Accordingly, it is presently believed that the PRO245 polypeptide disclosed in the present application may be a newly identified member of the transmembrane protein tyrosine kinase family.

11. Full-Length PRO220, PRO221 and PRO227 Polypeptides

The present invention provides newly identified and isolated nucleotide sequences encoding polypeptides referred to in the present application as PRO220, PRO221 and PRO227. In particular, Applicants have identified and isolated cDNAs encoding a PRO220, PRO221 and PRO227 polypeptide, respectively, as disclosed in further detail in the Examples below. Using BLAST and FastA sequence alignment computer programs, PRO220 has amino acid identity with the amino acid sequence of a leucine rich protein wherein the identity is 87%. PRO220 additionally has amino acid identity with the neuronal leucine rich protein wherein the identity is 55%. The neuronal leucine rich protein is further described in Taguchi, et al., *Mol. Brain Res.,* 35:3140 (1996).

PRO221 has amino acid identity with the SLIT protein precursor, wherein different portions of these two proteins have the respective percent identities of 39%, 38%, 34%, 31%, and 30%.

PRO227 has amino acid identity with the amino acid sequence of platelet glycoprotein V precursor. The same results were obtained for human glycoprotein V. Different portions of these two proteins show the following percent identities of 30%, 28%, 28%, 31%, 35%, 39% and 27%.

Accordingly, it is presently believed that PRO220, PRO221 and PRO227 polypeptides disclosed in the present application are newly identified members of the leucine rich repeat protein superfamily and that each possesses protein—protein binding capabilities typical of the leucine rich repeat protein superfamily. It is also believed that they have capabilities similar to those of SLIT, the leucine rich repeat protein and human glycoprotein V.

12. Full-Length PRO258 Polypeptides

The present invention provides newly identified and isolated nucleotide sequences encoding polypeptides referred to in the present application as PRO258. In particular, Applicants have identified and isolated cDNA encoding a PRO258 polypeptide, as disclosed in further detail in the Examples below. Using BLAST and FastA sequence alignment computer programs, Applicants found that various portions of the PRO258 polypeptide have significant homology with the CRTAM and poliovirus receptors. Accordingly, it is presently believed that PRO258 polypeptide disclosed in the present application is a newly identified member of the Ig superfamily and possesses virus receptor capabilities or regulates immune function as typical of this family.

13. Full-Length PRO266 Polypeptides

The present invention provides newly identified and isolated nucleotide sequences encoding polypeptides referred to in the present application as PRO266. In particular, Applicants have identified and isolated cDNA encoding a PRO266 polypeptide, as disclosed in further detail in the Examples below. Using BLAST and FastA sequence alignment computer programs, Applicants found that various portions of the PRO266 polypeptide have significant homology with the SLIT protein from Drosophilia. Accordingly, it is presently believed that PRO266 polypeptide disclosed in the present application is a newly identified member of the leucine rich repeat family and possesses ligand—ligand binding activity and neuronal development typical of this family. SLIT has been shown to be useful in the study and treatment of Alzheimer's disease, supra, and thus, PRO266 may have involvement in the study and cure of this disease.

14. Full-Length PRO269 Polypeptides

The present invention provides newly identified and isolated nucleotide sequences encoding polypeptides referred to in the present application as PRO269. In particular, Applicants have identified and isolated cDNA encoding a PRO269 polypeptide, as disclosed in further detail in the Examples below. Using BLAST, FastA and sequence alignment computer programs, Applicants found that the amino acid sequence encoded by nucleotides 314 to 1783 of the full-length native sequence PRO269 (shown in FIG. 35 and SEQ ID NO:95) has significant homology to human urinary thrombomodulin and various thrombomodulin analogues respectively, to which it was aligned. Accordingly, it is presently believed that PRO269 polypeptide disclosed in the present application is a newly identified member of the thrombomodulin family.

15. Full-Length PRO287 Polypeptides

The present invention provides newly identified and isolated nucleotide sequences encoding polypeptides referred to in the present application as PRO287. In particular, Applicants have identified and isolated cDNA encoding a PRO287 polypeptide, as disclosed in further detail in the Examples below. Using BLAST and FastA sequence alignment computer programs, Applicants found that various portions of the PRO287 polypeptide have significant homology with the type 1 procollagen C-proteinase enhancer protein precursor and type 1 procollagen C-proteinase enhancer protein. Accordingly, it is presently believed that PRO287 polypeptide disclosed in the present application is a newly identified member of the C-proteinase enhancer protein family.

16. Full-Length PRO214 Polypeptides

The present invention provides newly identified and isolated nucleotide sequences encoding polypeptides referred to in the present application as PRO214. In particular, Applicants have identified and isolated cDNA encoding a PRO214 polypeptide, as disclosed in further detail in the Examples below. Using BLAST and FastA sequence alignment computer programs, Applicants found that a full-length native sequence PRO214 polypeptide (shown in FIG. 40 and SEQ ID NO:109) has 49% amino acid sequence identity with HT protein, a known member of the EGF-family. The comparison resulted in a BLAST score of 920, with 150 matching nucleotides. Accordingly, it is presently believed that the PRO214 polypeptide disclosed in the present application is a newly identified member of the family comprising EGF domains and may possess activities or properties typical of the EGF-domain containing family.

17. Full-Length PRO317 Polypeptides

The present invention provides newly identified and isolated nucleotide sequences encoding polypeptides referred to in the present application as PRO317. In particular, cDNA encoding a PRO317 polypeptide has been identified and isolated, as disclosed in further detail in the Examples below. Using BLAST™ and FastA™ sequence alignment computer programs, it was found that a full-length native-sequence PRO317 (shown in FIG. 42 and SEQ ID NO:114) has 92% amino acid sequence identity with EBAF-1. Further, it is closely aligned with many other members of the TGF-superfamily.

Accordingly, it is presently believed that PRO317 disclosed in the present application is a newly identified member of the TGF-superfamily and may possess properties that are therapeutically useful in conditions of uterine bleeding, etc. Hence, PRO317 may be useful in diagnosing or treating abnormal bleeding involved in gynecological diseases, for example, to avoid or lessen the need for a hysterectomy. PRO317 may also be useful as an agent that affects angiogenesis in general, so PRO317 may be useful in anti-tumor indications, or conversely, in treating coronary ischemic conditions.

Library sources reveal that ESTs used to obtain the consensus DNA for generating PRO317 primers and probes were found in normal tissues (uterus, prostate, colon, and pancreas), in several tumors (colon, brain (twice), pancreas, and mullerian cell), and in a heart with ischemia. PRO317 has shown up in several tissues as well, but it does look to have a greater concentration in uterus. Hence, PRO317 may have a broader use by the body than EBAF-1. It is contemplated that, at least for some indications, PRO317 may have opposite effects from EBAF-1.

18. Full-Length PRO301 Polypeptides

The present invention provides newly identified and isolated nucleotide sequences encoding polypeptides referred to in the present application as PRO301. In particular, Applicants have identified and isolated cDNA encoding a PRO301 polypeptide, as disclosed in further detail in the Examples below. Using BLAST and FastA sequence alignment computer programs, Applicants found that a full-length native sequence PRO301 (shown in FIG. 44 and SEQ ID NO: 119) has a Blast score of 246 corresponding to 30% amino acid sequence identity with human A33 antigen precursor. Accordingly, it is presently believed that PRO301 disclosed in the present application is a newly identified member of the A33 antigen protein family and may be expressed in human neoplastic diseases such as colorectal cancer.

19. Full-Length PRO224 Polypeptides

The present invention provides newly identified and isolated nucleotide sequences encoding polypeptides referred to in the present application as PRO224. In particular, Applicants have identified and isolated cDNA encoding a PRO224 polypeptide, as disclosed in further detail in the Examples below. Using known programs such as BLAST and FastA sequence alignment computer programs, Applicants found that full-length native PRO224 (FIG. 46, SEQ ID NO:127) has amino acid identity with apolipoprotein E receptor 2906 from *homo sapiens*. The alignments of different portions of these two polypeptides show amino acid identities of 37%, 36%, 30%, 44%, 44% and 28% respectively. Full-length native PRO224 (FIG. 46, SEQ ID NO:127) also has amino acid identity with very low-density lipoprotein receptor precursor from gall. The alignments of different portions of these two polypeptides show amino acid identities of 38%, 37%; 42%, 33%, and 37% respectively. Additionally, full-length native PRO224 (FIG. 46, SEQ ID NO:127) has amino acid identity with the chicken oocyte receptor P95 from *Gallus gallus*. The alignments of different portions of these two polypeptides show amino acid identities of 38%, 37%, 42%, 33%, and 37% respectively. Moreover, full-length native PRO224 (FIG. 46, SEQ ID NO:127) has amino acid identity with very low density lipoprotein receptor short form precursor from humans. The alignments of different portions of these two polypeptides show amino acid identities of 32%, 38%, 34%, 45%, and 31%, respectively. Accordingly, it is presently believed that PRO224 polypeptide disclosed in the present application is a newly identified member of the low density lipoprotein receptor family and possesses the structural characteristics required to have the functional ability to recognize and endocytose low density lipoproteins typical of the low density lipoprotein receptor family. (The alignments described above used the following scoring parameters: T=7, S+65, S2=36, Matrix: BLOSUM62.)

20. Full-Length PRO222 Polypeptides

The present invention provides newly identified and isolated nucleotide sequences encoding polypeptides referred to in the present application as PRO222. In particular, Applicants have identified and isolated cDNA encoding a PRO222 polypeptide, as disclosed in further detail in the Examples below. Using BLAST and FastA sequence alignment computer programs, Applicants found that a sequence encoding full-length native sequence PRO222 (shown in FIG. 48 and SEQ ID NO:132) has 25–26% amino acid identity with mouse complement factor h precursor, has 27–29% amino acid identity with complement receptor, has 25–47% amino acid identity with mouse complement C3b receptor type 2 long form precursor, has 40% amino acid identity with human hypothetical protein kiaa0247. Accordingly, it is presently believed that PRO222 polypeptide disclosed in the present application is a newly identified member of the complement receptor family and possesses activity typical of the complement receptor family.

21. Full-Length PRO234 Polypeptides

The present invention provides newly identified and isolated nucleotide sequences encoding polypeptides referred to in the present application as PRO234. In particular, Applicants have identified and isolated cDNA encoding a PRO234 polypeptide, as disclosed in further detail in the Examples below. Using BLAST (FastA-format) sequence alignment computer programs, Applicants found that a cDNA sequence encoding full-length native sequence PRO234 has 31% identity and Blast score of 134 with E-selectin precursor. Accordingly, it is presently believed that the PRO234 polypeptides disclosed in the present application are newly identified members of the lectin/selectin family and possess activity typical of the lectin/selectin family.

22. Full-Length PRO231 Polypeptides

The present invention provides newly identified and isolated nucleotide sequences encoding polypeptides referred to in the present application as PRO231. In particular, Applicants have identified and isolated cDNA encoding a PRO231 polypeptide, as disclosed in further detail in the Examples below. Using BLAST and FastA sequence alignment computer programs, Applicants found that the full-length native sequence PRO231 polypeptide (shown in FIG. 52 and SEQ ID NO:142) has 30% and 31% amino acid identity with human and rat prostatic acid phosphatase precursor proteins, respectively. Accordingly, it is presently believed that the PRO231 polypeptide disclosed in the present application may be a newly identified member of the acid phosphatase protein family.

23. Full-Length PRO229 Polypeptides

The present invention provides newly identified and isolated nucleotide sequences encoding polypeptides referred to in the present application as PRO229. In particular, Applicants have identified and isolated cDNA encoding a PRO229 polypeptide, as disclosed in further detail in the Examples below. Using BLAST and FastA sequence alignment computer programs, Applicants found that various portions of the PRO229 polypeptide have significant homology with antigen wc1.1, M130 antigen, T cell surface glycoprotein CD6 and CD6. It also is related to Sp-alpha. Accordingly, it is presently believed that PRO229 polypeptide disclosed in the present application is a newly identified member of the family containing scavenger receptor homology, a sequence motif found in a number of proteins involved in immune function and thus possesses immune function and/or segments which resist degradation, typical of this family.

24. Full-Length PRO238 Polypeptides

The present invention provides newly identified and isolated nucleotide sequences encoding polypeptides referred to in the present application as PRO238. In particular, Applicants have identified and isolated cDNA encoding a PRO238 polypeptide, as disclosed in further detail in the Examples below. Using BLAST and FastA sequence alignment computer programs, Applicants found that various portions of the PRO238 polypeptide have significant homology with reductases, including oxidoreductase and fatty acyl-CoA reductase. Accordingly, it is presently believed that PRO238 polypeptide disclosed in the present application is a newly identified member of the reductase family and possesses reducing activity typical of the reductase family.

25. Full-Length PRO233 Polypeptides

The present invention provides newly identified and isolated nucleotide sequences encoding polypeptides referred to in the present application as PRO233. In particular, Applicants have identified and isolated cDNA encoding a PRO233 polypeptide, as disclosed in further detail in the Examples below. Using BLAST and FastA sequence alignment computer programs, Applicants found that various portions of the PRO233 polypeptide have significant homology with the reductase protein. Applicants have also found that the DNA encoding the PRO233 polypeptide has significant homology with proteins from *Caenorhabditis elegans*. Accordingly, it is presently believed that PRO233 polypeptide disclosed in the present application is a newly identified member of the reductase family and possesses the ability to effect the redox state of the cell typical of the reductase family.

26. Full-Length PRO223 Polypeptides

The present invention provides newly identified and isolated nucleotide sequences encoding polypeptides referred to in the present application as PRO223. In particular, Applicants have identified and isolated cDNA encoding a PRO223 polypeptide, as disclosed in further detail in the Examples below. Using BLAST and FastA sequence alignment computer programs, Applicants found that the PRO223 polypeptide has significant homology with various serine carboxypeptidase polypeptides. Accordingly, it is presently believed that PRO223 polypeptide disclosed in the present application is a newly identified serine carboxypeptidase.

27. Full-Length PRO235 Polypeptides

The present invention provides newly identified and isolated nucleotide sequences encoding polypeptides referred to in the present application as PRO235. In particular, Applicants have identified and isolated cDNA encoding a PRO235 polypeptide, as disclosed in further detail in the Examples below. Using BLAST and FastA sequence alignment computer programs, Applicants found that various portions of the PRO235 polypeptide have significant homology with the various plexin proteins. Accordingly, it is presently believed that PRO235 polypeptide disclosed in the present application is a newly identified member of the plexin family and possesses cell adhesion properties typical of the plexin family.

28. Full-Length PRO236 and PRO262 Polypeptides

The present invention provides newly identified and isolated nucleotide sequences encoding polypeptides referred to in the present application as PRO236 and PRO262. In particular, Applicants have identified and isolated cDNA encoding PRO236 and PRO262 polypeptides, as disclosed in further detail in the Examples below. Using BLAST and FastA sequence alignment computer programs, Applicants found that various portions of the PRO236 and PRO262 polypeptides have significant homology with various β-galactosidase and β-galactosidase precursor polypeptides. Accordingly, it is presently believed that the PRO236 and PRO262 polypeptides disclosed in the present application are newly identified β-galactosidase homologs.

29. Full-Length PRO239 Polypeptides

The present invention provides newly identified and isolated nucleotide sequences encoding polypeptides referred to in the present application as PRO239. In particular, Applicants have identified and isolated cDNA encoding a PRO239 polypeptide, as disclosed in further detail in the Examples below. Using BLAST and FastA sequence alignment computer programs, Applicants found that various portions of the PRO239 polypeptide have significant homology with densin proteins. Accordingly, it is presently believed that PRO239 polypeptide disclosed in the present application is a newly identified member of the densin family and possesses cell adhesion and the ability to effect synaptic processes as is typical of the densin family.

30. Full-Length PRO257 Polypeptides

The present invention provides newly identified and isolated nucleotide sequences encoding polypeptides referred to in the present application as PRO257. In particular, Applicants have identified and isolated cDNA encoding a PRO257 polypeptide, as disclosed in further detail in the Examples below. Using BLAST and FastA sequence alignment computer programs, Applicants found that various portions of the PRO257 polypeptide have significant homology with the ebnerin precursor and ebnerin protein. Accordingly, it is presently believed that PRO257 polypeptide disclosed in the present application is a newly identified protein member which is related to the ebnerin protein.

31. Full-Length PRO260 Polypeptides

The present invention provides newly identified and isolated nucleotide sequences encoding polypeptides referred to in the present application as PRO260. In particular, Applicants have identified and isolated cDNA encoding a PRO260 polypeptide, as disclosed in further detail in the Examples below. Using programs such as BLAST and FastA sequence alignment computer programs, Applicants found that various portions of the PRO260 polypeptide have significant homology with the alpha-1-fucosidase precursor. Accordingly, it is presently believed that PRO260 polypeptide disclosed in the present application is a newly identified member of the fucosidase family and possesses enzymatic activity related to fucose residues typical of the fucosidase family.

32. Full-Length PRO263 Polypeptides

The present invention provides newly identified and isolated nucleotide sequences encoding polypeptides referred to in the present application as PRO263. In particular, Applicants have identified and isolated cDNA encoding a PRO263 polypeptide, as disclosed in further detail in the Examples below. Using BLAST and FastA sequence alignment computer programs, Applicants found that various portions of the PRO263 polypeptide have significant homology with the CD44 antigen and related proteins. Accordingly, it is presently believed that PRO263 polypeptide disclosed in the present application is a newly identified member of the CD44 antigen family and possesses at least one of the properties associated with these antigens, i.e., cancer and HIV marker, cell—cell or cell-matrix interactions, regulating cell traffic, lymph node homing, transmission of growth signals, and presentation of chemokines and growth factors to traveling cells.

33. Full-Length PRO270 Polypeptides

The present invention provides newly identified and isolated nucleotide sequences encoding polypeptides referred to in the present application as PRO270. In particular, Applicants have identified and isolated cDNA encoding a PRO270 polypeptide, as disclosed in further detail in the Examples below. Using BLAST, FastA and sequence alignment computer programs, Applicants found that that various portions of the PRO270 polypeptide have significant homology with various thioredoxin proteins. Accordingly, it is presently believed that PRO270 polypeptide disclosed in the present application is a newly identified member of the thioredoxin family and possesses the ability to effect reduction-oxidation (redox) state typical of the thioredoxin family.

34. Full-Length PRO271 Polypeptides

The present invention provides newly identified and isolated nucleotide sequences encoding polypeptides referred to in the present application as PRO271. In particular, Applicants have identified and isolated cDNA encoding a PRO271 polypeptide, as disclosed in further detail in the Examples below. Using BLAST and FastA sequence alignment computer programs, Applicants found that the PRO271 polypeptide has significant homology with various link proteins and precursors thereof. Accordingly it is presently believed that PRO271 polypeptide disclosed in the present application is a newly identified link protein homolog.

35. Full-Length PRO272 Polypeptides

The present invention provides newly identified and isolated nucleotide sequences encoding polypeptides referred to in the present application as PRO272. In particular, Applicants have identified and isolated cDNA encoding a PRO272 polypeptide, as disclosed in further detail in the Examples below. Using BLAST and FastA sequence alignment computer programs, Applicants found that various portions of the PRO272 polypeptide have significant homology with the human reticulocalbin protein and its precursors. Applicants have also found that the DNA encoding the PRO272 polypeptide has significant homology with the mouse reticulocalbin precursor protein. Accordingly, it is presently believed that PRO272 polypeptide disclosed in the present application is a newly identified member of the reticulocalbin family and possesses the ability to bind calcium typical of the reticulocalbin family.

36. Full-Length PRO294 Polypeptides

The present invention provides newly identified and isolated nucleotide sequences encoding polypeptides referred to in the present application as PRO294. In particular, Applicants have identified and isolated cDNA encoding a PRO294 polypeptide, as disclosed in further detail in the Examples below. Using BLAST and FastA sequence alignment computer programs, Applicants found that various portions of the PRO294 polypeptide have significant homology with the various portions of a number of collagen proteins. Accordingly, it is presently believed that PRO294 polypeptide disclosed in the present application is a newly identified member of the collagen family.

37. Full-Length PRO295 Polypeptides

The present invention provides newly identified and isolated nucleotide sequences encoding polypeptides referred to in the present application as PRO295. In particular, Applicants have identified and isolated cDNA encoding a PRO295 polypeptide, as disclosed in further detail in the Examples below. Using BLAST and FastA sequence alignment computer programs, Applicants found that various portions of the PRO295 polypeptide have significant homology with integrin proteins. Accordingly, it is presently believed that PRO295 polypeptide disclosed in the present application is a newly identified member of the integrin family and possesses cell adhesion typical of the integrin family.

38. Full-Length PRO293 Polypeptides

The present invention provides newly identified and isolated nucleotide sequences encoding polypeptides referred to in the present application as PRO293. In particular, Applicants have identified and isolated cDNA encoding a PRO293 polypeptide, as disclosed in further detail in the Examples below. Using BLAST and FastA sequence alignment computer programs, Applicants found that portions of the PRO293 polypeptide have significant homology with the neuronal leucine rich repeat proteins 1 and 2, (NLRR-1 and NLRR-2), particularly NLRR-2. Accordingly, it is presently believed that PRO293 polypeptide disclosed in the present application is a newly identified member of the neuronal leucine rich repeat protein family and possesses ligand—ligand binding activity typical of the NRLL protein family.

39. Full-Length PRO247 Polypeptides

The present invention provides newly identified and isolated nucleotide sequences encoding polypeptides referred to in the present application as PRO247. In particular, Applicants have identified and isolated cDNA encoding a PRO247 polypeptide, as disclosed in further detail in the Examples below. Using BLAST and FastA sequence alignment computer programs, Applicants found that various portions of the PRO247 polypeptide have significant homology with densin. Applicants have also found that the DNA encoding the PRO247 polypeptide has significant homology with a number of other proteins, including KIAA0231. Accordingly, it is presently believed that PRO247 polypeptide disclosed in the present application is a newly identified member of the leucine rich repeat family and possesses ligand binding abilities typical of this family.

40. Full-Length PRO302, PRO303, PRO304, PRO307 and PRO343 Polypeptides

The present invention provides newly identified and isolated nucleotide sequences encoding polypeptides referred to in the present application as PRO302, PRO303, PRO304, PRO307 and PRO343. In particular, Applicants have identified and isolated cDNA encoding PRO302, PRO303, PRO304, PRO307 and PRO343 polypeptides, as disclosed in further detail in the Examples below. Using BLAST and FastA sequence alignment computer programs, Applicants found that various portions of the PRO302, PRO303, PRO304, PRO307 and PRO343 polypeptides have significant homology with various protease proteins. Accordingly, it is presently believed that the PRO302, PRO303, PRO304, PRO307 and PRO343 polypeptides disclosed in the present application are newly identified protease proteins.

41. Full-Length PRO328 Polypeptides

The present invention provides newly identified and isolated nucleotide sequences encoding polypeptides referred to in the present application as PRO328. In particular, Applicants have identified and isolated cDNA encoding a PRO328 polypeptide, as disclosed in further detail in the Examples below. Using BLAST and FastA sequence alignment computer programs, Applicants found that various portions of the PRO328 polypeptide have significant homology with the human glioblastoma protein ("GLIP"). Further, Applicants found that various portions of the PRO328 polypeptide have significant homology with the cysteine rich secretory protein ("CRISP") as identified by BLAST homology [ECCRISP3_1, S68683, and CRS3_HUMAN]. Accordingly, it is presently believed that PRO328 polypeptide disclosed in the present application is a newly identified member of the GLIP or CRISP families and possesses transcriptional regulatory activity typical of the GLIP or CRISP families.

42. Full-Length PRO335, PRO331 and PRO326 Polypeptides

The present invention provides newly identified and isolated nucleotide sequences encoding polypeptides referred to in the present application as PRO335, PRO331 or PRO326. In particular, Applicants have identified and isolated cDNA encoding a PRO335, PRO331 or PRO326 polypeptide, as disclosed in further detail in the Examples below. Using BLAST and FastA sequence alignment computer programs, Applicants found that various portions of the PRO335, PRO331 or PRO326 polypeptide have significant homology with LIG-1, ALS and in the case of PRO331, additionally, decorin. Accordingly, it is presently believed that the PRO335, PRO331 and PRO326 polypeptides disclosed in the present application are newly identified members of the leucine rich repeat superfamily, and particularly, are related to LIG-1 and possess the biological functions of this family as discussed and referenced herein.

43. Full-Length PRO332 Polypeptides

The present invention provides newly identified and isolated nucleotide sequences encoding polypeptides referred to in the present application as PRO332. In particular, Applicants have identified and isolated cDNA encoding PRO332 polypeptides, as disclosed in further detail in the Examples below. Using BLAST and FastA sequence alignment computer programs, Applicants found that a full-length native sequence PRO332 (shown in FIG. 108 and SEQ ID NO:310) has about 30–40% amino acid sequence identity with a series of known proteoglycan sequences, including, for example, fibromodulin and fibromodulin precursor sequences of various species (FMOD_BOVIN, FMOD_CHICK, FMOD_RAT, FMOD_MOUSE, FMOD_HUMAN, P_R36773), osteomodulin sequences (AB000114_1, AB007848_1), decorin sequences (CFU83141_1, OCU03394_1, P R42266, P_R42267, P_R42260, P_R89439), keratan sulfate proteoglycans (BTU48360_1, AF022890_1), corneal proteoglycan (AF022256_1), and bone/cartilage proteoglycans and proteoglycane precursors (PGS1_BOVIN, PGS2_MOUSE, PGS2_HUMAN). Accordingly, it is presently believed that PRO332 disclosed in the present application is a new proteoglycan-type molecule, and may play a role in regulating extracellular matrix, cartilage, and/or bone function.

44. Full-Length PRO334 Polypeptides

The present invention provides newly identified and isolated nucleotide sequences encoding polypeptides referred to in the present application as PRO334. In particular, Applicants have identified and isolated cDNA encoding a PRO334 polypeptide, as disclosed in further detail in the Examples below. Using BLAST and FastA sequence alignment computer programs, Applicants found that various portions of the PRO334 polypeptide have significant homology with fibulin and fibrillin. Accordingly, it is presently believed that PRO334 polypeptide disclosed in the present application is a newly identified member of the epidermal growth factor family and possesses properties and activities typical of this family.

45. Full-Length PRO346 Polypeptides

The present invention provides newly identified and isolated nucleotide sequences encoding polypeptides referred to in the present application as PRO346. In particular, Applicants have identified and isolated cDNA encoding a PRO346 polypeptide, as disclosed in further detail in the Examples below. Using BLAST and FastA sequence alignment computer programs, Applicants found that a full-length native sequence PRO346 (shown in FIG. 112 and SEQ ID NO:320) has 28% amino acid sequence identity with carcinoembryonic antigen. Accordingly, it is presently believed that PRO346 disclosed in the present application is a newly identified member of the carcinoembryonic protein family and may be expressed in association with neoplastic tissue disorders.

46. Full-Length PRO268 Polypeptides

The present invention provides newly identified and isolated nucleotide sequences encoding polypeptides referred to in the present application as PRO268. In particular, Applicants have identified and isolated cDNA encoding a PRO268 polypeptide, as disclosed in further detail in the Examples below. Using BLAST and FastA sequence alignment computer programs, Applicants found that portions of the PRO268 polypeptide have significant homology with the various protein disulfide isomerase proteins. Accordingly, it is presently believed that PRO268 polypeptide disclosed in the present application is a homolog of the protein disulfide isomerase p5 protein.

47. Full-Length PRO330 Polypeptides

The present invention provides newly identified and isolated nucleotide sequences encoding polypeptides referred to in the present application as PRO330. In particular, Applicants have identified and isolated cDNA encoding a PRO330 polypeptide, as disclosed in further detail in the Examples below. Using BLAST and FastA sequence alignment computer programs, Applicants found that various portions of the PRO330 polypeptide have significant homology with the murine prolyl 4-hydroxylase alpha-II subunit protein. Accordingly, it is presently believed that PRO330 polypeptide disclosed in the present application is a novel prolyl 4-hydroxylase subunit polypeptide.

48. Full-Length PRO339 and PRO310 Polypeptides

The present invention provides newly identified and isolated nucleotide sequences encoding polypeptides referred to in the present application as PRO339 and PRO310. In particular, Applicants have identified and isolated cDNA encoding a PRO339 polypeptide, as disclosed in further detail in the Examples below. Applicants have also identified and isolated cDNA encoding a PRO310 polypeptide, as disclosed in further detail in the Examples below. Using BLAST and FastA sequence alignment computer programs, Applicants found that various portions of the PRO339 and PRO310 polypeptides have significant homology with small secreted proteins from *C. elegans* and are distantly related to fringe. PRO339 also shows homology to collagen-like polymers. Sequences which were used to identify PRO310, designated herein as DNA40533 and DNA42267, also show homology to proteins from *C. elegans*. Accordingly, it is presently believed that the PRO339 and PRO310 polypeptides disclosed in the present application are newly identified member of the family of proteins involved in development, and which may have regulatory abilities similar to the capability of fringe to regulate serrate.

49. Full Length PRO244 Polypeptides

The present invention provides newly identified and isolated nucleotide sequences encoding C-type lectins referred to in the present application as PRO244. In particular, applicants have identified and isolated cDNA encoding PRO244 polypeptides, as disclosed in further detail in the Examples below. Using BLAST and FastA sequence alignment computer programs, Applicants found that a full-length native sequence PRO244 (shown in FIG. 122 and SEQ ID NO:377) has 43% amino acid sequence identity with the hepatic lectin *gallus gallus* (LECH-CHICK), and 42% amino acid sequence identity with an HIV gp120 binding C-type lectin (A46274). Accordingly, it is presently believed that PRO244 disclosed in the present application is a newly identified member of the C-lectin superfamily and may play a role in immune function, apoptosis, or in the pathogenesis of atherosclerosis. In addition, PRO244 may be useful in identifying tumor-associated epitopes.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem*., pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.* 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. Tn a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology

[Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456–457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968–975 (1991)) such as, e.g., *K. lactis* (MW98-8C, CBS683, CBS4574; Louvencourt et al., *J. Bacteriol.,* 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol.,* 28:265–278 [1988]); *Candida; Trichoderma reesia* (EP 244,234); *Neurospora crassa* (Case et al., *Proc. Natl. Acad. Sci. USA,* 76:5259–5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284–289 [1983]; Tilbum et al., *Gene,* 26:205–221 [1983]; Yelton et al., *Proc. Natl. Acad. Sci. USA,* 81: 1470–1474 [1984]) and *A. niger* (Kelly and Hynes, *EMBO J.,* 4:475–479 [1985]). Methylotropic yeasts are suitable herein and include, but are not limited to, yeast capable of growth on methanol selected from the genera consisting of *Hansenula, Candida, Kloeckera, Pichia, Saccharonyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR(CHO, Urlaub and Chasin, Proc. Natl. Acad. Sci. USA, 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293: 620–625 (1981); Mantei et al., *Nature,* 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein—protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 mg/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.,* 2:795–799 (1996); Yasuda, *Biomed. Ther.,* 27:1221–1223 (1993); Hora et al., *Bio/Technology,* 8:755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein—protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein—protein interactions. Such assays include traditional approaches, such as, e.g., cross-linking, co-immunoprecipitation, and co-purification through gradients or chromatographic columns. In addition, protein—protein interactions can be monitored by using a yeast-based genetic system described by Fields and co-workers (Fields and Song, *Nature* (*London*), 340:245–246 (1989); Chien et al., *Proc. Natl. Acad. Sci. USA,* 88:9578–9582 (1991)) as disclosed by Chevray and Nathans, *Proc. Natl. Acad. Sci. USA,* 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein—protein interaction. Colonies containing interacting polypeptides are detected with a chromogenic substrate for β-galactosidase. A complete kit (MATCHMAKER™) for identifying protein—protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

With regard to the PRO211 and PRO217 polypeptide, therapeutic indications include disorders associated with the preservation and maintenance of gastrointestinal mucosa and the repair of acute and chronic mucosal lesions (e.g., enterocolitis, Zollinger-Ellison syndrome, gastrointestinal ulceration and congenital microvillus atrophy), skin diseases associated with abnormal keratinocyte differentiation (e.g., psoriasis, epithelial cancers such as lung squamous cell carcinoma, epidermoid carcinoma of the vulva and gliomas.

Since the PRO232 polypeptide and nucleic acid encoding it possess sequence homology to a cell surface stem cell antigen and its encoding nucleic acid, probes based upon the PRO232 nucleotide sequence may be employed to identify other novel stem cell surface antigen proteins. Soluble forms of the PRO232 polypeptide may be employed as antagonists of membrane bound PRO232 activity both in vitro and in vivo. PRO232 polypeptides may be employed in screening assays designed to identify agonists or antagonists of the native PRO232 polypeptide, wherein such assays may take the form of any conventional cell-type or biochemical binding assay. Moreover, the PRO232 polypeptide may serve as a molecular marker for the tissues in which the polypeptide is specifically expressed.

With regard to the PRO187 polypeptides disclosed herein, FGF-8 has been implicated in cellular differentiation and embryogenesis, including the patterning which appears during limb formation. FGF-8 and the PRO187 molecules of the invention therefore are likely to have potent effects on cell growth and development. Diseases which relate to cellular growth and differentiation are therefore suitable targets for therapeutics based on functionality similar to FGF-8. For example, diseases related to growth or survival of nerve cells including Parkinson's disease, Alzheimer's disease, ALS, neuropathies. Additionally, disease related to uncontrolled cell growth, e.g., cancer, would also be expected therapeutic targets.

With regard to the PRO265 polypeptides disclosed herein, other methods for use with PRO265 are described in U.S. Pat. No. 5,654,270 to Ruoslahti et al. In particular, PRO265 can be used in comparison with the fibromodulin disclosed therein to compare its effects on reducing dermal scarring and other properties of the fibromodulin described therein including where it is located and with what it binds and does not.

The PRO219 polypeptides of the present invention which play a regulatory role in the blood coagulation cascade may be employed in vivo for therapeutic purposes as well as for in vitro purposes. Those of ordinary skill in the art will well know how to employ PRO219 polypeptides for such uses.

The PRO246 polypeptides of the present invention which serve as cell surface receptors for one or more viruses will find other uses. For example, extracellular domains derived from these PRO246 polypeptides may be employed therapeutically in vivo for lessening the effects of viral infection. Those PRO246 polypeptides which serves as tumor specific antigens may be exploited as therapeutic targets for anti-tumor drugs, and the like. Those of ordinary skill in the art will well know how to employ PRO246 polypeptides for such uses.

Assays in which connective growth factor and other growth factors are usually used should be performed with PRO261. An assay to determine whether TGF beta induces PRO261, indicating a role in cancer is performed as known in the art. Wound repair and tissue growth assays are also performed with PRO261. The results are applied accordingly.

PRO228 polypeptides should be used in assays in which EMR1, CD97 and latrophilin would be used in to determine their relative activities. The results can be applied accordingly. For example, a competitive binding assay with PRO228 and CD97 can be performed with the ligand for CD97, CD55.

Native PRO533 is a 216 amino acid polypeptide of which residues 1–22 are the signal sequence. Residues 3 to 216 have a Blast score of 509, corresponding to 53% homology to fibroblast growth factor. At the nucleotide level, DNA47412, the EST from which PCR oligos were generated to isolate the full length DNA49435-1219, has been observed to map to 11p15. Sequence homology to the 11p15 locus would indicate that PRO533 may have utility in the treatment of Usher Syndrome or Atrophia areata.

As mentioned previously, fibroblast growth factors can act upon cells in both a mitogenic and non-mitogenic manner. These factors are mitogenic for a wide variety of normal diploid mesoderm-derived and neural crest-derived cells, inducing granulosa cells, adrenal cortical cells, chondrocytes, myoblasts, corneal and vascular endothelial cells (bovine or human), vascular smooth muscle cells, lens, retina and prostatic epithelial cells, oligodendrocytes, astrocytes, chrondocytes, myoblasts and osteoblasts.

Non-mitogenic actions of fibroblast growth factors include promotion of cell migration into a wound area (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival. Baird, A. & Bohlen, P., *Handbook of Exp. Pharmacol.* 95(1): 369–418 (1990). These properties provide a basis for using fibroblast growth factors in therapeutic approaches to accelerate wound healing, nerve repair, collateral blood vessel formation, and the like. For example, fibroblast growth factors, have been suggested to minimize myocardium damage in heart disease and surgery (U.S. Pat. No. 4,378,437).

Since the PRO245 polypeptide and nucleic acid encoding it possess sequence homology to a transmembrane protein tyrosine kinase protein and its encoding nucleic acid, probes based upon the PRO245 nucleotide sequence may be employed to identify other novel transmembrane tyrosine kinase proteins. Soluble forms of the PRO245 polypeptide may be employed as antagonists of membrane bound PRO245 activity both in vitro and in vivo. PRO245 polypeptides may be employed in screening assays designed to identify agonists or antagonists of the native PRO245 polypeptide, wherein such assays may take the form of any conventional cell-type or biochemical binding assay. Moreover, the PRO245 polypeptide may serve as a molecular marker for the tissues in which the polypeptide is specifically expressed.

PRO220, PRO221 and PRO227 all have leucine rich repeats. Additionally, PRO220 and PRO221 have homology to SLIT and leucine rich repeat protein. Therefore, these proteins are useful in assays described in the literature, supra, wherein the SLIT and leucine rich repeat protein are used. Regarding the SLIT protein, PRO227 can be used in an assay to determine the affect of PRO227 on neurodegenerative disease. Additionally, PRO227 has homology to human glycoprotein V. In the case of PRO227, this polypeptide is used in an assay to determine its affect on bleeding, clotting, tissue repair and scarring.

The PRO266 polypeptide can be used in assays to determine if it has a role in neurodegenerative diseases or their reversal.

PRO269 polypeptides and portions thereof which effect the activity of thrombin may also be useful for in vivo therapeutic purposes, as well as for various in vitro applications. In addition, PRO269 polypeptides and portions thereof may have therapeutic use as an antithrombotic agent with reduced risk for hemorrhage as compared with heparin. Peptides having homology to thrombomodulin are particularly desirable.

PRO287 polypeptides and portions thereof which effect the activity of bone morphogenic protein "BMP1"/procollagen C-proteinase (PCP) may also be useful for in vivo therapeutic purposes, as well as for various in vitro applications. In addition, PRO287 polypeptides and portions thereof may have therapeutic applications in wound healing and tissue repair. Peptides having homology to procollagen C-proteinase enhancer protein and its precursor may also be used to induce bone and/or cartilage formation and are therefore of particular interest to the scientific and medical communities.

Therapeutic indications for PRO214 polypeptides include disorders associated with the preservation and maintenance of gastrointestinal mucosa and the repair of acute and chronic mucosal lesions (e.g., enterocolitis, Zollinger-Ellison syndrome, gastrointestinal ulceration and congenital microvillus atrophy), skin diseases associated with abnormal keratinocyte differentiation (e.g., psoriasis, epithelial cancers such as lung squamous cell carcinoma, epidermoid carcinoma of the vulva and gliomas.

Studies on the generation and analysis of mice deficient in members of the TGF-superfamily are reported in Matzuk, *Trends in Endocrinol. and Metabol.,* 6: 120–127 (1995).

The PRO317 polypeptide, as well as PRO317-specific antibodies, inhibitors, agonists, receptors, or their analogs, herein are useful in treating PRO317-associated disorders. Hence, for example, they may be employed in modulating endometrial bleeding angiogenesis, and may also have an effect on kidney tissue. Endometrial bleeding can occur in gynecological diseases such as endometrial cancer as abnormal bleeding. Thus, the compositions herein may find use in diagnosing and treating abnormal bleeding conditions in the endometrium, as by reducing or eliminating the need for a hysterectomy. The molecules herein may also find use in angiogenesis applications such as anti-tumor indications for which the antibody against vascular endothelial growth factor is used, or, conversely, ischemic indications for which vascular endothelial growth factor is employed.

Bioactive compositions comprising PRO317 or agonists or antagonists thereof may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems of the kidney, uterus, endometrium, blood vessels, or related tissue, e.g., in the heart or genital tract.

Dosages and administration of PRO317, PRO317 agonist, or PRO317 antagonist in a pharmaceutical composition may be determined by one of ordinary skill in the art of clinical pharmacology or pharmacokinetics. See, for example, Mordenti and Rescigno, *Pharmaceutical Research,* 9:17–25 (1992); Morenti et al., *Pharmaceutical Research,* 8:1351–1359 (1991); and Mordenti and Chappell, "The use of interspecies scaling in toxicokinetics" in *Toxicokinetics and New Drug Development*, Yacobi et al. (eds) (Pergamon Press: NY, 1989), pp. 42–96. An effective amount of PRO317, PRO317 agonist, or PRO317 antagonist to be employed therapeutically will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 μg/kg/day to 10 mg/kg/day. Typically, the clinician will administer PRO317, PRO317 agonist, or PRO317 antagonist, until a dosage is reached that achieves the desired effect for treatment of the above mentioned disorders.

PRO317 or an PRO317 agonist or PRO317 antagonist may be administered alone or in combination with another to achieve the desired pharmacological effect. PRO317 itself, or agonists or antagonists of PRO317 can provide different effects when administered therapeutically. Such compounds for treatment will be formulated in a nontoxic, inert, pharmaceutically acceptable aqueous carrier medium preferably at a pH of about 5 to 8, more preferably 6 to 8, although the pH may vary according to the characteristics of the PRO317, agonist, or antagonist being formulated and the condition to be treated. Characteristics of the treatment compounds include solubility of the molecule, half-life, and antigenicity/immunogenicity; these and other characteristics may aid in defining an effective carrier.

PRO317 or PRO317 agonists or PRO317 antagonists may be delivered by known routes of administration including but not limited to topical creams and gels; transmucosal spray and aerosol, transdermal patch and bandage; injectable, intravenous, and lavage formulations; and orally administered liquids and pills, particularly formulated to resist stomach acid and enzymes. The particular formulation, exact dosage, and route of administration will be determined by the attending physician and will vary according to each specific situation.

Such determinations of administration are made by considering multiple variables such as the condition to be treated, the type of mammal to be treated, the compound to be administered, and the pharmacokinetic profile of the particular treatment compound. Additional factors which may be taken into account include disease state (e.g. severity) of the patient, age, weight, gender, diet, time of administration, drug combination, reaction sensitivities, and tolerance/response to therapy. Long-acting treatment compound formulations (such as liposomally encapsulated PRO317 or PEGylated PRO317 or PRO317 polymeric microspheres, such as polylactic acid-based microspheres) might be administered every 3 to 4 days, every week, or once every two weeks depending on half-life and clearance rate of the particular treatment compound.

Normal dosage amounts may vary from about 10 mg/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting the uterus, for example, may necessitate delivery in a manner different from that to another organ or tissue, such as cardiac tissue.

Where sustained-release administration of PRO317 is desired in a formulation with release characteristics suitable for the treatment of any disease or disorder requiring administration of PRO317, microencapsulation of PRO317 is contemplated. Microencapsulation of recombinant proteins for sustained release has been successfully performed with human growth hormone (rhGH), interferon- (rhIFN-), interleukin-2, and MN rgp120. Johnson et al., *Nat. Med.,* 2: 795–799 (1996); *Yasuda, Biomed. Ther.,* 27: 1221–1223 (1993); Hora et al., *Bio/Technology,* 8: 755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

It is contemplated that conditions or diseases of the uterus, endometrial tissue, or other genital tissues or cardiac tissues may precipitate damage that is treatable with PRO317 or PRO317 agonist where PRO317 expression is reduced in the diseased state; or with antibodies to PRO317 or other PRO317 antagonists where the expression of PRO317 is increased in the diseased state. These conditions or diseases may be specifically diagnosed by the probing tests discussed above for physiologic and pathologic problems which affect the function of the organ.

The PRO317, PRO317 agonist, or PRO317 antagonist may be administered to a mammal with another biologically active agent, either separately or in the same formulation to treat a common indication for which they are appropriate. For example, it is contemplated that PRO317 can be administered together with EBAF-1 for those indications on which they demonstrate the same qualitative biological effects. Alternatively, where they have opposite effects, EBAF-1 may be administered together with an antagonist to PRO317, such as an anti-PRO317 antibody. Further, PRO317 may be administered together with VEGF for coronary ischemia where such indication is warranted, or with an anti-VEGF for cancer as warranted, or, conversely, an antagonist to PRO317 may be administered with VEGF for coronary ischemia or with anti-VEGF to treat cancer as warranted. These administrations would be in effective amounts for treating such disorders.

Native PRO301 (SEQ ID NO:119) has a Blast score of 246 and 30% homology at residues 24 to 282 of FIG. 44 with A33_HUMAN, an A33 antigen precursor. A33 antigen precursor, as explained in the Background is a tumor-specific antigen, and as such, is a recognized marker and therapeutic target for the diagnosis and treatment of colon cancer. The expression of tumor-specific antigens is often associated with the progression of neoplastic tissue disorders. Native PRO301 (SEQ ID NO:119) and A33_HUMAN also show a Blast score of 245 and 30% homology at residues 21 to 282 of FIG. 44 with A33_HUMAN, the variation dependent upon how spaces are inserted into the compared sequences. Native PRO301 (SEQ ID NO:119) also has a Blast score of 165 and 29% homology at residues 60 to 255 of FIG. 44 with HS46 KDA__1, a human coxsackie and adenovirus receptor protein, also known as cell surface protein HCAR. This region of PRO301 also shows a similar Blast score and homology with HSU90716__1. Expression of such proteins is usually associated with viral infection and therapeutics for the prevention of such infection may be accordingly conceived. As mentioned in the Background, the expression of viral receptors is often associated with neoplastic tumors.

Therapeutic uses for the PRO234 polypeptides of the invention includes treatments associated with leukocyte homing or the interaction between leukocytes and the endothelium during an inflammatory response. Examples include asthma, rheumatoid arthritis, psoriasis and multiple sclerosis.

Since the PRO231 polypeptide and nucleic acid encoding it possess sequence homology to a putative acid phosphatase and its encoding nucleic acid, probes based upon the PRO231 nucleotide sequence may be employed to identify other novel phosphatase proteins. Soluble forms of the PRO231 polypeptide may be employed as antagonists of membrane bound PRO231 activity both in vitro and in vivo. PRO231 polypeptides may be employed in screening assays designed to identify agonists or antagonists of the native PRO231 polypeptide, wherein such assays may take the form of any conventional cell-type or biochemical binding assay. Moreover, the PRO231 polypeptide may serve as a molecular marker for the tissues in which the polypeptide is specifically expressed.

PRO229 polypeptides can be fused with peptides of interest to determine whether the fusion peptide has an increased half-life over the peptide of interest. The PRO229 polypeptides can be used accordingly to increase the half-life of polypeptides of interest. Portions of PRO229 which cause the increase in half-life are an embodiment of the invention herein.

PRO238 can be used in assays which measure its ability to reduce substrates, including oxygen and Aceyl-CoA, and particularly, measure PRO238's ability to produce oxygen free radicals. This is done by using assays which have been-previously described. PRO238 can further be used to assay for candidates which block, reduce or reverse its reducing abilities. This is done by performing side by side assays where candidates are added in one assay having PRO238 and a substrate to reduce, and not added in another assay, being the same but for the lack of the presence of the candidate.

PRO233 polypeptides and portions thereof which have homology to reductase may also be useful for in vivo therapeutic purposes, as well as for various other applications. The identification of novel reductase proteins and related molecules may be relevant to a number of human disorders such as inflammatory disease, organ failure, atherosclerosis, cardiac injury, infertility, birth defects, premature aging, AIDS, cancer, diabetic complications and mutations in general. Given that oxygen free radicals and antioxidants appear to play important roles in a number of disease processes, the identification of new reductase proteins and reductase-like molecules is of special importance in that such proteins may serve as potential therapeutics for a variety of different human disorders. Such polypeptides may also play important roles in biotechnological and medical research, as well as various industrial applications. As a result, there is particular scientific and medical interest in new molecules, such as PRO233.

The PRO223 polypeptides of the present invention which exhibit serine carboxypeptidase activity may be employed in vivo for therapeutic purposes as well as for in vitro purposes. Those of ordinary skill in the art will well know how to employ PRO223 polypeptides for such uses.

PRO235 polypeptides and portions thereof which may be involved in cell adhesion are also useful for in vivo therapeutic purposes, as well as for various in vitro applications. In addition, PRO235 polypeptides and portions thereof may have therapeutic applications in disease states which involve cell adhesion. Given the physiological importance of cell adhesion mechanisms in vivo, efforts are currently being under taken to identify new, native proteins which are involved in cell adhesion. Therefore, peptides having homology to plexin are of particular interest to the scientific and medical communities.

Because the PRO236 and PRO262 polypeptides disclosed herein are homologous to various known β-galactosidase proteins, the PRO236 and PRO262 polypeptides disclosed herein will find use in conjugates of monoclonal antibodies and the polypeptide for specific killing of tumor cells by generation of active drug from a galactosylated prodrug (e.g., the generation of 5-fluorouridine from the prodrug β-D-galactosyl-5-fluorouridine). The PRO236 and PRO262 polypeptides disclosed herein may also find various uses both in vivo and in vitro, wherein those uses will be similar or identical to uses for which β-galactosidase proteins are now employed. Those of ordinary skill in the art will well know how to employ PRO236 and PRO262 polypeptides for such uses.

PRO239 polypeptides and portions thereof which have homology to densin may also be useful for in vivo therapeutic purposes, as well as for various in vitro applications. In addition, PRO239 polypeptides and portions thereof may have therapeutic applications in disease states which involve synaptic mechanisms, regeneration or cell adhesion. Given the physiological importance of synaptic processes, regeneration and cell adhesion mechanisms in vivo, efforts are currently being under taken to identify new, native proteins which are involved in synaptic machinery and cell adhesion. Therefore, peptides having homology to densin are of particular interest to the scientific and medical communities.

The PRO260 polypeptides described herein can be used in assays to determine their relation to fucosidase. In particular, the PRO260 polypeptides can be used in assays in determining their ability to remove fucose or other sugar residues from proteoglycans. The PRO260 polypeptides can be assayed to determine if they have any functional or locational similarities as fucosidase. The PRO260 polypeptides can then be used to regulate the systems in which they are integral.

PRO263 can be used in assays wherein CD44 antigen is generally used to determine PRO263 activity relative to that of CD44. The results can be used accordingly.

PRO270 polypeptides and portions thereof which effect reduction-oxidation (redox) state may also be useful for in vivo therapeutic purposes, as well as for various in vitro applications. More specifically, PRO270 polypeptides may affect the expression of a large variety of genes thought to be involved in the pathogenesis of AIDS, cancer, atherosclerosis, diabetic complications and in pathological conditions involving oxidative stress such as stroke and inflammation. In addition, PRO270 polypeptides and portions thereof may affect the expression of a genes which have a role in apoptosis. Therefore, peptides having homology to thioredoxin are particularly desirable to the scientific and medical communities.

PRO272 polypeptides and portions thereof which possess the ability to bind calcium may also have numerous in vivo therapeutic uses, as well as various in vitro applications. Therefore, peptides having homology to reticulocalbin are particularly desirable. Those with ordinary skill in the art will know how to employ PRO272 polypeptides and portions thereof for such purposes.

PRO294 polypeptides and portions thereof which have homology to collagen may also be useful for in vivo therapeutic purposes, as well as for various other applications. The identification of novel collagens and collage-like molecules may have relevance to a number of human disorders. Thus, the identification of new collagens and collage-like molecules is of special importance in that such proteins may serve as potential therapeutics for a variety of different human disorders. Such polypeptides may also play important roles in biotechnological and medical research as well as various industrial applications. Given the large number of uses for collagen, there is substantial interest in polypeptides with homology to the collagen molecule.

PRO295 polypeptides and portions thereof which have homology to integrin may also be useful for in vivo therapeutic purposes, as well as for various other applications. The identification of novel integrins and integrin-like molecules may have relevance to a number of human disorders such as modulating the binding or activity of cells of the immune system. Thus, the identification of new integrins and integrin-like molecules is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO295.

As the PRO293 polypeptide is clearly a leucine rich repeat polypeptide homologue, the peptide can be used in all applications that the known NLRR-1 and NLRR-2 polypeptides are used. The activity can be compared between these peptides and thus applied accordingly.

The PRO247 polypeptides described herein can be used in assays in which densin is used to determine the activity of PRO247 relative to densin or these other proteins. The results can be used accordingly in diagnostics and/or therapeutic applications with PRO247.

PRO302, PRO303, PRO304, PRO307 and PRO343 polypeptides of the present invention which possess protease activity may be employed both in vivo for therapeutic purposes and in vitro. Those of ordinary skill in the art will well know how to employ the PRO302, PRO303, PRO304, PRO307 and PRO343 polypeptides of the present invention for such purposes.

PRO328 polypeptides and portions thereof which have homology to GLIP and CRISP may also be useful for in vivo therapeutic purposes, as well as for various other applications. The identification of novel GLIP and CRISP-like molecules may have relevance to a number of human disorders which involve transcriptional regulation or are over expressed in human tumors. Thus, the identification of new GLIP and CRISP-like molecules is of special importance in that such proteins may serve as potential therapeutics for a variety of different human disorders. Such polypeptides may also play important roles in biotechnological and medical research as well as in various industrial applications. As a result, there is particular scientific and medical interest in new molecules, such as PRO328.

Uses for PRO335, PRO331 or PRO326 including uses in competitive assays with LIG-1, ALS and decorin to determine their relative activities. The results can be used accordingly. PRO335, PRO331 or PRO326 can also be used in assays where LIG-1 would be used to determine if the same effects are incurred.

PRO332 contains GAG repeat (GKEK) at amino acid positions 625–628 in FIG. 108 (SEQ ID NO:310). Slippage in such repeats can be associated with human disease. Accordingly, PRO332 can use useful for the treatment of such disease conditions by gene therapy, i.e. by introduction of a gene containing the correct GKEK sequence motif.

Other uses of PRO334 include use in assays in which fibrillin or fibulin would be used to determine the relative activity of PRO334 to fibrillin or fibulin. In particular, PRO334 can be used in assays which require the mechanisms imparted by epidermal growth factor repeats.

Native PRO346 (SEQ ID NO:320) has a Blast score of 230, corresponding to 27% homology between amino acid residues 21 to 343 with residues 35 to 1040 CGM6_HUMAN, a carcinoembryonic antigen cgm6 precursor. This homology region includes nearly all but 2 N-terminal extracellular domain residues, including an immunoglobulin superfamily homology at residues 148 to 339 of PRO346 in addition to several transmembrane residues (340–343). Carcinoembryonic antigen precursor, as explained in the Background is a tumor-specific antigen, and as such, is a recognized marker and therapeutic target for the diagnosis and treatment of colon cancer. The expression of tumor-specific antigens is often associated with the progression of neoplastic tissue disorders. Native PRO346 (SEQ ID NO:320) and P_W06874, a human carcinoembryonic antigen CEA-d have a Blast score of 224 and homology of 28% between residues 2 to 343 and 67 to 342, respectively. This homology includes the entire extracellular domain residues of native PRO346, minus the initiator methionine (residues 2 to 18) as well as several transmembrane residues (340–343).

PRO268 polypeptides which have protein disulfide isomerase activity will be useful for many applications where protein disulfide isomerase activity is desirable including, for example, for use in promoting proper disulfide bond formation in recombinantly produced proteins so as to increase the yield of correctly folded protein. Those of ordinary skill in the art will readily know how to employ such PRO268 polypeptides for such purposes.

PRO330 polypeptides of the present invention which possess biological activity related to that of the prolyl 4-hydroxylase alpha subunit protein may be employed both in vivo for therapeutic purposes and in vitro. Those of ordinary skill in the art will well know how to employ the PRO330 polypeptides of the present invention for such purposes.

Uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel-Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fe), typically that of a human immunoglobulin [Jones et al., *Nature,* 321:522–525 (1986); Riechmann et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al.; *Nature,* 332:323–327 (1988); Verhoeyen et al., *Science,* 239: 1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies [Cole et al., *Monoclonal Antibodies and Cancer Therapy*, Alan R. Liss, p. 77 (1985) and Boerner et al., *J. Immunol.,* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191–1195 (1992) and Shopes, *J. Immunol.,* 148:2918–2922 (1992). Homodimeric antibodies with enhanced anti-tumor activity may also be prepared using heterobifunctional cross-linkers as described in Wolff et al.

*Cancer Research,* 53: 2560–2565 (1993). Alternatively, an antibody can be engineered that has dual Fc regions and may thereby have enhanced complement lysis and ADCC capabilities. See Stevenson et al., *Anti-Cancer Drug Design,* 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286–288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889–7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST2 (Altschul, and Gish, *Methods in Enzymology* 266: 460–80 (1996); http://blast.wustl/edu/blast/README.html) as a comparison of the ECD protein sequences to a 6 frame translation of the EST sequences. Those comparisons with a Blast score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences. In addition, the consensus DNA sequences obtained were often (but not always) extended using repeated cycles of BLAST and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward (.f) and reverse (.r) PCR primers generally range from 20 to 30 nucleotides and are often designed to give a PCR product of about 100–1000 bp in length. The probe (.p) sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or PRKD; pRK5B is a precursor of pRK5D that does not contain the SfiI site; see, Holmes et al., *Science*, 253:1278–1280 (1991)) in the unique XhoI and NotI sites.

Example 2

Isolation of cDNA Clones Encoding PRO211 and PRO217

Consensus DNA sequences were assembled as described in Example 1 above and were designated as DNA28730 and DNA28760, respectively. Based on these consensus sequences, oligonucleotides were synthesized and used to identify by PCR a cDNA library that contained the sequences of interest and for use as probes to isolate a clone of the full-length coding sequence for the PRO211 and PRO217 polypeptides. The libraries used to isolate DNA32292-1131 and DNA33094-1131 were fetal lung libraries.

cDNA clones were sequenced in their entirety. The entire nucleotide sequences of PRO211 (DNA32292-1131) and PRO217 (UNQ191) are shown in FIG. 1 (SEQ ID NO:1)

and FIG. 3 (SEQ ID NO:3), respectively. The predicted polypeptides are 353 and 379 amino acid in length, respectively, with respective molecular weights of approximately 38,190 and 41,520 daltons.

The oligonucleotide sequences used in the above procedures were the following:

28730.p (OLI 516) (SEQ ID NO:5)

5'-AGGGAGCACGGACAGTGTGCAGATGTG-GACGAGTGCTCACTAGCA-3'

28730.f (OLI 517) (SEQ ID NO:6)

5'-AGAGTGTATCTCTGGCTACGC-3'

28730.r (OLI 518) (SEQ ID NO:7)

5'-TAAGTCCGGCACATTACAGGTC-3'

28760.p (OLI 617) (SEQ ID NO:8)

5'-CCCACGATGTATGAATGGTGGACTTTGT-GTGACTCCTGGTTTCTGCATC-3'

28760.f (OLI 618) (SEQ ID NO:9)

5'-AAAGACGCATCTGCGAGTGTCC-3'

28760.r (OLI 619) (SEQ ID NO:10)

5'-TGCTGATTTCACACTGCTCTCCC-3'

Example 3

Isolation of cDNA Clones Encoding Human PRO230

A consensus DNA sequence was assembled relative to the other identified EST sequences as described in Example 1 above, wherein the consensus sequence is designated herein as DNA30857. An EST proprietary to Genentech was employed in the consensus assembly. The EST is designated as DNA20088 and has the nucleotide sequence shown in FIG. 7 (SEQ ID NO:13).

Based on the DNA30857 consensus sequence, oligonucleotides were synthesized to identify by PCR a cDNA library that contained the sequence of interest and for use as probes to isolate a clone of the full-length coding sequence for PRO230.

A pair of PCR primers (forward and reverse) were synthesized:

forward PCR primer 5'-TTCGAGGCCTCTGAGAAGTG-GCCC-3' (SEQ ID NO:14)

reverse PCR primer 5'-GGCGGTATCTCTCTGGCCTCCC-3' (SEQ ID NO:15)

Additionally, a synthetic oligonucleotide hybridization probe was constructed from the consensus DNA30857 sequence which had the following nucleotide sequence hybridization probe

5'-TTCTCCACAGCAGCTGTGGCATC-CGATCGTGTCTCAATCCATTCTCTGGG-3' (SEQ ID NO:16)

In order to screen several libraries for a source of a full-length clone, DNA from the libraries was screened by PCR amplification with the PCR primer pair identified above. A positive library was then used to isolate clones encoding the PRO230 gene using the probe oligonucleotide and one of the PCR primers.

RNA for construction of the cDNA libraries was isolated from human fetal lung tissue. DNA sequencing of the clones isolated as described above gave the full-length DNA sequence for PRO230 (herein designated as DNA33223-1136 and the derived protein sequence for PRO230.

The entire nucleotide sequence of DNA33223-1136 is shown in FIG. 5 (SEQ ID NO:11). Clone DNA33223-1136 contains a single open reading frame with an apparent translational initiation site at nucleotide positions 100–103 and ending at the stop codon at nucleotide positions 1501–1503 (FIG. 5; SEQ ID NO:11). The predicted polypeptide precursor is 467 amino acids long (FIG. 6).

Example 4

Isolation of cDNA Clones Encoding Human PRO232

A consensus DNA sequence was assembled relative to the other identified EST sequences as described in Example 1 above, wherein the consensus sequence is designated herein as DNA30935. Based on the DNA30935 consensus sequence, oligonucleotides were synthesized to identify by PCR a cDNA library that contained the sequence of interest and for use as probes to isolate a clone of the full-length coding sequence for PRO232.

A pair of PCR primers (forward and reverse) were synthesized:

forward PCR primer 5'-TGCTGTGCTACTCCTG-CAAAGCCC-3' (SEQ ID NO:19)

reverse PCR primer 5-TGCACAAGTCGGTGTCACAG-CACG-3' (SEQ ID NO:20)

Additionally, a synthetic oligonucleotide hybridization probe was constructed from the consensus DNA30935 sequence which had the following nucleotide sequence hybridization probe

5'-AGCAACGAGGACTGCCTGCAGGTG-GAGAACTGCACCCAGCTGGG-3' (SEQ ID NO:21)

In order to screen several libraries for a source of a full-length clone, DNA from the libraries was screened by PCR amplification with the PCR primer pair identified above. A positive library was then used to isolate clones encoding the PRO232 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO232 [herein designated as DNA34435-1140] and the derived protein sequence for PRO232.

The entire nucleotide sequence of DNA34435-1140 is shown in FIG. 8 (SEQ ID NO:17). Clone DNA34435-1140 contains a single open reading frame with an apparent translational initiation site at nucleotide positions 17–19 and ending at the stop codon at nucleotide positions 359–361 (FIG. 8; SEQ ID NO:17). The predicted polypeptide precursor is 114 amino acids long (FIG. 9). Clone DNA34435-1140 has been deposited with ATCC on Sep. 16, 1997 and is assigned ATCC deposit no. ATCC 209250.

Analysis of the amino acid sequence of the full-length PRO232 suggests that it possesses 35% sequence identity with a stem cell surface antigen from *Gallus gallus*.

Example 5

Isolation of cDNA Clones Encoding PRO187

A proprietary expressed sequence tag (EST) DNA database (LIFESEQ™, Incyte Pharmaceuticals, Palo Alto, Calif.) was searched and an EST (#843193) was identified which showed homology to fibroblast growth factor (FGF-8) also known as androgen-induced growth factor. mRNA was isolated from human fetal lung tissue using reagents and protocols from Invitrogen, San Diego, Calif. (Fast Track 2). The cDNA libraries used to isolate the cDNA clones were constructed by standard methods using commercially available reagents (e.g., Invitrogen, San Diego, Calif., Life Technologies, Gaithersburg, Md.). The cDNA was primed with oligo dT containing a NotI site, linked with blunt to SalI hemikinased adaptors, cleaved with NotI, sized appropriately by gel electrophoresis, and cloned in a defined orientation into the cloning vector pRK5D using reagents and protocols from Life Technologies, Gaithersburg, Md. (Super Script Plasmid System). The double-stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

Several libraries from various tissue sources were screened by PCR amplification with the following oligonucleotide probes:

IN843193.f (OLI315) (SEQ ID NO:24)

5'-CAGTACGTGAGGGACCAGGGCGCCATGA-3'

IN843193.r (OLI 317) (SEQ ID NO:25)

5'-CCGGTGACCTGCACGTGCTTGCCA-3'

A positive library was then used to isolate clones encoding the PRO187 gene using one of the above oligonucleotides and the following oligonucleotide probe:

IN843193.p (OLI 316) (SEQ ID NO:26)

5'-GCGGATCTGCCGCCTGCTCANCTGGTCG-GTCATGGCGCCCT-3'

A cDNA clone was sequenced in entirety. The entire nucleotide sequence of PRO187 (DNA27864-1155) is shown in FIG. 10 (SEQ ID NO:22). Clone DNA27864-1155 contains a single open reading frame with an apparent translational initiation site at nucleotide position 1 (FIG. 10; SEQ ID NO:22). The predicted polypeptide precursor is 205 amino acids long. Clone DNA27864-1155 has been deposited with the ATCC (designation: DNA27864-1155) and is assigned ATCC deposit no. ATCC 209375.

Based on a BLAST and FastA sequence alignment analysis (using the ALIGN computer program) of the full-length sequence, the PRO187 polypeptide shows 74% amino acid sequence identity (Blast score 310) to human fibroblast growth factor-8 (androgen-induced growth factor).

Example 6

Isolation of cDNA Clones Encoding PRO265

A consensus DNA sequence was assembled relative to other EST sequences as described in Example 1 above using phrap. This consensus sequence is herein designated DNA33679. Based on the DNA33679 consensus sequence, oligonucleotides were synthesized: 1) to identify by PCR a cDNA library that contained the sequence of interest, and 2) for use as probes to isolate a clone of the full-length coding sequence for PRO265.

PCR primers (two forward and one reverse) were synthesized:

forward PCR primer A: 5'-CGGTCTACCTGTATG-GCAACC-3' (SEQ ID NO:29);

forward PCR primer B: 5'-GCAGGACAACCAGATAAAC-CAC-3' (SEQ ID NO:30);

reverse PCR primer 5'-ACGCAGATTTGAGAAGGCT-GTC-3' (SEQ ID NO:31)

Additionally, a synthetic oligonucleotide hybridization probe was constructed from the consensus DNA33679 sequence which had the following nucleotide sequence hybridization probe

5'-TTCACGGGCTGCTCTTGCCCAGCTCT-TGAAGCTTGAAGAGCTGCAC-3' (SEQ ID NO:32)

In order to screen several libraries for a source of a full-length clone, DNA from the libraries was screened by PCR amplification with PCR primer pairs identified above. A positive library was then used to isolate clones encoding the PRO265 gene using the probe oligonucleotide and one of the PCR primers.

RNA for construction of the cDNA libraries was isolated from human a fetal brain library.

DNA sequencing of the clones isolated as described above gave the full-length DNA sequence for PRO265 [herein designated as DNA36350-1158](SEQ ID NO:27) and the derived protein sequence for PRO265.

The entire nucleotide sequence of DNA36350-1158 is shown in FIG. 12 (SEQ ID NO:27). Clone DNA36350-1158 contains a single open reading frame with an apparent translational initiation site at nucleotide positions 352–354 and ending at the stop codon at positions 2332–2334 (FIG. 12). The predicted polypeptide precursor is 660 amino acids long (FIG. 13). Clone DNA36350-1158 has been deposited with ATCC and is assigned ATCC deposit no. ATCC 209378.

Analysis of the amino acid sequence of the full-length PRO265 polypeptide suggests that portions of it possess significant homology to the fibromodulin and the fibromodulin precursor, thereby indicating that PRO265 may be a novel member of the leucine rich repeat family, particularly related to fibromodulin.

Example 7

Isolation of cDNA Clones Encoding Human PRO219

A consensus DNA sequence was assembled relative to other EST sequences using phrap as described in Example 1 above. This consensus sequence is herein designated DNA28729. Based on the DNA28729 consensus sequence, oligonucleotides were synthesized: 1) to identify by PCR a cDNA library that contained the sequence of interest, and 2) for use as probes to isolate a clone of the full-length coding sequence for PRO219.

A pair of PCR primers (forward and reverse) were synthesized:

forward PCR primer 5'-GTGACCCTGGTTGT-GAATACTCC-3' (SEQ ID NO:35)

reverse PCR primer 5'-ACAGCCATGGTCTATAGCTTGG-3' (SEQ ID NO:36)

Additionally, a synthetic oligonucleotide hybridization probe, was constructed from the consensus DNA28729 sequence which had the following nucleotide sequence hybridization probe

5'-GCCTGTCAGTGTCCTGAGGGACACGT-GCTCCGCAGCGATGGGAAG-3' (SEQ ID NO:37)

In order to screen several libraries for a source of a full-length clone, DNA from the libraries was screened by PCR amplification with the PCR primer pair identified above. A positive library was then used to isolate clones encoding the PRO219 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO219 [herein designated as DNA32290-1164] (SEQ ID NO:33) and the derived protein sequence for PRO219.

The entire nucleotide sequence of DNA32290-1164 is shown in FIG. 14 (SEQ ID NO:33). Clone DNA32290-1164 contains a single open reading frame with an apparent translational initiation site at nucleotide positions 204–206 and ending at the stop codon at nucleotide positions 2949–2951 (FIG. 14). The predicted polypeptide precursor is 915 amino acids long (FIG. 15). Clone DNA32290-1164 has been deposited with ATCC and is assigned ATCC deposit no. ATCC 209384.

Analysis of the amino acid sequence of the full-length PRO219 polypeptide suggests that portions of it possess significant homology to the mouse and human matrilin-2 precursor polypeptides.

Example 8

Isolation of cDNA Clones Encoding Human PRO246

A consensus DNA sequence was assembled relative to other EST sequences using phrap as described in Example 1 above. This consensus sequence is herein designated DNA30955. Based on the DNA30955 consensus sequence, oligonucleotides were synthesized: 1) to identify by PCR a cDNA library that contained the sequence of interest, and 2) for use as probes to isolate a clone of the full-length coding sequence for PRO246.

A pair of PCR primers (forward and reverse) were synthesized:

forward PCR primer 5'-AGGGTCTCCAGGAGAAA-GACTC-3' (SEQ ID NO:40)

reverse PCR primer 5'-ATTGTGGGCCTTGCAGACATA-GAC-3' (SEQ ID NO:41)

Additionally, a synthetic oligonucleotide hybridization probe was constructed from the consensus DNA30955 sequence which had the following nucleotide sequence hybridization probe

5'-GGCCACAGCATCAAAACCTTAGAACT-CAATGTACTGGTTCCTCCAGCTCC-3' (SEQ ID NO:42)

In order to screen several libraries for a source of a full-length clone, DNA from the libraries was screened by PCR amplification with the PCR primer pair identified above. A positive library was then used to isolate clones encoding the PRO246 gene using the probe oligonucleotide and one of the PCR primers.

RNA for construction of the cDNA libraries was isolated from human fetal liver tissue. DNA sequencing of the clones isolated as described above gave the full-length DNA sequence for PRO246 [herein designated as DNA35639-1172] (SEQ ID NO:38) and the derived protein sequence for PRO246.

The entire nucleotide sequence of DNA35639-1172 is shown in FIG. 16 (SEQ ID NO:38). Clone DNA35639-1172 contains a single open reading frame with an apparent translational initiation site at nucleotide positions 126–128 and ending at the stop codon at nucleotide positions 1296–1298 (FIG. 16). The predicted polypeptide precursor is 390 amino acids long (FIG. 17). Clone DNA35639-1172 has been deposited with ATCC and is assigned ATCC deposit no. ATCC 209396.

Analysis of the amino acid sequence of the full-length PRO246 polypeptide suggests that it possess significant homology to the human cell surface protein HCAR, thereby indicating that PRO246 may be a novel cell surface virus receptor.

Example 9

Isolation of cDNA Clones Encoding Human PRO228

A consensus DNA sequence was assembled relative to other EST sequences using phrap as described in Example 1 above. This consensus sequence is herein designated DNA28758. An EST proprietary to Genentech was employed in the consensus assembly. This EST is shown in FIG. 20 (SEQ ID NO:50) and is herein designated as DNA21951.

Based on the DNA28758 consensus sequence, oligonucleotides were synthesized: 1) to identify by PCR a cDNA library that contained the sequence of interest, and 2) for use as probes to isolate a clone of the full-length coding sequence for PRO228.

PCR primers (forward and reverse) were synthesized:

forward PCR primer 5'-GGTAATGAGCTCCATTACAG-3' (SEQ ID NO:51)

forward PCR primer 5'-GGAGTAGAAAGCGCATGG-3' (SEQ ID NO:52)

forward PCR primer 5'-CACCTGATACCATGAATG-GCAG-3' (SEQ ID NO:53)

reverse PCR primer 5'-CGAGCTCGAATTAATTCG-3' (SEQ ID NO:54)

reverse PCR primer 5'-GGATCTCCTGAGCTCAGG-3' (SEQ ID NO:55)

reverse PCR primer 5'-CCTAGTTGAGTGATCCTTG-TAAG-3' (SEQ ID NO:56)

Additionally, a synthetic oligonucleotide hybridization probe was constructed from the consensus DNA28758 sequence which had the following nucleotide sequence hybridization probe

5'-ATGAGACCCACACCTCATGCCGCTG-TAATCACCTGACACATTTTGCAATT-3' (SEQ ID NO:57)

In order to screen several libraries for a source of a full-length clone, DNA from the libraries was screened by PCR amplification with the PCR primer pairs identified above. A positive library was then used to isolate clones encoding the PRO228 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO228 [herein designated as DNA33092-1202] (SEQ ID NO:48) and the derived protein sequence for PRO228.

The entire nucleotide sequence of DNA33092-1202 is shown in FIG. 18 (SEQ ID NO:48). Clone DNA33092-1202 contains a single open reading frame with an apparent translational initiation site at nucleotide positions 24–26 of SEQ ID NO:48 and ending at the stop codon after nucleotide position 2093 of SEQ ID NO:48. The predicted polypeptide precursor is 690 amino acids long (FIG. 19). Clone DNA33092-1202 has been deposited with ATCC and is assigned ATCC deposit no. ATCC 209420.

Analysis of the amino acid sequence of the full-length PRO228 polypeptide suggests that portions of it possess significant homology to the secretin-related proteins CD97 and EMR1 as well as the secretin member, latrophilin, thereby indicating that PRO228 may be a new member of the secretin related proteins.

Example 10

Isolation of cDNA Clones Encoding Human PRO533

The EST sequence accession number AF007268, a murine fibroblast growth factor (FGF-15) was used to search various public EST databases (e.g., GenBank, Dayhoff, etc.). The search was performed using the computer program BLAST or BLAST2 [Altschul et al., *Methods in Enzymology,* 266:460–480 (1996); http://blast.wustl/edu/blast/README.html] as a comparison of the ECD protein sequences to a 6 frame translation of the EST sequences. The search resulted in a hit with GenBank EST AA220994, which has been identified as stratagene NT2 neuronal precursor 937230.

Based on the Genbank EST AA220994 sequence, oligonucleotides were synthesized: 1) to identify by PCR a cDNA library that contained the sequence of interest, and 2) for use as probes to isolate a clone of the full-length coding sequence. Forward and reverse PCR primers may range from 20 to 30 nucleotides (typically about 24), and are designed to give a PCR product of 100–1000 bp in length. The probe sequences are typically 40–55 bp (typically about 50) in length. In order to screen several libraries for a source of a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the PCR primers.

In order to screen several libraries for a source of a full-length clone, DNA from the libraries was screened by PCR amplification with the PCR primer pair identified below. A positive library was then used to isolate clones encoding the PRO533 gene using the probe oligonucleotide and one of the PCR primers.

RNA for construction of the cDNA libraries was isolated from human fetal retina. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278–1280 (1991)) in the unique XhoI and NotI sites.

A cDNA clone was sequenced in its entirety. The full length nucleotide sequence of PRO533 is shown in FIG. 21 (SEQ ID NO:58). Clone DNA49435-1219 contains a single open reading frame with an apparent translational initiation site at nucleotide positions 459461 (FIG. 21; SEQ ID NO:58). The predicted polypeptide precursor is 216 amino acids long. Clone DNA47412-1219 has been deposited with ATCC and is assigned ATCC deposit no. ATCC 209480.

Based on a BLAST-2 and FastA sequence alignment analysis of the full-length sequence, PRO533 shows amino acid sequence identity to fibroblast growth factor (53%).

The oligonucleotide sequences used in the above procedure were the following:

FGF15.forward: 5'-ATCCGCCCAGATGGCTACAATGT-GTA-3' (SEQ ID NO:60);

FGF15.probe: 5'-GCCTCCCGGTCTCCCTGAGCAGT-GCCAAACAGCGGCAGTGTA-3' (SEQ ID NO:61);

FGF15.reverse: 5'-CCAGTCCGGTGACAAGCCCAAA-3' (SEQ ID NO:62).

Example 11

Isolation of cDNA Clones Encoding Human PRO245

A consensus DNA sequence was assembled relative to the other identified EST sequences as described in Example 1 above, wherein the consensus sequence is designated herein as DNA30954.

Based on the DNA30954 consensus sequence, oligonucleotides were synthesized to identify by PCR a cDNA library that contained the sequence of interest and for use as probes to isolate a clone of the full-length coding sequence for PRO245.

A pair of PCR primers (forward and reverse) were synthesized:

forward PCR primer 5'-ATCGTTGTGAAGTTAGTGC-CCC-3' (SEQ ID NO:65)

reverse PCR primer 5'-ACCTGCGATATCCAACA-GAATTG-3' (SEQ ID NO:66)

Additionally, a synthetic oligonucleotide hybridization probe was constructed from the consensus DNA30954 sequence which had the following nucleotide sequence hybridization probe

5'-GGAAGAGGATACAGTCACTCTGGAAG-TATTAGTGGCTCCAGCAGTTCC-3' (SEQ ID NO:67)

In order to screen several libraries for a source of a full-length clone, DNA from the libraries was screened by PCR amplification with the PCR primer pair identified above. A positive library was then used to isolate clones encoding the PRO245 gene using the probe oligonucleotide and one of the PCR primers.

RNA for construction of the cDNA libraries was isolated from human fetal liver tissue. DNA sequencing of the clones isolated as described above gave the full-length DNA sequence for PRO245 [herein designated as DNA35638-1141] and the derived protein sequence for PRO245.

The entire nucleotide sequence of DNA35638–1141 is shown in FIG. 23 (SEQ ID NO:63). Clone DNA35638-1141 contains a single open reading frame with an apparent translational initiation site at nucleotide positions 89–91 and ending at the stop codon at nucleotide positions 1025–1027 (FIG. 23; SEQ ID NO:63). The predicted polypeptide precursor is 312 amino acids long (FIG. 24). Clone DNA35638-1141 has been deposited with ATCC on Sep. 16, 1997 and is assigned ATCC deposit no. ATCC 209265.

Analysis of the amino acid sequence of the full-length PRO245 suggests that a portion of it possesses 60% amino acid identity with the human c-myb protein and, therefore, may be a new member of the transmembrane protein receptor tyrosine kinase family.

Example 12

Isolation of cDNA Clones Encoding Human PRO220, PRO221 and PRO227 (a) PRO220

A consensus DNA sequence was assembled relative to the other identified EST sequences as described in Example 1 above, wherein the consensus sequence is designated herein as DNA28749. Based on the DNA28749 consensus sequence, oligonucleotides were synthesized to identify by PCR a cDNA library that contained the sequence of interest and for use as probes to isolate a clone of the full-length coding sequence for PRO220.

A pair of PCR primers (forward and reverse) were synthesized:

forward PCR primer 5'-TCACCTGGAGCCTTTATTG-GCC-3' (SEQ ID NO:74)

reverse PCR primer 5'-ATACCAGCTATAACCAGGCT-GCG-3' (SEQ ID NO:75)

Additionally, a synthetic oligonucleotide hybridization probe was constructed from the consensus DNA28749 sequence which had the following nucleotide sequence:

hybridization probe

5'-CAACAGTAAGTGGTTTGATGCTCTTC-CAAATCTAGAGATTCTGATGATTGGG-3' (SEQ ID NO:76).

In order to screen several libraries for a source of a full-length clone, DNA from the libraries was screened by PCR amplification with the PCR primer pair identified above. A positive library was then used to isolate clones encoding the PRO220 gene using the probe oligonucleotide and one of the PCR primers.

RNA for construction of the cDNA libraries was isolated from human fetal lung tissue. DNA sequencing of the clones isolated as described above gave the full-length DNA sequence for PRO220 [herein designated as DNA32298-1132 and the derived protein sequence for PRO220.

The entire nucleotide sequence of DNA32298-1132 is shown in FIG. 25 (SEQ ID NO:68). Clone DNA32298-1132 contains a single open reading frame with an apparent translational initiation site at nucleotide positions 480482 and ending at the stop codon at nucleotide positions 2604–2606 (FIG. 25). The predicted polypeptide precursor is 708 amino acids long (FIG. 26). Clone DNA32298-1132 has been deposited with ATCC and is assigned ATCC deposit no. ATCC 209257.

Analysis of the amino acid sequence of the full-length PRO220 shows it has homology to member of the leucine rich repeat protein superfamily, including the leucine rich repeat protein and the neuronal leucine-rich repeat protein 1.

(b) PRO221

A consensus DNA sequence was assembled relative to the other identified EST sequences as described in Example 1 above, wherein the consensus sequence is designated herein as DNA28756. Based on the DNA28756 consensus sequence, oligonucleotides were synthesized to identify by PCR a cDNA library that contained the sequence of interest and for use as probes to isolate a clone of the full-length coding sequence for PRO221.

A pair of PCR primers (forward and reverse) were synthesized:

forward PCR primer 5-CCATGTGTCTCCTCCTA-CAAAG-3' (SEQ ID NO:77)

reverse PCR primer 5'-GGGAATAGATGTGATCTGAT-TGG-3' (SEQ ID NO:78)

Additionally, a synthetic oligonucleotide hybridization probe was constructed from the consensus DNA28756 sequence which had the following nucleotide sequence:

hybridization probe

5'-CACCTGTAGCAATGCAAATCTCAAG-GAAATACCTAGAGATCTTCCTCCTG-3' (SEQ ID NO:79)

In order to screen several libraries for a source of a full-length clone, DNA from the libraries was screened by PCR amplification with the PCR primer pair identified above. A positive library was then used to isolate clones encoding the PRO221 gene using the probe oligonucleotide and one of the PCR primers.

RNA for construction of the cDNA libraries was isolated from human fetal lung tissue. DNA sequencing of the clones isolated as described above gave the full-length DNA sequence for PRO221 [herein designated as DNA33089-1132 and the derived protein sequence for PRO221.

The entire nucleotide sequence of DNA33089-1132 is shown in FIG. 27 (SEQ ID NO:70). Clone DNA33089-1132 contains a single open reading frame with an apparent translational initiation site at nucleotide positions 179–181 and ending at the stop codon at nucleotide positions 956–958 (FIG. 27). The predicted polypeptide precursor is 259 amino acids long (FIG. 28). PRO221 is believed to have a transmembrane region at amino acids 206–225. Clone DNA33089-1132 has been deposited with ATCC and is assigned ATCC deposit no. ATCC 209262.

Analysis of the amino acid sequence of the full-length PRO221 shows it has homology to member of the leucine rich repeat protein superfamily, including the SLIT protein.

(c) PRO227

A consensus DNA sequence was assembled relative to the other identified EST sequences as described in Example 1 above, wherein the consensus sequence is designated herein as DNA28740. Based on the DNA28740 consensus sequence, oligonucleotides were synthesized to identify by PCR a cDNA library that contained the sequence of interest and for use as probes to isolate a clone of the full-length coding sequence for PRO227.

A pair of PCR primers (forward and reverse) were synthesized:

forward PCR primer 5'-AGCAACCGCCTGAAGCTCATCC-3' (SEQ ID NO:80)

reverse PCR primer 5'-AAGGCGCGGTGAAAGATGTAGACG-3' (SEQ ID NO:81)

Additionally, a synthetic oligonucleotide hybridization probe was constructed from the consensus DNA28740 sequence which had the following nucleotide sequence:

hybridization probe

5'GACTACATGTTTCAGGACCTGTACAACCTCAAGTCACTGGAGGTTGGCGA-3' (SEQ ID NO: 82).

In order to screen several libraries for a source of a full-length clone, DNA from the libraries was screened by PCR amplification with the PCR primer pair identified above. A positive library was then used to isolate clones encoding the PRO227 gene using the probe oligonucleotide and one of the PCR primers.

RNA for construction of the cDNA libraries was isolated from human fetal lung tissue. DNA sequencing of the clones isolated as described above gave the full-length DNA sequence for PRO227 [herein, designated as DNA33786–1132 and the derived protein sequence for PRO227.

The entire nucleotide sequence of DNA33786-1132 is shown in FIG. 29 (SEQ ID NO:72). Clone DNA33786-1132 contains a single open reading frame with an apparent translational initiation site at nucleotide positions 33–35 and ending at the stop codon at nucleotide positions 1893–1895 (FIG. 29). The predicted polypeptide precursor is 620 amino acids long (FIG. 30). PRO227 is believed to have a transmembrane region. Clone DNA33786-1132 has been deposited with ATCC and is assigned ATCC deposit no. ATCC 209253.

Analysis of the amino acid sequence of the full-length PRO221 shows it has homology to member of the leucine rich repeat protein superfamily, including the platelet glycoprotein V precursor and the human glycoprotein V.

Example 13

Isolation of cDNA Clones Encoding Human PRO258

A consensus DNA sequence was assembled relative to other EST sequences using phrap as described in Example 1 above. This consensus sequence is herein designated DNA28746.

Based on the DNA28746 consensus sequence, oligonucleotides were synthesized: 1) to identify by PCR a cDNA library that contained the sequence of interest, and 2) for use as probes to isolate a clone of the full-length coding sequence for PRO258.

PCR primers (forward and reverse) were synthesized:

forward PCR primer 5'-GCTAGGAATTCCACAGAAGCCC-3' (SEQ ID NO:85)

reverse PCR primer 5'-AACCTGGAATGTCACCGAGCTG-3' (SEQ ID NO:86)

reverse PCR primer 5'-CCTAGCACAGTGACGAGGGACTTGGC-3' (SEQ ID NO:87)

Additionally, synthetic oligonucleotide hybridization probes were constructed from the consensus DNA28740 sequence which had the following nucleotide sequence:

hybridization probe

5'-AAGACACAGCCACCCTAAACTGTCAGTCTTCTGGGAGCAAGCCTGCAGCC-3' (SEQ ID NO:88)

5'-GCCCTGGCAGACGAGGGCGAGTACACCTGCTCAATCTTCACTATGCCTGT-3' (SEQ ID NO: 89)

In order to screen several libraries for a source of a full-length clone, DNA from the libraries was screened by PCR amplification with the PCR primer pair identified above. A positive library was then used to isolate clones encoding the PRO258 gene using the probe oligonucleotide and one of the PCR primers.

RNA for construction of the cDNA libraries was isolated from human fetal lung tissue. DNA sequencing of the clones isolated as described above gave the full-length DNA sequence for PRO258 [herein designated as DNA35918-1174] (SEQ ID NO:83) and the derived protein sequence for PRO258.

The entire nucleotide sequence of DNA35918-1174 is shown in FIG. 31 (SEQ ID NO:83). Clone DNA35918-1174 contains a single open reading frame with an apparent translational initiation site at nucleotide positions 147–149 of SEQ ID NO: 83 and ending at the stop codon after nucleotide position 1340 of SEQ ID NO:83 (FIG. 31). The predicted polypeptide precursor is 398 amino acids long (FIG. 32). Clone DNA35918-1174 has been deposited with ATCC and is assigned ATCC deposit no. ATCC 209402.

Analysis of the amino acid sequence of the full-length PRO258 polypeptide suggests that portions of it possess significant homology to the CRTAM and the poliovirus receptor and have an Ig domain, thereby indicating that PRO258 is a new member of the Ig superfamily.

Example 14

Isolation of cDNA Clones Encoding Human PRO266

An expressed sequence tag database was searched for ESTs having homology to SLIT, resulting in the identification of a single EST sequence designated herein as T73996. Based on the T73996 EST sequence, oligonucleotides were synthesized: 1) to identify by PCR a cDNA library that contained the sequence of interest, and 2) for use as probes to isolate a clone of the full-length coding sequence for PRO266.

A pair of PCR primers (forward and reverse) were synthesized:

forward PCR primer 5'-GTTGGATCTGGGCAACAATAAC-3' (SEQ ID NO:92)

reverse PCR primer 5'-ATTGTTGTGCAGGCTGAGTTTAAG-3' (SEQ ID NO:93)

Additionally, a synthetic oligonucleotide hybridization probe was constructed which had the following nucleotide sequence hybridization probe

5'-GGTGGCTATACATGGATAGCAATTACCTGGACACGCTGTCCCGGG-3' (SEQ ID NO:94)

In order to screen several libraries for a source of a full-length clone, DNA from the libraries was screened by PCR amplification with the PCR primer pair identified above. A positive library was then used to isolate clones encoding the PRO266 gene using the probe oligonucleotide and one of the PCR primers.

RNA for construction of the cDNA libraries was isolated from human fetal brain tissue. DNA sequencing of the clones isolated as described above gave the full-length DNA sequence for PRO266 [herein designated as DNA37150-1178] (SEQ ID NO:90) and the derived protein sequence for PRO266.

The entire nucleotide sequence of DNA37150-1178 is shown in FIG. 33 (SEQ ID NO:90). Clone DNA37150-1178 contains a single open reading frame with an apparent translational initiation site at nucleotide positions 167–169 and ending at the stop codon after nucleotide position 2254 of SEQ ID NO:90. The predicted polypeptide precursor is 696 amino acids long (FIG. 34). Clone DNA37150-1178 has been deposited with ATCC and is assigned ATCC deposit no. ATCC 209401.

Analysis of the amino acid sequence of the full-length PRO266 polypeptide suggests that portions of it possess significant homology to the SLIT protein, thereby indicating that PRO266 may be a novel leucine rich repeat protein.

Example 15

Isolation of cDNA Clones Encoding Human PRO269

A consensus DNA sequence was assembled relative to other EST sequences using phrap as described in Example 1 above. This consensus sequence is herein designated DNA35705. Based on the DNA35705 consensus sequence, oligonucleotides were synthesized: 1) to identify by PCR a cDNA library that contained the sequence of interest, and 2) for use as probes to isolate a clone of the full-length coding sequence for PRO269.

Forward and reverse PCR primers were synthesized:

forward PCR primer (.f1) 5'-TGGAAGGAGATGCGATGCCACCTG-3' (SEQ ID NO:97)

forward PCR primer (.f2) 5'-TGACCAGTGGGGAAGGACAG-3' (SEQ ID NO:98)

forward PCR primer (.f3) 5'-ACAGAGCAGAGGGTGCCTTG-3' (SEQ ID NO:99)

reverse PCR primer (.r1) 5'-TCAGGGACAAGTGGTGTCTCTCCC-3' (SEQ ID NO:100)

reverse PCR primer (.r2) 5'-TCAGGGAAGGAGTGTGCAGTTCTG-3' (SEQ ID NO:101)

Additionally, a synthetic oligonucleotide hybridization probe was constructed from the consensus DNA35705 sequence which had the following nucleotide sequence:

hybridization probe

5'-ACAGCTCCCGATCTCAGTTACTTGCATCGCGGACGAAATCGGCGCTCGCT-3' (SEQ ID NO:102)

In order to screen several libraries for a source of a full-length clone, DNA from the libraries was screened by PCR amplification with the PCR primer pairs identified above. A positive library was then used to isolate clones encoding the PRO269 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO269 [herein designated as DNA38260-1180] (SEQ ID NO:95) and the derived protein sequence for PRO269.

The entire nucleotide sequence of DNA38260-1180 is shown in FIG. 35 (SEQ ID NO:95). Clone DNA38260-1180 contains a single open reading frame with an apparent translational initiation site at nucleotide positions 314–316 and ending at the stop codon at nucleotide positions 1784–1786 (FIG. 35; SEQ ID NO:95). The predicted polypeptide precursor is 490 amino acids long (FIG. 36). Clone DNA38260-1180 has been deposited with ATCC and is assigned ATCC deposit no. ATCC 209397.

Analysis of the amino acid sequence of the full-length PRO269 suggests that portions of it possess significant homology to the human thrombomodulin proteins, thereby indicating that PRO269 may possess one or more thrombomodulin-like domains.

Example 16

Isolation of cDNA Clones Encoding Human PRO287

A consensus DNA sequence encoding PRO287 was assembled relative to the other identified EST sequences as described in Example 1 above, wherein the consensus sequence is designated herein as DNA28728. Based on the DNA28728 consensus sequence, oligonucleotides were synthesized to identify by PCR a cDNA library that contained the sequence of interest and for use as probes to isolate a clone of the full-length coding sequence for PRO287.

A pair of PCR primers (forward and reverse) were synthesized:

forward PCR primer 5'-CCGATTCATAGACCTCGAGAGT-3' (SEQ ID NO:105)

reverse PCR primer 5'-GTCAAGGAGTCCTCCACAATAC-3' (SEQ ID NO:106)

Additionally, a synthetic oligonucleotide hybridization probe was constructed from the consensus DNA28728 sequence which had the following nucleotide sequence hybridization probe

5'-GTGTACAATGGCCATGCCAATGGCCAGCGCATTGGCCGCTTCTGT-3' (SEQ ID NO:107)

In order to screen several libraries for a source of a full-length clone, DNA from the libraries was screened by PCR amplification with the PCR primer pair identified above. A positive library was then used to isolate clones encoding the PRO287 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO287 [herein designated as DNA39969-1185, SEQ ID NO:103] and the derived protein sequence for PRO287.

The entire nucleotide sequence of DNA39969-1185 is shown in FIG. 37 (SEQ ID NO:103). Clone DNA39969-1185 contains a single open reading frame with an apparent translational initiation site at nucleotide positions 307–309 and ending at the stop codon at nucleotide positions 1552–1554 (FIG. 37; SEQ ID NO:103). The predicted polypeptide precursor is 415 amino acids long (FIG. 38). Clone DNA39969-1185 has been deposited with ATCC and is assigned ATCC deposit no. ATCC 209400.

Analysis of the amino acid sequence of the full-length PRO287 suggests that it may possess one or more procollagen C-proteinase enhancer protein precursor or procollagen C-proteinase enhancer protein-like domains. Based on a BLAST and FastA sequence alignment analysis of the full-length sequence, PRO287 shows nucleic acid sequence identity to procollagen C-proteinase enhancer protein precursor and procollagen C-proteinase enhancer protein (47 and 54%, respectively).

Example 17

Isolation of cDNA Clones Encoding Human PRO214

A consensus DNA sequence was assembled using phrap as described in Example 1 above. This consensus DNA sequence is designated herein as DNA28744. Based on this consensus sequence, oligonucleotides were synthesized: 1) to identify by PCR a cDNA library that contained the sequence of interest, and 2) for use as probes to isolate a clone of the full-length coding sequence.

In order to screen several libraries for a source of a full-length clone, DNA from the libraries was screened by PCR amplification with the PCR primer pair identified below. A positive library was then used to isolate clones encoding the PRO214 gene using the probe oligonucleotide and one of the PCR primers.

RNA for construction of the cDNA libraries was isolated from human fetal lung tissue.

A cDNA clone was sequenced in its entirety. The full length nucleotide sequence of DNA32286-1191 is shown in FIG. 39 (SEQ ID NO:108). DNA32286-1191 contains a single open reading frame with an apparent translational initiation site at nucleotide position 103 (FIG. 39; SEQ ID NO:108). The predicted polypeptide precursor is 420 amino acids long (SEQ ID NO:109).

Based on a BLAST and FastA sequence alignment analysis of the full-length sequence, PRO214 polypeptide shows amino acid sequence identity to HT protein and/or Fibulin (49% and 38%, respectively).

The oligonucleotide sequences used in the above procedure were the following:

28744.p (OLI555)

5'-CCTGGCTATCAGCAGGTGGGCTCCAAGT-GTCTCGATGTGGATGAGTGTGA-3' (SEQ ID NO:110)

28744.f (OLI556)

5'-ATTCTGCGTGAACACTGAGGGC-3' (SEQ ID NO: 111)

28744.r (OLI557)

5'-ATCTGCTTGTAGCCCTCGGCAC-3' (SEQ ID NO:112)

Example 18

Isolation of cDNA Clones Encoding Human PRO317

A consensus DNA sequence was assembled using phrap as described in Example 1 above, wherein the consensus sequence is herein designated as DNA28722. Based on this consensus sequence, oligonucleotides were synthesized: 1) to identify by PCR a cDNA library that contained the sequence of interest, and 2) for use as probes to isolate a clone of the full-length coding sequence. The forward and reverse PCR primers, respectively, synthesized for this purpose were:

5'-AGGACTGCCATAACTTGCCTG (OLI489) (SEQ ID NO:115) and

5'-ATAGGAGTTGAAGCAGCGCTGC (OLI490) (SEQ ID NO:116).

The probe synthesized for this purpose was:

5'-TGTGTGGACATAGACGAGTGCCGCTAC-CGCTACTGCCAGCACCGC (OLI488) (SEQ ID NO:117)

mRNA for construction of the cDNA libraries was isolated from human fetal kidney tissue.

In order to screen several libraries for a source of a full-length clone, DNA from the libraries was screened by PCR amplification, as per Ausubel et al., *Current Protocols in Molecular Biology* (1989), with the PCR primer pair identified above. A positive library was then used to isolate clones containing the PRO317 gene using the probe oligonucleotide identified above and one of the PCR primers.

A cDNA clone was sequenced in its entirety. The entire nucleotide sequence of DNA33461-1199 (encoding PRO317) is shown in FIG. 41 (SEQ ID NO:113). Clone DNA33461-1199 contains a single open reading frame with an apparent translational initiation site at nucleotide positions 68–70 (FIG. 41; SEQ ID NO:113). The predicted polypeptide precursor is 366 amino acids long. The predicted signal sequence is amino acids 1–18 of FIG. 42 (SEQ ID NO:114). There is one predicted N-linked glycosylation site at amino acid residue 160. Clone DNA33461-1199 has been deposited with ATCC and is assigned ATCC deposit no. ATCC 209367.

Based on BLAST™ and FastA™ sequence alignment analysis (using the ALIGN™ computer program) of the full-length PRO317 sequence, PRO317 shows the most amino acid sequence identity to EBAF-1 (92%). The results also demonstrate a significant homology between human PRO317 and mouse LEFTY protein. The C-terminal end of the PRO317 protein contains many conserved sequences consistent with the pattern expected of a member of the TGF-superfamily.

In situ expression analysis in human tissues performed as described below evidences that there is distinctly strong expression of the PRO317 polypeptide in pancreatic tissue.

Example 19

Isolation of cDNA Clones Encoding Human PRO301

A consensus DNA sequence designated herein as DNA35936 was assembled using phrap as described in Example 1 above. Based on this consensus sequence, oligonucleotides were synthesized: 1) to identify by PCR a cDNA library that contained the sequence of interest, and 2) for use as probes to isolate a clone of the full-length coding sequence.

In order to screen several libraries for a source of a full-length clone, DNA from the libraries was screened by PCR amplification with the PCR primer pair identified below. A positive library was then used to isolate clones encoding the PRO301 gene using the probe oligonucleotide and one of the PCR primers.

RNA for construction of the cDNA libraries was isolated from human fetal kidney.

A cDNA clone was sequenced in its entirety. The full length nucleotide sequence of native sequence PRO301 is shown in FIG. 43 (SEQ ID NO:118). Clone DNA40628-1216 contains a single open reading frame with an apparent translational initiation site at nucleotide positions 52–54 (FIG. 43; SEQ ID NO:118). The predicted polypeptide precursor is 299 amino acids long with a predicted molecular weight of 32,583 daltons and pI of 8.29. Clone DNA40628-1216 has been deposited with ATCC and is assigned ATCC deposit No. ATCC 209432.

Based on a BLAST and FastA sequence alignment analysis of the full-length sequence, PRO301 shows amino acid sequence identity to A33 antigen precursor (30%) and coxsackie and adenovirus receptor protein (29%).

The oligonucleotide sequences used in the above procedure were the following:

OLI2162 (35936.f1) 5'-TCGCGGAGCTGTGTTCT-GTTTCCC-3' (SEQ ID NO:120)

OLI2163 (35936.p1)

5'-TGATCGCGATGGGGACAAAGGCG-CAAGCTCGAGAGGAAACTGTTGTGCCT-3' (SEQ ID NO:121)

OLI2164 (35936.f2)

5'-ACACCTGGTTCAAAGATGGG-3' (SEQ ID NO:122)

OLI2165 (35936.r1)

5'-TAGGAAGAGTTGCTGAAGGCACGG-3' (SEQ ID NO:123)

OLI2166 (35936.f3)

5'-TTGCCTTACTCAGGTGCTAC-3' (SEQ ID NO:124)

OLI2167 (35936.r2)

5'-ACTCAGCAGTGGTAGGAAAG-3' (SEQ ID NO:125)

Example 20

Isolation of cDNA Clones Encoding Human PRO224

A consensus DNA sequence assembled relative to the other identified EST sequences as described in Example 1, wherein the consensus sequence is designated herein as DNA30845. Based on the DNA30845 consensus sequence, oligonucleotides were synthesized to identify by PCR a cDNA library that contained the sequence of interest and for use as probes to isolate a clone of the full-length coding sequence for PRO224.

A pair of PCR primers (forward and reverse) were synthesized:

forward PCR primer 5'-AAGTTCCAGTGCCGCAC-CAGTGGC-3' (SEQ ID NO:128)

reverse PCR primer 5'-TTGGTTCCACAGC-CGAGCTCGTCG-3' (SEQ ID NO:129)

Additionally, a synthetic oligonucleotide hybridization probe was constructed from the consensus DNA30845 sequence which had the following nucleotide sequence hybridization probe

5'-GAGGAGGAGTGCAGGATTGAGCCATG-TACCCAGAAAGGGCAATGCCCACC-3' (SEQ ID NO:130)

In order to screen several libraries for a source of a full-length clone, DNA from the libraries was screened by PCR amplification with the PCR primer pair identified above. A positive library was then used to isolate clones encoding the PRO224 gene using the probe oligonucleotide and one of the PCR primers.

RNA for construction of the cDNA libraries was isolated from human fetal liver tissue.

DNA sequencing of the clones isolated as described above gave the full-length DNA sequence for PRO224 [herein designated as DNA33221-1133] and the derived protein sequence for PRO224.

The entire nucleotide sequence of DNA33221-1133 is shown in FIG. 45 (SEQ ID NO:126). Clone DNA33221-1133 contains a single open reading frame with an apparent translational initiation site at nucleotide positions 33–35 and ending at the stop codon at nucleotide positions 879–899 (FIG. 45; SEQ ID NO:126). The start of a transmembrane region begins at nucleotide position 777. The predicted polypeptide precursor is 282 amino acids long (FIG. 46). Clone DNA33221-1133 has been deposited with ATCC and is assigned ATCC deposit no. ATCC 209263.

Analysis of the amino acid sequence of the full-length PRO224 suggests that it has homology to very low-density lipoprotein receptors, apolipoprotein E receptor and chicken oocyte receptors P95. Based on a BLAST and FastA sequence alignment analysis of the full-length sequence, PRO224 has amino acid identity to portions of these proteins in the range from 28% to 45%, and overall identity with these proteins in the range from 33% to 39%.

Example 21

Isolation of cDNA Clones Encoding Human PRO222

A consensus DNA sequence was assembled relative to the other identified EST sequences as described in Example 1 above, wherein the consensus sequence is designated herein as DNA28771. Based on the DNA28771 consensus sequence, oligonucleotides were synthesized to identify by PCR a cDNA library that contained the sequence of interest and for use as probes to isolate a clone of the full-length coding sequence for PRO222.

A pair of PCR primers (forward and reverse) were synthesized:

forward PCR primer 5'-ATCTCCTATCGCTGCTTTC-CCGG-3' (SEQ ID NO:133)

reverse PCR primer 5'-AGCCAGGATCGCAG-TAAAACTCC-3' (SEQ ID NO:134)

Additionally, a synthetic oligonucleotide hybridization probe was constructed from the consensus DNA28771 sequence which had the following nucleotide sequence:

hybridization probe

5'-ATTTAAACTTGATGGGTCTGCGTATCT-TGAGTGCTTACAAAACCTTATCT-3' (SEQ ID NO:135)

In order to screen several libraries for a source of a full-length clone, DNA from the libraries was screened by PCR amplification with the PCR primer pair identified above. A positive library was then used to isolate clones encoding the PRO222 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO222 [herein designated as DNA33107-1135] and the derived protein sequence for PRO222.

The entire nucleotide sequence of DNA33107-1135 is shown in FIG. 47 (SEQ ID NO:131). Clone DNA33107-1135 contains a single open reading frame with an apparent translational initiation site, at nucleotide positions 159–161 and ending at the stop codon at nucleotide positions 1629–1631 (FIG. 47; SEQ ID NO:131). The predicted polypeptide precursor is 490 amino acids long (FIG. 48). Clone DNA33107-1135 has been deposited with ATCC and is assigned ATCC deposit no. ATCC 209251.

Based on a BLAST and FastA sequence alignment analysis of the full-length sequence, PRO222 shows amino acid sequence identity to mouse complement factor h precursor (25–26%), complement receptor (27–29%), mouse complement C3b receptor type 2 long form precursor (25–47%) and human hypothetical protein kiaa0247 (40%).

Example 22

Isolation of cDNA clones Encoding PRO234

A consensus DNA sequence was assembled (DNA30926) using phrap as described in Example 1 above. Based on this consensus sequence, oligonucleotides were synthesized: 1) to identify by PCR a cDNA library that contained the sequence of interest, and 2) for use as probes to isolate a clone of the full-length coding sequence.

RNA for the construction of the cDNA libraries was isolated using standard isolation protocols, e.g., Ausubel et al., *Current Protocols in Molecular Biology*, from tissue or cell line sources or it was purchased from commercial sources (e.g., Clontech). The cDNA libraries used to isolate the cDNA clones were constructed by standard methods (e.g., Ausubel et al.) using commercially available reagents (e.g., Invitrogen). This library was derived from 22 week old fetal brain tissue.

A cDNA clone was sequenced in its entirety. The entire nucleotide sequence of PRO234 is shown in FIG. 49 (SEQ ID NO:136). The predicted polypeptide precursor is 382 amino acids long and has a calculated molecular weight of approximately 43.1 kDa.

The oligonucleotide sequences used in the above procedure were the following:

30926.p (OLI826) (SEQ ID NO:138): 5'-GTTCATTGAAAACCTCTTGCCATCTGATGGTGACTTCTGGATTGGGCTCA-3'

30926.f (OLI827) (SEQ ID NO:139): 5'-AAGCCAAAGAAGCCTGCAGGAGGG-3'

30926.r (OLI828) (SEQ ID NO:140): 5'-CAGTCCAAGCATAAAGGTCCTGGC-3'

Example 23

Isolation of cDNA Clones Encoding Human PRO231

A consensus DNA sequence was assembled relative to the other identified EST sequences as described in Example 1 above, wherein the consensus sequence was designated herein as DNA30933. Based on the DNA30933 consensus sequence, oligonucleotides were synthesized to identify by PCR a cDNA library that contained the sequence of interest and for use as probes to isolate a clone of the full-length coding sequence for PRO231.

Three PCR primers (two forward and one reverse) were synthesized:

forward PCR primer 1 5'-CCAACTACCAAAGCTGCTGGAGCC-3' (SEQ ID NO:143)

forward PCR primer 2 5'-GCAGCTCTATTACCACGGGAAGGA-3' (SEQ ID NO:144)

reverse PCR primer 5'-TCCTTCCCGTGGTAATAGAGCTGC-3' (SEQ ID NO:145)

Additionally, a synthetic oligonucleotide hybridization probe was constructed from the consensus DNA30933 sequence which had the following nucleotide sequence hybridization probe

5'-GGCAGAGAACCAGAGGCCGGAGGAGACTGCCTCTTTACAGCCAGG-3' (SEQ ID NO:146)

In order to screen several libraries for a source of a full-length clone, DNA from the libraries was screened by PCR amplification with the PCR primer pairs identified above. A positive library was then used to isolate clones encoding the PRO231 gene using the probe oligonucleotide and one of the PCR primers.

RNA for construction of the cDNA libraries was isolated from human fetal liver tissue.

DNA sequencing of the clones isolated as described above gave the full-length DNA sequence for PRO231 [herein designated as DNA34434-1139] and the derived protein sequence for PRO231.

The entire nucleotide sequence of DNA34434-1139 is shown in FIG. 51 (SEQ ID NO:141). Clone DNA34434-1139 contains a single open reading frame with an apparent translational initiation site at nucleotide positions 173–175 and ending at the stop codon at nucleotide positions 1457–1459 (FIG. 51; SEQ ID NO:141). The predicted polypeptide precursor is 428 amino acids long (FIG. 52). Clone DNA34434-1139 has been deposited with ATCC on Sep. 16, 1997 and is assigned ATCC deposit no. ATCC 209252.

Analysis of the amino acid sequence of the full-length PRO231 suggests that it possesses 30% and 31% amino acid identity with the human and rat prostatic acid phosphatase precursor proteins, respectively.

Example 24

Isolation of cDNA Clones Encoding Human PRO229

A consensus DNA sequence was assembled relative to other EST sequences using phrap as described in Example 1 above. This consensus sequence is herein designated DNA28762. Based on the DNA28762 consensus sequence, oligonucleotides were synthesized: 1) to identify by PCR a cDNA library that contained the sequence of interest, and 2) for use as probes to isolate a clone of the full-length coding sequence for PRO229.

A pair of PCR primers (forward and reverse) were synthesized:

forward PCR primer 5'-TTCAGCTCATCACCTTCACCTGCC-3' (SEQ ID NO:149)

reverse PCR primer 5'-GGCTCATACAAAATACCAC-TAGGG-3' (SEQ ID NO:150)

Additionally, a synthetic oligonucleotide hybridization probe was constructed from the consensus DNA28762 sequence which had the following nucleotide sequence hybridization probe

5'-GGGCCTCCACCGCTGTGAAGGGCGGGTG-GAGGTGGAACAGAAAGGCCAGT-3' (SEQ ID NO:151)

In order to screen several libraries for a source of a full-length clone, DNA from the libraries was screened by PCR amplification with the PCR primer pair identified above. A positive library was then used to isolate clones encoding the PRO229 gene using the probe oligonucleotide and one of the PCR primers.

RNA for construction of the cDNA libraries was isolated from human fetal liver tissue.

DNA sequencing of the clones isolated as described above gave the full-length DNA sequence for PRO229 [herein designated as DNA33100-1159] (SEQ ID NO:147) and the derived protein sequence for PRO229.

The entire nucleotide sequence of DNA33100-1159 is shown in FIG. 53 (SEQ ID NO:147). Clone DNA33100-1159 contains a single open reading frame with an apparent translational initiation site at nucleotide positions 98–100 and ending at the stop codon at nucleotide positions 1139–1141 (FIG. 53). The predicted polypeptide precursor is 347 amino acids long (FIG. 54). Clone DNA33100-1159 has been deposited with ATCC and is assigned ATCC deposit no. ATCC 209377

Analysis of the amino acid sequence of the full-length PRO229 polypeptide suggests that portions of it possess significant homology to antigen wc1.1, M130 antigen and CD6.

Example 25

Isolation of cDNA Clones Encoding Human PRO238

A consensus DNA sequence was assembled relative to other EST sequences using phrap as described above in Example 1. This consensus sequence is herein designated DNA30908. Based on the DNA30908 consensus sequence, oligonucleotides were synthesized: 1) to identify by PCR a cDNA library that contained the sequence of interest, and 2) for use as probes to isolate a clone of the full-length coding sequence for PRO238.

PCR primers (forward and reverse) were synthesized:

forward PCR primer 1 5'-GGTGCTAAACTGGTGCTCT-GTGGC-3' (SEQ ID NO:154)

forward PCR primer 2 5'-CAGGGCAAGATGAGCATTCC-3' (SEQ ID NO:155)

reverse PCR primer 5'-TCATACTGTTCCATCTCG-GCACGC-3' (SEQ ID NO:156)

Additionally, a synthetic oligonucleotide hybridization probe was constructed from the consensus DNA30908 sequence which had the following nucleotide sequence hybridization probe

5'-AATGGTGGGGCCCTAGAAGAGCTCATCA-GAGAACTCACCGCTTCTCATGC-3' (SEQ ID NO:157)

In order to screen several libraries for a source of a full-length clone, DNA from the libraries was screened by PCR amplification with the PCR primer pair identified above. A positive library was then used to isolate clones encoding the PRO238 gene using the probe oligonucleotide and one of the PCR primers.

RNA for construction of the cDNA libraries was isolated from human fetal liver tissue.

DNA sequencing of the clones isolated as described above gave the full-length DNA sequence for PRO238 and the derived protein sequence for PRO238.

The entire nucleotide sequence of DNA35600-1162 is shown in FIG. 55 (SEQ ID NO:152). Clone DNA35600-1162 contains a single open reading frame with an apparent translational initiation site at nucleotide positions 134–136 and ending prior to the stop codon at nucleotide positions 1064–1066 (FIG. 55). The predicted polypeptide precursor is 310 amino acids long (FIG. 56). Clone DNA35600-1162 has been deposited with ATCC and is assigned ATCC deposit no. ATCC 209370.

Analysis of the amino acid sequence of the full-length PRO238 polypeptide suggests that portions of it possess significant homology to reductase, particularly oxidoreductase, thereby indicating that PRO238 may be a novel reductase.

Example 26

Isolation of cDNA Clones Encoding Human PRO233

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460–480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.; http://bozeman.mbt.washington.edu/phrap.docs/phrap.html).

An expressed sequence tag (EST) was identified by the EST database search and a consensus DNA sequence was assembled relative to other EST sequences using phrap. This consensus sequence is herein designated DNA30945. Based on the DNA30945 consensus sequence, oligonucleotides were synthesized: 1) to identify by PCR a cDNA library that contained the sequence of interest, and 2) for use as probes to isolate a clone of the full-length coding sequence for PRO233.

Forward and reverse PCR primers were synthesized:

forward PCR primer 5'-GGTGAAGGCAGAAATTG-GAGATG-3' (SEQ ID NO:160)

reverse PCR primer 5'-ATCCCATGCATCAGCCTGTT-TACC-3' (SEQ ID NO:161)

Additionally, a synthetic oligonucleotide hybridization probe was constructed from the consensus DNA30945 sequence which had the following nucleotide sequence hybridization probe

5'-GCTGGTGTAGTCTATACATCA-GATTTGTTTGCTACACAAGATCCTCAG-3' (SEQ ID NO:162)

In order to screen several libraries for a source of a full-length clone, DNA from the libraries was screened by PCR amplification with the PCR primer pair identified above. A positive library was then used to isolate clones encoding the PRO233 gene using the probe oligonucleotide.

RNA for construction of the cDNA libraries was isolated from human fetal brain tissue.

DNA sequencing of the clones isolated as described above gave the full-length DNA sequence for PRO233 [herein designated as DNA34436-1238] (SEQ ID NO:158) and the derived protein sequence for PRO233.

The entire nucleotide sequence of DNA34436-1238 is shown in FIG. 57 (SEQ ID NO:158). Clone DNA34436-1238 contains a single open reading frame with an apparent translational initiation site at nucleotide positions 101–103 and ending at the stop codon at nucleotide positions 1001–1003 (FIG. 57). The predicted polypeptide precursor is 300 amino acids long (FIG. 58). The full-length PRO233 protein shown in FIG. 58 has an estimated molecular weight of about 32,964 daltons and a pI of about 9.52. Clone DNA34436-1238 has been deposited with ATCC and is assigned ATCC deposit no. ATCC 209523.

Analysis of the amino acid sequence of the full-length PRO233 polypeptide suggests that portions of it possess significant homology to reductase proteins, thereby indicating that PRO233 may be a novel reductase.

Example 27

Isolation of cDNA Clones Encoding Human PRO223

A consensus DNA sequence was assembled relative to other EST sequences using phrap as described in Example 1 above. This consensus sequence is herein designated DNA30836. Based on the DNA30836 consensus sequence, oligonucleotides were synthesized: 1) to identify by PCR a cDNA library that contained the sequence of interest, and 2) for use as probes to isolate a clone of the full-length coding sequence for PRO223.

PCR primer pairs (one forward and two reverse) were synthesized:

forward PCR primer 5'-TTCCATGCCACCTAGG-GAGACTC-3' (SEQ ID NO:165)

reverse PCR primer 1 5'-TGGATGAGGTGTGCAATG-GCTGGC-3' (SEQ ID NO:166)

reverse PCR primer 2 5'-AGCTCTCAGAGGCTGGTCAT-AGGG-3' (SEQ ID NO:167)

Additionally, a synthetic oligonucleotide hybridization probe was constructed from the consensus DNA30836 sequence which had the following nucleotide sequence hybridization probe

5'-GTCGGCCCTTTCCCAGGACTGAACAT-GAAGAGTTATGCCGGCTTCCTCAC-3' (SEQ ID NO:168)

In order to screen several libraries for a source of a full-length clone, DNA from the libraries was screened by PCR amplification with the PCR primer pair identified above. A positive library was then used to isolate clones encoding the PRO223 gene using the probe oligonucleotide and one of the PCR primers.

RNA for construction of the cDNA libraries was isolated from human fetal liver tissue.

DNA sequencing of the clones isolated as described above gave the full-length DNA sequence for PRO223. [herein designated as DNA33206-1165] (SEQ ID NO:163) and the derived protein sequence for PRO223.

The entire nucleotide sequence of DNA33206-1165 is shown in FIG. 59 (SEQ ID NO:163). Clone DNA33206-1165 contains a single open reading frame with an apparent translational initiation site at nucleotide positions 97–99 and ending at the stop codon at nucleotide positions 1525–1527 (FIG. 59). The predicted polypeptide precursor is 476 amino acids long (FIG. 60). Clone DNA33206-1165 has been deposited with ATCC and is assigned ATCC deposit no. ATCC 209372.

Analysis of the amino acid sequence of the full-length PRO223 polypeptide suggests that it possesses significant homology to various serine carboxypeptidase proteins, thereby indicating that PRO223 may be a novel serine carboxypeptidase.

Example 28

Isolation of cDNA Clones Encoding Human PRO235

A consensus DNA sequence was assembled relative to other EST sequences using phrap as described in Example 1 above. This consensus sequence is herein designated "DNA30927". Based on the DNA30927 consensus sequence, oligonucleotides were synthesized: 1) to identify by PCR a cDNA library that contained the sequence of interest, and 2) for use as probes to isolate a clone of the full-length coding sequence for PRO235.

A pair of PCR primers (forward and reverse) were synthesized:

forward PCR primer 5'-TGGAATACCGCCTCCTGCAG-3' (SEQ ID NO:171)

reverse PCR primer 5'-CTTCTGCCCTTTGGAGAA-GATGGC-3' (SEQ ID NO:172)

Additionally, a synthetic oligonucleotide hybridization probe was constructed from the consensus DNA30927 sequence which had the following nucleotide sequence hybridization probe

5'-GGACTCACTGGCCCAGGCCTTCAATAT-CACCAGCCAGGACGAT-3' (SEQ ID NO:173)

In order to screen several libraries for a source of a full-length clone, DNA from the libraries was screened by PCR amplification with the PCR primer pair identified above. A positive library was then used to isolate clones encoding the PRO235 gene using the probe oligonucleotide and one of the PCR primers.

RNA for construction of the cDNA libraries was isolated from human fetal liver tissue.

DNA sequencing of the clones isolated as described above gave the full-length DNA sequence for PRO235 [herein designated as DNA35558-1167] (SEQ ID NO:169) and the derived protein sequence for PRO235.

The entire nucleotide sequence of DNA35558-1167 is shown in FIG. 61 (SEQ ID NO:169). Clone DNA35558-1167 contains a single open reading frame with an apparent translational initiation site at nucleotide positions 667–669 and ending at the stop codon at nucleotide positions 2323–2325 (FIG. 61). The predicted polypeptide precursor is 552 amino acids long (FIG. 62). Clone DNA35558-1167 has been deposited with ATCC and is assigned ATCC deposit no. 209374.

Analysis of the amino acid sequence of the full-length PRO235 polypeptide suggests that portions of it possess significant homology to the human, mouse and *Xenopus* plexin protein, thereby indicating that PRO235 may be a novel plexin protein.

Example 29

Isolation of cDNA Clones Encoding Human PRO236 and Human PRO262

Consensus DNA sequences were assembled relative to other EST sequences using phrap as described in Example 1 above. These consensus sequences are herein designated DNA30901 and DNA30847. Based on the DNA30901 and DNA30847 consensus sequences, oligonucleotides were synthesized: 1) to identify by PCR a cDNA library that contained the sequence of interest, and 2) for use as probes to isolate a clone of the full-length coding sequence for PRO236 and PRO262, respectively.

Based upon the DNA30901 consensus sequence, a pair of PCR primers (forward and reverse) were synthesized:

forward PCR primer 5'-TGGCTACTCCAAGACCCTG-GCATG-3' (SEQ ID NO:178)

reverse PCR primer 5'-TGGACAAATCCCCTTGCT-CAGCCC-3' (SEQ ID NO:179)

Additionally, a synthetic oligonucleotide hybridization probe was constructed from the consensus DNA30901 sequence which had the following nucleotide sequence hybridization probe

5'-GGGCTTCACCGAAGCAGTGGACCTT-TATTTTGACCACCTGATGTCCAGGG-3' (SEQ ID NO:180)

Based upon the DNA30847 consensus sequence, a pair of PCR primers (forward and reverse) were synthesized:

forward PCR primer 5'-CCAGCTATGACTATGATG-CACC-3' (SEQ ID NO:181)

reverse PCR primer 5'-TGGCACCCAGAATGGTGTTG-GCTC-3' (SEQ ID NO:182)

Additionally, a synthetic oligonucleotide hybridization probe was constructed from the consensus DNA30847 sequence which had the following nucleotide sequence hybridization probe

5'-CGAGATGTCATCAGCAAGTTCCAG-GAAGTTCCTTTGGGACCTTTACCTCC-3' (SEQ ID NO:183)

In order to screen several libraries for a source of full-length clones, DNA from the libraries was screened by PCR amplification with the PCR primer pairs identified above. Positive libraries were then used to isolate clones encoding the PRO236 and PRO262 genes using the probe oligonucleotides and one of the PCR primers.

RNA for construction of the cDNA libraries was isolated from human fetal lung tissue for PRO236 and human fetal liver tissue for PRO262.

DNA sequencing of the clones isolated as described above gave the full-length DNA sequence for PRO236 [herein designated as DNA35599-1168] (SEQ ID NO:174), the derived protein sequence for PRO236, the full-length DNA sequence for PRO262 [herein designated as DNA36992-1168] (SEQ ID NO:176) and the derived protein sequence for PRO262.

The entire nucleotide sequence of DNA35599-1168 is shown in FIG. 63 (SEQ ID NO:174). Clone DNA35599-1168 contains a single open reading frame with an apparent translational initiation site at nucleotide positions 69–71 and ending at the stop codon at nucleotide positions 1977–1979 (FIG. 63). The predicted polypeptide precursor is 636 amino acids long (FIG. 64). Clone DNA35599-1168 has been deposited with ATCC and is assigned ATCC deposit no. ATCC 209373.

The entire nucleotide sequence of DNA36992-1168 is shown in FIG. 65 (SEQ ID NO:176). Clone DNA36992-1168 contains a single open reading frame with an apparent translational initiation site at nucleotide positions 240–242 and ending at the stop codon at nucleotide positions 2202–2204 (FIG. 65). The predicted polypeptide precursor is 654 amino acids long (FIG. 66). Clone DNA36992-1168 has been deposited with ATCC and is assigned ATCC deposit no. ATCC 209382.

Analysis of the amino acid sequence of the full-length PRO236 and PRO262 polypeptides suggests that portions of those polypeptides possess significant homology to β-galactosidase proteins derived from various sources, thereby indicating that PRO236 and PRO262 may be novel β-galactosidase homologs.

Example 30

Isolation of cDNA Clones Encoding Human PRO239

A consensus DNA sequence was assembled relative to other EST sequences using phrap as described in Example 1 above. This consensus sequence is herein designated DNA30909. Based on the DNA30909 consensus sequence, oligonucleotides were synthesized: 1) to identify by PCR a cDNA library that contained the sequence of interest, and 2) for use as probes to isolate a clone of the full-length coding sequence for PRO239.

A pair of PCR primers (forward and reverse) were synthesized:

forward PCR primer 5'-CCTCCCTCTATTACCCATGTC-3' (SEQ ID NO:186)

reverse PCR primer 5'-GACCAACTTTCTCTGGGAGT-GAGG-3' (SEQ ID NO:187)

Additionally, a synthetic oligonucleotide hybridization probe was constructed from the consensus DNA30909 sequence which had the following nucleotide sequence hybridization probe

5'-GTCACTTTATTTCTCTAACAACAAGCTC-GAATCCTTACCAGTGGCAG-3' (SEQ ID NO:188)

In order to screen several libraries for a source of a full-length clone, DNA from the libraries was screened by PCR amplification with the PCR primer pair identified above. A positive library was then used to isolate clones encoding the PRO239 gene using the probe oligonucleotide and one of the PCR primers.

RNA for construction of the cDNA libraries was isolated from human fetal lung tissue.

DNA sequencing of the clones isolated as described above gave the full-length DNA sequence for PRO239 [herein designated as DNA34407-1169] (SEQ ID NO:184) and the derived protein sequence for PRO239.

The entire nucleotide sequence of DNA34407-1169 is shown in FIG. 67 (SEQ ID NO:184). Clone DNA34407-1169 contains a single open reading frame with an apparent translational initiation site at nucleotide positions 72–74 and ending at the stop codon at nucleotide positions 1575–1577 (FIG. 67). The predicted polypeptide precursor is 501 amino acids long (FIG. 68). Clone DNA34407-1169 has been deposited with ATCC and is assigned ATCC deposit no. ATCC 209383.

Analysis of the amino acid sequence of the full-length PRO239 polypeptide suggests that portions of it possess significant homology to the densin protein, thereby indicating that PRO239 may be a novel molecule in the densin family.

Example 31

Isolation of cDNA Clones Encoding Human PRO257

A consensus. DNA sequence was assembled relative to other EST sequences using phrap as described in Example 1 above. This consensus sequence is herein designated DNA28731. Based on the DNA28731 consensus sequence, oligonucleotides were synthesized: 1) to identify by PCR a cDNA library that contained the sequence of interest, and 2) for use as probes to isolate a clone of the full-length coding sequence for PRO257.

A pair of PCR primers (forward and reverse) were synthesized:

forward PCR primer 5'-TCTCTATTCCAAACTGTGGCG-3' (SEQ ID NO:191)

reverse PCR primer 5'-TTTGATGACGATTCGAAG-GTGG-3' (SEQ ID NO:192)

Additionally, a synthetic oligonucleotide hybridization probe was constructed from the consensus DNA28731 sequence which had the following nucleotide sequence hybridization probe

5'-GGAAGGATCCTTCACCAGCCCCAATTAC-CCAAAGCCGCATCCTGAGC-3' (SEQ ID NO:193)

In order to screen several libraries for a source of a full-length clone, DNA from the libraries was screened by PCR amplification with the PCR primer pair identified above. A positive library was then used to isolate clones encoding the PRO257 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO257 [herein designated as DNA35841-1173] (SEQ ID NO:189) and the derived protein sequence for PRO257.

The entire nucleotide sequence of DNA35841-1173 is shown in FIG. 69 (SEQ ID NO:189). Clone DNA35841-1173 contains a single open reading frame with an apparent translational initiation site at nucleotide positions 964–966 and ending at the stop codon at nucleotide positions 2785–2787 (FIG. 69). The predicted polypeptide precursor is 607 amino acids long (FIG. 70). Clone DNA35841-1173 has been deposited with ATCC and is assigned ATCC deposit no. ATCC 209403.

Analysis of the amino acid sequence of the full-length PRO257 polypeptide suggests that portions of it possess significant homology to the ebnerin protein, thereby indicating that PRO257 may be a novel protein member related to the ebnerin protein.

Example 32

Isolation of cDNA Clones Encoding Human PRO260

A consensus DNA sequence was assembled relative to other EST sequences using phrap as described in Example 1 above. This consensus sequence is herein designated DNA30834. Based on the DNA30834 consensus sequence, oligonucleotides were synthesized: 1) to identify by PCR a cDNA library that contained the sequence of interest, and 2) for use as probes to isolate a clone of the full-length coding sequence for PRO260.

PCR primers (forward and two reverse) were synthesized:

forward PCR primer: 5'-TGGTTTGACCAGGCCAAGT-TCGG-3' (SEQ ID NO:196);

reverse PCR primer A: 5'-GGATTCATCCTCAAGGAA-GAGCGG-3' (SEQ ID NO:197); and reverse PCR primer B: 5'AACTTGCAGCATCAGC-CACTCTGC-3' (SEQ ID NO:198)

Additionally, a synthetic oligonucleotide hybridization probe was constructed from the consensus DNA30834 sequence which had the following nucleotide sequence:

hybridization probe:

5'-TTCCGTGCCCAGCTTCGGTAGCGAGTG-GTTCTGGTGGTATTGGCA-3' (SEQ ID NO:199)

In order to screen several libraries for a source of a full-length clone, DNA from the libraries was screened by PCR amplification with the PCR primer pair identified above. A positive library was then used to isolate clones encoding the PRO260 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO260 [herein designated as DNA33470-1175] (SEQ ID NO:194) and the derived protein sequence for PRO260.

The entire nucleotide sequence of DNA33470-1175 is shown in FIG. 71 (SEQ ID NO:194). Clone DNA33470-1175 contains a single open reading frame with an apparent translational initiation site at nucleotide positions 67–69 and ending at the stop codon 1468–1470 (see FIG. 71). The predicted polypeptide precursor is 467 amino acids long (FIG. 72). Clone DNA33470-1175 has been deposited with ATCC and is assigned ATCC deposit no. ATCC 209398.

Analysis of the amino acid sequence of the full-length PRO260 polypeptide suggests that portions of it possess significant homology to the alpha-1-fucosidase precursor, thereby indicating that PRO260 may be a novel fucosidase.

Example 33

Isolation of cDNA Clones Encoding Human PRO263

A consensus DNA sequence was assembled relative to other EST sequences using phrap as described in Example 1 above. This consensus sequence is herein designated DNA30914. Based on the DNA30914 consensus sequence, oligonucleotides were synthesized: 1) to identify by PCR a cDNA library that contained the sequence of interest, and 2) for use as probes to isolate a clone of the full-length coding sequence for PRO263.

PCR primers (tow forward and one reverse) were synthesized:

forward PCR primer 1: 5'-GAGCTTTCCATCCAGGTGTCATGC-3'. (SEQ ID NO:202);

forward PCR primer 2: 5'-GTCAGTGACAGTACCTACTCGG-3' (SEQ ID NO:203); reverse PCR primer:

5'-TGGAGCAGGAGGAGTAGTAGTAGG-3' (SEQ ID NO:204)

Additionally, a synthetic oligonucleotide hybridization probe was constructed from the consensus DNA30914 sequence which had the following nucleotide sequence:

hybridization probe:

5'-AGGAGGCCTGTAGGCTGCTGGGACTAAGTTTGGCCGGCAAGGACCAAGTT-3' (SEQ ID NO:205)

In order to screen several libraries for a source of a full-length clone, DNA from the libraries was screened by PCR amplification with the PCR primer pair identified above. A positive library was then used to isolate clones encoding the PRO263 gene using the probe oligonucleotide and one of the PCR primers.

RNA for construction of the cDNA libraries was isolated from human fetal liver tissue.

DNA sequencing of the clones isolated as described above gave the full-length DNA sequence for PRO263 [herein designated as DNA34431-1177] (SEQ ID NO:200) and the derived protein sequence for PRO263.

The entire nucleotide sequence of DNA34431-1177 is shown in FIG. 73 (SEQ ID NO:200). Clone DNA34431-1177 contains a single open reading frame with an apparent translational initiation site at nucleotide positions 160–162 of SEQ ID NO:200 and ending at the stop codon after the nucleotide at position 1126–1128 of SEQ ID NO:200 (FIG. 73). The predicted polypeptide precursor is 322 amino acids long (FIG. 74). Clone DNA34431-1177 has been deposited with ATCC and is assigned ATCC deposit no. ATCC 209399.

Analysis of the amino acid sequence of the full-length PRO263 polypeptide suggests that portions of it possess significant homology to CD44 antigen, thereby indicating that PRO263 may be a novel cell surface adhesion molecule.

Example 34

Isolation of cDNA Clones Encoding Human PRO270

A consensus DNA sequence was assembled relative to the other identified EST sequences as described in Example 1 above, wherein the consensus sequence was designated herein as DNA35712. Based on the DNA35712 consensus sequence, oligonucleotides were synthesized: 1) to identify by PCR a cDNA library that contained the sequence of interest, and 2) for use as probes to isolate a clone of the full-length coding sequence for PRO270. Forward and reverse PCR primers were synthesized:

forward PCR primer (.f1) 5'-GCTTGGATATTCGCATGGGCCTAC-3' (SEQ ID NO:208)

forward PCR primer (.f2) 5'-TGGAGACAATATCCCTGAGG-3' (SEQ ID NO:209)

reverse PCR primer (.r1) 5'-AACAGTTGGCCACAGCATGGCAGG-3' (SEQ ID NO:210)

Additionally, a synthetic oligonucleotide hybridization probe was constructed from the consensus DNA35712 sequence which had the following nucleotide sequence hybridization probe

5'-CCATTGATGAGGAACTAGAACGGGACAAGAGGGTCACTTGGATTGTGGAG-3' (SEQ ID NO:211)

In order to screen several libraries for a source of a full-length clone, DNA from the libraries was screened by PCR amplification with the PCR primer pair identified above. A positive library was then used to isolate clones encoding the PRO270 gene using the probe oligonucleotide and one of the PCR primers.

RNA for construction of the cDNA libraries was isolated from human fetal lung tissue.

DNA sequencing of the clones isolated as described above gave the full-length DNA sequence for PRO270 [herein designated as DNA39510-1181] (SEQ ID NO:206) and the derived protein sequence for PRO270.

The entire nucleotide sequence of DNA39510-1181 is shown in FIG. 75 (SEQ ID NO:206). Clone DNA39510-1181 contains a single open reading frame with an apparent translational initiation site at nucleotide positions 3–5 and ending at the stop codon at nucleotide positions 891–893 (FIG. 75; SEQ ID NO:206). The predicted polypeptide precursor is 296 amino acids long (FIG. 76). Clone DNA39510-1181 has been deposited with ATCC and is assigned ATCC deposit no. ATCC 209392.

Analysis of the amino acid sequence of the full-length PRO270 suggests that portions of it possess significant homology to the thioredoxin-protein, thereby indicating that the PRO270 protein may be a novel member of the thioredoxin family.

Example 35

Isolation of cDNA Clones Encoding Human PRO271

A consensus DNA sequence was assembled relative to other EST sequences using phrap as described in Example 1 above. This consensus sequence is herein designated DNA35737. Based on the DNA35737 consensus sequence, oligonucleotides were synthesized: 1) to identify by PCR a cDNA library that contained the sequence of interest, and 2) for use as probes to isolate a clone of the full-length coding sequence for PRO271.

Forward and reverse PCR primers were synthesized:

forward PCR primer 1 5'-TGCTTCGCTACTGCCCTC-3' (SEQ ID NO:214)

forward PCR primer 2 5'-TTCCCTTGTGGGTTGGAG-3' (SEQ ID NO:215)

forward PCR primer 3 5'-AGGGCTGGAAGCCAGTTC-3' (SEQ ID NO:216)

reverse PCR primer 1 5'-AGCCAGTGAGGAAATGCG-3' (SEQ ID NO:217)

reverse PCR primer 2 5'-TGTCCAAAGTACACACACCT-GAGG-3' (SEQ ID NO:218)

Additionally, a synthetic oligonucleotide hybridization probe was constructed from the consensus DNA35737 sequence which had the following nucleotide sequence hybridization probe

5'-GATGCCACGATCGCCAAGGTGGGA-CAGCTCTTTGCCGCCTGGAAG-3' (SEQ ID NO:219)

In order to screen several libraries for a source of a full-length clone, DNA from the libraries was screened by PCR amplification with the PCR primer pair identified above. A positive library was then used to isolate clones encoding the PRO271 gene using the probe oligonucleotide and one of the PCR primers.

RNA for construction of the cDNA libraries was isolated from human fetal brain tissue.

DNA sequencing of the clones isolated as described above gave the full-length DNA sequence for PRO271 [herein designated as DNA39423-1182] (SEQ ID NO:212) and the derived protein sequence for PRO271.

The entire nucleotide sequence of DNA39423-1182 is shown in FIG. 77 (SEQ ID NO:212). Clone DNA39423-1182 contains a single open reading frame with an apparent translational initiation site at nucleotide positions 101–103 and ending at the stop codon at nucleotide positions 1181–1183 (FIG. 77). The predicted polypeptide precursor is 360 amino acids long (FIG. 78). Clone DNA39423-1182 has been deposited with ATCC and is assigned ATCC deposit no. ATCC 209387.

Analysis of the amino acid sequence of the full-length PRO271 polypeptide suggests that it possess significant homology to the proteoglycan link protein, thereby indicating that PRO271 may be a link protein homolog.

Example 36

Isolation of cDNA Clones Encoding Human PRO272

A consensus DNA sequence was assembled relative to other EST sequences using phrap as described in Example 1 above. This consensus sequence is herein designated DNA36460. Based on the DNA36460 consensus sequence, oligonucleotides were synthesized: 1) to identify by PCR a cDNA library that contained the sequence of interest, and 2) for use as probes to isolate a clone of the full-length coding sequence for PRO272.

Forward and reverse PCR primers were synthesized:

forward PCR primer (.f 1) 5'-CGCAGGCCCTCATGGC-CAGG-3' (SEQ ID NO:222)

forward PCR primer (.f2) 5'-GAAATCCTGGGTAATTGG-3' (SEQ ID NO:223)

reverse PCR primer 5'-GTGCGCGGTGCTCACAGCT-CATC-3' (SEQ ID NO:224)

Additionally, a synthetic oligonucleotide hybridization probe was constructed from the consensus DNA36460 sequence which had the following nucleotide sequence hybridization probe

5'-CCCCCCTGAGCGACGCTCCCCCATGAT-GACGCCCACGGGAACTTC-3' (SEQ ID NO:225)

In order to screen several libraries for a source of a full-length clone, DNA from the libraries was screened by PCR amplification with the PCR primer pairs identified above. A positive library was then used to isolate clones encoding the PRO272 gene using the probe oligonucleotide and one of the PCR primers.

RNA for construction of the cDNA libraries was isolated from human fetal lung tissue.

DNA sequencing of the clones isolated as described above gave the full-length DNA sequence for PRO272 [herein designated as DNA40620-1183] (SEQ ID NO:220) and the derived protein sequence for PRO272.

The entire nucleotide sequence of DNA40620-1183 is shown in FIG. 79 (SEQ ID NO:220). Clone DNA40620-1183 contains a single open reading frame with an apparent translational initiation site at nucleotide positions 35–37 and ending at the stop codon at nucleotide positions 1019–1021 (FIG. 79). The predicted polypeptide precursor is 328 amino acids long (FIG. 80). Clone DNA40620-1183 has been deposited with ATCC and is assigned ATCC deposit no. ATCC 209388.

Analysis of the amino acid sequence of the full-length PRO272 polypeptide suggests that portions of it possess significant homology to the human and mouse reticulocalbin proteins, respectively, thereby indicating that PRO272 may be a novel reticulocalbin protein.

Example 37

Isolation of cDNA Clones Encoding Human PRO294

A consensus DNA sequence was assembled relative to other EST sequences using phrap as described in Example 1 above. This consensus sequence is herein designated DNA35731. Based on the DNA35731 consensus sequence, oligonucleotides were synthesized: 1) to identify by PCR a cDNA library that contained the sequence of interest, and 2) for use as probes to isolate a clone of the full-length coding sequence for PRO294.

Forward and reverse PCR primers were synthesized:

forward PCR primer (.f1) 5'-TGGTCTCGCACACCGATC-3' (SEQ ID NO:228)

forward PCR primer (.f2) 5'-CTGCTGTCCACAGGGGAG-3' (SEQ ID NO:229)

forward PCR primer (.f3) 5'-CCTTGAAGCATACTGCTC-3' (SEQ ID NO:230)

forward PCR primer (.f4) 5'-GAGATAGCAATTTCCGCC-3' (SEQ ID NO:231)

reverse PCR primer (.r1) 5'-TTCCTCAAGAGGGCAGCC-3' (SEQ ID NO:232)

reverse PCR primer (.r2) 5'-CTTGGCACCAATGTC-CGAGATTTC-3' (SEQ ID NO:233)

Additionally, a synthetic oligonucleotide hybridization probe was constructed from the consensus DNA35731 sequence which had the following nucleotide sequence hybridization probe

5'-GCTCTGAGGAAGGTGACGCGCGGGGC-CTCCGAACCCTTGGCCTTG-3' (SEQ ID NO:234)

In order to screen several libraries for a source of a full-length clone, DNA from the libraries was screened by PCR amplification with the PCR primer pairs identified above. A positive library was then used to isolate clones encoding the PRO294 gene using the probe oligonucleotide and one of the PCR primers.

RNA for construction of the cDNA libraries was isolated from human fetal brain tissue.

DNA sequencing of the clones isolated as described above gave the full-length DNA sequence for PRO294 [herein designated as DNA40604-1187] (SEQ ID NO:226) and the derived protein sequence for PRO294.

The entire nucleotide sequence of DNA40604-1187 is shown in FIG. 81 (SEQ ID NO:226). Clone DNA40604-1187 contains a single open reading frame with an apparent translational initiation site at nucleotide positions 396–398 and ending at the stop codon at nucleotide positions 2046–2048 (FIG. 81). The predicted polypeptide precursor is 550 amino acids long (FIG. 82). Clone DNA40604-1187 has been deposited with ATCC and is assigned ATCC deposit no. 209394.

Analysis of the amino acid sequence of the full-length PRO294 polypeptide suggests that portions of it possess significant homology to portions of various collagen proteins, thereby indicating that PRO294 may be collagen-like molecule.

Example 38

Isolation of cDNA Clones Encoding Human PRO295

A consensus DNA sequence was assembled relative to other EST sequences using phrap as described in Example 1 above. This consensus sequence is herein designated DNA35814. Based on the DNA35814 consensus sequence, oligonucleotides were synthesized: 1) to identify by PCR a cDNA library that contained the sequence of interest, and 2) for use as probes to isolate a clone of the full-length coding sequence for PRO295.

Forward and reverse PCR primers were synthesized:

forward PCR primer (.f1) 5'-GCAGAGCGGAGATG-CAGCGGCTTG-3' (SEQ ID NO:238)

forward PCR primer (.f2) 5'-CCCAGCATGTACTGCCAG-3' (SEQ ID NO:239)

forward PCR primer (.f3) 5'-TTGGCAGCTTCATGGAGG-3' (SEQ ID NO:240)

forward PCR primer (.f4) 5'-CCTGGGCAAAAATGCAAC-3' (SEQ ID NO:241)

reverse PCR primer (.r1) 5'-CTCCAGCTCCTGGCGCAC-CTCCTC-3' (SEQ ID NO:242)

Additionally, a synthetic oligonucleotide hybridization probe was constructed from the consensus DNA35814 sequence which had the following nucleotide sequence hybridization probe

5'-GGCTCTCAGCTACCGCGCAGGAGCGAG-GCCACCCTCAATGAGATG-3' (SEQ ID NO:243)

In order to screen several libraries for a source of a full-length clone, DNA from the libraries was screened by PCR amplification with the PCR primer pairs identified above. A positive library was then used to isolate clones encoding the PRO295 gene using the probe oligonucleotide and one of the PCR primers.

RNA for construction of the cDNA libraries was isolated from human fetal lung tissue.

DNA sequencing of the clones isolated as described above gave the full-length DNA sequence for PRO295 [herein designated as DNA38268-1188] (SEQ ID NO:235) and the derived protein sequence for PRO295.

The entire nucleotide sequence of DNA38268-1188 is shown in FIG. 83 (SEQ ID NO:235). Clone DNA38268-1188 contains a single open reading frame with an apparent translational initiation site at nucleotide positions 153–155 and ending at the stop codon at nucleotide positions 1202–1204 (FIG. 83). The predicted polypeptide precursor is 350 amino acids long (FIG. 84). Clone DNA38268-1188 has been deposited with ATCC and is assigned ATCC deposit no. 209421.

Analysis of the amino acid sequence of the full-length PRO295 polypeptide suggests that portions of it possess significant homology to the integrin proteins, thereby indicating that PRO295 may be a novel integrin.

Example 39

Isolation of cDNA Clones Encoding Human PRO293

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460–480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.; http://bozeman.mbt.washington.edu/phrap-.docs/phrap.html).

Based on an expression tag sequence designated herein as T08294 identified in the above analysis, oligonucleotides were synthesized: 1) to identify by PCR a cDNA library that contained the sequence of interest, and 2) for use as probes to isolate a clone of the full-length coding sequence for PRO293.

A pair of PCR primers (forward and reverse) were synthesized:

forward PCR primer 5'-AACAAGGTAAGATGCCATC-CTG-3' (SEQ ID NO:246)

reverse PCR primer 5'-AAACTTGTCGATGGAGAC-CAGCTC-3' (SEQ ID NO:247)

Additionally, a synthetic oligonucleotide hybridization probe was constructed from the expression sequence tag which had the following nucleotide sequence hybridization probe

5'-AGGGGCTGCAAAGCCTGGAGAGCCTCTC-CTTCTATGACAACCAGC-3' (SEQ ID NO:248)

In order to screen several libraries for a source of a full-length clone, DNA from the libraries was screened by PCR amplification with the PCR primer pair identified above. A positive library was then used to isolate clones encoding the PRO293 gene using the probe oligonucleotide and one of the PCR primers.

RNA for construction of the cDNA libraries was isolated from human fetal brain tissue.

DNA sequencing of the clones isolated as described above gave the full-length DNA sequence for PRO293 [herein designated as DNA37151-1193] (SEQ ID NO:244) and the derived protein sequence for PRO293.

The entire nucleotide sequence of DNA37151-1193 is shown in FIG. 85 (SEQ ID NO:244). Clone DNA37151-1193 contains a single open reading frame with an apparent translational initiation site at nucleotide positions 881–883 and ending at the stop codon after nucleotide position 3019 of SEQ ID NO:244, FIG. 85). The predicted polypeptide precursor is 713 amino acids long (FIG. 86). Clone DNA37151-1193 has been deposited with ATCC and is assigned ATCC deposit no. ATCC 209393.

Analysis of the amino acid sequence of the full-length PRO293 polypeptide suggests that portions of it possess significant homology to the NLRR proteins, thereby indicating that PRO293 may be a novel NLRR protein.

Example 40

Isolation of cDNA Clones Encoding Human PRO247

A consensus DNA sequence was assembled relative to other EST sequences using phrap as described in Example 1 above. This consensus sequence is herein designated DNA33480. Based on the DNA33480 consensus sequence, oligonucleotides were synthesized: 1) to identify by PCR a cDNA library that contained the sequence of interest, and 2) for use as probes to isolate a clone of the full-length coding sequence for PRO247.

A pair of PCR primers (forward and reverse) were synthesized:

forward PCR primer 5'-CAACAATGAGGGCACCAAGC-3' (SEQ ID NO:251)

reverse PCR primer 5'-GATGGCTAGGTTCTGGAGGTTCTG-3' (SEQ ID NO:252)

Additionally, a synthetic oligonucleotide hybridization probe was constructed from the DNA33480 expression sequence tag which had the following nucleotide sequence hybridization probe

5'-CAACCTGCAGGAGATTGACCTCAAGGACAACAACCTCAAGACCATCG-3' (SEQ ID NO:253)

In order to screen several libraries for a source of a full-length clone, DNA from the libraries was screened by PCR amplification with the PCR primer pair identified above. A positive library was then used to isolate clones encoding the PRO247 gene using the probe oligonucleotide and one of the PCR primers.

RNA for construction of the cDNA libraries was isolated from human fetal brain tissue.

DNA sequencing of the clones isolated as described above gave the full-length DNA sequence for PRO247 [herein designated as DNA35673-1201] (SEQ ID NO:249) and the derived protein sequence for PRO247.

The entire nucleotide sequence of DNA35673-1201 is shown in FIG. 89 (SEQ ID NO:249). Clone DNA35673-1201 contains a single open reading frame with an apparent translational initiation site at nucleotide positions 80–82 of SEQ ID NO:249 and ending at the stop codon after nucleotide position 1717 of SEQ ID NO:249 (FIG. 89). The predicted polypeptide precursor is 546 amino acids long (FIG. 88). Clone DNA35673-1201 has been deposited with ATCC and is assigned ATCC deposit no. 209418.

Analysis of the amino acid sequence of the full-length PRO247 polypeptide suggests that portions of it possess significant homology to the densin molecule and KIAA0231, thereby indicating that PRO247 may be a novel leucine rich repeat protein.

Example 41

Isolation of cDNA Clones Encoding Human PRO302, PRO303, PRO304, PRO307 and PRO343

Consensus DNA sequences were assembled relative to other EST sequences using phrap as described in Example 1 above. These consensus sequences are herein designated DNA35953, DNA35955, DNA35958, DNA37160 and DNA30895. Based on the DNA35953 consensus sequence, oligonucleotides were synthesized: 1) to identify by PCR a cDNA library that contained the sequence of interest, and 2) for use as probes to isolate a clone of the full-length coding sequence for PRO302.

PCR primers (forward and reverse) were synthesized:

forward PCR primer 1 5'-GTCCGCAAGGATGCCTACATGTTC-3' (SEQ ID NO:264)

forward PCR primer 2 5'-GCAGAGGTGTCTAAGGTTG-3' (SEQ ID NO:265)

reverse PCR primer 5'-AGCTCTAGACCAATGCCAGCTTCC-3' (SEQ ID NO:266)

Also, a synthetic oligonucleotide hybridization probe was constructed from the consensus DNA35953 sequence which had the following nucleotide sequence hybridization probe

5'-GCCACCAACTCCTGCAAGAACTTCTCAGAACTGCCCCTGGTCATG-3' (SEQ ID NO:267)

In order to screen several libraries for a source of a full-length clone, DNA from the libraries was screened by PCR amplification with the PCR primer pairs identified above. A positive library was then used to isolate clones encoding the PRO302 gene using the probe oligonucleotide and one of the PCR primers.

RNA for construction of the cDNA libraries was isolated from human fetal kidney tissue (LIB228).

DNA sequencing of the clones isolated as described above gave the full-length DNA sequence for PRO302 [herein designated as DNA40370-1217] (SEQ ID NO:254) and the derived protein sequence for PRO302.

The entire nucleotide sequence of DNA40370-1217 is shown in FIG. 89 (SEQ ID NO:254). Clone DNA40370-1217 contains a single open reading frame with an apparent translational initiation site at nucleotide positions 34–36 and ending at the stop codon at nucleotide positions 1390–1392 (FIG. 89). The predicted polypeptide precursor is 452 amino acids long (FIG. 90). Various unique aspects of the PRO302 protein are shown in FIG. 90. Clone DNA40370-1217 has been deposited with the ATCC on Nov. 21, 1997 and is assigned ATCC deposit no. ATCC 209485.

Based on the DNA35955 consensus sequence, oligonucleotides were synthesized: 1) to identify by PCR a cDNA library that contained the sequence of interest, and 2) for use as probes to isolate a clone of the full-length coding sequence for PRO303.

A pair of PCR primers (forward and reverse) were synthesized:

forward PCR primer 5'-GGGGAATTCACCCTATGACATTGCC-3' (SEQ ID NO:268)

reverse PCR primer 5'-GAATGCCCTGCAAGCATCAACTGG-3' (SEQ ID NO:269)

Additionally, a synthetic oligonucleotide hybridization probe was constructed from the consensus DNA35955 sequence which had the following nucleotide sequence:

hybridization probe

5'-GCACCTGTCACCTACACTAAACACATCCAGCCCATCTGTCTCCAGGCCTC-3' (SEQ ID NO:270)

In order to screen several libraries for a source of a full-length clone, DNA from the libraries was screened by PCR amplification with the PCR primer pairs identified above. A positive library was then used to isolate clones encoding the PRO303 gene using the probe oligonucleotide and one of the PCR primers.

RNA for construction of the cDNA libraries was isolated from human fetal lung tissue (LIB25).

DNA sequencing of the clones isolated as described above gave the full-length DNA sequence for PRO303 [herein designated as DNA42551-1217] (SEQ ID NO:256) and the derived protein sequence for PRO303.

The entire nucleotide sequence of DNA42551-1217 is shown in FIG. 91 (SEQ ID NO:256). Clone DNA42551-1217 contains a single open reading frame with an apparent translational initiation site at nucleotide positions 20–22 and ending at the stop codon at nucleotide positions 962–964 (FIG. 91). The predicted polypeptide precursor is 314 amino acids long (FIG. 92). Various unique aspects of the PRO303 protein are shown in FIG. 92. Clone DNA42551-1217 has been deposited on Nov. 21, 1997 with the ATCC and is assigned ATCC deposit no. ATCC 209483.

Based on the DNA35958 consensus sequence, oligonucleotides were synthesized: 1) to identify by PCR a cDNA library that contained the sequence of interest, and 2) for use as probes to isolate a clone of the full-length coding sequence for PRO304.

Pairs of PCR primers (forward and reverse) were synthesized:

forward PCR primer 1 5'-GCGGAAGGGCAGAATGGGACTCCAAG-3' (SEQ ID NO:271)

forward PCR primer 2 5'-CAGCCCTGCCACATGTGC-3' (SEQ ID NO:272)

forward PCR primer 3 5'-TACTGGGTGGTCAGCAAC-3' (SEQ ID NO:273)

reverse PCR primer 5'-GGCGAAGAGCAGGGTGAGACCCCG-3' (SEQ ID NO:274)

Additionally, a synthetic oligonucleotide hybridization probe was constructed from the consensus DNA35958 sequence which had the following nucleotide sequence hybridization probe

5'-GCCCTCATCCTCTCTGGCAAATGCAGTTACAGCCCGGAGCCCGAC-3' (SEQ ID NO:275)

In order to screen several libraries for a source of a full-length clone, DNA from the libraries was screened by PCR amplification with the PCR primer pairs identified above. A positive library was then used to isolate clones encoding the PRO304 gene using the probe oligonucleotide and one of the PCR primers.

RNA for construction of the cDNA libraries was isolated from 22 week human fetal brain tissue (LIB153).

DNA sequencing of the clones isolated as described above gave the full-length DNA sequence for PRO304 [herein designated as DNA39520-1217] (SEQ ID NO:258) and the derived protein sequence for PRO304.

The entire nucleotide sequence of DNA39520-1217 is shown in FIG. 93 (SEQ ID NO:258). Clone DNA39520-1217 contains a single open reading frame with an apparent translational initiation site at nucleotide positions 34–36 and ending at the stop codon at nucleotide positions 1702–1704 (FIG. 93). The predicted polypeptide precursor is 556 amino acids long (FIG. 94). Various unique aspects of the PRO304 protein are shown in FIG. 94. Clone DNA39520-1217 has been deposited with ATCC on Nov. 21, 1997 and is assigned ATCC deposit no. ATCC 209482.

Based on the DNA37160 consensus sequence, oligonucleotides were synthesized: 1) to identify by PCR a cDNA library that contained the sequence of interest, and 2) for use as probes to isolate a clone of the full-length coding sequence for PRO307.

Pairs of PCR primers (forward and reverse) were synthesized:

forward PCR primer 1 5'-GGGCAGGGATTCCAGGGCTCC-3' (SEQ ID NO:276)

forward PCR primer 2 5'-GGCTATGACAGCAGGTTC-3' (SEQ ID NO:277)

forward PCR primer 3 5'-TGACAATGACCGACCAGG-3' (SEQ ID NO:278)

reverse PCR primer 5'-GCATCGCATTGCTGGTAGAGCAAG-3' (SEQ ID NO:279)

Additionally, a synthetic oligonucleotide hybridization probe was constructed from the consensus DNA37160 sequence which had the following nucleotide sequence hybridization probe

5'-TTACAGTGCCCCCTGGAAACCCACTTGGCCTGCATACCGCCTCCC-3' (SEQ ID NO:280)

In order to screen several libraries for a source of a full-length clone, DNA from the libraries was screened by PCR amplification with the PCR primer pairs identified above. A positive library was then used to isolate clones encoding the PRO307 gene using the probe oligonucleotide and one of the PCR primers.

RNA for construction of the cDNA libraries was isolated from human fetal liver tissue (LIB229).

DNA sequencing of the clones isolated as described above gave the full-length DNA sequence for PRO307 [herein designated as DNA41225-1217] (SEQ ID NO:260) and the derived protein sequence for PRO307.

The entire nucleotide sequence of DNA41225-1217 is shown in FIG. 95 (SEQ ID NO:260). Clone DNA41225-1217 contains a single open reading frame with an apparent translational initiation site at nucleotide positions 92–94 and ending at the stop codon at nucleotide positions 1241–1243 (FIG. 95). The predicted polypeptide precursor is 383 amino acids long (FIG. 96). Various unique aspects of the PRO307 protein are shown in FIG. 96. Clone DNA41225-1217 has been deposited with ATCC on Nov. 21, 1997 and is assigned ATCC deposit no. ATCC 209491.

Based on the DNA30895 consensus sequence, oligonucleotides were synthesized: 1) to identify by PCR a cDNA library that contained the sequence of interest, and 2) for use as probes to isolate a clone of the full-length coding sequence for PRO343.

A pair of PCR primers (forward and reverse) were synthesized:

forward PCR primer 5'-CGTCTCGAGCGCTCCATA-CAGTTCCCTTGCCCCA-3' (SEQ ID NO:281)

reverse PCR primer

5'-TGGAGGGGGAGCGGGATGCT-TGTCTGGGCGACTCCGGGGGCCCCCT-CATGTGCCAGGTGGA-3' (SEQ ID NO:282)

Additionally, a synthetic oligonucleotide hybridization probe was constructed from the consensus DNA30895 sequence which had the following nucleotide sequence hybridization probe 5'-CCCTCAGACCCTGCAGAAGCTGAAGGT-TCCTATCATCGACTCGGAAGTCTGCAGC-CATCTGTACTGGCGGGGAGCAGGACAGG-GACCCATCACTGAGGACATGCTGTGTGCCGGCTACT-3' (SEQ ID NO:283)

In order to screen several libraries for a source of a full-length clone, DNA from the libraries was screened by PCR amplification with the PCR primer pairs identified above. A positive library was then used to isolate clones encoding the PRO343 gene using the probe oligonucleotide and one of the PCR primers.

RNA for construction of the cDNA libraries was isolated from human fetal lung tissue (LIB26).

DNA sequencing of the clones isolated as described above gave the full-length DNA sequence for PRO343 [herein designated as DNA43318-1217] (SEQ ID NO:262) and the derived protein sequence for PRO343.

The entire nucleotide sequence of DNA43318-1217 is shown in FIG. 97 (SEQ ID NO:262). Clone DNA43318-1217 contains a single open reading frame with an apparent translational initiation site at nucleotide positions 53–55 and ending at the stop codon at nucleotide positions 1004–1006 (FIG. 97). The predicted polypeptide precursor is 317 amino acids long (FIG. 98). Various unique aspects of the PRO343 protein are shown in FIG. 98. Clone DNA43318-1217 has been deposited with ATCC on Nov. 21, 1997 and is assigned ATCC deposit no. ATCC 209481.

Example 42

Isolation of cDNA Clones Encoding Human PRO328

A consensus DNA sequence was assembled relative to other EST sequences using phrap as described in Example 1 above. This consensus sequence is herein designated DNA35615. Based on the DNA35615 consensus sequence, oligonucleotides were synthesized: 1) to identify by PCR a cDNA library that contained the sequence of interest, and 2) for use as probes to isolate a clone of the full-length coding sequence for PRO328.

Forward and reverse PCR primers were synthesized:

forward PCR primer 5'-TCCTGCAGTTTCCTGATGC-3-' (SEQ ID NO:286)

reverse PCR primer 5'-CTCATATTGCACACCAGTAAT-TCG-3' (SEQ ID NO:287)

Additionally, a synthetic oligonucleotide hybridization probe was constructed from the consensus DNA35615 sequence which had the following nucleotide sequence hybridization probe

5'-ATGAGGAGAAACGTTTGATGGTGGAGCT-GCACAACCTCTACCGGG-3' (SEQ ID NO:288)

In order to screen several libraries for a source of a full-length clone, DNA from the libraries was screened by PCR amplification with the PCR primer pair identified above. A positive library was then used to isolate clones encoding the PRO328 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO328 [herein designated as DNA40587-1231] (SEQ ID NO:284) and the derived protein sequence for PRO328.

The entire nucleotide sequence of DNA40587-1231 is shown in FIG. 99 (SEQ ID NO:284). Clone DNA40587-1231 contains a single open reading frame with an apparent translational initiation site at nucleotide positions 15–17 and ending at the stop codon at nucleotide positions 1404–1406 (FIG. 99). The predicted polypeptide precursor is 463 amino acids long (FIG. 100). Clone DNA40587-1231 has been deposited with ATCC and is assigned ATCC deposit no. ATCC 209438.

Analysis of the amino acid sequence of the full-length PRO328 polypeptide suggests that portions of it possess significant homology to the human glioblastoma protein and to the cysteine rich secretory protein thereby indicating that PRO328 may be a novel glioblastoma protein or cysteine rich secretory protein.

Example 43

Isolation of cDNA Clones Encoding Human PRO335, PRO331 or PRO326

A consensus DNA sequence was assembled relative to other EST sequences using phrap as described in Example 1 above. This consensus sequence is herein designated DNA36685. Based on the DNA36685 consensus sequence, and Incyte EST sequence no. 2228990, oligonucleotides were synthesized: 1) to identify by PCR a cDNA library that contained the sequence of interest, and 2) for use as probes to isolate a clone of the full-length coding sequence for PRO335, PRO331 or PRO326.

Forward and reverse PCR primers were synthesized for the determination of PRO335:

forward PCR primer 5'-GGAACCGAATCTCAGCTA-3' (SEQ ID NO:295)

forward PCR primer 5'-CCTAAACTGAACTGGACCA-3' (SEQ ID NO:296)

forward PCR primer 5'-GGCTGGAGACACTGAACCT-3' (SEQ ID NO:297)

forward PCR primer 5'-ACAGCTGCACAGCTCAGAA-CAGTG-3' (SEQ ID NO:298)

reverse PCR primer 5'-CATTCCCAGTATAAAAATTTTC-3' (SEQ ID NO:299)

reverse PCR primer 5'-GGGTCTTGGTGAATGAGG-3' (SEQ ID NO:300)

reverse PCR primer 5'-GTGCCTCTCGGTTACCAC-CAATGG-3' (SEQ ID NO:301)

Additionally, a synthetic oligonucleotide hybridization probe was constructed for the determination of PRO335 which had the following nucleotide sequence hybridization probe

5'-GCGGCCACTGTTGGACCGAACTGTAAC-CAAGGGAGAAACAGCCGTCCTAC-3' (SEQ ID NO:302)

Forward and reverse PCR primers were synthesized for the determination of PRO331:

forward PCR primer 5'-GCCTTTGACAACCTTCAGT-CACTAGTGG-3' (SEQ ID NO:303)

reverse PCR primer 5'-CCCCATGTGTCCATGACTGT-TCCC-3' (SEQ ID NO:304)

Additionally, a synthetic oligonucleotide hybridization probe was constructed for the determination of PRO331 which had the following nucleotide sequence hybridization probe

5'-TACTGCCTCATGACCTCTTCACTCCCT-TGCATCATCTTAGAGCGG-3' (SEQ ID NO:305)

Forward and reverse PCR primers were synthesized for the determination of PRO326:

forward PCR primer 5'-ACTCCAAGGAAATCGGATC-CGTTC-3' (SEQ ID NO:306)

reverse PCR primer 5'-TTAGCAGCTGAGGATGGGCA-CAAC-3' (SEQ ID NO:307)

Additionally, a synthetic oligonucleotide hybridization probe was constructed for the determination of PRO331 which had the following nucleotide sequence hybridization probe

5'-GCCTTCACTGGTTTGGATGCATTGGAG-CATCTAGACCTGAGTGACAACGC-3' (SEQ ID NO:308)

In order to screen several libraries for a source of a full-length clone, DNA from the libraries was screened by PCR amplification with the PCR primer pairs identified above. A positive library was then used to isolate clones encoding the PRO335, PRO331 or PRO326 gene using the probe oligonucleotide and one of the PCR primers.

RNA for construction of the cDNA libraries was isolated from human fetal kidney tissue (PRO335 and PRO326) and human fetal brain (PRO331).

DNA sequencing of the clones isolated as described above gave the full-length DNA sequence for PRO335, PRO331 or PRO326 [herein designated as SEQ ID NOS:289, 291 and 293, respectively; see FIGS. 101, 103 and 105, respectively], and the derived protein sequence for PRO335, PRO331 or PRO326 (see FIGS. 102, 104 and 106, respectively; SEQ ID NOS:290, 292 and 294, respectively).

The entire nucleotide sequences are shown in FIGS. 101, 103 and 105, deposited with the ATCC on Jun. 2, 1998, Nov. 7, 1997 and Nov. 21, 1997, respectively.

Analysis of the amino acid sequence of the full-length PRO335, PRO331 or PRO326 polypeptide suggests that portions of it possess significant homology to the LIG-1 protein, thereby indicating that PRO335, PRO331 and PRO326 may be a novel LIG-1-related protein.

Example 44

Isolation of cDNA clones Encoding Human PRO332

Based upon an ECD homology search performed as described in Example 1 above, a consensus DNA sequence designated herein as DNA36688 was assembled. Based on the DNA36688 consensus sequence, oligonucleotides were synthesized to identify by PCR a cDNA library that contained the sequence of interest and for use as probes to isolate a clone of the full-length coding sequence for PRO332.

A pair of PCR primers (forward and reverse) were synthesized:

5'-GCATTGGCCGCGAGACTTTGCC-3' (SEQ ID NO:311)

5'-GCGGCCACGGTCCTTGGAAATG-3' (SEQ ID NO:312)

A probe was also synthesized:

5'-TGGAGGAGCTCAACCTCAGCTACAACCG-CATCACCAGCCCACAGG-3' (SEQ ID NO:313)

In order to screen several libraries for a source of a full-length clone, DNA from the libraries was screened by PCR amplification with the PCR primer pair identified above. A positive library was then used to isolate clones encoding the PRO332 gene using the probe oligonucleotide and one of the PCR primers.

RNA for construction of the cDNA libraries was isolated from a human fetal liver library (LIB229).

DNA sequencing of the clones isolated as described above gave the full-length DNA sequence for DNA40982-1235 and the derived protein sequence for PRO332.

The entire nucleotide sequence of DNA40982-1235 is shown in FIG. 107 (SEQ ID NO:309). Clone DNA40982-1235 contains a single open reading frame (with an apparent translational initiation site at nucleotide positions 342–344, as indicated in FIG. 107). The predicted polypeptide precursor is 642 amino acids long, and has a calculated molecular weight of 72,067 (pI: 6.60). Clone DNA40982-1235 has been deposited with ATCC and is assigned ATCC deposit no. ATCC 209433.

Based on a BLAST and FastA sequence alignment analysis of the full-length sequence, PRO332 shows about 30–40% amino acid sequence identity with a series of known proteoglycan sequences, including, for example, fibromodulin and fibromodulin precursor sequences of various species (FMOD_BOVIN, FMOD CHICK, FMOD_RAT, FMOD_MOUSE, FMOD_HUMAN, P_R36773), osteomodulin sequences (AB000114 1, AB007848_1), decorin sequences (CFU83141_1, OCU03394_1, P_R42266, P_R42267, P_R42260, P_R89439), keratan sulfate proteoglycans (BTU48360_1, AF022890_1), corneal proteoglycan (AF022256_1), and bone/cartilage proteoglycans and proteoglycane precursors (PGS1_BOVIN, PGS2_MOUSE, PGS2_HUMAN).

Example 45

Isolation of cDNA clones Encoding Human PRO334

A consensus DNA sequence was assembled relative to other EST sequences using phrap as described in Example 1 above. Based on the consensus sequence, oligonucleotides were synthesized: 1) to identify by PCR a cDNA library that contained the sequence of interest, and 2) for use as probes to isolate a clone of the full-length coding sequence for PRO334.

Forward and reverse PCR primers were synthesized for the determination of PRO334:

forward PCR primer 5'-GATGGTTCCTGCTCAAGTGCCCTG-3' (SEQ ID NO:316)

reverse PCR primer 5'-TTGCACTTGTAGGACCCACGTACG-3' (SEQ ID NO:317)

Additionally, a synthetic oligonucleotide hybridization probe was constructed for the determination of PRO334 which had the following nucleotide sequence hybridization probe

5'-CTGATGGGAGGACCTGTGTAGATGTTGATGAATGTGCTACAGGAAGAGCC-3' (SEQ ID NO:318)

In order to screen several libraries for a source of a full-length clone, DNA from the libraries was screened by PCR amplification with the PCR primer pair identified above. A positive library was then used to isolate clones encoding the PRO334 gene using the probe oligonucleotide and one of the PCR primers.

Human fetal kidney cDNA libraries used to isolate the cDNA clones were constructed by standard methods using commercially available reagents such as those from Invitrogen, San Diego, Calif.

DNA sequencing of the clones isolated as described above gave the full-length DNA sequence for PRO334 [herein designated as DNA41379-1236] (SEQ ID NO:314) and the derived protein sequence for PRO334.

The entire nucleotide sequence of DNA41379-1236 (also referred to as UNQ295) is shown in FIG. 109 (SEQ ID NO:314). Clone DNA41379-1236 contains a single open reading frame with an apparent translational initiation site at nucleotide positions 203–205 and ending at the stop codon at nucleotide positions 1730–1732 (FIG. 109). The predicted polypeptide precursor is 509 amino acids long (FIG. 110). Clone DNA41379-1236 has been deposited with ATCC and is assigned ATCC deposit no. ATCC 209488.

Analysis of the amino acid sequence of the full-length PRO334 polypeptide suggests that portions of it possess significant homology to the fibulin and fibrillin proteins, thereby indicating that PRO334 may be a novel member of the EGF protein family.

Example 46

Isolation of cDNA Clones Encoding Human PRO346

A consensus DNA sequence was identified using phrap as described in Example 1 above. Specifically, this consensus sequence is herein designated DNA38240. Based on the DNA38240 consensus sequence, oligonucleotides were synthesized: 1) to identify by PCR a cDNA library that contained the sequence of interest, and 2) for use as probes to isolate a clone of the full-length PRO346 coding sequence.

RNA for construction of the cDNA libraries was isolated from human fetal liver. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278–1280 (1991)) in the unique XhoI and NotI sites.

A cDNA clone was sequenced in entirety. The entire nucleotide sequence of DNA44167-1243 is shown in FIG. 111 (SEQ ID NO:319). Clone DNA44167-1243 contains a single open reading frame with an apparent translational initiation site at nucleotide positions 64–66 (FIG. 111; SEQ ID NO:319). The predicted polypeptide precursor is 450 amino acids long. Clone DNA44167-1243 has been deposited with ATCC and is assigned ATCC deposit no. ATCC 209434 (designation DNA44167-1243).

Based on a BLAST, BLAST-2 and FastA sequence alignment analysis (using the ALIGN computer program) of the full-length sequence, PRO346 shows amino acid sequence identity to carcinoembryonic antigen (28%).

The oligonucleotide sequences used in the above procedure were the following:

OLI2691 (38240.f1)

5'-GATCCTGTCACAAAGCCAGTGGTGC-3' (SEQ ID NO:321)

OLI2693 (38240.r1)

5'-CACTGACAGGGTTCCTCACCCAGG-3' (SEQ ID NO:322)

OLI2692 (3.8240.p1)

5'-CTCCCTCTGGGCTGTGGAGTATGTGGGGAACATGACCCTGACATG-3' (SEQ ID NO:323)

Example 47

Isolation of cDNA Clones Encoding Human PRO268

A consensus DNA sequence was assembled relative to other EST sequences using phrap as described in Example 1 above. This consensus sequence is herein designated DNA35698. Based on the DNA35698 consensus sequence, oligonucleotides were synthesized: 1) to identify by PCR a cDNA library that contained the sequence of interest, and 2) for use as probes to isolate a clone of the full-length coding sequence for PRO268.

Forward and reverse PCR primers were synthesized:

forward PCR primer 1 5'-TGAGGTGGGCAAGCGGCGAAATG-3' (SEQ ID NO:326)

forward PCR primer 2 5'-TATGTGGATCAGGACGTGCC-3' (SEQ ID NO:327)

forward PCR primer 3 5'-TGCAGGGTTCAGTCTAGATTG-3' (SEQ ID NO:328)

reverse PCR primer 5'-TTGAAGGACAAAGGCAATCTGCCAC-3' (SEQ ID NO:329)

Additionally, a synthetic oligonucleotide hybridization probe was constructed from the consensus DNA35698 sequence which had the following nucleotide sequence hybridization probe

5'-GGAGTCTTGCAGTTCCCCTGGCAGTCCTGGTGCTGTTGCTTTGGG-3' (SEQ ID NO: 330)

In order to screen several libraries for a source of a full-length clone, DNA from the libraries was screened by PCR amplification with the PCR primer pair identified above. A positive library was then used to isolate clones encoding the PRO268 gene using the probe oligonucleotide and one of the PCR primers.

RNA for construction of the cDNA libraries was isolated from human fetal lung tissue.

DNA sequencing of the clones isolated as described above gave the full-length DNA sequence for PRO268 [herein designated as DNA39427-1179] (SEQ ID NO:324) and the derived protein sequence for PRO268.

The entire nucleotide sequence of DNA39427-1179 is shown in FIG. 113 (SEQ ID NO:324). Clone DNA39427-1179 contains a single open reading frame with an apparent translational initiation site at nucleotide positions 13–15 and ending at the stop codon at nucleotide positions 853–855 (FIG. 113). The predicted polypeptide precursor is 280 amino acids long (FIG. 114). Clone DNA39427-1179 has been deposited with ATCC and is assigned ATCC deposit no. ATCC 209395.

Analysis of the amino acid sequence of the full-length PRO268 polypeptide suggests that it possess significant homology to protein disulfide isomerase, thereby indicating that PRO268 may be a novel protein disulfide isomerase.

Example 48

Isolation of cDNA Clones Encoding Human PRO330

A consensus DNA sequence was assembled relative to other EST sequences using phrap as described in Example 1 above. This consensus sequence is herein designated DNA35730. Based on the DNA35730 consensus sequence, oligonucleotides were synthesized: 1) to identify by PCR a cDNA library that contained the sequence of interest, and 2) for use as probes to isolate a clone of the full-length coding sequence for PRO330.

Forward and reverse PCR primers were synthesized:

forward PCR primer 1 5'-CCAGGCACAATTTCCAGA-3' (SEQ ID NO:333)

forward PCR primer 2 5'-GGACCCTTCTGTGTGCCAG-3' (SEQ ID NO:334)

reverse PCR primer 1 5'-GGTCTCAAGAACTCCTGTC-3' (SEQ ID NO:335)

reverse PCR primer 2 5'-ACACTCAGCATTGCCTGG-TACTTG-3' (SEQ ID NO:336)

Additionally, a synthetic oligonucleotide hybridization probe was constructed from the consensus sequence which had the following nucleotide sequence hybridization probe

5'-GGGCACATGACTGACCTGATTTATGCA-GAGAAAGAGCTGGTGCAG-3' (SEQ ID NO:337)

In order to screen several libraries for a source of a full-length clone, DNA from the libraries was screened by PCR amplification with the PCR primer pair identified above. A positive library was then used to isolate clones encoding the PRO330 gene using the probe oligonucleotide and one of the PCR primers.

RNA for construction of the cDNA libraries was isolated from human fetal liver tissue.

DNA sequencing of the clones isolated as described above gave the full-length DNA sequence for PRO330 [herein designated as DNA40603-1232] (SEQ ID NO:331) and the derived protein sequence for PRO330.

The entire nucleotide sequence of DNA40603-1232 is shown in FIG. 115 (SEQ ID NO:331). Clone DNA40603-1232 contains a single open reading frame with an apparent translational initiation site at nucleotide positions 167–169 and ending at the stop codon at nucleotide positions 1766–1768 (FIG. 115). The predicted polypeptide precursor is 533 amino acids long (FIG. 116). Clone DNA40603-1232 has been deposited with ATCC and is assigned ATCC deposit no. ATCC 209486 on Nov. 21, 1997.

Analysis of the amino acid sequence of the full-length PRO330 polypeptide suggests that portions of it possess significant homology to the mouse prolyl 4-hydroxylase alpha subunit protein, thereby indicating that PRO330 may be a novel prolyl 4-hydroxylase alpha subunit polypeptide.

Example 49

Isolation of cDNA Clones Encoding Human PRO310

A consensus DNA sequence was assembled relative to other EST sequences using phrap as described in Example 1 above. This consensus sequence is herein designated DNA40553. Based on the DNA40553 consensus sequence, oligonucleotides were synthesized: 1) to identify by PCR a cDNA library that contained the sequence of interest, and 2) for use as probes to isolate a clone of the full-length coding sequence for PRO310.

Forward and reverse PCR primers were synthesized:

forward PCR primer 1 5'-TCCCCAAGCCGTTCTA-GACGCGG-3' (SEQ ID NO:342)

forward PCR primer 2 5'-CTGGTTCTTCCTTGCACG-3' (SEQ ID NO:343)

reverse PCR primer 5'-GCCCAAATGCCCTAAGGCGG-TATACCCC-3' (SEQ ID NO:344)

Additionally, a synthetic oligonucleotide hybridization probe was constructed from the consensus sequence which had the following nucleotide sequence hybridization probe

5'-GGGTGTGATGCTTGGAAGCATTTTCTGT-GCTTTGATCACTATGCTAGGAC-3' (SEQ ID NO:345)

In order to screen several libraries for a source of a full-length clone, DNA from the libraries was screened by PCR amplification with the PCR primer pair identified above. A positive library was then used to isolate clones encoding the PRO310 gene using the probe oligonucleotide and one of the PCR primers.

RNA for construction of the cDNA libraries was isolated from human fetal liver tissue.

DNA sequencing of the clones isolated as described above gave the full-length DNA sequence for PRO310 [herein designated as DNA43046-1225] (SEQ ID NO:340) and the derived protein sequence for PRO310 (SEQ ID NO:341).

The entire nucleotide sequence of DNA43046-1225 is shown in FIG. 119 (SEQ ID NO:340). Clone DNA43046-1225 contains a single open reading frame with an apparent translational initiation site at nucleotide positions 81–83 and ending at the stop codon at nucleotide positions 1035–1037 (FIG. 119). The predicted polypeptide precursor is 318 amino acids long (FIG. 120) and has a calculated molecular weight of approximately 36,382 daltons. Clone DNA43046-1225 has been deposited with ATCC and is assigned ATCC deposit no. ATCC 209484.

Analysis of the amino acid sequence of the full-length PRO310 polypeptide suggests that portions of it possess homology to *C. elegans* proteins and to fringe, thereby indicating that PRO310 may be involved in development.

Example 50

Isolation of cDNA clones Encoding Human PRO339

An expressed sequence tag (EST) DNA database (LIFESEQ™, Incyte Pharmaceuticals, Palo Alto, Calif.) was searched and ESTs were identified. An assembly of Incyte clones and a consensus sequence was formed using phrap as described in Example 1 above.

Forward and reverse PCR primers were synthesized based upon the assembly-created consensus sequence:

forward PCR primer 15'-GGGATGCAGGTGGTGTCT-CATGGGG-3' (SEQ ID NO:346)

forward PCR primer 2 5'-CCCTCATGTACCGGCTCC-3' (SEQ ID NO:347)

forward PCR primer 3 5'-GTGTGACACAGCGTGGGC-3' (SEQ ID NO:43)

forward PCR primer 4 5'-GACCGGCAGGCTTCTGCG-3' (SEQ ID NO:44)

reverse PCR primer 1 5'-CAGCAGCTTCAGCCACCAG-GAGTGG-3' (SEQ ID NO:45)

reverse PCR primer 2 5'-CTGAGCCGTGGGCTG-CAGTCTCGC-3' (SEQ ID NO:46)

Additionally, a synthetic oligonucleotide hybridization probe was constructed from the consensus sequence which had the following nucleotide sequence hybridization probe

5'-CCGACTACGACTGGTTCTTCATCATG-CAGGATGACACATATGTGC-3' (SEQ ID NO:47)

In order to screen several libraries for a source of a full-length clone, DNA from the libraries was screened by PCR amplification with the PCR primer pairs identified above. A positive library was then used to isolate clones encoding the PRO339 gene using the probe oligonucleotide and one of the PCR primers.

RNA for construction of the cDNA libraries was isolated from human fetal liver tissue.

A cDNA clone was sequenced in entirety. The entire nucleotide sequence of DNA43466-1225 is shown in FIG. 117 (SEQ ID NO:338). Clone DNA43466-1225 contains a single open reading frame with an apparent translational initiation site at nucleotide positions 333–335 and ending at the stop codon found at nucleotide positions 2649–2651 (FIG. 117; SEQ ID NO:338). The predicted polypeptide precursor is 772 amino acids long and has a calculated molecular weight of approximately 86,226 daltons. Clone DNA43466-1225 has been deposited with ATCC and is assigned ATCC deposit no. ATCC 209490.

Based on a BLAST and FastA sequence alignment analysis (using the ALIGN computer program) of the full-length sequence, PRO339 has homology to *C. elegans* proteins and collagen-like polymer sequences as well as to fringe, thereby indicating that PRO339 may be involved in development or tissue growth.

Example 51

Isolation of cDNA Clones Encoding Human PRO244

A consensus DNA sequence was assembled relative to other EST sequences using phrap as described in Example 1 above. Based on this consensus sequence, oligonucleotides were synthesized to identify by PCR a cDNA library that contained the sequence of interest and for use as probes to isolate a clone of the full-length coding sequence for PRO244.

A pair of PCR primers (forward and reverse) were synthesized:

5'-TTCAGCTTCTGGGATGTAGGG-3' (30923. f1) (SEQ ID NO:378)

5'-TATTCCTACCATTTCACAAATCCG-3' (30923.r1) (SEQ ID NO:379)

A probe was also synthesized:

5'-GGAGGACTGTGCCACCATGAGAGACTCT-TCAAACCCAAGGCAAAATTGG-3' (30923. p 1) (SEQ ID NO:380)

In order to screen several libraries for a source of a full-length clone, DNA from the libraries was screened by PCR amplification with the PCR primer pair identified above. A positive library was then used to isolate clones encoding the PRO244 gene using the probe oligonucleotide and one of the PCR primers.

RNA for construction of the cDNA libraries was isolated from a human fetal kidney library. DNA sequencing of the clones isolated as described above gave the full-length DNA sequence and the derived protein sequence for PRO244.

The entire nucleotide sequence of PRO244 is shown in FIG. 121 (SEQ ID NO:376). Clone DNA35668-1171 contains a single open reading frame with an apparent translational initiation site at nucleotide positions 106–108 (FIG. 121). The predicted polypeptide precursor is 219 amino acids long. Clone DNA35668–1171 has been deposited with ATCC (designated as DNA35663-1171) and is assigned ATCC deposit no. ATCC209371. The protein has a cytoplasmic domain (aa 1–20), a transmembrane domain (aa 2146), and an extracellular domain (aa 47–219), with a C-lectin domain at aa 55–206.

Based on a BLAST and FastA sequence alignment analysis of the full-length sequence, PRO244 shows notable amino acid sequence identity to hepatic lectin *gallus gallus* (43%), HIC hp120-binding C-type lectin (42%), macrophage lectin 2 (HUMHML2-1, 41%) and sequence PR32188 (44%).

Example 52

Use of PRO Polypeptide-Encoding Nucleic Acid as Hybridization Probes

The following method describes use of a nucleotide sequence encoding a PRO polypeptide as a hybridization probe.

DNA comprising the coding sequence of a PRO polypeptide of interest as disclosed herein may be employed as a probe or used as a basis from which to prepare probes to screen for homologous DNAs (such as those encoding naturally-occurring variants of the PRO polypeptide) in human tissue cDNA libraries or human tissue genomic libraries.

Hybridization and washing of filters containing either library DNAs is performed under the following high stringency conditions. Hybridization of radiolabeled PRO polypeptide-encoding nucleic acid-derived probe to the filters is performed in a solution of 50% form amide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO polypeptide can then be identified using standard techniques known in the art.

Example 53

Expression of PRO Polypeptides in *E. Coli*

This example illustrates preparation of an unglycosylated form of a desired PRO polypeptide by recombinant expression in *E. coli*.

The DNA sequence encoding the desired PRO polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the specific PRO polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO polypeptide can then be purified using a metal chelating column under conditions that allow tight binding of the protein.

PRO187, PRO317, PRO301, PRO224 and PRO238 were successfully expressed in *E. coli* in a poly-His tagged form, using the following procedure. The DNA encoding PRO187, PRO317, PRO301, PRO224 or PRO238 was initially amplified using selected PCR primers. The primers contained restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences were then ligated into an expression vector, which was used to transform an *E. coli* host based on strain 52 (W3110 fuhA(tonA) lon galE rpoHts(htpRts) clpP(lacIq). Transformants were first grown in LB containing 50 mg/ml carbenicillin at 30° C. with shaking until an O.D. 600 of 3–5 was reached. Cultures were then diluted 50–100 fold into CRAP media (prepared by mixing 3.57 g $(NH_4)_2SO_4$, 0.71 g sodium citrate $2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30'.C with shaking. Samples were removed to verify expression by SDS-PAGE analysis, and the bulk culture is centrifuged to pellet the cells. Cell pellets were frozen until purification and refolding.

*E. coli* paste from 0.5 to 1 L fermentations (6–10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentifuge for 30 min. The supernatant was diluted with 3–5 volumes of metal chelate column buffer (6 M guanidine, 20 mM Tris, pH 7.4) and filtered through 0.22 micron filters to clarify. Depending the clarified extract was loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The proteins were refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes were chosen so that the final protein concentration was between 50 to 100 micrograms/ml. The refolding solution was stirred gently at 4° C. for 12–36 hours. The refolding reaction was quenched by the addition of TFA to a final concentration of 0.4% (pH of approximately 3). Before further purification of the protein, the solution was filtered through a 0.22 micron filter and acetonitrile was added to 2–10% final concentration. The refolded protein was chromatographed on a Poros R1/H reversed phase column using a mobile buffer of 0.1% TFA with elution with a gradient of acetonitrile from 10 to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO187, PRO317, PRO301, PRO224 and PRO238 proteins, respectively, were pooled and the acetonitrile removed using a gentle stream of nitrogen directed at the solution. Proteins were formulated into 20 mM Hepes, pH 6.8 with 0.14 M sodium chloride and 4% mannitol by dialysis or by gel filtration using G25 Superfine (Pharmacia) resins-equilibrated in the formulation buffer and sterile filtered.

Example 54

Expression of PRO Polypeptides in Mammalian Cells

This example illustrates preparation of a glycosylated form of a desired PRO polypeptide by recombinant expression in mammalian cells.

The vector, pRK5 (see EP 307,247, published Mar. 15, 1989), is employed as the expression vector. Optionally, the PRO polypeptide-encoding DNA is ligated into pRK5 with selected restriction enzymes to allow insertion of the PRO polypeptide DNA using ligation methods such as described in Sambrook et al., supra. The resulting vector is called pRK5-PRO polypeptide.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO polypeptide DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO polypeptide may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-PRO polypeptide DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO polypeptide can then be concentrated and purified by any selected method, such as dialysis and/or column chromatography.

In another embodiment, PRO polypeptides can be expressed in CHO cells. The pRK5-PRO polypeptide can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO polypeptide can then be concentrated and purified by any selected method.

Epitope-tagged PRO polypeptide may also be expressed in host CHO cells. The PRO polypeptide may be subcloned out of the pRK5 vector. The subclone insert can undergo PCR to fuse in frame with a selected epitope tag such as a poly-his tag into a Baculovirus expression vector. The poly-his tagged PRO polypeptide insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO polypeptide can then be concentrated and purified by any selected method, such as by $Ni^{2+}$-chelate affinity chromatography. PRO211, PRO217, PRO230, PRO219, PRO245, PRO221, PRO258, PRO301, PRO224, PRO222, PRO234, PRO229, PRO223, PRO328 and PRO332 were successfully expressed in CHO cells by both a transient and a stable expression procedure. In addition, PRO232, PRO265, PRO246, PRO228, PRO227, PRO220, PRO266, PRO269, PRO287, PRO214, PRO231, PRO233, PRO238, PRO244, PRO235, PRO236, PRO262, PRO239, PRO257, PRO260, PRO263, PRO270, PRO271, PRO272, PRO294, PRO295, PRO293, PRO247, PRO303 and PRO268 were successfully transiently expressed in CHO cells.

Stable expression in CHO cells was performed using the following procedure. The proteins were expressed as an IgG construct (immunoadhesin), in which the coding sequences for the soluble forms (e.g. extracellular domains) of the respective proteins were fused to an IgG1 constant region sequence containing the hinge, CH2 and CH2 domains and/or is a poly-His tagged form.

Following PCR amplification, the respective DNAs were subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24: 9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA were introduced into approximately 10 million CHO cells using commercially available transfection reagents Superfect® (Quiagen), Dosper® or Fugene® (Boehringer Mannheim). The cells were grown and described in Lucas et al., supra. Approximately $3\times10^{-7}$ cells are frozen in an ampule for further growth and production as described below.

The ampules containing the plasmid DNA were thawed by placement into water bath and mixed by vortexing. The contents were pipetted into a centrifuge tube containing 10 mLs of media and centrifuged at 1000 rpm for 5 minutes. The supernatant was aspirated and the cells were resuspended in 10 mL of selective media (0.2 μm filtered PS20 with 5% 0.2 μm diafiltered fetal bovine serum). The cells were then aliquoted into a 100 mL spinner containing 90 mL of selective media. After 1–2 days, the cells were transferred into a 250 mL spinner filled with 150 mL selective growth medium and incubated at 37° C. After another 2–3 days, a 250 mL, 500 mL and 2000 mL spinners were seeded with $3\times10^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 was actually used. 3 L production spinner is seeded at $1.2\times10^6$ cells/mL. On day 0, the cell number pH were determined. On day 1, the spinner was sampled and sparging with filtered air was commenced. On day 2, the spinner was sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion). Throughout the production, pH was adjusted as necessary to keep at around 7.2. After 10 days, or until viability dropped below 70%, the cell culture was harvested by centrifugation and filtering through a 0.22 μm filter. The filtrate was either stored at 4° C. or immediately loaded onto columns for purification.

For the poly-His tagged constructs, the proteins were purified using a Ni-NTA column (Qiagen). Before purification, imidazole was added to the conditioned media to a concentration of 5 mM. The conditioned media was pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M Imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of were purified from the conditioned media as follows. The conditioned medium was pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 μL of 1 M Tris buffer, pH 9. The highly purified protein was subsequently desalted into storage buffer as described above for the poly-His tagged proteins. The homogeneity was assessed by SDS polyacrylamide gels and by N-terminal amino acid sequencing by Edman degradation.

PRO211, PRO217, PRO230, PRO232, PRO187, PRO265, PRO219, PRO246, PRO228, PRO533, PRO245, PRO221, PRO227, PRO220, PRO258, PRO266, PRO269, PRO287, PRO214, PRO317, PRO301, PRO224, PRO222, PRO234, PRO231, PRO229, PRO233, PRO238, PRO223, PRO235, PRO236, PRO262, PRO239, PRO257, PRO260, PRO263, PRO270, PRO271, PRO272, PRO294, PRO295, PRO293, PRO247, PRO304, PRO302, PRO307, PRO303, PRO343, PRO328, PRO326, PRO331, PRO332, PRO334, PRO346, PRO268, PRO330, PRO310 and PRO339 were also successfully transiently expressed in COS cells.

Example 55

Expression of PRO Polypeptides in Yeast

The following method describes recombinant expression of a desired PRO polypeptide in yeast.

First, yeast expression vectors are constructed for intracellular production or secretion of PRO polypeptides from the ADH2/GAPDH promoter. DNA encoding a desired PRO polypeptide, a selected signal peptide and the promoter is inserted into suitable restriction enzyme sites in the selected plasmid to direct intracellular expression of the PRO polypeptide. For secretion, DNA encoding the PRO polypeptide can be cloned into the selected plasmid, together with DNA encoding the ADH2/GAPDH promoter, the yeast alpha-factor secretory signal/leader sequence, and linker sequences (if needed) for expression of the PRO polypeptide.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO polypeptide can subsequently be isolated and purified by removing the yeast cells from the fermentation medium by centrifugation and then concentrating the medium using selected cartridge filters. The concentrate containing the PRO polypeptide may further be purified using selected column chromatography resins.

Example 56

Expression of PRO Polypeptides in Baculovirus-Infected Insect Cells

The following method describes recombinant expression of PRO polypeptides in Baculovirus-infected insect cells.

The desired PRO polypeptide is fused upstream of an epitope tag contained with a baculovirus expression vector. Such epitope tags include poly-his tags and immunoglobulin tags (like Fe regions of IgG). A variety of plasmids may be employed, including plasmids derived from commercially available plasmids such as pVL1393 (Novagen). Briefly, the PRO polypeptide or the desired portion of the PRO polypeptide (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PRO polypeptide can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 0.5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO polypeptide are pooled and dialyzed against loading buffer.

Alternatively, purification of the IgG tagged (or Fe tagged) PRO polypeptide can be performed using known chromatography techniques, including for instance, Protein A or protein G column chromatography. PRO211, PRO217, PRO230, PRO187, PRO265, PRO246, PRO228, PRO533, PRO245, PRO221, PRO220, PRO258, PRO266, PRO269, PRO287, PRO214, PRO301, PRO224, PRO222, PRO234, PRO231, PRO229, PRO235, PRO239, PRO257, PRO272, PRO294, PRO295, PRO328, PRO326, PRO331, PRO334, PRO346 and PRO310 were successfully expressed in baculovirus infected Sf9 or high5 insect cells. While the expression was actually performed in a 0.5–2 L scale, it can be readily scaled up for larger (e.g. 8 L) preparations. The proteins were expressed as an IgG construct (immunoadhesin), in which the protein extracellular region was fused to an IgG1 constant region sequence containing the hinge, CH2 and CH3 domains and/or in poly-His tagged forms.

Following PCR amplification, the respective coding sequences were subcloned into a baculovirus expression vector (pb.PH.IgG for IgG fusions and pb.PH.His.c for poly-His tagged proteins), and the vector and Baculogold® baculovirus DNA (Pharmingen) were co-transfected into 105 *Spodoptera frugiperda* ("Sf9") cells (ATCC CRL 1711), using Lipofectin (Gibco BRL). pb.PH.IgG and pb.PH.His are modifications of the commercially available baculovirus expression vector pVL1393 (Pharmingen), with modified polylinker regions to include the His or Fe tag sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the constructs in the baculovirus expression vector was determined by batch binding of 1 ml of supernatant to 25 mL of Ni-NTA beads (QIAGEN) for histidine tagged proteins or Protein-A Sepharose CL4B beads (Pharmacia) for IgG tagged proteins followed by SDS-PAGE analysis comparing to a known concentration of protein standard by Coomassie blue staining.

The first viral amplification supernatant was used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. For the poly-His tagged constructs, the protein construct were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M Imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins were purified from the conditioned media as follows. The conditioned media were pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 mL of 1 M Tris buffer, pH 9. The highly purified protein was subsequently desalted into storage buffer as described above for the poly-His tagged proteins. The homogeneity of the proteins was verified by SDS polyacrylamide gel (PEG) electrophoresis and N-terminal amino acid sequencing by Edman degradation.

Example 57

Preparation of Antibodies that Bind to PRO Polypeptides

This example illustrates preparation of monoclonal antibodies which can specifically bind to a PRO polypeptide.

Techniques for producing the monoclonal antibodies are known in the art and are described, for instance, in Goding, supra. Immunogens that may be employed include purified PRO polypeptide, fusion proteins containing the PRO polypeptide, and cells expressing recombinant PRO polypeptide on the cell surface. Selection of the immunogen can be made by the skilled artisan without undue experimentation.

Mice, such as Balb/c, are immunized with the PRO polypeptide immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO polypeptide antibodies.

After a suitable antibody titer has been detected, the animals "positive" for antibodies can be injected with a final intravenous injection of PRO polypeptide. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the PRO polypeptide. Determination of "positive" hybridoma cells secreting the desired monoclonal antibodies against the PRO polypeptide is within the skill in the art.

The positive hybridoma cells can be injected intraperitoneally into syngeneic Balb/c mice to produce ascites containing the anti-PRO polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 58

Chimeric PRO Polypeptides

PRO polypeptides may be expressed as chimeric proteins with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS™ extension/affinity purification system (Immunex Corp., Seattle Wash.). The inclusion of a cleavable linker sequence such as Factor XA or enterokinase (Invitrogen, San Diego Calif.) between the purification domain and the PRO polypeptide sequence may be useful to facilitate expression of DNA encoding the PRO polypeptide.

Example 59

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 60

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 61

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology,* 9: 19–21(1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry.* 31:7796–7801 (1992) or which act as inhibitors, agonists, or antagonists of native peptides as shown by Athauda et al., *J. Biochem.,* 113: 742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 62

Diagnostic Test Using PRO317 Polypeptide-Specific Antibodies

Particular anti-PRO317 polypeptide antibodies are useful for the diagnosis of prepathologic conditions, and chronic or acute diseases such as gynecological diseases or ischemic diseases which are characterized by differences in the amount or distribution of PRO317. PRO317 has been found to be expressed in human kidney and is thus likely to be associated with abnormalities or pathologies which affect this organ. Further, since it is so closely related to EBAF-1, it is likely to affect the endometrium and other genital tissues. Further, due to library sources of certain ESTs, it appears that PRO317 may be involved as well in forming blood vessels and hence to be a modulator of angiogenesis.

Diagnostic tests for PRO317 include methods utilizing the antibody and a label to detect PRO317 in human body fluids, tissues, or extracts of such tissues. The polypeptide and antibodies of the present invention may be used with or without modification. Frequently, the polypeptide and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567.

A variety of protocols for measuring soluble or membrane-bound PRo317, using either polyclonal or monoclonal antibodies specific for that PRO317, are known in the art. Examples include enzyme-linked immunosorbent assay (ELISA), radioimmunoassay (RIA), radioreceptor assay (RRA), and fluorescent activated cell sorting (FACS). A two site monoclonal-based immunoassay utilizing monoclonal antibodies reactive to two non-interfering epitopes on PRO317 is preferred, but a competitive binding assay may be employed. These assays are described, among other places, in Maddox et al. *J. Exp. Med.,* 158:1211 (1983).

Example 63

Identification of PRO317 Receptors

Purified PRO317 is useful for characterization and purification of specific cell surface receptors and other binding molecules. Cells which respond to PRO317 by metabolic changes or other specific responses are likely to express a receptor for PRO317. Such receptors include, but are not limited to, receptors associated with and activated by tyrosine and serine/threonine kinases. See Kolodziejczyk and Hall, supra, for a review on known receptors for the TGF-superfamily. Candidate receptors for this superfamily fall into two primary groups, termed type I and type II receptors. Both types are serine/threonine kinases. Upon activation by the appropriate ligand, type I and type II receptors physically interact to form hetero-oligomers and subsequently activate intracellular signaling cascades, ultimately regulating gene transcription and expression. In addition, TGF-binds to a third receptor class, type III, a membrane-anchored proteoglycan lacking the kinase activity typical of signal transducing molecules.

PRO317 receptors or other PRO317-binding molecules may be identified by interaction with radiolabeled PRO317. Radioactive labels may be incorporated into PRO317 by various methods known in the art. A preferred embodiment is the labeling of primary amino groups in PRO317 with $^{125}I$ Bolton-Hunter reagent (Bolton and Hunter, *Biochem. J.,* 133:529 (1973)), which has been used to label other polypeptides without concomitant loss of biological activity (Hebert et al., *J. Biol. Chem.,* 266:18989 (1991); McColl et al., *J. Immunol.,* 150:4550–4555 (1993)). Receptor-bearing cells are incubated with labeled PRO317. The cells are then washed to removed unbound PRO317, and receptor-bound PRO317 is quantified. The data obtained using different concentrations of PRO317 are used to calculate values for the number and affinity of receptors.

Labeled PRO317 is useful as a reagent for purification of its specific receptor. In one embodiment of affinity purification, PRO317 is covalently coupled to a chromatography column. Receptor-bearing cells are extracted, and the extract is passed over the column. The receptor binds to the column by virtue of its biological affinity for PRO317. The receptor is recovered from the column and subjected to N-terminal protein sequencing. This amino acid sequence is then used to design degenerate oligonucleotide probes for cloning the receptor gene.

In an alternative method, mRNA is obtained from receptor-bearing cells and made into a cDNA library. The library is transfected into a population of cells, and those cells expressing the receptor are selected using fluorescently labeled PRO317. The receptor is identified by recovering and sequencing recombinant DNA from highly labeled cells.

In another alternative method, antibodies are raised against the surface of receptor bearing cells, specifically monoclonal antibodies. The monoclonal antibodies are screened to identify those which inhibit the binding of labeled PRO317. These monoclonal antibodies are then used in affinity purification or expression cloning of the receptor.

Soluble receptors or other soluble binding molecules are identified in a similar manner. Labeled PRO317 is incubated with extracts or other appropriate materials derived from the uterus. After incubation, PRO317 complexes larger than the size of purified PRO317 are identified by a sizing technique such as size-exclusion chromatography or density gradient centrifugation and are purified by methods known in the art. The soluble receptors or binding protein(s) are subjected to N-terminal sequencing to obtain information sufficient for database identification, if the soluble protein is known, or for cloning, if the soluble protein is unknown.

Example 64

Determination of PRO317-Induced Cellular Response

The biological activity of PRO317 is measured, for example, by binding of an PRO317 of the invention to an PRO317 receptor. A test compound is screened as an antagonist for its ability to block binding of PRO317 to the receptor. A test compound is screened as an agonist of the PRO317 for its ability to bind an PRO317 receptor and influence the same physiological events as PRO317 using, for example, the KIRA-ELISA assay described by Sadick et al., *Analytical Biochemistry,* 235:207–214 (1996) in which activation of a receptor tyrosine kinase is monitored by immuno-capture of the activated receptor and quantitation of the level of ligand-induced phosphorylation. The assay may be adapted to monitor PRO317-induced receptor activation through the use of an PRO317 receptor-specific antibody to capture the activated receptor. These techniques are also applicable to other PRO polypeptides described herein.

Example 65

Use of PRO224 for Screening Compounds

PRO224 is expressed in a cell stripped of membrane proteins and capable of expressing PRO224. Low density lipoproteins having a detectable label are added to the cells and incubated for a sufficient time for endocytosis. The cells are washed. The cells are then analysed for label bound to the membrane and within the cell after cell lysis. Detection of the low density lipoproteins within the cell determines that PRO224 is within the family of low density lipoprotein receptor proteins. Members found within this family are then used for screening compounds which affect these receptors, and particularly the uptake of cholesterol via these receptors.

Example 66

Ability of PRO Polypeptides to Inhibit Vascular Endothelial Growth Factor (VEGF) Stimulated Proliferation of Endothelial Cell Growth (Assay 9)

The ability of various PRO polypeptides to inhibit VEGF stimulated proliferation of endothelial cells was tested. Polypeptides testing positive in this assay are useful for inhibiting endothelial cell growth in mammals where such an effect would be beneficial, e.g., for inhibiting tumor growth.

Specifically, bovine adrenal cortical capillary endothelial cells (ACE) (from primary culture, maximum of 12–14 passages) were plated in 96-well plates at 500 cells/well per 100 microliter. Assay media included low glucose DMEM, 10% calf serum, 2 mM glutamine, and 1× penicillin/streptomycin/fungizone. Control wells included the following: (1) no ACE cells added; (2) ACE cells alone; (3) ACE cells plus 5 ng/ml FGF; (4) ACE cells plus 3 ng/ml VEGF; (5) ACE cells plus 3 ng/ml VEGF plus 1 ng/ml TGF-beta; and (6) ACE cells plus 3 ng/ml VEGF plus 5 ng/ml LIF. The test samples, poly-his tagged PRO polypeptides (in 100 microliter volumes), were then added to the wells (at dilutions of 1%, 0.1% and 0.01%, respectively). The cell cultures were incubated for 6–7 days at 37° C./5% $CO_2$. After the incubation, the media in the wells was aspirated, and the cells were washed 1× with PBS. An acid phosphatase reaction mixture (100 microliter; 0.1M sodium acetate, pH 5.5, 0.1% Triton X-100, 10 mM p-nitrophenyl phosphate) was then added to each well. After a 2 hour incubation at 37° C., the reaction was stopped by addition of 10 microliters 1N NaOH. Optical density (OD) was measured on a microplate reader at 405 nm.

The activity of PRO polypeptides was calculated as the percent inhibition of VEGF (3 ng/ml) stimulated proliferation (as determined by measuring acid phosphatase activity at OD 405 nm) relative to the cells without stimulation. TGF-beta was employed as an activity reference at 1 ng/ml, since TGF-beta blocks 70–90% of VEGF-stimulated ACE cell proliferation. The results are indicative of the utility of the PRO polypeptides in cancer therapy and specifically in inhibiting tumor angiogenesis. Numerical values (relative inhibition) are determined by calculating the percent inhibition of VEGF stimulated proliferation by the PRO polypeptides relative to cells without stimulation and then dividing that percentage into the percent inhibition obtained by TGF-β at 1 ng/ml which is known to block 70–90% of VEGF stimulated cell proliferation. The results are considered positive if the PRO polypeptide exhibits 30% or greater inhibition of VEGF stimulation of endothelial cell growth (relative inhibition 30% or greater).

The following polypeptides tested positive in this assay: PRO211, PRO217, PRO187, PRO219, PRO246, PRO228, PRO245, PRO221, PRO258, PRO301, PRO224, PRO272, PRO328, PRO331, PRO224, PRO328, PRO272, PRO301, PRO331 and PRO214.

Example 67

Retinal Neuron Survival (Assay 52)

This example demonstrates that certain PRO polypeptides have efficacy in enhancing the survival of retinal neuron cells and, therefore, are useful for the therapeutic treatment of retinal disorders or injuries including, for example, treating sight loss in mammals due to retinitis pigmentosum, AMD, etc.

Sprague Dawley rat pups at postnatal day 7 (mixed population: glia and retinal neuronal types) are killed by decapitation following $CO_2$ anesthesia and the eyes are removed under sterile conditions. The neural retina is dissected away from the pigment epithelium and other ocular tissue and then dissociated into a single cell suspension using 0.25% trypsin in $Ca^{2+}$, $Mg^{2+}$-free PBS. The retinas are incubated at 37° C. for 7–10 minutes after which the trypsin is inactivated by adding 1 ml soybean trypsin inhibitor. The cells are plated at 100,000 cells pet well in 96 well plates in DMEM/F12 supplemented with N2 and with or without the specific test PRO polypeptide. Cells for all experiments are grown at 37° C. in a water saturated atmosphere of 5% $CO_2$. After 2–3 days in culture, cells are stained with calcein AM then fixed using 4% paraformaldehyde and stained with DAPI for determination of total cell count. The total cells (fluorescent) are quantified at 20× objective magnification using CCD camera and NIH image software for Macintosh. Fields in the well are chosen at random.

The effect of various concentration of PRO polypeptides are reported herein where percent survival is calculated by dividing the total number of calcein AM positive cells at 2–3 days in culture by the total number of DAPI-labeled cells at 2–3 days in culture. Anything above 30% survival is considered positive.

The following PRO polypeptides tested positive in this assay using polypeptide concentrations within the range of 0.01% to 1.0% in the assay: PRO220 and PRO346.

Example 68

Rod Photoreceptor Cell Survival (Assay 56)

This assay shows that certain polypeptides of the invention act to enhance the survival/proliferation of rod photoreceptor cells and, therefore, are useful for the therapeutic treatment of retinal disorders or injuries including, for example, treating sight loss in mammals due to retinitis pigmentosum, AMD, etc. Sprague Dawley rat pups at 7 day postnatal (mixed population: glia and retinal neuronal cell types) are killed by decapitation following $CO_2$ anesthesis and the eyes are removed under sterile conditions. The neural retina is dissected away form the pigment epithelium and other ocular tissue and then dissociated into a single cell suspension using 0.25% trypsin in $Ca^{2+}$, $Mg^{2+}$-free PBS. The retinas are incubated at 37° C. for 7–10 minutes after which the trypsin is inactivated by adding 1 ml soybean trypsin inhibitor. The cells are plated at 100,000 cells per well in 96 well plates in DMEM/F12 supplemented with $N_2$. Cells for all experiments are grown at 37° C. in a water saturated atmosphere of 5% $CO_2$. After 2–3 days in culture, cells are fixed using 4% paraformaldehyde, and then stained using CellTracker Green CMFDA. Rho 4D2 (ascites or IgG 1:100), a monoclonal antibody directed towards the visual pigment rhodopsin is used to detect rod photoreceptor cells by indirect immunofluorescence. The results are calculated as % survival: total number of calcein–rhodopsin positive cells at 2–3 days in culture, divided by the total number of rhodopsin positive cells at time 2–3 days in culture. The total cells (fluorescent) are quantified at 20× objective magnification using a CCD camera and NIH image software for Macintosh. Fields in the well are chosen at random.

The following polypeptides tested positive in this assay: PRO220 and PRO346.

Example 69

Induction of Endothelial Cell Apoptosis (Assay 73)

The ability of PRO polypeptides to induce apoptosis in endothelial cells was tested in human venous umbilical vein endothelial cells (HUVEC, Cell Systems). A positive test in the assay is indicative of the usefulness of the polypeptide in therapeutically treating tumors as well as vascular disorders where inducing apoptosis of endothelial cells would be beneficial.

The cells were plated on 96-well microtiter plates (Amersham Life Science, cytostar-T scintillating microplate, RPNQ160, sterile, tissue-culture treated, individually wrapped), in 10% serum (CSG-medium, Cell Systems), at a density of $2\times10^4$ cells per well in a total volume of 100 μl. On day 2, test samples containing the PRO polypeptide were added in triplicate at dilutions of 1%, 0.33% and 0.11%. Wells without cells were used as a blank and wells with cells only were used as a negative control. As a positive control 1:3 serial dilutions of 50 μl of a 3× stock of staurosporine were used. The ability of the PRO polypeptide to induce apoptosis was determined by processing of the 96 well plates for detection of Annexin V, a member of the calcium and phospholipid binding proteins, to detect apoptosis.

0.2 ml Annexin V—Biotin stock solution (100 μg/ml) was diluted in 4.6 ml 2× $Ca^{2+}$ binding buffer and 2.5% BSA (1:25 dilution). 50 μl of the diluted Annexin V—Biotin solution was added to each well (except controls) to a final concentration of 1.0 μg/ml. The samples were incubated for 10–15 minutes with Annexin-Biotin prior to direct addition of $^{35}S$-Streptavidin. $^{35}S$-Streptavidin was diluted in 2×$Ca^{2+}$ Binding buffer, 2.5% BSA and was added to all wells at a final concentration of $3\times10^4$ cpm/well. The plates were then sealed, centrifuged at 1000 rpm for 15 minutes and placed on orbital shaker for 2 hours. The analysis was performed on a 1450 Microbeta Trilux (Wallac). Percent above background represents the percentage amount of counts per minute above the negative controls. Percents greater than or equal to 30% above background are considered positive.

The following PRO polypeptides tested positive in this assay: PRO228, PRO217 and PRO301.

Example 70

PDB12 Cell Inhibition (Assay 40)

This example demonstrates that various PRO polypeptides have efficacy in inhibiting protein production by PDB12 pancreatic ductal cells and are, therefore, useful in the therapeutic treatment of disorders which involve protein secretion by the pancreas, including diabetes, and the like.

PDB12 pancreatic ductal cells are plated on fibronectin coated 96 well plates at $1.5\times10^3$ cells per well in 100 μL/180 μL of growth media. 100 μL of growth media with the PRO polypeptide test sample or negative control lacking the PRO polypeptide is then added to well, for a final volume of 200 μL. Controls contain growth medium containing a protein shown to be inactive in this assay. Cells are incubated for 4 days at 37° C. 20 μL of Alamar Blue Dye (AB) is then added to each well and the flourescent reading is measured at 4 hours post addition of AB, on a microtiter plate reader at 530 nm excitation and 590 nm emission. The standard employed is cells without Bovine Pituitary Extract (BPE) and with various concentrations of BPE. Buffer or CM controls from unknowns are run 2 times on each 96 well plate.

These assays allow one to calculate a percent decrease in protein production by comparing the Alamar Blue Dye calculated protein concentration produced by the PRO polypeptide-treated cells with the Alamar Blue Dye calculated protein concentration produced by the negative control cells. A percent decrease in protein production of greater than or equal to 25% as compared to the negative control cells is considered positive.

The following polypeptides tested positive in this assay: PRO211, PRO287, PRO301 and PRO293.

Example 71

Stimulation of Adult Heart Hypertrophy (Assay 2)

This assay is designed to measure the ability of various PRO polypeptides to stimulate hypertrophy of adult heart. PRO polypeptides testing positive in this assay would be expected to be useful for the therapeutic treatment of various cardiac insufficiency disorders.

Ventricular myocytes freshly isolated from adult (250 g) Sprague Dawley rats are plated at 2000 cell/well in 180 μl volume. Cells are isolated and plated on day 1, the PRO polypeptide-containing test samples or growth medium only (negative control) (20 μl volume) is added on day 2 and the cells are then fixed and stained on day 5. After staining, cell size is visualized wherein cells showing no growth enhancement as compared to control cells are given a value of 0.0, cells showing small to moderate growth enhancement as compared to control cells are given a value of 1.0 and cells showing large growth enhancement as compared to control cells are given a value of 2.0. Any degree of growth enhancement as compared to the negative control cells is considered positive for the assay.

The following PRO polypeptides tested positive in this assay: PRO287, PRO301, PRO293 and PRO303.

Example 72

PDB12 Cell Proliferation (Assay 29)

This example demonstrates that various PRO polypeptides have efficacy in inducing proliferation of PDB12 pancreatic ductal cells and are, therefore, useful in the therapeutic treatment of disorders which involve protein secretion by the pancreas, including diabetes, and the like.

PDB12 pancreatic ductal cells are plated on fibronectin coated 96 well plates at $1.5\times10^3$ cells per well in 100 μL/180 μL of growth media. 100 μL of growth media with the PRO polypeptide test sample or negative control lacking the PRO polypeptide is then added to well, for a final volume of 200 μL. Controls contain growth medium containing a protein shown to be inactive in this assay. Cells are incubated for 4 days at 37° C. 20 μL of Alamar Blue Dye (AB) is then added to each well and the flourescent reading is measured at 4 hours post addition of AB, on a microtiter plate reader at 530 nm excitation and 590 nm emission. The standard employed is cells without Bovine Pituitary Extract (BPE) and with various concentrations of BPE. Buffer or growth medium only controls from unknowns are run 2 times on each 96 well plate.

Percent increase in protein production is calculated by comparing the Alamar Blue Dye calculated protein concentration produced by the PRO polypeptide-treated cells with the Alamar Blue Dye calculated protein concentration produced by the negative control cells. A percent increase in protein production of greater than or equal to 25% as compared to the negative control cells is considered positive.

The following PRO polypeptides tested positive in this assay: PRO301 and PRO303.

Example 73

Enhancement of Heart Neonatal Hypertrophy (Assay 1)

This assay is designed to measure the ability of PRO polypeptides to stimulate hypertrophy of neonatal heart. PRO polypeptides testing positive in this assay are expected to be useful for the therapeutic treatment of various cardiac insufficiency disorders.

Cardiac myocytes from 1-day old Harlan Sprague Dawley rats were obtained. Cells (180 μl at $7.5\times10^4$/ml, serum <0.1%, freshly isolated) are added on day 1 to 96-well plates previously coated with DMEM/F12+4% FCS. Test samples containing the test PRO polypeptide or growth medium only (negative control) (20 μl/well) are added directly to the wells on day 1. PGF (20 μl/well) is then added on day 2 at final concentration of $10^{-6}$ M. The cells are then stained on day 4 and visually scored on day 5, wherein cells showing no increase in size as compared to negative controls are scored 0.0, cells showing a small to moderate increase in size as compared to negative controls are scored 1.0 and cells showing a large increase in size as compared to negative controls are scored 2.0. A positive result in the assay is a score of 1.0 or greater.

The following polypeptides tested positive in this assay: PRO224 and PRO231.

Example 74

Stimulatory Activity in Mixed Lymphocyte Reaction (MLR) Assay (Assay 24)

This example shows that certain polypeptides of the invention are active as a stimulator of the proliferation of stimulated T-lymphocytes. Compounds which stimulate proliferation of lymphocytes are useful therapeutically where enhancement of an immune response is beneficial. A therapeutic agent may take the form of antagonists of the polypeptide of the invention, for example, murine-human chimeric, humanized or human antibodies against the polypeptide.

The basic protocol for this assay is described in Current Protocols in Immunology, unit 3.12; edited by J E Coligan, A M Kruisbeek, D H Marglies, E M Shevach, W Strober, National Institutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3\times10^6$ cells/ml of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads).

The assay is prepared by plating in triplicate wells a mixture of:

100:1 of test sample diluted to 1% or to 0.1%,

50:1 of irradiated stimulator cells, and

50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1\times10^7$ cells/ml of assay media. The assay is then conducted as described above.

Positive increases over control are considered positive with increases of greater than or equal to 180% being preferred. However, any value greater than control indicates a stimulatory effect for the test protein.

The following PRO polypeptides tested positive in this assay: PRO245, PRO269, PRO217, PRO301, PRO266, PRO335, PRO331, PRO533 and PRO326.

Example 75

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control=DME+5% serum+/−PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1× fungizone. Assay Media=low glucose DMEM +5% FBS.

The following polypeptides tested positive in this assay: PRO214, PRO219, PRO221 and PRO224.

Example 76

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4–6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) woth 0.1% BSA and 100 U/ml penicillin and 100 μg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, *Biochem. Biophys. Acta* 883:173–177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basely and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. The polypeptides testing positive in this assay are: PRO211.

Example 77

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grants or more are anesthetized with ketamine (75–80 mg/Kg) and 5 mg/Kg xylazine intramuscularly (IM). A sample of purified polypeptide of the invention or a conditioned media test sample is injected intradermally onto the backs of the test animals with 100 μl per injection site. It is possible to have about 10–30, preferably about 16–24, injection sites per animal. One μl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positive, no infiltrate at the site of injection is scored as negative.

The following polypeptides tested positive in this assay: PRO245, PRO217, PRO326, PRO266, PRO272, PRO301, PRO331 and PRO335.

Example 78

Enhancement of Heart Neonatal Hypertrophy Induced by F2a (Assay 37)

This assay is designed to measure the ability of PRO polypeptides to stimulate hypertrophy of neonatal heart. PRO polypeptides testing positive in this assay are expected to be useful for the therapeutic treatment of various cardiac insufficiency disorders.

Cardiac myocytes from 1-day old Harlan Sprague Dawley rats were obtained. Cells (180 μl at $7.5\times10^4$/ml, serum <0.1%, freshly isolated) are added on day 1 to 96-well plates previously coated with DMEM/F12+4% FCS. Test samples containing the test PRO polypeptide (20 μl/well) are added directly to the wells on day 1. PGF (20 μl/well) is then added on day 2 at a final concentration of $10^{-6}$ M. The cells are then stained on day 4 and visually scored on day 5. Visual scores are based on cell size, wherein cells showing no increase in size as compared to negative controls are scored 0.0, cells showing a small to moderate increase in size as compared to negative controls are scored 1.0 and cells showing a large increase in size as compared to negative controls are scored 2.0. A score of 1.0 or greater is considered positive.

No PBS is included, since calcium concentration is critical for assay response. Plates are coated with DMEM/F12 plus 4% FCS (200 μl/well). Assay media included: DMEM/F12 (with 2.44 gm bicarbonate), 10 μg/ml transferrin, 1 μg/ml insulin, 1 μg/ml aprotinin, 2 mmol/L glutamine, 100 U/ml penicillin G, 100 μg/ml streptomycin. Protein buffer containing mannitol (4%) gave a positive signal (score 3.5) at 1/10 (0.4%) and 1/100 (0.04%), but not at 1/1000 (0.004%). Therefore the test sample buffer containing mannitol is not run.

The following PRO polypeptides tested positive in this assay: PRO224.

Example 79

Inhibitory Activity in Mixed Lymphocyte Reaction (MLR) Assay (Assay 67)

This example shows that one or more of the polypeptides of the invention are active as inhibitors of the proliferation of stimulated T-lymphocytes. Compounds which inhibit proliferation of lymphocytes are useful therapeutically where suppression of an immune response is beneficial.

The basic protocol for this assay is described in Current Protocols in Immunology, unit 3.12; edited by J E Coligan, A M Kruisbeek, D H Marglies, E M Shevach, W Strober, National Institutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3\times10^6$ cells/ml of assay media (RPMI; 10% fetal bovine serum, 1% penicillin/streptomycin, 1% glutamine, 1% HEPES, 1% non-essential amino acids, 1% pyruvate). The stimulator PB MCs are prepared by irradiating the cells (about 3000 Rads).

The assay is prepared by plating in triplicate wells a mixture of:

100:1 of test sample diluted to 1% or to 0.1%,

50:1 of irradiated stimulator cells, and

50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1\times10^7$ cells/ml of assay media. The assay is then conducted as described above.

Any decreases below control is considered to be a positive result for an inhibitory compound, with decreases of less than or equal to 80% being preferred. However, any value less than control indicates an inhibitory effect for the test protein.

The following polypeptide tested positive in this assay: PRO235, PRO245 and PRO332.

Example 80

Induction of Endothelial Cell Apoptosis (ELISA) (Assay 109)

The ability of PRO polypeptides to induce apoptosis in endothelial cells was tested in human venous umbilical vein endothelial cells (HUVEC, Cell Systems) using a 96-well format, in 0% serum media supplemented with 100 ng/ml VEGF, 0.1% BSA, 1× penn/strep. A positive result in this assay indicates the usefulness of the polypeptide for therapeutically treating any of a variety of conditions associated with undesired endothelial cell growth, including, for example, the inhibition of tumor growth. The 96-well plates used were manufactured by Falcon (No. 3072). Coating of 96 well plates were prepared by allowing gelatinization to occur for >30 minutes with 100 μl of 0.2% gelatin in PBS solution. The gelatin mix was aspirated thoroughly before plating HUVEC cells at a final concentration of $2 \times 10^4$ cells/ml in 10% serum containing medium–100 µl volume per well. The cells were grown for 24 hours before adding test samples containing the PRO polypeptide of interest.

To all wells, 100 µl of 0% serum media (Cell Systems) complemented with 100 ng/ml VEGF, 0.1% BSA, 1× penn/strep was added. Test samples containing PRO polypeptides were added in triplicate at dilutions of 1%, 0.33% and 0.11%. Wells without cells were used as a blank and wells with cells only were used as a negative control. As a positive control, 1:3 serial dilutions of 50 µl of a 3× stock of staurosporine were-used. The cells were incubated for 24 to 35 hours prior to ELISA.

ELISA was used to determine levels of apoptosis preparing solutions according to the Boehringer Manual [Boehringer, Cell Death Detection ELISA plus, Cat No. 1 920 685]. Sample preparations: 96 well plates were spun down at 1 krpm for 10 minutes (200 g); the supernatant was removed by fast inversion, placing the plate upside down on a paper towel to remove residual liquid. To each well, 200 µl of 1× Lysis buffer was added and incubation allowed at room temperature for 30 minutes without shaking. The plates were spun down for 10 minutes at 1 krpm, and 20 µl of the lysate (cytoplasmic fraction) was transferred into streptavidin coated MTP. 80 µl of immunoreagent mix was added to the 20 µl lystate in each well. The MTP was covered with adhesive foil and incubated at room temperature for 2 hours by placing it on an orbital shaker (200 rpm). After two hours, the supernatant was removed by suction and the wells rinsed three times with 250 µl of 1× incubation buffer per well (removed by suction). Substrate solution was added (100 µl) into each well and incubated on an orbital shaker at room temperature at 250 rpm until color development was sufficient for a photometric analysis (approx. after 10–20 minutes). A 96 well reader was used to read the plates at 405 nm, reference wavelength, 492 µm. The levels obtained for PIN 32 (control buffer) was set to 100%. Samples with levels >130% were considered positive for induction of apoptosis.

The following PRO polypeptides tested positive in this assay: PRO235.

Example 81

Human Venous Endothelial Cell Calcium Flux Assay (Assay 68)

This assay is designed to determine whether PRO polypeptides of the present invention show the ability to stimulate calcium flux in human umbilical vein endothelial cells (HUVEC, Cell Systems). Calcium influx is a well documented response upon binding of certain ligands to their receptors. A test compound that results in a positive response in the present calcium influx assay can be said to bind to a specific receptor and activate a biological signaling pathway in human endothelial cells. This could ultimately lead, for example, to endothelial cell division, inhibition of endothelial cell proliferation, endothelial tube formation, cell migration, apoptosis, etc.

Human venous umbilical vein endothelial cells (HUVEC, Cell Systems) in growth media (50:50 without glycine, 1% glutamine, 10 mM Hepes, 10% FBS, 10 ng/ml bFGF), were plated on 96-well microtiter ViewPlates-96 (Packard Instrument Company Part #6005182) nucrotiter plates at a cell density of $2 \times 10^4$ cells/well. The day after plating, the cells were washed three times with buffer (HBSS plus 10 mM Hepes), leaving 100 µl/well. Then 100 µl/well of 8 µM Fluo-3 (2×) was added. The cells were incubated for 1.5 hours at 37° C./5% $CO_2$. After incubation, the cells were then washed 3× with buffer (described above) leaving 100 µl/well. Test samples of the PRO polypeptides were prepared on different 96-well plates at 5× concentration in buffer. The positive control corresponded to 50 µM ionomycin (5×); the negative control corresponded to Protein 32. Cell plate and sample plates were run on a FLIPR (Molecular Devices) machine. The FLIPR machine added 25 µl of test sample to the cells, and readings were taken every second for one minute, then every 3 seconds for the next three minutes.

The fluorescence change from baseline to the maximum rise of the curve (Δ change) was calculated, and replicates averaged. The rate of fluorescence increase was monitored, and only those samples which had a Δ change greater than 1000 and a rise within 60 seconds, were considered positive.

The following PRO polypeptides tested positive in the present assay: PRO245.

Example 82

Fibroblast (BHK-21) Proliferation (Assay 98)

This assay shows that certain PRO polypeptides of the invention act to induce proliferation of mammalian fibroblast cells in culture and, therefore, function as useful growth factors in mammalian systems. The assay is performed as follows. BHK-21 fibroblast cells plated in standard growth medium at 2500 cells/well in a total volume of 100 µl. The PRO polypeptide, P-FGF (positive control) or nothing (negative control) are then added to the wells in the presence of 1 µg/ml of heparin for a total final volume of 200 µl. The cells are then incubated at 37° C. for 6 to 7 days. After incubation, the media is removed, the cells are washed with PBS and then an acid phosphatase substrate reaction mixture (100 µl/well) is added. The cells are then incubated at 37° C. for 2 hours. 10 µl per well of 1N NaOH is then added to stop the acid phosphatase reaction. The plates are then read at OD 405 nm. A positive in the assay is acid phosphatase activity which is at least 50% above the negative control.

The following PRO polypeptide tested positive in this assay: PRO258.

Example 83

Inhibition of Heart Adult Hypertrophy (Assay 42)

This assay is designed to measure the inhibition of heart adult hypertrophy. PRO polypeptides testing positive in this assay may find use in the therapeutic treatment of cardiac disorders associated with cardiac hypertrophy.

Ventricular myocytes are freshly isolated from adult (250 g) Harlan Sprague Dawley rats and the cells are plated at 2000/well in 180 µl volume. On day two, test samples (20 µl) containing the test PRO polypeptide are added. On day five, the cells are fixed and then stained. An increase in ANP message can also be measured by PCR from cells after a few hours. Results are based on a visual score of cell size: 0=no inhibition, −1=small inhibition, −2=large inhibition. A score of less than 0 is considered positive. Activity reference corresponds to phenylephrin (PE) at 0.1 mM, as a positive control. Assay media included: M199 (modified)-glutamine free, $NaHCO_3$, phenol red, supplemented with 100 nM insulin, 0.2% BSA, 5 mM cretine, 2 mM L-carnitine, 5 mM taurine, 100 U/ml penicillin G, 100 µg/ml streptomycin (CCT medium). Only inner 60 wells are used in 96 well plates. Of these, 6 wells are reserved for negative and positive (PE) controls.

The following PRO polypeptides provided a score of less than 0 in the above assay: PRO269.

Example 84

Induction of c-fos in Endothelial Cells (Assay 34)

This assay is designed to determine whether PRO polypeptides show the ability to induce c-fos in endothelial cells. PRO polypeptides testing positive in this assay would be expected to be useful for the therapeutic treatment of conditions or disorders where angiogenesis would be beneficial including, for example, wound healing, and the like (as would agonists of these PRO polypeptides). Antagonists of the PRO polypeptides testing positive in this assay would be expected to be useful for the therapeutic treatment of cancerous tumors.

Human venous umbilical vein endothelial cells (HUVEC, Cell Systems) in growth media (50% Ham's F12 w/o GHT: low glucose, and 50% DMEM without glycine: with NaHCO3, 1% glutamine, 10 mM HEPES, 10% FBS, 10 ng/ml bFGF) were plated on 96-well microtiter plates at a cell density of $1\times10^4$ cells/well. The day after plating, the cells were starved by removing the growth media and treating the cells with 100 μl/well test samples and controls (positive control=growth media; negative control=Protein 32 buffer=10 mM HEPES, 140 mM NaCl, 4% (w/v) mannitol, pH 6.8). The cells were incubated for 30 minutes at 37° C., in 5% $CO_2$. The samples were removed, and the first part of the bDNA kit protocol (Chiron Diagnostics, cat. #6005-037) was followed, where each capitalized reagent/buffer listed-below was available from the kit.

Briefly, the amounts of the TM Lysis Buffer and Probes needed for the tests were calculated based on information provided by the manufacturer. The appropriate amounts of thawed Probes were added to the TM Lysis Buffer. The Capture Hybridization Buffer was warmed to room temperature. The bDNA strips were set up in the metal strip holders, and 100 μl of Capture Hybridization Buffer was added to each b-DNA well needed, followed by incubation for at least 30 minutes. The test plates with the cells were removed from the incubator, and the media was gently removed using the vacuum manifold. 100 μl of Lysis Hybridization Buffer with Probes were quickly pipetted into each well of the microtiter plates. The plates were then incubated at 55° C. for 15 minutes. Upon removal from the incubator, the plates were placed on the vortex mixer with the microtiter adapter head and vortexed on the #2 setting for one minute. 80 μl of the lysate was removed and added to the bDNA wells containing the Capture Hybridization Buffer, and pipetted up and down to mix. The plates were incubated at 53° C. for at least 16 hours.

On the next day, the second part of the bDNA kit protocol was followed. Specifically, the plates were removed from the incubator and placed on the bench to cool for 10 minutes. The volumes of additions needed were calculated based upon information provided by the manufacturer. An Amplifier Working Solution was prepared by making a 1:100 dilution of the Amplifier Concentrate (20 fm/μl) in AL Hybridization Buffer. The hybridization mixture was removed from the plates and washed twice with Wash A. 50 μl of Amplifier Working Solution was added to each well and the wells were incubated at 53° C. for 30 minutes. The plates were then removed from the incubator and allowed to cool for 10 minutes. The Label Probe Working Solution was prepared by making a 1:100 dilution of Label Concentrate (40 pmoles/μl) in AL Hybridization Buffer. After the 10-minute cool-down period, the amplifier hybridization mixture was removed and the plates were washed twice with Wash A. 50 μl of Label Probe Working Solution was added to each well and the wells were incubated at 53° C. for 15 minutes. After cooling for 10 minutes, the Substrate was warmed to room temperature. Upon addition of 3 μl of Substrate Enhancer to each ml of Substrate needed for the assay, the plates were allowed to cool for 10 minutes, the label hybridization mixture was removed, and the plates were washed twice with Wash A and three times with Wash D. 50 μl of the Substrate Solution with Enhancer was added to each well. The plates were incubated for 30 minutes at 37° C. and RLU was read in an appropriate luminometer.

The replicates were averaged and the coefficient of variation was determined. The measure of activity of the fold increase over the negative control (Protein 32/HEPES buffer described above) value was indicated by chemiluminescence units (RLU). The results are considered positive if the PRO polypeptide exhibits at least a two-fold value over the negative buffer control. Negative control=1.00 RLU at 1.00% dilution. Positive control=8.39 RLU at 1.00% dilution.

The following PRO polypeptides tested positive in this assay: PRO287.

Example 85

Guinea Pig Vascular Leak (Assays 32 and 51)

This assay is designed to determine whether PRO polypeptides of the present invention show the ability to induce vascular permeability. Polypeptides testing positive in this assay are expected to be useful for the therapeutic treatment of conditions which would benefit from enhanced vascular permeability including, for example, conditions which may benefit from enhanced local immune system cell infiltration.

Hairless guinea pigs weighing 350 grams or more were anesthetized with Ketamine (75–80 mg/kg) and 5 mg/kg Xylazine intramuscularly. Test samples containing the PRO polypeptide or a physiological buffer without the test polypeptide are injected into skin on the back of the test animals with 100 μl per injection site intradermally. There were approximately 16–24 injection sites per animal. One ml of Evans blue dye (1% in PBS) is then injected intracardially. Skin vascular permeability responses to the compounds (i.e., blemishes at the injection sites of injection) are visually scored by measuring the diameter (in mm) of blue-colored leaks from the site of injection at 1 and 6 hours post administration of the test materials. The mm diameter of blueness at the site of injection is observed and recorded as well as the severity of the vascular leakage. Blemishes of at least 5 mm in diameter are considered positive for the assay when testing purified proteins, being indicative of the ability to induce vascular leakage or permeability. A response greater than 7 mm diameter is considered positive for conditioned media samples. Human VEGF at 0.1 μg/100 μl is used as a positive control, inducing a response of 15–23 mm diameter.

The following PRO polypeptides tested positive in this assay: PRO302 and PRO533.

Example 86

Detection of Endothelial Cell Apoptosis (FACS) (Assay 96)

The ability of PRO polypeptides of the present invention to induce apoptosis in endothelial cells was tested in human venous umbilical vein endothelial cells (HUVEC, Cell Systems) in gelatinized T175 flasks using HUVEC cells below passage 10. PRO polypeptides testing positive in this assay are expected to be useful for therapeutically treating conditions where apoptosis of endothelial cells would be beneficial including, for example, the therapeutic treatment of tumors.

On day one, the cells were split [420,000 cells per gelatinized 6 cm dishes–($11\times10^3$ cells/$cm^2$ Falcon, Primaria)] and grown in media containing serum (CS-C, Cell System) overnight or for 16 hours to 24 hours.

On day 2, the cells were washed 1× with 5 ml PBS; 3 ml of 0% serum medium was added with VEGF (100 ng/ml); and 30 μl of the PRO test compound (final dilution 1%) or 0% serum medium (negative control) was added. The mixtures were incubated for 48 hours before harvesting.

The cells were then harvested for FACS analysis. The medium was aspirated and the cells washed once with PBS. 5 ml of 1× trypsin was added to the cells in a T-175 flask, and the cells were allowed to stand until they were released from the plate (about 5–10 minutes). Trypsinization was stopped by adding 5 ml of growth media. The cells were spun at 1000 rpm for 5 minutes at 4° C. The media was aspirated and the cells were resuspended in 10 ml of 10% serum complemented medium (Cell Systems), 5 μl of Annexin-FITC (BioVison) added and chilled tubes were submitted for FACS. A positive result was determined to be enhanced apoptosis in the PRO polypeptide treated samples as compared to the negative control.

The following PRO polypeptides tested positive in this assay: PRO331.

Example 87

Induction of c-fos in Cortical Neurons (Assay 83)

This assay is designed to determine whether PRO polypeptides show the ability to induce c-fos in cortical neurons. PRO polypeptides testing positive in this assay would be expected to be useful for the therapeutic treatment of nervous system disorders and injuries where neuronal proliferation would be beneficial.

Cortical neurons are dissociated and plated in growth medium at 10,000 cells per well in 96 well plates. After approximately 2 cellular divisions, the cells are treated for 30 minutes with the PRO polypeptide or nothing (negative control). The cells are then fixed for 5 minutes with cold methanol and stained with an antibody directed against phosphorylated CREB. mRNA levels are then calculated using chemiluminescence. A positive in the assay is any factor that results in at least a 2-fold increase in c-fos message as compared to the negative controls.

The following PRO polypeptides tested positive in this assay: PRO229 and PRO269.

Example 88

Stimulation of Endothelial Tube Formation (Assay 85)

This assay is designed to determine whether PRO polypeptides show the ability to promote endothelial vacuole and lumen formation in the absence of exogenous growth factors. PRO polypeptides testing positive in this assay would be expected to be useful for the therapeutic treatment of disorders where endothelial vacuole and/or lumen formation would be beneficial including, for example, where the stimulation of pinocytosis, ion pumping, vascular permeability and/or junctional formation would be beneficial.

HUVEC cells (passage <8 from primary) are mixed with type I rat tail collagen (final concentration 2.6 mg/ml) at a density of $6\times10^5$ cells per ml and plated at 50 μl per well of M199 culture media supplemented with 1% FBS and 1 μM 6-FAM-FITC dye to stain the vacuoles while they are forming and in the presence of the PRO polypeptide. The cells are then incubated at 37° C./5% $CO_2$ for 48 hours, fixed with 3.7% formalin at room temperature for 10 minutes, washed 5 times with M199 medium and then stained with Rh-Phalloidin at 4° C. overnight followed by nuclear staining with 4 μM DAPI. A positive result in the assay is when vacuoles are present in greater than 50% of the cells.

The following PRO polypeptides tested positive in this assay: PRO230.

Example 89

Detection of Polypeptides That Affect Glucose and/or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO-polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO187, PRO211, PRO221, PRO222, PRO224, PRO230, PRO239, PRO231, PRO245, PRO247, PRO258, PRO269, PRO328 and PRO533.

Example 90

Rod Photoreceptor Cell Survival Assay (Assay 46)

This assay shows that certain polypeptides of the invention act to enhance the survival/proliferation of rod photoreceptor cells and, therefore, are useful for the therapeutic treatment of retinal disorders or injuries including, for example, treating sight loss in mammals due to retinitis pigmentosum, AMD, etc.

Sprague Dawley rat pups (postnatal day 7, mixed population: glia and netinal neural cell types) are killed by decapitation following $CO_2$ anesthesia and the eyes removed under sterile conditions. The neural retina is dissected away from the pigment epithelium and other ocular tissue and then dissociated into a single cell suspension using 0.25% trypsin in $Ca^{2+}$, $Mg^{2+}$-free PBS. The retinas are incubated at 37° C. in this solution for 7–10 minutes after which the trypsin is inactivated by adding 1 ml soybean trypsin inhibitor. The cells are plated at a density of approximately 10,000 cells/ml into 96 well plates in DMEM/F12 supplemented with $N_2$. Cells for all experiments are grown at 37° C. in a water saturated atmosphere of 5% $CO_2$. After 7–10 days in culture, the cells are stained using calcein AM or CellTracker Green CMFDA and then fixed using 4% paraformaldehyde. Rho 4D2 (ascities or IgG 1:100) monoclonal antibody directed towards the visual pigment rhodopsin is used to detect rod photoreceptor cells by indirect immunofluorescence. The results are calculated as % survival: total number of calcein–rhodopsin positive cells at 7–10 days in culture, divided by the total number of rhodopsin positive cells at time 7–10 days in culture. The total cells (fluorescent) are quantified at 20× objective magnification using a CCD camera and NIH image software for MacIntosh. Fields in the well are chosen at random.

The following polypeptides tested positive in this assay: PRO245.

Example 91

In Vitro Antitumor Assay (Assay 161)

The antiproliferative activity of various PRO polypeptides was determined in the investigational, disease-oriented in vitro anti-cancer drug discovery assay of the National Cancer Institute (NCI), using a sulforhodamine B(SRB) dye binding assay essentially as described by Skehan et al., *J. Natl. Cancer Inst.* 82: 1107–1112 (1990). The 60 tumor cell lines employed in this study ("the NCI panel"), as well as conditions for their maintenance and culture in vitro have been described by Monks et al., *J. Natl. Cancer Inst.* 83:757–766 (1991). The purpose of this screen is to initially evaluate the cytotoxic and/or cytostatic activity of the test compounds against different types of tumors (Monks et al., supra; Boyd, *Cancer: Princ. Pract. Oncol. Update* 3(10): 1–12 [1989]).

Cells from approximately 60 human tumor cell lines were harvested with trypsin/EDTA (Gibco), washed once, resuspended in IMEM and their viability was determined. The cell suspensions were added by pipet (100 μL volume) into separate 96-well microtiter plates. The cell density for the 6-day incubation was less than for the 2-day incubation to prevent overgrowth. Inoculates were allowed a preincubation period of 24 hours at 37° C. for stabilization. Dilutions at twice the intended test concentration were added at time zero in 100 μL aliquots to the microtiter plate wells (1:2 dilution). Test compounds were evaluated at five half-log dilutions (1000 to 100,000-fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample is considered positive if it shows at least 50% growth inhibitory effect at one or more concentrations. PRO polypeptides testing positive in this assay are shown in Table 7, where the abbreviations are as follows:

TABLE 7

| Test compound | Tumor Cell Line Type | Cell Line Designation |
|---|---|---|
| PRO211 | NSCL | HOP62 |
| PRO211 | Leukemia | RPMI-8226 |
| PRO211 | Leukemia | HL-60 (TB) |
| PRO211 | NSCL | NCI-H522 |
| PRO211 | CNS | SF-539 |
| PRO211 | Melanoma | LOX IMVI |
| PRO211 | Breast | MDA-MB-435 |
| PRO211 | Leukemia | MOLT-4 |
| PRO211 | CNS | U251 |
| PRO211 | Breast | MCF7 |
| PRO211 | Leukemia | HT-60 (TB) |
| PRO211 | Leukemia | MOLT-4 |
| PRO211 | NSCL | EKVX |
| PRO211 | NSCL | NCI-H23 |
| PRO211 | NSCL | NCI-H322M |
| PRO211 | NSCL | NCI-H460 |
| PRO211 | Colon | HCT-116 |
| PRO211 | Colon | HT29 |
| PRO211 | CNS | SF-268 |
| PRO211 | CNS | SF-295 |
| PRO211 | CNS | SNB-19 |
| PRO211 | CNS | U251 |
| PRO211 | Melanoma | LOX IMVI |
| PRO211 | Melanoma | SK-MEL-5 |
| PRO211 | Melanoma | UACC-257 |
| PRO211 | Melanoma | UACC-62 |
| PRO211 | Ovarian | OVCAR-8 |
| PRO211 | Renal | RXF 393 |
| PRO211 | Breast | MCF7 |
| PRO211 | Breast | NCI/ADR-REHS 578T |
| PRO211 | Breast | T-47D |
| PRO211 | Leukemia | HL-60 (TB) |
| PRO211 | Leukemia | SR |
| PRO211 | NSCL | NCI-H23 |
| PRO211 | Colon | HCT-116 |
| PRO211 | Melanoma | LOX-IMVI |
| PRO211 | Melanoma | SK-MEL-5 |
| PRO211 | Breast | T-47D |
| PRO228 | Leukemia | MOLT-4 |
| PRO228 | NSCL | EKVX |
| PRO228 | Colon | KM12 |
| PRO228 | Melanoma | UACC-62 |
| PRO228 | Ovarian | OVCAR-3 |
| PRO228 | Renal | TK10 |
| PRO228 | Renal | SN12C |
| PRO228 | Breast | MCF7 |
| PRO228 | Leukemia | CCRF-CEM |
| PRO228 | Leukemia | HL-60 (TB) |
| PRO228 | Colon | COLO 205 |
| PRO228 | Colon | HCT-15 |
| PRO228 | Colon | KM12 |
| PRO228 | CNS | SF-268 |
| PRO228 | CNS | SNB-75 |
| PRO228 | Melanoma | LOX-IMVI |
| PRO228 | Melanoma | SK-MEL2 |
| PRO228 | Melanoma | UACC-257 |
| PRO228 | Ovarian | IGROV1 |
| PRO228 | Ovarian | OVCAR-4 |
| PRO228 | Ovarian | OVCAR-5 |
| PRO228 | Ovarian | OVCAR-8 |
| PRO228 | Renal | 786-0 |
| PRO228 | Renal | CAKI-1 |
| PRO228 | Renal | RXF 393 |
| PRO228 | Renal | TK-10 |
| PRO228 | Renal | UO-31 |
| PRO228 | Prostate | PC-3 |
| PRO228 | Prostate | DU-145 |
| PRO228 | Breast | MCF7 |

TABLE 7-continued

| Test compound | Tumor Cell Line Type | Cell Line Designation |
|---|---|---|
| PRO228 | Breast | NCI/ADR-REHS 578T |
| PRO228 | Breast | MDA-MB-435MDA-N |
| PRO228 | Breast | T-47D |
| PRO219 | Leukemia | SR |
| PRO219 | NSCL | NCI-H5222 |
| PRO219 | Breast | MCF7 |
| PRO219 | Leukemia | K-562; RPMI-8226 |
| PRO219 | NSCL | HOP-62; NCI-H322M |
| PRO219 | NSCL | NCI-H460 |
| PRO219 | Colon | HT29; KM12; HCT-116 |
| PRO219 | CNS | SF-539; U251 |
| PRO219 | Prostate | DU-145 |
| PRO219 | Breast | MDA-N |
| PRO219 | Ovarian | IGROV1 |
| PRO219 | NSCL | NCI-H226 |
| PRO219 | Leukemia | MOLT-4 |
| PRO219 | NSCL | A549/ATCC; EKVX; NCI-H23 |
| PRO219 | Colon | HCC-2998 |
| PRO219 | CNS | SF-295; SNB-19 |
| PRO219 | Melanoma | SK-MEL-2; SK-MEL-5 |
| PRO219 | Melanoma | UACC-257; UACC-62 |
| PRO219 | Ovarian | OCAR-4; SK-OV-3 |
| PRO219 | Renal | 786-0; ACHN; CAMI-1; SN12C |
| PRO219 | Renal | TK-10; UO-31 |
| PRO219 | Breast | NCI/ADR-RES; BT-549; T-47D |
| PRO219 | Breast | MDA-MB-435 |
| PRO221 | Leukemia | CCRF-CEM |
| PRO221 | Leukemia | MOLT-4 |
| PRO221 | NSCL | HOP-62 |
| PRO221 | Breast | MDA-N |
| PRO221 | Leukemia | RPMI-8226; SR |
| PRO221 | NSCL | NCI-H460 |
| PRO221 | Colon | HCC-2998 |
| PRO221 | Ovarian | IGROV1 |
| PRO221 | Renal | TK 10 |
| PRO221 | Breast | MCF7 |
| PRO221 | Leukemia | K-562 |
| PRO221 | Breast | MDA-MB-435 |
| PRO224 | Ovarian | OVCAR-4 |
| PRO224 | Renal | RXF 393 |
| PRO224 | Prostate | DU-145 |
| PRO224 | NSCL | HOP-62; NCI-H322M |
| PRO224 | Melanoma | LOX IMVI |
| PRO224 | Ovarian | OVCAR-8 |
| PRO224 | Leukemia | SR |
| PRO224 | NSCL | NCI-H460 |
| PRO224 | CNS | SF-295 |
| PRO224 | Leukemia | RPMI-8226 |
| PRO224 | Breast | BT-549 |
| PRO224 | Leukemia | CCRF-CEM; LH-60 (TB) |
| PRO224 | Colon | HCT-116 |
| PRO224 | Breast | MDA-MB-435 |
| PRO224 | Leukemia | HL-60 (TB) |
| PRO224 | Colon | HCC-2998 |
| PRO224 | Prostate | PC-3 |
| PRO224 | CNS | U251 |
| PRO224 | Colon | HCT-15 |
| PRO224 | CNS | SF-539 |
| PRO224 | Renal | ACHN |
| PRO328 | Leukemia | RPMI-8226 |
| PRO328 | NSCL | A549/ATCC; EKVX; HOP-62 |
| PRO328 | NSCL | NCI-H23; NCI-H322M |
| PRO328 | Colon | HCT-15; KM12 |
| PRO328 | CNS | SF-295; SF-539; SNB-19; U251 |
| PRO328 | Melanoma | M14; UACC-257; UCAA-62 |
| PRO328 | Renal | 786-0; ACHN |
| PRO328 | Breast | MCF7 |
| PRO328 | Leukemia | SR |
| PRO328 | Colon | NCI-H23 |
| PRO328 | Melanoma | SK-MEL-5 |
| PRO328 | Prostate | DU-145 |
| PRO328 | Melanoma | LOX IMVI |
| PRO328 | Breast | MDA-MB-435 |
| PRO328 | Ovarian | OVCAR-3 |
| PRO328 | Breast | T-47D |
| PRO301 | NSCL | NCI-H322M |
| PRO301 | Leukemia | MOLT-4; SR |

TABLE 7-continued

| Test compound | Tumor Cell Line Type | Cell Line Designation |
|---|---|---|
| PRO301 | NSCL | A549/ATCC; EKVX; |
| PRO301 | NSCL | NCI-H23; NCI-460; NCI-H226 |
| PRO301 | Colon | COLO 205; HCC-2998; |
| PRO301 | Colon | HCT-15; KM12; HT29; |
| PRO301 | Colon | HCT-116 |
| PRO301 | CNS | SF-268; SF-295; SNB-19 |
| PRO301 | Melanoma | MALMLE-3M; SK-MEL-2; |
| PRO301 | Melanoma | SK-MEL-5; UACC-257 |
| PRO301 | Melanoma | UACC-62 |
| PRO301 | Ovarian | IGROV1; OVCAR-4 |
| PRO301 | Ovarian | OVCAR-5 |
| PRO301 | Ovarian | OVCAR-8; SK0OV-3 |
| PRO301 | Renal | ACHN; CAKI-1; TK-10; UO-31 |
| PRO301 | Prostate | PC-3; DU-145 |
| PRO301 | Breast | NCI/ADR-RES; HS 578T |
| PRO301 | Breast | MDA-MB-435; MDA-N; T-47D |
| PRO301 | Melanoma | M14 |
| PRO301 | Leukemia | CCRF-CEM; HL-60(TB); K-562 |
| PRO301 | Leukemia | RPMI-8226 |
| PRO301 | Melanoma | LOX IMVI |
| PRO301 | Renal | 786-0; SN12C |
| PRO301 | Breast | MCF7; MDA-MB-231/ATCC |
| PRO301 | Breast | BT-549 |
| PRO301 | NSCL | HOP-62 |
| PRO301 | CNS | SF-539 |
| PRO301 | Ovarian | OVCAR-3 |
| PRO326 | NSCL | NCI-H322M |
| PRO326 | CNS | SF295 |
| PRO326 | CNS | ST539 |
| PRO326 | CNS | U251 |

NSCL = non-small cell lung carcinoma
CNS = central nervous system

The results of these assays demonstrate that the positive testing PRO polypeptides are useful for inhibiting neoplastic growth in a number of different tumor cell types and may be used therapeutically therefor. Antibodies against these PRO polypeptides are useful for affinity purification of these useful polypeptides. Nucleic acids encoding these PRO polypeptides are useful for the recombinant preparation of these polypeptides.

Example 92

Gene Amplification

This example shows that certain PRO polypeptide-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers and diagnostic determination of the presence of those cancers. Therapeutic agents may take the form of antagonists of the PRO polypeptide, for example, murine-human chimeric, humanized or human antibodies against a PRO polypeptide.

The starting material for the screen was genomic DNA isolated from a variety cancers. The DNA is quantitated precisely, e.g., fluorometrically. As a negative control, DNA was isolated from the cells of ten normal healthy individuals which was pooled and used as assay controls for the gene copy in healthy individuals (not shown). The 5' nuclease assay (for example, TaqMan™) and real-time quantitative PCR (for example, ABI Prizm 7700 Sequence Detection System" (Perkin Elmer, Applied Biosystems Division, Foster City, Calif.)), were used to find genes potentially amplified in certain cancers. The results were used to determine whether the DNA encoding the PRO polypeptide is over-represented in any of the primary lung or colon cancers or cancer cell lines or breast cancer cell lines that were screened. The primary lung cancers were obtained from individuals with tumors of the type and stage as indicated in Table 8. An explanation of the abbreviations used for the designation of the primary tumors listed in Table 8 and the primary tumors and cell lines referred to throughout this example are given below.

The results of the TaqMan™ are reported in delta (Δ) Ct units. One unit corresponds to 1 PCR cycle or approximately a 2-fold amplification relative to normal, two units corresponds to 4-fold, 3 units to 8-fold amplification and so on. Quantitation was obtained using primers and a TaqMan™ fluorescent probe derived from the PRO polypeptide-encoding gene. Regions of the PRO polypeptide-encoding gene which are most likely to contain unique nucleic acid sequences and which are least likely to have spliced out introns are preferred for the primer and probe derivation, e.g., 3'-untranslated regions. The sequences for the primers and probes (forward, reverse and probe) used for the PRO polypeptide gene amplification analysis were as follows:

| | |
|---|---|
| PRO187 (DNA27864-1155) | |
| 27864.tm.p: | |
| 5'-GCAGATTTTGAGGACAGCCACCTCCA-3' | (SEQ ID NO:381) |
| 27864.tm.f: | |
| 5'-GGCCTTGCAGACAACCGT-3' | (SEQ ID NO:382) |
| 27864.tm.r: | |
| 5'-CAGACTGAGGGAGATCCGAGA-3' | (SEQ ID NO:383) |
| 27864.tm.p2: | |
| 5'-CAGCTGCCCTTCCCCAACCA-3' | (SEQ ID NO:384) |
| 27864.tm.f2: | |
| 5'-CATCAAGCGCCTCTACCA-3' | (SEQ ID NO:385) |
| 27864.tm.r2: | |
| 5'-CACAAACTCGAACTGCTTCTG-3' | (SEQ ID NO:386) |
| PRO214 (DNA32286-1191): | |
| 32286.3utr-5: | |
| 5'-GGGCCATCACAGCTCCCT-3' | (SEQ ID NO:387) |
| 32286.3utr-3b: | |
| 5'-GGGATGTGGTGAACACAGAACA-3' | (SEQ ID NO:388) |
| 32286.3utr-probe: | |
| 5'-TGCCAGCTGCATGCTGCCAGTT-3' | (SEQ ID NO:389) |
| PRO211 (DNA32292-1131): | |
| 32292.3utr-5: | |
| 5'-CAGAAGGATGTCCCGTGGAA-3' | (SEQ ID NO:390) |
| 32292.3utr-3: | |
| 5'-GCCGCTGTCCACTGCAG-3' | (SEQ ID NO:391) |
| 32292.3utr-probe.rc: | |
| 5'-GACGGCATCCTCAGGGCCACA-3' | (SEQ ID NO:392) |
| PRO230 (DNA33223-1136): | |
| 33223.tm.p3: | |
| 5'-ATGTCCTCCATGCCCACGCG-3' | (SEQ ID NO:393) |
| 33223.tm.f3: | |
| 5'-GAGTGCGACATCGAGAGCTT-3' | (SEQ ID NO:394) |
| 33223.tm.r3: | |
| 5'-CCGCAGCCTCAGTGATGA-3' | (SEQ ID NO:395) |
| 33223.3utr-5: | |
| 5'-GAAGAGCACAGCTGCAGATCC-3' | (SEQ ID NO:396) |
| 33223.3utr-3: | |
| 5'-GAGGTGTCCTGGCTTTGGTAGT-3' | (SEQ ID NO:397) |
| 33223.3utr-probe: | |
| 5'-CCTCTGGCGCCCCCACTCAA-3' | (SEQ ID NO:398) |
| PRO317 (DNA33461-1199): | |
| 33461.tm.f: | |
| 5'-CCAGGAGAGCTGGCGATG-3' | (SEQ ID NO:399) |
| 33461.tm.r: | |
| 5'-GCAAATTCAGGGCTCACTAGAGA-3' | (SEQ ID NO:400) |
| 33461.tm.p: | |
| 5'-CACAGAGCATTTGTCCATCAGCAGTTCAG-3' | (SEQ ID NO:401) |

-continued

| | |
|---|---|
| PRO246 (DNA35639-1172): | |
| 35639.3utr-5: | |
| 5'-GGCAGAGACTTCCAGTCACTGA-3' | (SEQ ID NO:402) |
| 35639.3utr-3: | |
| 5'-GCCAAGGGTGGTGTTAGATAGG-3' | (SEQ ID NO:403) |
| 35639.3utr-probe: | |
| 5'-CAGGCCCCCTTGATCTGTACCCCA-3' | (SEQ ID NO:404) |
| PRO533 (DNA49435-1219): | |
| 49435.tm.f: | |
| 5'-GGGACGTGCTTCTACAAGAACAG-3' | (SEQ ID NO:405) |
| 49435.tm.r: | |
| 5'-CAGGCTTACAATGTTATGATCAGACA-3' | (SEQ ID NO:406) |
| 49435.tm.p: | |
| 5'-TATTCAGAGTTTTCCATTGGCAGTGCCAGTT-3' | (SEQ ID NO:407) |
| PRO343 (DNA43318-1217): | |
| 43318.tm.f1 | |
| 5'-TCTACATCAGCCTCTCTGCGC-3' | (SEQ ID NO:408) |
| 43318.tm.p1 | |
| 5'-CGATCTTCTCCACCCAGGAGCGG-3' | (SEQ ID NO:409) |
| 43318.tm.r1 | |
| 5'-GGAGCTGCACCCCCTTGC-3' | (SEQ ID NO:237) |
| PRO232 (DNA34435-1140): | |
| 34435.3utr-5: | |
| 5'-GCCAGGCCTCACATTCGT-3' | (SEQ ID NO:410) |
| DNA34435.3utr-probe: | |
| 5'-CTCCCTGAATGGCAGCCTGAGCA-3' | (SEQ ID NO:411) |
| DNA34435.3utr-3: | |
| 5'-AGGTGTTTATTAAGGGCCTACGCT-3' | (SEQ ID NO:412) |
| PRO269 (DNA38260-1180): | |
| 38260.tm.f: | |
| 5'-CAGAGCAGAGGGTGCCTTG-3' | (SEQ ID NO:413 |
| 38260.tM.p: | |
| 5'-TGGCGGAGTCCCCTCTTGGCT-3' | (SEQ ID NO:414) |
| 38260.tm.r: | |
| 5'-CCCTGTTTCCCTATGCATCACT-3' | (SEQ ID NO:415) |
| PRO304 (DNA39520-1217): | |
| 39520.tM.f: | |
| 5'-TCAACCCCTGACCCTTTCCTA-3' | (SEQ ID NO:416) |
| 39520.tm.p: | |
| 5'-GGCAGGGGACAAGCCATCTCTCCT-3' | (SEQ ID NO:417) |
| 39520.tm.r: | |
| 5'-GGGACTGAACTGCCAGCTTC-3' | (SEQ ID NO:418) |
| PRO339 (DNA43466-1225): | |
| 43466.tm.F1: | |
| 5'-GGGCCCTAACCTCATTACCTTT-3' | (SEQ ID NO:419) |
| 43466.tM.p1: | |
| 5'-TGTCTGCCTCAGCCCCAGGAAGG-3' | (SEQ ID NO:420) |
| 43466.tM.R1: | |
| 5'-TCTGTCCACCATCTTGCCTTG-3' | (SEQ ID NO:421) |

The 5' nuclease assay reaction is a fluorescent PCR-based technique which makes use of the 5' exonuclease activity of Taq DNA polymerase enzyme to monitor amplification in real time. Two oligonucleotide primers (forward [.f] and reverse [.r]) are used to generate an amplicon typical of a PCR reaction. A third oligonucleotide, or probe (.p), is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore.

One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700TM Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 8 describes the stage, T stage and N stage of various primary tumors which were used to screen the PRO polypeptide compounds of the invention.

TABLE 8

Primary Lung and Colon Tumor Profiles

| Primary Tumor Stage | Stage | Other Stage | Dukes Stage | T Stage | N Stage |
|---|---|---|---|---|---|
| Human lung tumor AdenoCa (SRCC724) [LT1] | IIA | | | T1 | N1 |
| Human lung tumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT79 | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735) [LT13] | IB | | | T2 | N0 |
| Human lung tumor SqCCa (SRCC736) 8 LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | IA | | | T1 | N0 |
| Human colon AdenoCa (SRCC742) [CT2] | | M1 | D | pT4 | N0 |

TABLE 8-continued

Primary Lung and Colon Tumor Profiles

| Primary Tumor Stage | Stage | Other Stage | Dukes Stage | T Stage | N Stage |
|---|---|---|---|---|---|
| Human colon AdenoCa (SRCC743) [CT3] | | | B | pT3 | N0 |
| Human colon AdenoCa (SRCC744) [CT8] | | | B | T3 | N0 |
| Human colon AdenoCa (SRCC745) [CT10] | | | A | pT2 | N0 |
| Human colon AdenoCa (SRCC746) [CT12] | | MO, R1 | B | T3 | N0 |
| Human colon AdenoCa (SRCC747) [CT14] | | pMO, RO | B | pT3 | pN0 |
| Human colon AdenoCa (SRCC748) [CT15] | | M1, R2 | D | T4 | N2 |
| Human colon AdenoCa (SRCC749) [CT16] | | pMO | B | pT3 | pN0 |
| Human colon AdenoCa | | | C1 | pT3 | pN1 |
| Human colon AdenoCa (SRCC751) [CT1] | | MO, R1 | B | pT3 | N0 |
| Human colon AdenoCa (SRCC752) [CT4] | | | B | pT3 | M0 |
| Human colon AdenoCa | | G2 | C1 | pT3 | pN0 |
| Human colon AdenoCa (SRCC754) [CT6] | | pMO, RO | B | pT3 | pN0 |
| Human colon AdenoCa (SRCC755) [C17] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | MO, RO | B | pT3 | pN0 |

DNA Preparation:

DNA was prepared from cultured cell lines, primary tumors, normal human blood. The isolation was performed using purification kit, buffer set and protease and all from Quiagen, according to the manufacturer's instructions and the description below.

Cell Culture Lysis:

Cells were washed and trypsinized at a concentration of $7.5\times10^{8}$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 ml PBS. Buffer C1 was equilibrated at 4° C. Qiagen protease #19155 was diluted into 6.25 ml cold $ddH_2O$ to a final concentration of 20 mg/ml and equilibrated at 4° C. 10 ml of G2 Buffer was prepared by diluting Qiagen RNAse A stock (100 mg/ml) to a final concentration of 200 μg/ml.

Buffer C1 (10 ml, 4° C.) and $ddH_2O$ (40 ml, 4° C.) were then added to the 10 ml of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 ml Buffer C1 (at 4° C.) and 6 ml $ddH_2O$, followed by a second 4° C. centrifugation at 2500 rpm for 15 minutes. The nuclei were then resuspended into the residual buffer using 200 μl per tip. G2 buffer (10 ml) was added to the suspended nuclei while gentle vortexing was applied. Upon completion of buffer addition, vigorous vortexing was applied for 30 seconds. Quiagen protease (200 μl, prepared as indicated above) was added and incubated at 50° C. for 60 minutes. The incubation and centrifugation was repeated until the lysates were clear (e.g., incubating additional 30–60 minutes, pelleting at 3000×g for 10 min., 4° C.).

Solid Human Tumor Sample Preparation and Lysis:

Tumor samples were weighed and placed into 50 ml conical tubes and held on ice. Processing was limited to no more than 250 mg tissue, per preparation (1 tip/preparation). The protease solution was freshly prepared by diluting into 6.25 ml cold $ddH_2O$ to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2 L $ddH_2O$, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000×g for 10 min., 4° C.).

Human Blood Preparation and Lysis:

Blood was drawn from healthy volunteers using standard infectious agent protocols and citrated into 10 ml samples per tip. Quiagen protease was freshly prepared by dilution into 6.25 ml cold $ddH_2O$ to a final concentration of 20 mg/ml and stored at 4° C. G2 buffer was prepared by diluting RNAse A to a final concentration of 200 μg/ml from 100 mg/ml stock. The blood (10 ml) was placed into a 50 ml conical tube and 10 ml C1 buffer and 30 ml $ddH_2O$ (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml $ddH_2O$ (4° C.). Vortexing was repeated until the pellet was white. The nuclei were then suspended into the residual buffer using a 200 μl tip. G2 buffer (10 ml) were added to the suspended nuclei while gently vortexing, followed by vigorous vortexing for 30 seconds. Quiagen protease was added (200 μl) and incubated at 50° C. for 60 minutes. The incubation and centrifugation was repeated until the lysates were clear (e.g., incubating additional 30–60 minutes, pelleting at 3000×g for 10 min., 4° C.).

Purification of Cleared Lysates:

(1) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

(2) Quantitation of Genomic DNA and Preparation for Gene Amplification Assay:

The DNA levels in each tube were quantified by standard $A_{260}$, $A_{280}$ spectrophotometry on a 1:20 dilution (5 μl DNA+95 μl $ddH_2O$) using the 0.1 ml quartz cuvetts in the Beckman DU640 spectrophotometer. $A_{260}/A_{280}$ ratios were in the range of 1.8–1.9. Each DNA samples was then diluted further to approximately 200 ng/ml in TE (pH 8.5). If the original material was highly concentrated (about 700 ng/μl), the material was placed at 50° C. for several hours until resuspended.

Fluorometric DNA quantitation was then performed on the diluted material (20–600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 μl, prepared within 12 hours of use) was diluted into 100 ml 1×TNE buffer. A 2 ml cuvette was filled with the fluorometer solution, placed into the machine, and the machine was zeroed. pGEM 3Zf(+) (2 μl, lot #360851026) was added to 2 ml of fluorometer solution and calibrated at 200 units. An additional 2 μl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometricly determined concentration was then used to dilute each sample to 10 ng/μl in $ddH_2O$. This was done simultaneously on all template samples for a single TaqMan plate assay, and with enough material to run 500–1000 assays. The samples were tested in triplicate with Taqman™ primers and probe both B-actin and GAPDH on a single plate with normal human DNA and no-template controls. The diluted samples were used provided that the CT value of normal human DNA subtracted from test DNA was +/−1 Ct. The diluted, lot-qualified genomic DNA was stored in 1.0 ml aliquots at −80° C. Aliquots which were subsequently to be used in the gene amplification assay were stored at 4° C. Each 1 ml aliquot is enough for 8–9 plates or 64 tests.

Gene Amplification Assay:

The PRO polypeptide compounds of the invention were screened in the following primary tumors and the resulting ΔCt values greater than or equal to 1.0 are reported in Table 9 below.

TABLE 9

Δ Ct values in lung and colon primary tumors and cell line models

| Primary Tumors or Cell lines | PRO-187 | PRO-533 | PRO-214 | PRO-343 | PRO-211 | PRO-230 | PRO-246 | PRO-317 | PRO-232 | PRO-269 | PRO-304 | PRO-339 |
|---|---|---|---|---|---|---|---|---|---|---|---|---|
| LT7 | | | | | | | | 1.52 | | 1.04 | | 1.08 |
| LT13 | 2.74 | | 1.85 | 2.71 | 1.88 | 3.42 | 1.63 | 1.90 | | 1.27 | 1.29 | 1.04 |
| | 2.98 | | 1.83 | 2.23 | 2.26 | 3.22 | 1.68 | 2.24 | | | | |
| | 2.44 | | | | | 2.84 | | 2.93 | | | | |
| | | | | | | 2.15 | | | | | | |
| | | | | | | 2.75 | | | | | | |
| | | | | | | 2.53 | | | | | | |
| | | | | | | 1.82 | | | | | | |
| LT3 | | | 1.57 | | 1.97 | | 1.06 | 1.86 | | | | 1.17 |
| LT4 | | | | | 1.17 | | | 1.18 | | | | |
| LT9 | | | | | 1.42 | | | 1.04 | | 1.80 | | 1.03 |
| LT12 | 2.70 | | 1.38 | 2.23 | 1.51 | 2.86 | 1.54 | 2.54 | 2.40 | 1.14 | 1.15 | 1.26 |
| | 2.90 | | 1.49 | 1.50 | 1.27 | 2.96 | 2.47 | 1.74 | | | | |
| | 2.27 | | | | | 2.92 | | | | | | |
| | | | | | | 1.25 | | | | | | |
| | | | | | | 2.68 | | | | | | |
| | | | | | | 2.28 | | | | | | |
| | | | | | | 1.34 | | | | | | |
| LT30 | 1.67 | | | | | 2.13 | | | | | | |
| | | | | | | 1.36 | | | | | | |
| LT21 | | | | | 1.26 | 1.09 | 1.50 | | | | | |
| LT1-a | | 1.02 | | | 1.18 | | | 1.29 | | | | |
| LT6 | | | | | | | | 1.93 | | | | |
| LT10 | | | | | 1.96 | | 1.07 | 2.57 | | | | |
| LT11 | | 1.09 | 1.67 | 1.00 | 2.05 | 1.32 | 3.43 | 2.20 | | 1.14 | 1.51 | 1.39 |
| | | | 1.80 | | 1.89 | 1.14 | 1.41 | 2.33 | | | | |
| | | | | | | 1.54 | | 1.02 | | | | |
| LT15 | 3.75 | | 1.77 | 3.62 | 2.44 | 4.32 | 2.11 | 2.06 | 1.86 | 1.36 | 1.34 | |
| | 3.92 | | 1.58 | 1.30 | 2.16 | 4.47 | 1.56 | 2.76 | | | | |
| | 3.49 | | | | | 3.64 | | 1.63 | | | | |
| | | | | | | 2.94 | | | | | | |
| | | | | | | 3.56 | | | | | | |
| | | | | | | 3.32 | | | | | | |
| | | | | | | 2.68 | | | | | | |
| LT16 | 2.10 | 1.66 | | 1.70 | 1.25 | 1.15 | | 1.55 | | | 1.00 | |
| | | | | | | 2.04 | | 1.08 | | | | |
| | | | | | | 1.83 | | 1.33 | | | | |
| LT17 | | 1.32 | 1.93 | 1.15 | 1.85 | 1.26 | 2.68 | 2.29 | 1.35 | 1.42 | 1.68 | 1.63 |
| | | | 1.87 | | 2.30 | 1.39 | 1.69 | 2.03 | | | | |
| | | | | | | 1.30 | | 1.10 | | | | |
| | | | | | | 1.33 | | | | | | |
| | | | | | | 1.30 | | | | | | |
| LT18 | | | | 1.17 | | | | | 1.04 | | | |
| LT19 | 4.05 | 1.67 | 2.09 | 3.82 | 2.42 | 4.05 | 1.91 | 2.51 | 1.21 | 1.60 | 1.15 | |
| | 3.99 | | 1.98 | | 2.55 | 4.92 | 1.68 | 2.03 | | | | |
| | | | | | | 4.93 | 1.16 | | | | | |
| | | | | | | 3.78 | | | | | | |
| | | | | | | 4.76 | | | | | | |
| HF-000840 | | | | | | 1.58 | | | | | | |
| Calu-1 | | | | | | 1.08 | | | | | | |
| SW900 | | | | | 1.86 | | | | | | | |
| CT2 | 3.56 | | 2.49 | 1.95 | 1.42 | | | 2.75 | | | | |
| | | | | 3.49 | | | | 2.36 | | | | |
| CT3 | | | 2.06 | 1.15 | | 1.34 | | | | | | |
| CT8 | 1.01 | | 1.48 | 1.29 | | | | | | | | |
| | | | | 1.58 | | | | | | | | |
| CT10 | 1.81 | | 1.84 | 1.88 | | 1.00 | | 1.88 | | | | |
| | | | | 1.49 | | | | 1.55 | | | | |
| CT12 | | | 1.81 | 1.74 | | 1.13 | | | | | | |
| CT14 | 1.82 | | 2.48 | 2.33 | | | | 1.36 | | | | |
| | | | | 1.72 | | | | 1.24 | | | | |
| CT15 | | | 1.63 | 2.06 | | | | 1.33 | | | | |
| | | | | 1.41 | | | | 1.04 | | | | |
| CT16 | | | 1.95 | 1.78 | | 1.40 | | | | | | |
| CT17 | | | 2.04 | 2.40 | | 1.74 | | | | | | |
| CT1 | 1.24 | | 1.22 | | 1.27 | 1.25 | | | 2.41 | | | |
| | 1.34 | | 1.46 | | 1.14 | | | | | | | |
| CT4 | | | 1.36 | 1.77 | 1.33 | 1.32 | 1.10 | 1.17 | 2.05 | | | |
| | | | 1.42 | | 1.02 | | | | | | | |
| CT5 | 2.96 | | 1.56 | 2.68 | 1.76 | 2.27 | 1.33 | | 1.59 | | | |
| | 2.99 | | 2.76 | | 1.64 | | 2.39 | | | | | |
| CT6 | 1.10 | | 1.33 | | 1.01 | | | | | | | |
| | | | | | 1.14 | | | | | | | |
| CT7 | 1.40 | | | 1.66 | | 1.39 | | | 1.00 | | | |

TABLE 9-continued

| | Δ Ct values in lung and colon primary tumors and cell line models | | | | | | | | | | | |
|---|---|---|---|---|---|---|---|---|---|---|---|---|
| Primary Tumors or Cell lines | PRO-187 | PRO-533 | PRO-214 | PRO-343 | PRO-211 | PRO-230 | PRO-246 | PRO-317 | PRO-232 | PRO-269 | PRO-304 | PRO-339 |
| CT9 | 1.39 | | 1.16 | | | | 1.09 | 1.24 | 1.13 | | | |
| CT11 | 2.22 | | 2.05 | 1.55 | 2.01 | 1.75 | 1.48 | | 1.92 | | | |
| | 2.26 | | 1.85 | | 1.83 | | 1.12 | | | | | |
| HF000539 | | | | | | 1.57 | | | | | | |
| SW620 | | | | | | 1.14 | | | | | | |
| HF000611 | | | | | | 4.64 | | | | | | |
| HF000733 | | | | | | 1.93 | | | | | | |
| | | | | | | 2.33 | | | | | | |
| HF000716 | | | | | | 1.68 | | | | | | |
| | | | | | | 2.82 | | | | | | |
| CT18 | | | | | | | | | 1.29 | | | |

Summary

Because amplification of the various DNA's as described above occurs in various tumors, it is likely associated with tumor formation and/or growth. As a result, antagonists (e.g., antibodies) directed against these polypeptides would be expected to be useful in cancer therapy.

Example 94

Detection of PRO Polypeptides that Affect Glucose or FFA Uptake by Primary Rat Adipocytes (Assay 94)

This assay is designed to determine whether PRO polypeptides show the ability to affect glucose or FFA uptake by adipocyte cells. PRO polypeptides testing positive in this assay would be expected to be useful for the therapeutic treatment of disorders where either the stimulation or inhibition of glucose uptake by adipocytes would be beneficial including, for example, obesity, diabetes or hyper- or hypo-insulinemia.

In a 96 well format, PRO polypeptides to be assayed are added to primary rat adipocytes, and allowed to incubate overnight. Samples are taken at 4 and 16 hours and assayed for glycerol, glucose and FFA uptake. After the 16 hour incubation, insulin is added to the media and allowed to incubate for 4 hours. At this time, a sample is taken and glycerol, glucose and FFA uptake is measured. Media containing insulin without the PRO polypeptide is used as a positive reference control. As the PRO polypeptide being tested may either stimulate or inhibit glucose and FFA uptake, results are scored as positive in the assay if greater than 1.5 times or less than 0.5 times the insulin control.

The following PRO polypeptides tested positive as stimulators of glucose and/or FFA uptake in this assay: PRO221, PRO235, PRO245, PRO295, PRO301 and PRO332.

The following PRO polypeptides tested positive as inhibitors of glucose and/or FFA uptake in this assay: PRO214, PRO219, PRO228, PRO222, PRO231 and PRO265.

Example 95

Chondrocyte Re-differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articulary cartilage of metacarpophalangeal joints of 4–6 month old female pigs. The isolated cells are then seeded at 25,000 cells/$cm^2$ in Ham F-12 containing 10% FBS and 4 μg/ml gentamycin. The culture media is changed every third day and the cells are then seeded in 96 well plates at 5,000 cells/well in 100 μl of the same media without serum and 100 μl of the test PRO polypeptide, 5 μM staurosporin (positive control) or medium alone (negative control) is added to give a final volume of 200 μl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO214, PRO219, PRO229, PRO222, PRO224, PRO230, PRO257, PRO272 and PRO301.

Example 96

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 μM hemin and as a negative control, the cells are untreated. After 5 days, cell lysates are prepared and analyzed for the expression of gamma globin (a fetal marker). A positive in the assay is a gamma globin level at least 2-fold above the negative control.

The following polypeptides tested positive in this assay: PRO221 and PRO245.

Example 97

Mouse Kidney Mesangial Cell Proliferation Assay (Assay 92)

This assay shows that certain polypeptides of the invention act to induce proliferation of mammalian kidney mesangial cells and, therefore, are useful for treating kidney disorders associated with decreased mesangial cell function such as Berger disease or other nephropathies associated with Schönlein-Henoch purpura, celiac disease, dermatitis herpetiformis or Crohn disease. The assay is performed as follows. On day one, mouse kidney mesangial cells are plated on a 96 well plate in growth media (3:1 mixture of Dulbecco's modified Eagle's medium and Ham's F12 medium, 95% fetal bovine serum, 5% supplemented with 14 mM HEPES) and grown overnight. On day 2, PRO polypeptides are diluted at 2 concentrations (1% and 0.1%) in serum-free medium and added to the cells. Control samples are serum-free medium alone. On day 4, 20 μl of the Cell Titer 96 Aqueous one solution reagent (Progema) was added to each well and the colormetric reaction was allowed to proceed for 2 hours. The absorbance (OD) is then measured at 490 nm. A positive in the assay is anything that gives an absorbance reading which is at least 15% above the control reading.

The following polypeptide tested positive in this assay: PRO227.

Example 98

Proliferation of Rat Utricular Supporting Cells (Assay 54)

This assay shows that certain polypeptides of the invention act as potent mitogens for inner ear supporting cells which are auditory hair cell progenitors and, therefore, are useful for inducing the regeneration of auditory hair cells and treating hearing loss in mammals. The assay is performed as follows. Rat UEC-4 utricular epithelial cells are aliquoted into 96 well plates with a density of 3000 cells/well in 200 μl of serum-containing medium at 33° C. The cells are cultured overnight and are then switched to serum-free medium at 37° C. Various dilutions of PRO polypeptides (or nothing for a control) are then added to the cultures and the cells are incubated for 24 hours. After the 24 hour incubation, $^3$H-thymidine (1 μCi/well) is added and the cells are then cultured for an additional 24 hours. The cultures are then washed to remove unincorporated radiolabel, the cells harvested and Cpm per well determined. Cpm of at least 30% or greater in the PRO polypeptide treated cultures as compared to the control cultures is considered a positive in the assay.

The following polypeptides tested positive in this assay: PRO310 and PRO346.

Example 99

Chondrocyte Proliferation Assay (Assay 111)

This assay is designed to determine whether PRO polypeptides of the present invention show the ability to induce the proliferation and/or redifferentiation of chondrocytes in culture. PRO polypeptides testing positive in this assay would be expected to be useful for the therapeutic treatment of various bone and/or cartilage disorders such as, for example, sports injuries and arthritis.

Porcine chondrocytes are isolated by overnight collagenase digestion of articular cartilage of the metacarpophalangeal joint of 4–6 month old female pigs. The isolated cells are then seeded at 25,000 cells/cm$^2$ in Ham F-12 containing 10% FBS and 4 μg/ml gentamycin. The culture media is changed every third day and the cells are reseeded to 25,000 cells/cm$^2$ every five days. On day 12, the cells are seeded in 96 well plates at 5,000 cells/well in 100 μl of the same media without serum and 100 μL of either serum-free medium (negative control), staurosporin (final concentration of 5 nM; positive control) or the test PRO polypeptide are added to give a final volume of 200 μl/well. After 5 days at 37° C., 20 μl of Alamar blue is added to each well and the plates are incubated for an additional 3 hours at 37° C. The fluorescence is then measured in each well (Ex:530 nm; Em: 590 nm). The fluorescence of a plate containing 200 μl of the serum-free medium is measured to obtain the background. A positive result in the assay is obtained when the fluorescence of the PRO polypeptide treated sample is more like that of the positive control than the negative control.

The following PRO polypeptides tested positive in this assay: PRO219, PRO222, PRO317, PRO257, PRO265, PRO287, PRO272 and PRO533.

Example 100

Inhibition of Heart Neonatal Hypertrophy Induced by LIF+ET−1 (Assay 74)

This assay is designed to determine whether PRO polypeptides of the present invention show the ability to inhibit neonatal heart hypertrophy induced by LIF and endothelin-1 (ET-1). A test compound that provides a positive response in the present assay would be useful for the therapeutic treatment of cardiac insufficiency diseases or disorders characterized or associated with an undesired hypertrophy of the cardiac muscle.

Cardiac myocytes from 1-day old Harlan Sprague Dawley rats (180 μl at $7.5\times10^4$/ml, serum <0.1, freshly isolated) are introduced on day 1 to 96-well plates previously coated with DMEM/F12+4% FCS. Test PRO polypeptide samples or growth medium alone (negative control) are then added directly to the wells on day 2 in 20 μl volume. LIF+ET−1 are then added to the wells on day 3. The cells are stained after an additional 2 days in culture and are then scored visually the next day. A positive in the assay occurs when the PRO polypeptide treated myocytes are visually smaller on the average or less numerous than the untreated myocytes.

The following PRO polypeptides tested positive in this assay: PRO238.

Example 101

Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200–600 base pair amplified fragment from the 3' end of its associated template in a standard PCR reaction. The oligonucleotide probes were employed in standard quantitative PCR amplification reactions with cDNA libraries isolated from different human adult and/or fetal tissue sources and analyzed by agarose gel electrophoresis so as to obtain a quantitative determination of the level of expression of the PRO polypeptide-encoding nucleic acid in the various tissues tested. Knowledge of the expression pattern or the differential expression of the PRO polypeptide-encoding nucleic acid in various different human tissue types provides a diagnostic marker useful for tissue typing, with or without other tissue-specific markers, for determining the primary tissue source of a metastatic tumor, and the like. These assays provided the following results.

| DNA Molecule | Tissues With Significant Expression | Tissues Lacking Significant Expression |
|---|---|---|
| DNA34436-1238 | lung, placenta, brain | testis |
| DNA35557-1137 | lung, kidney, brain | placenta |
| DNA35599-1168 | kidney, brain | liver, placenta |
| DNA35668-1171 | liver, lung, kidney | placenta, brain |
| DNA36992-1168 | liver, lung, kidney, brain | placenta |
| DNA39423-1182 | kidney, brain | liver |
| DNA40603-1232 | liver | brain, kidney, lung |
| DNA40604-1187 | liver | brain, kidney, lung |
| DNA41379-1236 | lung, brain | liver |
| DNA33206-1165 | heart, spleen, dendrocytes | substantia nigra, hippocampus, cartilage, prostate, HUVEC |
| DNA34431-1177 | spleen, HUVEC, cartilage, heart, uterus | brain, colon tumor, prostate, THP-1 macrophages |
| DNA41225-1217 | HUVEC, uterus, colon tumor, cartilage, prostate | spleen, brain, heart, IM-9 lymphoblasts |

Example 102

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169–176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed vac dried. To each tube containing dried $^{33}$P-UTP, the following ingredients were added:

2.0 μl 5× transcription buffer 1.0 μl DTT (100 mM)

2.0 μl NTP mix (2.5 mM: 10μ; each of 10 mM GTP, CTP & ATP+10 μl $H_2O$)

1.0 μl UTP (50 μM)

1.0 μl Rnasin 1.0 μl DNA template (1 μg)

1.0 μl $H_2O$ 1.0 μl RNA polymerase (for PCR products T3=AS, T7=S, usually)

The tubes were incubated at 37° C. for one hour. 1.0 μl RQ1 DNase were added, followed by incubation at 37° C. for 15 minutes. 90 μl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 μl TE were added. 1 μl of the final product was pipetted on DE81 paper and counted in 6 mil of Biofluor II.

The probe was run on a TBE/urea gel. 1–3 μl of the probe or 5 μl of RNA Mrk III were added to 3 μl of loading buffer. After heating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ $H_2O$). After deproteination in 0.5 μg/ml proteinase K for 10 minutes at 37° C. (12.5 μl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ $H_2O$, and rinsed twice in 2×SSC at room temperature, for 5 minutes each time. The sections were deproteinated in 20 μg/ml proteinase K (500 μl of 10 mg/ml in 250 ml RNase-free RNase buffer; 37° C., 15 minutes)–human embryo, or 8× proteinase K (100 μl in 250 ml Rnase buffer, 37° C., 30 minutes)–formalin tissues. Subsequent rinsing in 0.5×SSC and dehydration were performed as described above.

C. Prehybridization

The slides were laid out in a plastic box lined with Box buffer (4×SSC, 50% formamide)–saturated filter paper. The tissue was covered with 50 μl of hybridization buffer (3.75 g Dextran Sulfate+6 ml SQ $H_2O$), vortexed and heated in the microwave for 2 minutes with the cap loosened. After cooling on ice, 18.75 ml formamide, 3.75 ml 20×SSC and 9 ml SQ $H_2O$ were added, the tissue was vortexed well, and incubated at 42° C. for 1–4 hours.

D. Hybridization $1.0\times10^6$ cpm probe and 1.0 μl tRNA (50 mg/ml stock) per slide were heated at 95° C. for 3 minutes. The slides were cooled on ice, and 48 μl hybridization buffer were added per slide. After vortexing, 50 μl $^{33}$P mix were added to 50 μl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4L), followed by RNaseA treatment at 37° C. for 30 minutes (500 μl of 10 mg/ml in 250 ml Rnase buffer=20 μg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4L).

F. Oligonucleotides

In situ analysis was performed on a variety of DNA sequences disclosed herein. The oligonucleotides employed for these analyses are as follows.

(1) DNA33094-1131 (PRO217)

p1 5'-GGATTCTAATACGACTCACTATAGGGCT-CAGAAAAGCGCAACAGAGAA-3' (SEQ ID NO:348)

p2 5'-CTATGAAATTAACCCTCACTAAAGGGAT-GTCTTCCATGCCAACCTTC-3' (SEQ ID NO:349)

(2) DNA33223-1136 (PRO230)

p1 5'-GGATTCTAATACGACTCACTATAGGGCG-GCGATGTCCACTGGGGCTAC-3' (SEQ ID NO:350)

p2 5'-CTATGAAATTAACCCTCACTAAAGGGAC-GAGGAAGATGGGCGGATGGT-3' (SEQ ID NO:351)

(3) DNA34435-1140 (PRO232)

p1 5'-GGATTCTAATACGACTCACTAT-AGGGCACCCACGCGTCCGGCTGCTT-3' (SEQ ID NO:352)

p2 5'-CTATGAAATTAACCCTCACTAAAGG-GACGGGGGACACCACGGACCAGA-3' (SEQ ID NO:353)

(4) DNA35639-1172 (PRO246)

p1 5'-GGATTCTAATACGACTCACTATAGGGCT-TGCTGCGGTTTTTGTTCCTG-3' (SEQ ID NO:354)

p2 5'-CTATGAAATTAACCCTCACTAAAGG-GAGCTGCCGATCCCACTGGTATr-3' (SEQ ID NO:355)

(5) DNA49435-1219 (PRO533)

p1 5'-GGATTCTAATACGACTCACTATAGGGCG-GATCCTGGCCGGCCTCTG-3' (SEQ ID NO:356)

p2 5'-CTATGAAATTAACCCTCACTAAAGG-GAGCCCGGGCATGGTCTCAGTTA-3' (SEQ ID NO:357)

(6) DNA35638-1141 (PRO245)

p1 5'-GGATCTAATACGACTCACTATAGGGCGG-GAAGATGGCGAGGAGGAG-3' (SEQ ID NO:358)

p2 5'-CTATGAAATTAACCCTCACTAAAGGGAC-CAAGGCCACAAACGGAAATC-3' (SEQ ID NO:359)

(7) DNA33089-1132 (PRO221)

p1 5'-GGATTCTAATACGACTCACTATAGGGCT-GTGCTTTCATTCTGCCAGTA-3' (SEQ ID NO:360)

p2 5'-CTATGAAATTAACCCTCACTAAAGG-GAGGGTACAATTAAGGGGTGGAT-3' (SEQ ID NO:361)

(8) DNA35918-1174 (PRO258)

p1 5'-GGATTCTAATACGACTCACTATAGGGC-CCGCCTCGCTCCTGCTCCTG-3' (SEQ ID NO:362)

p2 5'-CTATGAAATTAACCCTCACTAAAGGGAG-GATTGCCGCGACCCTCACAG-3' (SEQ ID NO:363)

(9) DNA32286-1191 (PRO214)

p1 5'-GGATTCTAATACGACTCACTATAGGGC-CCCTCCTGCCTTCCCTGTCC-3' (SEQ ID NO:364)

p2 5'-CTATGAAATTAACCCTCACTAAAGG-GAGTGGTGGCCGCGATTATCTGC-3' (SEQ ID NO:365)

(10) DNA33221-1133 (PRO224)

p1 5'-GGATTCTAATACGACTCACTATAGGGCG-CAGCGATGGCAGCGATGAGG-3' (SEQ ID NO:366)

p2 5'-CTATGAAATTAACCCTCACTAAAGGGA-CAGACGGGGCAGAGGGAGTG-3' (SEQ ID NO:367)

(11) DNA35557-1137 (PRO234)

p1 5'-GGATFCTAATACGACTCACTATAGGGC-CAGGAGGCGTGAGGAGAAAC-3' (SEQ ID NO:368)

p2 5'-CTATGAAATTAACCCTCACTAAAGG-GAAAGACATGTCATCGGGAGTGG-3' (SEQ ID NO:369)

(12) DNA33100-1159 (PRO229)

p1 5'-GGATTCTAATACGACTCACTATAGGGC-CGGGTGGAGGTGGAACAGAAA-3' (SEQ ID NO:370)

p2 5'-CTATGAAATTAACCCTCACTAAAGGGA-CACAGACAGAGCCCCATACGC-3' (SEQ ID NO:371)

(13) DNA34431-1177 (PRO263)

p1 5'-GGATTCTAATACGACTCACTATAGGGC-CAGGGAAATCCGGATGTCTC-3' (SEQ ID NO:372)

p2 5'-CTATGAAATTAACCCTCACTAAAGGGAG-TAAGGGGATGCCACCGAGTA-3' (SEQ ID NO:373)

(14) DNA38268-1188 (PRO295)

p1 5'-GGATTCTAATACGACTCACTATAGGGC-CAGCrACCCGCAGGAGGAGG-3' (SEQ ID NO:374)

p2 5'-CTATGAAATTAACCCTCACTAAAGG-GATCCCAGGTGATGAGGTCCAGA-3' (SEQ ID NO:375)

G. Results

In situ analysis was performed on a variety of DNA sequences disclosed herein. The results from these analyses are as follows.

(1) DNA33094-1131 (PRO217)

Highly distinctive expression pattern, that does not indicate an obvious biological function. In the human embryo it was expressed in outer smooth muscle layer of the GI tract, respiratory cartilage, branching respiratory epithelium, osteoblasts, tendons, gonad, in the optic nerve head and developing dermis. In the adult expression was observed in the epidermal pegs of the chimp tongue, the basal epithelial/myoepithelial cells of the prostate and urinary bladder. Also expressed in the alveolar lining cells of the adult lung, mesenchymal cells juxtaposed to erectile tissue in the penis and the cerebral cortex (probably glial cells). In the kidney, expression was only seen in disease, in cells surrounding thyroidized renal tubules.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult human tissues examined: Kidney (normal and end-stage), adrenal, myocardium, aorta, spleen, lymph node, gall bladder, pancreas, lung, skin, eye (inc. retina), prostate, bladder, liver (normal, cirrhotic, acute failure).

Non-human primate tissues examined:

(a) Chimp Tissues: Salivary gland, stomach, thyroid, parathyroid, skin, thymus, ovary, lymph node.

(b) Rhesus Monkey Tissues: Cerebral cortex, hippocampus, cerebellum, penis.

(2) DNA33223-1136 (PRO230)

Sections show an intense signal associated with arterial and venous vessels in the fetus. In arteries the signal appeared to be confined to smooth-muscle/pericytic cells. The signal is also seen in capillary vessels and in glomeruli. It is not clear whether or not endothelial cells are expressing this mRNA. Expression is also observed in epithelial cells in the fetal lens. Strong expression was also seen in cells within placental trophoblastic villi, these cells lie between the trophoblast and the fibroblast-like cells that express HGF—uncertain histogenesis. In the adult, there was no evidence of expression and the wall of the aorta and most vessels appear to be negative. However, expression was seen over vascular channels in the normal prostate and in the epithelium lining the gallbladder. Insurers expression was seen in the vessels of the soft-tissue sarcoma and a renal cell carcinoma. In summary, this is a molecule that shows relatively specific vascular expression in the fetus as well as in some adult organs. Expression was also observed in the fetal lens and the adult gallbladder.

In a secondary screen, vascular expression was observed, similar to that observed above, seen in fetal blocks. Expression is on vascular smooth muscle, rather than endothelium. Expression also seen in smooth muscle of the developing oesophagus, so as reported previously, this molecule is not vascular specific. Expression was examined in 4 lung and 4 breast carcinomas. Substantial expression was seen in vascular smooth muscle of at least ¾ lung cancers and 2/4 breast cancers. In addition, in one breast carcinoma, expression was observed in peritumoral stromal cells of uncertain histogenesis (possibly myofibroblasts). No endothelial cell expression was observed in this study.

(3) DNA34435-1140 (PRO232)

Strong expression in prostatic epithelium and bladder epithelium, lower level of expression in bronchial epithelium. High background/low level expression seen in a number of sites, including among others, bone, blood, chondrosarcoma, adult heart and fetal liver. It is felt that this level of signal represents background, partly because signal at this level was seen over the blood. All other tissues negative.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis, testis and lower limb.

Adult human tissues examined: Kidney (normal and end-stage), adrenal, spleen, lymph node, pancreas, lung, eye (inc. retina), bladder, liver (normal, cirrhotic, acute failure).

Non-Human Primate Tissues Examined:

Chimp Tissues: adrenal

Rhesus Monkey Tissues: Cerebral cortex, hippocampus

In a secondary screen, expression was observed in the epithelium of the prostate, the superficial layers of the urethelium of the urinary bladder, the urethelium lining the renal pelvis and the urethelium of the ureter (1 out of 2 experiments). The urethra of a rhesus monkey was negative; it is unclear whether this represents a true lack of expression by the urethra, or if it is the result of a failure of the probe to cross react with rhesus tissue. The findings in the prostate and bladder are similar to those previously described using an isotopic detection technique. Expression of the mRNA for this antigen is NOT prostate epithelial specific. The antigen may serve as a useful marker for urethelial derived tissues. Expression in the superficial, post-mitotic cells, of the urinary tract epithelium also suggest that it is unlikely to represent a specific stem cell marker, as this would be expected to be expressed specifically in basal epithelium.

(4) DNA35639-1172 (PRO246)

Strongly expressed in fetal vascular endothelium, including tissues of the CNS. Lower level of expression in adult vasculature, including the CNS. Not obviously expressed at higher levels in tumor vascular endothelium. Signal also seen over bone matrix and adult spleen, not obviously cell associated, probably related to non-specific background at these sites.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis, testis and lower limb.

Adult human tissues examined: Kidney (normal and end-stage), adrenal, spleen, lymph node, pancreas, lung, eye (inc. retina), bladder, liver (normal, cirrhotic, acute failure).

Non-human primate tissues examined:

Chimp Tissues: adrenal

Rhesus Monkey Tissues: Cerebral cortex, hippocampus (5) DNA49435-1219 (PRO533)

Moderate expression over cortical neurones in the fetal brain. Expression over the inner aspect of the fetal retina, possible expression in the developing lens. Expression over fetal skin, cartilage, small intestine, placental villi and umbilical cord. In adult tissues there is an extremely high level of expression over the gallbladder epithelium. Moderate expression over the adult kidney, gastric and colonic epithelia. Low-level expression was observed over many cell types in many tissues, this may be related to stickiness of the probe, these data should therefore be interpreted with a degree of caution.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis, testis and lower limb.

Adult human tissues examined: Kidney (normal and end-stage), adrenal, spleen, lymph node, pancreas, lung, eye (inc. retina), bladder, liver (normal, cirrhotic, acute failure).

Non-Human Primate Tissues Examined:

Chimp Tissues: adrenal

Rhesus Monkey Tissues: Cerebral cortex, hippocampus, cerebellum.

(6) DNA35638-1141 (PRO245)

Expression observed in the endothelium lining a subset of fetal and placental vessels. Endothelial expression was confined to these tissue blocks. Expression also observed over intermediate trophoblast cells of placenta. Expression also observed tumor vasculature but not in the vasculature of normal tissues of the same type. All other tissues negative.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: Liver, kidney, adrenal, myocardium, aorta, spleen, lymph node, pancreas, lung, skin, cerebral cortex (rm), hippocampus (rm), cerebellum (rm), penis, eye, bladder, stomach, gastric carcinoma, colon, colonic carcinoma, thyroid (chimp), parathyroid (chimp) ovary (chimp) and chondrosarcoma. Acetominophen induced liver injury and hepatic cirrhosis (7) DNA33089-1132 (PRO221)

Specific expression over fetal cerebral white and grey matter, as well as over neurones in the spinal cord. Probe appears to cross react with rat. Low level of expression over cerebellar neurones in adult rhesus brain. All other tissues negative.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: Liver, kidney, adrenal, myocardium, aorta, spleen, lymph node, pancreas, lung, skin, cerebral cortex (rm), hippocampus (rm), cerebellum (rm), penis, eye, bladder, stomach, gastric carcinoma, colon, colonic carcinoma and chondrosarcoma. Acetominophen induced liver injury and hepatic cirrhosis (8) DNA35918-1174 (PRO258)

Strong expression in the nervous system. In the rhesus monkey brain expression is observed in cortical, hippocampal and cerebellar neurones. Expression over spinal neurones in the fetal spinal cord, the developing brain and the inner aspects of the fetal retina. Expression over developing dorsal root and autonomic ganglia as well as enteric nerves. Expression observed over ganglion cells in the adult prostate. In the rat, there is strong expression over the developing hind brain and spinal cord. Strong expression over interstitial cells in the placental villi. All other tissues were negative.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: Liver, kidney, renal cell carcinoma, adrenal, aorta, spleen, lymph node, pancreas, lung, myocardium, skin, cerebral cortex (rm), hippocampus (rm), cerebellum (rm), bladder, prostate, stomach, gastric carcinoma, colon, colonic carcinoma, thyroid (chimp), parathyroid (chimp) ovary (chimp) and chondrosarcoma. Acetominophen induced liver injury and hepatic cirrhosis.

(9) DNA32286-1191 (PRO214)

Fetal tissue: Low level throughout mesenchyme. Moderate expression in placental stromal cells in membranous tissues and in thyroid. Low level expression in cortical neurones. Adult tissue: all negative.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined include: Liver, kidney, adrenal, myocardium, aorta, spleen, lymph node, pancreas, lung and skin.

(10) DNA33221-1133 (PRO224)

Expression limited to vascular endothelium in fetal spleen, adult spleen, fetal liver, adult thyroid and adult lymph node (chimp). Additional site of expression is the developing spinal ganglia. All other tissues negative.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult human tissues examined: Kidney (normal and end-stage), adrenal, myocardium, aorta, spleen, lymph node, pancreas, lung, skin, eye (inc. retina), bladder, liver (normal, cirrhotic, acute failure).

Non-Human Primate Tissues Examined:

Chimp Tissues: Salivary gland, stomach, thyroid, parathyroid, skin, thymus, ovary, lymph node.

Rhesus Monkey Tissues: Cerebral cortex, hippocampus, cerebellum, penis.

(11) DNA35557-1137 (PRO234)

Specific expression over developing motor neurones in ventral aspect of the fetal spinal cord (will develop into ventral horns of spinal cord). All other tissues negative. Possible role in growth, differentiation and/or development of spinal motor neurons.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: Liver, kidney, adrenal, myocardium, aorta, spleen, lymph node, pancreas, lung, skin, cerebral cortex (rm), hippocampus (rm), cerebellum (rm), penis, eye, bladder, stomach, gastric carcinoma, colon, colonic carcinoma and chondrosarcoma. Acetominophen induced liver injury and hepatic cirrhosis

(12) DNA33100-1159 (PRO229)

Striking expression in mononuclear phagocytes (macrophages) of fetal and adult spleen, liver, lymph node and adult thymus (in tingible body macrophages). The highest expression is in the spleen. All other tissues negative. Localisation and homology are entirely consistent with a role as a scavenger receptor for cells of the reticuloendothelial system. Expression also observed in placental mononuclear cells.

Human fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult human tissues examined: Kidney (normal and end-stage), adrenal, myocardium, aorta, spleen, lymph node, gall bladder, pancreas, lung, skin, eye (inc. retina), prostate, bladder, liver (normal, cirrhotic, acute failure).

Non-Human Primate Tissues Examined:

Chimp Tissues: Salivary gland, stomach, thyroid, parathyroid, skin, thymus, ovary, lymph node.

Rhesus Monkey Tissues: Cerebral cortex, hippocampus, cerebellum, penis.

(13) DNA34431-1177 (PRO263)

Widepread expression in human fetal tissues and placenta over mononuclear cells, probably macrophages +/− lymphocytes. The cellular distribution follows a perivascular pattern in many tissues. Strong expression also seen in epithelial cells of the fetal adrenal cortex. All adult tissues were negative.

Fetal tissues examined (E12–E16 weeks) include: Placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: Liver, kidney, adrenal, spleen, lymph node, pancreas, lung, skin, cerebral cortex (rm), hippocampus (rm), cerebellum (rm), bladder, stomach, colon and colonic carcinoma. Acetominophen induced liver injury and hepatic cirrhosis.

A secondary screen evidenced expression over stromal mononuclear cells probably histiocytes.

(14) DNA38268-1188 (PRO295)

High expression over ganglion cells in human fetal spinal ganglia and over large neurones in the anterior horns of the developing spinal cord. In the adult there is expression in the chimp adrenal medulla (neural), neurones of the rhesus monkey brain (hippocampus [+++] and cerebral cortex) and neurones in ganglia in the normal adult human prostate (the only section that contains ganglion cells, ie expression in this cell type is presumed NOT to be confined to the prostate). All other tissues negative.

Human fetal tissues examined (E12–E16 weeks) include: Placenta, umbilical cord, liver, kidney, adrenals, thyroid, lungs, great vessels, stomach, small intestine, spleen, thymus, pancreas, brain, eye, spinal cord, body wall, pelvis, testis and lower limb.

Adult human tissues examined: Kidney (normal and end-stage), adrenal, spleen, lymph node, pancreas, lung, eye (inc. retina), bladder, liver (normal, cirrhotic, acute failure).

Non-Human Primate Tissues Examined:
Chimp Tissues: adrenal
Rhesus Monkey Tissues: Cerebral cortex; hippocampus, cerebellum.

Example 103

Isolation of cDNA clones Encoding Human PRO1868

A consensus DNA sequence was assembled relative to other EST sequences using phrap as described in Example 1 above. This consensus sequence is herein designated DNA49803. Based up an observed homology between the DNA49803 consensus sequence and an EST sequence contained within the Incyte EST clone no. 2994689, Incyte EST clone no. 2994689 was purchased and its insert obtained and sequenced. The sequence of that insert is shown in FIG. 123 and is herein designated DNA77624-2515.

The entire nucleotide sequence of DNA77624-2515 is shown in FIG. 123 (SEQ ID NO:422). Clone DNA77624-2515 contains a single open reading frame with an apparent translational initiation site at nucleotide positions 51–53 and ending at the stop codon at nucleotide positions 981–983 (FIG. 123). The predicted polypeptide precursor is 310 amino acids long (FIG. 124). The full-length PRO1868 protein shown in FIG. 124 has an estimated molecular weight of about 35,020 daltons and a pI of about 7.90. Analysis of the full-length PRO1868 sequence shown in FIG. 124 (SEQ ID NO:423) evidences the presence of the following: a signal peptide from about amino acid 1 to about amino acid 30, a transmembrane domain from about amino acid 243 to about amino acid 263, potential N-glycosylation sites from about amino acid 104 to about amino acid 107 and from about amino acid 192 to about amino acid 195, a cAMP- and cGMP-dependent protein kinase phosphorylation site from about amino acid 107 to about amino acid 110, casein kinase II phosphorylation sites from about amino acid 106 to about amino acid 109 and from about amino acid 296 to about amino acid 299, a tyrosine kinase phosphorylation site from about amino acid 69 to about amino acid 77 and potential N-myristolation sites from about amino acid 26 to about amino acid 31, from about amino acid 215 to about amino acid 220, from about amino acid 226 to about amino acid 231, from about amino acid 243 to about amino acid 248, from about amino acid 244 to about amino acid 249 and from about amino acid 262 to about amino acid 267. Clone DNA77624-2515 has been deposited with ATCC on Dec. 22, 1998 and is assigned ATCC deposit no. 203553.

An analysis of the Dayhoff database (version 35.45 SwissProt 35), using a WU-BLAST2 sequence alignment analysis of the full-length sequence shown in FIG. 124 (SEQ ID NO:423), evidenced significant homology between the PRO1868 amino acid sequence and the following Dayhoff sequences: HGS_RC75, P_W61379, A33_HUMAN, P_W14146, P_W14158, AMAL_DROME, P_R77437, 138346, NCM2_HUMAN and PTPD_HUMAN.

Example 104

Identification of Receptor/Ligand Interactions

In this assay, various PRO polypeptides are tested for ability to bind to a panel of potential receptor molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparation of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified: PRO245 binds to PRO1868.

DEPOSIT OF MATERIAL

The following materials have been deposited with the American Type Culture Collection, 12301 Parklawn Drive, Rockville, Md., USA (ATCC):

| Material | ATCC Dep. No. | Deposit Date |
|---|---|---|
| DNA32292-1131 | ATCC 209258 | Sep. 16, 1997 |
| DNA33094-1131 | ATCC 209256 | Sep. 16, 1997 |
| DNA33223-1136 | ATCC 209264 | Sep. 16, 1997 |
| DNA34435-1140 | ATCC 209250 | Sep. 16, 1997 |
| DNA27864-1155 | ATCC 209375 | Oct. 16, 1997 |
| DNA36350-1158 | ATCC 209378 | Oct. 16, 1997 |
| DNA32290-1164 | ATCC 209384 | Oct. 16, 1997 |
| DNA35639-1172 | ATCC 209396 | Oct. 17, 1997 |
| DNA33092-1202 | ATCC 209420 | Oct. 28, 1997 |
| DNA49435-1219 | ATCC 209480 | Nov. 21, 1997 |
| DNA35638-1141 | ATCC 209265 | Sep. 16, 1997 |
| DNA32298-1132 | ATCC 209257 | Sep. 16, 1997 |
| DNA33089-1132 | ATCC 209262 | Sep. 16, 1997 |
| DNA33786-1132 | ATCC 209253 | Sep. 16, 1997 |

-continued

| Material | ATCC Dep. No. | Deposit Date |
|---|---|---|
| DNA35918-1174 | ATCC 209402 | Oct. 17, 1997 |
| DNA37150-1178 | ATCC 209401 | Oct. 17, 1997 |
| DNA38260-1180 | ATCC 209397 | Oct. 17, 1997 |
| DNA39969-1185 | ATCC 209400 | Oct. 17, 1997 |
| DNA32286-1191 | ATCC 209385 | Oct. 16, 1997 |
| DNA33461-1199 | ATCC 209367 | Oct. 15, 1997 |
| DNA40628-1216 | ATCC 209432 | Nov. 7, 1997 |
| DNA33221-1133 | ATCC 209263 | Sep. 16, 1997 |
| DNA33107-1135 | ATCC 209251 | Sep. 16, 1997 |
| DNA35557-1137 | ATCC 209255 | Sep. 16, 1997 |
| DNA34434-1139 | ATCC 209252 | Sep. 16, 1997 |
| DNA33100-1159 | ATCC 209373 | Oct. 16, 1997 |
| DNA35600-1162 | ATCC 209370 | Oct. 16, 1997 |
| DNA34436-1238 | ATCC 209523 | Dec. 10, 1997 |
| DNA33206-1165 | ATCC 209372 | Oct. 16, 1997 |
| DNA35558-1167 | ATCC 209374 | Oct. 16, 1997 |
| DNA35599-1168 | ATCC 209373 | Oct. 16, 1997 |
| DNA36992-1168 | ATCC 209382 | Oct. 16, 1997 |
| DNA34407-1169 | ATCC 209383 | Oct. 16, 1997 |
| DNA35841-1173 | ATCC 209403 | Oct. 17, 1997 |
| DNA33470-1175 | ATCC 209398 | Oct. 17, 1997 |
| DNA34431-1177 | ATCC 209399 | Oct. 17, 1997 |
| DNA39510-1181 | ATCC 209392 | Oct. 17, 1997 |
| DNA39423-1182 | ATCC 209387 | Oct. 17, 1997 |
| DNA40620-1183 | ATCC 209388 | Oct. 17, 1997 |
| DNA40604-1187 | ATCC 209394 | Oct. 17, 1997 |
| DNA38268-1188 | ATCC 209421 | Oct. 28, 1997 |
| DNA37151-1193 | ATCC 209393 | Oct. 17, 1997 |
| DNA35673-1201 | ATCC 209418 | Oct. 28, 1997 |
| DNA40370-1217 | ATCC 209485 | Nov. 21, 1997 |
| DNA42551-1217 | ATCC 209483 | Nov. 21, 1997 |
| DNA39520-1217 | ATCC 209482 | Nov. 21, 1997 |
| DNA41225-1217 | ATCC 209491 | Nov. 21, 1997 |
| DNA43318-1217 | ATCC 209481 | Nov. 21, 1997 |
| DNA40587-1231 | ATCC 209438 | Nov. 7, 1997 |
| DNA41338-1234 | ATCC 209927 | Jun. 2, 1998 |
| DNA40981-1234 | ATCC 209439 | Nov. 7, 1997 |
| DNA37140-1234 | ATCC 209489 | Nov. 21, 1997 |
| DNA40982-1235 | ATCC 209433 | Nov. 7, 1997 |
| DNA41379-1236 | ATCC 209488 | Nov. 21, 1997 |
| DNA44167-1243 | ATCC 209434 | Nov. 7, 1997 |
| DNA39427-1179 | ATCC 209395 | Oct. 17, 1997 |
| DNA40603-1232 | ATCC 209486 | Nov. 21, 1997 |
| DNA43466-1225 | ATCC 209490 | Nov. 21, 1997 |
| DNA43046-1225 | ATCC 209484 | Nov. 21,1997 |
| DNA35668-1171 | ATCC 209371 | Oct. 16, 1997 |
| DNA77624-2515 | ATCC 203553 | Dec. 22, 1998 |

These deposit were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid comprising a nucleotide sequence having at least 95% sequence identity to:

(a) the nucleic acid sequence encoding the polypeptide of SEQ ID NO: 104;

(b) the nucleic acid sequence encoding the polypeptide of SEQ ID NO: 104, lacking its associated signal peptide;

(c) the nucleic acid sequence of SEQ ID NO: 103;

(d) the full-length coding sequence of the nucleic acid sequence of SEQ ID NO: 103; or (e) the full-length coding sequence of the cDNA deposited under ATCC accession number 209400;

wherein the polypeptide encoded by said nucleic acid is capable of inducing chondrocyte proliferation.

2. The isolated nucleic acid of claim 1 comprising a nucleotide sequence having at least 99% sequence identity to:

(a) the nucleic acid sequence encoding the polypeptide of SEQ ID NO: 104;

(b) the nucleic acid sequence encoding the polypeptide of SEQ ID NO: 104, lacking its associated signal peptide;

(c) the nucleic acid sequence of SEQ ID NO: 103;

(d) the full-length coding sequence of the nucleic acid sequence of SEQ ID NO: 103; or (e) the full-length coding sequence of the cDNA deposited under ATCC accession number 209400;

wherein the polypeptide encoded by said nucleic acid is capable of inducing chondrocyte proliferation.

3. A vector comprising the nucleic acid of claim 1.

4. The vector of claim 3, wherein said nucleic acid is operably linked to control sequences recognized by a host cell transformed with the vector.

5. A host cell comprising the vector of claim 3.

6. The host cell of claim 5, wherein said cell is a CHO cell, an *E. coli* or a yeast cell.

* * * * *